US009518097B2

(12) United States Patent
Hallen et al.

(10) Patent No.: US 9,518,097 B2
(45) Date of Patent: Dec. 13, 2016

(54) IDENTIFICATION AND USE OF GENES ENCODING AMATOXIN AND PHALLOTOXIN

(75) Inventors: Heather E. Hallen, Lincoln, NE (US); Jonathan D. Walton, East Lansing, MI (US); Hong Luo, Lansing, MI (US); John S. Scott-Craig, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 12/268,229

(22) Filed: Nov. 10, 2008

(65) Prior Publication Data

US 2010/0267019 A1 Oct. 21, 2010

Related U.S. Application Data

(60) Provisional application No. 61/002,650, filed on Nov. 9, 2007.

(51) Int. Cl.
*C07K 14/375* (2006.01)
*C07K 7/64* (2006.01)
*C12Q 1/68* (2006.01)

(52) U.S. Cl.
CPC ............... *C07K 14/375* (2013.01); *C07K 7/64* (2013.01); *C12Q 1/6895* (2013.01); *C12Q 2600/142* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 4,683,195 | A | 7/1987 | Mullis et al. | 435/6.11 |
| 4,683,202 | A | 7/1987 | Mullis et al. | 435/91.2 |
| 4,965,188 | A | 10/1990 | Mullis et al. | 435/6.12 |
| 5,928,906 | A | 7/1999 | Koster et al. | 435/91.2 |
| 9,273,100 | B2 | 3/2016 | Hallen-Adams et al. | |
| 2001/0014445 | A1* | 8/2001 | Urnovitz | 435/6 |
| 2004/0081978 | A1* | 4/2004 | Ziman et al. | 435/6 |
| 2005/0255486 | A1* | 11/2005 | Behlke et al. | 435/6 |
| 2006/0141495 | A1* | 6/2006 | Wu | 435/6 |
| 2008/0076677 | A1* | 3/2008 | Yershov et al. | 506/13 |
| 2009/0093620 | A1* | 4/2009 | Kovalic et al. | 536/23.1 |
| 2012/0276588 | A1 | 11/2012 | Hallen-Adams et al. | |

FOREIGN PATENT DOCUMENTS

CN 1341362 A * 3/2002

OTHER PUBLICATIONS

Zhang et al. Production and characterization of Amanitin toxins from a pure culture of Amanita exitialis. FEMS Microbiology Letters (2005) 252: 223-228.*

Walton et al. Ribosomal Biosynthesis of the Cyclic Peptide Toxins of Amanita Mushrooms. Peptide Science (2010) 94(5): 659-664.*

Machine translation of CN1341362 obtained on Dec. 21, 2010. 7 pages.*

Trigueros et al. Biochimica et Biophysica Acta (2003) 1621: 292-298.*

Rozen et al. Methods in Molecular Biology (2000) 132: 365-386.*

Ahn, et al., "An extended physical map of the TOX2 locus of Cochliobolus carbonum required for biosynthesis of HC-toxin." *Fungal Genet Biol.* 35(1):31-8 (2002).

Alexandra, et al., "Highly Efficient Production of Laccase by the Basidiomycete Pycnoporus cinnabarinus." *Appl Environ Microbiol.* 70(11):6379-638 (2004).

Bamburg, "Proteins of the ADF/cofilin family: essential regulators of actin dynamics." *Annu. Rev. Cell Dev. Biol.* 15:185-230 (1999).

Benedict, et al., "Fermentative production of amanita toxins by a strain of Galerina marginata." *J Bacteriol* 91:1380-1381 (1966).

Beutler and der Marderosian, "Chemical variation in Amanita." *J. Nat. Prod.* 44:422-431 (1981).

Brandt, et al., "Suggested functions for prolyl oligopeptidase: a puzzling paradox." *Clin Chim Acta.* 377(1-2):50-61. Epub Oct. 10, 2006 (2007).

Bulaj, et al., "Efficient oxidative folding of conotoxins and the radiation of venomous cone snails." *Proc Natl Acad Sci U S A.* 100(2):14562-8. Epub Oct 22, 2003.

Bushnell, et al., "Structural basis of transcription: alpha-amanitin-RNA polymerase II cocrystal at 2.8 A resolution." *Proc. Natl. Acad. Sci. USA* 99:1218-1222 (2002).

Craik, et al., "The chemistry and biology of cyclotides." *Curr Opin Drug Discov Devel* 10:176-184 (2007).

Craik, "Chemistry. Seamless proteins tie up their loose ends." *Science* 311:1563-1564 (2006).

Crooks, et al., "WebLogo: a sequence logo generator." Genome Res. Jun. 14, 2004(6):1188-90 (2004).

Cunningham and O'Connor, "Proline specific peptidases." *Biochim Biophys Acta* 1343:160-186 (1997).

Duquesne, et al., "Two enzymes catalyze the maturation of a lasso peptide in *Escherichia coli." Chem Biol.* 14(7):793-803 (2007).

Enjalbert, et al., "Treatment of Amatoxin Poisoning: 20-Year Retrospective Analysis, review of poisonings." *J. Toxicol. Clin. Toxicol.* 40:715-757 (2002).

Escoubas, "Molecular diversification in spider venoms: a web of combinatorial peptide libraries." *Mol Divers* 10:545-554 (2006).

(Continued)

*Primary Examiner* — Angela M Bertagna
(74) *Attorney, Agent, or Firm* — Schwegman Lundberg & Woessner, P.A.

(57) ABSTRACT

The present invention relates to compositions and methods comprising genes and peptides associated with cyclic peptide toxins and toxin production in mushrooms. In particular, the present invention relates to using genes and proteins from *Amanita* species encoding *Amanita* peptides, specifically relating to amatoxins and phallotoxins. In a preferred embodiment, the present invention also relates to methods for detecting *Amanita* peptide toxin genes for identifying *Amanita* peptide-producing mushrooms and for diagnosing suspected cases of mushroom poisoning. Further, the present inventions relate to providing kits for diagnosing and monitoring suspected cases of mushroom poisoning in patients.

9 Claims, 91 Drawing Sheets

(56) References Cited

OTHER PUBLICATIONS

Finking and Marahiel, "Biosynthesis of Nonribosomal Peptides." *Annu Rev Microbiol* 58:453-488 (2004).
Frohman, et al., "Rapid production of full-length cDNAs from rare transcripts: amplification using a single gene-specific oligonucleotide primer." *Proc Natl Acad Sci* 85:8998-9002 (1988).
Garcia-Horsman, et al., "Deficient activity of mammalian prolyl oligopeptidase on the immunoactive peptide digestion in coeliac disease." *Scand J Gastroenterol.* 42(5):562-71 (2007).
Gardiner, et al., "The sirodesmin biosynthetic gene cluster of the plant pathogenic fungus Leptosphaeria maculans." *Mol Microbiol.* 53(5):1307-18 (2004).
Gass and Khosla, "Prolyl endopeptidases." *Cell Mol Life Sci.* 64(3):345-55 (2007).
Hallen, et al., "Taxonomy and toxicity of Conocybe lactea and related species." *Mycol. Res.* 107:969-979 (2003).
Hallen, Walton, 159. The utility of the incomplete genome: the Amanita bisporigera genome project. Mar. 15-20, 2005 Asilomar Conference Center, *Pacific Grove Calif. Fungal Genetics Newsletter*, vol. 52—Supplement XXIII Fungal Genetics Conference.
Hallen, et al., "Gene expression shifts during perithecium development in Gibberella zea: (anamorph Fusarium graminearum), with particular emphasis on ion transport proteins." *Fung. Genet. Biol.*, 44:1146-1156 (2007).
Hallen, et al., "Gene family encoding the major toxins of lethal Amanita mushrooms." *Proc. Natl. Acad. Sci. USA* 104: 19097-19101 (2007).
Keller, et al., "Fungal secondary metabolism—from biochemistry to genomics." *Nat Rev Microbiol.* 3(12):937-47 (2005).
Kroncke, et al., "alpha-Amanitin uptake into hepatocytes. Identification of hepatic membrane transport systems used by amatoxins." *J. Biol. Chem.*, 261:12562-12567 (1986).
Kuo, *Galerina marginata*. Retrieved from the MushroomExpert. Com Web site: http://www.mushroomexpert.com/galerina_marginata.html, (Aug. 2004).
Le Quere, et al., "Size and complexity of the nuclear genome of the ectomycorrhizal fungus Paxillus involutus." *Fung. Genet. Biol.* 36:234-241 (2002).
Lengsfeld, et al., "Interaction of phalloidin with actin." *Proc. Natl. Acad. Sci. USA*, 71:2803-2807 (1974).
Letschert, et al., "Molecular characterization and inhibition of amanitin uptake into human hepatocytes." *Toxicol Sci.* 91:140-149 (2006).
Lindell, et al., "Specific inhibition of nuclear RNA polymerase II by alpha-amanitin." *Science* 170:447-449 (1970).
Lugones, et al., "Introns are necessary for mRNA accumulation in Schizophyllum commune." *Mol. Microbiol.* 32:681-700 (1999).
Malonek, et al., "Functional characterization of two cytochrome P450 monooxygenase genes, P450-1 and P450-4, of the gibberellic acid gene cluster in Fusarium proliferatum (Gibberella fujikuroi MP-D)." *Appl Environ Microbiol.* 71(3):1462-72 (2005).
Maniatis, et al., "Regulation of inducible and tissue specific gene expression." *Science* 236:1237-1245 (1987).
Margulies, et al., "Genome sequencing in microfabricated high-density picolitre reactors." *Nature* 437:376-380 (2005).
May and Perrin, "Tryptathionine bridges in peptide synthesis." *Biopolymers*, 88(5):714-24 (2007).
Muraoka, et al., "Detection and identification of amanitins in the wood-rotting fungi Galerina fasciculata and Galerina helvoliceps." *Appl. Environ. Microbiol.* 65:4207-4210 (1999).
Muraoka and Shinozawa, "Effective production of amanitins by two-step cultivation of the basidiomycete, Galerina fasciculata GF-060." *J Biosci Bioeng* 89:73-76 (2000).
Nikolskaya, et al., "Identification of peptide synthetase-encoding genes from filamentous fungi producing host-selective phytotoxins or analogs." *Gene* 165:207-211 (1995).
Novick and Geisinger, "Quorum sensing in staphylococci." *Annu Rev Genet.* 42:541-64 (2008) in the instant application.
Olivera, "Conus peptides: biodiversity-based discovery and exogenomics." *J. Biol. Chem.* 281:31173-31177 (2006).
Panaccione, "Multiple families of peptide synthetase genes from ergopeptine-producing fungi." *Mycological Research* 100:429-436 (1996).
Panaro Fabrizio, et al., "Liver transplantation represents the optimal treatment for fulminant hepatic failure from amanita phalloides poisoning." *Transplant International* 19(4):344-345 (2006).
Polgar, "The prolyl oligopeptidase family." *Cell. Mol. Life Sci.* 59:349-362 (2002).
Richter, et al., "cDNAs encoding [D-Ala2]deltorphin precursors from skin of Phyllomedusa bicolor also contain genetic information for three dermorphin-related opioid peptides." *Proc. Nat. Acad. Sci. USA* 87:4836-4839 (1990).
Rosengren, et al., "Microcin J25 has a threaded sidechain-to-backbone ring structure and not a head-to-tail cyclized backbone." *J Am. Chem. Soc.* 125:12464-12474 (2003).
Salamov and Solovyev, "Ab initio gene finding in *Drosophila* genomic DNA." *Genome Res.* 10:516-522 (2000).
Saska, et al., "An asparaginyl endopeptidase mediates in vivo protein backbone cyclization." *J Biol Chem.* 282(40):29721-8. Epub Aug. 13, 2007.
Schneider, "Mushroom in backyard kills curious puppy." *Lansing State Journal*, Sep. 30, 2008.
Schuren, et al., "Highly-efficient transformation of the homobasidiomycete Schizophyllum commune to phleomycin resistance." *Curr. Genet.* 26:179-183 (1994).
Shan, et al., "Structural Basis for Gluten Intolerance in Celiac Sprue." *Science* 27 297 No. 5590 pp. 2275-2279 (2002).
Shan, et al., "Identification and analysis of multivalent proteolytically resistant peptides from gluten: implications for celiac sprue." *J Proteome Res.* 4(5):1732-41 (2005).
Singh, et al., "The use of heparin as a simple cost-effective means of controlling background in nucleic acid hybridization procedures." *Nucl. Acids Res.* 12:5627-5638 (1984).
Szeltner, et al., "The noncatalytic beta-propeller domain of prolyl oligopeptidase enhances the catalytic capability of the peptidase domain." *J Biol Chem.* 275(20):15000-5 (2000).
Szeltner, et al., "Substrate- and pH-dependent contribution of oxyanion binding site to the catalysis of prolyl oligopeptidase, a paradigm of the serine oligopeptidase family." *Protein Sci.* 9(2):353-60 (2000).
Trabi and Craik, "Circular proteins—no end in sight." *Trends Biochem Sci.* 27(3):132-8 (2002).
Tudzynski and Holter, "Gibberellin biosynthetic pathway in Gibberella fujikuroi: evidence for a gene cluster." *Fungal Genet Biol.* 25(3):157-70 (1998).
Tudzynski et al., "Characterization of the final two genes of the gibberellin biosynthesis gene cluster of Gibberella fujikuroi: des and P450-3 encode GA4 desaturase and the 13-hydroxylase, respectively." *J Biol Chem.* 278(31):28635-43. Epub May 15, 2003.
Tulloss, et al., "Amanita-beauty, danger, and diversity-almost everywhere." *Boll. Gr. micol. G. Bres. (n.s.)* 43(2): 13-21 (2000).
Tyler, et al., "Occurrence of Amanita toxins in American collections of deadly amanitas." *J. Pharm. Sci.* 55:590-593 (1966).
Voss, et al., "The role of enhancers in the regulation of cell-type-specific transcriptional control." *Trends Biochem. Sci.*, 11:287-289 (1986).
Walton, "Horizontal gene transfer and the evolution of secondary metabolite gene clusters in fungi: an hypothesis." *Fungal Genet Biol.* 30(3):167-71 (2000).
Welzel, et al., "Characterization of the ferrichrome A biosynthetic gene cluster in the homobasidiomycete Omphalotus olearius." *FEMS Microbiol Lett.* 249(1):157-63 (2005).
Weiß, et al., "Molecular phylogenetic studies in the genus Amanita." *Can J. Bot.* 76:1170-1180 (1998).
Williams, et al., "Loss of a prolyl oligopeptidase confers resistance to lithium by elevation of inositol (1,4,5) trisphosphate." *EMBO J.* 18(10):2734-45 (1999).
Williams, "Pharmacogenetics in model systems: defining a common mechanism of action for mood stabilisers." *Prog Neuropsychopharmacol Biol Psychiatry* 29(6):1029-37 (2005).
Woodward, et al., "Constant and hypervariable regions in conotoxin propeptides." *EMBO J.* 9:1015-1020 (1990).

(56) References Cited

OTHER PUBLICATIONS

Yu, et al., "A draft sequence of the rice genome (*Oryza sativa L.* ssp. indica)." *Science* 296:79-92 (2002).

Butera, R., et al., "Diagnostic accuracy of urinary amanitin in suspected mushroom poisoning: a pilot study", Clinical Toxicology, 42(6), (2004), 901-912.

"U.S. Appl. No. 13/362,561, Response filed Oct. 16, 2013 to Restriction Requirement mailed Sep. 17, 2013", 7 pgs.

"U.S. Appl. No. 13/362,561, Restriction Requirement mailed Sep. 17, 2013", 7 pgs.

"U.S. Appl. No. 13/362,561, Response filed Apr. 8, 2014 to Non Final Office Action mailed Jan. 28, 2014", 8 pgs.

"U.S. Appl. No. 13/362,561, Restriction Requirement mailed Jun. 3, 2014", 6 pgs.

"U.S. Appl. No. 13/362,561, Non Final Office Action mailed Jan. 28, 2014", 8 pgs.

"U.S. Appl. No. 13/362,561, Response filed Aug. 4, 2014 to Restriction Requirement mailed Jun. 3, 2014", 14 pgs.

U.S. Appl. No. 13/362,561, PTO Response to Rule 312 Communication mailed Jan. 28, 2016, 2 pgs.

U.S. Appl. No. 14/933,239, Preliminary Amendment filed Apr. 11, 2016, 9 pgs.

\* cited by examiner

AMATOXINS
α-AMANITIN R=CH₂C(=O)NH₂
β-AMANITIN R=CH₂C(=O)OH

PHALLOTOXINS
PHALLOIDIN R¹=CH₃, R²=CH₃, R³=OH
PHALLACIDIN R¹=CH(CH₃)₂, R²=OH, R³=CO₂H

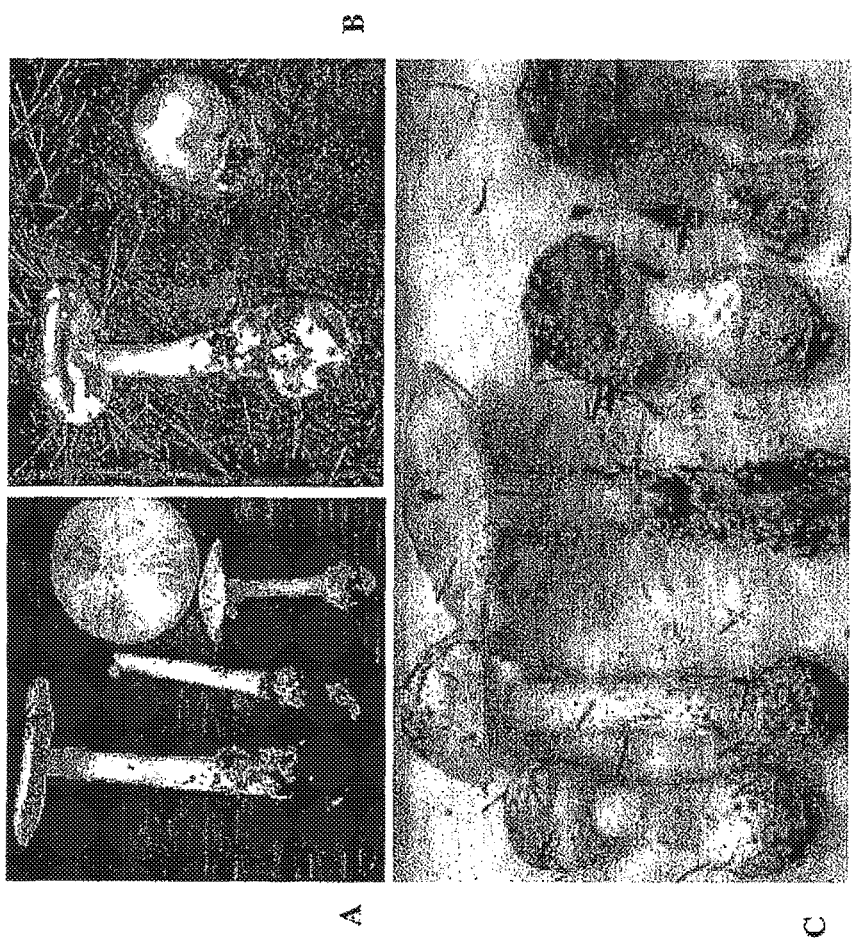

Fig. 4A
Amanitin

SEQ ID NO.

55  a ccc aac tcc cat tcg aac cta act cca aga cct cta aac ctc aca
    atc cca

617 M   S   D   I   N   A   T   R   L   P   <u>I   W   G   I   G   C</u>
    atg tct gac atc aat gct acc cgt ctt ccc <u>atc tgg ggt atc ggt tgc</u>

<u>N-  P</u>  C   I   G   D   D   V   T   T   L   L   T   R   G   E
    <u>aac ccg</u> tgc atc ggt gac gac gtc act aca ctc ctc act cgt ggc gag A   L   C   *
    gc^c ctt tgt taa attccccatccatttgtccgctgctatgacacgaag^tagtgggcgatacaagttgtggacgt
    tatcaggcttgggccgttgagcctgcatcggaa^acaacttatgttccttctttttctgttt
    tcatttgttaaaatacagaacccatgtcgatgatctgtgttgtagtcaatataaagttgtact
    gtgtttcttgtcaaaaaaaaaaaaaaaaaaaaa

Carats indicate the positions of three introns.

SEQ ID NO:55
a ccc aac tcc cat tcg aac cta act cca aga cct cta aac ctc aca
atc cca atg tct gac atc aat gct acc cgt ctt ccc atc tgg ggt atc
ggt tgc aac ccg tgc atc ggt gac gac gtc act aca ctc ctc act cgt
ggc gag gcc ctt tgt
taaattccccatccatttgtccgctgctatgacacgaagtagtgggcgatacaagttgtggacg
ttatcaggcttgggccgttgagcctgcatcggaaacaacttatgttccttctttttctgtttt
catttgttaaaatacagaacccatgtcgatgatctgtgttgtagtcaatataaagttgtactgt
gtttcttgtcaaaaaaaaaaa aaaaaaaaaa SEQ ID NO:56 (noncoding region of the propeptide)
atg tct gac atc aat gct acc cgt ctt ccc atc tgg ggt atc ggt tgc aac
ccg tgc atc ggt gac gac gtc act aca ctc ctc act cgt ggc gag gcc
ctt tgt

Fig. 4B

SEQ ID NO:57
Exemplary sequence of genomic DNA covering the amanitin gene. The nucleotides encoding the amanitin peptide are underlined.

CGATCGAAAACAGAAATCACACACTCGGCTAGATGTCCATTAAGTATGGGAGCGGAAGTCTGT
TGCCAAATATGGACGACCAGACGTTTTTTAAAATTATGAGTCGCGTGACTCGACCATTAAAGT
ACGAATACTCAGCATTGTATAGGTCCCGAATATCATCCGCAGTAGCCGCCATTGTTGGCGGCC
ACGAGAAGTTGGTAATCGCCGCTCAAACTATCAAACGTCGTGCACGTCGCACTATTGGCTGTG
CTATGTATATACAGTTCATACTGACATCACTGTGACCTCGTCACTTTCCACCTGTCGAACAAG
CCAAGGAAGCTTAAGACGGCCGACGATAGCCGAAAGTACAACCTAGAGGTATGGCAGTAGATA
AGTCGGACGAACCAAAGTCAAACTACTGACAGGAACTTCACCCTGAACTGTTGCCGCGCGATG
GTTCAACAGGGGTTGTCATAAGTTTAGCCTGACACGTAATGGTCGCCCAACCGGGCATGGATA
TATGGAGAGCGAGAGGTGTGTGAATGGACAACTACCGCCGAAAAAGGATAACCAGGCTCCCTT
GACCGAACAGCGGCGGGATCGCAGTTCGTATCACCGCACCATCTTGTCGCGTTTCACTCTGTC
AGAACATTCATGTAATGAGCTAGTGTGAATGGAAATATTTTCGCTATGTCGAAAAAGGATGAA
CTTCGGATAGAGAAAGCCAACGAATGCTTGACCGAACAACGGTAGTACCGCAGTACCACCGCA
CCAACTTGGTGCAATTCGCTCTGTCAGAAGATTCATATCAACTCCGCCGAGGAAATGAGTTGG
CAAGATGAAAAATTCGCAGATCCCATATGAGAGCGTGAGGAGACGCTCAGAAACTTCCAGCTT
GAAGCGCTTAGCCCAGCAGGCGGACAAGACGTGGTGGTCCTTAAGATTCCGAGGGAGAATGAA
ATGAGCCTCGGTCTTATCTTCGTCGAGCCGTGTGGGGAATTTAAGAGTACGGAAATATTCTTA
TAGCCTCAAAACACTCATCTCCGGCAAAAAGTGACCACCTACCCAGGGCACGTAACGATGTCC
TTGTTCACAGGCCTCTGATCGTGCCGTGCGCAGCAGCGGTCCATACCATAGAAGTCATGCTGC
GAGCCTTTGGATTGGCATGGTTGTCGTCGCCGATGGGGCATAGGTAAACGTGACCAATTTTAA
TCGATAATCATCGGATCAAAGTCGTTGAAACTTGAAGAGGATGAGCCGTTTTAACTGTGACGT
CAGTTTAGGAAAATAAGGAACTAGCCAACACGATGGTCGAGTAAATCATGAATGGAGAAAATA
TTTCACTATCACCAAGAAAGAATGACTAGGCGTGCATGGGAAGGGCTGGCTGATGGTTTGACG
AATGGGGGTCAACCACCGTAACGAAGTGGTCCCAGTCCCCGTTTCTCAAGGTGACTATAGCA
AAACCCTACGGATTTTGCAGGTAGTCCAACAAGATAAGGGTGAGATGTGTCTGTTGCCGAAAA
AAGGAATCCGCTCAAATGCTCACAAAATGTGTTGGACTCCTATCAAGATAACATACTTGATGT
CAAGTTACTCCGAGAATGGGGTCTTCTATTAGTTCCTTTTGATTCTCTCATTTCGATTGGGCG
AACTGGTGCGAATGGCGACAAGTACTTCGTTACTACCCCCATGGAATAACCAAATTTCTGTGG
AAAAAGAAGCATCTGCCCGCACCTTACGGTATACTACTTTTGTTCCGCATTCGCGCACTGATT
CTTCTATCTATTRTGTTTCTCAGGCTATTATACCAATTTCTGCGACTCATAGGATTGATTTTA
CCTCCAACCAACTAGGCAATGAYGTATAAAAGGGAYTGTGAATCTCAGCGTTCAGTACCCAAC
TaaatcCCATTCGAACCTAACTCCAAGACCTCTAAACCTCACAATCCCAATGTCTGACATCAA
TGCTACCCGTCTCCCC<u>ATCTGGGGTATCGGTTGCAACCCG</u>TGCGTCGGTGACGACGTCACTA
CRCTYCTCACTCGTGGCGAGGCGTAAGCACGATTTCTCTCCACTAATGTACTAGTGCACTTAT
GTGTGTATCAGCCTTTGTTAAATTCCCCWTCCATTTGTCCGCTGCTATGACACGAAGGTATCA
CCATCTCACTTCATAACGGTGATACAAGGCAGTTGTCCTGACTCAAGACGTAGTAGTGGGCGA
TACAAGTTGTGGACGTTATCAGGCTTGGACCGTTGAGCCTGCATCGGAAGTAAGGCCTTCAAG
TTATTATTTGTGGCAAACCACGAGGCTAAATTGTCTTTTGCCAGACAACTTACGTTCTTTCAT
TTTTTCTGTTCTCATTTGTAAAAATACAAAACCCATGTCGATGATCTGTGTTGTAGTCAATAT
AAAGTTGTACTGTGTTTCTTGTCAGCAGGAGTGCATTAACTTGTTCAGGAAACGTCACCCTCC
GAGTCTGCTCACGATTCATAGCAATACAAACTGTTTTTTTAAGCAGATGCGTCACTCTGAGA
ACAACTCCGATCG Fig. 5A
Phallacidin

SEQ ID NO. 619

```
                          M   S   D   I   N   A   T   R   L   P
ga cct ctg ctc taa atc aca atg tct gac atc aat gcc acc cgt ctt ccc A   W   L   V   D   C   P   C   V   G   D   D   V   N   R   L
get tgg ctt gta gat tgc cca tgc gtc ggt gac gat gtc aac cgt ctc L   T   R   G   E   S   L   C   *
ctc act cgt ggc gag ag^c ctt tgg taa atgtctcatccactagtcaag^gcaagttgttgacaatgtcaggcttgcggaccgttgagcctg
catcggaa^acgactcacgttctttctcattctttctgattctcatttgtaaacatataaaaccc
acgtaaatgatccgttgtgctatggaatgcaatatacttgtgaaaaaaaaaaaaaaaaaaaaa
aaaa
```

Carats indicate the positions of three introns.

```
SEQ ID NO:79
ga cct ctg ctc taa atc aca atg tct gac atc aat gcc acc cgt ctt
ccc gct tgg ctt gta gat tgc cca tgc gtc ggt gac gat gtc aac cgt
ctc ctc act cgt ggc gag agc ctt tgg taa
atgtctcatccactagtcaaggcaagttgttgacaatgtcaggcttgcggaccgttgagcctgc
atcggaaacgactcacgttctttctcattctttctgattctcatttgtaaacatataaaccca
cgtaaatgatccgttgtgctatggaatgcaatatacttgtgaaaaaaaaaaaaaaaaaaaaa
aaaa SEQ ID NO:81 (coding sequence of proprotein)
atg tct gac atc aat gcc acc cgt ctt ccc gct tgg ctt gta gat tgc
cca tgc gtc ggt gac gat gtc aac cgt ctc ctc act cgt ggc gag agc
ctt tgg
```

Fig. 5B

SEQ ID NO: 78

SacI and PvuI

GCTTGGCTTGTAGACTGCCCA

SEQ ID NO: 76
>phallacidin sequence #1. 1893 bp. SacI
GAGCTCAGCACGGAGGGTCTCTTGGATTTCTGGCCGGCGTGCAAGTTCAATGAGAGACCACTGA
GTGAAGGCTCAGTGATAGAACAGCTTGAACACTCGTAGGCGAAGATTACCGTTAGGGTGACTAT
GAGCAGCACCATTTCACTACATCGGTTATGACGGGGTTGTTTGATCGCTCTGATGACGGAGAAC
ATGAATCCCATGCTGGCCGATTGTTTTGAGACTGAAACCGTTCTAACCTGATGGGCAGAATTCA
AGCACACGGGAGTGAGATTGCGAATTGCTGAAACCGACAGTGGAGAAGACAGTCTCCGTAGTCT
GCGATCATGTTAAGTTTATGCCCTAATCGTTGAGCGATAAAGAGCGACCAACCGCTTGTGAGTC
TCGCGCTCAGAAATAGATATAACATCACCATACTGGAACGACAATGAGGCTGGCAGCTGAAAAA
TGGTGCAAAACAAAGACTCGCCAACCTGGCTCAAAGCGGTTGTCCCTGCGAGCCGAGGATATGT
GGTGGTATCCTCGGAATATATGTGTGTGAGCCTTGGGATCGCTCAATACAACATGGCTGTAGCC
GATGCCAGTGGGTATCTCGTAAGGCCCATACATTCGTTCCCAATCCCGATATACCACCGTACTG
AGGTTCGCGGAAGGGAAGATCTTGGTGTTACTGAATCTGAAGCTCTCGCTGCGTGGTCCTTGTA
GTCTGGGCGTTCTGATACCTCGGCATCTCCAATAGATAGAAATGACGACGAGCAATGTCAGAGG
TCACAATCCTTATCGAATTACCTTTGAGATACTCTGCCACATCAGGCCAGAGGCCGTTGGAGTT
GAGGTTCAACATCACGGGTGACGGAGTGGACGAGCCGTTATGCAAGGAAGGAAGGCCATCGCGG
ATAAGTACTAGTATAGCGACCAACCCAACCAGACGTGGAAATGCCATTGAAGGGTGGGAGTTGC
GCGAATACGAGGAAAACGTTTCTGAGGAGCCGAAACCGTAACCAGGCGCGAGAACTTGACCTAT
CTATCTCCGGGAACGGTGTTGGGGGTCCATGTTACCGTGAAGGTGGATAGGGGCGGATTCGATT
CCAGGAAAGTTAGAGCCACATAGTCATAAGTGATGCAACACGCCTGTGCGCGATGGAGATAATG
CGTCTTTGTTGCATCGGCAAACCGGGTCACACGGACGAAAATCATTACTACATGGTCCATTTCA
GGACAAAACCCCTATCTATTGATCCTACAAACTGCTTGACTGTTCAATCTGTGACCACCGGGAC
AGAGAAAGGCTGTGCTCAGTGGGGTGTTTAATCCAGCGAGAAACGCGTTAGGCCCAGTCGCCGA
TCAGGATACGACGAAAAAGTGTAAGGTCAAGACTCCCTTGATGCGATTCAACTATTCTTGACGG
GGGGTTGCCATTGTATTGCACCGTCTTGCCCGACTGGCTGTGCCCGCAAAGACAGAACGTCCCA
AAAACAGGAAAGAACAAAGAAGTTTTGTGGAGCCTGCCAAGAATGTGTGATGAACAGTGACTGA
CAGCATGAATGGGGATGAATATTGAATACCGAAAAGGATGATCAGACAACTGTTTATGGAGA
TTTTGCGCCAACTCGTCTTCATCTCCGTGTCAGGACAAGATTCTCTTATCTATCGTCCTTTCCG
CGGTTTTGCAACCATGCGAATTCGTGACTGAGACAGATAAAAGGCGTTGGATTCAGCTTAGCA
TTCAATATTCAATACTTACCTCCCATTCGAACTCGAGCCCAAGACCTCTGCTCTAAATCACAAT
GTCTGACATCAATGCCACCCGTCTTCCYGCTTGGCTTGTAGACTGCCCATGCGTCGGTGACGAT
GTCAACCGTCTCCTCACTCGTGGCGAGAGGTGAGCTC

Fig. 5B (Cont.)

SEQ ID NO:77
>phallacidin sequence #2. 1613 nt. PvuI

CGATCGGGTGGTATGAGCGACGTTGATGCATGGATTAGATAAAAAACTCATTTTTGCCTTGAC
ATTGTAACATGCGAATAAGAGAGCAAGGACCCCATCAGAGCAAAAAAGGAATCACGGATTTGA
TATCGACCTGACCCAAGTCGGCAACGGTAATAGGGGCTAGAGCCACATATGAGTGATGAGCGA
TGGAGATAATGTTGCATCGGGAAACCGGGTCACACGGCCGATAATCATTCTCATACATGTCCA
TTTCTATCTATTGGTCTGTAGGACTGCTTAACGGTTTAAATCTGTGACCACCAGGACAGACAA
AGAAAGGCTGTGCTGTTCGAAACGCGTTACTAATTAGGCCCAGTTCGGCATAAATCGCCGACA
CGCAGGATACGACGAAAAGTGTAAGCTTAAGGTCAAGACTCCTCTGATGTGATTCAACAACTTT
TGACGGGGGGTTGCCATTGTATGCACCGTCTTGCCCGGCTGGCCATGTCCGCAGAACCGAACGC
CCCTAACGACAGGAAAGAAGAAAGAAGTTCACGGATTCCATATAGTAAGCGTGGAGCCTGTGTG
ATAAACAGTCATGAATGATTCATGGGAATGAAGACCGATCAGACAAACGCTTATGGAGATTTTG
TGCCAATTTGTCTTTCCATCTACGATTCTCTTATCTATCGTCCTTTCTGCGGTTTTTGCAACCA
TGCGAAGTCGTGACTGAAACAGATAAAAGGCGTTGGATGTGGCTCAGTAGTCAATATTCAATAC
TTACCTCCCATTCGAACTCGAACCCAAGACCTCTGCTCTAAATCACAATGTCTGACATCAATGC
CACCCGTCTTCCT<u>GCTTGGCTTGTAGACTGCCCA</u>TGCGTCGGTGACGACGTCAACCGTCTCCTC
ACTCGTGGTGAGAGGTGAGCTCAAAATTCCATTTAATAATGTAGCAATGTACTCATGTGTCGTG
TATCAGCCTTTGTTAAATGTCTCATCCACTAGTCAAGGTATCCGCCTCTGATTTCTTGATGACA
ATGCATGGTCATGGTACTTACTTTGATGTAGTAGTGGACGACGCAAGTTGTTGACAATGTTAGG
CTTGGAGCGTTGAGCCTGCATCGGAAGTAAGGCCTTCAAATTTTTCTGTGATAAGCAGCGAGCT
AACTTGGGTTAGACGACTCACATTCTTTCTCATTCTTTCTCATTCTCATATAAAACCCACGTAA
ATGATCCGAGCTGTACTATGGAATGCAATGTACGCGTGTATATGTGTGTGTTGTCAGTAAGAGA
GCATTTAGCAATCCGAGCTTGCATGCCGCTGTCGCCAGAGCTGTCTACTTGTCAGCAACATATC
GCATATCACATAGGCAGCTGTTGTACCATTGAAAAGCCGTGGGGCGTATAACCTGGAGGAATTT
CAAAGAAGGGTCTTTTATGATGAGTTTGATAGCTCGCATAGTTGTGAAAGTCGGCAAGTTCACA
AAAAACAGTGATTTTATGTTACATGTGACGAGGAGCATGAGACACAACTTTGAACTGCACCCGG
GAGAAAGCAGGCTTAGCAACACCGATGACGAGGGGGAGGAGAAATACGGGAGAATGCCGATGA
TGTAGGCATAATGCGATCG

FIG. 6A

```
amanitin     M  S  D  I  N  A  T  R  L  P  I  W  G  I  G  C  N  P                    SEQ ID NO: 617
             ATGTCTGACATCAATGCTACCCGTCTCCCCATCTGGGGTATCGGTTGCAACCCG
             ||||||||||||||||| |||||||| ||||| ||| ||| ||  || ||
             ATGTCTGACATCAATGCCACCCGTCTTCCCGTTGCTTGGCTTGTTGACTGC---CCA    SEQ ID NO: 623
phallacidin  M  S  D  I  N  A  T  R  L  P  A  W  L  V  D  C     P C  I  G  D  D  V  T  T  L  L  T  R  A  L  C  *                          SEQ ID NO: 624
             TGCATCGGTGACGACGTCACTACTCTCCTCACTCGTGCCCTTTGTTAA
             ||  |||||||||||| ||  ||||||||||||| ||| ||| |||||
             TGCGTCGGTGACGATGTCAACGGTCTCCTCACTCGTAGCCTTTGGTAA             SEQ ID NO: 625
             C  V  G  D  D  V  N  R  L  L  T  R  S  L  C  *
```

FIG. 6B

| | A | B | Conserved Regions |
|---|---|---|---|
| SEQ ID NO: 626 | MSDINATRLP | IWGIGCNP CIGDDVTTLLTRALC | [amanitin] |
| SEQ ID NO: 627 | MSDINATRLP | -W   C P C  GDDV  LLTR LC | [consensus] |
| SEQ ID NO: 628 | MSDINATRLP | AWLVDC-P CVGDDVNRLLTRSLC | [phallacidin] |

FIG. 6C

| SEQ ID NO. | Comparisons of sequences BLAST | Identical amino acids | Percent identity |
|---|---|---|---|
| SEQ ID NO: 180 | Alpha-Amanitin<br>ATGTCTGACATCAATGCTACCCGTCTCCCCATCTGGGTATCGGTTGCAACCCGT<br>GCATCGGTGACGACGTCACTACTCCTCCACTCGTGCCCTTTGTAA | 102/102 | 100% |
| SEQ ID NO: 81 | Phallacidin<br>ATGTCTGACATCAATGCCACCCGTCTTCCCGGTTGGCTTGTAGACTGCCCA<br>TGCGTCGGTGACGATGTCAACGTCCCTCACTCGTAGCCTTGGTAA | 99/99 | 100% |
|  | Alpha-Amanitin vs. Phallacidin | 78/102 | 76% |

Fig. 7

SEQ ID NO:183 ECIM01V01AIXAG S length=115
TTGGGGTTTGGCAGTCGGTTAGTACCCAGTCCTCTTCGAACTCGGAAAACCTTTACTCT
CAATAAACCATGTCTGACATCAATGCCACCCGTCTTCCTATCTGGTGGTACATATA

SEQ ID NO: 184 GVWQSVSTQSSSNSENLYSQ-
TMSDINATRLPIWWYI

SEQ ID NO: 185 ECGK9L002IH938 R length=98
GTGGGTACGCGCCGGGGAGACGGGTGGCATTGATGTCCGACATTGCGATTGAGAGTAGA
GGATGCTGTAGGTTTCTGAGGGGTCTTGTGAGTATTGAA

SEQ ID NO: 186
SILTRPLRNLQHPLLSIAMSDINATRLPGAYP

SEQ ID NO: 187 ECGK9L001DOKJN R length=106
CTCACAAGACCCTCACGAAACCTACAGCATCCTCTACTTCTCAATCGCAATGTCGGACA
TCAATGCCACCCGTCTCCCCGGCGCGTACCCACCTGTTCCTTGGCCG

SEQ ID NO: 188 SQDPHETYSILYFSIAMSDINATRLPGAYPPVPWP

Fig. 7 (Cont.)

SEQ ID NO: 189 cn1104 1266 nt

TGAGGCACGGGAAGTATATGAACCAGAAGATAGGAAGACTGGTGACATTGATGTCAGAC
ATGGTTATCAGTAAAGAGTTTGACGAGGACTGGGTACTAATTGCCAAACCCCAGAACCT
TTATGTGATTCGACAAGAGCAAATATAATTGCAGAACTTGACCCAATGTTTCAGGTGTT
GGCGCTGTCTCAGGCAATGGTAGCGCCGCCTTGTGGGTGGCTCTAGGGTGTAACGTGTA
ACAGTTAGCAATTAGGCTATATGCTGCTCTGCGAAACAGGCTTGCGACGCCTGTCACCT
TGCCGACCGTACTATCTAGCACCATTCAACGCCATGTGATTATGATAGCGTCGGCATTC
CGTGCCAGTTGCATGTGCTTTGAGTTTTCCATGTTTAGTAACCGCGAGCCGCGAGCGTT
CAGAATCATAGTGGTGGCGGTGCTAGAGTTACAACATGTATGTAACATACGAGTCAGGA
ATAAATTACCATAGGAATCTAGTTCTGATGTCCATTGGTCAACTCGACCCAGTACCTTT
CCTCCCTCTCCTTCCACCGCCTTCGTCTCCTTCATTGTCCCCACCACTGGTATACAACG
CCGACGTCGACCGCTGCGCCGTCCTCTCAACAATAGACGTCCCGTCTCTAAATCTTGCC
CTAAACAGCACATTTGCGTTCGTAAACAGCCCTTCCTTCAGTGACACCACTATAAATTG
CGACCCCTTGAACCGCGTCCGGAACAGCTGTCCAATATGCTGCGTGTGCGATAGATCCA
GGGCAGCGTCGATCTCGTCGAGGATGTACATTGGCGCTGGTTTGAATTGGAGGAGCGCC
ATGATGAGCGAGAGCGCGATGAGAGATCTGCAGCATACCGTCAGACGAAGCAACTTGGG
TGTTCAAACGACATACCTCTGGCCCCCACTTAACTCAGTCAAGCTCTCCTTCCAAACGG
TGCCGAGTTGAACTTTGACTTCTAGACCGTCCATAAGATCTTGGCCTTCGGGCGGTACC
AGTTTGGCAAAATTGCCAGGCAAGAGTTCTGCAAAGATCCCGCCAAAGTCGCTTTACCA
CATGCCTTCAATCCCCTTGTCATACAAATGGTGACAAAGTGACTCACCCGTCAACCTTT
TCCCAAGTTTTTTGAAGCGCATCCCTCTTGTACCGGTCTAGTTCTTCGATAGTCTCTTC
AATCTTTTCTTTATCTTTCAGCACCTGACTAAGCATCTTTTTAAGATGTGCCTCTCTGC
TCACGACGCTAGACACGTGGCAGGAAA

Fig. 7 (Cont.)

SEQ ID NO:190
SCHVSSVVSREAHLKKMLSQVLKDKEKIEETIEELDRYKRDALQKTWEKVDG-
VTLSPFV-QGD-
RHVVKRLWRDLCRTLAWQFCQTGTARRPRSYGRSRSQSSTRHRLEGELD-
VKWGPEVCRLNTQVASSDGMLQISHRALAHHGAPPIQTSANVHPRRDRRCPGSIAHAAY
WTAVPDAVQGVAIYSGVTEGRAVYERKCAV-GKI-RRDVYCEDGAAVDVGVVYQWWGQ-
RRRRRWKEREERYWVELTNGHQN-IPMVIYSLVCYIHVVTLAPPPL-F-TLAARGY-
TWKTQSTCNWHGMPTLS-SHGVEWC-IVRSARQASQACFAEQHIA-
LLTVTRYTLEPPTRRRYHCLRQRQHLKHWVKFCNYICSCRIT-
RFWGLAISTQSSSNSLLITMSDINVTSLPIFWFIYFPCL

SEQ ID NO: 191 W7_54_B09 Length = 554
TATGCTTTTAGTCCAAGCTTTTACTTCACCTGGACGTTGGGATACGTCAGGAATATGTA
CTGACAATAAATATCACCGCAGCGGCGCCGAAACTCACCAATCTTTACTTCACCTGGAC
GTTGGGATAGATGACGTATTCACTGGAAAAGGGTTAGCGGATAACATGGGTCGCATGTC
ATCATGAATATAGTTAGTGCGTCTCCACTCACAATTGTCCAAGTTATTTCGCTTCCGTC
ATTCGCGGACAGTTGAGGTTTGCCCCTGCCCAACTCGGCAATGGGTCATGACTGAGACA
GATAAAGATGCTGGGGGCGCAAGCATTCAATACTCAGTTCCCCTCCAAATTTGAATCG
TTCAGAAACCTACTACTTCATTTACTCTCTCACAATGTCTGACATCAATACTGCTCGTC
TTCCTTTCTACCAGTTTCCCGATTTTAAGTATCCCTGCGTTGGTGACGACATCGAGATG
GTCCTCGCGCGTGGCGAGAGGTGAATACAACATCCGGCCAAGGCTGTATCAAACGACTT
ACGTGCTACGTATCAGCCTTTGC SEQ ID NO:192
MLLVQAFTSPGRWDTSGICTDNKYHRSGAETHQSLLHLDVGIDDVFTGKGLADNMGRMS
S-I-
LVRLHSQLSKLFRFRHSRTVEVCPCPTRQWVMTETDKRCWGRKHSILSSPPNLNRSETY
YPIYSLTMSDINTARLPFYQFPDFKYPCVGDDIEMVLARGERIQHPAKAVSNDLRATYQPL

Fig. 7 (Cont.)

SEQ ID NO: 193 w92k_04_H04_F 684 nt
AATTTGAATCTCTCAGAAACCTACTTACTCTCTCACAATGTCTGACATCAATACTGCTC
GTCTTCCTTTCTTCCAGCCTCCCGAATTTAGGCCTCCCTGCGTCGGTGACGACATCGAG
ATGGTCCTCACGCGTGGTGAGAGGTGAGTACACATCCGGCCAAGGATGTATCAAACCAC
TCACGTGCTACGTATCAGCCTTTGCTAAATGCACGGCCTATCGGTCCACTCCTATGGCA
TGAAGGTGTCGCCGTCGCATTTCAACTACAACGTAAGGCAATTGTACTGACTTGAATGT
AGTAGTGGTCATTATGTTGTTGACGATATCAGGCTTGGACCGTTGAGCCTGCATCAGAA
GTATGACTTTGCTTGTGGTGAAGAAGCACTGGATTTAACCCATCTTTTTTCCTAGATAA
CTCGCTTTCTTTTTCAAGTTTATGTCGAATCCGTTTTGTAGTAAACATATAAAACCCAC
GTCAACGATCCCGTGTTACTTGTTACTTGTTCTTTGTTCTTGAAACCCTCGTCAATGAT
CCGCGTTATAGTCAATAAACTTGTTCTTTGTTCTTGTCAGTGTGAGGGCATTTTGTACG
CGAGTGGTTTCAAGAAATCAGTCAAAAGGTGTCTTTCCAACATATCTGTTGAGCCTGTC
CGGTCCTGAAGCCTGATTGGAGAATCAATCAGTAT

SEQ ID NO: 194
I-ISQKPTYSLTMSDINTARLPFFQPPEFRPPCVGDDIEMVLTRGER-
VHIRPRMYQTTHVLRISLC-MHGLSVHSYGMKVSPSHFNYNVRQLY-
LECSSGHYVVDDIRLGPLSLHQKYDFACGEEALDLTHLFS-ITRPLFQVYVESVL-
TYKTHVNDPVLLVTCSLFLKPSSMIRVIVNKLVLCSCQCEGILYASGFKKSVKRCLSNI
SVEPVRS-SLIGESIS

SEQ ID NO: 195
ECGK9L001EMOC5 S length=96
CACAATGTCTGATATCAATACCGCTCGTCTTCCTTGCATCGGGTTCCTTGGCATTCCCT
CCGTCGGTGACGACATCGAGATGGTCCTCAGGCATGG

SEQ ID NO: 196
TMSDINTARLPCIGFLGIPSVGDDIEMVLRH

SEQ ID NO: 629 ECIM01V01BBKCW R length=110
ACCCTTCCGCAATGTCTGACGTCAATGACACCCGTCTTCCCTTCAACTTCTTCCGCTTT
CCCTACCCCTGCATCGGTGACGACAGCGGAAGTGTCCTCAGGCTCGGCGAG

SEQ ID NO: 197 PSAMSDVNDTRLPFNFFRFPYPCIGDDSGSVLRLGE

SEQ ID NO: 198 contig26848 length=93
CCTTCCGAaCCAAGAACCTACAGATACCTTTGCACTCTCACAATGTCTGACATCAATGC
CATCCGTGCTCCCATCCTGATGCTCGCAATTTTG

SEQ ID NO:199
PSEPRTYRYLCTLTMSDINAIRAPILMLAIL

Fig. 7 (Cont.)

SEQ ID NO:200 W7_17_xp_D11
TTCAATTTAATGCCCCCTGCGTCGGTGACGACATCAACATGGTCCTCACGCGTGGCGA
GAGGTGAGTACAAATTCCGGCCAACAATGTATCAAACCACTTACGTGCTACGTATTAGC
CTTTGCTAGATGCATTCTATCGGTCCACTCCTGTGGCATGAAGGTGTCGCCGTCTCACT
TAAATTACAACGTAAAGCAATTGTACTGACTTGGATGTAGTAGTGGACACTGTTGTTGA
CGATATCAGGCTCGGACCATTGAGCCTGCATCAGAAGTATGACTTTGGTTGTGGTAAAG
TACTGGGTTAACTCGTCTTTTCTTCCTAGATAACTCACGTTCGTTTTCATTTGAATCTG
CTTTGTAAACATATAAAACCCACGTCTACGATCCGTGCCATACTTGTTCTTTGTTCTTG
TCAGATTTCGAAATTGCCAACGATATGCCAGTTTTCCTGTGTCTGCAAGCTTGGAACTG
TGTGCGTCGGATACTGGATACTGGCGTTTCCTCGTCCTAAAGGTAGCAAAGTGCGCATG
CGGGTGCTAACGGTTGCATGATAAATCATCGCAAGCATCAATGGGTTTCGTTGGCAACG
ATCCAAATGAACGACTGAGGGCTTCGAAATGTGTAGATGGTTGCAAAAACAAAACAAAA
AAACCATTAGACCGTGAATATCGAATCTCTTAGTTACTATTGATTTCGACTTGGAGTAT
CAGCCGCGATCATTTCGTCCTCGGCCCTAGTATCACAACATATGTAATATCATCCTCAG
GATTACATGTATTCTTCAGGTAGCGTGACTGTGATACCTACCTCCCTTC

SEQ ID NO:201
FNLMPPCVGDDINMVLTRGER-VQIPANNVSNHLRATY-PLLDAFYRSTPVARCRRLT-
ITT-SNCTDLDVVVDTVVDDIRLGPLSLHQKYDFGCGKVLG-LVFSS-
ITHVRFHLNLLCKHIKPTSTIRAILVLCSCQISKLPTICQFSCVCKLGTVCVGYWILAF
PRPKGSKVRMRVLTVA--IIASINGFRWQRSK-TTEGFEMCRWLQKQNKKTIRP-
ISNLLVTIDFDLEYQPRSFRPRP-YHNICNIILRITCILQVA-L-YLPPF

SEQ ID NO:202 cn1466
TCTGGTAAAGGATGAGTTAACCCAATGCTTCACCACAAGGAAACTCATACTTCTGATGC
AGGCTCAACGGTCCAAGCCTGATATCGTCAACAACAGTGTCCACTACTACGTCCAAGTC
AGTACAATTGCCTTCAATGCGTTGAAGTTGAAAAGAGACGGCGACACCTTCATGCCATA
GGAGTGGATCGATATACTGTGCATTTAGGAAAGGCTAATAATACGTAGCACGTAAGTCA
TTTGATACATCGTTGGCCAGATGTTGTACTCACCTCTCGCCACGCGTGAGGACCATCTC
GATGTCGTCACCGACGCAGGGGGGCATCCGAACGGGAGGGAGGAAGAGAGGAAGACGAG
CAGTATTGATGTCAGACATCGTAAAAGGAAGCTGTAGGTTTCTGAAAGATTGAAGTTTG
GAGGGGAACTGAGTTTTGAACGCTCCGCCCCCAGCATCTTTTATCTGTCCCAGTCATGG
CCTATTGCTGATTTGGGCAGAGGCAAACCTCAATCCGCCGACGACGGAAGCGAATAACT
TGGATAAGCGACGGTGATTCTTTTTTTATTTATTTAGAGGAACTTCGGCATCAATCATG
TTGATATCTTGCAGAAGTCGTATATCATTGTGATATCATTGTGACAAATGTCACCCACT
ATCTCTTTCCTTGTGAATGTGCCATGTATCCAACGTCCAGGTGAAGTAAACCTTGGTGA
TTCTCGCCGCCGCTGCGGTGATATTGACAGCATAATGATCTGAAAACGTACTGATGGAA
GCGTACTTGACGGCCCGTCCAAACTGACATGGGAGTAATCGCACAGTATTACTATGCTA
TTTGTATTCAGATTCCACAATTCCATTACAGTCACCCGTGAGTTTTCCATATCTGC

Fig. 7 (Cont.)

SEQ ID NO:203
RYGKLTGDCNGIVESEYK-
HSNTVRLLPCQFGRAVKYASISTFSDHYAVNITAAAARITKVYFTWTLDTWHIHKERDS
G-HLSQ-YHNDIRLLQDINMIDAEVPLNK-KKNHRRLSKLFASVVGGLRFASAQISNRP-
LGQIKDAGGGAFKTQFPSKLQSFRNLQLPFTMSDINTARLPLFLPPVRMPPCVGDDIEMVLT
RGER-
VQHLANDVSNDLRATYY-PFLNAQYIDPLLWHEGVAVSFQLQRIEGNCTDLDVVVDTVVDD
IRLGPLSLHQKYEFPCGEALG-LILYQ

SEQ ID NO:204 cn1150 881 nt
CCTCTGAAACTTGCTGCGACGGCACGATCTGACTGGGAGATCTTCGTTGCATCTCTAGG
TTGAGTGAATTCACAATTCCAGTATTCAGTTCGGAGGAGCATGTTGGATCGATTACCGT
ACGTTCTGGCTCTTCATCGACTGGCTTTAGGAACGAACCTTACCAAACTTGTATATCGT
ATTGCAGGTGAATCGAGAAAACACCTTTTACGTCGAGTGTTGTAACCTGGCTCAAAGAT
TCAAAAACTCTCAACGACAAGCAGTTTATTGACTATAACACCGATCGTCGACGTGGGAT
TTGTGTTTACAGAACAAATTCGACAGAGAACGAGAAAGAATGTAAGTTATCTGGGAGAC
AAATTAGACCAGTGCTTCGTGACGAACAAAGTCATACTTCTGATGCAGGCTCAGCGGTC
CAAGCCTGGTATCGTCAACAGCAGAGTCCACTACTACATGCATTTAGCAAAGGCTATAC
GTAGCATGTAAGTGATTTGATACATCATTGGTCAGTTGTTGTACTCACTCCTCGCCACG
CGTGAGGACCACCTGGATGTCGTCATTGACACATGGGGGATGAAGCTCATGAAGACGA
CGTAAGGAAGACGAGCGGTATTGATGTCAGACATTGTGAGAGTTGGAGGGGAACTGAGT
ATTGAATATTGGATATTGAACGCTGCGTCCCAAGCACCTTTTATCTGTCCCAGCCATGG
CCCAGGCCCATTCCTAGTTGAGGCTCGATCTATTGCAAAATTTGACAGCCTGCGTGGTA
TGGAAGACGAAGGACTGACGATGATGCTTAGTTGACATGTGTCAAGCCCACGTACGATA
TCGAAGCCAGAGATAGATCGCGTATTCGTATATCGTACGAGGGATGCTTACTTGG

SEQ ID NO: 205
K-ASLVRYTNTRSISGFDIVRGLDTCQLSIIVSPSSSIPRRLSNFAIDRASTRNGPGPWLG
QIKGAWDAAFNIQYSILSSPPTLTMSDINTARLPYVVFMSFIPPCVNDDIQVVLTRGEE -
VQQLTNDVSNHLHATYSLC-MHVVVDSAVDDTRLGPLSLHQKYDFVRHEALV-
FVSQITYILSRSLSNLFCKHKSHVDDRCYSQ-TACR-EFLNL-ARLQHST-
KVFSRFTCNTIYKFGKVRS-SQSMKSQNVR-SIQHAPPN-ILEL-IHST-
RCNEDLPVRSCRRSKFQR

SEQ ID NO: 206 contig70115 length=172
GGACCATCAGGATGTCGTCACCGACGCAAGGAGGAGCATTGGCGAGGAGAGGGAAGA
CGAGCGGTATTGATGTCAGACATTGTGAGAGTAAAGGAAGTTGTAGGTTTCTGAAAG
ATTCAAGTTTGGAGGGGAGGTGAGTATTGAACGCTGCGCCCCAGCACCTCCAG

Fig. 7 (Cont.)

SEQ ID NO: 207
LEVLGAQRSILTSPPNLNLSETYNFLYSLTMSDINTARLPLSSPMLLPCVGDDILMV

SEQ ID NO: 208 contig38711 length=234
CCTTCCGAACCAAGAACCTACAGATACCTTTGCACTCTCACAATGTCTGACATCAATGC
CATCCGTGCTCCCATCCTGATGCTCGCAATTTTGCCCTGCGTCGGCGACGACATCGAGG
TCCTCAGGCGTGGCGAGGGGTGAGCCTAACATCCGTCAACGGCGTACAAATGTACTTAT
GCGCTGCGTATCAGCCTTTCCTAAATACCCGGTTCATCAGCTCGCTCCTATGGCATG SEQ ID NO: 209
PSEPRTYRYLCTLTMSDINAIRAPILMLAILPCVGDDIEVLRRGEG-A-
HPSTAYKCTYALRISLS-IPGSSARSYGM SEQ ID NO: 210 cnl006
CTTCTAACGTGGGCTTTACGTGTTTATAAATGTGAAAAACCTTAAAAGAAAAAAATCAG
AGTTGTCCCCCACAGACAAAATAAGGACTTACTCCGATGTAGGCTCAACGGTCCAAGCC
TCATATCGTGAACAACTTTGAAAATTTATCACTACATAATACATACGAGTCAGAACGGT
TGCCTTGTATTATACGAGGATGGCGACACCTTTAATGGCACCGAGTTCTCAGCAGAGAC
TAACGCACGCGACATAAGTGTACATCATTGGGTAGATGATATTGCTCACCTCTCGCCAC
GAGTGAGGGTAGGGTTGACGTCGTCACTGACGCACGGAATTCCGAGGGGTATCAAACCA
GGGATGGGAAGACGAGTGCCATTGATATCAGACATTGCGAATGAGAGTAAAGGAGGCTC
TGAGAGGTCTTGGATTCAAGTTGGGAGAGGAACTGGGTATTGTACGCCCTGCCCGATGC
CTTTTTATCTGTCTCAGCCAAGGCCAATTGCCTAGTTGGGCATAGGGAAACCCAAGAGG
CGCTTCGAGTTCGTCCGTGGTCATTCAAGCTCTTTTAGGAGAGCTGGAACCATGATGGG
CCTAATGTAGCTCAACCAGGTATGGAATGGCGCAAGAATTCCGGCCAGAACGGATGATA
TGAGTGGTTCTCATCACGCTGTTCGCTGACTTCCAACGTCCAACGTCTTTGGGTACATG
AAGTACGGCATGTCCTCTTAGAAAAAAGGCCGGTGGACGATGGACAGTAGCGAACATC
GTGGTGCCTATAGGCTATGGCGTAGCCGGATGTGGGTAGAACAAAGGAGCGGTGCATGT
TGGACAGTAGTGAACAGCGTGGCGTCCTCGTTTCGCACGAGGTACCGCCGCACTGACTC
GTTGTGCGCTGATAAAGGATATCGGCCCTCGATCGCGCACCGCCCCATCATGCGCTCCA
TTGCCACCACGAGGATGTGCATACAGTGCAACCCCCGAGGACTGCACGACCCAGTTGA
TCCGCGACAAGTACTCCGCGCAGAACGTGGTCGGGAGGTACTGGCGCATACATCACCCG
GCCCAAGCGCAAGCATCCGCGGCTGATCCGAGCTTGCACAAGCTGGTCGAAGACGTAGC
TCTCCCAAACATGTCTGTCCGCCCTTTCGCAAACTGGTCGCTCGACAGCCCTAAAATCT
GCTCCGCCTTCGAGTGCAGATCCGTCCAGCAGCCTTAGTCCAAGTGTCATCCACCCCA
GTGTCGTCGCGTGATGCATCCCAAATTGCGCATCCCCATACAGCTTGAAATCTACACTT
CCTCAGGGTCCATGTCCGCATCGACTATCGCGTGCCCAGGCGGCACGCACCATCACGGT
TCTGCTTCACATTCAACCACGTCTTTTCGATCGCGCGCCGCATGATGGCGCCTATCGTG
ATCGATGATCACCTGGGGAAGCCTGAAGATCATCCCCCACGTAGAGAAGCAAGAATCCA
CTTCATCGTGACATCGCACCACCAACCGCAAGCGGAAGAAGCTTCCTCCACCAGTCCCA
ACCAATGCCAAACATTCTCTTGTCTCTATTCCGCTTGTTGTCGTCGTCACCCTCGTCGT
CGCAGAGAGCAGGACTATTTGACTCGGGCGACCCGCCCAATCCTTCGATGCTGACGATC
TTATGACATTGCCCGCTTGCCTTCTCACATTAATTTGAGGACGAACTGGATTCG

Fig. 7 (Cont.)

SEQ ID NO: 211
RIQFVLKLM-EGKRAMS-DRQHRRIGRVARVK-SCSLRRRG-RRQQAE-
RQENVWHWLGLVEEASSACGWWCDVTMKWILASLRGG-SSGFPR-
SSITIGAIMRRAIEKTWLNVKQNRDGACRLGTR-
SMRTWTLRKCRFQAVWGCAIWDASRDDTGVDDTWTKAAGTDLHSKAEQILGLSSDQFAK
GRTDMFGRATSSTSLCKLGSAADACAWAG-
CMRQYLPTTFCAEYLSRINWVVQSSGGCTVCTSSWWQWSA-
WGGARSRADILYQRTTSQCGGTSCETRTPRCSLLSNMHRSFVLPTSGYAIAYRHHDVRY
CPSSTGLFF-EDMPYFMYPKTLDVGSQRTA--
EPLISSVLAGILAPFHTWLSYIRPIMVPALLKELE-PRTNSKRLLGFPMPN-AIGLGDR-
KGIGQGVQYPVPLPT-
IQDLSEPPLLSFAMSDINGTRLPIPGLIPLGIPCVSDDVNPTLTRGER-AISSTQ-
CTLMSRALVSAENSVPLKVSPSSYNTRQPF-LVCIM---
IFKVVHDMRLGPLSLHRSKSLFCLWGTTLIFFF-GFSHL-TRKAHVR

SEQ ID NO: 52 contig49252 length=146
AATCTCAGCGTTCAGTACCCAACTCCCATTCGAACCTAACTCCAAGACCTCTAAACCTC
ACAATCCCAATGTCTGACATCAATGCTACCCGTCTCCCCATCTGGGGTATCGGTTGCAA
CCCGTGCGTCGGTGACGACGTCACTACG

SEQ ID NO: 53
SQRSVPNSHSNLTPRPLNLTIPMSDINATRLPIWGIGCNPCVGDDVTT

SEQ ID NO: 214 EEISCGG02IQ8KO R length=103
GTCCGACATCAACGCCACTCGTCTTCCCATGATCCAACGCCCCTTCTACCCGTGCGCCA
GTGACGACGTCACCTCCACCCTCACTCGTGGCGAGAGGTGAGCG

SEQ ID NO: 215
SDINATRLPMIQRPFYPCASDDVTSTLTRGER-A

SEQ ID NO: 216 EEISCGG02HZJKJ R length=103
CCGAACTTAAATCCCAGACCTCACAAAGCCTCTTTATTCTTGAATCGCAATGTCTGATA
TCAATGCCGCTCGTCTTCCCATCATTTTTGAACCAATCATCCCG

SEQ ID NO: 217 RT-IPDLTKPLYS-IAMSDINAARLPIIFEPIIP

SEQ ID NO: 218 contig72700 length=168
TGCTGGGCTCACTTCTCGCCCCTAGTGAGGGTGAAATTGTCCGCGTCACCGACGCACGG
CATAGGAACAGGTGGGTACGCGCCGGGGAGACGGGTGGCATTGATGTCCGACATTGCGA
TTGAGAGTAGAGGATGCTGTAGGTTTCTGAGGGGTCTTGTGAGTATTGAA

SEQ ID NO: 219
SILTRPLRNLQHPLLSIAMSDINATRLPGAYPPVPMPCVGDADNFTLTRGEK-AQ

Fig. 7 (Cont.)

SEQ ID NO: 220
ATGTCTGACATCAATGCCACCCGTCTCCCCCATCCGTTTCCATTAGGATTGCAACCGTG
TGCCGGTGACGTGGACAATTTGACCCTCACTAAAGGCGAAGGGTGA

SEQ ID NO: 118
MSDINATRLPHPFPLGLQPCAGDVDNLTLTKGEG

SEQ ID NO: 220
ATGTCTGACATCAATGCCACCCGTCTCCCCCATCCGTTTCCATTAGGATTGCAACCGTG
TGCCGGTGACGTGGACAATTTGACCCTCACTAAAGGCGAAGGGTGA

SEQ ID NO: 118
MSDINATRLPHPFPLGLQPCAGDVDNLTLTKGEG.

SEQ ID NO: 224 Beta-amanitin_from_Amanita_phalloides [this sequence was found by PCR with degnerate primers]
ATGTCAGATATCAATGCGACGCGTCTTCCCATATGGGGAATAGGTTGCGACCCGTGCAT
CGGTGACGACGTCACCATACTCCTCACTCGTGGCGAG

SEQ ID NO: 225
MSDINATRLPIWGIGCDPCIGDDVTILLTRGE

SEQ ID NO: 226 Phalloidin_from_Amanita_ocreata [this sequence was also found by PCR with degenerate primers]

ATGTCAGACATTAACGCGACCCGTCTTCCCGCCTGGCTCGCCACCTGCCCGTGCGCCGG
TGACGACGTCAACCCTCTCCTCACTCGTGGCGAG

SEQ ID NO: 227 MSDINATRLPAWLATCPCAGDDVNPLLTRGE

FIG. 11

A) GmAMA1 Nucleic Acid Sequences.

SEQ ID NO:240
>gi|30874522||cl|E0UVDMS01BP3R9 length=248
Acacattcaacaaatactaacgcacaacgcatgagtacgtcgaacaagtcaacaacagaaattgagctcactcgttgccactaacgagagtttgatcgacgtgttcagcagtccatgg
Gttgcagccaataccccagattggaagacgagtggagttggtgtcgaacatggtagarattaaggcaagggcgaagatctttggctgattgagttgacggtcggaagattggagactc
ggttttcactgg SEQ ID NO:241: putative preproprotein:
atgttcgacaccaactccactcgtcttccaatctggggtattggctgcaacccatggactgctgaacacgtcgatcaaactctcgttagtggcaacgag SEQ ID NO:242: sequence of alpha-amanitin/gamma-amanitin:
atctggggtattggctgcaaccca B) GmAMA1 Amino acid sequences deduced from sequences in A.

SEQ ID NO:243: Translation of frame 3'5' Frame 2:
Q.KPSLQSSDRQLNQPKIFALALISTMFDTNSTRLPIWGIGCNPWTAEHVDQTLVSGNEAQFLLLTCSTYSCVVR.YLLNV
(where . = nonsense codon)

SEQ ID NO:244 : the putative preproprotein is underlined; predicted sequence of α-amanitin is in bold
MFDTNSTRLPIWGIGCNPWTAEHVDQTLVSGNE SEQ ID NO:50 : The bold, larger letters show a sequence of alpha-amanitin/gamma-amanitin:
IWGIGCNP

B

SEQ ID NO: 111 alpha-amanitin/gamma-amanitin from Amanita

MSDINATRLPIWGIGCNPCIGDDVTILLTRG-E

| : | | | ||||||||||||| | | | |

MFDTNSTRLPIWGIGCNPWTAEHVDQTLVSGNE

SEQ ID NO:244 alpha-amanitin/gamma-amanitin from Galerina GaAMA1

A

GmAMA1 (GalMFD2; MFD2) Nucleic Acid Sequences.

SEQ ID NO:246
>GalerinaMFD2(615_bp) GmAMA2
agctacgtcggcgacattgcccatagaactaacttgggtagtcgaatcgtacaatcacgactccacgctttgccactgtcggvtggaatcagg&ctatctcttataggagcct
cttttcgtatctcgaaaactccaagcacttccaagctgaggatcgccgcgacacctagtactctcttgccgtcgtcaaagtggacaaagatacacctcgccgagtttactgactta
ccaccgatct

FIG. 15

Prolyloligopeptidase (POP)-like genes in fungi identified using a human POP (GenBank accession no. NP002717) sequence for a BLAST search.

| | | score | e value |
|---|---|---|---|
| gi|116497644|gb|EAU80539.1| | Coprinus (Coprinopsis) cinereus | 526 | 1e-148 |
| gi|71022411|ref|XP_761435.1| | Ustilago maydis | 506 | 1e-142 |
| gi|58259797|ref|XP_567311.1| | Cryptococcus neoformans 1 | 299 | 2e-80 |
| gi|58259759|ref|XP_567292.1| | Cryptococcus neoformans 2 | 286 | 3e-76 |
| gi|111059876|gb|EAT80996.1| | Setosphaeria nodorum | 156 | 3e-40 |
| gi|123476937|emb|CAC87723.1| | Aspergillus niger | 53.1 | 4e-06 |
| gi|83773722|dbj|BAE63849.1| | Aspergillus niger | 50.4 | 3e-05 |

FIG. 16

SEQ ID NO: 160

SEQ ID NO: 228: ECGK9LO02JKSHR R Length = 112; Score = 47.8 bits (112), Expect = 4e-06
Identities = 26/33 (60%), Positives = 26/33 (78%) Frame = +3
Query: 436  Q+VQIFYPSKDGTKIPMFIVHKKSTKLDGSHPA 468
            ++ Q++Y PSKDGTK+PMF+V  KS K DG +PA
Sbjct: 3    ESTQVWYESKDGTKVPMFIVRHKSTKFDGTAPA 101

SEQ ID NO: 162

SEQ ID NO: 229: contig26093 length = 206 num Reads = 6; Score = 41.2 bits (95), Expect = 3e-04
Identities = 18/32 (56%), Positives = 23/32 (71%) Frame = +1
Query: 440  IFYPSKDGTKIPMFIVHKKSIKLDGSHPAFLY 471
            ++Y S DGTKIPMFIV  K +K +G+ PA Y
Sbjct: 109  VWVDSYUGTKIPMFIVRHKNTKFNGTAPAIQV 204

SEQ ID NO: 164

SEQ ID NO: 230: ECIMO1V0I2HO5 S Length = 107; Score = 35.8 bits (81), Expect = 0.014
Identities = 18/27 (66%), Positives = 21/27 (77%), Gaps = 1/27 (3%) Frame = +2
Query: 546  KRLTINGGSNGGLLVAAC-ANQRPDLF 571
            ++L I+GGSNGGLLV A  QRPDLF
Sbjct: 26   EKLAISGGSNGGLLVGASRLTQRPDLF 106

SEQ ID NO: 166

SEQ ID NO: 231: ECIMO1V01CKHES R Length = 94; Score = 35.4 bits (80), Expect = 0.019
Identities = 16/27 (59%), Positives = 19/27 (70%) Frame = +2
Query: 120  SDDGTVALRGYAFSEDGEYFAYGLSAS 146
            S DGT +L  Y FS  G+YFAYG S S
Sbjct: 2    SSDGTASLSMYDFSHCGKYFAYGISLS 82

SEQ ID NO: 168

SEQ ID NO: 232: EEISCGG02HTSV R Length = 106; Score = 33.1 bits (74), Expect = 0.093
Identities = 14/20 (70%), Positives = 15/20 (75%) Frame = -2
Query: 669  PLLIHVDTKAGHGAGKPTAK 688
            PLL+ VD KAGHG GK + K
Sbjct: 105  PLLIRVDKKAGHGGGKSTEK 46

SEQ ID NO: 169

SEQ ID NO: 233: ECIMO1V02H2WNR S Length = 78; Score = 28.9 bits (63), Expect = 1.7
Identities = 12/16 (75%), Positives = 13/16 (81%) Frame = +2
Query: 436  DGTKIPMFIVHKKSIK 45
            DGTK+PMFIV  KS K
Sbjct: 2    DGTKVPMFIVRHKSTK 49

SEQ ID NO: 173
POPA: genomic sequence ggacaccccaaccatgtaccttcgctcgccgttcagaccatatagacacatacagaggagcgaaacagagagagcgaagtcaagtgccggacccataccactgctcgtaggaat
attcagaagagacggacaagtggacgtccgaccaagagtccgacgagagttcacgaggacaatttggacagcaacccgatcgaagaagcagaagacgcattcagaagagtatggat
tatccaaggttcttcggcattctattcattcgatgagtgatggctgccaatcttcttcctttatatagttccgctcctcttttgaatgatgacaagcgatgtattgttttac
aatacggccttcaagcagcacaaacagtaaacacatcaagctctgtcgtgcgaaatattacaactttggtagtcatcgcagatacaaggatgagactcttcccgactctcagagag
tgactacgtcgggaaacattttgatgtagtttgtgctggcggtgttccgatatcaatgataagcgtttcgcagccgaacctattatctcgatgcacagcctgctctccatg
tatgatttctcacactgtggcaaatacttcgcatatgtatttctcttccgtatgtaattcaacgagcaaccatcctccgatgagatgaactctttcgtcacaggggagcgatttca
actatatacgttcggtcaacttcctctccactgcccctgcaacgacagcattagaaatgacgacggtagactccagaggactttccaaagacagactttcctccatcagctgaca
aaggactcccaaggatttcttatcagttactaacgtgatgggatcgaggacatcacactatacccgctcttgtccaatcctcattcgctctgccgatgatattctgtcatg
actcaaggcgatcgtgatgcagtctactgagggacatcacaatgtaaaatatgtggcctgtacaacagaagcacatcaaggtagctttaagtgtccacctgc
aagaccaggaacatctgatgggtatttggcgcagaagtcacggaagatggtaaatatgtggcctgtacaacagaagcacatcaaggtagctttaagtgtccacctgc
gttgctaaccggttctgtagaaaaatctattgtggattgctgatctgtgacagaattgcaacgacggtcattacttactacaagattgcaacgttcaacgttgactcacttagat
aagtccctgaacggtaatacggttgtttttgcttatttgcgacagaattgcgacagaatgtccaaaacgaagcatatctctcaaagtcaaaaattttaataaggatagcactacactgctgcaactaacactggtcacgactaagcgtaacgtga
atagaaaacacagaattaggtttaaggagttaaggaattcataccggaagatccaaaaatagttatagcgaactctacgtctactgctacaataacactggtcacgactaagcgtaacgtga
gtccagaacacggcaatatatgcaggagagcaatacgaatgcaaattgcagagcagcaaattggaagaactctgcagtccactgcaacagcaggaagaaca
tgttggctccatgacgtgaccgctcgagaacgaaacggagccatgttttttgccactcacgggcttcaatacccctgaatcgtatgcaggtacaatatccagcgaccggaagaaca
gcgttgagcgtatatcgaactgcaagtccaaggttaaatcgaacgattcgaggctcgacaacatttaatggacggcgccagctacacaaattaatggacggcgccagctacaaatatggacggctcaaagcaatttttcaaaagcaatttttcaaaagatgttcagtaggtaggt
gccttgagcgtatatcgaactgcaagtccaaggttaaatcgaacgattcgaggctcgacaacatttaatggacggcgccagctacaaatatggacggctcaaagcaatttttcaaaagcaatttttcaaaagatgttcagtaggtaggt
acggatgacaacaagcgaatgaacaaagattcaacatgtcatcgtcgtcacaagaataccaaaatccctcttagtcgacttcaggttcaggttgacagatttgtcgactagctagcttgtacta
atatccgaggaggcggcaagttcgcgagacatgccatgatgcgtggtatgcgggatagctctgacattatttccaggctaatg
ttacgatgatttcattgcgcaacgtacgtcagttgcctgttcaatttcacattgaatccaccctcagctctcattcttcacgagatatatgctcaaactagtgctcacacttgattttcgaccttgattatcttattgagtctccaaattaccataggtatatgacaaca
caacgggggtccaatgggtccctagactgctcttgcatgtcctcaaggtttgctcgatcgtgtctacagagatatgctgactacgcgatctcagaagccggatttctcgacgcgatcagaatgctccaagttggatttgacgaaccttgagctg
ccattgctgaagttgggtccatgagactgcatgtccatgtcttatccaactcagtctctcattatatgtgtgcgtcgaggcaaattaccataggtatatgtcatatcaaca
ctgctcatgactttgtcttaaggtcgatatcaggcaagcttgactacgcgatcaggcaagcttgactacgcgatcggccccatggttcatgagcgccccaattgtcaggcccaataga
aagaacatgtcttacctccgacgatgcttcgacgcgtcctgagttgcctccatgtataatttgctagttgctgaccgacctgagaccgacctgagaaaggcggagcaatactaaa
taagtatgctcaatgctacaaataccacccctgcaataatgctccgcataatgctctcacttcgtacagtgtagacaagaaggccgggcatggcgggcatggggggagcaaaatcactgaaaatactactgagaagaggtggttt
ttccgttgtcataactcgctgcaattaattatccc

FIG. 17A

SEQ ID NO: 174
POPB : genomic sequence accaatggctgaggaggaattcaaatgaagtagaacgaatgacgacggcgaatgacgaagcttcacgcaagctactctgataagaatgcgatagacagaagctcgaggagaaatt
tcgtcaagcaaggaactacgtcaaggtaatcgatgatacgttgtctgtgctgaattagccgttgtgtctgtgaagaccttgccaatagttttctgcgccaactctgcgtgatagtggacactgtattgttcta
caatagggcgtacaaatgcaagcagcagtggtactgtccatctgtctgccgatgccgaattcagacagtgttcagtccactcacctgaacgaaaaccgttcctgattctcaaagag
gacgaggaatggcgcgaagtactcgattgtaggatccacgacgttgaatactcttttgacttcactcttgaaagccaaactgtctgctgatgccacgcaactttatggcac
gtgccgattctccccagtggcgagtattgcgatatgcagtcaagtccactggtagtaaccagttccacatgggccaactctggtcttatttttgcacaggagttgattattttactatct
atgttcgccctcagtccatcattgctcaaggtccaccaaccatccgttcgtcatacagcggaccctgtcatacagcgttgaggatggtgaaggtgaaggtgaacaaatcagcgaaagatctcggtgacaagactcca
aaggattttctttaccagtatgatacatccagccacccatccgttcatacagcggaccctgtcatacagctatttggcgaaagatctggtgcgaaaagatcggataaagatcgtat
ggtatgctatcatagggtgaacgactcaatgtaggggattacttgccgttgcttgacttccccaaactgatccagctagtgtataaagaactgcaagatgtgaagatatatttccagcccgacatcaataaccttcata
agactggacatatggaacagatgcgtcagagaatcgacaaggatcgtcagagagacgtcaaggaacgggtccaaaatcaaatgaacagtatattactatctctagtgtataaagaactgcaagatgttaagttgggcgtgattaccatgtgagtctccgct
cctcacgtcccttcacgtcccctttaactggtcagaattcgacaaggatcgtcatggtccatggtatgattcacgagaaccacgatcttgatctatctcaaagtcctgcgaaaagtcatcataagagtttggccgattaccatgttcactcatcgacct
ttgacagagaaccccgaaattgatttcatccgtaaactctgattttgcatccgatcgtgtattcaaagtgaacatcaagtcactcagtcaaatgtcaaagaaatatatcttaccaaagcagcgatcaactcagtcgtctgcctggacttcattgcgtt
cattgacaattcgaattcctctaattcgatgcatccgggcaccatcatccaaagcagcgatcaactcagtcgtctgcctggacttcattgcgtt
gcatctataaactaacagagaagaaaacaaccctcattcttctgcatggtcaaagatgtccaaagcagcgatcaactctgattcaagctaatctgacaaccctcgtctgcatgattcatcgttcgtcactccagcacaacctctgacaaatcaacgaa
agaacgacgaagctaaatgctcgaatcgacgcgcgattcactcttatgcagacatatggcgcaatccgtatcgattcacaaccagtaggcgaatctgacaacctcgtcttgctccgcacaagttatgtgtttcgcgattacagccg
atccattcttagctccacatatgccatcatgctcaccttatgcagacatatggcgcaatccgtatcgtctccgaacatcagagtggaggtgaattcgcgagaatgccacaaggcaggagacg
agaaaccaaggttgtgccatgacgagtcttttgttgctacagtcaattctttgcccaaaaacaagtacgcggcggtcaaggtccaatcaaggtacgcggtcaatcactgtgcatcaatggcggtcaaagtgaccctcgt
atttcacaggctcacgagatctttggtcatccctgcgatgtggaataggttttcttgtgtgtgtcaattgtgtaattgaatagttttttctccaccagaggacattcggcgctgttgtcaccgctgatttgattaataccatcgtca
tcttgtttttcatccgtactcacctgcacgatatccgtgctcgtttcaattcgtcacagctttaagaaggactccggggtgagttgacatgtcctctgcataacgtaacgtgttcaaccttaagttcgtgaaccttcagtac
caaaggtatttggttgtcacgatgaatatgaaaaccctttattaaggagggacttgccagcattgcttggcttggtcatggtggttggcaagagaacgacagcagtaaatcgtgttccgattgattaattacatgctca
gggatggcgtgacgagtgaatctctgagcccagattaccagttgcctgatggctgcggatgttgctgggcgctttgtcaccgctgttttgattaattacatgctgattactgattctgattcattgctcgaaacctcagtac
accaatgcctcaaaatcctcatcctgagctgacacacgtcggtgtacatggtgattaatacatctcggaacaaagagaccagtaaatcggtttgcctcccccttcacgttcaattgctatttt
aatgtcctcaaaatcctcatccttcctgtggaactgttcctcactgccattggcttggtcatcagacggagcaaacgcagtaaaatcgtcccccttcacgttcaattgctatttt
tacagtactaaagatgcttcgagagcaaccaccgttcctcatcctgtggacaagtgggaattcgtagccaatgcctctaggcctagccgctgtaaattaacagatgtatgcggtgaaaatacggtcaac
gttagatgtattcaaccgtactctgtttcctgtaacctcgctgcgcctgtaccgcctagcggccggccaatacagccatg FIG. 17A (continued)

FIG. 17B cDNA sequences of POPA and POPB.
SEQ ID NO: 234
>PopA_cDNA_full-length

ACACGCGTCTCAAATTCAAGCCATGCGACCGTTTTTTGCAGCCCGTAAGAGAAACGCCTTGCCTCTGCTCTGCGCCGGTACTTTGGTTCG
CGGATCATGTCTTCTACACAGGTGGAGACACCCAACATGTACCCTTCGTCGCGTTCAGACATATAGACACTATACAGGAGCGAAAC
GAGAGGCGAAGTCAAGGTGCCGGACCCGTACCACTGGTCGGCTAGAAGGAATATTCAGAAGAGACGGACAAGTGGACGTCGACCAGGA
GGAGTTCACGAGGACATATTGGACAGCAACCCTGATCGAAGAAGCTAGAAGAAGACGCATTCAGAAGAGTATGGATTATCCAAGTT
CTCCGCTCCTTTTGAATGATGACAAGCGATGTGACTACGTCGGGGACAACATTGGTTTACAATACCGGCCTTCAAGCACAAACAGTCATCTGAGATCAAAG
GATGAGACTCTTCCGGACTTCTCACGTCTATGATTCTCAGATGTGGCAAATACTTGGCATTGACTGTGCAACAACAGCATTAGAAACGCAGGTTCCAGATGGCACAGCC
TGGCTCTCCATGTATGATTTCTCACGTCTATGATTCTCAGATGTGGCAAATACTTGGCATTGACTGTGCAACAACAGCATTAGAAACGACGCAGGTTCCAGATGGCACAGCC
AATTTCCTCAAGTTCGTCTCCATGCGTCCAGTGGCGACAAAGGAGCTGATGCTGTATCAGCGGATAGGGACATCACAACCGATGATATTCTTGTCGATGAAG
ACCAGGAACATCCTGATTGGCGTATTGGGACAAAACTATGGAAGTTCACGGAAGATGTAAATATGGCCTGTACACAAGATTGCAACGTTTGACT
AGGAAAATCTATGTGACCTAATTGGCAACGACGGTTCATTCTTACTATACAGGAAGCTAATACAAGAGATTGTCACCTTAGA
CAGAATACGACCTAATTGGCAACGACGGTTCATTCTTACTATACAGGAAGCTAATACAAGAGATTGTCACCTTAGA
TATAGAGAAACAGAATTAGGGTTAAGCGTAACGTTATACAGGCGAACCTACGTCTACAATAACACTGGGTCACGACTAATGCGCTAGCCGG
AGACTAGCACTAGTATACAAGACGTGACGGTGACCGCTCGAAGAACAGGGTTGGAGCCTCACGGGTTCAAGGTTCAAGGTTTAAATCCGGAAC
GGACTTTGTTGCAAGTACAATATCCAGGTGTGTTACAATATGGCTTAATATATCTATAAATCCCTTCTTAGTCGAACGATTTGACGTTCT
TCGTATGCAAGTACAATATCCAGGTGTGTTACAATATGGCTTAATATATCTATAAATCCCTTCTTAGTCGAACGATTTGACGTTCT
GATTTCGAGGCTCGACAGGTCTGTGATTACAATATGGCTGTACCTAATATCCGAGGAGCAACTCAGTTCGTGTCAATCGTGCACGTGAAGCTTGAAGACATATGCCGGGCAAAGTGGC
AATGGGACGGCGCCAGTATGGAGCAATGTTACGATGATTTCATTGGTCCGCGCCCAAATTTGTCTCCCAAGTTACCATGGAACACAAGTATGCCGGGCGGGCAAAGATCC
TGCAAAAGTATGGAGCAATGTTACGATGATTTCATTGGTCCGCGCCCAAATTTGTCTCCCAAGTTACCATGGAACACAAGTATGCCGGGCGGGCAAAGATCC
GAAGTTGGGGTCCTAGACTTGCTCAAGTTCCTCAGACTTAGCGACTACGGCGATCCAGAAGATCC
GCGTGATTTGATTTACAGACATTCACAACACCACTTCATAATATAATTAAGTATGTCGACAATACTGTGCTACAATACACCGGCGACAGGTTCTTCTGACAGCT
GATCATGATGATGACCGTGTCGTGCCAATGCATTCATTTAGTATGTCGCAATACTGTGCTACAATACACCGGCGACAGTTCTTCTGACAGCT
TGCTACGTGTAGACAAGAAGCGGGGACATGCGTTCTTGCGTGGAAGGATAAATGGGGAAAATGTACTGAGGAAGAGGCGTTAGAGAGGCTGCCGACAAATGGGGTTT
TGGTTACTGTTTGCCCAGTCCATGGGGGTCTTGCGGTGGAAGGATAAATGGGGAAAATGTACTGAGGAAGAGGCGTTAGAGAGGCTGCCGACAAATGGGGTTT
GTTTTACTGTTTGGGCTACAGATTTTAGGACACTACGATTCACGACTTTAACGCATTGCACTGTGCACTGCAGGCTAAAAAAAAAAA
AAAAAAAAAAA

FIG. 17B (continued)

SEQ ID NO: 235
>PopB_cDNA

ATGCCCCCTACACCATGGCTCCTCACAGTTATCCTCCACCGTCGTTCTGACCACGTTGATGTATATCAGAGCGCATCCAGAGGC
GAAGTACCAGTACCGGACCCGTACCAATGGCTGGAGGAGAATTCAATGAAGTCGACGAATGACGCGGCCAGACAGCTTTCACG
CAAGGCTATCTTGATAAGAATCGGATAGAGAAGCTCGAGGAGAAGCTACGTCCAAGTCCAAGTTTCTGCCCA
ACTCTGCTTGATAGTGGACACTGGTATTGGTTCTACAATGGCGAAGCAGTCCTCTACCGCTCCAAGAAACCCGTT
CTTCCTGATTTCTCAAGAGAGGACGAGGAAATCGGGAAGTATACTTCGATCGAAACGTACTCTCGCTGATGGCACCGCAATTATG
GGCACGTGCCGATTCTCCCCTAGTGGCGAGTATTTCGCATATGCAGTGTCCCACTTGGGAGTTGATTATTTACTATCTATGTTCGC
CCTACGAGTTCATCATTGTCTCAAGCTCCGGAGCTGAAGGTGGGATGGTCGATTGTCGGGAATCTCTGTGGGAAGATCGAAGATCGTGATAAA
ACTATAACGTGGACAAGGACTCCAAAGGATTCTTTACCAGCGGCTCAATTGGAAGATATCATTGGAAGATCATCAAGGATGCCTCCAAGCAAATCTTCTGTGGTTGCA
GATGCTATGGTATGCTATCATAGAGGACGGCTCAAGCGCGGCAAATATATCTCCCGGCGAAAGATCAAGATTGCCTCGAAGTAACGAAC
TATGGGACAGATGGCGTCAGGGGTCAAGCTAAGCTGAATGCGGCCCAATATAAAAGTCATCATAAAAGTTCACTAGCGGATTTGCTACTATCGAACCGAA
CACGGATCTTTGATCTATGTCAAGACTAAGCTGATGCGAAGCAGATGCCGAAGCTCACTCAACAGGAATATTCGTCGCGATCTACAAG
ATCGTGATTTCATCCCGGAACCAGAAGATGCGAAGCTCACTCAAGTCAAGTCAGTCGTCAGTTCAGTTCATTGGCGTTGCATCT
CGCAATGTCAAGATGAAGATGAAACAACCTCATTCTTCCCTAGGACTTTACGAAGCTAAATGGTCTGAATGACTTTGAGAGCACAAGTCTGG
ATAACTAACGACACAACGTCTGACCATCCTTAGGACTACGAAGCTAAATGGCTGAATGGCTCAAGTGACGGACACACAAGTCTGG
GCTCCAGACACAAGACGGAACGAAAGTCTCACATCTTCAATGTGCTCATGTCCATGTCCATGCTCACCTTATGCAGACATATGGCCGAATCCTG
TATAAGAGCAAAGACGGAACGAAAGTTCGGTTATTACAGCCGATCCGATTCGGCGGAGAATGGCACAGGCAGGGAGAGGAACAAGGAGTTGAT
ACCGGTTATGGTGGTTTCGGCTATTACAGCCGATCGAATTCGGCGGAGAATGGCACAGGCAGGGAGCAGATGGAGCTCGCATGGTAACCAAGGAAATACTTTGAT
GCTGTCCCGAACATCAGAGGTGAGTGATTTCTTGCTCAATTCTTGTCAAAAAAGAACAAGTACGGCGTCGGCAAGGTGCATCCAATGCGGGT
GATTCATCGCTGCCGCTCAATTTCTTGTCAAAAAACAAGTACGGCCGTCCAGGCAAGGTGCATCCGGCAAGGACTTGACTTGTCCAAGCATTG
TTTAATAAATTCACCGGGGATGCGTGGACATAGGGTTCTTCCTGCCACATTACTTATGACCATGGGGTGACGATGGTGTAGTTCAATG
TCTCCTGTGCATAACGTCGTCCGCAACCTTCAGTACCAAGCATACTAAGACATGCTCAAAATCCTCATCCATTGTCTCATCCGTGTGGATAAATCTTGGCTT
CATTCGCTCAAGTTCGTCGTCCGCAACCTTCAGTACCAAGCATACTAAGACATGCCGCAATGTCGCAATGCGTTAGGGCTAGAA
GGTCATGGTTTTGGCAAGACAACAAGACAAGACATACTAAGAGATGCCGGACAAGTGGAGTTCGTAGCGCAATGCGTTAGGGCTAGAA
TGGAAAACGGTTGA

FIG. 17C

Amino acid sequences of POPA and POPB

SEQ ID NO: 236
>PopA_amino_acid sequence

MHRFLQPVRERLRSALARYFGSRIMSSTQWTPNMYPSARRSDHIDTYRSETRGEVKVPDPYHWLEEYSEET
DKWTSDQEEFTRTYLDSNPDRKKLEDAPRKSMDYPKFSAPFLNDDKRWYWFYNTGLQAQTVICRSKDET
LPDFSESDYVGETFDPNLLSSIDGTASILSMYDFSHCGKYFAYGISLSGSDFSTIYVRSTSSPLAPGNNSIRNDD
GRLPDELRYVKFSSISWTKDSKGHFYQRYPGTGTVNGQNGIQTQGDRDAMIYYHRIGTSQSDDILVHEDQE
HPDWTFGAEVTEDGKYVALYTMKDTSRKNLLWIADLGQNEVGRNMKWNKICNVFDSEYDLIGNDGSLL
YIRTNKAAPQYKIVTLDIEKPELGFKEFPEDPKAYLSQVKHNKDRLALVYKRNVIGELYVYNNTGSRLMR
LARDFVGSMTVTARETEPWFFATLTGFNTPGIVCRYNIQRPEEQRWSVYRTAKVKGLNPNDFEARQVWYD
SYDGTKIPMFIVRHKNTQPNGTAPAIQYGYGGFNSINPFFSPTILTFLQKYGAILAVPNIRGGEFGETWHD
AGIREKRANVYDDFIAATQFLVKNKYAAGGKVAfiNGGSNGGLLVAACVNRAREGTFGAAIAEVGVLDLLK
FPKFTIGKAWISDYGDPEDPRDFDYTTHSPLHNIPKNMVLPPTMLITADHDRVVPMHSFKYAAMLQYTL
PHNRHPLLLRVDKKAGHGGGKSTEKRLQEAADKWGFAAQSMGLAWKDRQANL*

SEQ ID NO: 237
>PopB_amino_acid sequence

MPPTPWAPHSYPPTRRSDHVDVYQSASRGEVPVPDPYQWLEENSNEVDEWTTAQTAFTQGYLDKNADRQ
KLEEKFRASKDYVKFSAPTLLDSGHWTWFYNSGVQSQAVLYRSKKPVLPDFQRGTRKVGEVYFDPNVLS
ADGTAfMGTCRFSPSGEYFAYAVSHLGVDYFTIYVRPTSSSLSQAPEAEGDGRLSDGVKWCKFTITWTK
DSKGFLYQRYPARESLVAKDRDKDAMVCYHRVGTIQLEDIVQQDKENPDWTYGTDASEDGKYTYLVVY
KDASKQNLLWVAEFDKDGVKPEIPWRKVINEFGADYHVITNHGSLIYVKTNVNAPQYKVVTIDLSTGEPEI
RDFfPEQKDAKLTQVKCVNKGYFVAIYKRNVKDEIYLYSKAGDQLSRLASDFfIGVASITNREKQPHSFLTFS
GFNTPGTISRYDFTAPDTQRLSfILRTTKLNGLNADDFESTQVWYKSKDGTfKVPMFTVRHKSTKFDGTAPAIQ
NGYGGFAfATADPFFSPIMLTFMQTYGAILAVPNIRGGGEFGGEWHKAGRRETKGNTfDDFfAAAQFfLVKNK
YAAPGKVAfITGASNGGFLVCGSVVRAPEGTFGAAVSEGGVADLLKFNKFTGGMAWTSEYGNPFIKEDFDF
VQALSPVHNVPKIDRVLPATLLMITNAGfIDRVVPMHSLKFVANLQYNVPQNPHPLLIRVDKSWLGHGHGFKT
TDKHTKIDAADKWSFVAQSLGLEWKTVD

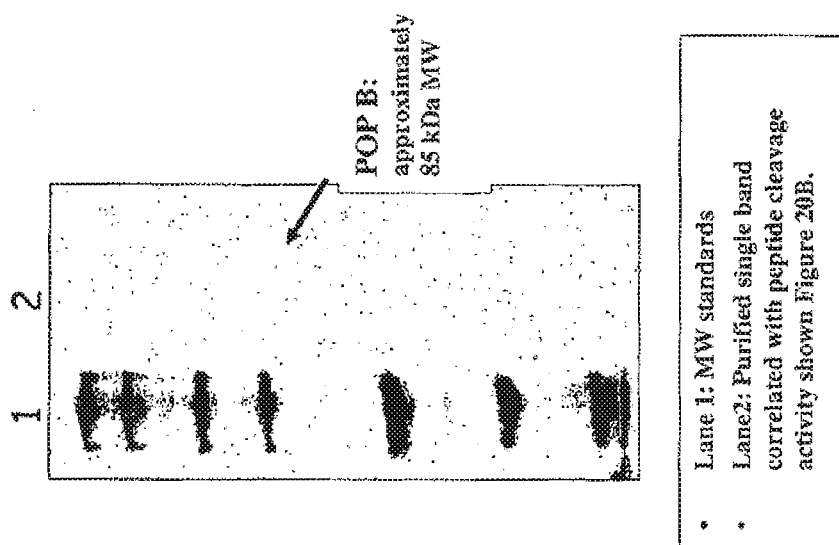

Lane 1: Markers.
Lane 2: POPB purified from inclusion bodies.
Lane 3: Soluble extract of *Amanita bisporigera*.
Lane 4: Immunoblot of POPB inclusion body.
Lane 5: Immunoblot of *Amanita* extract.

| GALERINA POPA SEQUENCES | LENGTH IN NUCLEIC ACIDS | NUMBER OF READS | RELATEDNESS RATING | | SEQ ID NO:XX |
|---|---|---|---|---|---|
| EOUVDMSO1DRXPF | LENGTH=241 | NA | 102 | 7e-23 | SEQ ID NO:250 |
| EOUVDMSO1AG5YR | LENGTH=221 | NA | 94 | 2e-20 | SEQ ID NO:251 |
| EOUVDMSO1CLJX8 | LENGTH=243 | NA | 84 | 2e-19 | SEQ ID NO:252 |
| CONTIG1013 | LENGTH=310 | NUMREADS=5 | 87 | 1e-18 | SEQ ID NO:253 |
| EOUVDMSO2HFQY | LENGTH=224 | NA | 80 | 4e-16 | SEQ ID NO:254 |
| EOUVDMSO2FASH | LENGTH=239 | NA | 57 | 6e-16 | SEQ ID NO:255 |
| EOUVDMSO1ANFQ8 | LENGTH=264 | NA | 64 | 3e-14 | SEQ ID NO:256 |
| CONTIG10675 | LENGTH=241 | NUMREADS=1 | 64 | 3e-14 | SEQ ID NO:256 |
| EOUVDMSO1EJV4E | LENGTH=254 | NA | 72 | 1e-13 | SEQ ID NO:258 |
| EOUVDMSO1C7LJ6 | LENGTH=267 | NA | 58 | 2e-13 | SEQ ID NO:259 |
| EOUVDMSO1EURXT | LENGTH=249 | NA | 65 | 1e-12 | SEQ ID NO:260 |
| EOUVDMSO2GNCLJ | LENGTH=254 | NA | 68 | 2e-12 | SEQ ID NO:261 |
| EOUVDMSO1A5NO8 | LENGTH=254 | NA | 67 | 3e-12 | SEQ ID NO:262 |
| CONTIG11529 | LENGTH=243 | NUMREADS=2 | 67 | 4e-12 | SEQ ID NO:263 |
| EOUVDMSO1D8CCX | LENGTH=230 | NA | 61 | 2e-10 | SEQ ID NO:264 |
| CONTIG48857 | LENGTH=169 | NUMREADS=3 | 57 | 3e-09 | SEQ ID NO:265 |
| EOUVDMSO1BH7S5 | LENGTH=262 | NA | 57 | 5e-09 | SEQ ID NO:266 |
| CONTIG60897 | LENGTH=242 | NUMREADS=4 | 57 | 5e-09 | SEQ ID NO:267 |
| EOUVDMSO2FGTBO | LENGTH=253 | NA | 52 | 9e-08 | SEQ ID NO:268 |
| EOUVDMSO2GQMEJ | LENGTH=280 | NA | 51 | 3e-07 | SEQ ID NO:269 |
| CONTIG43041 | LENGTH=170 | NUMREADS=2 | 47 | 1e-06 | SEQ ID NO:270 |
| EOUVDMSO2JY2X | LENGTH=130 | NA | 46 | 6e-06 | SEQ ID NO:271 |
| CONTIG08963 | LENGTH=360 | NUMREADS=6 | 46 | 6e-06 | SEQ ID NO:272 |
| CONTIG23635 | LENGTH=193 | NUMREADS=3 | 45 | 1e-05 | SEQ ID NO:273 |
| CONTIG34645 | LENGTH=176 | NUMREADS=2 | 43 | 2e-05 | SEQ ID NO:274 |
| CONTIG02145 | LENGTH=325 | NUMREADS=4 | 37 | 0.003 | SEQ ID NO:275 |
| EOUVDMSO2I6FQQ | LENGTH=220 | NA | 36 | 0.006 | SEQ ID NO:276 |
| EOUVDMSO1BQJH3 | LENGTH=263 | NA | 33 | 0.042 | SEQ ID NO: 69 |

```
>CONTIG01013; LENGTH=310; NUMREADS=5; SCORE = 87.4 BITS(215); EXPECT(2)=1e-18; IDENTITIES = 39/50(78%),
POSITIVES=44/50 (88%); FRAME=+2
QUERY: 526 GGFNISINPHSPTIIFFLQKYGALAVPNIRGGEEGETWEDAGIREKR 575
            GGF+ISI+PFFS TIIFFLQKYG + A+PNIRGGEFCE WH AG REK+
SBJCT: 2   GGFSISIDFFFSATIIFFLQKIGVVTALFNIRGGEFGEDWELAGCREKK 151

SCORE = 21.2 BITS (43), EXPECT(2) = 1e-18; IDENTITIES = 8/10 (80%), POSITIVES = 9/10 (90%); FRAME = +3
QUERY: 577 NVIDDFIAAT 586
            N +DDFIAAT
SBJCT: 210 NCFDDFIAAT 239

>EOUVDMS02HHTQY; LENGTH=224; SCORE = 80.1 BITS (196), EXPECT = 4e-16; IDENTITIES = 35/46 (76%),
POSITIVES = 42/46 (91%); FRAME = -2
QUERY: 690 DDRVVPMHSFKVAAMLQVTLPHNRHPLLLRVDKKAGHGGGKSTEKR 735
            DDRVVPMHSFK AA LQV+LPHN +PLL+R+DKKAGHG GKST+++
SBJCT: 202 DDRVVPMHSFKLAAELQYSLPHNPPLLIRIDKKAGHGAGKSTQQK 65

>EOUVDMS02PZASH; LENGTH=239; SCORE = 57.0 BITS(136), EXPECT(2)=6e-16; IDENTITIES=24/34(70%),
POSITIVES=30/34(88%); FRAME=-1
QUERY: 702 AAMLQVTLPHNRHPLLLRVDKKAGHGGGKSTEKR 735
            AA LQV+LPHN +PLL+R+DKK GHG GKST++R
SBJCT: 236 AAELQYSLPHNPPLLIRIDKKTGHGAGKSTQQR 135

SCORE = 42.7 BITS (99), EXPECT(2) = 6e-16; IDENTITIES = 16/22 (72%), POSITIVES = 20/22 (90%); FRAME = -3
QUERY: 735 RLQEAADKNGFAAQSNGLAMKD 756
            R++E+ADKNGF AQS+GL MKD
SBJCT: 78  RIKESADKNGFVAQSLGLIVMRD 13
```

SEQ ID NO: 367
SEQ ID NO: 368
SEQ ID NO: 369
SEQ ID NO: 370
SEQ ID NO: 371
SEQ ID NO: 372
SEQ ID NO: 373
SEQ ID NO: 374
SEQ ID NO: 375
SEQ ID NO: 376

FIG. 22A-3

```
SEQ ID NO: 377   >EOUVDMS01AWFQ8; LENGTH=264; SCORE = 63.9 BITS (154), EXPECT(2) = 3e-14; IDENTITIES = 27/34 (79%),
                 POSITIVES = 31/34 (91%); FRAME = +3
SEQ ID NO: 378   QUERY: 491 QVWYDSVDGTKIPMFIVRHKNTQFNGTAPAIQYG 524
                            QVWY+S DGT IPMFIVREK+T+F+GTAP IQYG
                 SBJCT: 108 QVWYESKDGTSIPMFIVRHKSTKFDGTAPVIQVG 209

SEQ ID NO: 379   SCORE=30.0 BITS(66), EXPECT(2)=3e-14; IDENTITIES=12/20(60%), POSITIVES=15/20(75%); FRAME=+2
                 QUERY: 473 VYRTAKVRGLNPNDFEARQV 492
                            +YRT K+ GLN DF+A QV
SEQ ID NO: 380   SBJCT: 2   IYRTKLNGLNTEDFKASQV 61

SEQ ID NO: 256   >CONTIG10675; LENGTH=241; NUMREADS=1; SCORE=63.9 BITS(154), EXPECT(2)=3e-14; IDENTITIES =27/34(79%),
                 POSITIVES=31/34(91%); FRAME = +3
SEQ ID NO: 382   QUERY: 491 QVWYDSVDGTKIPMFIVRHKNTQFNGTAPAIQYG 524
                            QVWY+S DGT IPMFIVREK+T+F+GTAP IQYG
                 SBJCT: 108 QVWYESKDGTSIPMFIVRHKSTKFDGTAPVIQVG 209

SEQ ID NO: 379   SCORE=30.0 BITS(66), EXPECT(2)=3e-14; IDENTITIES=12/20(60%), POSITIVES=15/20(75%); FRAME=+2
                 QUERY: 473 VYRTAKVRGLNPNDFEARQV 492
                            +YRT K+ GLN DF+A QV
SEQ ID NO: 380   SBJCT: 2   IYRCIKLNGLNTEDFKASQV 61

SEQ ID NO: 385   >EOUVDMS01ELV4E; LENGTH=254; SCORE = 72.0 BITS (175), EXPECT = 1e-13; IDENTITIES = 36/60 (60%),
                 POSITIVES = 44/60 (73%); FRAME = -2
                 QUERY: 189 SDFSTIVRSTSSPLAPSNNSIRNDGRLPEDLRYVKRSSISWTKDSKGFYQRYPCTGT 248
                            SDF TIVV S+ SPL     +S +ND GRLP+E++VKRSSI WT DSKGFF + P T +
SEQ ID NO: 386   SBJCT: 253 SDFVTIVVNSTDSSPLTNDVDS-ZNBKGRLPERIKFVKRESIGWTPDSKGPFIRSIPRTAS 77
```

FIG. 22A-4

```
>EUUVDMS01C7LJ6; LENGTH=267; SCORE = 58.2 BITS (139), EXPECT(2) = 2e-13; IDENTITIES = 23/35 (65%),
POSITIVES = 30/35 (85%); FRAME = -2

QUERY: 211  KNDGCRLPDELRYVKFSSISWEKDSKGFYQRYPG  245
             +ND GRLP+E+++VKFSSI WT DSKGFF + +PG
SBJCT: 218  KNDRGRLPEEIRFVRFSSIGWFDDSKGFFIRSFPG  114

SCORE = 32.7 BITS (73), EXPECT(2) = 2e-13; IDENTITIES = 15/26 (57%), POSITIVES = 18/26 (69%),
GAPS = 1/25 (3%); FRAME = -3

QUERY: 242  RYPGTGTVNGGNG-IQTQGDRDAMIY  266
             RYP T T   +NG I  T+GD DAM+Y
SBJCT: 79   RYPDTSTATQEMGPIATEGDLDAMVY  2
```

SEQ ID NO: 387

SEQ ID NO: 388

SEQ ID NO: 389

SEQ ID NO: 390

```
>EUUVDMS0LEUNXT; LENGTH=249; SCORE = 65.1 BITS (157), EXPECT(2) = 1e-12; IDENTITIES = 29/47 (61%),
POSITIVES = 37/47 (78%), GAPS = 1/47 (2%); FRAME = -2

QUERY: 690  DDRVPMHSFKYAAMLQYTLPHHRHPILLRVDKK-AGHGGGKSTEAR  735
             DDRVPMHSF+ A LQ+ +P N HPLL+++DK   GHG GK T+R+
SBJCT: 230  DDRVPMHSFRFIATIQNRVPQNPHPLLKIDKSNLGHGMGGKFTDKR  90

SCORE = 23.5 BITS (49), EXPECT(2) = 1e-12; IDENTITIES = 8/12 (66%),
POSITIVES = 11/12 (91%); FRAME = -1

QUERY: 736  LQEAADKWGFAA  747
             +++AADKWGF A
SBJCT: 36   VKDAADKWGFIA  1
```

SEQ ID NO: 371

SEQ ID NO: 394

SEQ ID NO: 396

SEQ ID NO: 395

```
>EUUVDMS01D8CX; LENGTH=230; SCORE = 60.8 BITS (146), EXPECT = 2e-10; IDENTITIES = 31/74 (41%),
POSITIVES = 43/74 (58%), GAPS = 19/74 (25%); FRAME = +2
QUERY: 643 TIGKAWISDYGPDEDPRDEDYITHSPLRNIPKNMVLPPIMLLTAD------------------ 688
            ++G+AWIS+YG+P  P +PDYIY   SP+HN+   + V+ P ML+T +
SBJCT:  11 SLGQAWISEYGNPSIPEEPDYIYPLSPVHNVQRDVM-PAMLITVNIGRQLTSSNLIMPH 187

QUERY: 689 --------HDDRVVPMH 697
                    DDRVVPME
SBJCT: 188 TRPSPGDDRVVPMH 229

>CONTIG48857; LENGTH=169; NUMREADS=3; SCORE = 57.4 BITS (137), EXPECT = 3e-09; IDENTITIES = 24/34 (70%),
POSITIVES = 31/34 (91%); FRAME = -1
QUERY: 702 AAMLQYTLPHNREPLLLRVDKKAGHGGGKSTEKR 735
            AA LQY+LPHN +PLL+R+DKKAGHG GAST+++
SBJCT: 166 AAELQYSLPHRPNPLLIRIDKKAGHGAGKSTQQK 65

>EQUVDMS01BH755; LENGTH=262; SCORE = 56.6 BITS (135), EXPECT = 5e-09; IDENTITIES = 31/86 (36%),
POSITIVES = 45/86 (53%); FRAME = -2
QUERY: 552 AVPNIRGGGEFGEINHDAGIREKRANVIDDPIAATQFLIVANKVIAGGKVIAINGSNGGLL 611
            AV +IRGG E G  N  G ++K+ N + DFIA  + L+  Y  G++   G S GG+L
SBJCT: 261 AVTHIRGSSEKGWGNFLDGRKDKKPNSFDFIACARALIAEGYGTAGRIVAEGRSAGGML 82

QUERY: 612 VAACVARAREGTPGAAIAEVGVLDLL 637
            + A  R +  I V +D+L
SBJCT:  81 MGAVAN-LRPLWAGVIGGVPFVDVL 7
```

FIG. 22A-7

SEQ ID NO: 407
SEQ ID NO: 408
SEQ ID NO: 409
SEQ ID NO: 410

SEQ ID NO: 373
SEQ ID NO: 412

SEQ ID NO: 413
SEQ ID NO: 414

SEQ ID NO: 415
SEQ ID NO: 416

```
>CONTIG50097; LENGTH=242; NUMREALS=4; SCORE = 56/6 BITS (135), EXPECT = 5e-09; IDENTITIES = 30/77 (38%),
POSITIVES = 42/77 (54%), GAPS = 20/77 (25%); FRAME = +3
QUERY: 107 KFSAPFLNDDRKWTWYNTGLQAQT--------------------VICRSKDETLPDSES 147
           ++ AP+L+DD RKTW+YN+G++ QT                    + RSKD LPD S +
SBJCT: 12  QYTAPYLHDDRWTWYYNSGLFQCGERSKQPPRPRWATSVPAKALYRSKDSNLPQLSTR 191

QUERY: 148 D-YGETFPDFNLLSSD 163
           D  G+ FFD  LS++
SBJCT: 192 DCGSGDLFFDVGPLSAM 242

>EUVDMS02FGJBD LENGTH=253; SCORE = 52.4 BITS (124)M EXPECT = 9e-08; IDENTITIES = 19/38 (50%),
POSITIVES = 31/38 (81%); FRAME = +2
QUERY: 275 SDDILVHEDQEHPDWTFGAEVTEDGKYVALYPMKDTSR 312
           ++D L+++D+EH DW+F +VT+DG Y+ LY +KD+SR
SBJCT: 77  AEDSLIYQDREHRDWMFSIDVTDDGNYLLLYILKDSSR 190

>EUVDMS02GQMEJ LENGTH=80; SCORE = 50.8 BITS (120), EXPECY = 3e-07; IDENTITIES = 24/30 (80%),
POSITIVES = 27/30 (90%); FRAME = -3
QUERY: 609 GLLVAACVNRAREGTFGAAIAEVGVLDLLK 638
           GLLV+ACVNRA EGTFG A+A+VGV DLLK
SBJCT: 269 GLLVSACVNRAPEGTFGCAVADVGVHDLLK 180

>CONTIG43041; LENGTH=170; NUMREADS=2; SCORE = 47.0 BITS (110), EXPECT(2) = 1e-06;IDENTITIES = 15/27 (55%),
POSITIVES = 25/27 (92%); FRAME = -1
QUERY: 276 DDILVHEDQEHPDWVFGARVTEDGKNV 302
           +D+V++D EHP+W++GA+ +EDGK++
SBJCT: 83  EDILVYQDNREHREWIFGADITEDGKYL 3

SCORE = 21.2 BITS (43), EXPECT(2) = 1e-06; IDENTITIES = 6/13 (46%), POSITIVES = 11/13 (84%); FRAME = -2
QUERY: 264 NIYTHRIGTSOSD 276
           N+ YH++GT+Q +
SBJCT: 169 NMCYHKVGTTQGE 131

>EUVDMS02JYIZ4; LENGTH=130; SCORE = 46.2 BITS (108), EXPECT = 6e05; IDENTITIES = 18/30 (60%),
POSITIVES = 23/30 (76%); FRAME = +2
QUERY: 25  MSSTQWTPNMYPSARESDHIDTYRSEPGE 54
           MSS  W P  YPS ARSDH+D+Y+S ++GE
SBJCT: 41  MSSIAWAPGWYPSTRRSDHVDSYQSASKGE 130
```

FIG. 22A-8

SEQ ID NO: 417
SEQ ID NO: 418
SEQ ID NO: 419
SEQ ID NO: 420
SEQ ID NO: 421
SEQ ID NO: 422
SEQ ID NO: 423
SEQ ID NO: 424
SEQ ID NO: 425
SEQ ID NO: 427
SEQ ID NO: 428
SEQ ID NO: 429
SEQ ID NO: 430
SEQ ID NO: 431
SEQ ID NO: 432

FIG. 22A-9

| GALLERIA PQPA SEQUENCES | LENGTH IN NUCLEIC ACIDS | NUMBER OF READS | RELATEDNESS RATING | SEQ ID NO:XX |
|---|---|---|---|---|
| EQUVDMS01CLJX8 | LENGTH=243 | NA | 118 5e-30 | SEQ ID NO:338 |
| EQUVDMS01DRXPF | LENGTH=241 | NA | 123 3e-29 | SEQ ID NO:280 |
| EQUVDMS01EUNXT | LENGTH=249 | NA | 92 3e-21 | SEQ ID NO:339 |
| EQUVDMS01AG5VR | LENGTH=221 | NA | 88 1e-18 | SEQ ID NO:282 |
| EQUVDMS01ANFO8 | LENGTH=264 | NA | 67 3e-16 | SEQ ID NO:332 |
| CONTIG10675 | LENGTH=241 | NUMREADS=1 | 67 3e-16 | SEQ ID NO:332 |
| EQUVDMS02GNCLJ | LENGTH=254 | NA | 80 5e-16 | SEQ ID NO:253 |
| CONTIG01013 | LENGTH=310 | NUMREADS=5 | 77 3e-15 | SEQ ID NO:343 |
| EQUVDMS01ASNC8 | LENGTH=254 | NA | 74 3e-14 | SEQ ID NO:286 |
| CONTIG11529 | LENGTH=243 | NUMREADS=2 | 74 3e-14 | SEQ ID NO:286 |
| EQUVDMS01D8GCX | LENGTH=230 | NA | 70 4e-13 | SEQ ID NO:288 |
| EQUVDMS02HHTQY | LENGTH=224 | NA | 67 3e-12 | SEQ ID NO:289 |
| EQUVDMS02F2ASH | LENGTH=239 | NA | 45 9e-11 | SEQ ID NO:337 |
| CONTIG34645 | LENGTH=176 | NUMREADS=2 | 53 3e-10 | SEQ ID NO:345 |
| EQUVDMS01BQJH3 | LENGTH=263 | NA | 45 4e-09 | SEQ ID NO:346 |
| EQUVDMS01BH7S5 | LENGTH=262 | NA | 57 4e-09 | SEQ ID NO:293 |
| CONTIG43041 | LENGTH=170 | NUMREADS=2 | 48 1e-08 | SEQ ID NO:336 |
| EQUVDMS02I6P0Q | LENGTH=220 | NA | 52 8e-08 | SEQ ID NO:276 |
| EQUVDMS01ELV4E | LENGTH=254 | NA | 50 3e-07 | SEQ ID NO:296 |
| CONTIG08963 | LENGTH=360 | NUMREADS=6 | 50 3e-07 | SEQ ID NO:297 |
| EQUVDMS02JY12X | LENGTH=130 | NA | 48 2e-06 | SEQ ID NO:271 |
| CONTIG60897 | LENGTH=242 | NUMREADS=4 | 48 2e-06 | SEQ ID NO:267 |
| CONTIG23635 | LENGTH=193 | NUMREADS=3 | 48 2e-06 | SEQ ID NO:273 |
| CONTIG48857 | LENGTH=169 | NUMREADS=3 | 45 2e-05 | SEQ ID NO:290 |
| EQUVDMS02FGJBO | LENGTH=253 | NA | 43 5e-05 | SEQ ID NO:302 |

FIG. 22B-1

```
>EQUVDMS01CLJX8; LENGTH=243; SCORE=118 BITS (295), EXPECT(2)=5e-30; IDENTITIES = 55/70 (78%),
POSITIVES = 61/70 (87%); FRAME = -1
QUERY: 403 GVASITNREKQPHSFLTFSSGFNTPGTIGRYDFTAPDTQRLSILRTKLNGLNADDFESTQ 462
            G ASI NR+KQ H FL+ SGFNTPGTI+RYDFTAP+TQR SILRTK+N L+ DDFESTQ
SBJCT: 243 GAASIANRQKQTRFFHLSGFNTPGTIARYDFTAPETQRFSILRTKVNELDPDDFESTQ 64

QUERY: 463 VNYKSKDGNK 472
            VNY+SKDG K
SBJCT: 63  VNYESKDGNK 34

SCORE=28.9 BITS 63), EXPECT(2)=5e-30; IDENTITIES=12/15(80%); POSITIVES=13/15(86%); FRAME=-2
QUERY: 468 KDGTKVPMFIVRHKS 482
            K  K+PMFIVRHKS
SBJCT: 47  KMATKIPMFIVRHKS 3

>EQUVDMS01BRXPF; LENGTH=241; SCORE = 123 BITS (309), EXPECT = 3e-29; IDENTITIES = 55/75 (73%),
POSITIVES = 65/75 (86%); FRAME = -1
QUERY: 6   WAPHSTPFTRRSDHVDVYQSASRGEVPVPDPYQNLRFNSNEVDRKTTAQTQFTQGYLDKN 65
            WAP +TP TRRSDHVD YQSAS+GEVPVPDPYQWLEE++EVD+KTTAQ  Q YLD+N
SBJCT: 226 WAPGNTPSTRRSDHVDSYQSASKGEVPVPDPYQWLEESTDEVDRKNITAQADLAQAYLDQN 47

QUERY: 66  ADROKLLGKFRASKD 80
            AD  KL +KFRAS++
SBJCT: 46  ADIQKLADRFRASRN 2

>EQUVDMS01EUNKT; LENGTH=249; SCORE = 92.0 BITS (227), EXPECT(2) = 3e-21; identities = 35/47 (82%),
POSITIVES = 43/47 (91%); FRAME = -2
QUERY: 660 GDDRVVPMHSLKFVANLQYNVPQNPHPLLIRVDKSWLGHGFGKTFDK 706
            GDDRVVPMHS KF+A LQ+NVPQNPHPLLI+DKSWLGHG GK FDK
SBJCT: 233 GDDRVVPMHSFKFIATLQHNVPQRNPHPLLIKIDKSWLGHGWGKPFDK 93

SCORE=25.4 BITS(54), EXPECT(2)=3e-21; IDENTITIES=9/11(81%), POSITIVES=10/11(90%); FRAME = -1
QUERY: 709 KDAADKNSFVA 719
            KDAADKN F+A
SBJCT: 33  KDAADKNGFIA 1
```

FIG. 22B-2

```
>EOUVDMS01AGSVR; LENGTH=221; SCORE = 88.2 BITS (217), EXPECT = 1e-18; IDENTITIES = 40/70 (57%),
POSITIVES = 52/70 (74%); FRAME = +3
QUERY:  20  VDYVQSARGEVPDVPDPYQWLEENSNEVDEWTTAQEAPTQGYLDRNADRQKLEEKPRASK  79
            VDY+SA RG+V V DPYQWLEE ++E D+WTTAQ FT+ YLDKN D  +LS+ F+A
SBJCT:   3  VDIYKSALRGDVHVQDPVQWLEPYTDETDKWTTAQWVFTRKTYLDKNPLLPREEKAPQACN 182

QUERY:  80  DYVFSAETL 89
            DY R + T+
SBJCT: 183 DYPRVLSATI 212

>EOUVDMS01AMFQ8; LENGTH=264; SCORE = 67.0 BITS (162), EXPECT(2)=3e-16; IDENTITIES = 29/34 (85%),
POSITIVES = 31/34 (91%); FRAME=+3
QUERY: 462  QWYKSKDGTKVPNFIVRHKSTKFDGTAPAIQNG 495
            QWY+SKDGT +PNFIVRHKSTKFDGTAP IQ G
SBJCT: 108  QWYESKDGTSIPNFIVRHKSTKFDGTAPVIQYG 209

SCORE=33.5 BITS(75), EXPECT(2)=3e-16; IDENTITIES=14/20(70%), POSITIVES=18/20(90%); FRAME=+2
QUERY: 444  ILRTTKLNGLNADFESTQV 463
            I RTTKLNGLN +DF+++QV
SBJCT:   2  IYRTTKLNGLNTEDFKASQV 61

>CONTIG10675; LENGTH=241; NUMREALS=1; SCORE = 67.0 BITS (162), EXPECT(2) = 3e-16; IDENTITIES 29/34 (85%),
POSITIVES = 31/34 (91%); FRAME = +3
QUERY: 462  QWYKSKDGTKVPNFIVRHKSTKFDGTAPAIQNG 495
            QWY+SKDGT +PNFIVRHKSTKFDGTAP IQ G
SBJCT: 108  QWYESKDGTSIPNFIVRHKSTKFDGTAPVIQYG 209

SCORE=33.5 BITS(75), EXPECT(2)=3e-16;IDENTITIES=14/20(70%), POSITIVES=18/20(90%); FRAME=+2
QUERY: 444  ILRTTKLNGLNADFESTQV 463
            I RTTKLNGLN +DF+++QV
SBJCT:   2  IYRTTKLNGLNTEDFKASQV 61

>EOUVDMS02GWNLG; LENGTH=254; SCORE=79.7 BITS(195), EXPECT=3e-16; IDENTITIES=39/53(73%),
POSITIVES = 42/53 (79%); FRAME = -2
QUERY: 165  GVDYFTIVRPTSSSLSQAPEABGGDGRLSDGVRKCKFTTITHWKDSXGRIVQ 217
            G DY T+VR TSS LSQ+ A+G DGRLSD VKR KF+TI WTKD KGFLVQ
SBJCT: 226  GGDYSTIVRSTSSTPLSQSSVAQSVDGRLSDEVKNFKFSTIIWTKDPKGFLIQ 68
```

SEQ ID NO: 595
SEQ ID NO: 360
SEQ ID NO: 594
SEQ ID NO: 595
SEQ ID NO: 455
SEQ ID NO: 378
SEQ ID NO: 455
SEQ ID NO: 380
SEQ ID NO: 455
SEQ ID NO: 378
SEQ ID NO: 455
SEQ ID NO: 380
SEQ ID NO: 461
SEQ ID NO: 398

```
SEQ ID NO: 477   QUERY: 659 -AGDDRVVPMH 668
SEQ ID NO: 478   SBJCT: 197 SPGDDRVVPMH 229
                            GDDRVVPMH

>EOUVDMS02RHTQV; LENGTH=224; SCORE = 67.0 BITS (162), EXPECT = 3e-12; IDENTITIES = 31/49 (63%),
                 POSITIVES = 37/49 (75%); FRAME = -2
SEQ ID NO: 479   QUERY: 659 NAGDDRVVPMHSLKFVAMLQYNVPQNPHPLLIRVDKSWLGHGFGKTDK 706
                            N  DRVVPMHS K A LQY++P NP+PLLIR+DK    GHG GK+T +
SEQ ID NO: 480   SBJCT: 211 NLDSDRVPMHSFKLAAELQYSLPHNPWPLLIRIDKK-AGHGAGKSTQG 68

>EOUVDMS02FZASH; LENGTH=239; SCORE = 44.7 BITS (104), EXPECT(2) = 9e-11; IDENTITIES = 20/33(60%),
                 POSITIVES = 26/33(78%); FRAME = -1
SEQ ID NO: 481   QUERY: 674 ANLQYNVPQNPHPLLIRVDKSWLGHGFGKTDK 706
                            A LQY++P NP+PLLIR+DK   GHG GK+T +
SEQ ID NO: 482   SBJCT: 233 AELQYSLPHNPWPLLIRIDKK-TGHGAGKSICQ 138

SCORE=37.4 BITS(85) , EXPECT(2)=9e-11; IDENTITIES=15/19(78%); POSITIVES=17/19(89%); FRAME=-3
SEQ ID NO: 483   QUERY: 709 KDAADKWSFVAQSLGLWK 727
                            K++ADKW FVAQSLGL WK
SEQ ID NO: 484   SBJCT: 72  KESADKWGFVAQSLGLVWK 16

>CONTIG34645; LENGTH=176; NUMREADS=2; SCORE = 52.8 BITS (125), EXPECT(2) = 3e-10; IDENTITIES = 21/27 (77%),
                 POSITIVES = 23/72 (85%); FRAME = -3
SEQ ID NO: 485   QUERY: 84  FSAPTLLSSGHWTWFYNSGVGSQAVLY 110
                            FSAPTLLD GHWTWF+N G+QS + Y
SEQ ID NO: 486   SBJCT: 162 FSAPTLLDDGHWTWFYNRGLQSQSGRY 82

SCORE=27.7 BITS(60), EXPECT(2)=3e-10; IDENTITIES=11/13(84%), POSITIVES=12/13(92%); FRAME=-2
SEQ ID NO: 487   QUERY: 108 VLYRSKKPVLPDF 120
                            VLYRSK+P LPDF
SEQ ID NO: 442   SBJCT: 40  VLYRSKEPALPDF 2

>EOUVDMS01BQJH3; LENGTH=263; SCORE = 45.1 BITS (105), EXPECT(2) = 4e-09; IDENTITIES = 26/46 (55%),
                 POSITIVES = 27/46 (58%), GAPS = 18/46 (39%); FRAME = +3
SEQ ID NO: 489   QUERY: 589 RAPEGTFGAAVSEGGVADLLK------------FMKRIGG 615
                            RAPEGTFGAAV EGGVADLLK            F+K++GG
SEQ ID NO: 490   SBJCT: 3   RAPEGTFGAAVPEGGVADLLKNVFVFQLCNSQSLLIELQPHKFTGG 140
```

```
>CONTIG08963; LENGTH=360; NUMREADS=6; SCORE = 50.4 BITS (119), EXPECT = 3e-07; IDENTITIES = 32/95 (33%),
POSITIVES = 45/95 (47%), GAPS = 1/95 (1%); FRAME = -3
```
SEQ ID NO: 505    QUERY: 415 HSFLTSGNTRGTISRVDFTAPFTQRLSILRTKLNGLNADPESTQVWYKSKDGTKVP 474
                             H L+    N P I R   D+ +  T  L   NADD+ S  +N  S DGT+VP
SEQ ID NO: 506    SBJCT: 283 HIRLRVEALNRPAQIRR---LALARGAQVLAKETPVLGVPNADDVSQRLWANSVDGTQVP 110

SEQ ID NO: 508    QUERY: 475 M-PIVRRKSTKFGTAPAIQNGYGGPAFTADPFFS 508
                             + +VRR  P   GYG + +  DP+FS
SEQ ID NO: 507    SBJCT: 109 ISLWRH--DQLGQPTPLIIGVGAYGHSLDPWFS 11

```
>EUVDKS0LYTIX; LENGTH=130; SCORE = 48.1 BITS (113), EXPECT = 2e-06; IDENTITIES = 21/30 (70%),
POSITIVES = 23/30 (76%), GAPS = 0/30; FRAME = +2
```
SEQ ID NO: 509    QUERY: 1   MPPTPWAPHSYPPTRRSDHVHVYQSASRGE 30
                             M    WAP +YP  TRRSDHVD YQSAS+GE
SEQ ID NO: 432    SBJCT: 41  NSSTRWAPGNYPSTRRSDHVDSYQSASKGE 130

```
>CONTIG60897; LENGTH=242; SCORE = 48.1 BITS (113), EXPECT = 2e-06; IDENTITIES = 25/77 (33%),
POSITIVES = 35/77 (45%), GAPS = 19/77 (24%); FRAME = +3
```
SEQ ID NO: 511    QUERY: 83  KFSAPTLLDSGHWTWFYNSGVQSQA-------------VLYRSKKPVLPDFQRG 123
                             ++ AP L D       WTW+YNSG ++            LYRSK    LPD
SEQ ID NO: 418    SBJCT: 12  QYYAPYLHDDNEWTWYYNSGLEPQTGERFKQPRPRWLISVPAKALYRSKIDSNLPDLSTA 191

SEQ ID NO: 513    QUERY: 124 TRKVGEVFFDPNVLSAD 140
                             G+++FD   LSA+
SEQ ID NO: 420    SBJCT: 192 DGSGGDLFFDVGPLSAN 242

```
>CONTIG23635; LENGTH=193; NUMREADS=3; SCORE = 47.8 BITS (112), EXPECT = 2e-06; IDENTITIES = 22/23 (95%),
POSITIVES = 22/23 (95%); FRAME = -1
```
SEQ ID NO: 515    QUERY: 558 QFLVNKYAAPGKVAITGASNGG 580
                             QFLVNKYAAPG VAI GASNGG
SEQ ID NO: 438    SBJCT: 145 QFLVNKYAAPGKVAINGASNGG 77

```
>CONTIG3635; LENGTH=193; NUMREADS=3; SCORE = 47.8 BITS (112), EXPECT = 2e-06; IDENTITIES = 22/23 (95%);
POSITIVES = 22/23 (95%); FRAME = -1
```
SEQ ID NO: 515    QUERY: 558 QFLVKKKYAAPGKVAITGASNGG 580
                              QFLVKKYAAPGKVAI GASNGG
SEQ ID NO: 438    SBJCT: 145 QFLVKKKYAAPKGVAINGASNEG 77

```
>CONTIG48857; LENGTH=169  NUMREADS=3; SCORE = 44.7 BITS (104), EXPECT = 2e-05; IDENTITIES = 20/33
(60%);
POSITIVES = 26/33 (78%); FRAME = -1
```
SEQ ID NO: 481    QUERY: 674 AHLQYNVPQNPHPLLIRVDKSWLGHFGKTDK 706
                              A LQY++P NP+PLLIR+DK   GHG GK+T +
SEQ ID NO: 482    SBJCT: 163 AELQYSLPHNPNPLLIRIDKR-AGHGAGKSTQQ 68

```
>E0UVDMS02FGJBD; LENGTH=253; SCORE = 43.1 BITS (100, EXPECT = 5e-05; IDENTITIES = 15/37 (40%);
POSITIVES = 26/37 (70%); FRAME = +2
```
SEQ ID NO: 519    QUERY: 247 EDIIVQQDKENPDNTYGTDASEDGKYIYLVWYRDASK 283
                              ED ++ QD+E+ DN + D ++DG Y+ + L + KD+S+
SEQ ID NO: 520    SBJCT: 80  EDSLIYQDREHRQWNFSIDVFDDGNYLLYILKDSSR 190

```
>E0UVDMS01C7LT6; LENGTH=267; SCORE = 42.4 BITS (98), EXPECT =9e-05; IDENTITIES = 18/43 (41%);
POSITIVES = 29/43 (67%); FRAME = -2
```
SEQ ID NO: 391    QUERY: 178 SSLSQAPEAEGGDGRLSDGVRACKFTTIWTKDSKGPLYQRVP 220
                              S L++ +A+   GRL + +K+ KF++I WT DSKGF + +P
SEQ ID NO: 392    SBJCT: 245 SPLTKDVDAKNDKGRLPEIKFVKESSIGWTPDSKGFIRSFP 117

```
>E0UVDMS02GQMEJ; LENGTH=280; SCORE = 40.0 BITS (92), EXPECT = 4e-04; IDENTITIES = 20/30 (66%);
POSITIVES = 22/30 (73%); FRAME = -3
```
SEQ ID NO: 425    QUERY: 580 GFLVCSSVVRAPEGTFGAAVSEGGVADLLK 609
                              G LV  V RAPEG FG AV++ GV DLLK
SEQ ID NO: 424    SBJCT: 269 GLLVSACVNRRAPESTFGCAVADVGVHDLLK 180

A 13,254 bp lambda clone [red/underlined sequences (portions) are two copies of PHA1 encoding phallacidin] 5' - 3' orientation SEQ ID NO: 327
GATCGGAGAGAAGTCAGAGAAGTTTCACTATTTTCAGCACATCGCAGCCGAAGGGCGGCGATGT
CCATGATGGGAGCGTAGCATAACCAGAAATGGATAGAATCGATAATCGATGATGGAAAGTGGAG
ACGGTGACAGGGGGGAGCTAGTAAATCCAAAAGATACAGTAATGAAGATAATGTGTCTCTCACC
GAAAAAAAGGGACGAATCGGAACCATCAGTGCAACCTACGAAACTCAGCATCATCTTCAATCGG
AGATTTAACCGATCCACCTACAAGTTTGAAACGTTTGCCCGTTACCAAGTTAATAACAATGGTC
GACTTGCACACCATCTCGTATTCAGCTCTCGTCACTTTCAGGCTTATATTCCAATTCCTCAAGC
TATCTGCAGCTGCATTGACTATCTATGGACTTTACAGAGTCACTCGTGTAATTTATGTTGAGCT
GACTTCTCCAATACGCCATCTCCCCGGTCCAGCAAACGCCAATATATTTCTTGGTAATCTCAAA
CAGCTCTGGACAGATGTAAGTACAAAATCACCCACCTACCCACCCATTGTTAACCACTATTACC
ACAGACATATCATTGGCATTCACAATATGGGCCGATGATAAGACTAAATGGATTTCTCGGTGTA
AGAACCAATCCATTTATTCTGATATAGATAACAATCAAGTTTAGCTTTCGCATTTATATGTGAC
GGATCCGCAGGCCTTGAACCACATTTTGACGAATGGTTACGTTTACACCAAACCATCGTTTACT
CGCCGCCAGATCGGCAAGTTGTGGGGTCCAGGTGCTTTTTCACCTACCATACTTAAGAGGCGAT
GATCCAACCATACGTCAGGTCTCCCTTTTGTCGAAGGGGATCAACATAAAAAGCAGGTGCGTAC
TTCCGTTGCCTCAACCTAGTTCGTATTATGATATATTACGTTTAACAGCGGAAGATTTTGGTGA
CTATCTATCCATTCCAAATCGTGGTCCATCAGTGTCTCAATCACAACCAGAATCCTGCCTTTGG
TCCGGTCCGCATTCGCGAATTCACAGATTGCTTCGTAAAAAAATCAAAACGGGTCGGTTTTTAC
TACTCATCCATGCTACCAGTGATGAACTTCGCCTAGCTCCAAGACTCTTGGGCTACTGAATGCT
CGAAACAAGGTGGTACTTGCCGCTTAGACATTATGGTAGGCCTTGGTAAGGTGGTGATGGACAT
CATCAGCTCAACAGGTATGTCTGATGTTGCCAGCATACTTATTAGTGTTTACCGATGCCATTCG
ATGGAAAGGCTTCCGTTACGAGCTTGATTCCCTGGATCGTGAAAGTGACTTTAGCCGTGTGGCT
ACAATTTATCTCAATTGAACCTGATTCGTTGGCAACTCCGAAGATTCATCCCACTTCTATGGT
TCATAGTATGGAAATTCCAAATCACTGTAACGGAGTTCTCATCGCGTTGTCTAGCCTGATCCTG
TAGAGACACAACTAGACGATATCAAGCAGACCCTTTCTCGGATTACGAGTCGGCTTCTGAACGA
GAGCAAGGGATCCGTACGTACGAATAATGACAATTCCGGCAGTCGAGATCTCCTATCGCTTTTG
GTTCGCACCAATATGTCCCCCGATGTGCCAGAGCACCGTCGTCTATCCGATGACGAAGTCAAAG
CGCGTGAGGCTGATGTATTTGTCACTGCGAGTATACCTGATCTTTTTATTTAGAGGTTATCTCA
TTTGTAATTGCTGGACGTGAAAGTCCGATGTAAGTCTGAGTCTGTTTATCTGTTTAAGGACTAT
TCTCGAATATTTGATTGGTAGTAACGTAATGGCGTGGGCTTTATTTTCTCTGGCAAAAAACCGT
GAAATCCAGGCTAAGCTGCGTAGAGAGCTGCTCACGGTCGATACCTGTCAGCCAACGACGGACC
AGCTCAATGCACTTTCATATTTGGATATGGTAATTAGGGAGACGCTACGTCTGTATCCTTCATC
TAGGCCACTCGAGGGTGTGTGCCAAGGACGACATTTTACCTTTGGCTAAGCCGATCACCGACCG
GAGAGGAAACCTATTCTCCAGTATTAGGTGAGGATTCGGTCGTTCCCATATTTCTTTTTAGCGT
TCACCGGTCTTATAGTATCAAAAGAGGGCAAGTAGTCATAATTCCCATTTCTGCCATCACAAG
GACAAGTCGATATGGGTGAAGATGCTTTAGACTTCAGGTAAATATTGCACGTCGCTGTTGGCT
CCTGAGTCATTCAGTTTTGATAGACCAGAACGATGGAATGTCTACCTGAAGGCGTCAATACCA
TCCCAGGCGTCTGGAGCCATTTGCTCAGTTTTTGGGGTGGTCCACGTTCGTGTATCGGATTCAG
ATTTGCTATCGCCGAGTGAGCAAGTTTTCTCTAGCATTTCGAAGATATAGTGCTGACACTGGTA
ACGACAAGAATGAAAGCTCTACTCTTCACACTAGTCCGTGCCCTCGAATTTGACTTGGCTGTGC

Fig. 23 (Cont.)

CAGCGGAGCAAATTTCTGTGGAAAGTGGACTAAGTAACCGACCGATTTTGACCACGGACCCGGG
CCGTTATCAGCTCCCGCTGCTCATCAAGCCATATAAAGCTCGAAGTTAACGCGCCTCGTGGTTC
ATTATACCTAGAGGTCTAGGGACCACTGTGTGGAGTTTGTACTGGCATCTATGATATTACATAG
CAGTCAATTACGAACTGAGTTCGGGGCTGAGAAATGATGAGAGTAAAATGTGGAGGATGGAAAA
GAGCTTGAGCATGCGAGCTGCCGCCGAAGTTTAGTTCATAACCAGGGTTCTAGCCCGTCAAAGA
ACCGGTTAGCGATTGAATTTGACAGAAGCTTCTTGCCACTACTAAATGCGTTCTGACGGTGCAG
GCACTGCGGATGACGCAGCATTGGAACGCGGCGTTAATGGCGGGAGACTTTAGCGCAAGCCTCG
AGATGTCGGTTGGTTGAATGACATCAGTGGGGCCAACTGTTGCGACATGCCATGACTTCCCAA
GCAAAAATTTACAATACGACTCGTATGAGTCACCACCGACTTCATCGCCCAATGTCGTGGTCT
CTTATGCCCGTCATCGATTGACATGGTGTTTCGCACGAGTCTGCTTATCAAGTAGGCGAGCACC
ACCACCATGTTTTCTACCCTAGTACAAAAACAGTGGTACGGGGAACGCCTATGTTAACTTTCGC
ACAAGAAGAGGAACTTTTGTACCATCCTCGCCAGCTACCTTGGGGCGCGTAAAATGCCAACTCA
GTTCCGTCGATGGCCCATTGGGGAGCTCAAAGGCAAAATATCTGACCAGAACCGACAGCACAGC
CTAGAGATTGTGCAGTCAAACAACCAAACCGCTGACATGGGGTTCAATCGTACCTTCACCTCCA
GTACGGCGAGGTCTCTGCCTGGACACATCCTGGGACCAGCACCGAAAGTTAAGAGACCCCGGTA
GCCAGCTAGTTCTCCCTTGTTTCCTTTCTTATGACCCTCAGCGTCCAGCCATCTGCTTGGATCG
AACATGCCCGCGTCTGGCCCCCACAACGCTTCCGACATATTCACTCCCCCAAGGGTATACGGA
CGACCATACCTTTCTTCAAAAACAAGCTATCGATCGTCGCTCCAGATGCAATACGTATGGGATT
TGTCAACGGTATCACATCGTCTTCGGCTGCCTGCCAAGATAATAGGGGGATGCGGGAAGGAATT
AAACAATGAAGACGAACCACACGGATTGATTGCATTTCGGGGCATGGAGTCTCAGTATCTCGG
CTATAAAAGCATCGAGGTATTTCAGATCCTTTGTTAGCTGGTCGTATGTAGGACGTTCTCCCTT
TGCCAAACATTCTGAGAGCTCAGCACGGAGGCTCTCTTGGATTTCTGGCCGGCGTGCAAGTTCA
ATGAGAGACCACTGAGTGAAGGCTCAGTAATAGAACAGCTTGAACACTCGTAGGCGAAGATTAC
CGTTAAGGTGACTATGAGCAGCACGGGTCATAGTTTATGAGATCTTTGATAAACAAGGACAACC
GTTCGCAGAACTTACTTGCTGTTGTTTCATATGCAGCCATGAAAAGGAAACTCTTCGGTTATAT
TAACTTACAGAGAATATCAGAGGAGTGGCAAAGGTACGTACGGCCTACAAAGTATGTTGATTAG
GCATCAAGCCGATGTGCACTTGGGCTACATACCTGGGCCGTGATCTCGGAGAGTGACAAACGGC
TGTTGGGATTTGCGTTTTCTGACTTGACTATACAGGGAAGCGTAGGCACGAAGAAACATCACCT
CATATATTGGTGACATACCCAGAATCCCAAGGACTGATTCGTTGACAGTATCTTCCGGTTCCTT
ACATGCCTTGTTCAGGCTGTTAGTTGTAAGCCTATTCAAGTGTGCTACTGATTGTGCGAGCTTC
TCTTCTCTGACGCTCATGAGGGTAACTTTAAACAGGGCATAGAGTATCGGTGACAGAAAGTGAA
TAAGCCTTATAAAGGGGGAAGGCTTGACTGTGTGGATAGAGTCAAAGGCGGCCATCATCAAGGA
CGTGCGGCCCCTTAGAGTTCCAAAGTCATGCGACAATATAGCTTTCCCTATAGTGTCCAATCTA
GGAACATTTCAGGGCAAGGGCGGAATGAAGGCTGCGCAACGTACGTGACAGAATTCATCCTTGG
GCACAGAGAACAAGGTTAACTAACAATGGGGGAGATAGATACAGCAACTTGCCATTTCACGACA
TCAATTATGACGGGGTTGTTTGAGTGCTCTGATGACGGAGAACATGAATCCCATGCTGCTTTGA
GCTGTCATTTATGTTGGTCAATCGGCCGATTGTTTAAGAATGGAACCATTCTAACCTGATAGG
CAGAATCCAAGCACACGGGAGTGAGATTGCGAATTGCTGAGACCGACAGTGGAGAAGACAGGCC
TCTCCGTAGTCTGCGATCATGTTAAGTTTATGCCCTGATCGTTGAGCGATAAAGAGTGACCGAC
CGCTTGTGAGTCTCGCCCTCAGAAATAGATACAACATCACCATACTGGAACGTAAATAAGGCTG
GCAGCTAAGAAAATGGTGCAAAACAGATACTCGCCAACTTCCGGCTCAAAGCGGTTGTCCCTG
CGAGCCGACAATATGTGGTGGTATCCTTGGAATATATGTGTGTGAGAGCCTTGGGATCGCTTAA
TACAACATGGCTGGAGCCGATGCCAGTGGGTATCTCGTAAACGGGCCCATACATTCGTTCCCAA
TCCCGATATACCACACTGAGGTTCGCCGAAGGGAAGATCTTCTTGGTGTTACCGAAGATGAAGC
TCTCGCTGCGTGGTCCTTGCAGTCTGGGCGTTCTGATACCTCGGCGTCTTCGATAGATAGAAAT
GACGACGAGCAACGTAAAGGCAGAGGTCACAATCCTCATCGAATCGCCTTTGAAATACTCTGCT

Fig. 23 (Cont.)

```
ACATCAGGCCAGAGGCCGTTGAAGTTGAGGTTCAACATCACGAAGTGGACGAGCCGTGGAAGGC
GATCAAGTTGCGCGAATGCGAGGAAAATGTTTCTGAGGACCCGAAACCGTAACCAGGCGCGATA
AATGCTTGACCTATCTATCTCCGGGGACGGTGTTGGGGGTCCATCTTACCGTGAAGGTGGATAG
GGACAGATCCGATTCCGGGAAAGAACAGACGAAACGTTCGTATGATGCAACACAAGTGTGAGC
GCAAGATGGAGCCGAATGATCGGGAACTCGGCCGAAGGGATTCTTAAATACACACGCCCGATA
ATCATTCTCATACATGTCCATTTTGGGACAAAACACCTATCTATCGGTCTGTAGGACTGCCAC
TTAACTGTTTAATCTGTGACCACCAGGACAGACAAAGAGAGGCTGTGCTAAGTGGTGTTCGAAA
CGCGTTATGCCCAGTTCGGCATAAATCGCCAACACGCAGGATACGATGAAAAGTGTAAGCTTAA
GGTCAAGACTCCCTTGATGTGATTCAACAACTTTTGACGGGGTTGCCATTGTATTGCACCGTCT
TGCCCGGCTGAATGTCCGCAGAAACCGAACGCCCCTAAAAACAAAGAAGTTCACGGATTCCATA
TAGTAAGCGTGGAGCCTGTGTGATAAAGAGTGGGGGACAGCATGAATGATTCATGGGAAGACCG
ATCAGACAAACGCTTATGGAGATTTTGCGCCAATTTGTCTTCTCATCTCCGTGTCAGGACAAGA
TTCTCTTATCTATCGTACTTTCTGCGGTTTTCCAATCTTGCGAATTCGTGACTGAAACAGATAA
AAGGCGTTGGATGCGGCTCAGCTGTCAATATTACTTACCTCCCATTCGAACTCGAACCCAAGAC
CTCTACTCTAAATCACAATGTCTGACATCAATGCCACCCGTCTTCCTGCTTGGCTTGTAGACTG
CCCATGCGTCGGTGACGACGTCAACCGTCTCCTCACTCGTGGTGAGAGGTGAGCTCAAAATTCC
ATTTAATAATGTAGCAATGTACTTATGTGTCGTGTACCAGCCTTTGCTAAATGTCTCATCCACT
AGTCAAGGTATCCGCCTCTGATTTCTTGATGACAATGCATGGTCATGGTACTTACTTCGATGTA
GTAGTGGACGACGCAAGTTGTTGACAATGTTAGGCTTGGAGCGTTGAGCCTGCATCGGAAGTAA
GGCCTTCAAGTTTTTCTGTGATAAGCAGCGAGCCAACTTGGATTAGACGACTCACGTTATTTCT
CATTCTTTCTCATTCTCATATAAAACCCACGTAAATGATCCGAGCTGTACTATGGAATGCAATA
TACTTGTGTGTATGTGTGTGTTGTCAGTAAGAGAGCGTTTAGCAATCCGAGCGCATGCTG
CTGTCGCCAGAGCTTGACCGTCCTGACTGTCCTTATCATTGCTACTTGTCAGCAACATATCACA
TATCACATAGGCAGCTGTTGTACCATTGAAAAGCCGTGGGGCGTATAACCTGGAGGAATTTCAA
AGAAGGGTCTTTTATGATGAGTTTGATAGCTCGCATAGTTGTGGAAGTCGGCAAGTTCACAAAA
ACAGTGAATTTATGTTACATTGCGTGACGAGGAGCATGAGACGAGCAATTTGCAACTTTGAACT
ACACCCGGGAAAAAGCAGGCTCAGCAACCCCGATGACGAGGGGGAGGAGAGAATGGCGATGATG
TAGGCATAATGCGATCGCATGTGTGTAGGCGAACACGGGCGACGATTGGAGAGATAGACACGCT
ACGCGATTACTACGCCAGTCTCTCAAGGGCCGTTCATTAAAGTTGGCTAAAGTCGCGGGGGAAG
GGCTGGTGATGAGGTATCTTGTGTCGACGCGGGCACAATGGACCATGGGAGGCAGTCGCCGCAT
ATCTGAAAAGCTGGGCTCCCGACGTGAAGTGAGGAATCACGAAAATCATATTTGCTTGGAAGGA
AAGCCCATGCAGCTCAGCAAACTCTAGTAAGACAACGGAACGAAATCACTGGCGATGTTTGCGA
CATCAGATCTCTGGTATGAAGTCAGCCTGAAACCTGCCCTGTCAAGGACATGCGGCCGCAACCG
CGACTGGTTGATGGTAAATCCAAATGCGACGCCCAGTTCGAAAGATGAGACATACCTGCGCCAA
ACAGTGATTACCACAGCCACCTACGAGGCCTCGTGAGTTGGCCTCAATATTCATTAGCTATCAG
TAGATGAGCACCGAAGTAGGGCTTCTGCGTGTAGTTAGGGTGCGTGAATCCGCAGTGACGCTCA
TTTGTTTGGCTCAGCGTGGCCAGTCGCGCCTCGGGATTTACCGGCGCGATACAAACGGAAAGTT
CTTTCGCAGCGTTCCCACCCGCGCGGCCGTAAGCGTGCAAACCGTCACCCATAGGAAATAAACC
GTCGGCAAGAATAGAATGTGATCCCTTCGGCCGAATCGTCGAAAGCAATCTGATCATAGATCAT
CAGTGACCTTTCATCCTTTTTCAGCGACAGATCTTGCATTCATGCTGTCCGCCACTCATCATCT
TCTTCTTCACAATATTATACTATTCACCCCACACTATCCATATCCAGTTGGGCCAATAGTAAAT
CCCGCTGAGGCTGTCCGCCCTTGATGGAAATGACTTGGAGACTCGCCAGTTTGGCATCCTTTTT
TGGTGAGGACCCCATTTTCTATCTTGAGTCGTATCCATATCTGGATGGCCTACTGGTGGTCTCA
CCTCTGTAACGGCCCGCGATCGCTCTCTTCGCGATGTTGAACCTCAATTTCAGCAGCCTTTGGC
CTTATGTCGCGGAGTACCTCAAAGTCAATTCGATGAGGATAATAGCCTCTGGCATATCCTTGCT
```

Fig. 23 (Cont.)

```
CGTCGTTGTTTCCATTTACCGAAGCCGTCGAGGTCCTAGAACGCCGAGACTGCAAGGACCACAC
ATGGAGAGCTTCATCCTCGGCAATGCTAGGAAGATCTTCCCTTCAGCCAACCTCAGTTTGGTGT
ATCAAGGTTTGGAGCAGACTTACGGGCCCGTCTATGAAATAGCCTCTGGCTTTGGCTCCAACCA
CGTCGTATTGAACGATCCCAAGGCTCTCACACACTTATTTTCCAAGGACACTGTCACATATTCT
CAGCCTGCTAGGCAGAAAGACATGGGGCGGAAGTTGGTGAGCGTTTGTTCCAGCGTTTTCCCGA
GCTGTCAGACTTAACTTGTTCCAGTTTGGTGATATTTTGGTGCTCACGGAAGGGGAGACCCACA
AGAGGTTGGTCGCTCTTGACTGCTTGAAAACATGGCATAAATTTAATATTGAACGGATTATAGA
ATACGGAGGGTCTTGTCTTCTCCCCTGTCGGTCTCGGCAATCCGCAATTTCACTCCTATGTGT
TTGGATTCCGCCTATCAGGTCAGGACGGTTCCAGCTTTGAGAGTCAGTCGATTGAACAGCACAA
ATGATAGCTCAAAGCATCATGGGATTCATGTTTCCAGTTGTCAAACAATTCGAACCGTGCTATC
GTGCTTGATGCAGAGAAATGGTGAGTTGCTTTCCTTCTAGCCTTCATTTAATTGGTTCATTATG
TGCCCAAGGATGAACTGTTACACGTATGACTCGCAACCTTTACTCTGCCCATTCTTCTCACCT
GCAATATATTCCTAGCATGGATAATATTGGAAAAGCTGTATTGTCGTATGACTTCGGCAACATG
AGGGGCCATACGTGTTCGATCTTAGCTGACTTGGATGCTTTCCACGCAGTCAGCCCTTCAGGCC
TTTACATAAGGTTTATTGTGTTTACCCGCGAGATACTTTATAACCTCTTCAAGATTACCTTACC
GAATGCCAAAGAAAAGCAGTTTGAGGAACTGGCAGCGCACTTTAAAGTACTCGCGACTGGCTTT
CTGCGGGAAGCACGTGAGGCGCCTGAAGATAGCGCCGTTCACCAATCAATCCTTGGGGTTATGC
GTATGTTACCTCTATCCTGACCACGTGTAAGGAGATTTCAGCTTTCCTATATATAGTCAAGTCC
AAAAATGAAAATGCTAACGTCCGTTTATCACTTCCCGAGATCACGGCCCAGGTAAGTTGCTTCA
CACATCGGCGTCGGTGCTCGATCAACATCCTTTGTAGGCTGTATGTCCCTATGCAATCTCTTTT
GTATCCACTCTGACCTGATATAACCGAAGGGTGGTCTTGTCTTGGCCGGGTATGAAACTACGGC
AAGTAAGTTCTATGACTAGCAGTCCGATGATCTCATAATCCACTAACTATGCTGTTCACAGTTG
CCATGACGGTAATGTTATTTATCTACAAGAGATCCATCGCCGAGCTTTCCCTCAGTGGTCCCTC
ATTGAGCTTGCTCGCCGGGCAGAAATTCAAGAGACTCTCCGTGCCGAACTCAAGGAGTGCTTGG
CAGACGGAGAACGCCCTACATACGACCAGCTGACAAAGGATCTGAAATACCTCGATGCTTTTAT
ATCCGAGATACTGAGGTTACATCCCTCAGAAATGGTACTAACCCGCGTGGTTCGTCCCTTCCTT
TCATCCCTATCTTTTTATGATGACGATCTTTTCGACTAGGCAGCCGAAGACGATGTGATACCGC
TGACGGATCCCATACGAACTGCATCTGGAGCGATGATCGACAGCTTGTTCGTGAGGAAAGGCAC
CGTCTCCGCATCCCTTTAGGAGGAATGAATATATCAGAGACGTTGTGGGGACCGGATGCGGCGA
CATTCGATCCAAGCAGGTGGCTGGAAGTTGATGGTCATAAGAAAGGAAGAAGGGAGAAAGTACC
CGGCTACCGAAATCTATTGACTTTCGGTGCTGGCCAAAGGCTGTGTCCGGGAAGAGACCTCGCC
TTGCTGGAGATGAAGGTATGGCGAAACTCCTGCCGGTTTTTATTCATTTTTGACTTGACAATTG
CCAGGCTGCGCTTGTGATTCTGGTCCTCCATTTCAGTTTTGAGTTCCCCAATGGACCATCGACG
GAACTGAGTTGGCAGTTCGGGCGGCCCAAGGTAGCCGGCGAGGATGGTCCGAAAGTGCCTATGC
TGTGCGAGACTGACATAGGATCTCATGTGCAACATCGTTCGTTTCGTGTCTTAGTAGAGTTTAC
TGAGTCGCATGGGCTTTCCTTCCAAGCAAAAATGACTTTCATGATTCCTCACTTCACGTGGAGG
ACCAGCTTTTCAGATGTGTGGCGATGAGGCTTAGCATCGTGACGTAAATGGTAGGTTGGATGAC
TGGCATACCCACATATTTCACATCATCCTTATAGACCTACTAGTACGCCAAACTTGCCTCCCAT
AGTCCATCGTGCCACGCACCGACACAAGATGCATCATCACCAGCCCACTCTAACCAACTTTGAT
GAACGATCATTACAGCCTGAGAGGGCTGGCGTAGTAATCACGTAGCGTGTCTATCTCTCCTCGA
GCACGCCTGCAGCCTGCAGTGTTTTCCCGCCCAAGCGACCCTTCCGCCTCTTCCCAATCGTCG
CCAGCACATGCCATCGCATGCCTATACATACATCATCACCATGATTCTTCCTCATCGGCGTTGC
ATCTTTCTCTCAGGTGCTCGGCCCAGTTCAAGGTTGCAAAATGCTCGTCTCATGCTCTCATTAC
CTCCTCGTCACGCAATGTAACATAAAATCGCTGTTTTTGTGGACTTGCCGCTTTTACAACTATG
CGAGCTGTCAAACTCATCAGGAAGGACCCCTGCTGGAAATTCTTCCAGGCTACACGCCGCAGGA
```

Fig. 23 (Cont.)

```
CTCTTAAACGGTACAAAAGCTGCCAATGTTGTATGTGATATGTTCAAGTAGGCAAGTAGCAATG
ACACGGTCGGTCAGGTCGGTCTGCTGTGGATCGCGGCATACAAGCTGGCATTGATAAATGTTGA
GATGCTATCTCTCACACCTCCCCCCCCTTCTCTAGTGCATTGCATTGCACAGCTCAGAGCATCA
TTGAGGGGGGTATTAGAGATTGACAAAGGAGAATCAGTAAGAAGGGTAATGTACTTCAGTCGTG
TTAGCCAAGTGTCCCCGATGATTATCACGACAATCTTTAAGACGCTGGTTCAGCGGCACGATCA
TCGCTTTGCAAGCAAGACGTGTTCTACAATTTGCCTTCGTCATAGTCAGCACAATCACCCTTCG
TTATCATGAAATCCGAGGCGGGTACCTTGACTAGTGGATGAGACATTTAGCAAAGGCTGATACA
CGACACATGAGTCCATTGCTACATTATTAAATGGAATTTTGAGCTCACCTCTCGCCACGAGTGA
GGAGACGGTTGACATCGTCACCGACGCATGGGCAATCTACAAGCCAAGCGGGAAGACGGGTGGC
ATTGATGTCAGACATTGTGATTTAGAGCAGAGGTCTTGGGCTCGAGTTCGAATGGGAGGTAAG
TATTGAATATTGAATGCTAAGCTGAATCCAACGCCTTTTATCTGTCTCAGTCACGAATTCGCAT
GGTTGCAAAAACCGCGGAAAGGACGATAGATAAGAGAATCTTGTCCTGACACGGAGATGAAGAC
GAGTTGGCGCAAAATCTCCATAAACAGTTGTCTGATCATCCTTTTTCGGTATTCAATATTCATC
CCCCATTCATGCTGTCAGTCACTGTTCATCACACATTCTTGGCAGGCTCCACAAAACTTCTTTG
TTCTTTCCTGTTTTTGGGACGTTCTGTCTTTGCGGGCACAGCCAGTCGGGCAAGACGGTGCAA
TACAATGGCAACCCCCCGTCAAGAATAGTTGAATCGCATCAAGGGAGTCTTGACCCTACACTT
TTTCGTCGTATCCTGATCGGCGACTGGGCCTAACGCGTTTCTCGCTGGATTAAACACCCCACTG
AGCACAGCCTTTCTCTGTCCCGGTGGTCACAGATTGAACAGTCAAGCAGTTTGTAGGATCAATA
GATAGGGGTTTTGTCCTGAAATGGACCATGTAGTAATGATTTTCGTCCGTGTGACCCGGTTTGC
CGATGCAACAAAGACGCATTATCTCCATCGCGCACAGGCGTGTTGCATCACTTATGACTATGTG
GCTCTAACTTTCCTGGAATCGAATCCGCCCCTATCCACCTTCACGGTAACATGGACCCCAACA
CCGTTCCCGGAGATAGATAGGTCAAGTTCTCGCGCCTGGTTACGGTTTCGGCTCCTCAGAAACG
TTTTCCTCGTATTCGCGCAACTCCCACCCTTCAATGGCATTTCCACGTCTGGTTGGGTTGGTTG
CTATACTAGTACTTATCCGCGATGGCCTTCCTTCCTTGCATAACGGCTCGTCCACTCCGTCACC
CGTGATGTTGAACCTCAACTCCAACGGCCTCTGGCCTGATGTGGCAGAGTATCTCAAAGGTAAT
TCGATAAGGATTGTGACCTCTGACATTGCTCGTCGTCATTTCTATCTATCGGAGATGCCGAGGT
ATCAGAACGCCCAGACTACAAGGACCACGCAGCGAGAGCTTCAGATTCAGTAACACCAAGATCT
TCCCTTCCGCGAACCTCAGTACGGTGGTATATCGGGATTGGGAACGAATGTATGGCCTTACGA
GATACCCACTGGCATCGGCTACAGCCATGTTGTATTGAGCGATCCCAAGGCTCACACACATATA
TTCCGAGGATACCACCACATATCCTCGGCTCGCAGGGACAACCGCTTTGAGCCAGGTTGGCGAG
TCTTTGTTTTGCACCATTTTTCAGCTGCCAGCCTCATTGTCGTTCCAGTATGGTGATGTTATAT
CTATTTCTGAGCGCGAGACTCACAAGGGGTTGGTCGCTCTTTATCGCTCAACGATTAGGGCAT
AAACTTAACATGATC
```

FIG. 24

FGENESH 2.5 Prediction of potential genes in Coprinus genomic DNA

Time     :   Wed Oct 3 12:42:52 2007
Seq name:    test sequence
Length of sequence: 13254
Number of predicted genes 6 in +chain 2 in -chain 4
Number of predicted exons 45 in +chain 26 in -chain 19
Positions of predicted genes and exons: Variant   1 from   1,
Score: 219.729370

| G | Str | Feature | Start | End | Score | ORF | | Len |
|---|-----|---------|-------|-----|-------|-----|---|-----|
| 1 | +   | 1 CDSf  | 315 - | 527 | 13.80 | 315 - | 527 | 213 |
| 1 | +   | 2 CDSi  | 685 - | 799 | 2.33  | 685 - | 798 | 114 |
| 1 | +   | 3 CDSi  | 851 - | 888 | 3.39  | 853 - | 888 | 36  |
| 1 | +   | 4 CDSi  | 945 - | 1028| 5.81  | 945 - | 1028| 84  |
| 1 | +   | 5 CDSi  | 1125 -| 1230| 9.26  | 1125 -| 1229| 105 |
| 1 | +   | 6 CDSi  | 1262 -| 1413| -4.15 | 1264 -| 1413| 150 |
| 1 | +   | 7 CDSi  | 1463 -| 1667| 5.33  | 1463 -| 1666| 204 |
| 1 | +   | 8 CDSi  | 1718 -| 1757| 12.55 | 1720 -| 1755| 36  |
| 1 | +   | 9 CDSi  | 1814 -| 1968| 3.84  | 1815 -| 1967| 153 |
| 1 | +   | 10 CDSi | 1988 -| 2075| 6.28  | 1990 -| 2073| 84  |
| 1 | +   | 11 CDSi | 2129 -| 2214| -0.10 | 2129 -| 2212| 84  |
| 1 | +   | 12 CDSi | 2264 -| 2383| 2.36  | 2265 -| 2381| 117 |
| 1 | +   | 13 CDSl | 2441 -| 2609| -0.46 | 2442 -| 2609| 168 |
| 1 | +   | PolA    | 2730  |     | -4.02 |       |     |     |
| 2 | -   | PolA    | 2782  |     | -5.12 |       |     |     |
| 2 | -   | 1 CDSl  | 2802 -| 3153| 11.90 | 2802 -| 3152| 351 |
| 2 | -   | 2 CDSi  | 3194 -| 3337| -1.50 | 3196 -| 3337| 132 |
| 2 | -   | 3 CDSi  | 3381 -| 3677| 13.49 | 3381 -| 3677| 297 |
| 2 | -   | 4 CDSi  | 3729 -| 3914| 7.51  | 3729 -| 3914| 186 |
| 2 | -   | 5 CDSi  | 4047 -| 4049| 2.72  | 4047 -| 4049| 3   |
| 2 | -   | 6 CDSi  | 4104 -| 4139| 8.59  | 4104 -| 4139| 36  |
| 2 | -   | 7 CDSi  | 4192 -| 4250| 6.14  | 4192 -| 4248| 57  |
| 2 | -   | 8 CDSi  | 4306 -| 4590| 11.14 | 4307 -| 4588| 282 |
| 2 | -   | 9 CDSi  | 4856 -| 4937| 7.69  | 4857 -| 4937| 81  |
| 2 | -   | 10 CDSf | 5037 -| 5477| 24.96 | 5037 -| 5477| 441 |
| 2 | -   | TSS     | 5711  |     | -2.92 |       |     |     |
| 3 | -   | PolA    | 5828  |     | -0.32 |       |     |     |
| 3 | -   | 1 CDSl  | 5972 -| 6046| 9.41  | 5972 -| 6046| 75  |
| 3 | -   | 2 CDSi  | 6223 -| 6255| -0.04 | 6223 -| 6255| 33  |
| 3 | -   | 3 CDSi  | 6307 -| 6339| 6.29  | 6307 -| 6339| 33  |
| 3 | -   | 4 CDSi  | 6359 -| 6522| 3.06  | 6359 -| 6520| 162 |
| 3 | -   | 5 CDSi  | 6580 -| 6667| 10.19 | 6581 -| 6667| 87  |
| 3 | -   | 6 CDSf  | 6708 -| 6719| -1.18 | 6708 -| 6719| 12  |
| 3 | -   | TSS     | 6939  |     | -1.73 |       |     |     |
| 4 | +   | TSS     | 7029  |     | -7.71 |       |     |     |
| 4 | +   | 1 CDSf  | 7173 -| 7184| -3.79 | 7173 -| 7184| 12  |
| 4 | +   | 2 CDSi  | 7247 -| 7446| 10.90 | 7247 -| 7444| 198 |
| 4 | +   | 3 CDSi  | 7510 -| 7644| 7.81  | 7511 -| 7642| 132 |
| 4 | +   | 4 CDSi  | 7755 -| 7832| 1.96  | 7756 -| 7830| 75  |

FIG. 24 (continued)

| | | | | | | | | |
|---|---|---|---|---|---|---|---|---|
| 4 | + | 5 | CDSi | 8245 – | 8608 | 25.32 | 8246 – | 8608 | 363 |
| 4 | + | 6 | CDSi | 8764 – | 8869 | 15.02 | 8764 – | 8868 | 105 |
| 4 | + | 7 | CDSi | 8906 – | 8975 | 2.99 | 8908 – | 8973 | 66 |
| 4 | + | 8 | CDSi | 9099 – | 9403 | 8.93 | 9100 – | 9402 | 303 |
| 4 | + | 9 | CDSi | 9460 – | 9518 | 11.93 | 9462 – | 9518 | 57 |
| 4 | + | 10 | CDSi | 9569 – | 9571 | 3.53 | 9569 – | 9571 | 3 |
| 4 | + | 11 | CDSi | 9625 – | 9661 | 10.61 | 9625 – | 9660 | 36 |
| 4 | + | 12 | CDSi | 9753 – | 9964 | 11.55 | 9755 – | 9964 | 210 |
| 4 | + | 13 | CDSi | 10019 – | 10126 | 2.83 | 10019 – | 10126 | 108 |
| 4 | + | | PolA | 10135 | | -4.02 | | | |
| 5 | – | | PolA | 10338 | | 1.88 | | | |
| 5 | – | 1 | CDSi | 11626 – | 11635 | 1.39 | 11626 – | 11634 | 9 |
| 5 | – | 2 | CDSf | 11692 – | 11786 | 18.50 | 11694 – | 11786 | 93 |
| 5 | – | | TSS | 11838 | | -1.30 | | | |
| 6 | – | | PolA | 12087 | | -5.12 | | | |
| 6 | – | 1 | CDSo | 12872 – | 13129 | 13.78 | 12872 – | 13129 | 258 |
| 6 | – | | TSS | 13184 | | -1.30 | | | |

Fig. 25A

Predicted cDNA: P450-1 (OP451)

SEQ ID NO: 596

```
>FGENESH:[mRNA]1 13 exon (s)315 - 2609 1572 bp, chain +
ATGGTCGACTTGCACACCATCTCGTATTCAGCTCTCGTCACTTTCAGGCTTATATTCCAATTC
CTCAAGCTATCTGCAGCTGCATTGACTATCTATGGACTTTACAGAGTCACTCGTGTAATTTAT
GTTGAGCTGACTTCTCCAATACGCCATCTCCCCGGTCCAGCAAACGCCAATATATTTCTTGGT
AATCTCAAACAGCTCTGGACAGATCTTTCGCATTTATATGTGACGGATCCGCAGGCCTTGAAC
CACATTTTGACGAATGGTTACGTTTACACCAAACCATCGTTTACTCGCCGCCAGATCGGCAAG
TTGTGGGGTCCAGGTCTCCCTTTTGTCGAAGGGGATCAACATAAAAAGCAGCGGAAGATTTTG
GTGACTATCTATCCATTCCAAATCGTGGTCCATCAGTGTCTCAATCACAACCAGAATCCTGCC
TTTGGTCCGCTCCAAGACTCTTGGGCTACTGAATGCTCGAAACAAGGTGGTACTTGCCGCTTA
GACATTATGGTAGGCCTTGGTAAGGTGGTGATGGACATCATCAGCTCAACAGTGTTTACCGAT
GCCATTCGATGGAAAGGCTTCCGTTACGAGCTTGATTCCCTGGATCGTGAAAGTGACTTTAGC
CGTGTGGCTACAATTTTATCTCAATTGAACCTGATTCGTTGGCAACTCCGAAGATTCATCCCA
CTTCTATGGTTCATACCTGATCCTGTAGAGACACAACTAGACGATATCAAGCAGACCCTTTCT
CGGATTACGAGTCGGCTTCTGAACGAGAGCAAGGGATCCGTACGTACGAATAATGACAATTCC
GGCAGTCGAGATCTCCTATCGCTTTTGGTTCGCACCAATATGTCCCCGATGTGCCAGAGCAC
CGTCGTCTATCCGATGACGAAGTCAAAGCGCAGGTTATCTCATTTGTAATTGCTGGACGTGAA
AGTCCGATTAACGTAATGGCGTGGGCTTTATTTTCTCTGGCAAAAAACCGTGAAATCCAGGCT
AAGCTGCGTAGAGAGCTGCTCACGGTCGATACCTGTCAGCCAACGACGGACCAGCTCAATGCA
CTTTCATATTTGGATATGGTAATTAGGGAGACGCTACGCCACTCGAGGGTGTGTGCCAAGGAC
GACATTTTACCTTTGGCTAAGCCGATCACCGACCGGAGAGGAAACCTATTCTCCAGTATTAGT
ATCAAAAGAGGGCAAGTAGTCATAATTCCCATTTCTGCCATCCACAAGGACAAGTCGATATGG
GGTGAAGATGCTTTAGACTTCAGACCAGAACGATGGGAATGTCTACCTGAAGGCGTCAATACC
ATCCCAGGCGTCTGGAGCCATTTGCTCAGTTTTTGGGGTGGTCCACGTTCGTGTATCGGATTC
AGATTTGCTATCGCCGAAATGAAAGCTCTACTCTTCACACTAGTCCGTGCCCTCGAATTTGAC
TTGGCTGTGCCAGCGGAGCAAATTTCTGTGGAAAGTGGACTAAGTAACCGACCGATTTTGACC
ACGGACCCGGGCCGTTATCAGCTCCCGCTGCTCATCAAGCCATATAAAGCTCGAAGTTAA
```

Fig. 25A (Cont.)

Predicted protein(s): P450-1 (OP451)

SEQ ID NO: 597

>FGENESH: 1  13 exon(s)   315 - 2609   523 aa, chain +
MVDLHTISYSALVTFRLIFQFLKLSAAALTIYGLYRVTRVIYVELTSPIRHLPGPANANIFLG
NLKQLWTDLSHLYVTDPQALNHILTNGYVYTKPSFTRRQIGKLWGPGLPFVEGDQHKKQRKIL
VTIYPFQIVVHQCLNHNQNPAFGPLQDSWATECSKQGGTCRLDIMVGLGKVVMDIISSTVFTD
AIRWKGFRYELDSLDRESDFSRVATILSQLNLIRWQLRRFIPLLWFIPDPVETQLDDIKQTLS
RITSRLLNESKGSVRTNNDNSGSRDLLSLLVRTNMSPDVPEHRRLSDDEVKAQVISFVIAGRE
SPINVMAWALFSLAKNREIQAKLRRELLTVDTCQPTTDQLNALSYLDMVIRETLRHSRVCAKD
DILPLAKPITDRRGNLFSSISIKRGQVVIIPISAIHKDKSIWGEDALDFRPERWECLPEGVNT
IPGVWSHLLSFWGGPRSCIGFRFAIAEMKALLFTLVRALEFDLAVPAEQISVESGLSNRPILT
TDPGRYQLPLLIKPYKARS

FIG. 25B blastp results of Predicted protein(s): P450-1 (OP451) SEQ ID NO: 597

| | | | |
|---|---|---|---|
| gb\|AAW43969.1\| | Cytochrome P450, putative [Cryptococcus neof... | 232 | 2e-59 |
| gb\|EAL20013.1\| | hypothetical protein CNBF3400 [Cryptococcus ... | 229 | 2e-58 |
| ref\|XP_760336.1\| | hypothetical protein UM04189_1 [Ustilago m... | 179 | 3e-43 |
| ref\|XP_756349.1\| | hypothetical protein UM00202_1 [Ustilago m... | 162 | 3e-38 |
| ref\|XP_758127.1\| | hypothetical protein UM01980_1 [Ustilago m... | 154 | 1e-35 |
| ref\|NP_918020.1\| | putative cytochrome P450 [Oryza sativa (ja... | 149 | 3e-34 |
| gb\|AAR11387.1\| | cytochrome P450 [Triticum aestivum] | 145 | 3e-33 |
| * gb\|AAT68297.1\| | cytochrome P450 CYP709C1 [Triticum aestivum] | 145 | 4e-33 |
| ref\|NP_918024.1\| | putative cytochrome P450 [Oryza sativa (ja... | 144 | 8e-33 |
| ref\|XP_477684.1\| | putative cytochrome P450 [Oryza sativa (ja... | 143 | 2e-32 |
| gb\|EAA52219.1\| | hypothetical protein MG04911.4 [Magnaporthe ... | 142 | 2e-32 |
| gb\|EAA78616.1\| | hypothetical protein FG11303.1 [Gibberella z... | 135 | 3e-30 |
| ref\|NP_918022.1\| | putative cytochrome P450 [Oryza sativa (ja... | 132 | 3e-29 |

Fig. 25B (Cont.)

* putative homolog shown to have Hydroxylase activity: SEQ ID NO: 598

```
LOCUS       AAT68297   514 aa   linear   PLN 24-OCT-2005
DEFINITION  cytochrome P450 CYP709C1 [Triticum aestivum].
ACCESSION   AAT68297
VERSION     AAT68297.1  GI:49660018
DBSOURCE    accession AY641449.1
  ORGANISM     Triticum aestivum
  AUTHORS      Kandel,S., Morant,M., Benveniste,I., Blee,E.,
               Werck-Reichhart,D. and Pinot,F.
  TITLE        Cloning, Functional Expression, and
               Characterization of CYP709C1,the First Sub-
               terminal Hydroxylase of Long Chain Fatty Acid
               inPlants: INDUCTION BY CHEMICALS AND METHYL
               JASMONATE
  JOURNAL     J. Biol. Chem. 280 (43), 35881-35889 (2005)
   PUBMED      16120613
REFERENCE   2 (residues 1 to 514)
  AUTHORS      Morant,M., Werck-Reichhart,D. and Pallett,K.
  TITLE        Direct Submission
FEATURES          Location/Qualifiers
     source        1..514
                   /organism="Triticum aestivum"
                   /cultivar="Darius"
                   /note="Cytochrome P450. Cytochrome P450s are haem-
thiolate proteins involved in the oxidative degradation of
various compounds. They are particularly well known for their
role in the degradation of environmental toxins and mutagens;
pfam00067"

1  mglvwmvaaa  vaavlaswaf  dalvylvwrp  raitrqlraq  gvggpgyrff
      agnlaeikql  61 radsagaald igdhdfvprv  qphfrkwipi  hgrtflywfg
      akptlciadv  nvvkqvlsdr 121 gglypksign phiarllgkg  lvltdgddwk
      rhrkvvhpaf  nmdklkmmtv  tmsdcagsmm 181 sewkakmdkg gsveidlssq
      feeltadvis  htafgssyeq  gkkvflaqre  lqflafstvf 241 nvqipsfryl
      pteknlkiwk  ldkevrtmlm niikgrlatk  dtmgygndll  glmleacape 301
      dgqnpllsmd  eiidecktff  faghdtsshl  ltwtmfllst  hpewqeklre
      evlrecgngi 361 ptgdmlnklq lvnmflletl  rlyapvsaiq  rkagsdlevg
      gikvtegtfl  tipiatihrd 421 kevwgedank fkpmrfengv  tragkhpnal
      lsfssgprsc  igqnfamiea  kaviavilqr 481 fsfslspkyv  hapmdvitlr
      pkfglpmilk  slem
```

Fig. 25B (Cont.)

1: J Biol Chem. 2005 Oct 28;280(43):35881-9. Epub 2005 Aug 23.

Cloning, functional expression, and characterization of CYP709C1, the first sub-terminal hydroxylase of long chain fatty acid in plants. Induction by chemicals and methyl jasmonate.

Kandel S, Morant M, Benveniste I, Blée E, Werck-Reichhart D, Pinot F.

Département Réponse Métabolique à l'Environnement Biotique, IBMP-CNRS, UPR 2357, 28 Rue Goethe, F-67083 Strasbourg Cedex, France.

We cloned and characterized CYP709C1, a new plant cytochrome P450 belonging to the P450 family, that so far has no identified function except for clustering with a fatty acid metabolizing clade of P450 enzymes. We showed here that CYP709C1 is capable of hydroxylating fatty acids at the omega-1 and omega-2 positions. This work was performed after recoding and heterologous expression of a full-length cDNA isolated from a wheat cDNA library in an engineered yeaststrain. Investigation on substrate specificity indicates that CYP709C1 metabolizes different fatty acids varying in their chain length (C12 to C18) and unsaturation. CYP709C1 is the first identified plant cytochrome P450 that can catalyze sub-terminal hydroxylation of C18 fatty acids. cis-9,10-Epoxystearic acid is metabolized with the highest efficiency, i.e. K((m)(app)) of 8 microM and V(max(app)) of 328 nmol/min/nmol P450. This, together with the fact that wheat possesses a microsomal peroxygenase able to synthesize this compound from oleic acid, strongly suggests that it is a physiological substrate. Hydroxylated fatty acids are implicated in plant defense events. We postulated that CYP709C1 could be involved in plant defense by producing such compounds. This receives support from the observation that (i) sub-terminal hydroxylation of 9,10-epoxystearic acid is induced (15-fold after 3 h) in microsomes of wheat seedlings treated with the stress hormone methyl jasmonate and (ii) CYP709C1 is enhanced at the transcriptional level by this treatment. CYP709C1 transcript also accumulated after

Fig. 25B (Cont.)

treatment with a combination of the safener naphthalic acid anhydride and phenobarbital. This indicates a possible detoxifying function for CYP709C1 that we discussed.

FIG. 25C

BLASTP of OP45-1 against Coprinus at Broad: the top ID is contemplated to be significant.

| | | |
|---|---|---|
| CC1G_09160: hypothetical protein | 365 | e-101 |
| CC1G_03738: hypothetical protein | 191 | 4e-49 |
| CC1G_06332: hypothetical protein | 183 | 1e-46 |
| CC1G_06814: hypothetical protein | 178 | 4e-45 |
| CC1G_02050: hypothetical protein | 176 | 2e-44 |
| CC1G_00121: hypothetical protein | 160 | 1e-39 |
| CC1G_05306: hypothetical protein | 157 | 8e-39 |
| CC1G_12478: hypothetical protein | 157 | 8e-39 |
| CC1G_04749: hypothetical protein | 156 | 1e-38 |
| CC1G_00122: hypothetical protein | 154 | 5e-38 |
| CC1G_06334: predicted protein | 140 | 7e-34 |
| CC1G_05310: hypothetical protein | 136 | 2e-32 |
| CC1G_12971: predicted protein | 99 | 2e-21 |
| CC1G_02813: predicted protein | 99 | 2e-21 |

FIG. 25D

BLASTP of OP451 against Laccaria

Sequences producing significant alignments:

| Sequence | Score (bits) | Value | N |
|---|---|---|---|
| * jgi\|Lacbi1\|315739\|eu2.Lbscf0006g04230 | 215 | e-123 | 10 |
| jgi\|Lacbi1\|315758\|eu2.Lbscf0006g04420 | 186 | e-111 | 9 |
| jgi\|Lacbi1\|339056\|estExt_fgenesh3_pg.C_60271 | 215 | e-110 | 9 |
| jgi\|Lacbi1\|142996\|gww1.6.117.1 | 215 | e-109 | 8 |
| jgi\|Lacbi1\|324809\|fgenesh3_pg.C_scaffold_6000303 | 155 | 7e-99 | 11 |
| jgi\|Lacbi1\|232844\|e_gwh1.6.118.1 | 215 | 1e-93 | 7 |
| jgi\|Lacbi1\|324790\|fgenesh3_pg.C_scaffold_6000284 | 159 | 1e-92 | 8 |
| jgi\|Lacbi1\|157726\|gwh1.6.118.1 | 215 | 1e-92 | 6 |
| jgi\|Lacbi1\|178207\|estExt_Genewise1_worm.C_60117 | 215 | 1e-88 | 5 |
| jgi\|Lacbi1\|189508\|estExt_GeneWisePlus_worm.C_60357 | 215 | 1e-88 | 5 |
| jgi\|Lacbi1\|183804\|estExt_GeneWisePlus_human.C_6027 | 215 | 1e-88 | 5 |
| jgi\|Lacbi1\|172792\|estExt_Genewise1_human.C_60118 | 215 | 1e-88 | 5 |
| jgi\|Lacbi1\|315756\|eu2.Lbscf0006g04400 | 200 | 2e-85 | 3 |
| jgi\|Lacbi1\|324807\|fgenesh3_pg.C_scaffold_6000301 | 200 | 5e-77 | 4 |

* Best Laccaria protein hit:

SEQ ID NO: 599

```
>jgi|Lacbi1|315739|eu2.Lbscf0006g04230
MGRTCLLVVSATATLGVYGLYKIAGIVYREWLSPLRVLPGTKSPSFLYGDLKELW
EEEDTGTSGILVEKYGTTFRYKSLLGISRLYTADTRALNHILMNSYDYEKLPESR
AALTNILGAGLLVVEGDKHKQQRKIMNPAFGPAQIRELTDIFVRKSIQLRDLWAE
ECTKQGGQGRIEILSWLTWTTLDVIGLAGFNYKFNALMRDSKANELSEAFNTIFQ
AGTSVNVMLILRAFIPALSWILPEAGDVEAKKASSTMSRIGKELLSNSKAAVSQQ
ESLEKDTWKTRDLLSLLVRANVATDLTESQRMLDEDVLAQIPTFIVAGHETTSNA
TTWALFALNSQNPDAQIKLRNELLTVSTDNPTMDELNALPYLDAVVRETLRLHAP
VSMTSRVAMKDDVLPLAIPFTDSKGVIHHEIRIRKGEPLLIPILALNRDKSIWGE
DAHEFRPERWESIPDAASSIPGVWGHMLTFLGGPHSCIGYRFALVEMKALLFTLI
RSFEFELAVPASDIGKKAGIVHRPILLSNPEGGSQMPLFVKAYQPPLEEA*
```

FIG. 25E

OP451 as a query sequence for a BLASTP against nr, showing an excellent hit against a Coprinus protein:

gb|EAU81974.1| hypothetical protein CC1G_09160 [Coprinopsis c... 607  6e-172

Predicted cDNA: P450-2 (OP452)

SEQ ID NO: 600

```
>FGENESH: [mRNA]   2  10 exon(s)   2802  -   5477  1875 bp,  chain -
ATGTTGAACCTCAACTTCAACGGCCTCTGGCCTGATGTAGCAGAGTATTTCAAAGGCGAT
TCGATGAGGATTGTGACCTCTGCCTTTACGTTGCTCGTCGTCATTTCTATCTATCGAAGA
CGCCGAGGTATCAGAACGCCCAGACTGCAAGGACCACGCAGCGAGAGCTTCATCTTCGGT
AACACCAAGAAGATCTTCCCTTCGGCGAACCTCAGTGTCGTATATCGGGATTGGGAACGA
ATGTATGGGCCCGTTTACGAGATACCCACTGGCATCGGCTCCAGCCATGTTGTATTAAGC
GATCCCAAGGCTCTCACACACATATATTCCAAGGATACCACCACATATTGTCGGCTCGCA
GGGACAACCGCTTTGAGCCGGAAGTTGGCGAGTATCTGTTTTGCACCATTTTCTTAGCT
GCCAGCCTTATTTACGTTCCAACTACGGAGAGGCCTGTCTTCTCCACTGTCGGTCTCAGC
AATTCGCAATCTCACTCCCGTGTGCTTGGATTCTGCCTATCAGGGAAAGCTATATTGTCG
CATGACTTTGGAACTCTAAGGGGCCGCACGTCCTTGATGATGGCCGCCTTTGACTCTATC
CACACAGTCAAGCCTTCCCCCTTTATAAGGCTTATTCACTTTCTGTCACCGATACTCTAT
GCCCTGTTTAAAGTTACCCTCATGAGCGTCAGAGAAGAGAAGCTCGCACAATCAGTAGCA
CACTTGAATAGGCTTACAACTAACAGCCTGAACAAGGCATGTAAGGAACCGGAAGATACT
GTCAACGAATCAGTCCTTGGGATTCTGGTCAAGTCAGAAAACGCAAATCCCAACAGCCGT
TTGTCACTCTCCGAGATCACGGCCCAGGCCGTACGTACCTTTGCCACTCCTCTGATATTC
TCTCAATGGTCTCTCATTGAACTTGCACGCCGGCCAGAAATCCAAGAGAGCCTCCGTGCT
GAGCTCTCAGAATGTTTGGCAAAGGGAGAACGTCCTACATACGACCAGCTAACAAAGGAT
CTGAAATACCTCGATGCTTTTATAGCCGAGATACTGAGACTCCATGCCCCCGAAATGCAA
TCAATCCGTGTGGCAGCCGAAGACGATGTGATACCGTTGACAAATCCCATACGTATTGCA
TCTGGAGCGACGATCGATAGCTTGTTTTTGAAGAAAGGTATGGTCGTCCGTATACCCTTG
GGGGGAGTGAATATGTCGGAAGCGTTGTGGGGGCCAGACGCGGGCATGTTCGATCCAAGC
AGATGGCTGGACGCTGAGGGTCATAAGAAAGGAAACAAGGGAGAACTAGCTGGCTACCGG
GGTCTCTTAACTTTCGGTGCTGGTCCCAGGATGTGTCCAGGCAGAGACCTCGCCGTACTG
GAGGTGAAGGCTGTGCTGTCGGTTCTGGTCAGATATTTGCCTTTGAGCTCCCCAATGGG
CCATCGACGGAACTGAGTTGGCATTTTACGCGCCCCAAGGTAGCTGGCGAGGATGGTACA
AAAGTTCCTCTTCTTGTGCGAAAGGTAGAAAACATGGTGGTGGTGCTCGCCTACTTGATA
AGCAGACTCGTGCGAAACACCATGTCAATCGATGACGGGCATAAGAGACCACGACATTGG
GGCGATGAAGTCGGTGGTGACTCATACGAGTCGTATTGTAAATTTTTGCTTGGGAAGTCA
TGGCATGTCGCAACAGTTGGCCCCACTGATGTCATTCAACCAACCGACATCTCGAGGCTT
GCGCTAAAGTCTCCCGCCATTAACGCCGCGTTCCAATGCTGCGTCATCCGCAGTGCCTGC
ACCGTCAGAACGCATTTAGTAGTGGCAAGAAGCTTCTGTCAAATTCAATCGCTAACCGGT
TCTTTGACGGGCTAG
```

FIG. 26A

Predicted protein(s): P450-2 (OP452)

SEQ ID NO: 601

```
>FGENESH:   2  10 exon(s)   2802  -   5477   624 aa, chain -
MLNLNFNGLWPDVAEYFKGDSMRIVTSAFTLLVVISIYRRRRGIRTPRLQGPRSESFIFG
NTKKIFPSANLSVVYRDWERMYGPVYEIPTGIGSSHVVLSDPKALTHIYSKDTTTYCRLA
GTTALSRKLASICFAPFFLAASLIYVPTTERPVFSTVGLSNSQSHSRVLGFCLSGKAILS
HDFGTLRGRTSLMMAAFDSIHTVKPSPFIRLIHFLSPILYALFKVTLMSVREEKLAQSVA
HLNRLTTNSLNKACKEPEDTVNESVLGILVKSENANPNSRLSLSEITAQAVRTFATPLIF
SQWSLIELARRPEIQESLRAELSECLAKGERPTYDQLTKDLKYLDAFIAEILRLHAPEMQ
SIRVAAEDDVIPLTNPIRIASGATIDSLFLKKGMVVRIPLGGVNMSEALWGPDAGMFDPS
RWLDAEGHKKGNKGELAGYRGLLTPGAGPRMCPGRDLAVLEVKAVLSVLVRYFAFELPNG
PSTELSWHFTRPKVAGEDGTKVPLLVRKVENMVVVLAYLISRLVRNTMSIDDGHKRPRHW
GDEVGGDSYESYCKFLLGKSWHVATVGPTDVIQPTDISRLALKSPAINAAFQCCVIRSAC
TVRTHLVVARSFCQIQSLTGSLTG
```

P450-2 (OP452), see 26A.

| | | | |
|---|---|---|---|
| gb\|AAW43969.1\| | Cytochrome P450, putative [Cryptococcus neof... | 138 | 5e-31 |
| gb\|EAL20013.1\| | hypothetical protein CNBF3400 [Cryptococcus ... | 137 | 9e-31 |
| ref\|XP_758127.1\| | hypothetical protein UM01980_1 [Ustilago m... | 118 | 6e-25 |
| ref\|XP_760336.1\| | hypothetical protein UM06189_1 [Ustilago m... | 106 | 2e-21 |
| gb\|EAA77720.1\| | hypothetical protein FG09671.1 [Gibberella z... | 98 | 8e-19 |
| gb\|EAL92111.1\| | cytochrome P450 monooxygenase, putative [Asp... | 98 | 1e-18 |
| gb\|EAA69194.1\| | hypothetical protein FG01048.1 [Gibberella z... | 94 | 2e-17 |
| gb\|EAL91101.1\| | cytochrome P450, putative [Aspergillus fumig... | 93 | 3e-17 |
| ref\|XP_317263.1\| | ENSANGP00000021820 [Anopheles gambiae str... | 93 | 3e-17 |
| gb\|AAK32957.1\| | cytochrome P450 [Anopheles gambiae] | 92 | 4e-17 |
| ref\|NP_918024.1\| | putative cytochrome P450 [Oryza sativa (ja... | 92 | 6e-17 |
| dbj\|BAB09357.1\| | cytochrome P450-like protein [Arabidopsis t... | 92 | 5e-17 |
| gb\|EAA52219.1\| | hypothetical protein MG04911.4 [Magnaporthe ... | 92 | 6e-17 |
| gb\|EAA73429.1\| | hypothetical protein FG03961.1 [Gibberella z... | 91 | 1e-16 |

BlastP against Coprinus

CC1G_09160: hypothetical protein    144    1e-34
CC1G_02050: hypothetical protein    143    1e-34
CC1G_03738: hypothetical protein    124    1e-28
CC1G_04749: hypothetical protein    115    3e-26
CC1G_06332: hypothetical protein    113    2e-25
CC1G_12478: hypothetical protein    108    7e-24
CC1G_05306: hypothetical protein    107    1e-23
CC1G_06814: hypothetical protein    107    1e-23
CC1G_00121: hypothetical protein    102    3e-22
CC1G_00122: hypothetical protein     97    2e-20

FIG. 26D
Blast against Laccaria. Again, hits are relatively weak compared to P450-1
Sequences producing significant alignments:                              (bits) Score    E Value  N jgi|Lacbi1|315756|eu2.Lbscf0006g04400                                       91    6e-28   3
jgi|Lacbi1|324807|fgenesh3_pg.C_scaffold_6000301                            91    1e-27   3
jgi|Lacbi1|339066|estExt_fgenesh3_pg.C_60288                                91    1e-27   3
jgi|Lacbi1|314449|eu2.Lbscf0061g00300                                       97    1e-27   3
jgi|Lacbi1|315758|eu2.Lbscf0006g04420                                       91    2e-25   2
jgi|Lacbi1|334243|fgenesh3_pg.C_scaffold_61000021                           94    4e-24   2
jgi|Lacbi1|300937|eu2.Lbscf0001g03860                                       51    4e-24   5
jgi|Lacbi1|320702|fgenesh3_pg.C_scaffold_1000272                            51    4e-24   5

FIG. 27

SEQ ID NO: 602

>FGENESH:[mRNA] 3 6 exon(s) 5972 - 6719 405 bp, chain -
ATGAGAAATAACAAAAACTTGAAGGCCTTACTTCCGATGCAGGCTCAACGCTCCAAGCCTAAC
ATTGTCAACAACTTGCGTCGTCCACTACTACATCGAATGGATGAGACATTTAGCAAAGGCTGG
TACACGACACATAAGTACATTGCTACATTATTAAATGGAATTTTGAGCTCACCTCTCACCACG
AGTGAGGAGACGGTTGACGTCGTCACCGACGCATGGGCAGTCTACAAGCCAAGCAGGAAGACG
GGTGGCATTGATAGTAGAGGTCTTGGGTTCGAGTTCGAATGGGAGTCACGAATTCGCAAGATT
GGAAAACCGCAGAAAGGGCGTTCGGTTTCTGCGGACATTCAGCCGGGCAAGACGGTGCAATAC
AATGGCAACCCCGTCAAAAGTTGTTG SEQ ID NO: 603
>FGENESH: 3 6 exon(s) 5972 - 6719 134 aa, chain -
MRNNKNLKALLPMQAQRSKPNIVNNLRRPLLHRMDETFSKGWYTTHKYIATLL
NGILSSPLTTSEETVDVVTDAWAVYKPSRKTGGIDSRGLGFEFEWESRIRKIG
KPQKGRSVSADIQP GKTVQYNGNPVKSC protein 3: No hits at all. This region overlaps with PHA1-1, which is on + strand (gene 3 is on - strand).

FIG. 28A

P450-3 (OP453) SEQ ID NO: 604

>FGENESH:[mRNA] 4 13 exon(s)   7173 - 10126 1689 bp, chain +
ATGCGATCGCATTCTCTCAAGGGCCGTTCATTAAAGTTGGCTAAAGTCGCGGGGGAAGGG
CTGGTGATGAGGTATCTTGTGTCGACGCGGGCACAATGGACCATGGGAGGCAGTCGCCGC
ATATCTGAAAAGCTGGGCTCCCGACGTGAAGTGAGGAATCACGAAAATCATATTTGCTTG
GAAGGAAAGCCCATGCAGCTCAGCAAACTCTACCTGAAACCTGCCCTGTCAAGGACATGC
GGCCGCAACCGCGACTGGTTGATGGTAAATCCAAATGCGACGCCCAGTTCGAAAGATGAG
ACATACCTGCGCCAAACAGTGATTACCACAGCCACCTACGAGGCCTCCGTGGCCAGTCGC
GCCTCGGGATTTACCGGCGCGATACAAACGGAAAGTTCTTTCGCAGCGTTCCCACCCGCG
CGGCCCCTTTGGCCTTATGTCGCGGAGTACCTCAAAGTCAATTCGATGAGGATAATAGCC
TCTGGCATATCCTTGCTCGTCGTTGTTTCCATTTACCGAAGCCGTCGAGGTCCTAGAACG
CCGAGACTGCAAGGACCACACATGGAGAGCTTCATCCTCGGCAATGCTAGGAAGATCTTC
CCTTCAGCCAACCTCAGTTTGGTGTATCAAGGTTTGGAGCAGACTTACGGGCCCGTCTAT
GAAATAGCCTCTGGCTTTGGCTCCAACCACGTCGTATTGAACGATCCAAGGCTCTCACA
CACTTATTTTCCAAGGACACTGTCACATATTCTCAGCCTGCTAGGCAGAAAGACATGGGG
CGGAAGTTGAATACGGAGGGTCTTGTCTTCTCCCTGTCGGTCTCGGCAATCCGCAATTT
CACTCCTATGTGTTTGGATTCCGCCTATCAGGTCAGGACGGTTCCAGCTTTGAGACATCA
TGGGATTCATGTTTCCAGTTGTCAAACAATTCGAACCGTGCTATCGTGCTTGATGCAGAG
AAATGCATGGATAATATTGGAAAAGCTGTATTGTCGTATGACTTCGGCAACATGAGGGGC
CATACGTGTTCGATCTTAGCTGACTTGGATGCTTTCCACGCAGTCAGCCCTTCAGGCCTT
TACATAAGGTTTATTGTGTTTACCCGCGAGATACTTTATAACCTCTTCAAGATTACCTTA

Fig. 28A (Cont.)

```
CCGAATGCCAAAGAAAAGCAGTTTGAGGAACTGGCAGCGCACTTTAAAGTACTCGCGACT
GGCTTTCTGCGGGAAGCACGTGAGGCGCCTGAAGATAGCGCCGTTCACCAATCAATCCTT
GGGGTTATGCTCAAGTCCAAAAATGAAAATGCTAACGTCCGTTTATCACTTCCCGAGATC
ACGGCCCAGGCTGGTGGTCTTGTCTTGGCCGGGTATGAAACTACGGCAAAGATCCATCGC
CGAGCTTTCCCTCAGTGGTCCCTCATTGAGCTTGCTCGCCGGGCAGAAATTCAAGAGACT
CTCCGTGCCGAACTCAAGGAGTGCTTGGCAGACGGAGAACGCCCTACATACGACCAGCTG
ACAAAGGATCTGAAATACCTCGATGCTTTTATATCCGAGATACTGAGGTTACATCCCTCA
GAAATGGTACTAACCCGCGTGGCAGCCGAAGACGATGTGATACCGCTGACGGATCCCATA
CGAACTGCATCTGGAGCGATGATCGACAGCTTGTTCGTGAGGAAAGGCACCGTCTCCGCA
TCCCTTTAG
```

P450-3 (OP453) SEQ ID NO: 605
>FGENESH: 4 13 exon(s) 7173 - 10126 562 aa, chain +

```
MRSHSLKGRSLKLAKVAGEGLVMRYLVSTRAQWTMGGSRRISEKLGSRREVRNHENHICL
EGKPMQLSKLYLKPALSRTCGRNRDWLMVNPNATPSSKDETYLRQTVITTATYEASVASR
ASGFTGAIQTESSFAAFPPARPLWPYVAEYLKVNSMRIIASGISLLVVVSIYRSRRGPRT
PRLQGPHMESFILGNARKIFPSANLSLVYQGLEQTYGPVYEIASGFGSNHVVLNDPKALT
HLFSKDTVTYSQPARQKDMGRKLNTEGLVFSPVGLGNPQFHSYVFGFRLSGQDGSSFETS
WDSCFQLSNNSNRAIVLDAEKCMDNIGKAVLSYDFGNMRGHTCSILADLDAFHAVSPSGL
YIRFIVFTREILYNLFKITLPNAKEKQFEELAAHFKVLATGFLREAREAPEDSAVHQSIL
GVMLKSKNENANVRLSLPEITAQAGGLVLAGYETTAKIHRRAFPQWSLIELARRAEIQET
LRAELKECLADGERPTYDQLTKDLKYLDAFISEILRLHPSEMVLTRVAAEDDVIPLTDPI
RTASGAMIDSLFVRKGTVSASL
```

FIG. 28B

| | | | |
|---|---|---|---|
| gb\|AAW41954.1\| | conserved hypothetical protein [Cryptococcus... | 86 | 3e-15 |
| gb\|EAL22841.1\| | hypothetical protein CNBB0620 [Cryptococcus ... | 79 | 6e-13 |
| gb\|AAW43969.1\| | Cytochrome P450, putative [Cryptococcus neof... | 72 | 5e-11 |
| gb\|EAL20013.1\| | hypothetical protein CNBF3400 [Cryptococcus ... | 72 | 5e-11 |
| gb\|AAT28222.1\| | putative 97B2-like cytochrome P450 [Ginkgo b... | 70 | 2e-10 |
| ref\|NP_959532.1\| | hypothetical protein MAP0598c [Mycobacteri... | 69 | 4e-10 |
| ref\|YP_118800.1\| | cytochrome P450 monooxygenase [Nocardia fa... | 69 | 6e-10 |
| ref\|XP_758127.1\| | hypothetical protein UM01980_1 [Ustilago m... | 68 | 1e-09 |
| gb\|AAT40578.1\| | putative cytochrome p450 [Mycobacterium vanb... | 65 | 6e-09 |
| ref\|NP_031846.1\| | cytochrome P450, family 3, subfamily a, po... | 65 | 8e-09 |
| gb\|EAL26035.1\| | GA10190-PA [Drosophila pseudoobscura] | 65 | 8e-09 |
| dbj\|BAB43954.1\| | cytochrome P450 [Musca domestica] | 65 | 8e-09 |
| ref\|XP_312050.1\| | ENSANGP00000016967 [Anopheles gambiae str.... | 64 | 1e-08 |

Fig. 28C

| BLASTP against Coprinus Sequences producing significant alignments: | Score (bits) | E Value |
|---|---|---|
| CC1G_02050: hypothetical protein | 127 | 7e-30 |
| CC1G_06332: hypothetical protein | 100 | 2e-21 |
| CC1G_09160: hypothetical protein | 95 | 5e-20 |
| CC1G_12478: hypothetical protein | 79 | 5e-15 |
| CC1G_04749: hypothetical protein | 73 | 2e-13 |
| CC1G_05306: hypothetical protein | 62 | 5e-10 |
| CC1G_06334: predicted protein | 62 | 6e-10 |
| CC1G_00122: hypothetical protein | 61 | 8e-10 |
| CC1G_00121: hypothetical protein | 60 | 2e-09 |
| CC1G_02813: predicted protein | 58 | 7e-09 |

FIG. 28D

| BLASTP aginast Laccaria: Sequences producing significant alignments: | Score (bits) | E Value | N |
|---|---|---|---|
| jgi\|Lacbi1\|314449\|eu2.Lbscf0061g00300 | 73 | 2e-17 | 2 |
| jgi\|Lacbi1\|255411\|e_gww1.61.27.1 | 73 | 4e-12 | 1 |
| jgi\|Lacbi1\|240704\|e_gwh1.61.30.1 | 73 | 4e-12 | 1 |
| jgi\|Lacbi1\|148184\|gww1.61.27.1 | 73 | 4e-12 | 1 |
| jgi\|Lacbi1\|163014\|gwh1.61.30.1 | 73 | 4e-12 | 1 |
| jgi\|Lacbi1\|334243\|fgenesh3_pg.C_scaffold_61000021 | 71 | 2e-11 | 1 |
| jgi\|Lacbi1\|334242\|fgenesh3_pg.C_scaffold_61000020 | 48 | 2e-11 | 3 |
| jgi\|Lacbi1\|341522\|estExt_fgenesh3_pg.C_610019 | 48 | 2e-11 | 3 |
| jgi\|Lacbi1\|309740\|eu2.Lbscf0041g01500 | 42 | 7e-10 | 3 |
| jgi\|Lacbi1\|318101\|eu2.Lbscf0008g02830 | 47 | 1e-09 | 2 |

FIG. 29A

SEQ ID NO: 606
>FGENESH:[mRNA]   5 2 exon (s) 11626 - 11786 105 bp, chain -
ATGTCTGACATCAATGCCACCCGTCTTCCCGCTTGGCTTGTAGATTGCCCATGCGTCGGT
GACGATGTCAACCGTCTCCTCACTCGTGGCGAGAGCCTTTGCTAA SEQ ID NO: 607 >FGENESH:  5 2 exon (s) 11626 - 11786 (160 nt) 34 aa, chain -
MSDINATRLPAWLVDCPCVGDDVNRLLTRGESLC No identity hits in any of the genomes of the nontoxic
mushrooms. This is a sequence encoding PHA1-2.

SEQ ID NO: Gene 5 rc:   SEQ ID NO: 608
TTAGCAAAGGCTCTCGCCACGAGTGAGGAGACGGTTGACATCGTCACCGACGCATGGGCAATC
TACAAGCCAAGCGG GAAGACGGGTGGCATTGATGTCAGACAT

FIG. 29B

SEQ ID NO: 609
>FGENESH:[mRNA]   6 1 exon (s) 12872 - 13129 258 bp, chain -
ATGGTGCAAAACAAAGACTCGCCAACCTGGCTCAAAGCGGTTGTCCCTGCGAGCCGAGGA
TATGTGGTGGTATCCTCGGAATATATGTGTGTGAGCCTTGGGATCGCTCAATACAACATG
GCTGTAGCCGATGCCAGTGGGTATCTCGTAAGGCCCATACATTCGTTCCCAATCCCGATA
TACCACCGTACTGAGGTTCGCGGAAGGGAAGATCTTGGTGTTACTGAATCTGAAGCTCTC
GCTGCGTGGTCCTTGTAG SEQ ID NO: 610 >FGENESH:  6 1 exon (s) 12872 - 1312985 aa, chain -
MVQNKDSPTWLKAVVPASRGYVVVSSEYMCVSLGIAQYNMAVADASGYLVRPIHSFPIPI
YHRTEVRGREDLGVTESEALAAWSL No identity hits in any of the mushroom genomes.

THE ALIGNMENTS OF P450 GENES 1, 2, 4 ARE:

| | | | |
|---|---|---|---|
| GB\|AAW43969.1\| | CYTOCHROME P450, PUTATIVE [CRYPTOCOCCUS NEOF... | 232 | 2e-59 |
| FB\|EAL20013.1\| | HYPOTHETICAL PROTEIN CNBF3400 [CRYPTOCOCCUS... | 229 | 2e-58 |
| REF\|XP_760336.1\| | HYPOTHETICAL PROTEIN UM04189_1 [USTILAGO M... | 179 | 3e-43 |
| REF\|XP_756349.1\| | HYPOTHETICAL PROTEIN UM00202_1 [USTILAGO M... | 162 | 3e-38 |
| REF\|XP_758127.1\| | HYPOTHETICAL PROTEIN UM01980_1 [USTILAGO M... | 154 | 1e-35 |
| REF\|NP_918020.1\| | PUTATIVE CYTOCHROME P450 [ORYZA SATIVA (JA... | 149 | 3e-34 |
| GB\|AAR11387.1\| | CYTOCHROME P450 [TRITICUM AESTIVUM] | 145 | 3e-33 |
| GB\|AAT68297.1\| | CYTOCHROME P450 CYP709C1 [TRITICUM AESTIVUM] | 145 | 4e-33 |
| REF\|NP_918024.1\| | PUTATIVE CYTOCHROME P450 [ORYZA SATIVA (JA... | 144 | 8e-33 |
| REF\|XP_477684.1\| | PUTATIVE CYTOCHROME P450 [ORYZA SATIVA (JA... | 143 | 2e-32 |
| GB\|EAA52219.1\| | HYPOTHETICAL PROTEIN MG04911.4 [MAGNAPORTHE... | 142 | 2e-32 |
| GB\|EAA78616.1\| | HYPOTHETICAL PROTEIN FG11303.1 [GIBBERELLA Z... | 135 | 3e-30 |
| REF\|NP_918022.1\| | PUTATIVE CYTOCHROME P450 [ORYZA SATIVA (JA... | 132 | 3e-29 |
| | | | |
| GB\|AAW43969.1\| | CYTOCHROME P450, PUTATIVE [CRYPTOCOCCUS NEOF... | 138 | 5e-31 |
| GB\|EAL20013.1\| | HYPOTHETICAL PROTEIN CNBF3400 [CRYPTOCOCCUS ... | 137 | 9e-31 |
| REF\|XP_758127.1\| | HYPOTHETICAL PROTEIN UM01980_1 [USTILAGO M... | 118 | 6e-25 |
| REF\|XP_760336.1\| | HYPOTHETICAL PROTEIN UM04189_1 [USTILAGO M... | 106 | 2e-21 |
| GB\|EAA77720.1\| | HYPOTHETICAL PROTEIN FG09671.1 [GIBBERELLA Z... | 98 | 8e-19 |
| GB\|EAL92111.1\| | CYTOCHROME P450 MONOOXYGENASE, PUTATIVE [ASP... | 98 | 1e-18 |
| GB\|EAA69194.1\| | HYPOTHETICAL PROTEIN FG01048.1 [GIBBERELLA Z... | 84 | 2e-17 |
| | | | |
| GB\|EAL91101.1\| | CYTOCHROME P450, PUTATIVE [ASPERGILLUS FUMIG... | 93 | 3e-17 |
| REF\|XP_317263.1\| | ENSANGP00000021820 [ANOPHELES GAMBIAE STR.... | 93 | 3e-17 |
| GB\|AAK32957.1\| | CYTOCHROME P450 [ANOPHELES GAMBIAE] | 92 | 4e-17 |
| REF\|NP_918024.1\| | PUTATIVE CYTOCHROME P450 [ORYZA SATIVA (JA... | 92 | 6e-17 |
| DBJ\|BAB09357.1\| | CYTOCHROME P450-LIKE PROTEIN [ARABIDOPSIS T... | 92 | 6e-17 |
| GB\|EAA52219.1\| | HYPOTHETICAL PROTEIN MG04911.4 [MAGNAPORTHE ... | 92 | 6e-17 |
| GB\|EAA73429.1\| | HYPOTHETICAL PROTEIN FG03961.1 [GIBBERELLA Z... | 91 | 1e-16 |
| | | | |
| GB\|AAW41954.1\| | CONSERVED HYPOTHETICAL PROTEIN [CRYPTOCOCCUS... | 86 | 3e-15 |
| GB\|EAL22841.1\| | HYPOTHETICAL PROTEIN CNBB0620 [CRYPTOCOCCUS... | 79 | 6e-13 |
| *GB\|AAW43969.1\| | CYTOCHROME P450, PUTATIVE [CRYPTOCOCCUS NEOF... | 72 | 5e-11 |
| GB\|EAL20013.1\| | HYPOTHETICAL PROTEIN CNBF3400 [CRYPTOCOCCUS ... | 72 | 5e-11 |
| GB\|AAT28222.1\| | PUTATIVE 97B2-LIKE CYTOCHROME P450 [GINKGO B... | 70 | 2e-10 |
| REF\|NP_959532.1\| | HYPOTHETICAL PROTEIN MAP0598c [MYCOBACTERI... | 69 | 4e-10 |
| REF\|YP_118800.1\| | CYTOCHROME P450 MONOOXYGENASE [NOCARDIA FA... | 69 | 6e-10 |
| REF\|XP_758127.1\| | HYPOTHETICAL PROTEIN UM01980_1 [USTILAGO M... | 68 | 1e-09 |
| GB\|AAT40578.1\| | PUTATIVE CYTOCHROME P450 [MYCOBACTERIUM VANB... | 65 | 6e-09 |
| REF\|NP_031846.1\| | CYTOCHROME P450, FAMILY 3, SUBFAMILY A, PO... | 65 | 8e-09 |
| GB\|EAL26035.1\| | GA10190-PA [DROSOPHILA PSEUDOOBSCURA] | 65 | 8e-09 |
| DBJ\|BAB43954.1\| | CYTOCHROME P450 [MUSCA DOMESTICA] | 65 | 8e-09 |
| REF\|XP_312050.1\| | ENSANGP00000016967 [ANOPHELES GAMBIAE STR.... | 64 | 1e-08 |

FIG. 30A

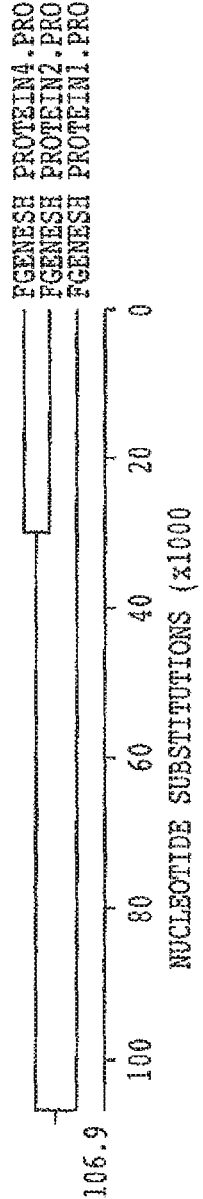

TWO AND FOUR ARE CLOSER THAN EITHER IS TO ONE.
SHOWING APPROXIMATELY 36% IDENTICAL, HOWEVER MAY NOT BE PRECISE DUE TO
UNMATCHED N AND C TERMINI. THERE ARE NO IDENTITY HITS TO KNOWN COPRINUS P45 GENES.

* IDENTITY TO CYTOCHROME P450, PUTATIVE [CRYPTOCOCCUS
>CRYPTO AAW43969

SEQ ID NO: 611

Mtmellkvinneasqlfpncirsspvacivlvsfqgiailllfsvylwlwpfqyaklyfrnlpgppsdswfwgvvptl
ikspppsvphsmwtdevgptwvryrvalgaqrfitidptalnviishadifbkpsivrkalsdifgnglitaeghtkk
qrkalnpispaavrgmipvfvdkayelkakligiiegdetegasptpckeedeyeggkidvmkylqktidvigi
vgfsydikalseprnelseaysmfgagmdantwdfirgaiplvnkipnkratelaadrkavtirskkivedkkrev
msahseqlekredidgglislilikanmasdvkpegklsdeevIdqittfmiagnetsstaltwiiysltqnpecqtr
lreevlavpddrpsletinnipymdavireairihapapgtmreakedtvipIsmpvigrdgkqidsvkinkgtmvf
ipIityntspaiwgpdarvfnpdrhiktssdsfgganmhvpgvwgnmlsfiggarncigvklafaeistlifvlirs
fefgelkskpevekkasvvmrprikgeesagIqmplrvvkpiIm

Whole lambda clone, reverse complement:
SEQ ID NO: 612
GATCATGTTAAGTTTATGCCCTAATCGTTGAGCGATAAAGAGGACCAACCCTTGTGAGTCTCGCGCTCAGAAATAGAT
ATAACATCACCATACTGGAACGACAATGAGGCTGGCAGCTGAAAAATGGTGCAAAACAAGACTCGCCAACCTGGCTCAA
AGCGGTTGTCCCTGCGAGCCCAGGATATGTGGTATCCTCGGAATATATGTGTTGTGAGCCTTGGATCCGCTCAATACA
ACATGGCTGTAGCCCATGCCAGTGGGTATCTCGTAAGGCCCATACATTCGCTCCGTCCCATCCGATATACCACCGTACTGAG
GTTCGCCGGAAGGGAAGATCTTGGTGTTACTGAGAATCGGAGCTCTCGAGCTGTCAGAGGTCAACATCGGGTGACGGAGTGCACAATCCTTATCGAATTACCTTTGAGATACTC
CTCGGCATCTCCGATAGATAGAAATGACGACGGACGGCAATGCAGGTTGAGTTCAACATCACGGGTGACGGAGTGGACGAGCCATTGAATGCCAATTGAAGGGTGGAAGGTTGCGC
TGCCACATCAGGCCGGATAAGTACTAGTATAGCAACCAGCCGAAACCGTAACCAGGCGGAAACTTGACCTATCTATCTCCGGAACGGTG
GAAGGCCATCGCGGATAAGTACTAGTATAGCAACCAGCCGAAACCGTAACCAGGCGGAGAACTTAGAGCCACATAGTCATAAGTGAT
GAATACGAGGAAAACGTTTCTGAGGACGTGGATAATGCGTCTTTTGTTGCATCGGCAAACTGCTTGACTGTTCAAACCGGGACACAG
TTGGGGGTCCATGTTACCGTGCGCGATGGAGATAGGGCGGATTGGATTGCATCGGCAAACTGCTTGACTGTTCAAACCGGGACACAG
GCAACACCCCTGTGCGCGATGGAGATAATGCGTCTTTTGTTGCATCGGCAAACTGCTTGACTGTTCAAACCGGGACACAG
CATGGTCCATTTCAGGACAAACCCCTATCTATTGATCTACAAACTGCTTAGGCCCAGTCGCCAGTCGGATCAGGATACGACGACGAAAA
AGAAAGGCTGTGCTCAGTGGGGTGTTTAATCCAGCGAGAAACCGCGTTAGGCCCAGTCGCCAGTCGGATCAGGATACGACGACGAAAA
GTGTAGGGTCAAGACTCCCCTTGATGCGATTCAACTATTCTTGACGGGGGTTGCCATTGTATTGCAGCCTGCCAAGAATGTGTGA
TGGCTGTGCCCGCAAGACAGAACGTCCAAAAACAGGAAAGAACAAGAAGTTTGTGGAGCCTGCCAAGAATGTGTGA
TGAACAGTGACTGACACGATGAATGGGGGATGAATATTGTAGACCAAGATGATCAGACAACTGTTTATGGAGATT
TTGCGGCCAACTCGTCTTCATCTCCGTGTCAGGACAAGATTCTCTTATCTATCAATTCAATATTCAATATTCAATACTCACCTCCCATTCGAACTCGAACTC
GAATTCGTGACTGAGACAGATAAAGGCGTTGGATTCAGCTTAGCATTGACATTCAATAATGCCACCCCGTCTTGGCTTGTAGATTGCCCAT
GAGCCCAAGACCCTCTGCCTCTAAATCAACAATGTCGACATCAATGCCACCCCGTCTTGGCTTGTAGATTGCCCAT
GCGTCGGTGACGATGTCAACCGTCTCAACCGTCTCCACTCGGTGGCAGAGGTGAGCTCAAGATTCATTAATAATGTAGCAATGGA
CTCATGTGTCGTGTATCAGCCTTTGCTAAATGTCTCATCCACTAGTCAAGTACCCGCTCGGATTTCATGATAACGAAG
GGTGATTGTGCTGACTATGCAGAAGCAATATGACGAAGCAAATTGTAGAACACGTCTTGCTTGCAAAGCGATGATCGTGCGCTGAACCAGC
GTCTTAAAGATTGCGTGATAATACCCCCCATGATGCTCGAGCTGTGCAATGCAATGCAATGCACTAGAGAACCTGACCGACCGTGTCATTG
TTTGTCAATCTCTAATACCCCCCATGATGCTCGAGCTGTGCAATGCAATGCAATGCACTAGAGAACCTGACCGACCGTGTCATTG
GAGATAGCATCTCAACATTCGACATCAACATTCGCCACATTATACGGTTCGGTGGCGCAGCCTTGAAGAGTCCTGCGGCGGTGTAGCCTGGA
CTACTTGCCTACTTGACTGAACATATACACAACATTGTGACAGCTCGCCATATGAGTTTGACAGGCCATGTTGCAACCTTGAACTGGCGATGCCATGTTGCTGGCGACG
AGAATTTCCAGCAGGGGGCTCCTGACATCGCCGGAGAATATTGTGACAGCTCGCCATATGAGTTTGTAAGCGGCCAGTCCACAAAACAGCGA
TTTATGTTACATGCGTGACGCAGGGATGAGGAGAATCATGTGATGATGTATATAGCCAGGCCATGCCGATGGACATGTGCTGGCGACG
GAGAGAAAGATGCACGCCCGATGAGGAAGAATCATGTGATGATGTATATAGCCAGGCCATGCCGATGGACATGTGCTGGCGACG
ATTGGGAAGGAGGGCGGAAGGTCGCTTGGGCGGGAAAACACTGCAGGCTGCAGGCCGTGCTCGAGGAGGAGATAGACACCGCT

FIG 30B CONT

```
ACGTGATTACTACGCCAGCCCTCTCAGGCTGTAATGATCGTTCATCAAAGTTGGTTAGAGTGGGCTGGTGATGATGCATC
TTGTGTCGGTGCGTGGCGACGATGGGACTATGGGAGGCAAGTTTGGCTACTAGTAGGTCTATAAGGATGATGTGAAATATG
TGGGTATGCCAGTCATCCAACCTACGCCGATGCTGACGATCCTAAGCCTAAGCCTCACGATGTAAGGCCACACATCTGAAAAGTGGTCCTCC
ACGTGAAGTGAGAATGCACATGAGATCATGAAAGTCATTTTTGCTTGGAAGGAAAGCCATATCTGGACTCAGTAACTCTACTAAGACACGA
AACGAACGATGTTGCACATGAGATCATGAAGTCATTTTTGCTTGGAAGGAAAGCCATATCTGGACTCAGTAACTCTACTAAGACACGA
GCGCCGCCCGAACTGCCAACTCAGTTCCGTCGATGGTCCATTGGGAACTCAAAACTGAAAATGAGGACCAGAATCACAA
GGGCAGCCTGGCGATTTGTCAAGTCAAAAATGAATAAAAACGGCACGGAGTTTCGCCATACCTTCATCTCAGCAAGGCGA
GGTCTCTTCCGGACACAGCCTTGGCCAGCACCGAAAGTCAATAGATTCGGTAGCCGGGTACTTCTCCCTTCTCCT
TTCTTATGACCATCAACTTCCAGCACCTGCTCGATCGGAATGTCGCCCGCATCCGTCCCCACACGTCTCTGATATATT
CATTCCTCCTAAAGCATGCCGAGACGGTGCCTTCTCGGCTGCCTAGTGCAAAAGATCGTCATCATAAAAGATAGGCATGAAGGA
GGGATCGTCAGCGGTATCACATCGTCTGGCTGCCTAGTGCAAAAGATCGTCATCATAAAAGATAGGCATGAAGGA
AGGGACGAACCACGCGGTTAGTACCATTCTGAGGGATGTAACCTCAGTATCTCGGATAAAAGCATCGAGGTATTTC
AGATCCTTTGTCAGCTGGTCGTATGTAGGGCGTTCTCCGTCTGCCAAGCCACTCCTCGAGCTCCGGCACGAGAGTCTTTG
AATTTCTGCCCGCGAGCAAGCTCAATGAGCGACCACTGAGCGAAAGCTCGGCGGATCTCTTGTAGATAAATAACAT
TACCGTCATGCCAACTGTGAACAGCATAGTTAGTGGATTATGAGATCATCGGGTGATACAAAGAGATTGCATAGGGACA
AGTTCATACCCGCCCAAGACCAAGACCACCCCTCGGTTAATCCAGGTCGATACAAAAGAGATTGCATAGGGACA
TACAGCCTACAAGGATGTTGATCGAGCACCGACGGCCAGTTGACTATATAGGAAAGCCGTATATACCGGTCCAGGATAG
TAAACGACGTTAGCATTTCATTTTGGACTTGACTATATGGTGAACGGCCGTATCTCAGGCGCCTCAGTGGCAGAAGC
AGGTAACATACGGATAACCCCAAGGATTGATTGGTGAACGGCCGTATCTCAGGCGCCTCAGTGGCAGAAGC
CAGTCGCGAGTACTTTAAAGTGCGCTGCCAGTTCCGCTACAACTGCTTTCTTGGCATTCCGTAAGGTAATCTTGAAGAGG
TTATAAAGTATCTCCCGGGTAAACACAATAACTTAGTAAGGCCTGAAGGCCTGACTGCCTGAAGCATCCAAGTC
AGCTAAGATCGAACACGTATGGCCCCTCATGTTGCCGAGTCATACGACAATACGAGTTTTCCAATATTATCCATGCTAG
GAATATTGCAGGTGAAGAAGAATGGGGCAGAGTAAAGGTTGCGAGTAAAGTTGCGGAGTGTAACAGTTCATCCTTGGGCACATAA
TGAACCAATTAAATGAGCCTAGAAGGAAGGAAAGCAACTCACCATTTCTCTGCATCAAGCACGAAGACGCGGTTCGAATTGTT
TGACAAACTGGAAACATGAATCCATGAGTCCTTTGAGCTATCATTTGCTCGTTCAATCGACTGACTCTCAAAGCTGGAAC
CGTCCTGACCTGATAGGCGGAATCCAAACACATAGGAGTGAAATTGCCGATTGCCGAGACCCGACAGGGGAGAAGACAAGA
CCCTCCGTATTCTATAATCCGTTCAATATATCCACCAAACTGGACCAAGTTAAGTCTGACACAGTCTGACAGCTGGGAGAAACCGGACCAGCCGAAGCTGTCTGGG
TCCCCCCCCGAGCACCAAACAGTCTTTCGCCTAGCAGGCTGAATATGTGACAGGCTATTTCATAGACGGCCCGTAAGTGTGTGA
GAGCCCTGGGATGGTCAATACGACGTGGCCAAGCCAAAGCCAGAGATTTCCAGGATCATTTGCCAGCCAGGGATGAAGCTCTCCATGTGCCTGCTCTCC
AAACCTTGATACACCAAACTGAGGTTGGCTGAAGGGGAAGATCCCTCCTAGGAGGCGGAGGATGAAGCTTCCATGTGTGG
TCCTTGCCAGTCTCGCGTCTAGGCAGCTCGAAATGCAAAGGCTCGGTCATAGCCAAAGCTCTGAAATTGAGGTTCAACATCCGAAG
TTATCCTCATCGAATTGACTTTGAGGTACCTCCGGACACCAGTAGCCATCCAGATATGGAATCAGCACAGGCTGCAGAGGCTA
AGAGCGATGCGGGCCGTTACAGAGGTGAGACCACCAGGCTACGAGGCACCAGCAGATGGATACGACTCAAGATAGAAAATGGG
GTCCTCACCCAAAAAAGATGCCAAACTGGCCAGTCTCCAAGTCATTTCCATCAAGGGCGACAGCCTCAGCGGGATTTAC
```

FIG 30B CONT

```
GGCTCGCTCCACTTCGTGATGTTGAACCTCACTTCAAGGCCTCTGGCCTGATGTAGCAGAGTATTTCAAGGGCGATTCG
ATGAGGATTGTGACCCTGACCCTGCCTTTACGTTGCTCGTCGTCATTCTATCTGTGAAGAAGACGCGAGGTATCAGAACGCCCAG
ACTGCAAGGACCACCCAGCGAGAGCTTCATCTTCGGTAACACCAAGAAGATCTTCCCTTCGGCGAACCTCAGTGTGGTAT
ATCGGGATTGGGAACGGAATGTATGGCCCGTTTACGAGGATACCCACTGGCATCGGCTCCAGGGACAACCGGCTTTGAGCCGGAA
CCCAAGGCCTCACCACACATATATTGCACCATTTTCTTAGCTGCCAGCCTTATTTACGTTCAGTCAGTATGGTGATGTTGATCTATT
GTTGCCGAGTATCGTTTTGCACACAGTCGGCATCGGTCGGTCACTCTTATCGCTCAACGATCAGGGCATAAACTTAACATGATCGCAGACT
TCTGAGGGCGAGACTCACAAGCGGTCGGTCGGTCTCCACTGTCGTCTCAGTGAGCTCAACGATCGGTCGTTGGATTCTGCCTATCAGG
ACGGAGAGGCCCGTCTCTCCACTGTCGGTCCAATTGACCAACTAACATAAATGACCAGCGTCAAGCAGCAGTCGGATTCATGTTC
TTAGAATGGTTCCATTCTTAAAACAATCGGCCATTGACTCATAATTGATGTCGTGAAATGGCAAGTTGCTGTATCTATCTCCCATTG
TCCGTCATCAGAGGCACTCAAACACCCGGTCATAATTGATGTCGCAGTGCGCAGCCTCATTCCGCCCTTGCCGCGAA
TTAGTTAAACTTGTTCTCGTGCCAAGGATGAATTCGTCACGTACGTTGCGATGACTTTGGAACTCTAGGGGCGCAGTCCTGATG
ATGTTCCTAGATTGGACACTATAGGGCAAAGCTATATGTCGATGGACTTTTCCCCCTTTATAAGGCTTATTCACTTTCTGTCACCGATACTCTA
TGCCCTGTTTTAAAGTTACCCTCATGAGACGTCAAGCTCCAGAAGAGAGATACTGTCAACGATCAGTCCTTGAATAGGCTTACAA
ATGGCCCCGTTTGACTCTATCCACACAGTGTAAGGGAACAGGCATGTAAGGAACCGGAAGATACTGTCAACGAATCAGTCTTGGATTCTGGGTATGTCACCA
CTAACAGCCTGAACAAGGCATGTAAGGAACCGGAAGATACTGTCAACGAATCAGTCGTCGAGAAAACCAATCCCAACAGCCGTTTGT
ATATATGAGGTGATGTTCTTGGTGCCTAGCCGCTACGCTTCCCGTATAGTCAGTCAGACAGAAAACCAATCCCAACAGCCGTTTGT
CACTCCCGGAGATCAGGCCCCAGGTATGTAGCCCAAGTGACGCACCGTCTGATGCCAATCAACATACTTTGTAGGCCGT
ACTACCTTTGCCACTCCCTCTGATATTCCTGTAAGTTAATATAACCGAAGAGTTTCCTTTCATGCTGCATATGAAAC
AACAGCAAGTAAGTTCTGCGAAGCGGTTGCTGCTTGTTATCAAAGATCCATAAACTATGACCCGTGCTCTCATAGTCAC
CTTAACGGTAATCTTCGCCCTACGAGTGTTCAAGCTGTCTCTCGAGCTCTCGAGATGTTTGCAAAGGGAGAAGCGTGTCTCATTGAACTTGC
ACGCCGGCCAGAAATCCAAGAGAGATCCAAGAGAGAATACCTCGATGCTTTTATAGCCGGAGAGTACTGAGACTCGAGACTTGGCAAAGTTTGGCAAAGGGAGAACGTCCATGCCCCGAAATGCAATCAATC
AGCTAACAAGGAATCGAAATACCTCGAAATACGTCGAAGAATCGAAATACCTCGAAGAGTCGGCATCCTCGAGTCAGACTTGATATTTTATAGCCGGAGATCGTGCGAAATGCAATCAATC
CGTGTGGTTCGTCTTCATTGTTTAATTCCTTCCCGATCCCCTATTATTGTGCAGGCAGGCCGAAGACGATGATACC
GTTGACAAATCCCATACGTATGCATCGGGCGGACGATGCATCGCTTGTTAGAAGAAGGTATGGTGCTCGTATAC
CCTGGGGGGAGTGAATGTCGGAAGCGTGTGGGGGCCAGACGCGGCATGTTCGACTTCTTAACTTTCGTTCGTGCTGGCTTCCAGGATGTG
GAGGGTCATAAGACAAGGAAAGGAGAAGAACTACGCTGGCATACCGGGGTCTTACCGGGTTTGGTTGGTTGATGGTTGACTGCACAA
TCCAGGCAGAGACCTCGCCTACTGAGGTCTGGTCAGATATTGCCTTGAGCTCCAATGGGCATCGACGAAGTCATCGAGCGGTTGGC
TCTCTAGGCTGTCGTCGGTTCTGGTCAGATATTTGCCTTGAGCTCCAATGGGCATCGACGAAGTCATCGAGCGGTTGGC
ATTTACGCCCCAAGTAGCTGGCGAGGATGGGTAGAAAACATGTGGTGCCCCGCTAATAAGCAGACTCGTGCGAAACACCA
GTACCACTGTTTGTCTAGGGCATAAGAGACGACCACCACACACATTGGGGCGACTCATACGAGTCGTATTGTAAA
TGTCAATCGATGACGGCATAAGAGACGACCACCACACATTGGGGCGACTCATACGAGTCGTATTGTAAA
```

FIG 30B CONT

```
TATTGGCCCAACTCGATATGGATAGTGTGGGGTGAATAGTATATATTGTGAAGAAGAAGATGATGAGTGCGGACAGCA
TGAATGCAAGATCTGCGCTGAAAAAGGATGAAAGGTCACTGATGATCTATGATGAATCAGAATTGCTTTGACGCGATTCGGCCGA
AGGGATCACATTCTATTCTTGCCGACGGTTTATTTCCTATGGGTGACGGTTTGCACGCTTACGGCCGGCGGGTGGGAAC
GCTGCCAAAGAACTTTCCGTTTGTATCGGCGGTAAATCCCGAGGCCGACTTCGGTGCTCATCTACTGATAGCTAATGAATATTGAG
TCACTGCGGATTCACGCACCCTAACTACGGCAGAAGCCCTACTTCGGTGCTCATCTACTGATAGCTAATGAATATTGAG
GCCAACTCACGAGGCCTCGTAGGTGGCTGTGGTAATCACTGTTTGCGCCAAGTATGCTCATCTTTCGAACTGGGCGTCG
CATTTGGATTTACCATCAACCATCGCCAGTCCCGGTTCGCGCCCATGCCTTGACCAGGGCAGGTTTGCGAGCTGCATGGGCTTCCTTC
AGATCTGATGTCGCAAACATCGCCAGTATTCGTCCACTCACGTCAGATATGCGGGACTGCCTCCATGG
CAAGCAAATATGATTTCGTGATTCCTCACTTCACCTCACGTCAGATATGCGGGCAACTTTAATGAACGGCCC
TCCATTGTGCCCGCGTCGACTAGTAATCGCGTAGCGGTGTCATCTCGCCAATCCGGTTGCTCGAGCCTGCTTTTTCCCGGGTGTAGTTCA
TTGAGACTGCCGGTAGTAATCGCGTAGCGGTGTCATCTCGCCAATCCGGTTGCTCGAGCCTGCTTTTTCCCGGGTGTAGTTCA
ATTATGCCTACACATCGCCATTCTCATGCTCGCAAATGATCATCATAAAGACCCTTCTTGAATTCACTGTTTTTGTGAACTTGCCGACTTCA
ACAACTAIGCGAGCTATCAAACTCAATCATCATAAAGACCCTTCTTGAATTCCCAGTATAGGACAGTCAGGACGCGTCAAGCT
ATGGTACAACAGCTGCCTATGTGATATGTGATATGTTGCTGACAAGTAGCAATGATAGGACAGTCAGGACGCGTCAAGCT
CTGGCGACAGCAGCAGCAGATGCGCTCGGATTGCTAAACCGCTTCTGTTTATATGAGAATGAGAAAGAAATAACGTGAGTCGTCTAA
AITCCATAGTACAGCTCGGATCATTTACGTCGGATTCATTTACGTCCGATGGCGTGAGGTAGGAATAGCCGATGCACTATGTATCTTGATTCGATGCCAAGCCTAACAT
TGTCAACAACTTGGCTCGCTGCTTATCACTACTAGAAGAAAAAACTGAAGGCCTTACTTCCGATGCAGGCTCATCAGTAGCTCATCAAGAATCAGAGGCGGA
TACCTTGACTAGTGGATGAGACATTTAGCAAGGCTGGTACAGACGGTTGACGTCGTCACCGACGCATCTAACAAGCTACAAGCCAAGCAGGAA
TTGAGCTCACCTCTCACCACGAGTGAGGAGACATTGTGATTTAGAGGTAGAGGTCTTGGGTTCGAAGCAATGGGAGGTAAGTAATATT
GACGGGTGGCATTGATGTCAGACGCCATCCAACGCTCGAGGCCGATCCAACGCCATCCAACGCCTTTATCTGTTTCAGTCACGAATTGCCAAGATTGGAAAACTCAGAAAAGTACGATA
GATAAGAGAATCTGTCCTGACACGGAGATGAGGAGAGACAAATTGGCGCAAAATCTGCAAAATCTCCATAAGCGTTTGTCTGATCGCTTT
TCCCATGAATCATTCATTGCGTCGGTTCGGGTTCTGGGACATTCAGCCGGGACACCGAGCGACAATGCAACCCCGCGAACTGT
GTTTTAGGGGGGCGTTCGGTTCGGTTCTGGGACATTCAGCCGGGACACCGAGCGACAATGCAACCCCGCGAACTGTT
GCATAACGCGTTCCAACATCAAGGAGTCTTGACCTTAAGCAAGCCTCTCTTTTGTCTGTCGTGGTCGTCACGAATTATGCCGAACTGG
GTCCTAGACGCATGATAGGTGTTTGTGCCGATCATTCGGCTCCAATCGACATTGCCCTAAAATGGACATGTATAGAATGATTATCGGCGGTGTGTATTAAGAA
TCCCTTCGGCCGAGTTCGATCGTCCATCGCCATGTGCCTCCACCTTCAGGTAAGATGGACCCCCAACACCGTCCCGGAGATAGATACGTC
CTTTCCGGAATCGATCGATCGTCCATCGCCATGTGCCTCCACCTTCAGGTAAGATGGACCCCCAACACCGTCCCGGAGATAGATACGTC
AAGCATTTATCGGCCCTGGTTACGGCCCTGGTTACGGTTTCGGGTCCTCAGAAAACATTTCCTCCGCATTCGCGCCAACTTGATCGCCTTCCAC
```

FIG 30B CONT

```
TTTTTGCTTGGGAAGTCATGCCATGTCGCAACAGTTGGCCCCACTGATGTCATTCAACCAACCGACATCTCGAGGCTTGC
GCTAAAGTCTCCCGCCATTAACGCCGGTTCCAATCTGCCGGTCATCCGACTGCCTCCACCGTCAGAACGCATTAGTAG
TGGCAAGAAGCTTCTGTCAAATTCAATCGCTAACCGGTTCTTGACGGGCTAGAACCCTGGTTATGAACTAACTTCGGC
GGCAGCTCGCATGCTCAACCTCTTTCCATCCCCACATTTACCTCCATCATTTCTCAGCCGAACTCAGTTCGTAAT
TGACTGCTATGTAATATCATAGACGCTTGATGGCGTTGATGAGCAGCGGGAGCTGCTAGCCTCTAGGTCTATAATGAACCACGAG
GCGCGTTAACTTCGAGCTTTATATGGCTTGATGAGCCGACAAACTCCACACAGTGTCCCTAGACCTGGTCAAAATCGGTCG
GTTACTTAGTCCACTTCATTCTGTCGTTACCAGTGCTGAGCAGTGTGACGACTATATCTTCGAAATCTAGAGAAAACTGCTACTCGGCGATA
GTAGAGCTTTCATTCTGTCGTTACCAGTGCTGAGCAGTGTGACGACTATATCTTCGAAATCTAGAGAAAACTGCTACTCGGCGATA
GCAAATCTGAATCCGATACACGAACGTGGACCACCCCAAAACTGAGCAAATGGCTCCAGACGCCAACACGCACGTGCAATATTTAC
GCCTCAGGTAGACATTCCATCGTTCTGGTCTATCAAAGACTGTGTCCTTGTGGATGGCAGAAATGGAATATGACTACTGCCCTCT
CTGAAGTCTAAAGCATCTTCACCCATATGGACTTTCCTTGTGGATGGCAGAAATGGAATATGACTACTGCCCTCT
TTTGATACTATAAGACCGGTGAACGCTAAAGATATGGGAACGACCGAATCCTCACCTAATACTGGAGAATAGGTTT
CCTTCCGGTCGGTGATCGGCTTAGCGAACAATGTTGCGTCCTTGGCACACACCCTCGAGTGCCGTGGCTGACAGGTATCG
ACAGAACGTAGCGTCTCCCCTTAATTTACCATATTCCCCAAATATGGAATCCAGGTTTTTGCCAGAGAATACGGATTTCCAGCATCCGTCGCCATTACGTT
ACCGTGAGCAGCTCCTAGCGAGCTTAGCCTCGGATTTGCAGGGTTTTTGCCAGAGAATATAAAGCCTTCACGTCCAGCAAT
ACTACCAATCAATAATTCGAGATAGTCCTAAACAGATAAACAGACTCAGACTTACATCGGACTTCATCGGACTCACGTCCAGCAAT
TACAAATGAGATAAACCCTAAATAAAAGATCAGTTATCTCGCAGTATCAAATACATCAGCCTCACGCGCTTTGACTTC
GTCATCGGATAGACGACGGTGCTCTGCTACGGATTCGCACATCGGGGACTATTGGTGCGAACCAAAGCGATAGGAGATCTCGACTGC
CGGAATTGTCATTATTCGTACGTCGTGTCTCTACAGGATCAGGCTAGACAACGCGATAGAGAATCCGTTACAGTGATTTGGAATTTCCATA
ATATGCTCTAGTTGTGCTCTACGGATCAGGCTAGACAACGCGATAGAGAATCCGTTACAGTGATTTGGAATTTCCATA
CTATGAACCATAGAAGTGGATGAATCTTGGAGTCGAAGCTCGTAACGGAGCCTTCCATCGAATGGCATCGGTAGCACACGG
GTATCTGGCACATCGGACATCAGAGCAAGCGATCCAGGGAATCAAGCTCGTAACGGAGCCTTCCATCGAATGGCATCGGTAGCACACGG
CGGCAAGTACCACCCTGTTCGAGCATTCAGAGCCCTGAGTGATGATGTCCGAATCGGCGGAAGTTCACTGTAGCATGGA
TGAGTAGTAAAAACGACCCGTTTGATTTTTTACGAGGACCACGATTGGAAATGGATAGATAGTCACCAAAATCTTCCGCTGTTAAACG
GATTCTGGTTGTGATTGAGACTGAGGACTAGTTGAGGCAACGGAAGTACGCCACCTGCTTTTAAGTTGATCCCCTCGACAAAGGG
TAATTATCATAATAGCGAACTAGTTGAGGCAACGGAAGTACGCCACCTGCTTTTAAGTTGATCCCCTCGACAAAGGG
AGACCTGACGTAGGTGGATCATCGCCCTCTTAAGTATGGTAGGTGAAAAGCACCTGAAAAAGCACCTGCCGATCTG
GCGGCGAGTAAACGATGGTTGGTGTAAACGTAACCATTCGTCAAAATGTGTTCAAGGCCTGCGGATCCGTCACATATA
AATGCGAAAGCTAAACTGATTGGTTATCTATATCAGAATAAATGGATTGGTTCTTACACCGAGAATCCATTTAGTCTTA
TCAGCGGCCATATTGAATGCCAATGATATGTCTGGTAACATAGTGGTTAACAATGGGTGGTAGTGGGTGATTTG
TACTTACACATTCTCAGACGTGTTTGAGATTACGAGATGACTGCTGTAAAATACCAGAGCAGCTGAGATAGCTTGATGGA
GAAGTCAGCTCAACATAATTACACGAGTGACTGAGCTGAAACAGATGGTGTGCAAGTCGACCATTGTTATTAACTTGGTAACGG
TTGGAATATAAGCCTGAAAGTGACGAGGAGCGGATGGAGATGCTTAAATCCCGATTGAGAGATGATGCTGAGTTCGTAGGTTCACTGATGG
GCAAACGTTTCAAACTGTAGGTGGATCGGTGAGAGACACATATCTCATTACTCGTATCTTTTGATTTACTAGCTCCCCCTGT
TTCCGATTCGTCCCTTTTCCATCATCGATTATCGATTTCTGGTTATGCTCGGTTAGCTATCGTTATCGTATTGGCACTGCTCCCCCTGT
CACCGTCTCCACTTCCATCATCGATTATCGATTTCTGGTTATGCTCGGTTAGCTATCGCCATCATGGACATCGCGCGC
CCTTCGGCTGCAGTGCGAATGTGAAAATAGTGAAACTTCTGAACTCTGACTTCTCGGATC
```

FIG 30B CONT

SEQ ID NO: sequence at ~11,000 (in original orientation): SEQ ID NO: 613

APTRLHLRVRTRFSYLSSPRELQPCEFVTETDKRRWIQLSIQYSILTSHSNSSPRPLL-
ITMSDINATRLPAWLVDCPCVGDDVNRLLTRGER-AQNSI---CSNGLMCRVSAFAKCLIH
-SRYPPRIS---RRVIVLIMTKANCRTRLACKAMIVPLNQRLKDCRDNHRGHLANTTEVHY
PSY-FSFVNL-YPPQ--CSELCNAMH-RRGGRCER--HLNIYQCQLVCRDPQQTDLTDRV

SEQ ID NO: sequence at ~6400 in original sequence: SEQ ID NO: 614

LCDKEWGTA-MIHGKTDQTNAYGDFAPICLLISVSGQDSLIYRTFCGSPPILRIRD-NR-K
ALDAAQLSILLISHSNSNPRPLL-ITMSDINATRLPAWLVDCPCVGDDVNRLLTRGER-A
QNSI---CSNVLMCRVPAFAKCLIH-SRYPPLIS---QCMVMVLTSM-WTTQVVDNVRLGA
LSLHRK-GLQVFL--AASQLGLDDSRYFSFFLILI-NPRK-SELYYGMQYTCVCMCVCCQ
-ESV-QSERMLLSPELIDRPDCPYHCYLSATYHISHRQLL

FIG. 30C
FGENESH of reverse complement:

Compared to normal (5'- 3') complement, genes 1,2,3,5,6 are the same, but gene 4 (gene 3 in RC) is different:

SEQ ID NO: 615
>FGENESH: [mRNA]   3   11 exon (s)   3129 -   5780   1512 bp, chain -
ATGTTTGCGACATCAGATCTCTGGTATGAAGTCAGCCTGAAACCTGCCCTGTCAAGGACA
TGCGGCCGCAACCGCGACTGTGGTTGATGGTAAATCAAATGCGACGCCCAGTTCGAAAGAT
GAGACATACCTGCGCAAACAGTGATTACCACCAGCGACCTACGAGGCCTCCGTGCCAGT
CGCGCCTCGGGATTTACCGCGATGATACAAACGGAAAGTTCTTTCGCAGCGTTCCCACCC
GCGGCGGCCCCTTTGGCTTATGTCGCGGAGTACCTCAAGTCAATTCGATGAGGATAATA
GCCTCTGGCATATCCTTGCTCGTCGTTCCATTTACCGAGCGTCGAGGTCCTAGA
ACGCCGAAGACTGCAAGGACCACATGGAGAGCCTCATCCTCGGCAATGCTAGGAAGATC
TTCCCTTCAGCCAACCTCAGTTTGGTCTATCAAGGTTGGAGCAGACTTACGGCCCGTC
TATGAAATAGCCTCTGGCTTTGGCTCCAACCAGTCGTATTGAACGATCCCAAGGCTCTC
ACACACTTATTTCCAAGGACACTGTCACATATTCCTCAGCCTGCTAGGCAGAAGACATG
GGGCGAAGTTGAATAGGGAGGGTCTGTCTTCCCCCTGTCGGTCTCAGGCAATCCGCAA
TTTCACTCCTATGTGTTTGGATTCCGCCATCAGTCAGGACGGTTCCAGCTTTGAGACA
TCATGGGATTCATGTTTCCAGTTGTCAAAGCTGTATTGTCGTATGACTTCGCAACATGAGG
GAGAAATGCAGGGATAAATATTGGAAAAGCTGTATTGTCGTATGACTTCGGCAACATGAGG
GGCCATACGGTTGATCTTAGCTGACTTGGACTGCTTCCAGCAGTCAGCCCTTCAGGC
CTTACATAAGGTTTATTGTGTTAACCGCGAGAACTGGCAGGCACTTTAAAGTACTCGCG
TTACCGAAATGCCAAAGAAAGCAGTTTGAGGAGCGGCCTGAAGATAGCCCGTTCACCAATCAATC
ACTGGCTTTTCTGCGGGGGAAGCACGTGAGGCGCCCTGAAGATAGCTAACGTCCGTTATCACTTCCGAG
CTTTGGGTATGCTCAAGTCCAAAATGAAAATGCTAACGTCCGTTTATCACTTCCGAG
ATCACGGCCCAAGCTGGTGGTCTCAGTGGTCCCTCATTGAGCTTGCTGCCCGGGCAGAAATTCAAGAG
CGCCGAGCTTCCCTGCCGAACTCAAGGAGTGCTTGGCAGACGGAGAACGCCCTACATACGACCAG
ACTCTCCGTGCCAAGGATCTGAAATACCTCGATGCTTTTATATCCGAAGACCGATGTGATACCGTGACGGATCCC
CTGACAAGGATCTGAAATACCTCGATGCTTTTATATCCGAAGACCGATGTGATACCGTGACGGATCCC
TCAGAAATGGTACTAACCCGCGTGGCAGCCGAAGACGATCGACAGAGCTTGTTCGTGAGGAAAGGCCACCGTCTCC
ATACGAACTGCATCTGGAGCCGATGATCGACAGCTTGTTCGTGAGGAAAGGCCACCGTCTCC
GCATCCCTTTAG

FIG 30C CONT

SEQ ID NO: 616
>FGENESH:   3   11 exon(s)   3129 - 5780   503 aa, chain
MFATSDLWYEVSLKPALSRTCGRNRDWLMVNPNATPSSKDETYLRQTVITTATYEASVAS
RASGFTGAIQTESSPAAFPPARPLWPYVAEYLKVNSMRIIASGISLLVVVSIYRSRRGPR
TPRLQGPHMESFILGNARKIFPSANLSLVYQGLEQTYGPVYEIASGFGSNHVVLNDPKAL
THLFSKDIVTYSQPARQKDMGRKLNTEGLVFSPVGLGNPQFHSYVFGFRLSGQDGSSFET
SWDSCFQLSNNSNRAIVLDAEKCMDNIGKAVLSYDFGNMRGHTCSILADLDAFHAVSPSG
LYIRFIVFTREILYNLFKITLPNAKEKQFEELAAHFKVLATGFLREAREAPEDSAVHQSI
LGVMLKSKMENANVRLSLPEITAQAGGIVLAGYETTAKIHRRAFPQWSLIELARRAEIQE
TLRAELKECLADGERPTYDQLIKDLKYLDAFISEILRLHPSEMVLTRVAAEDDVIPLTDP
IRIASGAMIDSLFVRKGTVSASL

FIG. 30D

New blastp result: (quite different)

```
gb|EAU91561.1|   hypothetical protein CC1G_02050 [Coprinopsis c...    127    2e-27
gb|EAU85619.1|   hypothetical protein CC1G_06332 [Coprinopsis c...    97.8   1e-18
gb|EAU81974.1|   hypothetical protein CC1G_09160 [Coprinopsis c...    92.8   6e-17
ref|XP_569261.1| hypothetical protein [Cryptococcus neoforman...      84.0   2e-14
ref|XP_777488.1| hypothetical protein CNBB0620 [Cryptococcus ...      80.9   2e-13
gb|EAU84038.1|   hypothetical protein CC1G_12478 [Coprinopsis c...    76.6   4e-12
ref|XP_001622363.1| hypothetical protein NEMVEDRAFT_v1g176175...      74.7   2e-11
ref|XP_001602787.1| PREDICTED: similar to cytochrome P450 [Nason     73.6   3e-11
gb|AAY20974.1|   astaxanthin synthetase [Xanthophyllomyces dend...    72.8   6e-11
ref|XP_571276.1| Cytochrome P450 [Cryptococcus neoformans var...      72.4   6e-11
gb|EAU83493.1|   hypothetical protein CC1G_04749 [Coprinopsis c...    72.4   8e-11
ref|XP_774660.1| hypothetical protein CNBF3400 [Cryptococcus ...      72.0   8e-11
ref|XP_001603146.1| PREDICTED: similar to cytochrome P450 [Nason     71.6   1e-10
ref|XP_970215.1| PREDICTED: similar to Probable cytochrome P4...      71.6   1e-10
```

IDENTIFICATION AND USE OF GENES ENCODING AMATOXIN AND PHALLOTOXIN

This application claims priority to U.S. Provisional Application Ser. No. 61/002,650, filed on Nov. 9, 2007.

GOVERNMENT INTERESTS

This invention was made with government support under DE-FG02-91ER20021 awarded by the U.S. Department of Energy. The government has certain rights in the invention.

FIELD OF THE INVENTION

The present invention relates to compositions and methods comprising genes and peptides associated with cyclic peptide toxins and toxin production in mushrooms. In particular, the present invention relates to using genes and proteins from *Amanita* species encoding *Amanita* peptides, specifically relating to amatoxins and phallotoxins. In a preferred embodiment, the present invention also relates to methods for detecting *Amanita* peptide toxin genes for identifying *Amanita* peptide-producing mushrooms and for diagnosing suspected cases of mushroom poisoning. Further, the present inventions relate to providing kits for diagnosing and monitoring suspected cases of mushroom poisoning in patients.

BACKGROUND

More than 90% of human deaths resulting from mushroom poisoning are due to peptide toxins found in *Amanita* species of mushrooms, such as *A. phalloides, A. bisporigera, A. ocreata*, and *A. virosa*. Animals, especially dogs, are frequent victims of poisoning by *Amanita* mushrooms. Recently, two dogs died after eating toxin containing mushrooms in Michigan in the last few months, See Schneider: Mushroom in backyard kills curious puppy, Lansing State Journal, Sep. 30, 2008 (at lansingstatejournal.com.apps/pbcs.dll/article?AID=/20080930/COLUMNISTS09/809300321.

High concentrations of peptide toxins are found in the above ground mushroom portion (otherwise known as carpophores or fruiting bodies) of the toxin producing *Amanita* species. These toxins include two major families of compounds called amatoxins (for example, α-amanitin, FIG. 1A) and phallotoxins (for example, phalloidin, phallacidin, FIG. 1B). Both classes of compounds are bicyclic peptides with a Cys-Trp cross-bridge. In general, amatoxins are 8 amino acids in length while phallotoxins are 7 amino acids in length. Although phallotoxins are toxic when injected, phallotoxins do not survive the human intestinal tract and therefore are usually not responsible for deadly mushroom poisonings in humans and animals. On the other hand, amatoxins do survive cooking and remain intact in the intestinal tract where they are absorbed into the body where large doses irreversibly damage the liver. Liver failure due to poisoning by amatoxins can be "cured" only with a liver transplant (Enjalbert et al., (2002) J. Toxicol. Clin. Toxicol. 40:715; herein incorporated by reference).

There are an estimated 900-1000 species of *Amanita*, of which the majority do not produce amatoxins or phallotoxins and some are actually safe for humans to eat (Bas, (1969) Persoonia 5:285; Tulloss et al., (2000) Micologico G. Bresadola, 43:13; Weiβ et al., (1998) Can J. Bot. 76:1170; all of which are herein incorporated by reference). Thus mere ingestion of an *Amanita* mushroom may not herald the need for the extreme medical treatment necessary to save a patient.

Even experienced mycologists may not be able to distinguish edible from poisonous mushrooms even with microscopic examination (EMedicine webmd at hypertext transfer protocol site: emedicine.com/ and hypertext transfer protocol site: emedicine.com/emerg/topic874.htm.

Thus physicians and veterinarians need to be able to directly and quickly confirm whether a patient or an animal showing gastrointestinal symptoms of unknown origin, or who has accidentally eaten an unknown mushroom, is in danger of serious illness or death from eating a deadly poisonous mushroom containing amatoxins.

SUMMARY OF THE INVENTION

The present invention relates to compositions and methods comprising genes and peptides associated with cyclic peptide toxins and toxin production in mushrooms. In particular, the present invention relates to using genes and proteins from *Amanita* species encoding *Amanita* peptides, specifically relating to amatoxins and phallotoxins. In a preferred embodiment, the present invention also relates to methods for detecting *Amanita* peptide toxin genes for identifying *Amanita* peptide-producing mushrooms and for diagnosing suspected cases of mushroom poisoning. Further, the present inventions relate to providing kits for diagnosing and monitoring suspected cases of mushroom poisoning in patients.

The present invention provides an isolated nucleic acid sequence comprising at least one sequence set forth in SEQ ID NOs: 1-4, 55-56, 79-81, 85-86, and 95-96. In one embodiment, the nucleic acid encodes a polypeptide comprising at least one sequence set forth in SEQ ID NOs: 50, 113, 118, 121-132, and 135. In one embodiment, the nucleic acid sequence comprises a sequence at least 50% identical to any sequence set forth in SEQ ID NOs: 82-87. In one embodiment, the nucleic acid sequence encodes a peptide set forth in any one of SEQ ID NOs: 136-151 and 80. In one embodiment, the nucleic acid sequence comprises SEQ ID NOs: 86-87. In one embodiment, the polypeptide is selected from the group consisting of IWGIGCNP (SEQ ID NO: 50) and AWLVDCP (SEQ ID NO: 69). In one embodiment, the invention provides a polypeptide encoded by the nucleic acid sequences SEQ ID NOs: 55-56, 79-81, and 85-86.

The present invention provides a composition comprising a nucleic acid sequence, wherein said nucleic acid sequence comprises at least one sequence set forth in SEQ ID NOs: 1-4, 55-56, 79-81, 85-86, and 95-96.

The present invention provides a composition comprising a polypeptide, wherein said polypeptide is encoded by a nucleic acid sequence comprising at least one sequence set forth in SEQ ID NOs: 55-56, 79-81, and 85-86.

The present invention provides a set of at least two polymerase chain reaction primer sequences, wherein said primers are capable of amplifying a mushroom nucleic acid sequence associated with encoding an *Amanita* toxin. In one embodiment, the two polymerase chain reaction primer sequences are selected from the group SEQ ID NOs: 1-4, 95-96.

The present invention provides a method of identifying a toxin producing mushroom, comprising, a) providing, i) a sample, ii) a set of at least two polymerase chain reaction primers, wherein said primers are capable of amplifying a mushroom nucleic acid sequence associated with encoding a toxin, and iii) a polymerase chain reaction, b) mixing said sample with said set of polymerase chain reaction primers, c) completing a polymerase chain reaction under conditions capable of amplifying a mushroom nucleic acid sequence associated with encoding a toxin, and d) testing for an amplified toxin associated sequence for identifying a toxin producing mushroom. In one embodiment, the testing comprises detecting the presence or absence of an amplified mushroom nucleic acid sequence. In one embodiment, the sample is selected from the group consisting of a raw sample, a cooked sample, and a digested sample. In one embodiment, the sample comprises a mushroom sample. In one embodiment, the sample is obtained from a subject. The subject may be any mammal, e.g., the subject may be a human. In one embodiment, the set of polymerase chain reaction primer sequences may identify any *Amanita* peptide. In one embodiment, the set of polymerase chain reaction primer sequences may identify an amanitin peptide. In one embodiment, the set of polymerase chain reaction primer sequences are selected from the group consisting of SEQ ID NOs: 1-4, 95-96.

The present invention provides a diagnostic kit for identifying a poisonous mushroom, providing, comprising, a set of at least two polymerase chain reaction primers, wherein said primers are capable of amplifying a mushroom nucleic acid sequence associated with producing a toxin. In one embodiment, the two polymerase chain reaction primer sequences are selected from the group consisting of SEQ ID NOs: 1-4, 95-96. In one embodiment, the kit further comprises a nucleic acid sequence associated with producing a mushroom toxin, wherein said nucleic acid sequence is capable of being amplified by said polymerase chain reaction primers. In one embodiment, the kit further comprises instructions for amplifying said mushroom nucleic acid sequence. In one embodiment, the kit further comprises instructions for detecting the presence or absence of an amplified mushroom nucleic acid sequence. In one embodiment, the kit further comprises instructions for identifying the species of an amplified mushroom nucleic acid sequence.

The present invention provides a polypeptide, wherein said polypeptide is encoded by a sequence derived from a fungal species. In one embodiment, the polypeptide is an isolated polypeptide. In one embodiment, the isolated polypeptide is isolated from a cell. In one embodiment, the cell includes but is not limited to a fungal cell and a bacterial cell. In one embodiment, the isolated polypeptide is a synthetic polypeptide. It is not meant to limit the sequence of the polypeptide. In one embodiment, the polypeptide includes but is not limited to a polypeptide comprising a toxin sequence. In one embodiment, the polypeptide comprises at least one preprotein sequence set forth in SEQ ID NOs: 50, 110, 113, 118, 121-132, 135, 249, 303-306, 308-318. In one embodiment, the polypeptide is a MDIN amino acid sequence. In one embodiment, the polypeptide comprises a toxin amino acid sequence. In one embodiment, the polypeptide comprises IWGIGCNP (SEQ ID NO: 50) and AWLVDCP (SEQ ID NO: 69). In one embodiment, the polypeptide comprises at least one sequence set forth in SEQ ID NOs: 249, and 318. In one embodiment, the polypeptide is linear. In one embodiment, the polypeptide is cyclic. In one embodiment, the polypeptide comprises at least one sequence set forth in 110, 303-306, 308-317. In one embodiment, the polypeptide includes but is not limited to a polypeptide comprising a prolyloligopeptidase sequence. In one embodiment, the prolyloligopeptidase sequence comprises at least one sequence set forth in SEQ ID NOs: 54, 69, 236, 237, 250-256, 258-276.

A composition, comprising a polypeptide, wherein said polypeptide is encoded by a sequence derived from a fungal species.

A method, comprising a polypeptide, wherein said polypeptide is encoded by a sequence derived from a fungal species.

The present invention provides an antibody having specificity for a preproprotein comprising a toxin sequence, wherein said preproprotein is encoded by a nucleotide sequence derived from a fungal species. In one embodiment, the preproprotein includes but is not limited to SEQ ID NOs: 50, 110, 113, 118, 121-132, 135, 249, 303-306, 308-318. In one embodiment, the toxin includes but is not limited to a cyclic toxin, a linear amino acid sequence of a cyclic toxin, a portion of a linear amino acid sequence of a cyclic toxin. In one embodiment, the toxin includes but is not limited to an amatoxin and phallotoxin. In one embodiment, the toxin includes but is not limited to an amanitin. In one embodiment, the toxin includes but is not limited to an alpha, beta, gamma, etc., amanitin. In one embodiment, the toxin includes but is not limited to 110, 246, 303-306, 308-117.

A composition, comprising an antibody having specificity for a preproprotein comprising a toxin sequence, wherein said preproprotein is encoded by a nucleotide sequence derived from a fungal species.

A method, comprising an antibody having specificity for a preproprotein comprising a toxin sequence, wherein said preproprotein is encoded by a nucleotide sequence derived from a fungal species.

The present invention provides an antibody having specificity for a toxin encoded by a nucleotide sequence derived from a fungal species. In one embodiment, the toxin includes but is not limited to a cyclic toxin, a linear amino acid sequence of a cyclic toxin, a portion of a linear amino acid sequence of a cyclic toxin. In one embodiment, the toxin includes but is not limited to an amanitin and a phallotoxin. In one embodiment, the toxin includes but is not limited to an alpha, beta, gamma, etc., amanitin. In one embodiment, the toxin includes but is not limited to SEQ ID NOs. 110, 303-306, 308-317. In one embodiment, the antibody includes but is not limited to a polyclonal antibody and a monoclonal antibody. In one embodiment, the antibody includes but is not limited to a rat, rabbit, mouse, chicken antibody.

A composition, comprising an antibody having specificity for a toxin encoded by a nucleotide sequence derived from a fungal species.

A method, comprising an antibody having specificity for a toxin encoded by a nucleotide sequence derived from a fungal species.

The present invention provides an isolated prolyloligopeptidase protein, wherein said prolyloligopeptidase protein is encoded by nucleic acid sequence derived from a fungal species. In one embodiment, the prolyloligopeptidase includes but is not limited to a prolyloligopeptidase, prolyloligopeptidase A, prolyloligopeptidase B, and fragments thereof. In one embodiment, the prolyloligopeptidase A comprises any one sequence set forth in SEQ ID NOs. 69, 250-256, 258-276. In a preferred embodiment, the prolyloligopeptidase B comprises any one sequence set forth in SEQ ID NOs. 54, 252, 256, 261, 267, 270, 271, 273, 276, 280-282, 286, 288-293, 296-297, 302.

A composition, comprising an isolated prolyloligopeptidase protein, wherein said prolyloligopeptidase protein is encoded by nucleic acid sequence derived from a fungal species.

A method, comprising an isolated prolyloligopeptidase protein, wherein said prolyloligopeptidase protein is encoded by nucleic acid sequence derived from a fungal species.

The present invention provides an antibody having specificity to a prolyloligopeptidase protein, wherein said prolyloligopeptidase protein is encoded by a nucleotide sequence derived from a fungal species. In one embodiment, the prolyloligopeptidase includes but is not limited to a prolyloligopeptidase, prolyloligopeptidase A prolyloligopeptidase B, and fragments thereof. In one embodiment, the prolyloligopeptidase A comprises any one sequence set forth in SEQ ID NOs. 69, 250-256, 258-276. In a preferred embodiment, the prolyloligopeptidase B comprises any one sequence set forth in SEQ ID NOs. 54, 252, 256, 261, 267, 270, 271, 273, 276, 280-282, 286, 288-293, 296-297, 302.

A composition, comprising a mushroom P450 protein.

A method, comprising a mushroom P450 protein.

DESCRIPTION OF THE FIGURES

FIG. 2 shows exemplary fungi of the genus Amanita. A. A. bisporigera (collected in Oakland County, Michigan). B: A. phalloides (Alameda County, California). C: Non-deadly species of Amanita. From left to right: three specimens of A. gemmata, A. muscaria, and two specimens of A. franchetii (Mendocino County, California).

FIG. 4 shows exemplary amanitin (an amatoxin) cDNA sequences, genomic DNA sequences, prepropolypeptide sequences, and polypeptide sequences coding for peptide toxins, A) shows exemplary cDNA sequences of the α-amanitin gene and predicted amino acid sequence, where 5' and 3' ends were determined by Rapid amplification of cDNA ends (RACE). * indicates a stop codon. The string of A's at the end are a contemplated poly-A tail. The amatoxin peptide sequence is underlined. B) shows an exemplary sequence of genomic DNA covering the amanitin gene based on inverse PCR. The nucleotides encoding the amanitin peptide are underlined.

FIG. 5 shows exemplary phallacidin cDNA, genomic DNA, propolypeptide, and polypeptide sequences encoding phallacidin peptide toxin. A) shows exemplary cDNA sequences and predicted amino acid sequence, where 5' and 3' ends were determined by RACE, * indicates the stop codon. The string of A's at the end are the poly-A tail and were not found encoded within the genomic DNA, and B) shows an exemplary genomic nucleic acid coding regions for phallacidin sequence #1, 1893 bp. SacI and phallacidin sequence #2, 1613 nt. PvuI where the nucleotides encoding a phallacidin peptide were underlined. These two genomic sequences encoding a phallacidin peptide were obtained by inverse PCR and confirmed by sequencing both strands.

FIG. 6 shows an exemplary alignment of a (A) cDNA nucleotide and (B) predicted amino acid sequences of exemplary coding regions of AMA1 and PHA1 proproteins, the mature toxin sequences were underlined, and (C) shows homologous regions in nucleic acids from other species to coding regions of AMA1 and PHA1 proproteins (BLAST results).

FIG. 7 shows exemplary fragment DNA sequences from *A. bisporigera* that contain conserved motifs of the amanitin and phallacidin genes. Each DNA sequence is followed by the translation of the presumed correct reading frame. Conserved upstream and downstream amino acid sequences with known and putative toxin sequences underlined.

FIG. 8 shows exemplary DNA blots of different species of *Amanita*. (A) Probed with AMA1 cDNA. (B) Probed with PHA1 cDNA. (C) Probed with a fragment of the β-tubulin gene isolated from *A. bisporigera* (19). (D) Ethidium-stained gel showing relative lane loading. Markers are lambda cut with BstEII. Species and provenances: Lane 1, *A.* aff. *suballiacea* (Ingham County, Michigan); lane 2, *A. bisporigera* (Ingham County); lane 3, *A. phalloides* (Alameda County, California); lane 4, *A. ocreata* (Sonoma County, California); lane 5, *A. novinupta* (Sonoma County); lane 6, *A. franchetii* (Mendocino County, California); lane 7, *A. porphyria* (Sonoma County); lane 8, a second isolate of *A. franchetii* (Sonoma County); lane 9, *A. muscaria* (Monterey County, California); lane 10, *A. gemmata* (Mendocino County); lane 11, *A. hemibapha* (Mendocino County); lane 12, *A. velosa* (Napa County, California); lane 13, *A.* sect. *Vaginatae* (Mendocino County). Mushrooms represent sect. Phalloideae (#'s 1-4), sect. Validae (#'s 5-8), sect. *Amanita*(#'s 9-10), sect. *Caesarea* (#11), sect. *Vaginatae* (#'s 12-13). Four separate gels were run; the lanes are in the same order on each gel and approximately the same amount of DNA was loaded per lane. A and B are to the same scale, and C and D are to the same scale.

FIG. 9 shows an exemplary schematic of a WebLogo (Crooks et al., 2004, herein incorporated by reference) showing a representation of amino acid frequency within at least 15 predicted "MSDIN" sequences from DNA sequences of *Amanita* species.

FIG. 10 shows an exemplary correlation of toxin genes and expression with toxin producing species of mushrooms in addition to a schematic of types of genes discovered near toxin producing genes in at least one lambda clone from a toxin producing mushroom. A) and B) Southern blot of DNA from species of *Amanita* that do (*A. bisporigera* and *A. phalloides*) or do not (*A. gemmata, A. muscaria, A. flavoconia, A. section Vaginatae*, and *A. hemibapha*) make amatoxin (probe used in A) and phallotoxin (probe used in B); C) PCR amplification of the gene for α-amanitin. Primers were based on the sequences in FIG. 4. *A. gemmata* and *A. muscaria* are species of *Amanita* that do not make amatoxins (or phallotoxins). *A. bisporigera* #'s 1-3 are three different isolates of *A. bisporigera*; and D) Exemplary Schematic Map of *Amanita* bisporigera genes in a lambda clone (13.4 kb) isolated using PHA1 as probe; showing two copies of PHA1 clustered with each other and with three P450 genes, NOTE: p450 genes were predicted using the *Coprinus* model however *Coprinus* doesn't have a PHA1 gene.

FIG. 11 shows exemplary sequences found in genomic sequencing of *Galerina* (*G. marginata*, Gm) A) Nucleic Acid Sequences (GmAM1) and B) Amino acid sequences deduced from sequences in A (GmAM1). (.=nonsense codon)

FIG. 12 shows exemplary *Galerina marginata* amanitin (GmAM1) preproprotein amino acid sequence alignment between *Galerina* and *Amanita* including A) alpha-amanitin toxins alpha-amanitin/gamma-amanitin from *Amanita* compared to alpha-amanitin/gamma-amanitin from *Galerina* and B) a Southern blot of *Galerina* (*G.*) *marginata* (m) (Gm) DNA probed with GmAM1 under high stringency conditions.

Figure 13:
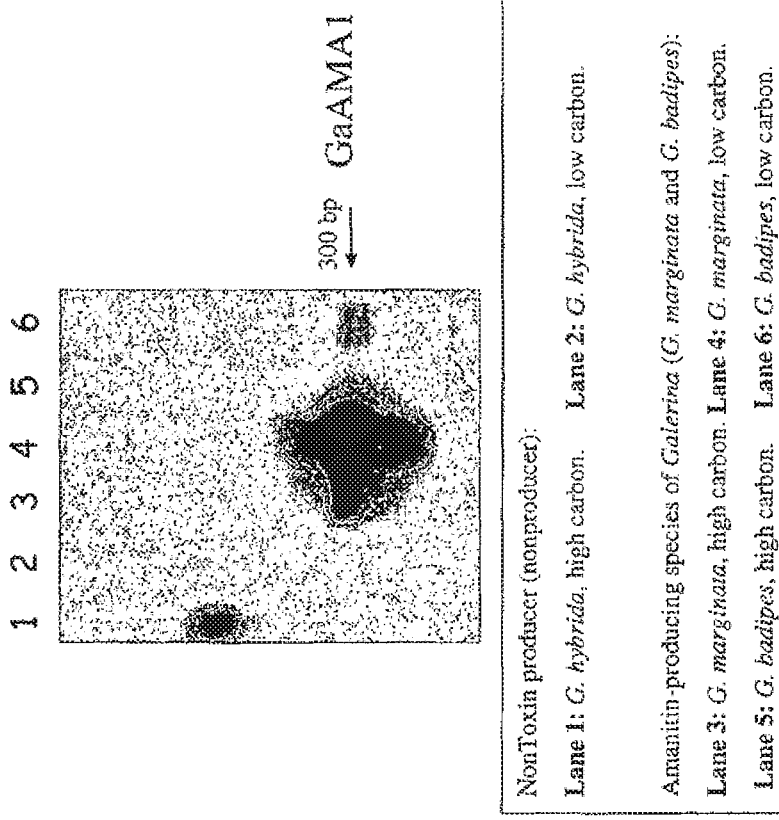

FIG. 13 shows an exemplary RNA blot of the *Galerina marginata* amanitin gene (GmAMA1). The results show that the gene is expressed in two known amanitin-producing species of *Galerina* (*G. marginata* and *G. badipes*) but not in a species that is a nonproducer of toxin (*G. hybrida*). Induction of gene expression was triggered by low carbon growth conditions. Lane 1: *G. hybrida*, high carbon. Lane 2: *G. hybrida*, low carbon. Lane 3: *G. marginata*, high carbon. Lane 4: *G. marginata*, low carbon. Lane 5: *G. badipes*, high carbon. Lane 6: *G. badipes*, low carbon. The probe was *G. marginata* AMA1 gene (GmAMA1) predicted to encode alpha-amanitin (FIG. 4). Each lane was loaded with 15 ug total RNA. Fungi were grown in liquid culture for 30 d on 0.5% glucose (high carbon) then switched to fresh culture of 0.5% glucose or 0.1% glucose (low carbon) for 10 d before harvest. The major band in lanes 3-6 is ~300 bp. The high MW signal in lane 1 is spurious.

FIG. 14 shows exemplary *Galerina marginata* amanitin sequences (GmAMA1) found in genomic sequencing of *Galerina* (*G. marginata*, Gm). A) Nucleic Acid Sequences (GmAM1), B) Amino acid sequences deduced from sequences in A (GmAM1). (.=nonsense codon), and C) amino acid sequence alignment of two *Galerina* amanitins (GaAMA1 above SEQ ID NO.244, GmAMA2 below, SEQ ID NO.248).

FIG. 15 shows exemplary BLASTP results using human prolyloligopeptidase (POP) as query against fungi in GenBank. The results indicate that an ortholog of human POP exists in at least some Homobasidiomycetes (*Coprinus*) and Heterobasidiomycetes (*Ustilago* and *Cryptococcus*) and few other fungal species showing various levels of significant identity and where scores and e-values of the two *Aspergillus* fungal sequences were considered statistically insignificant.

FIG. 16 shows exemplary prolyloligopeptidase (POP)-like homologs in fungi with strong amino acid sequence similarity to human prolyloligopeptidase (gi:41349456). Shown are the DNA sequences and the alignments of the human protein (query) with each predicted translation product from *A. bisporigera* (subject).

FIG. 17 shows A) two exemplary prolyloligopeptidase (POP)-like *A. bisporigera* genome sequences POPA and POPB, B) two exemplary cDNA sequences for POPA and POPB, and C) two exemplary amino acid sequences for POPA and POPB.

FIG. 18 shows exemplary Southern blot of different *Amanita* species probed with (A) POPA or (B) POPB of *A. bisporigera*. DNA was from the same species of mushroom in lanes of the same order as FIG. 8, herein, and FIG. 5 in Hallen et al., 2007, *Proc. Natl. Acad. Sci. USA* 104: 19097-19101, herein incorporated by reference. Lanes 1-4 are *Amanita* species in sect. Phalloideae and the others are toxin non-producers. Note the presence of POPA and absence of POPB in sect. Validae (lanes 5-8), the sister group to sect. Phalloideae (lanes 1-4). the weaker hybridization of POPA to the *Amanita* species outside sect. Phalloideae (lanes 5-13) to lower DNA loading and/or lower sequence identity due to taxonomic divergence (cf. FIG. 5 in Hallen et al., 2007, *Proc. Natl. Acad. Sci. USA* 104: 19097-19101, herein incorporated by reference). POPB does not hybridize to any species outside sect. Phalloideae even after prolonged autoradiographic exposure.

FIG. 19 shows exemplary purified POPB protein isolated from *Conocybe albipes* separated by standard SDS-PAGE gel electrophoresis and Coomassie dye stained to show the location of protein.

Figure 20:
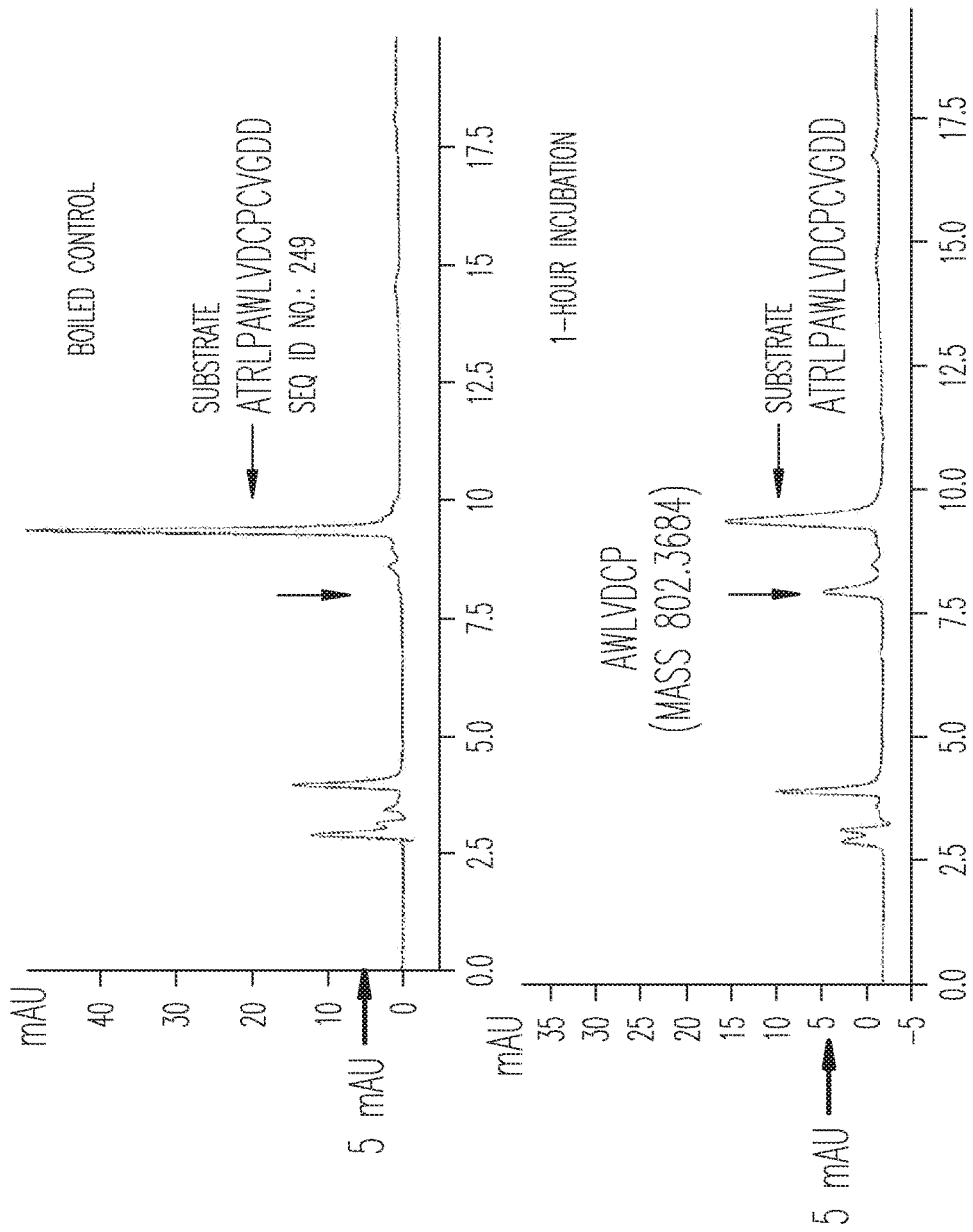

FIG. 20 shows exemplary A) HPLC analysis of an enzymatic reaction of POPB with a boiled isolate of POPB showing no cleavage product at the vertical arrow where a AWLVDCP (SEQ ID NO: 69) should be found and B) cleavage of a synthetic phallacidin precursor by purified *Conocybe albipes* POPB enzyme (see, FIG. 19) showing a cleavage product matching AWLVDCP (SEQ ID NO: 69) at the vertical arrow. The results show that purified POPB cuts a synthetic amanatin peptide precisely at the expected flanking Pro residues.

FIGS. 21A-21B shows exemplary expression of POPB in *E. coli* and production of anti-POPB antibodies. FIG. 21A shows Lanes 1-3: stained with Coomassie Blue. FIG. 21B shows Lanes 4-5 with antibody binding visualized by enhanced chemiluminescence. Lane 1: Markers. Lane 2: POPB purified from inclusion bodies. Lane 3: Soluble extract of Amanita bisporigera. Lane 4: immunoblot of POPB inclusion body. Lane 5: immunoblot of Amanita extract. Crude antiserum was used at 1:5000 dilution.

Figure 22A-2:
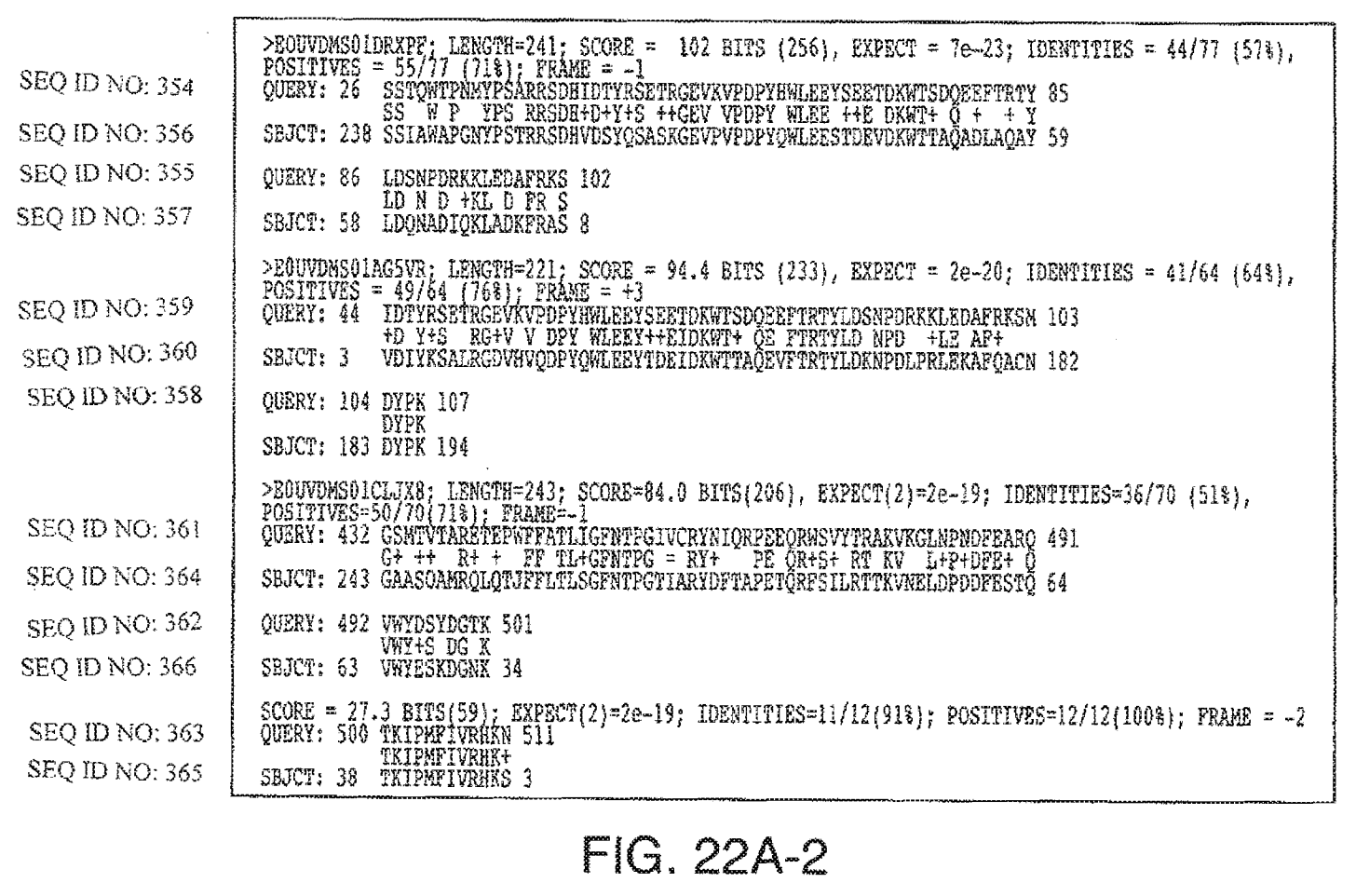
Figure 22A-6:
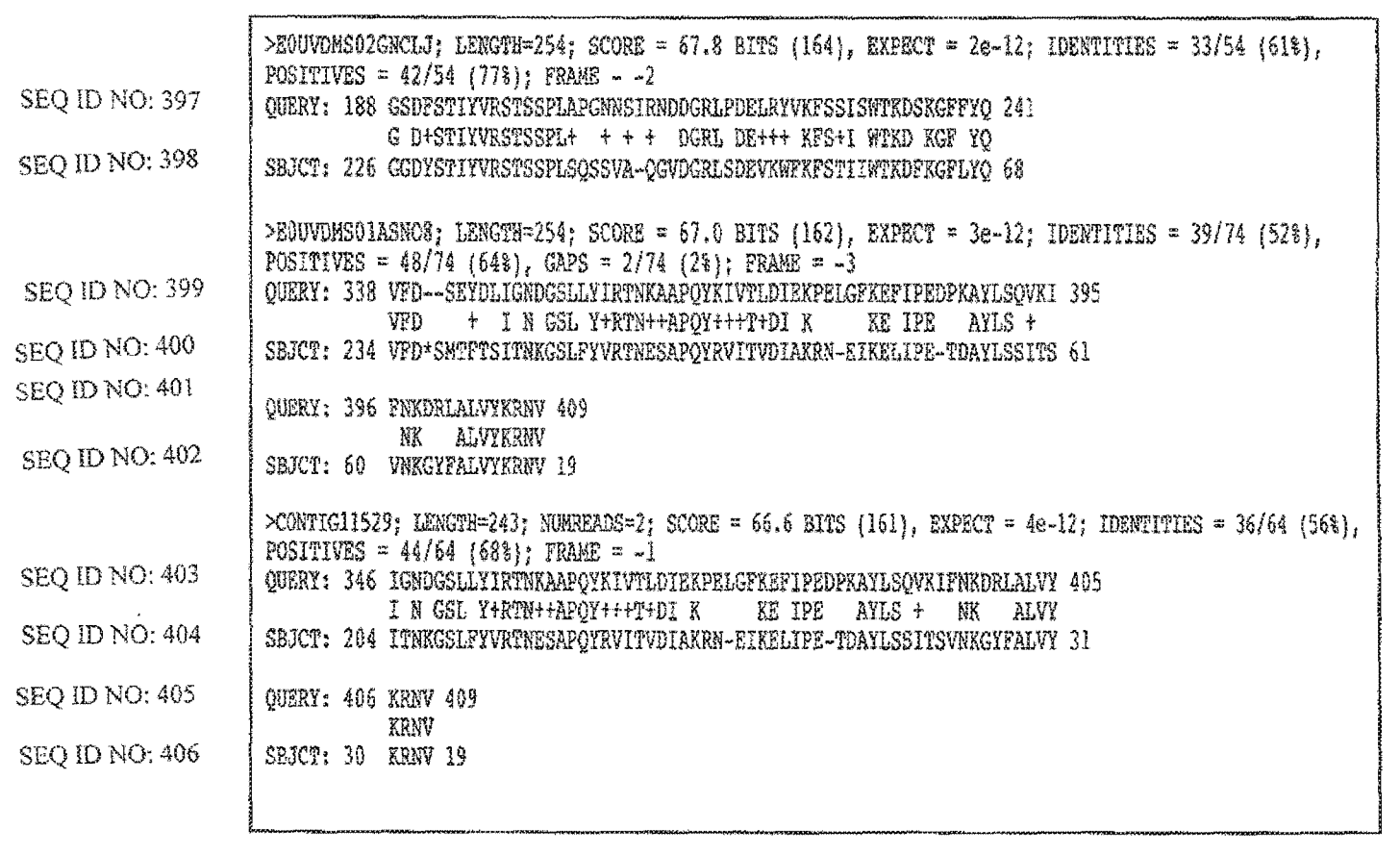
Figure 22A-9:
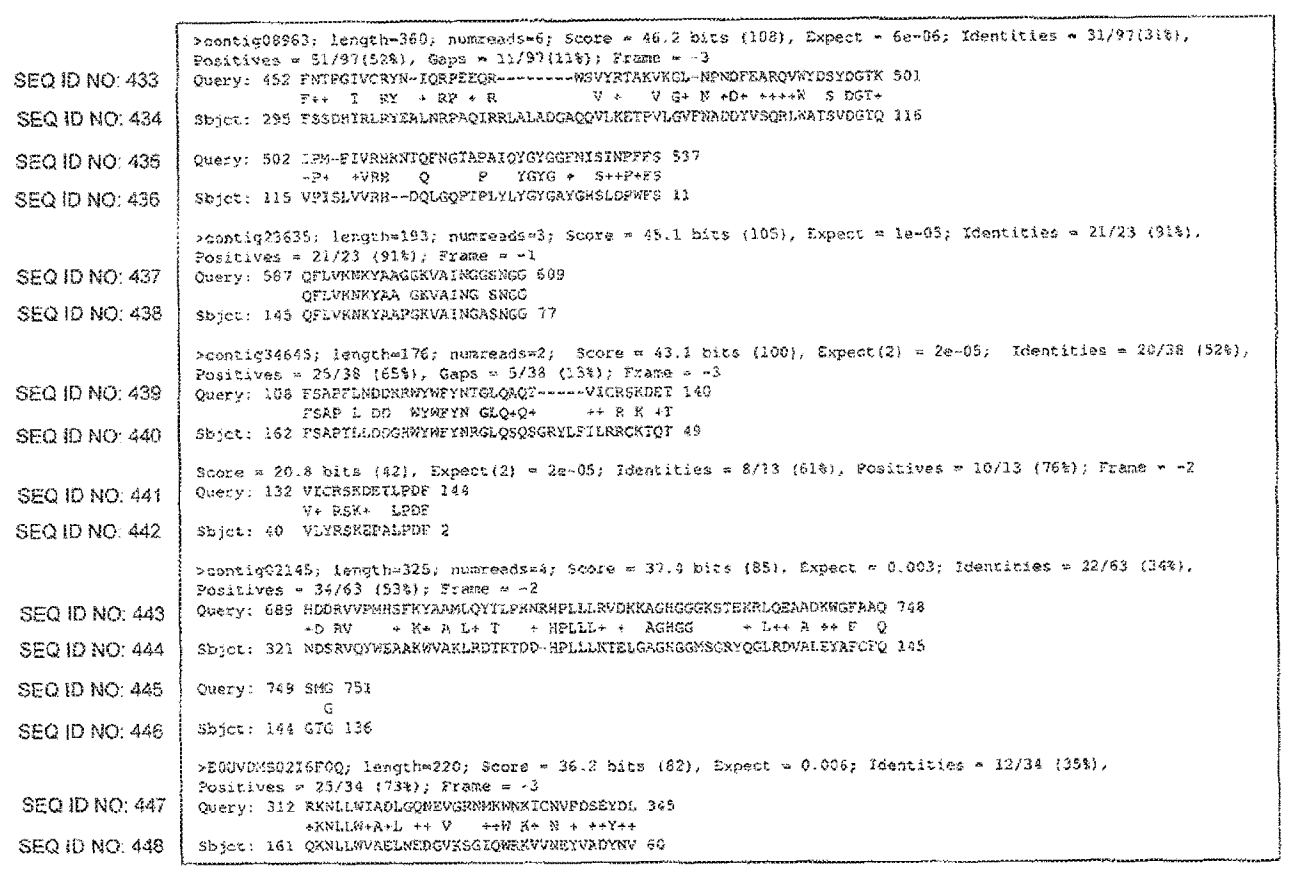
Figure 22B-4:
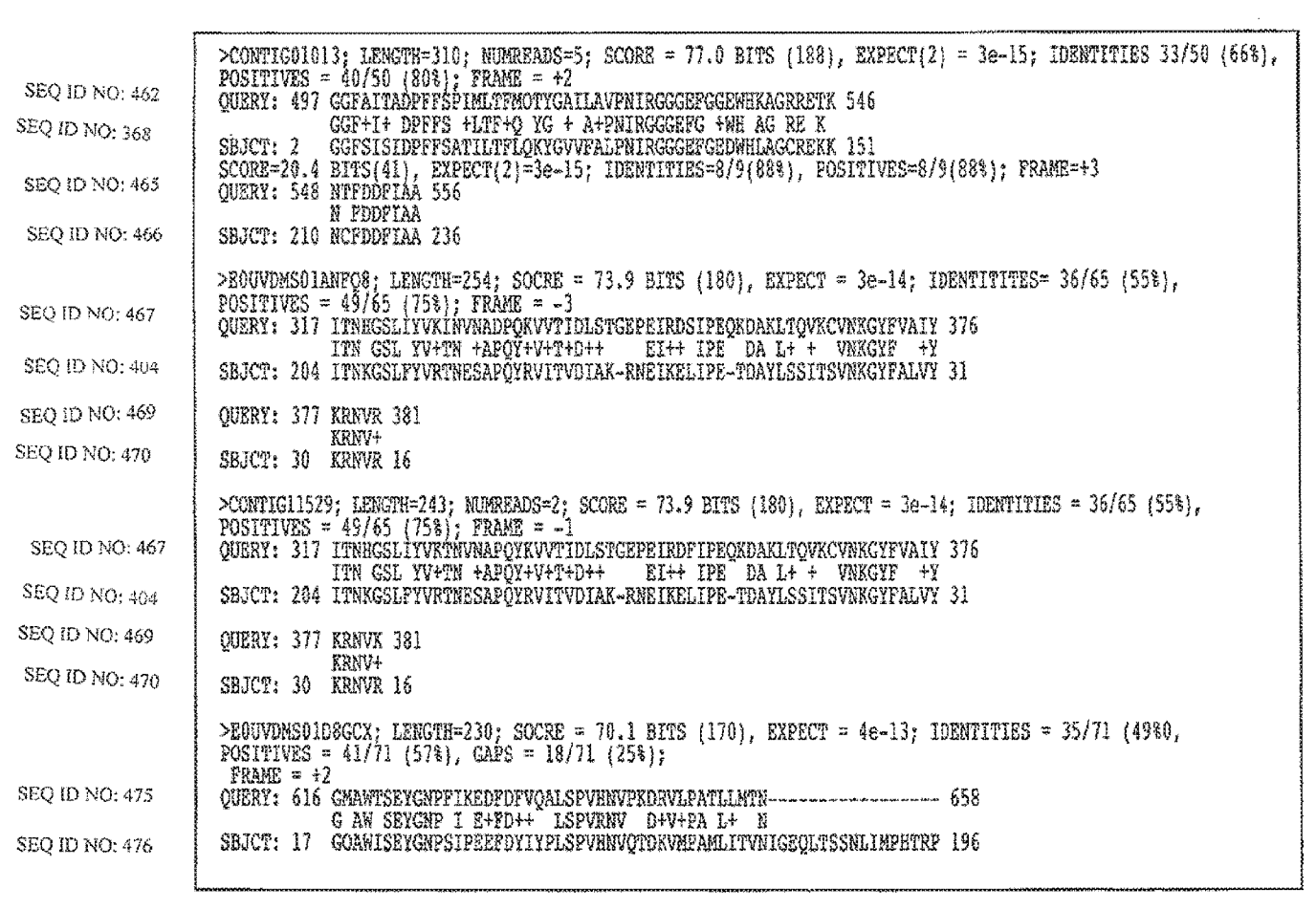
Figure 22B-6:
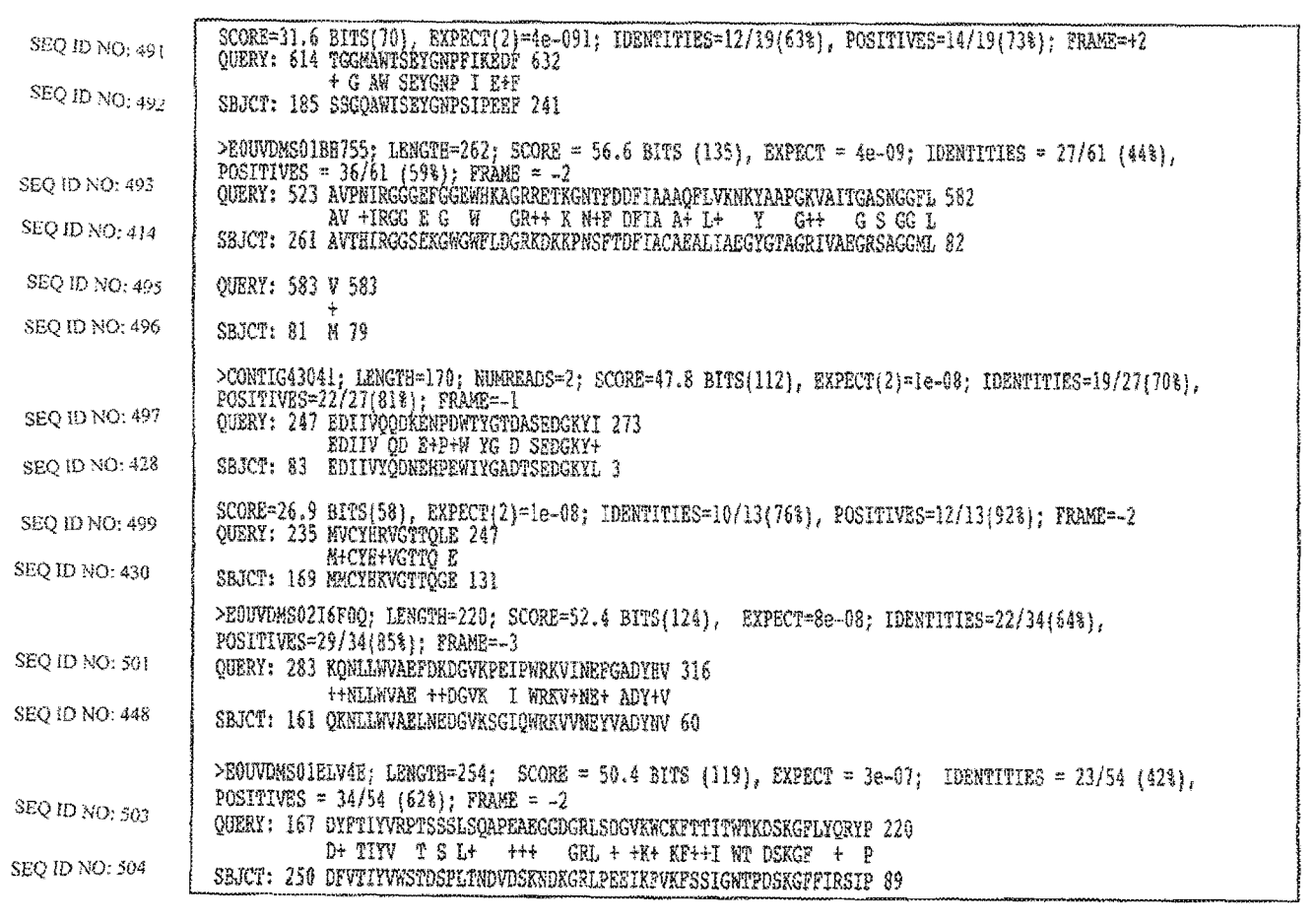

FIG. 22 shows exemplary *Galerina* POP sequences identified using *Amanita* bisporigera A) POPA and B) POPB as query sequences for searching a library of *Galerina* sequences created by the inventors for their use during the development of the present inventions. The higher scoring hits were strong evidence that the *Galerina* genome contains at least two POP genes.

FIG. 23 shows exemplary sequences found in the genomic schematic sequence of FIG. 10D inserted into a lambda clone; 13,254 bp lambda clone [red/underlined sequences (portions) are two copies of PHA1 encoding phallacidin] 5'-3' orientation, (SEQ ID NO: 327).

FIG. 24 shows an exemplary FGENESH 2.5 Prediction of potential genes in *Coprinus* genomic DNA of SEQ ID NO:XX.

FIG. 25 shows an exemplary contemplated P450 gene sequence, A) P450-1 (OP451) and putative encoded amino acid sequences, B) blastp results of Predicted protein(s): P450-1 (OP451), C), BLASTP of OP45-1 against *Coprinus* sequences at Broad, D) BLASTP of OP451 against *Laccaria* genomic sequences and E), OP451 as a query sequence for a BLASTP against nr, showing an excellent hit against a *Coprinus* protein.

Figure 26C:

FIG. 26 shows an exemplary contemplated P450 gene sequence, A) P450-2 (OP452) and putative encoded amino acid sequences, B) blastp results of Predicted protein(s): P450-2 (OP452), C), BLASTP of P450-2 (OP452) against *Coprinus* at Broad, and D) BLASTP of P450-2 (OP452) against *Laccaria* genomic sequences.

FIG. 27 shows an exemplary FGENESH mRNA and protein 3 resulting in no hits to any of the BLAST searches. This region overlaps with PHA1-1, which is on + strand (gene 3 is on − strand).

FIG. 28 shows an exemplary contemplated P450 gene sequence, A) P450-3 (OP453) and putative encoded amino acid sequences, B) blastp results of Predicted protein(s): P450-3 (OP453), C), BLASTP of P450-3 (OP453) against *Coprinus* at Broad, and D) BLASTP of P450-3 (OP453) against *Laccaria* genomic sequences.

FIG. 29 shows exemplary A) PHA1-2 as described herein (5th identified sequence) and B) a 6th identified sequence FIG. 30 shows exemplary A) alignments of P450 genes 1,2,4 corresponding to OP451, OP452 and OP453 and B) exemplary sequences from the entire lambda clone reverse complement (3'-5') and C) FGENESH of reverse complement showing a different gene 4, which is gene 3 in the reverse complement, resulting in D) a new set of exemplary gene identities.

DEFINITIONS

To facilitate an understanding of the present invention, a number of terms and phrases as used herein are defined below:

The use of the article "a" or "an" is intended to include one or more.

As used herein, terms defined in the singular are intended to include those terms defined in the plural and vice versa.

As used herein the term "microorganism" refers to microscopic organisms and taxonomically related macroscopic organisms within the categories of algae, bacteria, fungi (including lichens), protozoa, viruses, and subviral agents.

The terms "eukaryotic" and "eukaryote" are used in the broadest sense. It includes, but is not limited to, any organisms containing membrane bound nuclei and membrane bound organelles. Examples of eukaryotes include but are not limited to animals, plants, algae, diatoms, and fungi.

The terms "prokaryote" and "prokaryotic" are used in the broadest sense. It includes, but is not limited to, any organisms without a distinct nucleus. Examples of prokaryotes include but are not limited to bacteria, blue-green algae (cyanobacteria), archaebacteria, actinomycetes and mycoplasma. In some embodiments, a host cell is any microorganism.

As used herein, the term "fungi" is used in reference to eukaryotic organisms such as mushrooms, rusts, molds and yeasts, including dimorphic fungi. "Fungus" or "fungi" also refers to a group of lower organisms lacking chlorophyll and dependent upon other organisms for source of nutrients.

As used herein, "mushroom" refers to the fruiting body of a fungus.

As used herein, "fruiting body" refers to a reproductive structure of a fungus which produces spores, typically comprising the whole reproductive structure of a mushroom including cap, gills and stem, for example, a prominent fruiting body produced by species of Ascomycota and Basidiomycota, examples of fruiting bodies are "mushrooms," "carpophores," "toadstools," "puffballs", and the like.

As used herein, "fruiting body cell" refers to a cell of a cap or stem which may be isolated or part of the structure.

As used herein, "spore" refers to a microscopic reproductive cell or cells.

As used herein, "mycelium" refers to a mass of fungus hyphae, otherwise known as a vegetative portion of a fungus.

As used herein, "Basidiomycota" in reference to a Phylum or Division refers to a group of fungi whose sexual reproduction involves fruiting bodies comprising basidiospores formed on club-shaped cells known as basidia.

As used herein, "Basidiomycetes" in reference to a class of Phylum Basidiomycota refers to a group of fungi. Basidiomycetes include mushrooms, of which some are rich in cyclopeptides and/or toxins, and includes certain types of yeasts, rust and smut fungi, gilled-mushrooms, puffballs, polypores, jelly fungi, brackets, coral, mushrooms, boletes, puffballs, stinkhorns, etc.

As used herein, "Homobasidiomycetes" in reference to fungi refers to a recent classification of fungi, including *Amanita* spp. and all other gilled fungi (commonly known as mushrooms), based upon cladistics rather than morphology.

As used herein, "Heterobasidiomycetes" in reference to fungi refers to those basidiomycete fungi that are not Homobasidiomycetes.

As used herein, "Ascomycota" or "ascomycetes" in reference to members of a fungal Phylum or Division refers to a "sac fungus" group. Of the Ascomycota, a class "Ascomycetes" includes *Candida albicans*, unicellular yeast, *Morchella esculentum*, the morel, and *Neurospora crassa*. Some ascomycetes cause disease, for example, *Candida albicans* causes thrush and vaginal infections; or produce chemical toxins associated with diseases, for example, *Aspergillus flavus* produces a contaminant of nuts and stored grain called aflatoxin, that acts both as a toxin and a deadly natural carcinogen.

As used herein, the term "toxin" in reference to a poison refers to any substance (for example, alkaloids, cyclopeptides, coumarins, and the like) that is detrimental (i.e., poisonous) to cells and/or organisms, in particular a human organism. In particularly preferred embodiments of the present inventions, the term "toxin" encompasses toxins, suspected toxins, and pharmaceutically active peptides produced by various fungal species, including, but not limited to, a cyclic peptide toxin such as an amanitin, that provides toxic activity towards cells and humans. However, it is not intended that the present invention be limited to any particular fungal toxin or fungal species. Indeed, it is intended that the term encompass fungal toxins produced by any organism. As used herein, a toxin encompasses linear sequences of cyclic pharmaceutically active peptides and linear sequences showing identity to known toxins regardless of whether these sequences are known to be toxic.

As used herein, the term "*Amanita* peptide" or "*Amanita* toxin" or "*Amanita* peptide toxin" refers to any linear or cyclic peptide produced by a mushroom, including but not limited to species of *Lepiota, Conocybe, Galerina*, and the like. However, it is not intended that the present invention be limited to a toxin or a peptide produced by an *Amanita* mushroom and includes similar peptides and toxins produced by other fungi. In particular, an *Amanita* peptide toxin resembles any of the amatoxins and phallotoxins, such as similarity of amino acid sequences, matching toxin motifs as shown herein, encoded between the conserved regions (A and B) of their proproteins, encoded by hypervariable regions of their proproteins (P), and the like. For example, an exemplary Amanatin peptide toxin is 7-11 amino acids in length.

As used herein, the term "toxic" refers to any detrimental or harmful effects on a cell or tissue.

As used herein, "*Amanita*" refer to a genus of fungus whose members comprise poisonous mushrooms, e.g., *Amanita*(A.) *bisporigera, A. virosa, A. ocreata, A. suballiacea*, and *A. tenuifolia* which are collectively referred to as "death angels" or "Destroying Angels" and "*Amanita phalloides*" or "*A. phalloides* var. *alba*" or "*A. phalloides* var. *verna*" or "*A. verna*", referred to as "death cap." The toxins of these mushrooms frequently cause death through liver and kidney failure in humans. Not all species of this genus are deadly, for example, *Amanita muscaria*, the fly agaric, induces gastrointestinal distress and/or hallucinations while others do not induce detectable symptoms.

Figure 1A:
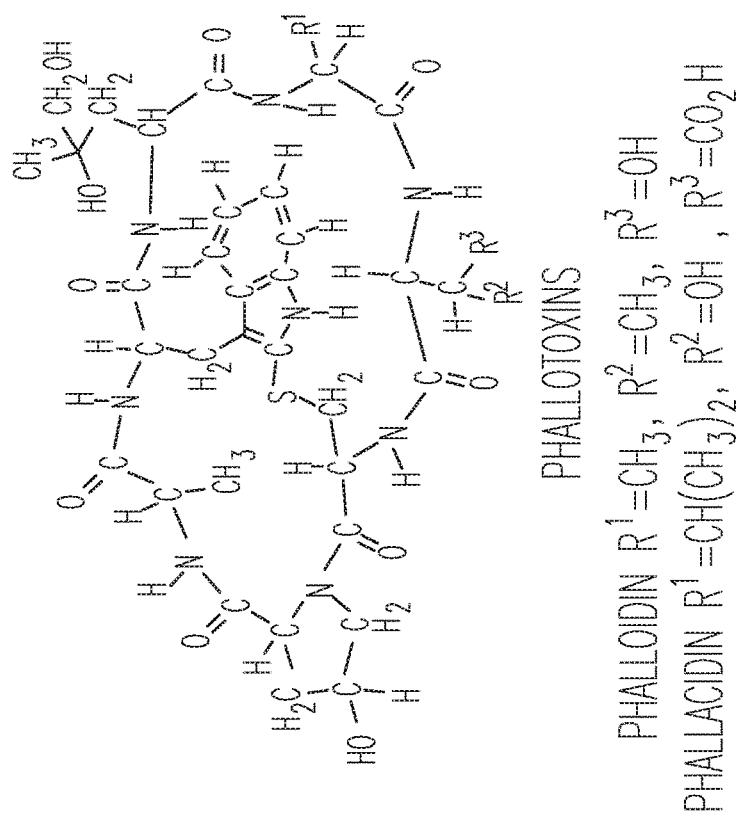
FIG. 1 shows exemplary structures of (A) amatoxins and (B) phallotoxins. Exemplary amino acids have the L configuration except hydroxyAsp in phallacidin and Thr in phalloidin.

As used herein, "amatoxin" generally refers to a family of peptide compounds, related to and including the amanitins. For the purposes of the present inventions, an amatoxin refers to any small peptide, linear and cyclic, comprising an exemplary chemical structure as shown in FIG. 1 or encoded by nucleic acid sequence of the present invention, wherein the nucleic acid sequence and/or proprotein has a higher sequence homology to AMA1 than to an analogous sequence of PHA1.

As used herein, "phallotoxin" generally refers to a family of peptide compounds, related to and including phallacidin and phalloidin. For the purposes of the present inventions, a phallotoxin refers to any small peptide encoded by nucleic acid sequences where the nucleic acid sequence and/or proprotein has a higher sequence homology to PHA1 than to an analogous sequence of AMA1.

As used herein, nonribosomal peptide synthetase (NRPS) is an enzyme that catalyzes the biosynthesis of a small (20 or fewer amino acids) peptide or depsipeptide, linear or circular, and is composed of one or more domains (modules) typical of this class of enzyme. Each domain is responsible for aminoacyl adenylation of one component amino acid. NRPSs can also contain auxiliary domains catalyzing, e.g., N-methylation and amino acid epimerization (Walton, et al., in Advances in Fungal Biotechnology for Industry, Agriculture, and Medicine, et al., Eds. (Kluwer Academic/Plenum, N.Y., 2004, pp. 127-162; Finking, et al., (2004) Annu Rev Microbiol 58:453-488, all of which are herein incorporated by reference). Examples are gramicidin synthetase, HC-toxin synthetase, cyclosporin synthetase, and enniatin synthetase.

As used herein, "prolyl oligopeptidase" or "POP" or "prolyloligopeptidase" refers to a member of a family of enzymes classified and referred to as EC 3.4.21.26-enzymes that are capable of cleaving a peptide sequence, such that hydrolysis of Pro-l-Xaa>>Ala-l-Xaa in oligopeptides, also referred to as any one of "post-proline cleaving enzyme," "proline-specific endopeptidase," "post-proline endopeptidase," "proline endopeptidase," "endoprolylpeptidase," "prolyl endopeptidase," "post-proline cleaving enzyme," "post-proline endopeptidase," and "prolyl endopeptidase." A POPA of the present inventions refers to a mushroom sequne found in the majority of mushrooms. A POPB of the present inventions refers to a sequence which in one embodiment has approximately a 55% amino acid homology to POPA, wherein said POPB sequence is primarily found in toxin producing mushroom species.

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. Several types of fungi and cultures are available for use as a host cell, such as those described for use in fungal expression systems, described below. Prokaryotes include but are not limited to gram negative or positive bacterial cells. Numerous cell lines and cultures are available for use as a host cell, and they can be obtained through the American Type Culture Collection (ATCC), an organization that serves as an archive for living cultures and genetic materials (world wide web.atcc.org). An appropriate host can be determined by one of skill in the art based on the vector nucleic acid sequence and the desired result. A plasmid or cosmid, for example, can be introduced into a prokaryote host cell for replication of many vectors. Bacterial cells used as host cells for expression vector replication and/or expression include, among those listed elsewhere herein, DH5α, JM109, and KC8, as well as a number of commercially available bacterial hosts such as SURE™ Competent Cells and SOLOPACK™ Gold Cells (Stratagene, La Jolla). Alternatively, bacterial cells such as *E. coli* LE392 can be used as host cells for phage viruses. In some embodiments, a host cell is used as a recipient for vectors. A host cell may be "transfected" or "transformed," which refers to a process by which exogenous nucleic acid is transferred or introduced into the host cell. For example, a host cell may be located in a transgenic mushroom. A transformed cell includes the primary subject cell and its progeny.

As used herein, "host fungus cell" refers to any fungal cell, for example, a yeast cell, a mold cell, and a mushroom cell (such as *Neurospora crassa, Aspergillus nidulans, Cochliobolus carbonum, Coprinus cinereus*, and the like).

As used herein, the term "Fungal expression system" refers to a system using fungi to produce (express) enzymes and other proteins. Examples of filamentous fungi which are currently used or proposed for use in such processes are *Neurospora crassa, Acremonium chrysogenum, Tolypocladium geodes, Mucor circinelloides, Trichoderma reesei, Aspergillus nidulans, Aspergillus niger, Coprinus cinereus, Aspergillus oryzae*, etc. Further examples include an expression system for basidiomycete genes (for example, Gola, et al., (2003) J Basic Microbiol. 43(2):104-12; herein incorporated by reference) and fungal expression systems using, for example, a monokaryotic laccase-deficient *Pycnoporus cinnabarinus* strain BRFM 44 (Banque de Resources Fongiques de Marseille, Marseille, France), and *Schizophyllum commune*, (for example, Alexandra, et al., (2004) Appl Environ Microbiol. 70(11):6379-638; Lugones, et al., (1999) Mol. Microbiol. 32:681-700; Schuren, et al., (1994) Curr. Genet. 26:179-183; all of which are herein incorporated by reference).

The term "transgene" as used herein refers to a foreign gene, such as a heterologous gene, that is placed into an organism by, for example, introducing the foreign gene into cells or primordial tissue. The term "foreign gene" refers to any nucleic acid (e.g., gene sequence) that is introduced into the genome of a host cell by experimental manipulations and may include gene sequences found in that cell so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." A vector "backbone" comprises those parts of the vector which mediate its maintenance and enable its intended use (e.g., the vector backbone may contain sequences necessary for replication, genes imparting drug or antibiotic resistance, a multiple cloning site, and possibly operably linked promoter and/or enhancer elements which enable the expression of a cloned nucleic acid). The cloned nucleic acid (e.g., such as a cDNA coding sequence, or an amplified PCR product) is inserted into the vector backbone using common molecular biology techniques.

A "recombinant vector" indicates that the nucleotide sequence or arrangement of its parts is not a native configuration, and has been manipulated by molecular biological techniques. The term implies that the vector is comprised of segments of DNA that have been artificially joined.

The terms "expression vector" and "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, "recombinant nucleic acid" or "recombinant gene" or "recombinant DNA molecule" indicates that the nucleotide sequence or arrangement of its parts is not a native configuration, and has been manipulated by molecular biological techniques. The term implies that the DNA molecule is comprised of segments of DNA that have been artificially joined together, for example, a lambda clone of the present inventions. Protocols and reagents to manipulate nucleic acids are common and routine in the art (See e.g, Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]; all of which are herein incorporated by reference). Similarly, a "recombinant protein" or "recombinant polypeptide" refers to a protein molecule that is expressed from a recombinant DNA molecule. Use of these terms indicates that the primary amino acid sequence, arrangement of its domains or nucleic acid elements which control its expression are not native, and have been manipulated by molecular biology techniques. As indicated above, techniques to manipulate recombinant proteins are also common and routine in the art.

The terms "exogenous" and "heterologous" are sometimes used interchangeably with "recombinant." An "exogenous nucleic acid," "exogenous gene" and "exogenous protein" indicate a nucleic acid, gene or protein, respectively, that has come from a source other than its native source, and has been artificially supplied to the biological system. In contrast, the terms "endogenous protein," "native protein," "endogenous gene," and "native gene" refer to a protein or gene that is native to the biological system, species or chromosome under study. A "native" or "endogenous" polypeptide does not contain amino acid residues encoded by recombinant vector sequences; that is, the native protein contains only those amino acids found in the polypeptide or protein as it occurs in nature. A "native" polypeptide may be produced by recombinant means or may be isolated from a naturally occurring source. Similarly, a "native" or "endogenous" gene is a gene that does not contain nucleic acid elements encoded by sources other than the chromosome on which it is normally found in nature.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the untranslated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "an oligonucleotide having a nucleotide sequence encoding a gene" and "polynucleotide having a nucleotide sequence encoding a gene," mean a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

The terms "in operable combination," "in operable order," "operably linked" and similar phrases when used in reference to nucleic acid herein are used to refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence (e.g., a nucleic acid sequence encoding a fusion protein of the present invention) to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference). It is further contemplated that control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment (e.g., comprising nucleic acid encoding a fusion protein of the present invention) in the cell type, organelle, and organism chosen for expression. Those of skill in the art of microbiology and molecular biology generally know the use of promoters, enhancers, and cell type combinations for protein expression, for example, see Sambrook et al. (1989); herein incorporated by reference. The promoters employed may be constitutive, tissue-specific, inducible, and/or useful under the appropriate conditions to direct the desired level of expression of the introduced DNA segment comprising a target protein of the present invention (e.g., high levels of expression that are advantageous in the large-scale production of recombinant proteins and/or peptides). The promoter may be heterologous or endogenous.

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236: 1237 [1987]; herein incorporated by reference). Promoter and enhancer elements have been isolated from a variety of eukaryotic sources including genes in yeast, insect and mammalian cells, as well as viruses. Analogous control elements (i.e., promoters and enhancers) are also found in prokaryotes. The selection of a particular promoter and enhancer to be operably linked in a recombinant gene depends on what cell type is to be used to express the protein of interest. Some eukaryotic promoters and enhancers have a broad host range while others are functional only in a limited subset of cell types (for review, see, Voss et al., Trends Biochem. Sci., 11: 287 [1986] and Maniatis et al., Science 236:1237 [1987]; all of which are herein incorporated by reference).

The term "promoter/enhancer region" is usually used to describe this DNA region, typically but not necessarily 5' of the site of transcription initiation, sufficient to confer appropriate transcriptional regulation. The word "promoter" alone is sometimes used synonymously with "promoter/enhancer." A promoter may be constitutively active, or alternatively, conditionally active, where transcription is initiated only under certain physiological conditions or in the presence of certain drugs. The 3' flanking region may contain additional sequences for regulating transcription, especially the termination of transcription.

The term "introns" or "intervening regions" or "intervening sequences" are segments of a gene which are contained in the primary transcript (i.e., hetero-nuclear RNA, or hnRNA), but are spliced out to yield the processed mRNA form. Introns may contain transcriptional regulatory elements such as enhancers. The mRNA produced from the genomic copy of a gene is translated in the presence of ribosomes to yield the primary amino acid sequence of the polypeptide.

Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "promoter/enhancer" denotes a segment of DNA which contains sequences capable of providing both promoter and enhancer functions (i.e., the functions provided by a promoter element and an enhancer element). For example, the long terminal repeats of retroviruses contain both promoter and enhancer functions. The promoter/enhancer may be "endogenous," or "exogenous," or "heterologous." An "endogenous" promoter/enhancer is one which is naturally linked with a given gene in the genome. An "exogenous" or "heterologous" promoter/enhancer is one placed in juxtaposition to a gene by means of genetic manipulation (i.e., molecular biological techniques such as cloning and recombination) such that transcription of the gene is controlled by the linked promoter/enhancer.

As used herein, the term "subject" refers to both humans and animals.

As used herein, the term "patient" refers to a subject whose care is under the supervision of a physician/veterinarian or who has been admitted to a hospital.

The term "sample" is used in its broadest sense. In one sense it can refer to a mushroom cell or mushroom tissue. In another sense, it is meant to include a specimen or culture obtained from any source, as well as biological and environmental samples that may comprise mushroom toxins. Biological samples may be obtained from mushrooms or animals (including humans) and encompass fluids, such as gastrointestinal fluids, solids, tissues, and the like. Environmental samples include environmental material such as mushrooms, hyphae, soil, water, such as cooking water, and the like. These terms encompasses all types of samples obtained from humans and other animals, including but not limited to, body fluids such as digestive system fluid, saliva, stomach contents, intestinal contents, urine, blood, fecal matter, diarrhea, as well as solid tissue, partially and fully digested samples. These terms also refers to swabs and other sampling devices which are commonly used to obtain samples for culture of microorganisms. Biological samples may be food products and ingredients, such as a mushroom sample, a raw sample, a cooked sample, a canned sample, animal, including human, fluid or tissue and waste. Environmental samples include environmental material such as surface matter, soil, water, and industrial samples, as well as samples obtained from food processing instruments, apparatus, equipment, disposable, and non-disposable items. These examples are not to be construed as limiting the sample types applicable to the present invention.

Whether biological or environmental, a sample suspected of containing a poisonous mushroom cell or mushroom toxin, may (or may not) first be subjected to an enrichment means. By "enrichment means" or "enrichment treatment," the present invention contemplates (i) conventional techniques for isolating a particular mushroom cell or mushroom toxin or mushroom sequence of interest away from other components by means of liquid, solid, semi-solid based separation technique or any other separation technique, and (ii) novel techniques for isolating particular cells or toxins away from other components. It is not intended that the present invention be limited only to one enrichment step or type of enrichment means. For example, it is within the scope of the present invention, following subjecting a sample to a conventional enrichment means, such as HPLC, to subject the resultant preparation to further purification such that a pure sample or culture of a strain of a species of interest is produced. This pure sample or culture may then be analyzed by the compositions and methods of the present inventions.

The terms "peptide," "prepropolypeptide," "propolypeptide," "polypeptide" and "protein" all refer to a primary sequence of amino acids that are joined by covalent "peptide linkages." In general, a peptide consists of a few amino acids, typically from 2-25 amino acids, and is shorter than a protein. Polypeptides may encompass either peptides or proteins. Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. Thus, a polynucleotide of the present invention may encode a polypeptide, a polypeptide plus a leader sequence (which may be referred to as a prepolypeptide), a precursor of a polypeptide having one or more prosequences which are not the leader sequences of a prepolypeptide, or a prepropolypeptide, which is a precursor to a propolypeptide, having a leader sequence and one or more prosequences, which generally are removed during processing steps that produce active forms of the polypeptide.

As used herein, the term "portion" when in reference to a protein (as in "a portion of a given protein") refers to fragments of that protein. The fragments may range in size from four amino acid residues to the entire amino acid sequence minus one amino acid.

As used herein, the term "target protein" or "protein of interest" when used in reference to a protein or nucleic acid refers to a protein or nucleic acid encoding a protein of interest for which structure or toxicity is to be analyzed and/or altered of the present invention, such as a gene encoding a mushroom toxin or a mushroom toxin. The term "target protein" encompasses both wild-type proteins and those that are derived from wild type proteins (e.g., variants of wild-type proteins or polypeptides, or, chimeric genes constructed with portions of target protein coding regions), and further encompasses fragments of a wild-type protein. Thus, in some embodiments, a "target protein" is a variant or mutant. The present invention is not limited by the type of target protein analyzed.

As used herein, the term "endopeptidase" refers to an enzyme that catalyzes the cleavage of peptide bonds within a polypeptide or protein. Peptidase refers to the fact that it acts on peptide bonds and endopeptidase refers to the fact that these are internal bonds. An exopeptide catalyzes the cleavage of the terminal or penultimate peptide bond, releasing a single amino acid or dipeptide from the peptide chain.

In particular, the terms "target protein gene" or "target protein genes" refer to the full-length target protein sequence, such as a prepropolypeptide. However, it is also intended that the term encompass fragments of the target protein sequences, mutants of the target protein sequences, as well as other domains within the full-length target protein nucleotide sequences. Furthermore, the terms "target protein nucleotide sequence" or "target protein polynucleotide sequence" encompasses DNA, cDNA, and RNA (e.g., mRNA) sequences.

The term "gene of interest" as used herein refers to the gene inserted into the polylinker of an expression vector whose expression in the cell is desired for the purpose of performing further studies on the transfected cell. The gene of interest may encode any protein whose expression is desired in the transfected cell at high levels. The gene of interest is not limited to the examples provided herein; the gene of interest may include cell surface proteins, secreted proteins, ion channels, cytoplasmic proteins, nuclear proteins (e.g., regulatory proteins), mitochondrial proteins, etc.

As used herein, the term "gene" refers to a DNA sequence that comprises control and coding sequences necessary for the production of a polypeptide or protein precursor. The polypeptide can be encoded by a full-length coding sequence, or by a portion of the coding sequence, as long as the desired protein activity is retained. Genes can encode a polypeptide or any portion of a polypeptide within the gene's "coding region" or "open reading frame." The polypeptide produced by the open reading frame of a gene may or may not display functional activity or properties of the full-length polypeptide product (e.g., toxin activity, enzymatic activity, ligand binding, signal transduction, etc.).

In addition to the coding region of the nucleic acid, the term "gene" also encompasses the transcribed nucleotide sequences of the full-length mRNA adjacent to the 5' and 3' ends of the coding region. These noncoding regions are variable in size, and sometimes extend for distances up to or exceeding 1 kb on both the 5' and 3' ends of the coding region. The sequences that are located 5' and 3' of the coding region and are contained on the mRNA are referred to as 5' and 3' untranslated regions (5' UTR and 3' UTR). Both the 5' and 3' UTR may serve regulatory roles, including translation initiation, post-transcriptional cleavage and polyadenylation. The term "gene" encompasses mRNA, cDNA and genomic forms of a gene.

It is contemplated that the genomic form or genomic clone of a gene may contain the sequences of the transcribed mRNA, as well as other non-coding sequences which lie outside of the mRNA. The regulatory regions which lie outside the mRNA transcription unit are sometimes called "5' or 3' flanking sequences." A functional genomic form of a gene must contain regulatory elements necessary for the regulation of transcription.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the"3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "nucleic acid molecule encoding," "DNA sequence encoding," and "DNA encoding" and similar phrases refer to the order or sequence of deoxyribonucleotides along a strand of deoxyribonucleic acid. The order of these deoxyribonucleotides determines the order of amino acids along the polypeptide (e.g., protein) chain. The DNA sequence thus codes for the amino acid sequence.

As used herein, the terms "an oligonucleotide having a nucleotide sequence encoding a gene," "polynucleotide having a nucleotide sequence encoding a gene," and similar phrases are meant to indicate a nucleic acid sequence comprising the coding region of a gene (i.e., the nucleic acid sequence which encodes a gene product). The coding region may be present in either a cDNA, genomic DNA or RNA form. When present in a DNA form, the oligonucleotide, polynucleotide or nucleic acid may be single-stranded (i.e., the sense strand or the antisense strand) or double-stranded.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of the mRNA. Gene expression can be regulated at many stages. "Up-regulation" or "activation" refers to regulation that increases the production of gene expression products (i.e., RNA or protein), while "down-regulation" or "repression" refers to regulation that decreases mRNA or protein production. Molecules (e.g., transcription factors) that are involved in up-regulation or down-regulation are often called "activators" and "repressors," respectively.

As used herein, the term "hybridization" is used in reference to the pairing of complementary nucleic acids. Hybridization can be demonstrated using a variety of hybridization assays (Southern blot, Northern Blot, slot blot, phage plaque hybridization, and other techniques). These protocols are common in the art (See e.g., Sambrook et al. (eds.), Molecular Cloning: A Laboratory Manual, Second Edition, Volumes 1-3, Cold Spring Harbor Laboratory Press, NY, [1989]; Ausubel et al. (eds.), Current Protocols in Molecular Biology, Vol. 1-4, John Wiley & Sons, Inc., New York [1994]; all of which are herein incorporated by reference).

Hybridization is the process of one nucleic acid pairing with an antiparallel counterpart which may or may not have 100% complementarity. Two nucleic acids which contain 100% antiparallel complementarity will show strong hybridization. Two antiparallel nucleic acids which contain no antiparallel complementarity (generally considered to be less than 30%) will not hybridize. Two nucleic acids which contain between 31-99% complementarity will show an intermediate level of hybridization. A single molecule that contains pairing of complementary nucleic acids within its structure is said to be "self-hybridized."

During hybridization of two nucleic acids under high stringency conditions, complementary base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less. As used herein, two nucleic acids which are able to hybridize under high stringency conditions are considered "substantially homologous." Whether sequences are "substantially homologous" may be verified using hybridization competition assays. For example, a "substantially homologous" nucleotide sequence is one that at least partially inhibits a completely complementary probe sequence from hybridizing to a target nucleic acid under conditions of low stringency. This is not to say that conditions of low stringency are such that non-specific binding is permitted; low stringency conditions require that the binding of two sequences to one another be a specific (i.e., selective) interaction. The absence of non-specific binding may be verified by the use of a second target that lacks even a partial degree of complementarity (e.g., less than about 30% identity); in the absence of non-specific binding the probe will not hybridize to the second non-complementary target. When used in reference to a double-stranded nucleic acid sequence such as a cDNA or genomic clone, the term "substantially homologous" refers to any probe that can hybridize to either or both strands of the double-stranded nucleic acid sequence under conditions of high stringency.

Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "stringency" is used in reference to the conditions of temperature, ionic strength, and the presence of other compounds such as organic solvents, under which nucleic acids hybridize. "Low or weak stringency" conditions are reaction conditions which favor the complementary base pairing and annealing of two nucleic acids. "High stringency" conditions are those conditions which are less optimal for complementary base pairing and annealing. The art knows well that numerous variables affect the strength of hybridization, including the length and nature of the probe and target (DNA, RNA, base composition, present in solution or immobilized, the degree of complementary between the nucleic acids, the $T_m$ of the formed hybrid, and the G:C ratio within the nucleic acids). Conditions may be manipulated to define low or high stringency conditions: factors such as the concentration of salts and other components in the hybridization solution (e.g., the presence or absence of formamide, dextran sulfate, polyethylene glycol) as well as temperature of the hybridization and/or wash steps. Conditions of "low" or "high" stringency are specific for the particular hybridization technique used.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less. "High stringency conditions" when used in reference to nucleic acid hybridization comprise conditions equivalent to binding or hybridization at 65° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% sodium dodecyl sulfate (SDS), 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 55° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

As used herein, the term "$T_m$" is used in reference to the "melting temperature." The melting temperature is the temperature at which a population of double-stranded nucleic acid molecules becomes half dissociated "denatures") into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein, the terms "complementary" or "complementarity" are used in reference to polynucleotides (i.e., a sequence of nucleotides) related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in polymerase chain reaction (PCR) amplification reactions, as well as detection methods that depend upon binding between nucleic acids.

As used herein, the terms "antiparallel complementarity" and "complementarity" are synonymous. Complementarity can include the formation of base pairs between any type of nucleotides, including non-natural bases, modified bases, synthetic bases and the like.

The following definitions are the commonly accepted definitions of the terms "identity," "similarity" and "homology." Percent identity is a measure of strict amino acid conservation. Percent similarity is a measure of amino acid conservation which incorporates both strictly conserved amino acids, as well as "conservative" amino acid substitutions, where one amino acid is substituted for a different amino acid having similar chemical properties (i.e. a "conservative" substitution). The term "homology" can pertain to either proteins or nucleic acids. Two proteins can be described as "homologous" or "non-homologous," but the degree of amino acid conservation is quantitated by percent identity and percent similarity. Nucleic acid conservation is measured by the strict conservation of the bases adenine, thymine, guanine and cytosine in the primary nucleotide sequence. When describing nucleic acid conservation, conservation of the nucleic acid primary sequence is sometimes expressed as percent homology. In the same nucleic acid, one region may show a high percentage of nucleotide sequence conservation, while a different region can show no or poor conservation. Nucleotide sequence conservation can not be inferred from an amino acid similarity score. Two proteins may show domains that in one region are homologous, while other regions of the same protein are clearly non-homologous.

Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other. When used in reference to a single-stranded nucleic acid sequence, the term "substantially homologous" refers to any probe that can hybridize (i.e., it is the exact or substantially close to the complement of) the single-stranded nucleic acid sequence under conditions of low stringency as described above.

The term "amplification" is defined as the production of additional copies of a nucleic acid sequence and is generally carried out using polymerase chain reaction technologies well known in the art (Dieffenbach and G S Dvekler, PCR Primer, a Laboratory Manual, Cold Spring Harbor Press, Plainview N.Y. [1995]; herein incorporated by reference).

As used herein, the term "polymerase chain reaction" ("PCR") refers to the methods disclosed in U.S. Pat. Nos.

4,683,195, 4,683,202 and 4,965,188, all of which are incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled or biotinylated deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc. Reverse transcription PCR (RT-PCR) refers to amplification of RNA (preferably mRNA) to generate amplified DNA molecules (i.e. cDNA). RT-PCR may be used to quantitate mRNA levels in a sample, and to detect the presence of a given mRNA in a sample. RT-PCR may be carried out "in situ", wherein the amplification reaction amplifies mRNA, for example, present in a tissue section.

As used herein, the term "amplifiable nucleic acid" is used in reference to nucleic acids which may be amplified by any amplification method. It is contemplated that "amplifiable nucleic acid" will usually comprise "template." As used herein, the term "template" refers to nucleic acid originating from a sample that is to be used as a substrate for the generation of the amplified nucleic acid.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "primer" refers to an oligonucleotide, typically but not necessarily produced synthetically, that is capable of acting as a point of initiation of nucleic acid synthesis when placed under conditions in which synthesis of a primer extension product that is complementary to a nucleic acid strand is induced, (i.e., in the presence of nucleotides, an inducing agent such as DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "amplification reagents" refers to those reagents (e.g., deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "sample template" refers to a nucleic acid originating from a sample which is analyzed for the presence of "target," such as a positive control DNA sequence encoding a mushroom toxin. In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other than those to be detected may be present as background in a test sample.

As used herein, the term "probe" refers to a polynucleotide sequence (for example an oligonucleotide), whether occurring naturally (e.g., as in a purified restriction digest) or produced synthetically, recombinantly or by PCR amplification, which is capable of hybridizing to another nucleic acid sequence of interest, such as a nucleic acid attached to a membrane, for example, a Southern blot or a Northern blot. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label.

The terms "reporter molecule" and "label" are used herein interchangeably. In addition to probes, primers and deoxynucleoside triphosphates may contain labels; these labels may comprise, but are not limited to, $^{32}$P, $^{33}$P, $^{35}$S, enzymes, fluorescent molecules (e.g., fluorescent dyes) or biotin.

As used herein, the term "rapid amplification of cDNA ends" or "RACE" refers to methods such as "classical anchored" or "single-sided PCR" or "inverse PCR" or "ligation-anchored PCR" or "RNA ligase-mediated RACE" for amplifying a 5' or 3' end of a DNA sequence (Frohman et al., (1988) Proc Natl Acad Sci 85:8998-9002; herein incorporated by reference).

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a mushroom toxin includes, by way of example, such nucleic acid in cells ordinarily expressing a mushroom toxin, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may be single-stranded), but may contain both the sense and anti-sense strands (in other words, the oligonucleotide may be double-stranded).

As used herein, the term "purified" or "to purify" refers to the removal of contaminants from a sample. For example, recombinant nucleotides are expressed in bacterial host cells and the nucleotides are purified by the removal of host cell nucleotides and proteins; the percent of recombinant nucleotides is thereby increased in the sample.

As used herein, the term "kit" is used in reference to a combination of reagents and other materials. It is contemplated that the kit may include reagents such as PCR primer sets, positive DNA controls, such as a DNA encoding a propolypeptide of the present inventions, diluents and other aqueous solutions, and instructions. The present invention contemplates other reagents useful for the identification and/or determination of the presence of an amplified sequence encoding a mushroom toxin, for example, a colorimetric reaction product.

DESCRIPTION OF THE INVENTION

The present invention relates to compositions and methods comprising genes and peptides associated with cyclic peptide toxins and toxin production in mushrooms. In particular, the present invention relates to using genes and proteins from *Amanita* species encoding *Amanita* peptides, specifically relating to amatoxins and phallotoxins. In a preferred embodiment, the present invention also relates to methods for detecting *Amanita* peptide toxin genes for identifying *Amanita* peptide-producing mushrooms and for diagnosing suspected cases of mushroom poisoning. Further, the present inventions relate to providing kits for diagnosing and monitoring suspected cases of mushroom poisoning in patients.

The present inventions further relate to compositions and methods associated with screening a genomic library in combination with 454 pyro-sequencing for obtaining sequences of interest. In particular, the present invention relates to providing and using novel PCR primers for identifying and sequencing *Amanita* genes, including methods comprising RACE PCR primers and degenerate primers for identifying *Amanita* mushroom peptides. Specifically, the present inventions relate to identifying and using sequences of interest associated with the production of small peptides, including linear peptides representing cyclic peptides, for example, compositions and methods comprising *Amanita* amanitin toxin sequences.

The present inventions further relate to compositions and methods associated with conserved genomic regions of the present inventions, in particular those conserved regions located upstream and downstream of small peptide encoding regions of the present inventions. Specifically, degenerate PCR primers based upon these conserved regions are used to identifying toxin producing mushrooms.

Unlike genetically based disease susceptibility, every human is susceptible to lethal mushroom toxins due to the direct action of toxins, primarily amatoxins, on ubiquitous cellular organelles. Furthermore, unlike poisonous plants, poisonous mushroom species are ubiquitously found throughout the world. For example, mushrooms in the genus *Amanita* section Phalloideae are responsible for more than 90% of global (worldwide) fatal mushroom poisonings. Perspectively, there are an estimated 900-1000 species of *Amanita* wherein the majority do not produce amatoxins (or phallotoxins) of which some are actually safe for humans to eat (FIG. 2C) (Bas, (1969) Persoonia 5:285; Tulloss et al., (2000) Micologico G. Bresadola, 43:13; Weiβ et al., (1998) Can J. Bot. 76:1170; all of which are herein incorporated by reference). Thus an accurate pre-ingestion determination of toxic species would prevent accidental poisoning in 100% of cases. However, there are a large number of toxin producing mushrooms commonly misidentified as an edible mushroom, see Tables 1 and 2. Therefore, accurately detecting toxic mushrooms in the wild based upon morphology in order to avoid or identify mushroom poisoning primarily depends upon expert mycological examination of an intact mushroom.

Expert identification opinions are necessary due to the large number of "look-a-like" mushrooms, such as exemplary mushroom in the following Table 1. For example, the Early False Morel *Gyromitra esculenta* is easily confused with the true Morel *Morchella esculenta*, and poisonings have occurred after consumption of fresh or cooked *Gyromitra*. *Gyromitra* poisonings have also occurred after ingestion of commercially available "morels" contaminated with *G. esculenta*. The commercial sources for these fungi (which have not yet been successfully cultivated on a large scale) are field collection of wild morels by semi-professionals. Cultivated commercial mushrooms of whatever species are almost never implicated in poisoning outbreaks unless there are associated problems such as improper canning (which lead to bacterial food poisoning).

TABLE 1

Poisonous Mushrooms and their Edible Look-Alikes.*
Mushrooms Containing Amatoxins

| Poisonous species | Appearance | Mistaken for |
|---|---|---|
| *Amanita tenuifolia* (Slender Death Angel) | pure white | *Leucoagaricus naucina* (Smoothcap Parasol) |

TABLE 1-continued Poisonous Mushrooms and their Edible Look-Alikes.*
Mushrooms Containing Amatoxins

| Poisonous species | Appearance | Mistaken for |
|---|---|---|
| Amanita bisporigera (Death Angel) | pure white | Amanita vaginata (Grisette), Leucoagaricus naucina (Smoothcap Parasol), white Agaricus spp. (field mushrooms), Tricholoma resplendens (Shiny Cavalier) |
| Amanita verna (Fool's Mushroom) | pure white | A. vaginata, L. naucina, white Agaricus spp., T. resplendens |
| Amanita virosa (Destroying Angel) | pure white | A. vaginata, L. naucina, Agaricus spp., T. resplendens |
| Amanita phalloides (Deathcap) | pure white variety | Amanita citrina (False Deathcap), A. vaginata, L. naucina, Agaricus spp., T. resplendens |
| Buttons of A. bisporigera,. A. verna, A. virosa | pure white | Buttons of white forms of Agaricus spp. Puffballs such as Lycoperdon perlatum, etc. |
| Amanita phalloides (Deathcap) | green = normal cap color | Russula virescens (Green Brittlegill), Amanita calyptrodermia (Hooded Grisette), Amanita fulva (Tawny Grisette), Tricholoma flavovirens (Cavalier Mushroom), Tricholoma portentosum (Sooty Head) |
| Amanita phalloides (Deathcap) | yellow variety | Amanita caesarea (Caesar's Mushroom) |
| Amanita brunnescens (Cleft Foot Deathcap) | na | Amanita rubescens (Blusher), Amanita pantherina (Panthercap) |
| Galerina autumnalis (Autumn Skullcap) | LBM | "Little Brown Mushrooms," including Gymnopilus spectabilis (Big Laughing Mushroom) and other Gymnopilus spp., Armillaria mellea (Honey Mushroom) |
| Leucoagaricus brunnea (Browning Parasol) | LBM | Lepiota spp., Leucoagaricus spp., Gymnopilus spp. and other Parasol Mushrooms and LBM's |
| Lepiota josserandii, L. helveola, L. subincarnata | LBM | Lepiota spp., Leucoagaricus spp., Gymnopilus spp. and other Parasol Mushrooms and LBM's |

Na = not available.

Mushrooms whose intact proteins produces mild gastroenteritis are too numerous to list here, where exemplary examples are shown which include members of many of the most abundant genera, including Agaricus, Boletus, Lactarius, Russula, Tricholoma, Coprinus, Pluteus, and others. The Inky Cap Mushroom (Coprinus atrimentarius) is considered both edible and delicious, and only the unwary who consume alcohol after eating this mushroom need be concerned. Some other members of the genus Coprinus (Shaggy Mane, C. comatus; Glistening Inky Cap, C. micaceus, and others) and some of the larger members of the Lepiota family such as the Parasol Mushroom (Leucocoprinus procera) do not contain coprine and do not cause this effect. The potentially deadly Sorrel Webcap Mushroom (Cortinarius orellanus) is not easily distinguished from nonpoisonous webcaps belonging to the same distinctive genus.

Individual specimens of poisonous mushrooms are characterized by individual variations in toxin content based on mushroom genetics, geographic location, and growing conditions. For example, mushroom intoxications may be more or less serious, depending not on the number of mushrooms consumed, but of the total dose of toxin delivered. In addition, although most cases of poisoning by higher plants occur in children, toxic mushrooms are consumed most often by adults. Adults who consume mushrooms are more likely to recall what was eaten and when, and are able to describe their symptoms more accurately than are children. Occasional accidental mushroom poisonings of children and pets have been reported, but adults are more likely to actively search for and consume wild mushrooms for culinary purposes.

TABLE 2

Mushrooms Producing Severe Gastroenteritis.
Mushrooms Producing Severe Gastroenteritis

| | |
|---|---|
| Chlorophyllum molybdites (Green Gill) | Leucocoprinus rachodes (Shaggy Parasol), Leucocoprinus procera (Parasol Mushroom) |
| Entoloma lividum (Gray Pinkgill) | Tricholomopsis platyphylla (Broadgill) |
| Tricholoma pardinum (Tigertop Mushroom) | Tricholoma virgatum (Silver Streaks), Tricholoma myomyces (Waxygill Cavalier) |
| Omphalotus olearius (Jack O'Lantern Mushroom) | Cantharellus spp. (Chanterelles) |
| Paxillus involutus (Naked Brimcap) | Distinctive, but when eaten raw or undercooked, will poison some people |

*Bad Bug Book published by the U.S. Food & Drug Administration Center for Food Safety & Applied Nutrition Foodborne Pathogenic Microorganisms and Natural Toxins Handbook http://www.cfsan.fda.gov/~mow/table3.html; herein incorporated by reference.

In part because of their smaller body mass, children are usually more seriously affected by normally nonlethal mushroom toxins than are adults and are more likely to suffer very serious consequences from ingestion of relatively smaller doses. Similar to the elder population and debilitated persons who are more likely to become seriously ill from all types of mushroom poisoning, even those types of toxins which are generally considered to be mild.

Recently, dogs and other animals are becoming frequent victims of poisonous mushrooms. Body mass plays a role here in that smaller animals, such as puppies and small dogs are likely to be more susceptible to smaller amounts of toxins.

I. Dangers of Mushroom Poisoning.

Mushroom poisoning in subjects, particularly humans, is caused by the consumption of raw or cooked fruiting bodies of toxin producing mushrooms, also known as toadstools (from the German Todesstuhl, death's stool) to distinguish toxic from nontoxic mushrooms. There is no general rule of thumb for distinguishing edible mushrooms from toxic mushrooms (poisonous toadstools). There are generally no easily recognizable differences between poisonous and nonpoisonous species to individuals who are not experts in mushroom identification (mycologists).

Toxins involved in and responsible for mushroom poisoning are produced naturally by the fungi, with each individual specimen within a toxic species considered equally poisonous. Most mushrooms that cause human poisoning cannot be made nontoxic by cooking, canning, freezing, or any other means of processing. Thus, the only way to completely avoid poisoning is to avoid consumption of the toxic species. Mushroom poisonings are almost always caused by ingestion of wild mushrooms that have been collected by nonspecialists (although specialists have also been poisoned). Most cases occur when toxic species are confused with edible species, and a useful question to ask of the victims or their mushroom-picking benefactors is the identity of the mushroom they thought they were picking. In the absence of a well-preserved specimen, the answer to this question could narrow the possible suspects considerably. Intoxication has also occurred when reliance was placed on some folk method of distinguishing poisonous and safe species. Outbreaks have occurred after ingestion of fresh, raw mushrooms, stir-fried mushrooms, home-canned mushrooms, mushrooms cooked in tomato sauce (which rendered the sauce itself toxic, even when no mushrooms were consumed), and mushrooms that were blanched and frozen at home. Cases of poisoning by home-canned and frozen mushrooms are especially insidious because a single outbreak may easily become a multiple outbreak when the preserved toadstools are carried to another location and consumed at another time.

Poisonings in the United States occur most commonly when hunters of wild mushrooms (especially novices) misidentify and consume a toxic species, when recent immigrants collect and consume a poisonous American species that closely resembles an edible wild mushroom from their native land, or when mushrooms that contain psychoactive compounds are intentionally consumed by persons who desire these effects.

A. Symptoms of Poisoning.

Mushroom poisonings are generally acute and are manifested by a variety of symptoms and prognoses, depending on the amount and species consumed. Because the chemistry of many of the mushroom toxins (especially the less deadly ones) is unknown and positive identification of the mushrooms is often difficult or impossible, mushroom poisonings are generally categorized by their physiological effects. There are four categories of mushroom toxins: protoplasmic poisons (poisons that result in generalized destruction of cells, followed by organ failure); neurotoxins (compounds that cause neurological symptoms such as profuse sweating, coma, convulsions, hallucinations, excitement, depression, spastic colon); gastrointestinal irritants (compounds that produce rapid, transient nausea, vomiting, abdominal cramping, and diarrhea); and disulfuram-like toxins. Mushrooms in this last category are generally nontoxic and produce no symptoms unless alcohol is consumed within 72 hours after eating them, in which case a short-lived acute toxic syndrome is produced.

In one embodiment, the inventors provide herein compositions and methods for providing molecular biology based diagnostic tests for accurately and reproducibly identifying DNA sequences encoding lethal fungal toxins. Thus accurate identification of mushroom toxins may be made from samples of uneaten mushrooms, including raw, cooked, frozen, dried, samples, and patient samples of undigested and partially digested, as in gastric contents, such as from human and dogs.

For comparison, current methods for diagnosing mushroom poisonings are briefly described below.

B. Current Diagnostic Methods.

Symptoms of mushroom poisoning may mimic other types of diseases, abnormal conditions or ingestion of other types of toxins which would trigger different and likely less drastic treatments. Exemplary differentials include, Adrenal Insufficiency and Adrenal Crisis, Alcohol and Substance Abuse Evaluation, Anorexia Nervosa, Delirium Tremens, Gastroenteritis, Hepatitis, Methemoglobinemia, Pediatrics, Dehydration, Pediatrics, Gastroenteritis, *Salmonella* Infection, Toxicity, Anticholinergic, Toxicity, Antihistamine, Disulfuram, Disulfuramlike Toxins, Gyromitra, Mushroom Hallucinogens, Mushroom—Orellanine, Organophosphate, Carbamate, Theophylline, Idiosyncratic reaction, patients with trehalase deficiency are unable to break down trehalose, a disaccharide found in mushrooms thus these patients present with diarrhea after ingestion, immune reaction (Paxillus syndrome)—patients may develop an acquired hypersensitivity-type reaction after repeated ingestions of specific mushrooms. This may result in hemolytic crisis and most commonly involves ingestion of *Paxillus involutus*. *Suillus luteus* also has been implicated, psychosomatic syndrome—Some patients have been reported to develop anxiety-related symptoms after learning that they have eaten wild mushrooms, Mushroom-drug interaction-symptoms may occur with ingestion of mushrooms contaminated with bacteria, sprayed with pesticides, or supplemented with drugs such as phencyclidine.

As described above, the protoplasmic poisons are the most likely to be fatal or to cause irreversible organ damage. In the case of poisoning by the deadly *Amanitas*, important laboratory indicators of liver (elevated LDH, SGOT, and bilirubin levels) and kidney (elevated uric acid, creatinine, and BUN levels) damage will be present. Unfortunately, in the absence of dietary history, these signs could be mistaken for symptoms of liver or kidney impairment as the result of other causes (e.g., viral hepatitis). It is important that this distinction be made as quickly as possible, because the delayed onset of symptoms will generally mean that the organ has already been damaged. The importance of rapid diagnosis is obvious: victims who are hospitalized and given aggressive support therapy almost immediately after ingestion have a mortality rate of only 10%, whereas those admitted 60 or more hours after ingestion have a 50-90% mortality rate.

1. Intact Mushrooms.

Ideally, once a mushroom poisoning is suspected, identification of suspect toxic mushroom, identical to the one ingested, should be made by a local medical toxicologist (certified through the American Board of Medical Toxicology or the American Board of Emergency Medicine) or at a regional poison control center.

If a pre-digested mushroom sample is available, the following information would be helpful to a mycologist or physician with mushroom poisoning experience for determining the mushroom's identity: Provide any available information, for example, size, shape, and color of the mushroom including a description of the surface and the underside of the cap, the stem, gills, veil, ring, spores and the color and texture of the flesh. It would be helpful to know the location and conditions in which the mushroom grew (eg, wood, soil). Further, it is suggested that any mushroom samples saved for mycological examinination are wrapped in foil or wax paper and stored in a paper bag in a cool dry place, pending transport to the mycologist or other professional. Moreover it is discouraged to store mushroom samples for mycological identification in a plastic bag or container where the mushroom's features may be altered due to moisture condensation and further freezing which is likely to alter or destroy any distinguishing identification features of the mushroom. Alternative methods for identifying mushrooms may be done by referring to the *Poisindex* or a mycology handbook.

Currently there are several research laboratory tests used for identifying mushroom toxins, examples of which are briefly described as follows. The Meixner test also known as the "Weiland Test" assay is qualitative assay used to detect amatoxins (eg, alpha-amanitin, beta-amanitin) in the mushroom. It is not recommended for use with stomach contents nor to determine edibility of a mushroom because false-positive and false-negative results have been described. Kuo, M. (2004, November). Meixner test for amatoxins. Retrieved from the MushroomExpert.Com Web site: mushroomexpert.com/meixner; herein incorporated by reference).

Further, an intact or partial undigested mushroom may be analyzed for actual toxic peptides, using biochemical tests such as HPLC. In order to rule out other types of food poisoning and to conclude that the mushrooms eaten were the cause of the poisoning, it must be established that everyone who ate the suspect mushrooms became ill and that no one who did not eat the mushrooms became ill. Wild mushrooms eaten raw, cooked, or processed should always be regarded as prime suspects. After ruling out other sources of food poisoning and positively implicating mushrooms as the cause of the illness, further diagnosis is necessary to provide an early indication of the seriousness of the disease and its prognosis.

Therefore, an initial diagnosis is based entirely on symptomology and recent dietary history. Despite the fact that cases of mushroom poisoning may be broken down into a relatively small number of categories based on symptomatology, positive botanical identification of the mushroom species consumed remains the only means of unequivocally determining the particular type of intoxication involved, and it is still vitally important to obtain such accurate identification as quickly as possible. Cases involving ingestion of more than one toxic species in which one set of symptoms masks or mimics another set are among many reasons for needing this information.

2. Post-Ingested and Pre-Digested Mushroom Samples.

If the actual mushroom is unavailable, which is frequent in post-ingestion cases with delayed onset of symtomps, the following information may be helpful for determining the mushroom's identity. Save emesis or gastric lavage fluid for microscopic examination for spores. If mushroom fragments are available, they can be stored in a 70% solution of ethyl alcohol, methanol, or formaldehyde and placed in the refrigerator. Otherwise, emesis can be centrifuged and the heavier layer on the bottom can be examined under a microscope for the presence of spores.

Despite the availability of laboratory tests for identifying toxins, diagnosing a mushroom poisoning remains primarily limited to botanical identification of the mushroom that was eaten. Accurate post-ingestion analyses for specific toxins when no botanical identification is possible is essential for cases of suspected poisoning by toxin containing mushrooms, such as *Amanitas*, since prompt and aggressive therapy (including lavage, activated charcoal, and plasmapheresis) can greatly reduce the mortality rate.

Samples of actual mushroom toxins may be recovered from poisonous fungi, cooking water of poisonous fungi, stomach contents with poisonous fungi, serum, and urine from poisoned patients. Procedures for extraction and quantitation of toxins are generally elaborate and time-consuming. In the case of using toxin based diagnostic procedures the patient will in most cases either have recovered or died by the time an analysis is made on the basis of toxin chemistry. However even with toxin chemistry, the exact chemical natures of many toxins, including toxins that produce milder symptoms are unknown. Lethal toxins are identified using chromatographic techniques (TLC, GLC, HPLC) for amanitins, orellanine, muscimol/ibotenic acid, psilocybin, muscarine, and the gyromitrins. Recently, amanitins were determined by commercially available $^3$H-RIA kits. Amanitin EIA Kit from Alpco Diagnostics of American Laboratory Products Company PO Box 451 Windham, N.H. 03087 Sample Type Urine, Serum, Plasma α- and γ-amanitin present in human urine, serum and plasma. For Research Use Only. Not For Use In Diagnostic Procedures. A polyclonal antibody (Ab) specific for a- and g-Amanitin Diagnostic Accuracy of Urinary Amanitin in Suspected Mushroom Poisoning: A Pilot Study Butera et al., Clinical Toxicology, Volume 42, Issue 6 Dec. 2004, pages 901-912; herein incorporated by reference).

II. Mushroom Toxins

A large variety of toxins are produced by mushrooms, including amatoxins, phallotoxins, virotoxins, phallolysins, ibotenic acid/muscimol, which include alkaloids, cyclopeptides, coumarins, etc. Many of these compounds are active at extremely low concentrations and have a rapid effect including death. Milder toxins such as ibotenic acid and muscimol bind to glutamic acid and GABA receptors, respectively, and thereby interfere with CNS receptors.

Amatoxins, phallotoxins, and virotoxins are found in *A. bisporigera, A. ocreata, A. phalloides, A. phalloides* var. *alba, A. suballiacea, A. tenuifolia, A. virosa*, and some other mushrooms. The phallolysins are a recently discovered group of toxins as yet observed in *A. phalloides*. Many of the cyclic and noncyclic peptides found in *Amanita* and other toxin producing genera are toxic to humans and other mammals ranging from mild symptoms to death.

A. Amanitin Toxins:

Several mushroom species, including the Death Cap or Destroying Angel (*Amanita phalloides, A. virosa*), the Fool's Mushroom (*A. verna*) and several of their relatives, along with the Autumn Skullcap (*Galerina marginata*, formerly called *Galerin autumnalis*) and some of its relatives, produce a family of cyclic octapeptides called amanitins. However because of changes in taxonomic designations, some or all of the amatoxins alpha-, beta- and gamma-amanitin are produced by named mushrooms such as *Galerina marginata=G. autumnalis=G. venenata=G. Unicolor* (*G. beinrothii, G. sulciceps, G. fasciculata, G. helvoliceps*—these four may be groupes as the same species as *G. marginata*) and *G. badipes*.

Amanitins are lethal toxins. A human $LD_{50}$ for α-amanitin is approximately 0.1 mg/kg (see, FIG. 1 for exemplary structures). Such that a fatal dose fatal for at least 50% of people weighing approximately 100-110 kgs (200-220 pounds) and around 100% for people weighing 100 or less pounds is 10-12 mgs. For example, one mature destroying angel (*A. bisporigera* [FIG. 2A], *A. virosa, A. suballiacea*, and allied species) or death cap (*A. phalloides*; FIG. 2B) can contain a fatal dose of 10-12 mgs of α-amanitin (Wieland, Peptides of Poisonous *Amanita* Mushrooms (Springer, N.Y., 1986); herein incorporated by reference). The news get worse. Toxin producing mushrooms typically demonstrate a higher toxicity than these estimates. An estimated 50% of the amatoxin content of a toxin-producing mushroom is α-amanitin. Toxic mushrooms also produce other major amatoxins, such as beta-amanitin (in *Amanita* spp.) and gamma-amanitin (in *Galerina* and *Lepiota*) resulting in a high death rate from mushroom poisonings.

Amatoxins are a member of a family of related molecules of which at least 9 members are known. Alpha-amanitin is one of the principle amatoxins, comprising approximately 50% of the amatoxin content of an amatoxin-producing mushroom. Beta-amanitin (also found in *Amanita* spp.) and gamma-amanitin (found in *Galerina* and *Lepiota* spp) are toxic in addition to other types of amatoxins, including but not limited to epsilon-Amanitin, Amanin, Amanin amide, Amanullin, Amanullinic acid, and Proamanullin. Members of this toxin family differ in whether they have asparagine (the position 1 amino acid) or aspartic acid, and in the degree of hydroxylation of the position 3 isoleucine and the tryptophan.

Amatoxins can be solely responsible for fatal human poisonings. After ingestion, amatoxins are taken up by the liver where they begin to cause damage. They are then secreted by the bile into the blood where they are taken up by the liver again, causing a cycle of damage and excretion. In the liver, amatoxins inhibit RNA-polymerase II. The liver is slowly destroyed and is unable to repair itself due to the inactivation of the RNA-polymerase. Thus, the liver slowly dissolves with no hope of repair. Thus, one of the few effective treatments is liver transplantation (Enjalbert et al., (2002) (Treatment of Amatoxin Poisoning: 20-Year Retrospective Analysis, review of poisonings) J. Toxicol. Clin. Toxicol. 40:715; Fabrizio, et al., (2006) Transplant International 19(4):344-345; all of which are herein incorporated by reference).

Poisoning by amanitins is clinically characterized by a long latent period (range 6-48 hours, average 6-15 hours) during which the patient shows no symptoms. Symptoms appear at the end of the latent period in the form of sudden, severe seizures of abdominal pain, persistent vomiting and watery diarrhea, extreme thirst, and lack of urine production which lasts for about 24 hours. If this early phase is survived, the patient may appear to recover for a short time, 2-3 days, during which liver damage is ongoing. This second latent period will generally be followed by a rapid and severe loss of strength, prostration, and pain-caused restlessness. During the last stages, hepatic and renal damage becomes clinically evident typically resulting in a coma. Death usually follows a period of comatose condition and occasionally causes convulsions. If recovery occurs, it generally requires at least a month and is accompanied by enlargement of the liver. Autopsy will usually reveal fatty degeneration and necrosis of the liver and kidney.

Amatoxins are particularly deadly because they are taken up by cells lining the gut where protein synthesis is immediately inhibited. The toxins are then released into the blood stream and transported to the liver. Once inside the liver cells, amatoxins inhibit RNA-polymerase II which slows or stops new protein production which begins to cause cellular damage. Bushnell et al., (2002) Proc. Natl. Acad. Sci. USA 99:1218; Kröncke et al., (1986) J. Biol. Chem., 261:12562; Letschert et al., (2006) Toxicol Sci. 91:140; Lindell et al., (1970) Science 170:447; all of which are herein incorporated by reference). The liver secretes excess toxins into bile and into the blood stream where they are taken up by the liver again, causing a cycle of damage and excretion. Thus the liver is slowly destroyed and is unable to repair itself. Amanitin toxins are excreted in the urine and evacuated from the body within hours of ingestion. However, if sufficient liver tissue is affected, liver failure will ensure death.

Death occurs in 50-90% of the cases from progressive and irreversible liver, kidney, cardiac, and skeletal muscle damage may follow within 48 hours (large dose), but effects typically lasts 6 to 8 days in adults and 4 to 6 days in children.

A dose that is likely to kill an average adult human is in the range of 6-7 mg, easily found in the cap of one mature *A. phalloides*. However, like other fungal toxins, the concentration which is fatal for individuals differs and relates to the concentration in different specimens, environment influences on concentration of toxin produced in one basidiocarp. These examples clearly show that any fungus collected from the field should be properly identified before it is consumed.

B. Phallotoxins.

Figure 1B:
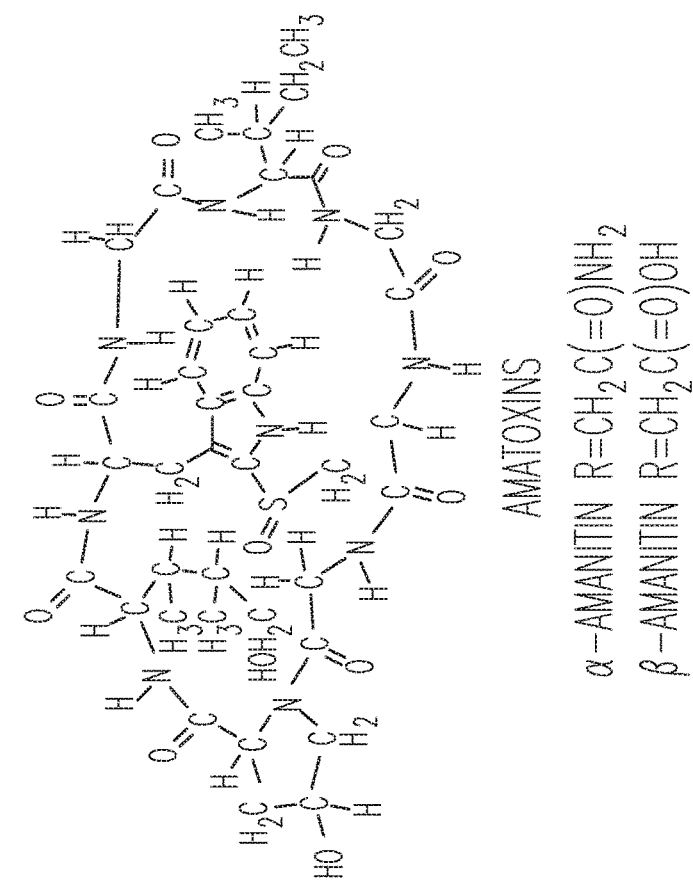

In addition to bicyclic octapeptide amatoxins, mushrooms naturally produce several bicyclic heptapeptides. In particular, members of *Amanita* sect. Phalloideae produce bicyclic heptapeptides specifically called phallotoxins (FIG. 1B). Although structurally related to amatoxins, phallotoxins were found to exert a different mode of toxic action in mammalian cells, which was to stabilize F-actin (Enjalbert et al., (2002) J. Toxicol. Clin. Toxicol. 40:715, Lengsfeld et al., (1974) Proc. Natl. Acad. Sci. USA, 71:2803; Bamburg, (1999) Annu. Rev. Cell Dev. Biol. 15:185; all of which are herein incorporated by reference). Phallotoxins were found to destroy liver cells by disturbing the equilibrium of G-actin with F-actin, causing it to shift entirely to F-actin. This leads to numerous exvaginations on the liver cell's membrane which render the cell susceptible to deformity by low-pressure gradients, even those of the portal vein in vivo. This is followed by loss of potassium ions and cytoplasmic enzymes which leads to depletion of ATP and glycogen causing the final failure of the liver.

Phallotoxins, such as phalloidin and phallacidin, are poisonous when administered parenterally, for example, when administered in a manner other than through the digestive tract, such as by inhalation, intravenous or intramuscular injection, however because they do not appear to be absorbed by the mammalian digestive tract, they are unlikely to play a primary role in clinical mushroom poisonings.

Biochemically, there are at least seven naturally occurring phallotoxins: phalloin, phalloidin, phallisin, prophalloin, phallacin, phallacidin, and phallisacin apparently derived from the same seven amino acid cyclic peptide backbone.

The phallotoxins are all derived from the same seven amino acid cyclic peptide backbone. There are two groups of phallotoxins, neutral and acidic. The neutral phallotoxins contain D-threonine, while the acidic ones contain beta-hydroxy-succinic acid.

Phallotoxin was once thought to be responsible for the usual symptoms of amatoxins. The compound acts to inhibit F actin in the cell cytoskeleton. It acts immediately, and probably does not move beyond the lining of the gut.

C. Virotoxins.

Although they have the same toxicological effects as and appear to be derived from the phallotoxins, the virotoxins are monocyclic heptapeptides, not bicyclic peptides.

There are at least six virotoxins, viroidin desoxoviroidin, a1a1-viroidin, a1a1-desoxoviroidin, viroisin, and desoxoviroisin.

Although they have the same toxicological effects as and appear to be derived from the phallotoxins, the virotoxins are monocyclic heptapeptides, not bicyclic peptides.

D. Other Types of Mushroom Toxins.

Phallolysins There are at least three phallolysins that are hemolytically active proteins, but, as previously stated, they are heat and acid labile and do not pose a threat to humans.

Ibotenic acid/Muscimol Ibotenic acid is an Excitatory Amino Acid (EAA) and muscimol is its derivative. These toxins act by mimicking the natural transmitters glutamic acid and aspartic acid on neurons in the central nervous system with specialized receptors for amino acids. These toxins may also cause selective death of neurons sensitive to EAAs.

III. *Amanita* Toxin Peptides in Relation to Other Peptides.

Small, modified, and biologically active peptides synthesized on ribosomes were previously identified from many sources, including bacteria, spiders, snakes, cone snails, and amphibian skin (Escoubas, 2006; Olivera, 2006; Simmaco et al., 1998). Like the *Amanita* toxins, these peptides are synthesized as precursor proteins and often undergo posttranslational modifications, including hydroxylation and epimerization.

The focus of the following discussion is focused on other types of toxins in relation to *amanita* toxins howerver several classes of cyclic proteins/peptides are not considered (Trabi and Craik, 2002).

Lantibiotics.

Lantibiotics, such as nisin, subtilin, and cinnamycin, are produced by species of *Lactobacillus, Streptococcus*, and other bacteria. They contain 19-38 amino acids. They are characterized by the presence of lanthionine, which is formed biosynthetically by dehydration of an Ala residue followed by intramolecular addition of Cys (Willey and van der Donk, 2007). The lantibiotics are similar to the *Amanita* toxins in containing a modified, cross-linked Cys residue. However, instead of Ala in the case of lantibiotics, the Cys in the *Amanita* toxins is cross-linked to a Trp residue. Furthermore, thorough BLAST searching of the genome of *Amanita* and of all other fungi whose genomes have been sequenced (available in GenBank NR or the DOE Joint Genome Institute) did not identify any orthologs of any of the known lantibiotic dehydratases or cyclases (Willey and van der Donk, 2007).

Cone Snail Toxins.

Cone snail toxins (conotoxins) are 12-40 amino acids. They are linear but contain multiple disulfide bonds (Bulaj et al., 2003). Like the *Amanita* toxins, the cone snail toxins exist as gene families, the members of which have hyper-variable regions, corresponding to the amino acids present in the mature toxins, and conserved regions found in all members (Olivera, 2006; Woodward et al., 1990). Conotoxins and *Amanita* toxins differ in many key respects. First, the *Amanita* toxins are smaller (7-10 amino acids vs. 12-40 for the conotoxins) (Bulaj et al., 2003). Second, the mature conotoxins are at the carboxy termini of the preproproteins and are predicted to be cleaved by a protease that cuts at basic amino acids (Arg or Lys). In contrast, the mature *Amanita* toxin sequences are internal to the proprotein and are predicted to require two cleavages by one or more prolyl peptidases. Third, the conotoxins are "cyclized" by multiple disulfide bonds, whereas the *Amanita* toxins are cyclized by N-terminus to C-terminus (head-to-tail) peptide bonds and do not have disulfide bonds. Fourth, the conotoxin preproproteins have signal peptides to direct secretion into the venom duct, whereas the *Amanita* toxins are not secreted (Zhang et al., 2005) and their proproteins lack predicted signal peptides (FIG. 4).

Amphibian, Snake, and Spider Toxins.

Like the conotoxins, these peptides are synthesized on ribosomes as preproproteins, undergo posttranslational modifications, and contain multiple disulfide bonds. None of them are truly cyclic nor as small as the *Amanita* toxins.

Cyclotides.

Cyclotides such as kalata are 28-37 amino acids in size (Trabi and Craik, 2002; Craik et al., 2007). The precursor structure contains an N-terminal signal peptide followed by a proprotein region and a conserved "N-terminal repeat region" containing a highly conserved domain of ~20 amino acids, one to three cyclotide domains, and a short C-terminal sequence. An Asn-endopeptidase is responsible for removing the C-terminal peptide from the proprotein and cyclizing the peptide (Saska et al., 2007), but the protease that cuts the N-terminus is apparently not known. The mature cyclotides are true head-to-tail cyclic peptides but, like some linear peptides, also have multiple disulfide bonds.

Bacterial Auto-Inducing Peptides (AIPs).

Quorum sensing by certain pathogenic Gram-positive bacteria, such as species of *Staphylococcus*, involves the secretion and recognition of small (7-9 amino acid) ribosomally-encoded peptides called AIPs (Novicku and Geisinger, 2008). AIPs are posttranslationally cyclized by formation of a thiolactone between the carboxyl group of the C-terminal amino acid and an internal Cys. AIP proproteins are processed at the C-terminus by agrB with simultaneous condensation to form the thiolactone ring (Lyon and Novick, 2004). The inventors determined that there are no proteins related to agrB in *Amanita, Galerina*, or any fungus in GenBank.

Microcin and related molecules. Microcin J25 is a 21-amino acid peptide cyclized between an N-terminal Gly or Cys residue and an internal Glu or Asp residue. It is produced by *E. coli*; other enterobacteria produce related peptides. Processing of the primary translation product (58 amino acids) involves cleavage of a 37-residue leader peptide and cyclization. Cyclization requires two genes, mcjA and mcjB, which are part of the microcin operon (Duquesne et al., 2007). The maturation reaction requires ATP for amide bond formation. The inventors did not find any orthologs of mcjA or mcjB by BLAST searching of all available fungal genomes, including *Amanita* and *Galerina*. Comparison of the *Amanita* toxins to all other known small cyclic peptides indicates that they are unique among microbial natural products in regard to their chemistry, modes of action, and biosynthesis.

A summary of several unique characteristics of *Amanita* toxins and peptides, linear and cyclic, includes but is not limited to: (1) The *Amanita* toxins are true head-to-tail cyclic peptides, unlike lantibiotics, cone snail toxins, microcins, or AIPs. (2) The tryptathionine moiety (Trp-Cys cross-bridge) is not found in any other natural molecule (May and Perrin, 2007). (3) The *Amanita* toxins are the only known ribosomally synthesized cyclic peptides from the Kingdom Mycota (Fungi), the source of many important secondary metabolites that affect human health. (4) The known *Amanita* toxins have unique modes of action, which contributes to their toxicity and also makes them widely used tools for basic biomedical research. The interaction of alpha-amanitin with pol II is understood in detail (Bushnell et al., 2002). It is therefore possible that other cyclic peptides known or predicted to be made by *Amanita*(for example, see, FIG. 4) might also have biologically significant modes of action that would make them useful as pharmaceutical agents or research reagents. (5) Amatoxins are not secreted (Zhang et al., 2005). Consistent with this the proproteins do not have predicted signal peptides. In this regard they differ from conotoxins, lantibiotics, snake and spider venoms, amphibian peptides, or microcins. Determination of the cellular location of toxin biosynthesis and accumulation is one Aim of this proposal. (6) The *Amanita* toxins are among the smallest known ribosomally synthesized peptides. Their proproteins (34 and 35 amino acids) are also very small by the standards of typical ribosomally synthesized proteins. (7) No other known peptides are predicted to be processed from their proproteins by a Pro-specific peptidase, and (8) Although *Amanita* has advantages over other eukaryotic synthesizers of small peptides. Snakes, amphibians, cone snails, and spiders are difficult to obtain or cultivate and their toxins are made only in small venom ducts.

As described herein the inventors discovered the presence of conserved and hypervariable regions in genes encoding small peptide mushroom toxins. After the inventors compared the *Amanita* toxin genes of the present inventions to known conotoxin genes they discovered that genomic sequences of both organisms are characterized by the presence of conserved and hypervariable regions, however with notable significant differences in the size and structure of the coding regions. Cone snails appear to have the capacity to synthesize a large number of peptides on the same fundamental biosynthetic scaffold, however the toxin producing pathway is not known (Richter et al., (1990) Proc. Nat. Acad. Sci. USA 87:4836; Woodward et al. (1990), EMBO J. 9:1015; all of which are herein incorporated by reference). However, in contrast to the conotoxins (Olivera, (2006) J. Biol. Chem. 281:31173; herein incorporated by reference), the *Amanita* toxins genes encode smaller peptides from shorter regions of conserved and hypervariable regions in addition to showing other significant differences, Benjamin, Denis R. 1995. Mushrooms. Poisons and panaceas. (W.H. Freeman, New York). xxvi+422 pp; herein incorporated by reference).

IV. Contemplated Role of Prolyl Oligopeptidase Family (POP) in Mushroom Toxin Production.

Prolyl oligopeptidase family (POPs) from other organisms are known to cleave several classes of Pro-containing peptides including mammalian hormones such as vasopressin (Brandt et al., 2007; Cunningham and O'Connor, 1997; Garcia-Horsman et al., 2007; Polgar, 2002; Shan et al., 2005). Changes in human blood serum levels of POP have been associated with depression, mania, schizophrenia, and response to lithium (Williams, 2005). A POP inhibitor reverses scopolamine-induced amnesia in rats (Brandt et al., 2007). Mutation of a POP gene in *Drosophila* results in resistance to lithium (Williams et al., 1999). POPs have been proposed as a treatment for celiac-sprue disease, which is caused by failure to properly digest Pro-rich peptides in gluten (Shan et al., 2002, 2005). Despite the demonstration that POP will cleave many small peptides, such as mammalian hormones, apparently the native, endogenous substrates of POPs are not known in any system (Brandt et al., 2007).

The *Amanita* toxin system is contemplated to represent the first time a native substrate of a POP was identified, as shown during the development of the present inventions (see below and FIG. 20). Specifically, because alpha-Amanitin and phallacidin are synthesized as proproteins of 35 and 34 amino acids, respectively, from which the inventors contemplate undergo cleaving by a prolyl oligopeptidase.

The inventors further identified sequences related to human POP (GenBank accession no. NP002717) in the genome survey sequences of *A. bisporigera*. Orthologs of human POP (POP-like genes) were also found in every other basidiomycete for which whole genome sequences were available (*Laccaria bicolor, Coprinus cinereus, Phanerochaete chrysosporium, Ustilago maydis, Sporobolomyces roseus, Puccinia graminis*, and *Cryptococcus neoformans*). A POP-like gene has been characterized from the mushroom *Lyophyllum cinerascens*. In contrast, orthologs of human POP are rare or nonexistent in fungi outside of the basidiomycetes. Thus, it appears that at least one component of the biochemical machinery necessary for the biosynthesis of the *Amanita* toxins is both widespread in, and restricted to, the basidiomycetes (Hallen, et al., Gene family encoding the major toxins of lethal *Amanita* mushrooms, Proc. Natl. Acad. Sci. USA 104: 19097-19101, herein incorporated by reference all of which is herein incorporated by reference).

V. Genomic Structure of *Amanita* Peptide Encoding Genes of the Present Inventions.

The inventors discovered *Amanita* peptides genes and translated peptides relating to *Amanita* toxins during the development of the present inventions. In particular, the inventors discovered a genomic structure of *Amanita* peptides, AMA1 and PHA1, relating to amatoxin and phallotoxin toxins. Both types of peptides comprise a conserved stretch (A) of about 9 homologous amino acids, followed by a hypervariable region of at least 2, 7, 8 and up to 10 amino acids that are specific for either the two types of toxin peptides, a-amanitin and phallacidin, in addition to longer peptides. These hypervariable regions were followed by an additional conserved stretch (B) of approximately 2-7 homologous amino acids. The inventors contemplate that the coding sequences of the toxins are part of a larger preproprotein that is translated and then undergoes post-translational processing to release the active peptide, similar to processing mechanisms of neuropeptides and other small peptide toxins (e.g., conotoxins).

The genome of *A. bisporigera* contains at least 10 copies of genes coding for the first highly conserved stretch of amino acids (A), followed by a hypervariable region (P), then another conserved region (B). The primary sequences derived from the cDNA encode peptides AWLVDCP (SEQ ID NO: 69) and IWGIGCNP (SEQ ID NO: 50) which are contemplated to be capable of cyclization into related cylic toxin peptides. Neither of these peptides were found after searching the entire GenBank NR database. Therefore, by statistical coincidence they are unlikely to be present in *A.*

*bisoporigera*; however, experimental results shown herein demonstrate that nucleic acid sequences are present that may encode these linear peptides.

The *Amanita* toxins differ from the other known naturally occurring small peptides in several ways. First, the animal peptides are not cyclized by peptide bonds known to be present in *Amanita* toxins but acquire their essential rigidity by extensive disulfide bonds. Ribosomally synthesized cyclic peptides are known from bacteria, plants, and animals, e.g., the cyclotides and microcin J25 (Craik, (2006) Science 311:1563, Rosengren, et al., (2003), J. Am. Chem. Soc. 125:12464; all of which are herein incorporated by reference), but to the best of the inventor's knowledge known fungal cyclic peptides are synthesized by nonribosomal peptide synthetases (Walton, et al., (2004) in *Advances in Fungal Biotechnology for Industry, Agriculture, and Medicine*, J. S. Tkacz, L. Lange, Eds. (Kluwer Academic/Plenum, N.Y., pp. 127-162; Finking, et al., (2004) *Annu. Rev. Microbiol.* 58:453; all of which are herein incorporated by reference). Second, the *Amanita* toxins are not secreted, and consistent with this they lack predicted signal peptides in their sequences (FIGS. 4 and 5) (Muraoka, et al., (1999) *Appl. Environ. Microbiol.* 65:4207, Zhang et al., (2005) *FEMS Microbiol. Lett.* 252:223; all of which are herein incorporated by reference). Third, whereas the other known peptides are processed from their respective proproteins by proteases that recognize basic amino acid residues (Arg or Lys) (Olivera, J. Biol. Chem. 281:31173 (2006), Richter et al., (1990) Proc. Nat. Acad. Sci. USA 87:4836; all of which are herein incorporated by reference), the toxins of *Amanita* are predicted to be cleaved from their proproteins by a proline-specific protease. As shown herein, the inventors were able to begin confirming their predictions by demonstrating the cleavage of a small peptide using an isolated POPB sequence, see, FIG. 20.

Further, the inventors contemplate that genes for *Amanita* toxin biosynthesis will be clustered within the *Amanita* genome. As shown herein, an example of genomic organization of PHA genes in relation to adjacent genes encoding potential enzymes.

VI. Contemplated Role of P450 Homologes in Mushroom Toxin Production.

Hydroxylation of the *Amanita* toxins might be catalyzed by cytochrome P450 monooxygenases, which are known to catalyze hydroxylation of many other fungal secondary metabolites (e.g., Malonek et al., 2005; Tudzynski et al., 2003). Filamentous fungi differ widely in their numbers of P450's. Whereas some filamentous fungi have >100, the Basidiomycete *Ustilago maydis* has only ~17 (hypertext transfer protocol site:drnelson.utmem.edu/CytochromeP450.html). The inventors found three P450 genes clustered with two copies of PHA1 (FIG. 10D and in Example).

In terms of identifying new P450 genes contemplated to be involved in *Amanita* toxin biosynthesis, three candidates in the three P450's were found on a lambda clone clustered with two copies of PHA1 (FIG. 10D). Since secondary metabolites appear to be rare in Basidiomycetes compared to Ascomycetes, the number of P450's in *A. bisporigera* is probably closer to the Basidiomycete *Ustilago* (.about.17) than the Ascomycete *Fusarium* (>100) (hypertext transfer protocol site:drnelson.utmem.edu/CytochromeP450.html).

Sequencing of the genome to 20× should also yield all of the other members of the "MSDIN" toxin family yielding a complete picture of the number and diversity of potential cyclic peptides that *Amanita* could synthesize. The inventors calculate that there are >30 MSDIN sequences in *A. bisporigera*.

VII. *Galerina* Mushrooms for Use in the Present Inventions.

Further, the present invention relates to using genes and proteins from *Galerina* species encoding mushroom toxins, specifically amatoxins but not phallotoxins. *Galerina* sequences and *Galerina* mushrooms are particularly contemplated for use in the present inventions because *Galerina* is the only known culturable fungus that produces amanitins. Amatoxins may be induced by cultured *Galerina*, by several methods, for example, Benedict R G, V E Tyler Jr., L R Brady, L J Weber (1966) Fermentative production of *amanita* toxins by a strain of *Galerina marginata*. J Bacteriol 91:1380-1381; and preferably using methods described in Muraoka S, T Shinozawa (2000) Effective production of amanitins by two-step cultivation of the basidiomycete, *Galerina fasciculata* GF-060. J Biosci Bioeng 89:73-76.

Thus the present inventions further relate to compositions and methods associated with creating and screening genomic libraries from *Galerina* and other species for sequences of interest. In particular, the present invention relates to providing and using PCR primers for identifying and sequencing *Galerina* genes, including methods comprising RACE PCR primers. Specifically, the present inventions relate to identifying and using sequences of interest associated with the production of small peptides, including cyclic peptides, for example, compositions and methods comprising *Galerina* POP homologes and amatoxins.

The procedures used to ligate the DNA construct of the invention, the promoter, terminator and other elements, respectively, and to insert them into suitable cloning vehicles containing the information necessary for replication, are well known to persons skilled in the art (see, e.g., Sambrook et al., 1989; herein incorporated by reference).

The polypeptide may be detected using methods known in the art that are specific for the polypeptide. These detection methods may include use of specific antibodies, formation of an enzyme product, disappearance of an enzyme substrate, or SDS-PAGE gel blotted onto membranes for immunoblotting. For example, an enzyme assay may be used to determine the activity of the polypeptide. Procedures for determining enzyme activity are known in the art for many enzymes.

VIII. Recombinant Products of *Amanita* and *Galerina* Genes.

The desired end product, i.e., the polypeptide of interest, such as a POP enzyme, may be expressed by a host cell, such as a bacterium, i.e. *E. coli*, as a heterologous protein or peptide. Thus the polypeptide may be any polypeptide heterologous to the bacterial cell. The term "polypeptide" is not meant herein to refer to a specific length of the encoded product and, therefore, encompasses peptides, oligopeptides, and proteins. The heterologous polypeptide may also be an engineered variant of a polypeptide. The term "heterologous polypeptide" is defined herein as a polypeptide, which is not native to the host cell. Preferably, the host cell is modified by methods known in the art for the introduction of an appropriate cloning vehicle, i.e., a plasmid or a vector, comprising a DNA fragment encoding the desired polypeptide of interest. The cloning vehicle may be introduced into the host cell either as an autonomously replicating plasmid or integrated into the chromosome. Preferably, the cloning vehicle comprises one or more structural regions operably linked to one or more appropriate regulatory regions.

The structural regions are regions of nucleotide sequences encoding the polypeptide of interest. The regulatory regions include promoter regions comprising transcription and translation control sequences, terminator regions comprising stop signals, and polyadenylation regions. The promoter, i.e., a nucleotide sequence exhibiting a transcriptional activity in the host cell of choice, may be one derived from a gene encoding an extracellular or an intracellular protein, preferably an enzyme, such as an amylase, a glucoamylase, a protease, a lipase, a cellulase, a xylanase, an oxidoreductase, a pectinase, a cutinase, or a glycolytic enzyme.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and l (liters); ml (milliliters); μl (microliters); cm (centimeters); mm (millimeters); μm (micrometers); nm (nanometers); U (units); min (minute); s and sec (second); deg (degree); ° C. (degrees Centigrade/Celsius).

Example I

Materials and Methods

The following is a description of exemplary materials and methods that were used in subsequent Examples during the development of the present inventions.
Exemplary Mushroom Species of the Present Inventions (FIG. 2).

The inventors selected the genome of *Amanita bisporigera* to provide sequences of interest because of reports on consistently high, albeit somewhat variable, levels of amatoxins and phallotoxins within individual fruiting bodies combined with the relative ease of obtaining exemplary wild growing mushrooms by merely identifying and harvesting the mushrooms.
Exemplary Basic Molecular Biology Techniques.

The inventors contemplated that a cDNA sequencing project or sequencing an EST library was impracticable for obtaining sequences of interest, in part due to the observations that amatoxin biosynthesis appeared to take place in a narrow window at or near the time of button initiation rendering transcription of amatoxin biosynthetic genes unlikely to be observable in the macroscopic organism (Preston et al., Investigations on the function of amatoxins in *Amanita* species: a case for amatoxins as potential regulators of transcription. In: Peptide Antibiotics—Biosynthesis and Functions. H Kleinkauf & H von Döhren, eds. Berlin, Germany: Walter de Gruyter. pp. 399-426; herein incorporated by reference and observed by inventor Hallen).
Genomic DNA Isolation.

Although the carpophores (fruiting bodies) contain high concentrations of the toxins, like other ectomycorrhizal Basidiomycetes, species of *Amanita* grow slowly and do not form carpophores in culture (Muraoka et al., (1999) Appl. Environ. Microbiol. 65:4207; Zhang et al., (2005) FEMS Microbiol Lett. 252:223; all of which are herein incorporated by reference). Therefore, *A. bisporigera* mushrooms, an amatoxin- and phallotoxin-producing species native to North America, were harvested from the wild in 2002, 2006 and 2007. Caps and undamaged stems were cleaned of soil and debris, frozen at −80° C., and lyophilized.

Genomic DNA was extracted from the lyophilized fruiting bodies using cetyl trimethyl ammonium bromide-phenol-chloroform isolation (Hallen, et al., (2003) *Mycol. Res.* 107:969; herein incorporated by reference). For studies requiring RNA, RNA was extracted using TRIZOL (Invitrogen) (Hallen, et al., (2007) *Fung. Genet. Biol.*, 44:1146; herein incorporated by reference in its entirety). Specifically, DNA for genomic blotting was cut with PstI and electrophoresed in 0.7% agarose.
Probe Labeling, DNA Blotting, and Filter Hybridization.

Standard protocols were followed for these and similar molecular biology procedures (see, Maniatis, et al., Molecular Cloning: A Laboratory Manual, (Cold Spring Harbor, N.Y., 1982) and Singh, et al., (1984) Nucl. Acids Res. 12:5627; herein incorporated by reference). In general, hybridization was done overnight at 65° C. in 4×SET (600 mM NaCl, 120 mM Tris-HCl, pH 7.4, 8 mM EDTA), 0.1% sodium pyrophosphate, 0.2% SDS, 10% dextran sulfate, 625 μg/ml heparin. Washing: twice in 2×SSPE (300 mM NaCl, 20 mM $NaH_2PO_4$, 2 mM EDTA, pH 7.4), 0.1% SDS at 21° C., then twice in 0.1×SSPE and 0.1% SDS at 60° Celcius.
PCR Amplification of Peptide Encoding Genes.

PCR primers for amanitin and phallacidin were based on fragments within sequences shown in FIGS. 4-6. The primer sequences used are shown in Table 3.

TABLE 3

PCR primers for amanitin (AMA1) and phallacidin (PHA1).

| Sequence Name | SEQ ID NO: | SEQUENCE |
|---|---|---|
| AMA1, forward | SEQ ID NO: 1 | 5' CCATCTGGGGTATCGGTTGC 3' |
| AMA1, reverse | SEQ ID NO: 2 | 5' TTGGGATTGTGAGGTTTAGAGGTC 3' |
| PHA1, forward | SEQ ID NO: 3 | 5' CGTCAACCGTCTCCTC 3' |
| PHA1, reverse | SEQ ID NO: 4 | 5' ACGCATGGGCAGTCTAC 3' |

A 551-bp fragment of the *A. bisporigera* β-tubulin gene was amplified using primers 5'-ACCTCCATCTCGTCCAT-ACCTTCC-3' (SEQ ID NO: 5) and 5'-TGTTTGCCACGCT-GCATACTA-3' (SEQ ID NO: 6) was used as a control probe on DNA blots. PCR amplification was done using REDTaq ReadyMix DNA polymerase (Sigma) and appropriate reagents under 30 cycles of denaturation (94° C., 30 sec), annealing (55° C., 30 sec), and extension (72° C., 5 min).
Target Genes for Sequencing.

PCR target gene products were purified using Wizard SV Gel and PCR Clean-Up System (Promega) and then cloned into TOPO pCR 4 (Invitrogen) for sequencing.

Example II

This example describes exemplary methods for providing a fungal genomic library, specifically an *Amanita* spp., library.

The inventors initially contemplated the existence of an amatoxin synthetase gene that was a member of the class of enzyme known as nonribosomal peptide synthetases. However after extensive unsuccessful attempts to obtain amatoxin synthetase genes or gene fragments through PCR-based techniques using isolated genomic DNA, see, Example III, and biochemical methods (such as, ATP-pyrophosphate exchange assay; amino acid feeding studies, etc.), the inventors subsequently initiated a shotgun genome sequencing project for obtaining genes of interest, such as genes associated with cyclized peptide production, toxin production, peptide encoding genes, toxin encoding genes, etc. One genomic library was generated by the Genomics Technology Support Facility at Michigan State University and one was generated by Macrogen, Inc. Each library yielded genomic fragments of approximately 2-kb in length. Random clones were end sequenced by automated dideoxy sequencing.

Approximately 5.7 Mb sequence was generated in approximately 10,000 unidirectional sequencing reads using dideoxy sequencing using an ABI 3730 Genetic Analyzer and an ABI Prism 3700 DNA Analyzer (sequencing performed at the Research Technologies Support Facility at Michigan State University, and by Macrogen, Inc.).

The inventors originally began a public *Amanita* sequence database; however, after a brief posting of the above-described sequencing results, the inventors removed those sequences from public access (see, Examining amatoxins: The *Amanita* Genome Project. Hallen, Walton, 159. The utility of the incomplete genome: the *Amanita* bisporigera genome project. Mar. 15-20, 2005 Asilomar Conference Center, Pacific Grove Calif. Fungal Genetics Newsletter, Volume 52-Supplement XXIII FUNGAL GENETICS CONFERENCE; herein incorporated by reference). Moreover, to the inventors' knowledge, sequences of the present inventions were never publicly available.

The inventors subsequently also completed at least four runs on a Genome Sequencer 20 from 454 Life Sciences (Margulies et al., (2005) Nature 437:376; herein incorporated by reference). This generated approximately 70 MB of sequence data, which is approximately 2× coverage of the genome of *A. bisporigera*, based on the known size of other Homo basidiomycetes, (Le Quere et al., *Fung. Genet. Biol.* 36, 234 (2002), which is herein incorporated by reference; *Coprinus cinereus* Sequencing Project. Broad Institute of MIT and Harvard (broad.mit.edu/annotation/genome/coprinus_cinereus/Home.html)).

The inventors structured and maintained the sequenced DNA in a password-protected, private BLAST-searchable format. The sequences were compared to GenBank's non-redundant database.

BLASTX (translated query against protein database) was used in searching the non-redundant database (NR) at GenBank, and TBLASTX (translated query against translated database) and BLASTN (nucleotide query against nucleotide database) were used in searching the genomes of *Coprinopsis* (also known as *Coprinus*) and *Phanerochaete*, the two closest relatives to *Amanita* for which complete genome sequence was available[1]. BLAST results were examined, catalogued, and automatically annotated.

[1] The genome sequence of *Coprinus* is available in GenBank, but Phanerochate is currently available only at the DOE JGI website.

Example III

This example describes the failure of the inventors to obtain a gene homologous to a fungal nonribosomal peptide synthetases (NRPSs) in *Amanita bisporigera*, which produces amatoxins, phallotoxins, and other putative *Amanita* peptide toxins. Details are shown in a poster entitled "Examining amatoxins: The *Amanita* Genome Project" Hallen Walton 159. The utility of the incomplete genome: the *Amanita bisporigera* genome project. Mar. 15-20, 2005 Asilomar Conference Center Pacific Grove Calif. Fungal Genetics Newsletter, Volume 52—Supplement XXIII FUNGAL GENETICS CONFERENCE; herein incorporated by reference.

Because known fungal cyclic peptides are biosynthesized by methods comprising nonribosomal peptide synthetases (NRPSs) (Walton, et al., in Advances in Fungal Biotechnology for Industry, Agriculture, and Medicine, et al., Eds. (Kluwer Academic/Plenum, New York, 2004, pp. 127-162; Finking, et al., (2004) Arum Rev Microbiol 58:453-488, all of which are herein incorporated by reference), the inventors initiated an attempt to identify by PCR in the total genomic DNA of *Amanita bisporigera* sequences encoding an NRPS using PCR primers based on known bacterial and fungal NRPSs and total *A. bisporigera* DNA as template. The inventors contemplated that any NRPS genes sequences within the *Amanita bisporigera* genome should have been readily amplified using two or more of PCR primers and identifiable due to its large size, presence of 8 amino acid adenylating domains, and other conserved regions present in all known NRPS-encoding sequences.

TABLE 4

| PCR primers used that failed to obtain a NRPS sequence (See FIG. 3). | | | |
|---|---|---|---|
| Forward Primers 5'-3' | | Reverse Primers 5'-3' | |
| AIxKAGxA: SEQ ID NO: 7 | GCN ATH TNN AAR GCN GGN NCN GC | AIxKAGx: SEQ ID NO: 8 | GCN GNN CCN GCY TTN NAD ATN GC |
| FTSGSTG (JA4F): SEQ ID NO: 9 | TTY ACI TCI GGI TCI ACI GG¹na | na | |
| YTSGSTG1: SEQ ID NO: 10 | TAY ACN AGY GGN AGY ACN GG na | na | |

TABLE 4-continued

Figure 3:
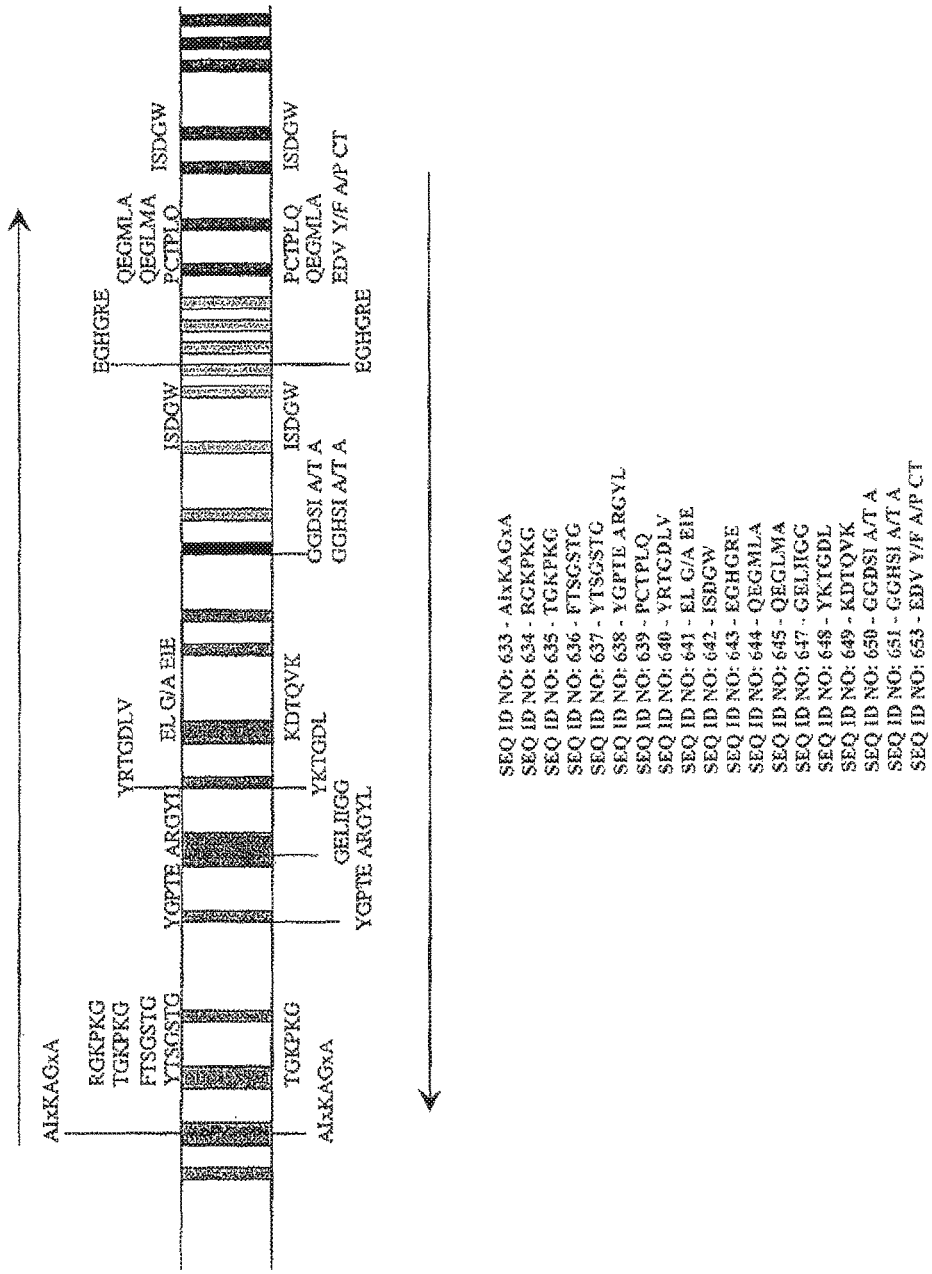
FIG. 3 shows an exemplary hypothetical peptide synthetase showing conserved motifs found in many NRPS proteins that served as the basis for the design of PCR primers (see, Table 4).

PCR primers used that failed to obtain a NRPS sequence (See FIG. 3).

| Forward Primers 5'-3' | | Reverse Primers 5'-3' | |
|---|---|---|---|
| YTSGSTG2: SEQ ID NO: 11 | TAY ACN AGY GGN TCN ACN GG | na | na |
| YTSGSTG3: SEQ ID NO: 12 | TAY ACN TCN GGN TCN ACN GG | na | na |
| YTSGSTG4: SEQ ID NO: 13 | TAY ACN TCN GGN AGY ACN GG | na | na |
| SRGKPKG: SEQ ID NO: 14 | TCT AGA GGN AAR CCN AAR GG[2] | na | na |
| TGKPKG: SEQ ID NO: 15 | ACN GGN AAR CCN AAR GG[4] | TGKPKG: SEQ ID NO: 16 | CCY TTN GGY TTN CCN GT |
| YGPTE: SEQ ID NO: 17 | TAY GGN CCN ACN GA[4] | YGPTE: SEQ ID NO: 18 | TTC NGT NGG NCC RTA |
| YGPTE2: SEQ ID NO: 19 | TAC GGN CCN ACN GAN | na | na |
| na | na | GELIIGG: SEQ ID NO: 20 | CCN CCN ATN ATN AGY TCN CC |
| ARGY: SEQ ID NO: 21X | TBG CNC GNG GNT ACN | ARGY: SEQ ID NO: 22 | GTA NCC NCG NGC GAN |
| Y K/R TGDL: SEQ ID NO: 23 | TAC ARR ACN GGN GAY CT | YKTGDL: SEQ ID NO: 24 | ARR TCN CCN GTY TTR TAT CTA GA[2] |
| YRTGDLV: SEQ ID NO: 25 | TAY MGI ACI GGI GAY YTI GT | na | na |
| Y/F RTGD L/R G/V R(TGD): SEQ ID NO: 26 | TWY GCI ACI GGI GAY YKI GKI CG[3] | na | na |
| ELGEIE: SEQ ID NO: 27 | GAR YTN GSN GAR ATH GA | KDTQVK (JA5): SEQ ID NO: 28 | GGI ACY TGI TGR TCY TT[1] |
| na | na | LLXLGGX S (LGG): SEQ ID NO: 29 | AWI GAR KSI CCI CCI RRS IMR AAR AA[3] |
| GGDSI A/T: SEQ ID NO: 30 | GGN GGN GAY TCN ATY RCN | GGDSI A/T A: SEQ ID NO: 31 | GCN GYD ATN SWR TCN CCN CC |
| na | na | GGHSI A/T A: SEQ ID NO: XX | GCN GYR ATN GAR TGN CCN CC |
| na | na | GDSITA Cochliobolus victoriae: SEQ ID NO: 32 | CGC CGT GAT CGA ATC CCC |
| ISGDW: SEQ ID NO: 33 | CAY CAY NNN ATH WSN GAY GGN TGG | ISGDW: SEQ ID NO: 34 | CCT NCC RTC NSW NAT NNN RTG RTG |
| EGHGRE: SEQ ID NO: 35 | GAR GGN CAY GGN MGN GA | EGHGRE: SEQ ID NO: 36 | TCN CKN CCR TGN CCY TC |
| DAYPCS C. victoriae: SEQ ID NO: 37 | GAT GCC TAC CCA TGC TCG | DVYPCTP: SEQ ID NO: 38 | GTK CAN GSR WAN ACR TCY TC |

TABLE 4-continued

PCR primers used that failed to obtain a NRPS sequence (See FIG. 3).

| Forward Primers 5'-3' | | Reverse Primers 5'-3' | |
|---|---|---|---|
| PCTPLQ: SEQ ID NO: 39 | CCN TGY ACN CCN YTN CA | PCTPLQ: SEQ ID NO: 40 | TGN ARN GGN GTR CAN GG |
| na | na | PCTPLQ2: SEQ ID NO: 41 | TGI ARI GGI GTR CAI GG |
| QEGLMA(JA1): SEQ ID NO: 42 | CAR GAR GGI YTI ATG GC[1] | QEGLMA: SEQ ID NO: 43 | CGC ATN AGN CCY TCC TG |
| QEGMLA: SEQ ID NO: 44 | KAR GGN ATG AWN GC | QEGMLA: SEQ ID NO: 45 | GCN WTC ATN CCY TMY TG |

[1]Primer sequences that the inventors obtained from Dr. Aric Weist
[2]Primers referenced in Panaccione, (1996) Mycological Research 100: 429-436; herein incorporated by reference.
[3]Primers referenced in Turgay & Marahiel (1994), Peptide Research 7: 238-241; herein incorporated by reference.
[4]Primers references in Nikolskaya et al. (1995) Gene 165: 207-211
Abbreviations: A, adenine; T, thymine; G, guanine; C, cytosine; I, inosine, K, G or T; R, A or G; M, A or C; W, A or T; Y, C or T.
Na = not available In order to find an NRPS in *A. bisporigera*, the inventors first contemplated that amatoxins were synthesized via a non-ribosomal peptide synthetase (NRPS) as found in other types of fungi (see, example in FIG. 3). Specifically, the inventors further contemplated that a NRPS responsible for biosynthesizing amatoxins would be encoded by a gene of approximately 30 kb in size. Because amatoxins contain eight amino acids, and in NRPS enzymes one domain activates by adenylation one amino acid, the enzyme should be approximately one MDa. Such a protein was predicted to be encoded by a 30-kb gene. The inventors further contemplated random (shotgun) sequencing of the genome and an average read size of 600 bp and calculated a >99% probability of hitting a 30 kb target in a 40 Mb genome in 7,000 random, independent sequences.

The inventors generated more than 70 MB of DNA sequence and searched using BLAST and more than 20 known NRPS genes and proteins from prokaryotes and eukaryotes for evidence for an NRPS in the genome of *A. bisporigera*. However, the inventors did not find evidence for any NRPS-like sequence in *A. bisporigera*. In contrast, the inventors discovered that the most closely related sequences to NRPSs were orthologs of aminoadipate reductase and acyl-CoA synthase, which, like bacterial and fungal NRPSs, are classified within the aminoacyl-adenylating superfamily (Finking et al., (2004) Annu. Rev. Microbiol. 58:453; herein incorporated by reference).

Approximately 59% of the *Amanita bisporigera* sequences of the present inventions did not show a hit to the GenBank NR database. This is consistent with results from other fungal genome projects (see, e.g. Schulte, U (2004) Genomics of filamentous fungi. In Advances in Fungal Biotechnology for Industry, Agriculture, and Medicine (JS Tkacz & L Lange, eds.):15-29. Kluwyer Academic/Plenum Publishers, New York; herein incorporated by reference). Little annotation is yet available for fungal genomes, so the proportion of unidentified sequences is high. Three thousand eight sequences that produced no hits to NR, did yield hits to the *Phanerochaete* and/or *Coprinopsis* genomes. The following known genes were identified using BLAST comparisons of the *Amanita* fragments of the present inventions.

The inventors found matches contemplated to be *Amanita* homologs to members of the aminoacyl-adenylating superfamily (Finking et al., (2004) Annu Rev Microbiol 58:453-488; herein incorporated by reference) which includes but is not limited to exemplary sequences of L-aminoadipate-semialdehyde dehydrogenase. In particular, L-aminoadipate-semialdehyde dehydrogenase is related to but is not a non-ribosomal peptide synthetase (NRPS), an enzyme originally contemplated to be responsible for *Amanita* peptide toxin biosynthesis. The inventors ruled out a NRPS identity of this match after they sequenced the remainder of the clone 16_c01KoreaM13Rrc, then extended the sequence by approximately 700 bp using inverse PCR.

Cap64 is a capsule formation protein first identified in the pathogenic basidiomycete *Filobasidiella neoformans* with a known homolog in the saprophytic basidiomycete *Pleurotus ostreatus*, of which the later does not form capsules associated with mammalian pathogenicity. The discovery of an *Amanita*Cap64 homologous sequence was not expected because like *Pleurotus*, *Amanita* species are not known to form capsules associated with mammalian pathogenicity.

Laccases, like Cap64, were not expected even though they were previously found to be widespread in saprophytic fungi (*Coprinopsis*, *Melanocarpus*, and the white rot fungus *Trametes*), and in both asco- and basidiomycetes. Their role in an ectomycorrhizal fungus such as *Amanita*, which is expected to obtain most of its nutrients in the form of photosynthate and would therefore lack the need to degrade plant tissue, is unknown.

Therefore, despite predictions to the contrary, the inventors did not find evidence of an NRPS gene that would likely be involved with synthesizing amatoxins and phallotoxins (Walton et al. (2004) Peptide synthesis without ribosomes. In: *Advances in Fungal Biotechnology for Industry, Agriculture, and Medicine*. J Tkacz, L Lange, eds, Kluwer Academic, New York, pp. 127-162; herein incorporated by reference). Yet on the other hand surprisingly discovered other types of genes.

Example IV

This example describes exemplary compositions and methods for identifying amatoxin genes. The inventors initially focused on amatoxins, in particular amanitins, bicyclic octapeptides which are more potent toxins to humans than any of the other mushroom toxins and are directly responsible for the majority of fatal human mushroom poisonings. Specifically, this example describes the discovery of an *A. bisporigera* gene sequence contemplated to encode alpha amanitin.

An exemplary structure of .alpha.-amanitin is cyclic(L-asparaginyl-4-hydroxy-L-prolyl-(R)-4,5-dihydroxy-L-isoleucyl-6-h-ydroxy-2-mercapto-L-tryptophylglycyl-L-isoleucylglycyl-L-cysteinyl), cyclic (4-8)-sulfide, (R)—S-oxide (ChemIDplus), wherein the amino acids have the L configuration and several amino acids are modified by hydroxylation. This structure was apparently simplified to the 20 proteogenic amino acids, wherein the chemical name became cyclic (NPIWGIGC) (SEQ ID NO: 46) (ChemIDplus). However because this is a cyclized peptide, the order in which the amino acids are assembled biosynthetically was unknown. Moreover, the structure of β-amanitin, RN: 21150-22-1 was based upon the known chemical structure of α-amanitin RN: 23109-05-9 and named in a similar manner.

Therefore, the inventors searched the DNA sequences from their *A. bisporigera* genome seeking DNA fragments capable of encoding amino acid sequences of amanitins, such as predicted sequences comprising a known predicted sequence of NPIWGIGC (SEQ ID NO: 46). Thus the inventors discovered an exemplary sequence encoding α-amanitin, ECIMO1V02FKY4Z S CCCAACTAAATCCCATTCGAACCTAACTCCAAGACCTCTAAACCTCACAATCC CAATGTCTGACATCAATGCTACCCGTCTCCCCATCTGGGGTATCGGTTGCAAC CCGTGCG, length=113 (SEQ ID NO:48) encoding PTKSHSNLTPRPLNLTIPMSDINATRLP IWGIGCNPC C (SEQ ID NO:49), see FIG. 4.

The inventors' exemplary sequence translates into a IWGIGCNP, SEQ ID NO:50, which the inventors contemplate would be capable of forming a, cyclo(IWGIGCNP), SEQ ID NO:51, wherein the inventors further contemplated several posttranslational hydroxylations and a sulfoxide crossbridge between the Trp and the Cys in order to form the bicyclic peptide known as alpha-amanitin. The inventors used the amino acid sequence and the nucleic acid sequences encoding IWGIGCNP (SEQ ID NO: 50) for searching known sequences in GenBank's non-redundant database. There was no evidence of any gene encoding or protein with IWGIGCNP (α- and γ-amanitins) (SEQ ID NO: 50). Therefore, the inventors contemplated that these sequences are unique for *A. bisporigera* and further these sequence orders were unlikely to be present in an *Amanita* genome by statistical coincidence.

The inventors also obtained a second and longer sequence comprising nucleotides encoding IWGIGCNP (SEQ ID NO: 50) using inverse PCR (AMA1 forward and reverse primers, see above) and obtained a genomic sequence contig 49252 AATCTCAGCGTTCAGTACCCAACTCCCATTCGAACCTAACTCCAAGACCTCTAAACC TCACAATCCCAATGTCTGACATCAATGCTACCCGTCTCCCCATCTGGGGTATCGGTT GCAACCCGTGCGTCGGTGACGACGTCACTACG, length=146 (SEQ ID NO:4) encoding SQRSVPNSHSNLTPRPLNLTIPMSDINATRLPIWGIGCNP CVGDDVTT (SEQ ID NO:5).

Therefore the inventors found nucleotide sequences that encode the amino acid sequence of α-amanitin with the sequence order of IWGIGCNP (SEQ ID NO: 50), in single letter code, and further identified two larger genomic sequences encoding an IWGIGCNP (SEQ ID NO: 50) amanitin peptide in the genome of *A. bisporigera*. The inventors contemplated that amanitins would be a cyclic permutation of linear peptides of IWGIGCNP (SEQ ID NO: 50) (α- and γ-amanitins) and IWGIGCDP (SEQ ID NO:54) (β- and ϵ-amanitins).

Example V

This example demonstrates using amino acid and nucleic acid information of the present inventions, inverse PCR and RACE methods to identify a cDNA and a large genomic fragment that comprises an amanitin gene as indicated in FIG. 4.

The inventors initiated a genomic survey using nucleic acid coding regions encoding the AMA1 gene, as described in the previous Example. SEQ ID NOs: 48, 49, 52, and 53, encoding an AMA1 polypeptide, were used to design AMA1 forward and reverse primers that were used in an inverse PCR reaction to obtain a larger genomic fragment of the AMA1 gene. Specifically, inverse PCR, using circularized PvuI generated genomic fragments as target (template) DNA resulted in the isolation of a 2.5-kb fragment of flanking genomic DNA.

RACE (Rapid Amplification of cDNA Ends) (for example, see, Frohman et al., (1988) Proc Natl Acad Sci 85:8998-9002; herein incorporated by reference), was used to obtain a full-length cDNA copy of AMA.1, SEQ ID NO:55, or SEQ ID NO:56. When compared to the AMA1 genomic sequence, SEQ ID NO:57, the cDNA indicated that AMA1 contains three introns (53, 59, and 58 nt in length), with canonical GT/AG boundaries. Two of the introns were in the 3' untranslated region, while the first intron was in the third codon from the end of the coding region (FIG. 4A). The inventors contemplated that translation started at the first ATG downstream of the transcriptional start site thus encoding a proprotein of 35 amino acids (FIG. 4A). The string of A's at the end represents the poly-A tail typical of eukaryotic mRNAs and their corresponding cDNAs (though not encoded within the genomic sequence). The amatoxin prepropeptide sequences is shown, where the amanitin peptide sequence is underlined, FIG. 4B.

TABLE 5

Examples of RACE primers used herein.

| SEQUENCE Name | SEQUENCE | SEQ ID NO: XX |
|---|---|---|
| GeneRacer ™ 5' Primer | 5'-GCACGAGGACACUGACAUGGACUGA-3' | SEQ ID NO: 58 |
| GeneRacer ™ 5' Nested Primer | 5'-GGACACTGACATGGACTGAAGGAGTA-3' | SEQ ID NO: 59 |
| GeneRacer ™ 3' Primer | 5'-GCTGTCAACGATACGCTACGTAACG-3' | SEQ ID NO: 60 |

TABLE 5-continued

Examples of RACE primers used herein.

| SEQUENCE Name | SEQUENCE | SEQ ID NO: XX |
|---|---|---|
| 3' AMA1 RACE initial primer | 5' CCCATTCGAACCTAACTCCAAGAC 3' | SEQ ID NO: 61 |
| 3' AMA1 RACE primer, nested primer | 5' CCTCTAAACCTCACAATCCCAATG 3' | SEQ ID NO: 62 |
| 5' AMA1 RACE cDNA, primer | 5' GCCCAAGCCTGATAACGTCCACAACT 3' | SEQ ID NO: 63 |
| 5' AMA1 RACE cDNA, nested primer | 5' TATCGCCCACTACTTCGTGTCATA 3' | SEQ ID NO: 64 |
| 3' PHA1, initial primer | 5' GACCTCTGCTCTAAATCACAATG 3' | SEQ ID NO: 65 |
| 3' PHA1, nested primer | 5' ATCAATGCCACCCGTCTTCCTG 3' | SEQ ID NO: 66 |
| 5' PHA1 initial primer | 5' CGGATCATTTACGTGGGTTTTA 3' | SEQ ID NO: 67 |
| 5' nested primer | 5' AACTTGCCTTGACTAGTGGATGAGAC 3' | SEQ ID NO: 68 |

Thus an exemplary amino acid sequence of the preproprotein of AMA1 is MSDINATRLPIWGIGCNPCIGDDVT-TLLTRGEALC (SEQ ID NO: 559). The inventors further contemplated an exemplary structure of β-amanitin, wherein Asn is replaced by Asp to provide IWGIGCDP (SEQ ID NO: 54). Indeed, further investigations described below, did result in the finding of an *Amanita* PCR product encoding a β-amanitin sequence.

An RNA blot of total RNA extracted from mushrooms of *Amanita* bisporigera probed with DNA fragment SEQ ID NO:48 showed an approximately 400 nt band contemplated as an AMA1 mRNA. Minor discrepancies between the genomic and cDNA sequences are likely due to natural variation among the amatoxin genes.

Example VI

This example describes the discovery of an *A. bisporigera* gene sequence contemplated to encode a phallotoxin, specifically a phallacidin toxin sequence.

An exemplary structure of phallacidin is a cyclic(L-alanyl-2-mercapto-L-tryptophyl-4,5-dihydroxy-L-leucyl-L-valyl-erythro-3-hydroxy-D-alpha-aspartyl-L-cysteinyl-cis-4-hydroxy-L-prolyl)cyclic (2-6)-sulfide, RN: 26645-35-2, with predicted amino acid sequences simplified to the 20 proteogenic amino acids comprising cycloAWLVDCP, SEQ ID NO:69. Another phallotoxin, phalloidin, RN: 17466-45-4, is a cyclic(L-alanyl-D-threonyl-L-cysteinyl-cis-4-hydroxy-L-prolyl-L-alanyl-2-mercapto-L-tryptophyl-4,5-dihydroxy-L-leucyl), cyclic (3,6)-sulfide, which translates into the sequence cycloATCPAWL, SEQ ID NO:70. Several of the phallacidin and phalloidin amino acids are hydroxylated. The Asp residue (which is replaced by Thr in phalloidin) has the D configuration at the alpha carbon.

A genomic survey of *A. bisporigera* sequences yielded at least 2 nucleic acid sequences encoding a predicted sequence comprising a linear AWLVDCP, SEQ ID NO:71, which would encode phallacidin, for example, SEQ ID NO:72, ECGK9LO01B8L63 S TGAGGAGACGGTT-GACGTCGTCACCGACGCATGGGCAGTCTACAAGC-CAAGC AGGAAGACGGGTGGCATTGATGTCAGA-CATTGTGATTTAGAGTAG, length=97 encoding LLIT MSDINATRLP<u>AWLVDCP</u>CVGDDVNRLL, SEQ ID NO:73, and SEQ ID NO:74, contig73170, TGAGGA-GACGGTTGACGTCGTCACCGACGCATGGGCAGTC-TACAAGCCAAGC AGGAAGACGGGTGGCATTGAT-GTCAGACATTGTGATTTAGAGTAGAGGTCTT GGGTTCGAGTTCGAATGGGAGGTAAG, length 130, encoding LTSHSNSNPRPLLITMSDINATRLP <u>AWLVDCP</u>CVGDDVNRLL, SEQ ID NO:75.

Inverse PCR following PvuI and SacI digestion of whole genomic DNA and ligation was used to isolate genomic fragments of 1.6 kb and 1.9 kb, respectively, named phallacidin sequence PHA1#1-1893 bp. SacI, SEQ ID NO:76, and phallacidin-sequence PHA1#2-1613 nt. PvuI, SEQ ID NO:77, collectively named PHA1, comprising phallacidin amino acid sequences. These were two different classes of sequences, identical in the region of phallacidin, SEQ ID NO:78, but diverged approximately 135 nt upstream. These two sequences showed that *A. bisporigera* genome has at least two copies of the PHA1 gene, both of which encode a phallacidin toxin sequence, FIG. 5. Furthermore, a cDNA for PHA1, SEQ ID NO:79, was isolated by 5' and 3' RACE (FIG. 5) using methods similar to those used in Example IV in combination with PHA1 RACE primers listed above. Nucleotide sequences of a cDNA for PHA1 are shown in FIG. 5A. When the genomic sequence (FIG. 5, #2) was compared to a cDNA sequence, the inventors found three introns (50-69 nt). Two of the introns were in the 3' untranslated region, while the first intron was in the third codon from the end of the coding region. Carats marked within the sequence indicate the positions of introns. The cDNA sequence, SEQ ID NO:79, is predicted to encode an amino acid sequence as a proprotein of PHA1 that is 34 amino acids in length, SEQ ID NO:80, translating into MSDI-NATRLP<u>AWLVDCP</u>CVGDDVNRLLTRSLC (phallacidin sequence, SEQ ID NO: 350), whose coding sequence was underlined in FIG. 5A. Because two different phallacidin genomic sequences were obtained, the inventors contemplate that *A. bisporigera* has at least two copies of PHA1. Further, the inventors concluded that these two PHA1 sequences represent natural variants of the phallacidin gene because both are present in the same isolate of *A. bisporigera*. The inventors further contemplate that these two PHA1 genes arose as a gene duplication event.

Example VII

This example describes methods and results from exemplary comparisons of AMA1 and PHA1 for obtaining exemplary consensus sequences.

Based on the cDNA sequence, the inventors chose the first ATG sequence as the translational start site of the proprotein polypeptides and the first in-frame stop codon as the translational stop. AMA1 and PHA1 nucleic acid and predicted amino acid sequences were compared by alignment of each set of two target sequences using a BLAST engine for local alignment through the NCBI website, (world wide web.ncbi.nlm.nih.gov/blast/b12 seq/wblast2.cgi).

Alignment of the predicted proproteins, amanitin to phallacidin sequences, is shown in FIG. 6A. Proproteins of amanitin and phallacidin were 35 and 34 amino acids in length, respectively. Sequences corresponding to amanitin and phallacidin are underlined, and for clarity are separated by spaces from the upstream and downstream amino acid sequences.

When the inventors compared the structures of an AMA1 cDNA to a cDNA identified as PHA1, the inventors observed that both comprise 3 introns (approximately 57, 70, and 51 nt in length), in approximately the same positions. Furthermore, AMA1 and PHA1 gene sequences and their translation products were found to be similar in overall size and sequence (FIG. 6 and Table 6).

Within amino acid encoding regions (the proproteins), nucleic acid sequence regions upstream of IWGIGCNP (amanitin) (SEQ ID NO: 50) and AWLVDCP (phallotoxin) (SEQ ID NO: 69) comprise 28 of 30 identical nt (93%), while regions downstream of IWGIGCNP (SEQ ID NO: 50) and AWLVDCP (SEQ ID NO: 69) comprise 41 of 50 identical nt (82%). However, these findings were in contrast to the amatoxin and phallotoxin-encoding regions themselves (IWGIGCNP, SEQ ID NO: 50 and AWLVDCP, SEQ ID NO: 69) where merely 12 of 24 nt were identical (50%). Thus the inventors designated these proprotein areas of α-amanitin and phallacidin as being composed of three domains, one conserved upstream region (A), one conserved downstream region (B), and a hypervariable peptide region (P) encoding amatoxin and phallotoxin. In other words, proprotein sequences of the present inventions consist of an upstream conserved region (A), a downstream conserved region (B) in relation to a variable region (P), such that the variable *Amanita* cyclic peptide toxin region is flanked by two conserved regions, (FIG. 6B). Because amatoxins contain 8 amino acids and phallotoxins contain 7 amino acids, the inventors inserted a 3-nucleotide gap (---) in the cDNA sequence and a one-amino acid space (-) in the proprotein sequence in order to emphasize the alignment of the conserved sequences down stream of the amatoxin and phallotoxin-encoding regions (FIG. 7A).

TABLE 6

Exemplary comparisons between AMA1 and PHA1 using BLASTN.

| SEQ ID NO: | Sequence | Comparison and Identity No. aa/No. aa (percent identity) |
|---|---|---|
| AMA1 A, SEQ ID NO: 81 | atg tct gac atc aat gct acc cgt ctt ccc (30 aa) | |
| PHA1 A, SEQ ID NO: 82 | atg tct gac atc aat gcc acc cgt ctt ccc (30aa) | AMA1A v. PHA1 A 29/30 (96%), |
| AMA1 B, SEQ ID NO: 83 | tgc atc ggt gac gac gtc act aca ctc ctc act cgt ggc gag gcc ctt tgt (51 aa) | |
| PHA1 B, SEQ ID NO: 84 | tgc gtc ggt gac gat gtc aac cgt ctc ctc act cgt ggc gag agc ctt tgg (48 aa) | AMA1 B v. PHA1 B 41/50 (82%) |
| AMA1 toxin, SEQ ID NO: 85 | atc tgg ggt atc ggt tgc aac ccg (24 aa) | |
| PHA1 toxin, SEQ ID NO: 86 | gct tgg ctt gta gat tgc --- cca (21 aa) | AMA1 toxin v. PHA1 toxin 12/24 (50%) |

TABLE 7A

Exemplary BLAST searches for AMA1 and PHA1 using BLASTN.

| Query SEQ | Hit | Comparison and Identity No. na/No. na | percent identity |
|---|---|---|---|
| Alpha-Amanitin | *Rhodococcus sp.* gb\|CP000431.1\| CGGGTACAACACGTGCATCGGTGACGCCGTCA | 28/32 | 87% |
| | Zebrafish DNA sequence emb\|CR385042.30\| CGACACTACCCTCACCACTCGTGCCCTTAGTTA | 28/33 | 84% |
| Phallacidin | *Agrobacterium tumefaciens* gb\|AE009415.1\| TCTGTGACGATGTCATCCAGTCTC-TCACTCGTA | 31/35 | 88% |
| | CP000479.1 *Mycobacterium avium* 104 CGTCGGTGACGATGTACACCGTCGCCACGCTCG | 28/33 | 84% |
| | AC112739.5 *Rattus norvegicus* 7 BAC CH230-108A12 TGTCAACCGTCTCCTCTGTCGTTTCCTTTG | 26/30 | 86% |
| | XM_382946.1 *Gibberella zeae* PH-1 chromosome 1 | 25/28 | 89% |

TABLE 7A-continued

Exemplary BLAST searches for AMA1 and PHA1 using BLASTN.

| Query SEQ | Hit | Comparison No. na/No. na | Identity percent identity |
|---|---|---|---|
| | conserved hypothetical protein (FG02770.1) partial mRNA CGTCGGTGACGATGTCCTCCGTCTCTTC | | |
| | AM444890.2 *Vitis vinifera* contig TTGTAGACTGCCCATGCGTCTGT | 22/23 | 95% |
| | gb\|AAQY01001277.1\|*Phytophthora sojae* strain P6497 CGGTGACGATGTCAACCGTCT | 21/21 | 100% |
| | gb\|AAQR01490933.1\|*Otolemur garnettii* cont1.490932 TGTCTGACATCAATGCCACCC | 21/21 | 100% |

TABLE 7B

Exemplary BLAST searches for AMA1 and PHA1 using BLASTN

| Query SEQ | Hit | Comparison No. na/No. na | Identity percent identity |
|---|---|---|---|
| Amanitin A | ATGTCTGACATCAATGCTACCCGTCTCCC | 30/30 | 100%

TABLE 7B-continued

Exemplary BLAST searches for AMA1 and PHA1 using BLASTN

| Query SEQ | Hit | Comparison No. na/No. na | and Identity percent identity |
|---|---|---|---|
| | ref\|XM_652576.1\|*Aspergillus nidulans* FGSC A4 hypothetical protein (AN0064.2), TGTCTGACATCAATGCCA | 18/18 | 100% |
| | dbj\|AP008214.1\|*Oryza sativa* (japonica cultivar-group) genomic TCTGACATCAATGCCACC | 18/18 | 100% |
| | gb\|EF469872.1\|*Helianthus annuus* RFLP probe ZVG13 mRNA sequence AATGCCACCCGTCTTCC | 17/17 | 100% |
| | emb\|CR619305.1\|B cells (Ramos cell line) GTCTGACATCAATGCCA | 17/17 | 100% |
| | emb\|CR595196.1\|T cells (Jurkat cell line) GTCTGACATCAATGCCA | 17/17 | 100% |
| | emb\|CR592893.1\|Neuroblastoma of *Homo sapiens* (human) GTCTGACATCAATGCCA | 17/17 | 100% |
| | dbj\|AK173931.1\|*Ciona intestinalis* or Sea squirt. ATGTCTGACATCAATGC | 17/17 | 100% |
| Amanitin B | TGCATCGGTGACGACGTCACTACTCTCCT CACTCGTGCCCTTTGT | 45 | 100% |
| | *Strongylocentrotus purpuratus* CATCGGTGACGACGTCACT | 19/19 | 100% |
| | *Ostreococcus lucimarinus* unicellular coccoid green alga GCATCGGTGACGACGTCA | 18/18 | 100% |
| | *Chaetomium globosum* dematiaceous filamentous fungus infectious in humns CTCCTCACTCGTGCCCTT | 18/18 | 100% |
| | Human DNA sequence from clone XXyac-60D10 TCACTACTCTCCTCACTC | 18/18 | 100% |
| | *Rattus norvegicus* LEA_4 domain containing protein ACGTCACTACTCTCCTC | 17/17 | 100% |
| | Atlantic Salmon CTCCTCACTCGTGCCCT | 17/17 | 100% |
| | *Burkholderia cenocepacia* Gram-negative bacteria Pathogen ATCGGTGACGACGTCAC | 17/17 | 100% |
| | *Ornithorhynchus anatinus* Platypus ACGTCACTACTCTCCTC | 17/17 | 100% |
| Phallacidin B | TGCGTCGGTGACGATGTCAACCGTCTCCT CACTCGTAGCCTTTGG | 45 | 100% |
| | *Chaetomium globosum* CBS 148.51 GGTGACGATGACAACCGCCTCCTCAC | 24/26 | 92% |
| | *Gibberella zeae* CGTCGGTGACGATGTCCTCCGTCTC | 23/25 | 92% |
| | *Rhizobium leguminosarum* bv. *viciae* chromosome CGTCGGTGACGAGGTCAACCG | 20/21 | 95% |
| | *Tetraodon nigroviridis* GATGTCAACCGTCTCCTCA | 19/19 | 100% |

The conserved amino acid regions encoded by conserved domains A and B and consensus region B were used as query sequences for BLAST searching the GenBank public NR database. These sequences per se were not found within the database, however somewhat similar sequences were discovered, with exemplary sequences shown below.

TABLE 8

Exemplary homology comparisons using Consensus MSDINATRLP, XWXXXCXP, and CVGDDVXLLTRALC as query sequences using BLASTP (MSDINATRLPXWXXXCXPCVGDDVXXLLTRALC, SEQ ID NO: 87).

| SEQUENCE | Identity No. aa/ matching No. aa | GenBank sequence hit |
|---|---|---|
| AMA1 Conserved A MSDINATRL P SEQ ID NO: 88 | 7/10 (70%), | gb\|EDN21666.1\|predicted protein [*Botryotinia fuckeliana* B05.10] |
|  | 7/8 (87%), | gb\|EAT86097.1\|hypothetical protein SNOG_06266 [*Phaeosphaeria nodorum* SN15] |
|  | 7/9 (77%), | gb\|EAK82279.1\|hypothetical protein UM01662.1 [*Ustilago maydis* 521] |
|  | 6/9 (66%), | gb\|EAU90435.1\|predicted protein [*Coprinopsis cinerea* okayama7#130] |
|  | MREINSTRLP 7/10 (70%) | predicted protein [*Botryotinia fuckeliana* B05.10]. Pathogenic fungus (aka *Botrytis cinerea*) that causes gray mold rot in plants |
|  | MSNIAAPRLP 7/10 (70%) | gb\|ABD10583.1\|Endopeptidase Clp [*Frankia* sp. CcI3] |
|  | MSDIAWHPDNATR 8/13 (61%) | hypothetical protein CC1G_09232 [*Coprinopsis cinerea* okayama7#130] |
|  | SDVNAPRLP 7/9 (77%) | hypothetical protein UM01662.1 [*Ustilago maydis* 521] |
|  | SDI-ATRLP 8/9 (88%) | non-ribosomal peptide synthetase [*Saccharopolyspora erythraea* NRRL 2338] |
| AMA1 Conserved Region B CIGDDVTTL LTRGEALC SEQ ID NO: 89 | 8/11 (72%) | gb\|ABF87913.1\|ATP-binding protein, ClpX family [*Myxococcus xanthus* DK 1622] |
|  | 8/10 (80%) | emb\|CAG61741.1\|unnamed protein product [*Candida glabrata* CBS 138] |
|  | 10/16 (62%) | gb\|EAK84527.1\|hypothetical protein UM03624.1 [*Ustilago maydis* 521] |
|  | 11/16 (68%) | gb\|EAU39589.1\|conserved hypothetical protein [*Aspergillus terreus* NIH2624] |
|  | 8/8 (100%) | dbj\|BAE56937.1\|unnamed protein product [*Aspergillus oryzae*] |
| PHA1 Conserved Region B CVGDDVNR LLTRGESLC SEQ ID NO: 90 | 14/21 (66%) | gb\|AAZ10451.1\|hypothetical protein Tb927.3.4180 [*Trypanosoma brucei*] |
|  | 11/18 (61%) | gb\|EAQ84320.1\|hypothetical protein CHGG_10724 [*Chaetomium globosum* CBS 148.51] |
|  | 9/11 (81%) | gb\|ABE92653.1\|Peptidase, cysteine peptidase active site; Aromatic-ring hydroxylase [*Medicago truncatula*] |
|  | 9/14 (64%) | gb\|EDN63642.1\|conserved protein [*Saccharomyces cerevisiae* YJM789] |

TABLE 8-continued

Exemplary homology comparisons using
Consensus MSDINATRLP, XWXXXCXP, and CVGDDVXXLLTRALC as query
sequences using BLASTP (MSDINATRLPXWXXXCXPCVGDDVXXLLTRALC,
SEQ ID NO: 87).

| SEQUENCE | Identity No. aa/ matching No. aa | GenBank sequence hit |
|---|---|---|
| Consensus B CXGDDVXX LLTRXLC | 9/14 (64%) GDDVAALLSRRVLC | ref\|XP_760134.1\|hypothetical protein UM03987.1 [*Ustilago maydis* 521] |
| SEQ ID NO: 91 | 8/12 (66%) GDDVETILTRLL | ref\|ZP_00591779.1\|ClpX, ATPase regulatory subunit [*Prosthecochloris aestuarii* DSM 271] green sulfur bacterium |

Example VIII

This example describes materials and methods for determining whether the amatoxin and phallotoxin-encoding nucleic acids are specific for *Amanita* mushroom species that produce amatoxins and phallotoxins.

Many secondary metabolites such as mushroom toxins are limited in their taxonomic distribution; for example, most species of *Amanita* do not make amatoxins or phallotoxins. Thus the inventors contemplated whether the lack of amatoxin and phallotoxin production among other species of *Amanita* was due to absence of the encoding genes or due to the absence of productive translation of the genes. The inventors tested for the presence of amatoxins such as alpha-amanitin and phallotoxins such as phallacidin and in the same mushrooms tested for the presence of DNA encoding alpha amanitin (AMA1) and phallacidin (PHA1). The inventors tested for the presence of AMA1 and PHA1 in the genomes of known amatoxin and phallotoxin-producing mushroom species and non-producing mushroom species in order to associate the AMA1 and PHA1 sequences with amatoxin and phallotoxin production.

Preparation and Isolation of *Amanita* Genomic Sequences.

DNA was extracted from a variety of species of *Amanita* that were either known as amatoxin and phallotoxin-producers (*A. bisporigera, A. ocreata, A.* aff. *suballiacea* and *A. phalloides*) or were known to not produce amatoxins (*A. novinupta, A. franchetti, A. porphyria, A. velosa, A. gemmata, A. muscaria, A. flavoconia, A.* section *Vaginatae*, and *A. hemibapha*). DNA was extracted from lyophilized fruiting bodies using cetyl trimethyl ammonium bromide-phenol-chloroform isolation (Hallen, (2003) *Mycol. Res.* 107: 969; herein incorporated by reference). Following the usual preparation methods, sequences were separated by gel electrophoresis and then transferred to blotting media for subsequent probe hybridization.

Southern blots of DNA were probed with AMA1 and PHA1 as described. As shown in FIG. 8, Panel A was probed with an amanitin geneAMA1 (nt 1710-2175 as numbered in FIG. 5) while Panel B was probed with a phallacidin gene PHA1 (nt 635-1115 in phallacidin #2, see, FIG. 6). For references on amatoxin and phallotoxin production in relation to *Amanita* taxonomy, see website hypertext transfer protocol site: pluto.njcc.com/.about.ret/amanita/mainaman.html; Hallen (2002) Studies in amatoxin-producing genera of fungi: phylogenetics and toxin distribution. Ph.D. dissertation, East Lansing, Mich.: Michigan State University. 192 pp.; and Arora D (1986) Mushrooms Demystified, Second Edition. Ten Speed Press, Berkeley; (Bas, Persoonia 5, 285 (1969); Tulloss et al., Boll Gruppo Micologico G Bresadola, 43, 13 (2000); WeiB et al., Can J. Bot. 76, 1170 (1998).

The results show that AMA1 and PHA1 sequences hybridized to DNA from known amatoxin and phallotoxin-producing species but did not hybridize to the species known to not produce these compounds. The inventors concluded that these genes were present in amatoxin and phallotoxin-producing species and absent in non-producers, thus providing additional evidence that the genes described herein encode amatoxins and phallotoxins.

Extraction and Analysis of Amatoxins and Phallotoxins.

Variability in toxin content is known even within species of *Amanita* that normally produce amatoxins and phallotoxins (Beutler, et al., (1981) J. Nat. Prod. 44:422 and Tyler, et al., (1966) J. Pharm. Sci. 55:590; all of which are herein incorporated by reference in its entirety). Therefore in order to confirm that the presence of AMA1 and PHA1-encoding sequences correlates with actual production of amatoxins and phallotoxins, the inventors tested the same mushrooms that were used for extraction of DNA and Southern blotting (FIG. 11) for the presence of amatoxins and phallotoxins. Thus amatoxins and phallotoxins were extracted from these mushrooms then analyzed by established HPLC methods (Hallen, et al., Mycol. Res. 107:969 (2003), Enjalbert, (1992) J. Chromatogr. 598:227; all of which are herein incorporated by reference in its entirety). Standards of α-amanitin, β-amanitin, phalloidin, and phallacidin were purchased from Sigma.

Each of the tested mushrooms that contain amatoxins and phallotoxins, but none of the nonproducers, hybridize to AMA1 and PHA1. This is consistent with AMA1 and PHA1 as being responsible for alpha-amanitin and phallacidin biosynthesis and provides a molecular explanation for why *Amanita* species outside of sect. Phalloideae are not deadly poisonous. Some of the species of *Amanita* that do not make amatoxins or phallotoxins are edible, but others make toxic compounds chemically unrelated to the *Amanita* cyclic peptide toxins.

Example IX

This Example demonstrates PCR amplification of an α-amanitin gene in mushroom species known to produce alpha-amanitin while failing to amplify DNA from species that do not produce alpha-amanatin (FIG. 10).

PCR amplification of the gene for α-amanitin. Primers were based on the sequences in FIGS. 4, 5 and 6. The primer sequences used were: forward primer: 5'-AGCATCTGC-CCGCACCTTACG-3', SEQ ID NO:92; Reverse primer: 5'

ACTGCCTTGTATCACCGTTATG-3', SEQ ID NO:93. PCR mixtures and running conditions were REDTaq ReadyMix DNA polymerase (Sigma), 30 cycles of denaturation (94° C., 30 sec), annealing (55° C., 30 sec), and extension (72° C., 5 min).

Figure 10:
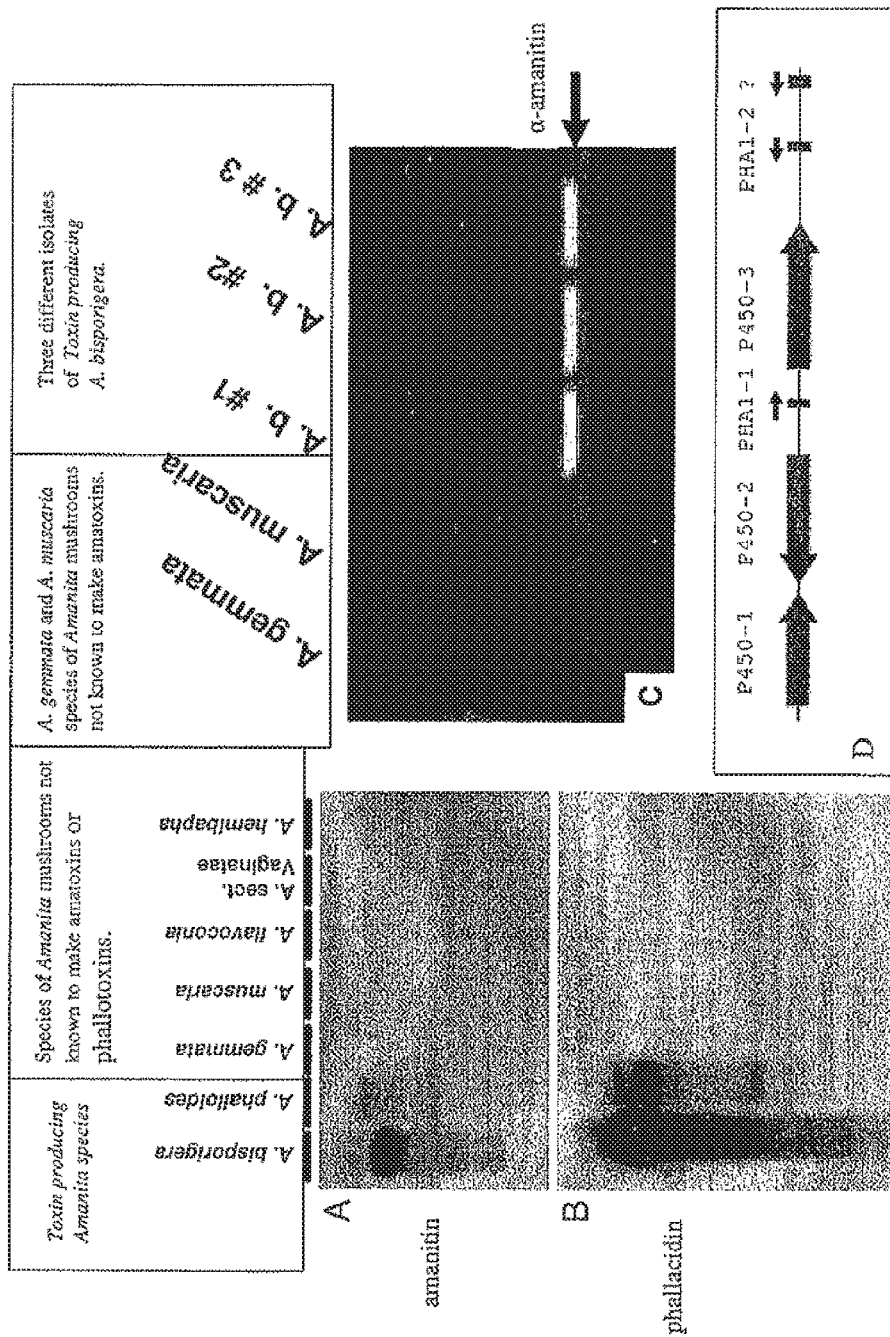
Figure 12:
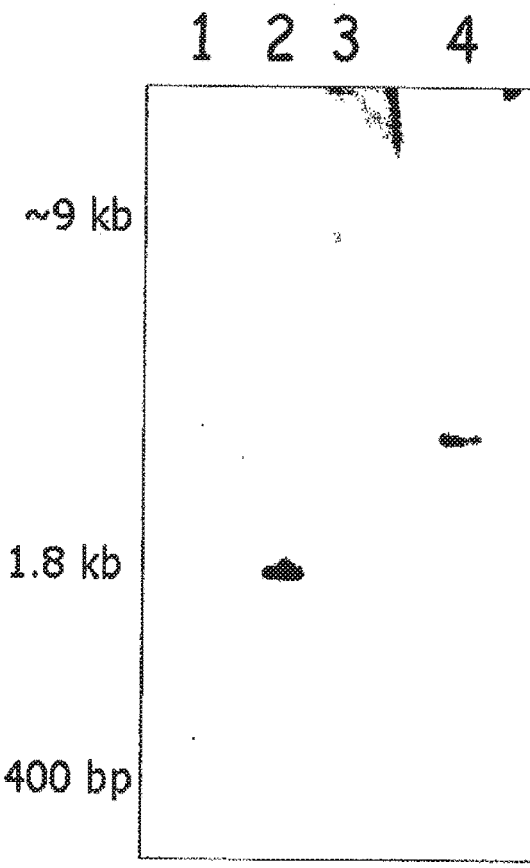

A. gemmata and A. muscaria are species of Amanita that do not make amatoxins (or phallotoxins) and did not yield a PCR product using these primers (FIG. 10). A. b. #'s 1-3 indicate three different isolates of A. bisporigera, all of which produced alpha-amanitin, and all of which yielded PCR products, indicating the presence of the gene for alpha-amanitin (FIG. 10).

Example X

This Example shows the development of conserved regions upstream and downstream of Amanita peptide encoding regions.

Figure 8:
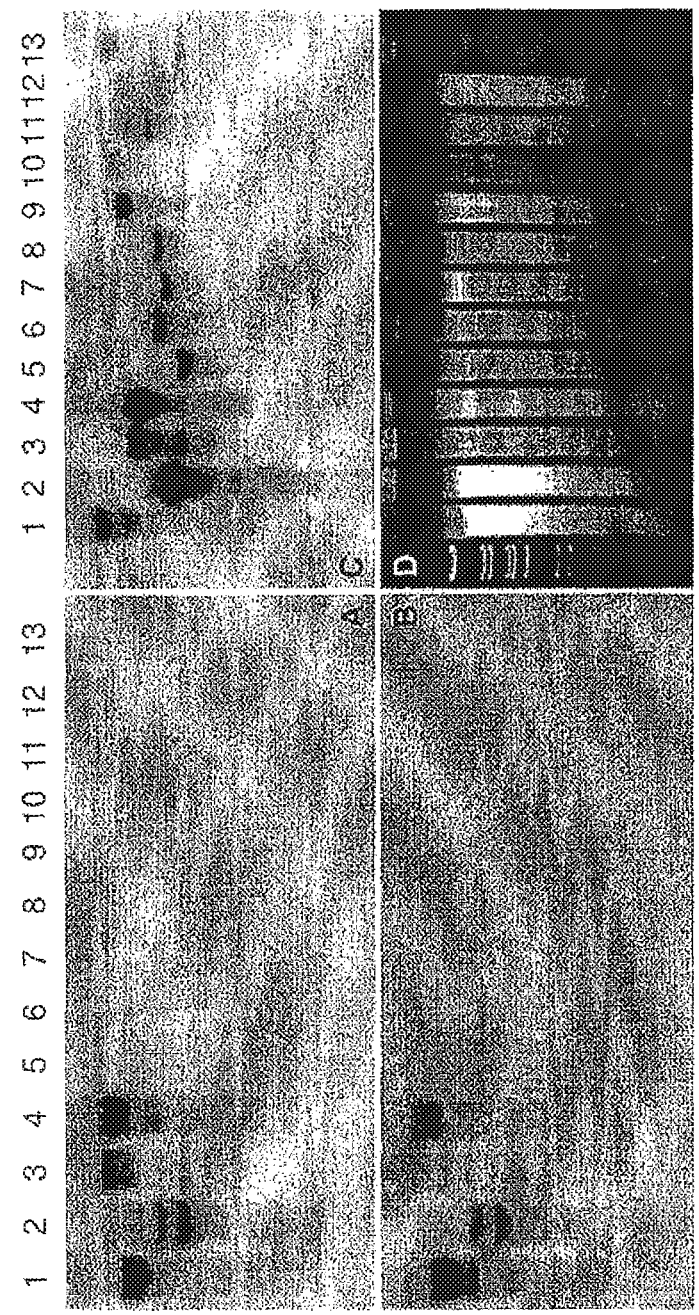

The unexpected complex hybridizaton patterns shown in FIG. 8 led the inventors to contemplate that AMA1 and PHA1 are members of gene families such that additional short peptides related to AMA1 and PHA1 should be encoded by genes in A. bisporigera.

The conserved upstream and downstream amino acid sequences of AMA1 and PHA1 were used as queries using BLASTP to search for additional related sequences in the A. bisporigera genome sequence database. The inventors thereby found at least 12 new related DNA sequences that could proproteins as long or longer than the proproteins of AMA1 and PHA1 (FIG. 7) and another 10-15 partial sequences (missing the upstream or the downstream conserved sequences). These new sequences comprise an upstream conserved sequence MSDINTARLP (SEQ ID NO: 575) MSDIN (SEQ ID NO: 587), R, and P are invariant yielding an exemplary consensus sequence MSDINXXRXP, SEQ ID NO: 94), and a downstream conserved sequence CVGDDV (SEQ ID NO: 534), wherein the first D is invariant, for a consensus sequence CVGDXV, SEQ ID NO: 95, and a consensus sequence CVGDDVXXXDXX, SEQ ID NO: 96. The regions capable of comprising interesting peptides are those in the same positions relative to the upstream and downstream conserved regions in AMA1 and PHA1, namely, starting immediately downstream of the first invariant Pro residue and ending just after a second invariant Pro residue. These regions between these two absolutely conserved Pro residues are much more variable ("hypervariable") in predicted amino acid sequence compared to the upstream and downstream conserved sequences. The "hypervariable regions" between the two invariant Pro residues are predicted to contain from seven to ten amino acids. Among the described putative new hypervariable regions (FIG. 7) all twenty proteinogenic amino acids are represented in at least one. These new hypervariable sequences might represent previously unknown linear and cyclic peptides made by A. bisporigera.

Example XI

This example describes methods and results of using conserved regions of AMA1 and PHA1 for obtaining additional regions encoding potentially biologically active linear or cyclic peptides from A. bisporigera, A. phalloides, and other species of Amanita. In particular, a DNA sequence encoding amino acid sequences was found that was highly similar to α-amanitin and comprising the amino acid sequence found in β-amanitin, and a DNA that was highly similar to phallacidin and comprising the amino acid sequence found in phalloidin.

During the course of developing the present inventions, the inventors discovered regions of conserved sequence whose use resulted in the discovery of additional sequences contemplated to encode proproteins related to amatoxin and phallotoxin proproteins, which could encode novel small linear or cyclic peptides. Degenerate primers were designed against the conserved sequences of AMA1 and PHA1. DNA extracted from A. phalloides and A. ocreata was used as template. This also shows that the AMA1 and PHA1 genes and related genes are conserved in other species of amatoxin and phallotoxin-producing Amanita species, and that PCR primers designed against one species (A. bisporigera) function to identify amatoxin and phallotoxin genes in other species of Amanita.

New degenerate PCR primer sequences that the inventors developed and used on genomic DNA as a template were 5'-ATGTCNGAYATYAAYGCNACNCG (forward), SEQ ID NO: 97, and 5'-AAGGSYCTCGCCACGAGTGAG-GAGWSKRKTGAC (reverse), SEQ ID NO: 98, W indicates A or T, S indicates C or G, K indicates G or T, R indicates A or G, and Y indicates T or C. The resulting PCR products (approximately 100 nt) were cloned and sequenced. Exemplary sequences of three amplicons are:

number 1:
SEQ ID NO: 99
ATGTCTGATATTAATGCAACGCGTCTTCCCTTCAATATTCTGCCATTCAT

GCTTCCCCCGTGCGTCAGTGACGATGTCAATATACTCCTCACTCGTGGCG

AG,, translation:
SEQ ID NO: 100
MSDINATRLPFNILPFMLPPCVSDDVNILLTRGE,,

[predicted to encode a unique linear and cyclic peptide, underlined];

number 2:
ATGTCAGATATCAATGCGACGCGTCTTCCCATATGGGGAATAGGTTGCGA

CCCGTGCATCGGTGACGACGTCACCATACTCCTCACTCGTGGCGAG translation,,
SEQ ID NO: 101
SEQ ID NO: 102
MSDINATRLPIWGIGCDPCIGDDVTILLTRGE,,

[predicted to encode beta-amanitin];

number 3:
SEQ ID NO: 103
ATGTCGGATATTAATGCTACACGTCTTCCAATTATTGGGATCTTACTTCC

CCCGTGCATCGGTGACGATGTCACCCTACTCCTCACTCGTGGCGAG,,

SEQ ID NO: 104
MSDINATRLPIIGILLPPCIGDDVTLLLTRGE,,

[predicted to encode a unique linear or cyclic peptide, underlined];
and number 4:
SEQ ID NO: 105
ATGTCAGACA TTAACGCGACCCGTCTTCCCGCCTGGCTCGCCACCTGC

CCGTGCGCCGGTGACGACGTCAACCCTCTCCT CACTCGTGGC GAG,,

-continued translation:

SEQ ID NO: 106

MSDINATRLP<u>AWLATCP</u>CAGDDVNPLLTRGE,,

[predicted to encode phalloidin, underlined].

TABLE 9

Exemplary comparisons of Amanita peptide sequences.

| Preprotprotein nucleic acid | Identity No. na/matching No. na | Percent Identity |
| --- | --- | --- |
| Alpha-Amanitin vs. new peptide 1 | 35/41 | 85% |
| Alpha-Amanitin vs. new peptide 2, beta-Amanitin | 79/91 | 86% |
| Alpha-Amanitin vs. new peptide 3 | 36/41 | 87% |
| Phallacidin vs. new peptide 1 | 34/40 | 85% |
| Phallacidin vs. new peptide 2 | 33/40 | 82% |
| Phallacidin vs. new peptide 3 | 35/40 | 87% |

The inventors then initiated a BLASTN and TBLASTN search of the *Amanita* genome DNA sequences using conserved region A for identifying homologous sequences. The inventors discovered numerous nucleic acid sequences encoding MSDINVTRLP or versions thereof, followed by variable short regions that were in turn followed by regions homologous to regions B of AMA1 and PHA1, see, FIG. 9, and the Table below. The inventors contemplated that these sequences encode additional proproteins and biologically active linear or cyclic peptides, such as toxins.

TABLE 10A

Exemplary comparisons to AMA1 and PHA1.

| Name | Proprotein | Identity |
| --- | --- | --- |
| [amanitin] peptide, SEQ ID NO: 107 | MSDINATRLP IWGIGCNP CVGDDVTTLLTRGE | 100% |
| [phallacidin], SEQ ID NO: 108 | MSDINATRLP AWLVDCP CVGDDVNRLLTRGE | 25/32 (78.1%) |
| [consensus], SEQ ID NO: 109 | MSDINATRLP XWXXXCXP CVGDDVXXLLTRGE | |
| new potential peptide 1, SEQ ID NO: 110 | MSDINATRLP FNILPFMLPP CVSDDVNILLTRGE | AMA1 23/34 (67%) PHA1 22/34 (64%) |
| new potential peptide 2, SEQ ID NO: 111 | MSDINATRLP IWGIGCDP CIGDDVTILLTRGE | AMA1 29/32 (90%) PHA1 24/32 (75%) |
| new potential peptide 3, SEQ ID NO: 112 | MSDINATRLP IIGILLPP CIGDDVTLLLTRGE | AMA1 26/32 (81%) PHA1 22/32 (68%) |
| new potential peptide 4, SEQ ID NO: 113 | MSDINATRLP AWLATCPC AGDDVNPLLTRGE | AMA1 26/32 (81%) PHA1 22/32 (68%) |

TABLE 10B

Exemplary comparisons using Amanita peptide sequences as query sequences in GenBank (BLASTP).

| Alpha-amanitin (AMA1) | <u>IWGIGCNP</u> (8) | 6/8 (75%) | gb|AAZ19981.1|conserved hypothetical protein [*Psychrobacter arcticus* 273-4] |
| --- | --- | --- | --- |
| | | IWGIGCVL 6/8 (75%) | gb|EAU82808.1|hypothetical protein CC1G_11325 [*Coprinopsis cinerea okayama*7#130] |
| Alpha-amanitin (AMA1) | <u>IWGIGCNP</u> (8) | 5/8 (40.0%) | <u>AWLVDCP</u> (PHA1) |
| phallacidin (PHA1) | <u>AWLVDCP</u> (7) | AWLVDC 6/7 (85.5%) | GB|EAV54171.1|SIGMA54 SPECIFIC TRANSCRIPTIONAL REGULATOR, FIS FAMILY [*BURKHOLDERIA AMBIFARIA* MC40-6] gb|AAG04585.1|AE004550_1 probable transcriptional regulator [*Pseudomonas aeruginosa* PAO1] |
| | | AWVVDCP 6/7 (85.5%) | gb|EAL84365.1|conserved hypothetical protein [*Aspergillus fumigatus* Af293] |
| Peptide 1 SEQ ID NO: 114 | <u>FNILPFMLPP</u> (10) SEQ ID NO: 115 | 2/10 (20%) 2/10 (20%) 8/10 (80%) | AMA1 PHA1 ref|ZP_01047917.1|hypothetical protein NB311A_09386 [*Nitrobacter* sp. Nb-311A] |
| beta-amanitin SEQ ID NO: 116 | <u>IWGIGCDP</u> (8) | 7/8 (87%) 5/8 (40.0%) 7/8 (87%) | AMA1 PHA1 ref|YP_265415.1|hypothetical protein Psyc_2134 [*Psychrobacter arcticus* 273-4] |

TABLE 10B-continued

Exemplary comparisons using Amanita peptide sequences as query sequences in GenBank (BLASTP).

```
Peptide 3 SEQ IIGILLPP (8)   4/8 (50%)    AMA1
ID NO: 117                   1/8 (12.5%)  PHA1
                             7/8 (87%)    gb|ABR79950.1|hypothetical protein
                                          [Klebsiella pneumoniae subsp. pneumoniae
                                          MGH 78578]
                             7/7 (100%)   ref|YP_001292803.1|hypothetical protein
                                          [Haemophilus influenzae PittGG]
                                          ref|XP_001139896.1|PREDICTED: prolyl
                                          4-hydroxylase, alpha I subunit isoform 2
                                          [Pan troglodytes]
```

TABLE 10C

Exemplary sequences related to AMA1 and PHA1.

| SEQ ID NO: | Exemplary Amanita peptides |
|---|---|
| SEQ ID NO: 118 | MSDINATRLP HPFPLGLQP CAGDVDNLTLTKGEG |
| SEQ ID NO: 119 | MSDINATRLP IWGIGCDP CIGDDVTILLTRGE |
| SEQ ID NO: 120 | MSDINATRLP AWLATCP CAGDDVNPLLTRGE |
| SEQ ID NO: 121 | MSDINVTRLP GFVPILFP CVGDDVNTALT |
| SEQ ID NO: 122 | MSDINTARLP FYQFPDFKYP CVGDDIEMVLARGER* |
| SEQ ID NO: 123 | MSDINTARLP FFQPPEFRPP CVGDDIEMVLTRG* |
| SEQ ID NO: 124 | MSDINTARLP LFLPPVRMPP CVGDDIEMVLTRGER* |
| SEQ ID NO: 125 | MSDINTARLP LFLPPVRLPP CVGDDIEMVLTR |
| SEQ ID NO: 126 | MSDINTARLP YVVFMSFIPP CVNDDIQVVLTRGEE* |
| SEQ ID NO: 127 | MSDINTARLP CIGFLGIP SVGDDIEMVLRH |
| SEQ ID NO: 128 | MSDINTARLP LSSPMLLP CVGDDILMV |
| SEQ ID NO: 129 | MSDINAIRAP ILMLAILP CVGDDIEVLRRGEG* |
| SEQ ID NO: 130 | MSDINGTRLP IPGLIPLGIP CVSDDVNPTLTRGER* |
| SEQ ID NO: 131 | MSDINATRLP GAYPPVPMP CVGDADNFTLTRGEK* |
| SEQ ID NO: 132 | MSDINATRLP GMEPPSPMP CVGDADNFTLTRGN |
| SEQ ID NO: 133 | MSDINATRLP HPFPLGLQP CAGDVDNLTLTKGEG* |

Predicted amino acid sequences encoded by genomic survey sequences of *A. bisporigera* (FIG. 7). Spaces were inserted before and after the peptide/toxin regions (underlined) in order to emphasize the conservation of the upstream and downstream sequences. *indicates stop codon. These are genomic survey sequences. Based on the cDNA sequences of AMA1 and PHA1, there is probably an intron near the C-terminus of the indicated proproteins.

In particular, the inventors analyzed three sequences encoding short peptides and potential toxins including comparing sequence homology to α-amanitin and phallacidin.

TABLE 11

Exemplary Amanita peptides.

| Peptide sequence | SEQ ID Number. |
|---|---|
| IWGIGCNP | SEQ ID NO: 134 |
| AWLVDCP | SEQ ID NO: 80 |
| XWXXXCXP | SEQ ID NO: 135 |
| FNILPFMLPP | SEQ ID NO: 121 |
| IWGIGCDP | SEQ ID NO: 122 |
| IIGILLPP | SEQ ID NO: 123 |
| AWLATCP | SEQ ID NO: 136 |
| GFVPILFP | SEQ ID NO: 137 |
| FYQFPDFKYP | SEQ ID NO: 138 |
| FFQPPEFRPP | SEQ ID NO: 139 |
| LFLPPVRMPP | SEQ ID NO: 140 |
| LFLPPVRLPP | SEQ ID NO: 141 |
| YVVFMSFIPP | SEQ ID NO: 142 |
| CIGFLGIP | SEQ ID NO: 143 |
| LSSPMLLP | SEQ ID NO: 144 |
| ILMLAILP | SEQ ID NO: 145 |
| IPGLIPLGIP | SEQ ID NO: 146 |
| GAYPPVPMP | SEQ ID NO: 147 |
| GMEPPSPMP | SEQ ID NO: 148 |
| HPFPLGLQP | SEQ ID NO: 149 |

Example XII

This example shows the complex hybridization patterns of Example VIII, FIG. 8, that indicated that AMA1 and PHA1 are members of gene families.

Using the conserved upstream and downstream amino acid sequences of AMA1 and PHA1 as queries, the invenors found at least 15 new related sequences (Table 16) and another 10-15 partial sequences in the genome survey sequence of *A. bisporigera*. Each of them had an upstream conserved consensus sequence MSDINATRLP (SEQ ID NO: 88) (MSD, N, R, and P are invariant), and a downstream conserved consensus CVGDDXXXXLTRGE (SEQ ID NO:

239) (D is invariant). The putative toxin regions, which start immediately downstream of an invariant Pro residue and end just after an invariant Pro residue, are more variable compared to the upstream and downstream sequences. The hypervariable regions contain seven to ten amino acids, while twenty proteinogenic amino acids are represented at least once (FIG. 4). With specific 5' PCR primers and oligo-dT, the inventors demonstrated that at least two of the new "MSDIN" sequences (FIG. 4) are expressed at the mRNA level.

TABLE 16

AMA1 and PHA1 related sequences.

| Fifteen additional AMA1 and PHA1 related sequences found in a genome survey of *A. bisporigera* using conserved upstream and downstream amino acid sequences of AMA1 and PHA1 as queries. | SEQ ID NO: XX |
|---|---|
| MSDINATRLPIWGIGCNxxPCVGDDVTTLLTRGE | SEQ ID NO: 303 |
| MSDINATRLPAWLVDCxxxPCVGDDVNRLLTRGE | SEQ ID NO: 304 |
| MSDINATRLPIWGIGCDxxPCIGDDVTILLTRGE | SEQ ID NO: 305 |
| MSDINATRLPIIGILLPxxPCIGDDVTLLLTRGE | SEQ ID NO: 306 |
| MSDINATRLPFNILPFMLPPCVSDDVNILLTRGE | SEQ ID NO: 307 |
| MSDINTARLPFYQFPDFKYPCVGDDIEMVLARGE | SEQ ID NO: 308 |
| MSDINTARLPFFQPPEFRPPCVGDDIEMVLTRGE | SEQ ID NO: 309 |
| MSDVNDTRLPFNFFRFPYxPCIGDDSGSVLRLGE | SEQ ID NO: 310 |
| MSDINTARLPLFLPPVRMPPCVGDDIEMVLTRGE | SEQ ID NO: 311 |
| MSDINTARLPYVVFMSFIPPCVNDDIQVVLTRGE | SEQ ID NO: 312 |
| MSDINAIRAPILMLAILxxPCVGDDIEVLRRGEG | SEQ ID NO: 313 |
| MSDINGTRLPIPGLIPLGIPCVSDDVNPTLTRGE | SEQ ID NO: 314 |
| MSDINATRLPGAYPPVPMxPCVGDADNFTLTRGE | SEQ ID NO: 315 |
| MSDINATRLPHPFPLGLQxPVAGDVDNLTLTKGE | SEQ ID NO: 316 |
| MSDINATRLPAWLATCxxxPCAGDDVNPLLTRGE | SEQ ID NO: 317 |

Fifteen sequences listed in Table 16 were used for providing a WebLogo (Crooks et al., 2004) showing the relative conservation by Letter size representing amino acids, such that highly conserved amino acids are represented by Large Letters (for example, MSDIN; positions 1-5, and P; positions 10 and 20) while less conserved amino acids have smaller letters (for example A/T, G/S; positions 6 and 23, respectively) and low areas of conserved amino acids have small letters (for example, in regions 11-18). These results showed upstream MSDINATRLP (SEQ ID NO: 88) (MSD, N, R, and P are invariant) and downstream conserved consensus CVGDDXXXXLTRGE (SEQ ID NO: 239) (D is invariant). FIG. 9. Because WebLogo requires that all sequences have the same length, one, two, or three X's were placed within the toxin region before the second conserved Pro residue for toxin peptides of nine, eight, or seven amino acids, respectively. Therefore the actual sequences do not contain x.

Example XIII

*Galerina marginata* (=*G. autumnalis*) produces amatoxins but not phallotoxins (Benedict et al., 1966). This fungus is contemplated as a potentially valuable experimental system for elucidating the biosynthesis and regulation of amatoxin biosynthesis because, unlike *Amanita*, it is saprophytic and grows and produces amatoxins in culture (Muraoka and Shinozawa, 2000). *Galerina* spp. are relatively small and rare, but they nonetheless sometimes cause mushroom poisonings (e.g., Kaneko et al, 2001).

Therefore, the inventors sequenced ~40 MB of *G. marginata* and identified a genomic sequence that could encode alpha-amanitin (GmAMA1) (FIGS. 11 and 12). Comparison of the DNA and amino acid sequences of AMA1 and GmAMA1 (FIG. 12A) indicates that amatoxins are also made on ribosomes in *Galerina* and probably processed similarly. DNA probed with GmAM1 under high stringency conditions showed at least 2 sequences, a Southern blot of *G. autumnalis* FIG. 12B. Lanes 1-4 are total genomics DNA cut with PstI, HindIII, EcoRV, and BamHI. The blot shows that there are two copies of GmAMA1. This corresponds to the two copies of GmAM1. One was identified by 454 sequencing and the other by inverse PCR (see herein). However, the upstream and downstream sequences are much less well conserved. The four amino acids immediately upstream of the toxin region (TRLP) are conserved (FIG. 11). This might be an indication that these amino acids are important for processing of the proproteins (see below).

An RNA blot of the *Galerina marginata* amanitin gene (GmAMA1) showed that the gene is expressed in two known amanitin-producing species of *Galerina* (*G. marginata* and *G. badipes*) and not in a nonproducer (*G. hybrida*), and that the gene is induced by low carbon. Lane 1: *G. hybrida*, high carbon. Lane 2: *G. hybrida*, low carbon. Lane 3: *G. marginata*, high carbon. Lane 4: *G. marginata*, low carbon. Lane 5: *G. badipes*, high carbon. Lane 6: *G. badipes*, low carbon. Each lane was loaded with 15 ug total RNA. The agarose gel was blotted to nitrocellulose by standard methods and probed with the *G. marginata* AMA1 gene (GmAMA1) predicted to encode alpha-amanitin. Fungi were grown in liquid culture for 30 d on 0.5% glucose (high carbon) then switched to fresh culture of 0.5% glucose or 0.1% glucose (low carbon) for 10 d before harvest. The major band in lanes 3-6 is ~300 bp. The high MW signal in lane 1 is spurious.

Therefore, by RNA blotting, the inventors found that GmAMA1 is expressed in culture and is induced by carbon starvation, as has been reported for the toxin itself (Muraoka and Shinozawa, 2000) (FIG. 13).

Genomic DNA Isolation.

*Galerina marginata*, an amatoxin producing species of circumboreal distribution, was harvested from the wild in 2007. Caps and undamaged stems were cleaned of soil and debris, frozen at −80° C., and lyophilized.

Genomic DNA was extracted from the lyophilized fruiting bodies using cetyl trimethyl ammonium bromide-phenol-chloroform isolation (Hallen, et al., (2003) Mycol. Res. 107:969; herein incorporated by reference). For studies requiring RNA, RNA was extracted using TRIZOL (Invitrogen) (Hallen, et al., (2007) Fung. Genet. Biol., 44:1146; herein incorporated by reference in its entirety). The inventors used a Genome Sequencer FLX from 454 Life Sciences (Margulies, et al., (2005) Nature 437:376; herein incorporated by reference) for generating sequences from *Galerina* species genomic DNA. There was no subcloning necessary. The inventors structured and maintained the sequenced DNA in a password-protected, private BLAST-searchable format.

Therefore, the inventors searched the DNA sequences from their *Galerina* genome seeking DNA fragments capable of encoding amino acid sequences of amanitins, such as predicted sequences comprising a known predicted sequence of IWGIGCNP (SEQ ID NO: 50). Thus the inventors discovered an exemplary DNA sequence encoding α-amanitin or γ-amanitin (these two forms of amanitin have the same amino acid sequence). The sequences were compared (BLAST) to *Amanita* sequences previously discovered by the inventor and disclosed in a Provisional U.S. Patent Application Ser. No. 61/002,650 (FIG. 12B). Therefore the inventors found nucleotide sequences that encode the amino acid sequence of α-amanitin or γ-amanitin with the sequence order of IWGIGCNP (SEQ ID NO: 50), in single letter code, in the genome of *Galerina*. The inventors contemplate that IWGIGCNP (SEQ ID NO: 50) would form a cyclic α-amanitin and/or γ-amanitin, which is also known to be present in *Galernia*.

Specifically, PCR primers were designed based on the full-length (248 bp) Genome Sequencer 454 FLX read encoding IWGIGCNP (SEQ ID NO: 50) and were used successfully to amplify the predicted amanitin coding region from *G. marginata* genomic DNA for use as probes in Southern and Northern blots. Primers were also designed for inverse PCR, in order to isolate and sequence DNA upstream and downstream of the amanitin-encoding region. Primers are as follows: A) Gal 454 start F: CCA GTG AAA ACC GAG TCT CCA; SEQ ID NO: 319, B) Gal before MFD F: CAA AGA TCT TCG CCC TTG CCT; SEQ ID NO: 320; C) Gal CDS MFD F: ATG TTC GAC ACC AAC TCC ACT, SEQ ID NO: 321; D) Gal end 454 R: ACA CAT TCA ACA AAT ACT AAC; SEQ ID NO: 322,; E) Gal inverse->: GCT GAA CAC GTC GAT CAA ACT; SEQ ID NO: 323; F) Gal inverse<-: TCC ATG GGT TGC AGC CAA TAC; SEQ ID NO: 324. Primer combinations A:D, B:D, and C:D amplify unique PCR products from *G. marginata* of sizes 244, 201 and 169 bp, respectively; when cloned and sequenced, these PCR products are perfect matches to the Genome Technologies 454 FLX sequence. FIG. 14.

Unlike GmAMA1, GmAMA2 (MFD2) was obtained by inverse PCR on genomic DNA of *Galerina* using primers GCT GAA CAC GTC GAT CAA ACT; SEQ ID NO: 323 and TCC ATG GGT TGC AGC CAA TAC; SEQ ID NO: 324. This yielded one PCR product (MFD2). Thus the inventors showed was that *Galerina* has at least two genes encoding for amanitin.

Example IVX

This Example describes identifying a potential prolyl oligopeptidase (POP)—like genes in fungal species.

The inventors discovered during the development of the present inventions, that both sequences of the present inventions and the structurally resolved *Amanita* cyclic peptides (amatoxins and phallotoxins) contained conserved Prolines. In particular, the inventors found in each predicted peptide sequence a Proline was located downstream of a 5' conserved region where proline (Pro) was the last amino acid of the peptide, while the last amino acid in the upstream conserved region was also Pro (for examples, FIGS. 5, 7). Thus the inventors contemplated that during processing of the propeptides of AMA1 and PHA1 to smaller peptides representing the amino acids found in the final mature amatoxins and phallotoxins, there would be a role for a proline-specific peptidase, known as a prolyl oligopeptidase enzyme, for example, a fungal peptidase or protease that cuts peptide bonds specifically after Pro residues. It was contemplated that such an enzyme also processes the other proproteins related to AMA1 and PHA1, resulting in the release of a small (7-10 amino acid) peptide that could be subsequently modified by, e.g., cyclization, hydroxylation, epimerization, and other posttranslational modifications.

Based on the conservation of a Pro residue immediately upstream of the toxin region, and of a Pro as the last amino acid in the toxin region of all *Amanita* toxin family members the inventors contemplated that an enzyme that recognizes and cleaves peptides at the carboxy side of Pro residues catalyzes the first post-translational step in *Amanita* toxin biosynthesis. Further, Based on the properties of the known proline-specific peptidases (Cunningham, et al., (1997) Biochim Biophys Acta 1343:160, Polgar, (2002) Cell. Mol. Life Sci. 59:349; all of which are herein incorporated by reference), the inventors contemplated that a member of the prolyl oligopeptidase family (POP) (EC 3.4.21.26) family was the most likely to be involved in the processing of the proproteins encoded by AMA1 and PHA1.

POPs are known to be widespread in animals, plants, and bacteria. However, none of the other known Pro-recognizing proteases specifically cleave at internal Pro residues of small peptides (Cunningham and O'Connor, 1997; Gass and Khosla, 2007).

Thus, the inventors used a human POP sequence (GenBank NP_002717, SEQ ID NO: 150) as a query sequence to search GenBank and known fungal genomes in order to identify a candidate fungal POP (see Table 12 below). A TBLASTN search was conducted using human POP (GenBank NP_002717) as query. BLASTP (default parameters) identified no orthologs of human POP with a score >53 and E value <e-06 in any fungus outside the Basidiomycetes, except *Phaeosphaeria nodorum* (SNOG_11288; score=166; E value=3e-40) (FIG. 15).

Orthologs of human POP are were present in other Basidiomycetes including *Coprinopsis cinereus* (GenBank CC1G.sub.-09936), *Ustilago maydis* (UM05288), *Cryptococcus neoformans* (XP.sub.-567311 and XP.sub.-567292), *Laccaria bicolor* (Lacbi1|303722) (hypertext transfer protocol site:genome.jgi-psf.org/Lacbi1/Lacbi1.home.html), *Phanerochaete chrysosporium* (Phchr1|1293) (hypertext transfer protocol site:genome.jgi-psf.org/Phchr1/Phchr1.home.html), and *Sporobolomyces roseus* (Sporo1|33368) (hypertext transfer protocol site:genome.jgi-psf.org/Sporo1/Sporo1.home.html). A POP enzyme has been previously purified from the mushroom *Lyophyllum cinerascens* (Yoshimoto, et al., (1988) *J. Biochem.* 104:622; herein incorporated by reference). Surprisingly, POP orthologs (POP-like genes and proteins) are rare or nonexistent in fungi outside of the Basidiomycetes, a possible exception being one in the Ascomycete *Phaeosphaeria* (*Septoria*) *nodorum* (SNOG_11288). However, this single potential Ascomycete POP-like gene is much less similar to human POP than any of the POP-like genes found in Basidiomycetes.

TABLE 12

Exemplary results using human prolyloligopeptidase (POP; (GenBank NP_002717, SEQ ID NO: 238) as a query sequence for fungal sequences (BLAST of GenBank unless otherwise noted).

| Fungal sequences related to human POP found in public databanks | Sequence Reference No. | SEQ ID NO: XX |
|---|---|---|
| human prolyloligopeptidase (POP). | (GenBank NP_002717) | SEQ ID NO: 150 |

TABLE 12-continued Exemplary results using human prolyloligopeptidase (POP; (GenBank NP_002717, SEQ ID NO: 238) as a query sequence for fungal sequences (BLAST of GenBank unless otherwise noted).

| Fungal sequences related to human POP found in public databanks | Sequence Reference No. | SEQ ID NO: XX |
|---|---|---|
| *Coprinopsis* (*Coprinus*) *cinereus* | (GenBank CC1G_09936) | SEQ ID NO: 151 |
| *Ustilago maydis* | (GenBank UM05288) | SEQ ID NO: 152 |
| *Cryptococcus neoformans* | (GenBank XP_567311) | SEQ ID NO: 153 |
| *Cryptococcus neoformans* | (GenBank XP_567292) | SEQ ID NO: 154 |
| *Laccaria bicolor*\* | (The DOE Joint Genome Institute (JGI) Lacbi1\|303722) | SEQ ID NO: 155 |
| *Phanerochaete chrysosporium*\* | (The DOE Joint Genome Institute (JGI) Phchr1\|1293) | SEQ ID NO: 156 |
| *Puccinia graminis* | PGTG_14822.2 | na |
| *Sporobolomyces roseus*\* | (The DOE Joint Genome Institute (JGI) 1\|33368; Sporo1\|33368) | SEQ ID NO: 157 |
| mushroom *Lyophyllum cinerascens* | Yoshimoto, et al., (1988) J. Biochem. 104: 622; herein incorporated by reference | na |
| Ascomycete *Phaeosphaeria* (*Septoria*) *nodorum* | (GenBank SNOG_11288) | SEQ ID NO: 158 |

*The genome sequences of *L. bicolor*, *P. chrysosporium*, and *S. roseus* are available at http://genome.jgi-psf.org. The genome sequence of *P. graminis* is available at www.broad-.mit.edu/annotation/genome/puccinia_graminis.
Na = sequence not available Based upon these discoveries the inventors contemplated that a POP-like protease was rare or nonexistent in the Ascomycota yet found widespread within the Basidiomycota.

Example XV

This example describes the identification and isolation of an *Amanita bisporigera* orthologous to human prolyloligopeptidase (POP). The inventors used the sequence for human POP (GenBank NP_002717) for screening their *A. bisporigera* genomic DNA sequence database.

Genome survey sequences were identified in the *A. bisporigera* genome (subject) by TBLASTN using human POP (GenBank accession no. NP_002717, SEQ ID NO: 150) as a query sequence (FIG. 16 and Table 13).

TABLE 13

Exemplary homology results using human prolyloligopeptidase (POP) as a query sequence (BLAST of *A. bisporigera* genome).

| Amanitin sequences related to human POP found in the Amanita genome of the present inventions | SEQUENCE | SEQ ID NO: |
|---|---|---|
| ECGK9LO02JKSHR | TTGAGAGCACACAAGTCTGGTATGAGAGCAAAGACGGAACGAAAGTTCCAATGTTCATCGTTCGTCACAAATCAACGAAATTTGACGGAACGGCGCCGGCGATTCAAAACGG | SEQ ID NO: 159 |

TABLE 13-continued

Exemplary homology results using human prolyloligopeptidase (POP) as a query sequence (BLAST of *A. bisporigera* genome).

| Amanitin sequences related to human POP found in the Amanita genome of the present inventions | SEQUENCE | SEQ ID NO: |
|---|---|---|
| ECGK sequences of POPA and POPB are shown (FIG. 14B). The amino acid sequences of POPA and POPB are shown in (FIG. 17C), SEQ ID NOs: 236 and 237.

TABLE 14A

PCR primers used to amplify prolyloligopeptidas-
likeA (POPA) genomic sequences and for 5' and 3'
RACE to identify full-length cDNA clones of POPA.

| Primer | Sequence | SEQ ID NO: |
|---|---|---|
| PopA genomic forward primer | 5' GAAACGAGAGGCGAAGTCAAGGTG 3' | SEQ ID NO: 172 |
| PopA genomic reverse primer | 5' AAGTGGATGACGATTATGCGGCAG 3' | SEQ ID NO: 173 |
| PopA gene-specific primer for 3' RACE (used with GeneRacer 3' primer) | 5' GATTGGGTATTTGGCGCAGAAGTCACG 3' | SEQ ID NO: 174 |
| PopA gene-specific primer for 5' RACE (used with GeneRacer 5' primer) | 5' ATGTCTCGCCGAACTCGCCGCCTCCTC 3' | SEQ ID NO: 175 |

TABLE 14B

PCR primers used to amplify prolyloligopeptidaes-
like B (POPB) genomic sequences and for 5' and 3'
RACE to identify full-length cDNA clones of POPB.

| Primer | Sequence | SEQ ID NO: |
|---|---|---|
| PopB genomic forward primer | 5' TCAAATGAAGTAGACGAATGGAC 3' | SEQ ID NO: 176 |
| PopB genomic reverse primer | 5' CACACGGATGAGCAATGGATGAG 3' | SEQ ID NO: 177 |
| PopB gene-specific primer for 3' RACE (used with GeneRacer 3' primer) | 5' AAAGTTCCAATGTTCATCGTTCGTCA 3' | SEQ ID NO: 178 |
| PopB gene-specific primer for 5' RACE (used with GeneRacer 5' Primer) | 5' TGGGACTAAAGAATGGATCGGCTGTAAT 3' | SEQ ID NO: 179 |

Figure 18A:
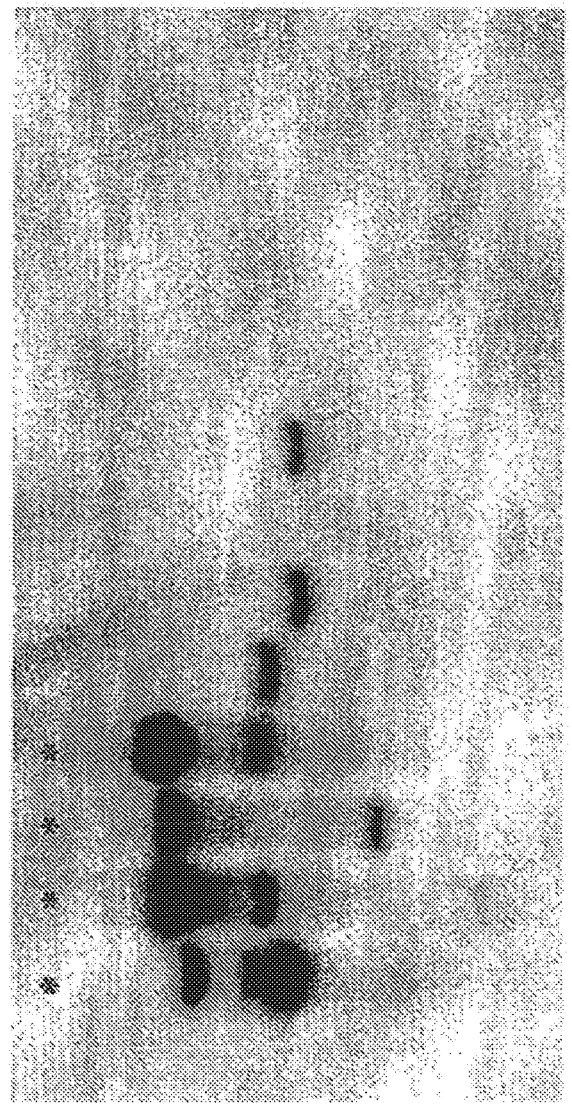
Figure 18B:

The finding of a second POP gene was unexpected. Furthermore, the inventors found at least two POP genes in *A. bisporigera*, while the majority of other mushrooms whose genomes were tested had one POP (i.e., *Coprinus cinerea, Laccaria bicolor, Phanerochaete chrysosporium*, and *Agaricus bisporus*). Based on genome survey sequences, *Galerina* species are contemplated to contain genes for the two types of POPs (see above). By Southern blotting, POPA is present in all *Amanita* species (FIG. 18A). POPB, on the other hand, is present only in toxin-producing species, corresponding to the discovery of genes encoding its putative substrates, AMA1 and PHA1 (FIG. 18B). In these experiments, the Southern blot of different *Amanita* species probed with (A) POPA or (B) POPB of *A. bisporigera*. DNA was from the same species in the same order as FIG. 5 in Hallen et al., 2007, *Proc. Natl. Acad. Sci. USA* 104: 19097-19101, herein incorporated by reference. Lanes 1-4 are *Amanita* species in sect. Phalloideae and the others are toxin non-producers. Note the presence of POPA and absence of POPB in sect. Validae (lanes 5-8), the sister group to sect. Phalloideae (lanes 1-4). We attribute the weaker hybridization of POPA to the *Amanita* species outside sect. Phalloideae (lanes 5-13) to lower DNA loading and/or lower sequence identity due to taxonomic divergence (cf. FIG. 5 in Hallen et al., 2007, *Proc. Natl. Acad. Sci. USA* 104: 19097-19101, herein incorporated by reference).

POPB was not found to hybridize to any species tested outside of sect. Phalloideae even after prolonged autoradiographic exposure. Therefore, the inventors contemplate that while POPA appears to be present in the genomes of toxin producing and nontoxin producing mushrooms, the presence of POPB appears to be limited to toxin producing mushroom species.

Example XVI

This example describes the expression and isolation of prolyl oligopeptidase (POP) of the present inventions.

The inventors first tried to express mushroom POP genes in a heterologous system, which has been successful with porcine and bacterial POPs (Szeltner et al., 2000; Shan et al., 2005). Exhaustive attempts were made to express these fungal proteins in *E. coli* or *Pichia* in a soluble, active form but were unsuccessful. However the inventors were able to use the inclusion bodies to raise antibodies; see below.

Therefore, the inventors purified POP from the mushroom *Conocbye lactea*. *Conocbye lactea* was chosen as a source of POP because (1) it produces phalloidin, one of the phallotoxins; (2) it grows abundantly in the lawns of Michigan State University while *Amanita* mushrooms themselves are less common and more restricted in their fruiting season. Proteins isolated from *Conocybe* were assayed for POP activity with a standard colorimetric substrate (Z-Gly-Pro-pNA) and was inhibited by a specific POP inhibitor, Z-Pro-Prolinal.

The inventors synthesized model peptides, ATRLPIW-GIGCNPCVGDD (SEQ ID NO:318), and ATRLPAWLVD-CPCVGDD (SEQ ID NO:249), i.e., the mature toxin peptides flanked by five amino acids on each end. Based on other successful synthetic POP substrates (e.g., Shan et al., 2005; Szeltner et al., 2000), these were contemplated as test mimics of the proproteins. The peptides IWGIGCNP (SEQ ID NO: 50) and AWLVDCP (SEQ ID NO: 69) were also synthesized as standards.

Specifically, *Conocybe* mushrooms were freeze-dried, ground in buffer, and the extracts concentrated by ammonium sulfate precipitation. After desalting, the proteins were fractionated by anion exchange High-performance liquid chromatography (or High pressure liquid chromatography, HPLC). FIG. 19. This fungus produces phallotoxins but not amatoxins. It grows abundantly in lawns and can be cultured in the laboratory (unlike *Amanita*). HPLC conditions were: C18 reverse phase column, 20% B to 60% B in 20 min. A was water+0.1% TFA and B was acetonitrile+0.075% TFA. Fractions were assayed using Z-Gly-Pro-pNA and the model phallacidin substrate. Reaction products were separated by reverse phase HPLC (FIG. 20). In some experiments the HPLC eluant was analyzed by MS, while in other cases the peaks of UV absorption were collected and analyzed by MS in the inventors lab and the central LC/MS facility, in particular for long HPLC run times. The MSU Proteomics and Mass Spectrometry facilities are equipped with several suitable mass spectrometers, including a Waters Quattro Premier XE LC MS/MS (for simultaneous separation and identification), vMALDI MS/MS, and a Shimadzu MALDI TOF MS/MS (for analysis of collected HPLC fractions). PepSeq within the MassLynx program was used to determine peptide sequences. The peptides were monitored at 280 nm.

After incubation of the test propeptide and the isolated POPB, the inventos consistently observed the production of a mature seven-amino acid product (FIG. 20B), whose identity was confirmed by the high resolution mass of the parent compound and the deduced amino acid sequence derived from MS/MS fragmentation. The inventors did not detect either of the two predicted intermediate products (i.e., AWLVDCPCVGDD, SEQ ID NO: 350, or ATRL-PAWLVDCP, SEQ ID NO: 351) nor a compound of the right mass to be the cyclized product. The cleavage activity was sensitive to boiling of the mushroom extract (FIG. 20A) and was inhibited by Z-Pro-Prolinal, a specific POP inhibitor. The same fractions showed activity against the colorimetric generic POP substrate Z-Gly-Pro-pNA and against the synthetic peptide. Confirmation of reaction product structures was accomplished by MS/MS.

The results show that purified POP cuts a synthetic amanatin peptide precisely at the expected flanking Pro residues.

Further contemplated products (shown in Table 15) for alpha-amanitin; phalloidin precursors where natural or synthetic propeptide sequences will be the substrates for *Conocybe* POPB protein.

TABLE 15

Peptides and their corresponding molecular mass for use in the present inventions.

| Peptide No. | AMA1 peptides | Mr (molecular mass) |
|---|---|---|
| 1 | TRLPIWGIGCNPCIGD (substrate) | 1714.99 |
| 2 | TRLPIWGIGCNPCIGD (substrate, oxidized) | 1712.99 |
| 3 | TRLPIWGIGCNP (cut at C side) | 1326.55 |
| 4 | IWGIGCNPCIGD (cut at N side) | 1247.42 |
| 5 | IWGIGCNPCIGD (cut at N side, oxidized) | 1245.42 |
| 6 | IWGIGCNP (final product, cut both sides) | 858.98 |
| 7 | IWGIGCNP (cyclized) | 840.97 |

Thus, the inventors found production of the mature heptapeptide of phalloidin by extracts of *Conocybe*, i.e. isolated POPB extracts (FIG. 20). Thus purified POPs from *Amanita* and *Galerina* are contemplated to release peptides 3, 4, and/or 6 from an amanitin precursor (prepropeptide or portion thereof).

Figure 9:
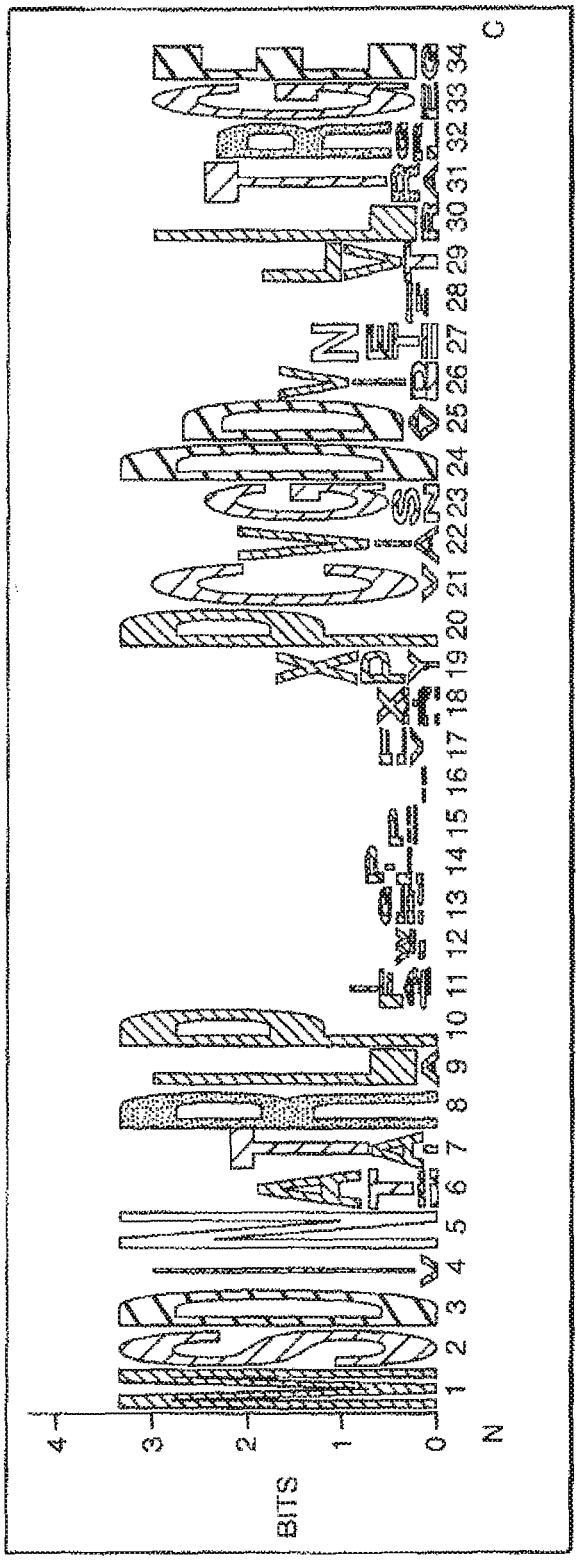

*Amanita* species in sect. Phalloideae, and perhaps *Galerina*, have two predicted POP genes (FIG. 9). This raises several possible experimental outcomes. POPB, which is only in toxin producing species, might be specialized for cutting the toxin precursors and POPA might have no role. Alternatively, POPA might make one cut and POPB the other. To address these possibilities, we will also assay toxin nonproducing species of *Amanita*(such as *A. muscaria* or *A. velosa*) for POP activity using chromogenic and peptide substrates. If POPB is responsible for one or both of the proteolytic processing steps, then only extracts of sect. Phalloideae should be able to fully cut the synthetic *Amanita* toxin peptides. If POPA and/or POPB also catalyze cyclization, a compound of the appropriate mass should be observed (Table 16).

The inventors cloned and sequenced two POP genes from *A. bisporigera*. One (POPB) was found only in the same species that can make amatoxins and phallotoxins, whereas POPA is widespread in *Amanita*. However, many species of mushrooms have POP genes as do animals and bacteria and plants.

In order to show that POP is the enzyme that catalyzes the peptide cleavage of the linear toxin peptide, a step in processing of the amatoxins and phallotoxins, the inventors synthesized a peptide representing the proprotein of phallacidin (sequence: ATRLPAWLVDCPCVGDD, SEQ ID NO: 560). The inventors incubated this with extracts of *Conocybe albipes* and found that cleavage of the peptide occurred to the predicted mature product AWLVDCP (SEQ ID NO: 69). The inventors purified the enzyme to a single band on an SDS-PAGE gel. Sequencing of this protein showed sequence identity to POPA and POPB from *A. bisporigera*. *Conocybe albipes* (this is the same species as *C. lactea*) as the source of the enzyme because it is found growing in lawns at Michigan State University in great abundance and it can be cultured. It produces phallotoxins such as phallacidin. The evidence strongly suggests that *Galerina autumnalis* has two POP genes (like toxin-producing *Amanita* species)

Example XVII

In this Example, POPA and POPB of *A. bisporigera* were expressed in inclusion bodies, purified and used to provide rat anti POPA and POPB antibodies for use in the present inventions.

*E. coli* were engineered for expressing POPA and POPB (in separate bacterium). Expression of recombinant POP was done by the procedures outlined in the pET handbook (Novagen). Briefly, a pET vector engineered to comprise a POP coding sequence of the present inventions was transformed into *Escherichia coli* AD494 cells, and cultures were grown according to the manufacturer's instructions in Luria-Bertani medium and then induced with isopropyl-D-thiogalactoside (final concentration of 1 mM) for 3 h. Pelleted cells were lysed with a French press (16,000 p.s.i.) and recentrifuged, and the pellet was extracted with B-Per II reagent (Pierce, Rockford, Ill.). The resulting purified inclusion bodies were solubilized and refolded using the Protein Refolding Kit (Novagen) according to the manufacturer's instructions.

Figure 21:
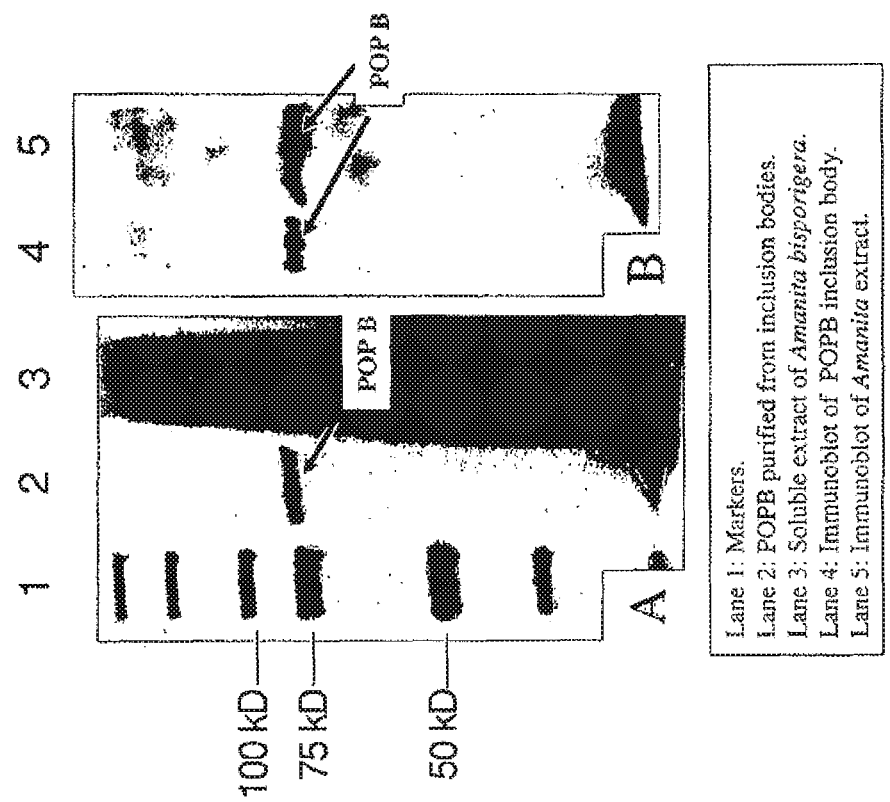

The inventors raised antibodies against POPA and POPB of *A. bisporigera* (POPB shown in FIG. 21A) showing immunoreactivity to a band of approximately the same MW as POPB (arrows) (FIG. 21B). The inventors observed that anti-POPB antibodies did not cross-react with POPA. cross-reactivity between POPB and POPA was not contemplated to be a concern because POPA and POPB are merely 55% identical at the amino acid level, and the immunoblot showed a single band (FIG. 21; Lane 1: Markers. Lane 2: POPB purified from inclusion bodies. Lane 3: Soluble extract of *Amanita bisporigera*. Lane 4: immunoblot of POPB inclusion body. Lane 5: immunoblot of *Amanita* extract. Crude antiserum was used at 1:5000 dilution.

Example XVIII

In this example, exemplary *Galerina* POP sequences identified using *Amanita bisporigera* POPA and POPB were used as query sequences for searching a library of *Galerina* sequences created by the inventors for their use during the development of the present inventions, and additional mushroom libraries. These *Galerina* sequences were obtained by the inventors from 454 sequencing (45 Mb total), see above. Not every sequence with identity to these genes are shown, merely what are considered the best examples.

*Galerina* POP sequences identified using *Amanita bisporigera* POPA (FIG. 22A) and POPB (FIG. 22B) as query sequences. The specific regions of identity and corresponding sequences are listed. The higher scoring hits (areas of identity) were strong evidence that the *Galerina* genome contains at least two POP genes. The inventors contemplate using these fragments for isolating full-length sequences for use in the present inventions.

Example IXX

Genes for fungal secondary metabolites are typically clustered (Walton, 2000; Keller et al., 2005). Examples include aflatoxin, penicillin, HC-toxin, fumonisin, sirodesmin, and gibberellins (Ahn et al., 2002; Gardiner et al., 2004; Tudzynski and Holter, 1998). From Basidiomycetes, an example of clustering are the genes for ferrichrome (Welzel et al., 2005).

To test clustering of *Amanita* toxin genes, the inventors constructed a partial lambda genomic library of *A. bisporigera* (insert size ~15 kb) and screened it with PHA1. One exemplary lambda clone was found to contain two copies of PHA1 and three putative cytochrome P450 genes (FIG. 10D). (Based on inverse PCR results, the inventors also discovered two copies of PHA1 in *A. bisporigera*; Hallen et al., 2007, *Proc. Natl. Acad. Sci. USA* 104: 19097-19101, herein incorporated by reference). Thus, at least two *Amanita* toxin genes are Clustered in the genome of *A. bisporigera*. Furthermore, because *Amanita* toxins undergo three to five hydroxylations (FIG. 1), which reactions are often catalyzed by P450's in fungi and other organisms (e.g., Malonek et al., 2005; Tudzynski et al., 2003), one or all of these three genes also has a plausible role in the biosynthesis of the *Amanita* toxins. Therefore, on both theoretical and experimental grounds the inventors contemplated finding additional *Amanita* toxin biosynthetic genes by examining regions of DNA adjacent to the known *Amanita* toxin genes.

In this Example, a software program and system, FGENESH, Salamov and Solovyev, Genome Res. 2000. 10:516-522, at world wide web.softberry.com, hypertext transfer protocol site:linux1.softberry.com/berry.phtml?topic=fgenesh&group=programs&subgroup=gfind. was used to identify and predict novel sequences adjacent to PHA genes of a 13,254 by lambda clone (SEQ ID NO:327). This software predicts genes (by which we mean predicting where the gene starts and stops and where intron and exons are) when the gene is pasted in as genomic sequence. In recent rice genome sequencing projects, this software was cited "the most successful (gene finding) program (Yu et al. (2002) Science 296:79) and was used to produce 87% of all high-evidence predicted genes (Goff et al. (2002) Science 296:79).

However, gene prediction is an inexact science, so the FGENESH software is "trained" with known gene structures from different organisms. That is, different organisms' have different (and poorly understood) rules for gene structure. Gene structure in humans isn't the same as plants, etc. To get the best prediction, an organism on which the software has been trained that is taxonomically closest to the source of the DNA was used. Therefore, the inventors used a known *Coprinus* (*Coprinopsis*) *cinerea* model for their *Amanita* genes.

Using this type of analysis as shown in FIGS. 24-30, the inventors found in an adjacent piece of genomic DNA, two PHA1 genes (one by FENESH) and 3 P450's, P450-1 (OP451), P450-2 (OP452) and P450-3 (OP453). For comparison, an estimated number of P450 genes in other organisms are provided as follows: Human 50, *Arabidopsis* 273, *phanerochaete* 149, *Fusarium* 110, *ustilago* 17, while there are 282 families of fungal P450's. For each contemplated gene, a BLASTp search was made in the inventors mushroom libraries and publicly available libraries including NCBI GENBANK and *Coprinus cinereus* genome annotations (Broad contigs) hypertext transfer protocol site:genome.semo.edu/cgi-bin/gbrowse/cc/?reset=1, Genomic sequence data from the Broad Institute (world wide web-.broad.mit.edu/annotation/genome/coprinus_cinereus/Home.html). The predictions may not find every sequence, however the inventors at this time show that the lambda clone analyzed herein contains at least three P450 genes, genes 1, 2, and 4, at least one PHA gene, gene 5, and at least one unidentified gene that is not PHA1-2, Gene 6 (85 amino acids) (?), Gene 6 has no significant match to any protein in NCBI GenBank. In addition to the genes listed in the Figures, a PHA1-2 was found (where the software analysis showed a start, stop, and introns correctly) but it did not find PHA1-1.

This example shows that two copies of PHA1 are clustered with each other and with three P450 genes. A Map of predicted genes in this lambda clone (13.4 kb), isolated using PHA1 as probe is shown in FIG. 10D.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in mycology, molecular biology, biochemistry, chemistry, botany, and medicine, or related fields are intended to be within the scope of the following claims.

The invention claimed is:

1. A nucleic acid consisting essentially of one of the sequences set forth in SEQ ID NOs: 55, 56, or 79.

2. A composition comprising at least one isolated nucleic acid consisting of SEQ ID NO: 55, 56, or 79.

3. A method of identifying a toxin-producing mushroom, comprising,
   a) providing,
      (i) a sample,
      (ii) a set of at least two polymerase chain reaction primers with sequences selected from SEQ ID NOs: 1-4, wherein said primers are capable of amplifying an amanitin or phallacidin nucleic acid, and
      (iii) a DNA polymerase,
   b) mixing said sample with said set of polymerase chain reaction primers,
   c) completing a polymerase chain reaction under conditions capable of amplifying an amanitin or phallacidin nucleic acid, and
   d) detecting the presence or absence of an amplified amanitin or phallacidin nucleic acid.

4. The method of claim 3, wherein said sample is selected from the group consisting of a raw sample, a cooked sample, and a digested sample.

5. The method of claim 3, wherein said sample comprises a mushroom sample.

6. The method of claim 3, wherein said sample is obtained from a subject.

7. A diagnostic kit for identifying a poisonous mushroom comprising one or more nucleic acids consisting essentially of SEQ ID NO: 55, 56, or 79 and instructions for identifying an amanitin or phallacidin nucleic acid.

8. The kit of claim 7, wherein said kit further comprises an amanitin or phallacidin nucleic acid consisting of SEQ ID NO: 57, 76, 77, or 81, wherein said nucleic acid is a positive control that can be amplified by a DNA polymerase and polymerase chain reaction primers, a label or a colorimetric reaction product, and instructions for detecting the presence or absence of an amplified nucleic acid.

9. A labeled nucleic acid consisting of any of the sequences set forth in SEQ ID NOs: 57, 76, 77, and 81, and a label.

* * * * *

SEQUENCE LISTING

```
<160> NUMBER OF SEQ ID NOS: 677

<210> SEQ ID NO 1
<211> LENGTH: 20
<212> TYPE: DNA
<213> ORGANISM: Amanita bisporigera

<400> SEQUENCE: 1
ccatctgggg tatcggttgc                                                  20

<210> SEQ ID NO 2
<211> LENGTH: 24
<212> TYPE: DNA
<213> ORGANISM: Amanita bisporigera

<400> SEQUENCE: 2
ttgggattgt gaggtttaga ggtc                                             24

<210> SEQ ID NO 3
<211> LENGTH: 16
<212> TYPE: DNA
<213> ORGANISM: Amanita bisporigera

<400> SEQUENCE: 3
cgtcaaccgt ctcctc                                                      16

<210> SEQ ID NO 4
<211> LENGTH: 17
<212> TYPE: DNA
<213> ORGANISM: Amanita bisporigera

<400> SEQUENCE: 4
acgcatgggc agtctac                                                     17

<210> SEQ ID NO 5
<211> LENGTH: 24
<212> TYPE: DNA
<213> ORGANISM: Amanita bisporigera

<400> SEQUENCE: 5
acctccatct cgtccatacc ttcc                                             24

<210> SEQ ID NO 6
<211> LENGTH: 21
<212> TYPE: DNA
<213> ORGANISM: Amanita bisporigera

<400> SEQUENCE: 6
tgtttgccac gctgcatact a                                                21

<210> SEQ ID NO 7
<211> LENGTH: 8
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: (1)...(8)
<223> OTHER INFORMATION: Xaa can be any amino acid
```

```
<400> SEQUENCE: 7

Ala Ile Xaa Lys Ala Gly Xaa Ala
1               5

<210> SEQ ID NO 8
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: (1)...(7)
<223> OTHER INFORMATION: Xaa can be any amino acid

<400> SEQUENCE: 8

Ala Ile Xaa Lys Ala Gly Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: A synthetic peptide

<400> SEQUENCE: 9

Phe Thr Ser Gly Ser Thr Gly
1               5

<210> SEQ ID NO 10
<211> LENGTH: 7
<212> TYPE: PRT
<213> ORGANISM: Artificial Sequence
<220> FEATURE:
<223> OTHER INFORMATION: A synthetic peptide

<400> SEQUENCE: 10

Tyr Thr Ser Gly Ser Thr Gly
1               5

<210> SEQ ID NO 11
<211> LENGTH: 7
<212> TYPE: PRT
<213> ORGANISM: Artificial Sequence
<220> FEATURE:
<223> OTHER INFORMATION: A synthetic peptide

<400> SEQUENCE: 11

Ser Arg Gly Lys Pro Lys Gly
1               5

<210> SEQ ID NO 12
<211> LENGTH: 6
<212> TYPE: PRT
<213> ORGANISM: Artificial Sequence
<220> FEATURE:
<223> OTHER INFORMATION: A synthetic peptide

<400> SEQUENCE: 12

Thr Gly Lys Pro Lys Gly
1               5

<210> SEQ ID NO 13
<211> LENGTH: 5
<212> TYPE: PRT
<213> ORGANISM: Artificial Sequence
```

```
<220> FEATURE:
<223> OTHER INFORMATION: A synthetic peptide

<400> SEQUENCE: 13

Tyr Gly Pro Thr Glu
 1               5

<210> SEQ ID NO 14
<211> LENGTH: 7
<212> TYPE: PRT
<213> ORGANISM: Artificial Sequence
<220> FEATURE:
<223> OTHER INFORMATION: A synthetic peptide

<400> SEQUENCE: 14

Gly Glu Leu Ile Ile Gly Gly
 1               5

<210> SEQ ID NO 15
<211> LENGTH: 4
<212> TYPE: PRT
<213> ORGANISM: Artificial Sequence
<220> FEATURE:
<223> OTHER INFORMATION: A synthetic peptide

<400> SEQUENCE: 15

Ala Arg Gly Tyr
 1

<210> SEQ ID NO 16
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: (1)...(6)
<223> OTHER INFORMATION: Xaa can be Lys or Arg

<400> SEQUENCE: 16

Tyr Xaa Thr Gly Asp Leu
 1               5

<210> SEQ ID NO 17
<211> LENGTH: 6
<212> TYPE: PRT
<213> ORGANISM: Artificial Sequence
<220> FEATURE:
<223> OTHER INFORMATION: A synthetic peptide

<400> SEQUENCE: 17

Tyr Lys Thr Gly Asp Leu
 1               5

<210> SEQ ID NO 18
<211> LENGTH: 7
<212> TYPE: PRT
<213> ORGANISM: Artificial Sequence
<220> FEATURE:
<223> OTHER INFORMATION: A synthetic peptide

<400> SEQUENCE: 18

Tyr Arg Thr Gly Asp Leu Val
 1               5

<210> SEQ ID NO 19
```

```
<211> LENGTH: 11
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 1
<223> OTHER INFORMATION: Xaa can be Tyr or Phe
<220> FEATURE:
<221> NAME/KEY: VARIANT
<222> LOCATION: 6
<223> OTHER INFORMATION: Xaa can be Leu or Arg
<220> FEATURE:
<221> NAME/KEY: VARIANT
<222> LOCATION: 7
<223> OTHER INFORMATION: Xaa can be Gly or Val

<400> SEQUENCE: 19

Xaa Arg Thr Gly Asp Xaa Xaa Arg Thr Gly Asp
 1               5                   10

<210> SEQ ID NO 20
<211> LENGTH: 6
<212> TYPE: PRT
<213> ORGANISM: Artificial Sequence
<220> FEATURE:
<223> OTHER INFORMATION: A synthetic peptide

<400> SEQUENCE: 20

Glu Leu Gly Glu Ile Glu
 1               5

<210> SEQ ID NO 21
<211> LENGTH: 6
<212> TYPE: PRT
<213> ORGANISM: Artificial Sequence
<220> FEATURE:
<223> OTHER INFORMATION: A synthetic peptide

<400> SEQUENCE: 21

Lys Asp Thr Gln Val Lys
 1               5

<210> SEQ ID NO 22
<211> LENGTH: 11
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: (1)...(11)
<223> OTHER INFORMATION: Xaa can be any amino acid

<400> SEQUENCE: 22

Leu Leu Xaa Leu Gly Gly Xaa Ser Leu Gly Gly
 1               5                   10

<210> SEQ ID NO 23
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 6
<223> OTHER INFORMATION: Xaa can be Ala or Thr

<400> SEQUENCE: 23
```

```
Gly Gly Asp Ser Ile Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 6
<223> OTHER INFORMATION: Xaa can be Ala or Thr

<400> SEQUENCE: 24

Gly Gly Asp Ser Ile Xaa Ala
1               5

<210> SEQ ID NO 25
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 7
<223> OTHER INFORMATION: Xaa can be Ala or Thr

<400> SEQUENCE: 25

Gly Gly His Ser Ile Xaa Ala
1               5

<210> SEQ ID NO 26
<211> LENGTH: 6
<212> TYPE: PRT
<213> ORGANISM: Artificial Sequence
<220> FEATURE:
<223> OTHER INFORMATION: A synthetic peptide

<400> SEQUENCE: 26

Gly Asp Ser Ile Thr Ala
1               5

<210> SEQ ID NO 27
<211> LENGTH: 5
<212> TYPE: PRT
<213> ORGANISM: Artificial Sequence
<220> FEATURE:
<223> OTHER INFORMATION: A synthetic peptide

<400> SEQUENCE: 27

Ile Ser Gly Asp Trp
1               5

<210> SEQ ID NO 28
<211> LENGTH: 6
<212> TYPE: PRT
<213> ORGANISM: Artificial Sequence
<220> FEATURE:
<223> OTHER INFORMATION: A synthetic peptide

<400> SEQUENCE: 28

Glu Gly His Gly Arg Glu
1               5

<210> SEQ ID NO 29
```

```
<211> LENGTH: 6
<212> TYPE: PRT
<213> ORGANISM: Artificial Sequence
<220> FEATURE:
<223> OTHER INFORMATION: A synthetic peptide

<400> SEQUENCE: 29

Asp Ala Tyr Pro Cys Ser
1               5

<210> SEQ ID NO 30
<211> LENGTH: 7
<212> TYPE: PRT
<213> ORGANISM: Artificial Sequence
<220> FEATURE:
<223> OTHER INFORMATION: A synthetic peptide

<400> SEQUENCE: 30

Asp Val Tyr Pro Cys Thr Pro
1               5

<210> SEQ ID NO 31
<211> LENGTH: 6
<212> TYPE: PRT
<213> ORGANISM: Artificial Sequence
<220> FEATURE:
<223> OTHER INFORMATION: A synthetic peptide

<400> SEQUENCE: 31

Pro Cys Thr Pro Leu Gln
1               5

<210> SEQ ID NO 32
<211> LENGTH: 6
<212> TYPE: PRT
<213> ORGANISM: Artificial Sequence
<220> FEATURE:
<223> OTHER INFORMATION: A synthetic peptide

<400> SEQUENCE: 32

Gln Glu Gly Leu Met Ala
1               5

<210> SEQ ID NO 33
<211> LENGTH: 23
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(23)
<223> OTHER INFORMATION: N is any nucleic acid
<220> FEATURE:
<221> NAME/KEY: misc_feature
<222> LOCATION: 6
<223> OTHER INFORMATION: H is A, C, or T
<220> FEATURE:
<221> NAME/KEY: misc_feature
<222> LOCATION: 12
<223> OTHER INFORMATION: R is A or G

<400> SEQUENCE: 33
gcnathtnna argcnggnnc ngc                                              23

<210> SEQ ID NO 34
<211> LENGTH: 23
<212> TYPE: DNA
<213> ORGANISM: Artificial Sequence
```

```
<220> FEATURE:
<223> OTHER INFORMATION: A synthetic primer
<220> FEATURE:
<221> NAME/KEY: misc_feature
<222> LOCATION: (1)...(23)
<223> OTHER INFORMATION: N is any nucleic acid
<220> FEATURE:
<221> NAME/KEY: misc_feature
<222> LOCATION: 12
<223> OTHER INFORMATION: Y is C or T
<220> FEATURE:
<221> NAME/KEY: misc_feature
<222> LOCATION: 18
<223> OTHER INFORMATION: D is A, G, or T

<400> SEQUENCE: 34
gcngnnccng cyttnnadat ngc                                              23

<210> SEQ ID NO 35
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is inosine
<220> FEATURE:
<221> NAME/KEY: misc_feature
<222> LOCATION: 3
<223> OTHER INFORMATION: Y is C or T

<400> SEQUENCE: 35
ttyacntcng gntcnacngg                                                  20

<210> SEQ ID NO 36
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: (1)...(20)
<223> OTHER INFORMATION: Y is C or T

<400> SEQUENCE: 36
tayacnagyg gnagyacngg                                                  20

<210> SEQ ID NO 37
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: 3
<223> OTHER INFORMATION: Y is C or T
<220> FEATURE:
<221> NAME/KEY: misc_feature
<222> LOCATION: (1)...(20)
<223> OTHER INFORMATION: N is any nucleic acid

<400> SEQUENCE: 37
tayacnagyg gntcnacngg                                                  20
```

```
<210> SEQ ID NO 38
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: 3
<223> OTHER INFORMATION: Y is C or T

<400> SEQUENCE: 38
tayacntcng gntcnacngg                                            20

<210> SEQ ID NO 39
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: Y is C or T
<220> FEATURE:
<221> NAME/KEY: misc_feature
<222> LOCATION: (1)...(20)
<223> OTHER INFORMATION: N is any nucleic acid

<400> SEQUENCE: 39
tayacntcng gnagyacngg                                            20

<210> SEQ ID NO 40
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: (1)...(20)
<223> OTHER INFORMATION: R is A or G

<400> SEQUENCE: 40
tctagaggna arccnaargg                                            20

<210> SEQ ID NO 41
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: R is A or G

<400> SEQUENCE: 41
acnggnaarc cnaargg                                               17
```

```
<210> SEQ ID NO 42
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: Y is C or T
<220> FEATURE:
<221> NAME/KEY: misc_feature
<222> LOCATION: (1)...(17)
<223> OTHER INFORMATION: N is any nucleic acid

<400> SEQUENCE: 42
ccyttnggyt tnccngt                                                      17

<210> SEQ ID NO 43
<211> LENGTH: 14
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: 3
<223> OTHER INFORMATION: Y is C or T
<220> FEATURE:
<221> NAME/KEY: misc_feature
<222> LOCATION: (1)...(20)
<223> OTHER INFORMATION: N is any nucleic acid

<400> SEQUENCE: 43
tayggnccna cnga                                                         14

<210> SEQ ID NO 44
<211> LENGTH: 15
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: 13
<223> OTHER INFORMATION: R is A or G
<220> FEATURE:
<221> NAME/KEY: misc_feature
<222> LOCATION: (1)...(15)
<223> OTHER INFORMATION: N is any nucleic acid

<400> SEQUENCE: 44
ttcngtnggn ccrta                                                        15

<210> SEQ ID NO 45
<211> LENGTH: 15
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(15)
<223> OTHER INFORMATION: N is any nucleic acid

<400> SEQUENCE: 45
tacggnccna cngan                                                        15

<210> SEQ ID NO 46
```

-continued

```
<211> LENGTH: 8
<212> TYPE: PRT
<213> ORGANISM: Amanita bisporigera
<220> FEATURE:
<221> NAME/KEY: VARIANT
<222> LOCATION: (1)...(8)
<223> OTHER INFORMATION: Cyclic peptide
<220> FEATURE:
<221> NAME/KEY: VARIANT
<222> LOCATION: 2
<223> OTHER INFORMATION: 4-hydroxy-L-prolyl
<220> FEATURE:
<221> NAME/KEY: VARIANT
<222> LOCATION: 3
<223> OTHER INFORMATION: (R)-4,5-dihydroxy-L-isoleucyl
<220> FEATURE:
<221> NAME/KEY: VARIANT
<222> LOCATION: 4
<223> OTHER INFORMATION: 6-hydroxy-2-mercapto-L-tryptophyl

<400> SEQUENCE: 46

Asn Pro Ile Trp Gly Ile Gly Cys
 1               5

<210> SEQ ID NO 47
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: (1)...(20)
<223> OTHER INFORMATION: Y is C or T

<400> SEQUENCE: 47
ccnccnatna tnagytcncc                                                   20

<210> SEQ ID NO 48
<211> LENGTH: 113
<212> TYPE: DNA
<213> ORGANISM: Amanita bisporigera

<400> SEQUENCE: 48
cccaactaaa tcccattcga acctaactcc aagacctcta aacctcacaa tcccaatgtc       60
tgacatcaat gctacccgtc tccccatctg gggtatcggt tgcaacccgt gcg            113

<210> SEQ ID NO 49
<211> LENGTH: 37
<212> TYPE: PRT
<213> ORGANISM: Amanita bisporigera

<400> SEQUENCE: 49

Pro Thr Lys Ser His Ser Asn Leu Thr Pro Arg Pro Leu Asn Leu Thr
 1               5                  10                  15

Ile Pro Met Ser Asp Ile Asn Ala Thr Arg Leu Pro Ile Trp Gly Ile
                20                  25                  30

Gly Cys Asn Pro Cys
         35

<210> SEQ ID NO 50
<211> LENGTH: 8
<212> TYPE: PRT
<213> ORGANISM: Amanita bisporigera
```

-continued

<400> SEQUENCE: 50

Ile Trp Gly Ile Gly Cys Asn Pro
1               5

<210> SEQ ID NO 51
<211> LENGTH: 8
<212> TYPE: PRT
<213> ORGANISM: Amanita bisporigera
<220> FEATURE:
<221> NAME/KEY: VARIANT
<222> LOCATION: (1)...(8)
<223> OTHER INFORMATION: This sequence is a cyclic peptide with a
      sulfoxide crossbridge between the Trp (position 2) and the
      Cys (position 6).

<400> SEQUENCE: 51

Ile Trp Gly Ile Gly Cys Asn Pro
1               5

<210> SEQ ID NO 52
<211> LENGTH: 146
<212> TYPE: DNA
<213> ORGANISM: Amanita bisporigera

<400> SEQUENCE: 52
aatctcagcg ttcagtaccc aactcccatt cgaacctaac tccaagacct ctaaacctca      60
caatcccaat gtctgacatc aatgctaccc gtctccccat ctggggtatc ggttgcaacc     120
cgtgcgtcgg tgacgacgtc actacg                                         146

<210> SEQ ID NO 53
<211> LENGTH: 48
<212> TYPE: PRT
<213> ORGANISM: Amanita bisporigera

<400> SEQUENCE: 53

Ser Gln Arg Ser Val Pro Asn Ser His Ser Asn Leu Thr Pro Arg Pro
1               5                   10                  15

Leu Asn Leu Thr Ile Pro Met Ser Asp Ile Asn Ala Thr Arg Leu Pro
            20                  25                  30

Ile Trp Gly Ile Gly Cys Asn Pro Cys Val Gly Asp Asp Val Thr Thr
        35                  40                  45

<210> SEQ ID NO 54
<211> LENGTH: 8
<212> TYPE: PRT
<213> ORGANISM: Amanita bisporigera

<400> SEQUENCE: 54

Ile Trp Gly Ile Gly Cys Asp Pro
1               5

<210> SEQ ID NO 55
<211> LENGTH: 381
<212> TYPE: DNA
<213> ORGANISM: Amanita bisporigera

<400> SEQUENCE: 55
acccaactcc cattcgaacc taactccaag acctctaaac ctcacaatcc caatgtctga      60
catcaatgct acccgtcttc ccatctgggg tatcggttgc aacccgtgca tcggtgacga     120
cgtcactaca ctcctcactc gtggcgaggc cctttgttaa attccccatc catttgtccg     180

```
ctgctatgac acgaagtagt gggcgataca agttgtggac gttatcaggc ttgggccgtt      240
gagcctgcat cggaaacaac ttatgttcct tctttttct gttttcattt gttaaaatac       300
agaacccatg tcgatgatct gtgttgtagt caatataaag ttgtactgtg tttcttgtca      360
aaaaaaaaaa aaaaaaaaaa a                                                381
```

<210> SEQ ID NO 56
<211> LENGTH: 105
<212> TYPE: DNA
<213> ORGANISM: Amanita bisporigera

<400> SEQUENCE: 56

```
atgtctgaca tcaatgctac ccgtcttccc atctggggta tcggttgcaa cccgtgcatc       60
ggtgacgacg tcactacact cctcactcgt ggcgaggccc tttgt                      105
```

<210> SEQ ID NO 57
<211> LENGTH: 2532
<212> TYPE: DNA
<213> ORGANISM: Amanita bisporigera

<400> SEQUENCE: 57

```
cgatcgaaaa cagaaatcac acactcggct agatgtccat taagtatggg agcggaagtc       60
tgttgccaaa tatggacgac cagacgtttt ttaaaattat gagtcgcgtg actcgaccat      120
taaagtacga atactcagca ttgtataggt cccgaatatc atccgcagta gccgccattg      180
ttggcggcca cgagaagttg gtaatcgccg ctcaaactat caaacgtcgt gcacgtcgca      240
ctattggctg tgctatgtat atacagttca tactgacatc actgtgacct cgtcactttc      300
cacctgtcga acaagccaag gaagcttaag acggccgacg atagccgaaa gtacaaccta      360
gaggtatggc agtagataag tcggacgaac caaagtcaaa ctactgacag gaacttcacc      420
ctgaactgtt gccgcgcgat ggttcaacag gggttgtcat aagtttagcc tgacacgtaa      480
tggtcgccca accgggcatg gatatatgga gagcgagagg tgtgtgaatg acaactacc       540 gccgaaaaag gataaccagg ctcccttgac cgaacagcgg cgggatcgca gttcgtatca      600
ccgcaccatc ttgtcgcgtt tcactctgtc agaacattca gtaatgagc tagtgtgaat       660 ggaaatattt tcgctatgtc gaaaaaggat gaacttcgga tagagaaagc caacgaatgc      720
ttgaccgaac aacggtagta ccgcagtacc accgcaccaa cttggtgcaa ttcgctctgt      780
cagaagattc atatcaactc cgccgaggaa atgagttggc aagatgaaaa attcgcagat      840
cccatatgag agcgtgagga gacgctcaga aacttccagc ttgaagcgct tagcccagca      900
ggcggacaag acgtggtggt ccttaagatt ccgagggaga atgaaatgag cctcggtctt      960
atcttcgtcg agccgtgtgg ggaatttaag agtacggaaa tattcttata gcctcaaaac     1020
actcatctcc ggcaaaaagt gaccacctac ccagggcacg taacgatgtc cttgttcaca     1080
ggcctctgat cgtgccgtgc gcagcagcgg tccataccat agaagtcatg ctgcgagcct     1140
ttggattggc atggttgtcg tcgccgatgg ggcataggta aacgtgacca attttaatcg     1200
ataatcatcg gatcaaagtc gttgaaactt gaagaggatg agccgtttta actgtgacgt     1260
cagtttagga aaataaggaa ctagccaaca cgatggtcga gtaaatcatg aatggagaaa     1320
atatttcact atcaccaaga aagaatgact aggcgtgcat gggaagggct ggctgatggt     1380
ttgacgaatg gggggtcaac caccgtaacg aagtggtccc agtccccgtt tctcaaggtg     1440
actatagcaa aaccctacgg atttttgcagg tagtccaaca agataagggt gagatgtgtc     1500
tgttgccgaa aaaaggaatc cgctcaaatg ctcacaaaat gtgttggact cctatcaaga     1560
```

-continued

```
taacatactt gatgtcaagt tactccgaga atggggtctt ctattagttc cttttgattc    1620
tctcatttcg attgggcgaa ctggtgcgaa tggcgacaag tacttcgtta ctaccccat     1680 ggaataacca aatttctgtg gaaaagaag catctgcccg caccttacgg tatactactt     1740
ttgttccgca ttcgcgcact gattcttcta tctattrtgt ttctcaggct attataccaa    1800
tttctgcgac tcataggatt gattttacct ccaaccaact aggcaatgay gtataaaagg    1860
gaytgtgaat ctcagcgttc agtacccaac taaatcccat tcgaacctaa ctccaagacc    1920
tctaaacctc acaatcccaa tgtctgacat caatgctacc cgtctcccca tctggggtat    1980
cggttgcaac ccgtgcgtcg gtgacgacgt cactacrcty ctcactcgtg gcgaggcgta    2040
agcacgattt ctctccacta atgtactagt gcacttatgt gtgtatcagc ctttgttaaa    2100
ttccccwtcc atttgtccgc tgctatgaca cgaaggtatc accatctcac ttcataacgg    2160
tgatacaagg cagttgtcct gactcaagac gtagtagtgg gcgatacaag ttgtggacgt    2220
tatcaggctt ggaccgttga gcctgcatcg gaagtaaggc cttcaagtta ttatttgtgg    2280
caaaccacga ggctaaattg tcttttgcca gacaacttac gttctttcat tttttctgtt    2340
ctcatttgta aaaatacaaa acccatgtcg atgatctgtg ttgtagtcaa tataaagttg    2400
tactgtgttt cttgtcagca ggagtgcatt aacttgttca ggaaacgtca ccctccgagt    2460
ctgctcacga ttcatagcaa tacaaactgt tttttttaag cagatgcgtc actctgagaa    2520
caactccgat cg                                                        2532
```

<210> SEQ ID NO 58
<211> LENGTH: 25
<212> TYPE: DNA
<213> ORGANISM: Artificial Sequence
<220> FEATURE:
<223> OTHER INFORMATION: A synthetic primer

<400> SEQUENCE: 58
gcacgaggac acugacaugg acuga                                           25

<210> SEQ ID NO 59
<211> LENGTH: 26
<212> TYPE: DNA
<213> ORGANISM: Artificial Sequence
<220> FEATURE:
<223> OTHER INFORMATION: A synthetic primer

<400> SEQUENCE: 59
ggacactgac atggactgaa ggagta                                          26

<210> SEQ ID NO 60
<211> LENGTH: 25
<212> TYPE: DNA
<213> ORGANISM: Artificial Sequence
<220> FEATURE:
<223> OTHER INFORMATION: A synthetic primer

<400> SEQUENCE: 60
gctgtcaacg atacgctacg taacg                                           25

<210> SEQ ID NO 61
<211> LENGTH: 24
<212> TYPE: DNA
<213> ORGANISM: Artificial Sequence
<220> FEATURE:
<223> OTHER INFORMATION: A synthetic primer

```
<400> SEQUENCE: 61
cccattcgaa cctaactcca agac                                              24

<210> SEQ ID NO 62
<211> LENGTH: 24
<212> TYPE: DNA
<213> ORGANISM: Artificial Sequence
<220> FEATURE:
<223> OTHER INFORMATION: A synthetic primer

<400> SEQUENCE: 62
cctctaaacc tcacaatccc aatg                                              24

<210> SEQ ID NO 63
<211> LENGTH: 26
<212> TYPE: DNA
<213> ORGANISM: Artificial Sequence
<220> FEATURE:
<223> OTHER INFORMATION: A synthetic primer

<400> SEQUENCE: 63
gcccaagcct gataacgtcc acaact                                            26

<210> SEQ ID NO 64
<211> LENGTH: 24
<212> TYPE: DNA
<213> ORGANISM: Artificial Sequence
<220> FEATURE:
<223> OTHER INFORMATION: A synthetic primer

<400> SEQUENCE: 64
tatcgcccac tacttcgtgt cata                                              24

<210> SEQ ID NO 65
<211> LENGTH: 23
<212> TYPE: DNA
<213> ORGANISM: Artificial Sequence
<220> FEATURE:
<223> OTHER INFORMATION: A synthetic primer

<400> SEQUENCE: 65
gacctctgct ctaaatcaca atg                                               23

<210> SEQ ID NO 66
<211> LENGTH: 22
<212> TYPE: DNA
<213> ORGANISM: Artificial Sequence
<220> FEATURE:
<223> OTHER INFORMATION: A synthetic primer

<400> SEQUENCE: 66
atcaatgcca cccgtcttcc tg                                                22

<210> SEQ ID NO 67
<211> LENGTH: 22
<212> TYPE: DNA
<213> ORGANISM: Artificial Sequence
<220> FEATURE:
<223> OTHER INFORMATION: A synthetic primer

<400> SEQUENCE: 67
cggatcattt acgtgggttt ta                                                22

<210> SEQ ID NO 68
<211> LENGTH: 26
```

```
<212> TYPE: DNA
<213> ORGANISM: Artificial Sequence
<220> FEATURE:
<223> OTHER INFORMATION: A synthetic primer

<400> SEQUENCE: 68
aacttgcctt gactagtgga tgagac                                        26

<210> SEQ ID NO 69
<211> LENGTH: 7
<212> TYPE: PRT
<213> ORGANISM: Amanita bisporigera
<220> FEATURE:
<221> NAME/KEY: VARIANT
<222> LOCATION: (1)...(7)
<223> OTHER INFORMATION: Cyclic peptide
<220> FEATURE:
<221> NAME/KEY: VARIANT
<222> LOCATION: 2
<223> OTHER INFORMATION: 2-mercapto-L-tryptophyl
<220> FEATURE:
<221> NAME/KEY: VARIANT
<222> LOCATION: 3
<223> OTHER INFORMATION: 4,5-dihydroxy-L-leucyl
<220> FEATURE:
<221> NAME/KEY: VARIANT
<222> LOCATION: 5
<223> OTHER INFORMATION: erythro-3-hydroxy-D-alpha-aspartyl
<220> FEATURE:
<221> NAME/KEY: VARIANT
<222> LOCATION: 7
<223> OTHER INFORMATION: cis-4-hydroxy-L-prolyl

<400> SEQUENCE: 69

Ala Trp Leu Val Asp Cys Pro
 1               5

<210> SEQ ID NO 70
<211> LENGTH: 7
<212> TYPE: PRT
<213> ORGANISM: Amanita bisporigera
<220> FEATURE:
<221> NAME/KEY: VARIANT
<222> LOCATION: (1)...(8)
<223> OTHER INFORMATION: Cyclic peptide
<220> FEATURE:
<221> NAME/KEY: VARIANT
<222> LOCATION: 4
<223> OTHER INFORMATION: cis-4-hydroxy-L-prolyl
<220> FEATURE:
<221> NAME/KEY: VARIANT
<222> LOCATION: 6
<223> OTHER INFORMATION: 2-mercapto-L-tryptophyl
<220> FEATURE:
<221> NAME/KEY: VARIANT
<222> LOCATION: 7
<223> OTHER INFORMATION: 4,5-dihydroxy-L-leucyl

<400> SEQUENCE: 70

Ala Thr Cys Pro Ala Trp Leu
 1               5

<210> SEQ ID NO 71
<211> LENGTH: 7
<212> TYPE: PRT
<213> ORGANISM: Amanita bisporigera

<400> SEQUENCE: 71

Ala Trp Leu Val Asp Cys Pro
 1               5
```

-continued

```
<210> SEQ ID NO 72
<211> LENGTH: 97
<212> TYPE: DNA
<213> ORGANISM: Amanita bisporigera

<400> SEQUENCE: 72
tgaggagacg gttgacgtcg tcaccgacgc atgggcagtc tacaagccaa gcaggaagac     60
gggtggcatt gatgtcagac attgtgattt agagtag                             97

<210> SEQ ID NO 73
<211> LENGTH: 31
<212> TYPE: PRT
<213> ORGANISM: Amanita bisporigera

<400> SEQUENCE: 73

Leu Leu Ile Thr Met Ser Asp Ile Asn Ala Thr Arg Leu Pro Ala Trp
 1               5                  10                  15

Leu Val Asp Cys Pro Cys Val Gly Asp Asp Val Asn Arg Leu Leu
             20                  25                  30

<210> SEQ ID NO 74
<211> LENGTH: 130
<212> TYPE: DNA
<213> ORGANISM: Amanita bisporigera

<400> SEQUENCE: 74
tgaggagacg gttgacgtcg tcaccgacgc atgggcagtc tacaagccaa gcaggaagac     60
gggtggcatt gatgtcagac attgtgattt agagtagagg tcttgggttc gagttcgaat   120
gggaggtaag                                                          130

<210> SEQ ID NO 75
<211> LENGTH: 42
<212> TYPE: PRT
<213> ORGANISM: Amanita bisporigera

<400> SEQUENCE: 75

Leu Thr Ser His Ser Asn Ser Asn Pro Arg Pro Leu Leu Ile Thr Met
 1               5                  10                  15

Ser Asp Ile Asn Ala Thr Arg Leu Pro Ala Trp Leu Val Asp Cys Pro
             20                  25                  30

Cys Val Gly Asp Asp Val Asn Arg Leu Leu
         35                  40

<210> SEQ ID NO 76
<211> LENGTH: 1893
<212> TYPE: DNA
<213> ORGANISM: Amanita bisporigera

<400> SEQUENCE: 76
gagctcagca cggagggtct cttggatttc tggccggcgt gcaagttcaa tgagagacca     60
ctgagtgaag gctcagtgat agaacagctt gaacactcgt aggcgaagat taccgttagg   120
gtgactatga gcagcaccat ttcactacat cggttatgac ggggttgttt gatcgctctg   180
atgacggaga acatgaatcc catgctggcc gattgttttg agactgaaac cgttctaacc   240
tgatgggcag aattcaagca cacgggagtg agattgcgaa ttgctgaaac cgacagtgga   300
gaagacagtc tccgtagtct gcgatcatgt taagtttatg ccctaatcgt tgagcgataa   360
agagcgacca accgcttgtg agtctcgcgc tcagaaatag atataacatc accatactgg   420
aacgacaatg aggctggcag ctgaaaaatg gtgcaaaaca aagactcgcc aacctggctc   480
```

```
aaagcggttg tccctgcgag ccgaggatat gtggtggtat cctcggaata tatgtgtgtg    540
agccttggga tcgctcaata caacatggct gtagccgatg ccagtgggta tctcgtaagg    600
cccatacatt cgttcccaat cccgatatac caccgtactg aggttcgcgg aagggaagat    660
cttggtgtta ctgaatctga agctctcgct gcgtggtcct tgtagtctgg gcgttctgat    720
acctcggcat ctccaataga tagaaatgac gacgagcaat gtcagaggtc acaatcctta    780
tcgaattacc tttgagatac tctgccacat caggccagag gccgttggag ttgaggttca    840
acatcacggg tgacggagtg gacgagccgt tatgcaagga aggaaggcca tcgcggataa    900
gtactagtat agcgaccaac ccaaccagac gtggaaatgc cattgaaggg tgggagttgc    960
gcgaatacga ggaaaacgtt tctgaggagc cgaaaccgta accaggcgcg agaacttgac    1020
ctatctatct ccgggaacgg tgttgggggt ccatgttacc gtgaaggtgg ataggggcgg    1080
attcgattcc aggaaagtta gagccacata gtcataagtg atgcaacacg cctgtgcgcg    1140
atggagataa tgcgtctttg ttgcatcggc aaaccgggtc acacggacga aaatcattac    1200
tacatggtcc atttcaggac aaaaccccta tctattgatc ctacaaactg cttgactgtt    1260
caatctgtga ccaccgggac agagaaaggc tgtgctcagt ggggtgttta atccagcgag    1320
aaacgcgtta ggcccagtcg ccgatcagga tacgacgaaa aagtgtaagg tcaagactcc    1380
cttgatgcga ttcaactatt cttgacgggg ggttgccatt gtattgcacc gtcttgcccg    1440
actggctgtg cccgcaaaga cagaacgtcc caaaaacagg aaagaacaaa gaagttttgt    1500
ggagcctgcc aagaatgtgt gatgaacagt gactgacagc atgaatgggg gatgaatatt    1560
gaataccgaa aaggatgat cagacaactg tttatggaga ttttgcgcca actcgtcttc    1620
atctccgtgt caggacaaga ttctcttatc tatcgtcctt tccgcggttt ttgcaaccat    1680
gcgaattcgt gactgagaca gataaaaggc gttggattca gcttagcatt caatattcaa    1740
tacttacctc ccattcgaac tcgagcccaa gacctctgct ctaaatcaca atgtctgaca    1800
tcaatgccac ccgtcttccy gcttggcttg tagactgccc atgcgtcggt gacgatgtca    1860
accgtctcct cactcgtggc gagaggtgag ctc    1893
```

<210> SEQ ID NO 77
<211> LENGTH: 1613
<212> TYPE: DNA
<213> ORGANISM: Amanita bisporigera

<400> SEQUENCE: 77

```
cgatcgggtg gtatgagcga cgttgatgca tggattagat aaaaaactca tttttgcctt     60
gacattgtaa catgcgaata agagagcaag accccatca gagcaaaaaa ggaatcacgg    120
atttgatatc gacctgaccc aagtcggcaa cggtaatagg ggctagagcc acatatgagt    180
gatgagcgat ggagataatg ttgcatcggg aaaccgggtc acacggccga taatcattct    240
catacatgtc catttctatc tattggtctg taggactgct taacggttta aatctgtgac    300
caccaggaca gacaaagaaa ggctgtgctg ttcgaaacgc gttactaatt aggcccagtt    360
cggcataaat cgccgacacg caggatacga cgaaaagtgt aagcttaagg tcaagactcc    420
tctgatgtga ttcaacaact tttgacgggg ggttgccatt gtatgcaccg tcttgcccgg    480
ctggccatgt ccgcagaacc gaacgcccct aacgacagga agaagaaag aagttcacgg    540 attccatata gtaagcgtgg agcctgtgtg ataaacagtc atgaatgatt catgggaatg    600
aagaccgatc agacaaacgc ttatggagat tttgtgccaa tttgtctttc catctacgat    660
```

```
tctcttatct atcgtcctttt ctgcggttttt tgcaaccatg cgaagtcgtg actgaaacag   720
ataaaaggcg ttggatgtgg ctcagtagtc aatattcaat acttacctcc cattcgaact     780
cgaacccaag acctctgctc taaatcacaa tgtctgacat caatgccacc cgtcttcctg     840
cttggcttgt agactgccca tgcgtcggtg acgacgtcaa ccgtctcctc actcgtggtg     900
agaggtgagc tcaaaattcc atttaataat gtagcaatgt actcatgtgt cgtgtatcag     960
cctttgttaa atgtctcatc cactagtcaa ggtatccgcc tctgatttct tgatgacaat    1020
gcatggtcat ggtacttact ttgatgtagt agtggacgac gcaagttgtt gacaatgtta    1080
ggcttggagc gttgagcctg catcggaagt aaggccttca aattttttctg tgataagcag    1140
cgagctaact tgggttagac gactcacatt ctttctcatt ctttctcatt ctcatataaa    1200
acccacgtaa atgatccgag ctgtactatg gaatgcaatg tacgcgtgta tatgtgtgtg    1260
ttgtcagtaa gagagcattt agcaatccga gcttgcatgc cgctgtcgcc agagctgtct    1320
acttgtcagc aacatatcgc atatcacata ggcagctgtt gtaccattga aaagccgtgg    1380
ggcgtataac ctggaggaat tcaaagaag ggtctttat gatgagtttg atagctcgca    1440
tagttgtgaa agtcggcaag ttcacaaaaa acagtgattt tatgttacat gtgacgagga    1500
gcatgagaca caactttgaa ctgcacccgg gagaaagcag gcttagcaac accgatgacg    1560
agggggagga gaaatacggg gagaatgccg atgatgtagg cataatgcga tcg            1613

<210> SEQ ID NO 78
<211> LENGTH: 21
<212> TYPE: DNA
<213> ORGANISM: Amanita bisporigera

<400> SEQUENCE: 78
gcttggcttg tagactgccc a                                                21

<210> SEQ ID NO 79
<211> LENGTH: 319
<212> TYPE: DNA
<213> ORGANISM: Amanita bisporigera

<400> SEQUENCE: 79
gacctctgct ctaaatcaca atgtctgaca tcaatgccac ccgtcttccc gcttggcttg     60
tagattgccc atgcgtcggt gacgatgtca accgtctcct cactcgtggc gagagccttt    120
ggtaaatgtc tcatccacta gtcaaggcaa gttgttgaca atgtcaggct tgcggaccgt    180
tgagcctgca tcggaaacga ctcacgttct ttctcattct ttctgattct catttgtaaa    240
catataaaac ccacgtaaat gatccgttgt gctatggaat gcaatatact tgtgaaaaaa    300
aaaaaaaaaa aaaaaaaaa                                                  319

<210> SEQ ID NO 80
<211> LENGTH: 32
<212> TYPE: PRT
<213> ORGANISM: Amanita bisporigera

<400> SEQUENCE: 80

Met Ser Asp Ile Asn Ala Thr Arg Leu Pro Ala Trp Leu Val Asp Cys
 1               5                  10                  15

Pro Cys Val Gly Asp Asp Val Asn Arg Leu Leu Thr Arg Ser Leu Cys
            20                  25                  30

<210> SEQ ID NO 81
<211> LENGTH: 102
```

```
<212> TYPE: DNA
<213> ORGANISM: Amanita bisporigera
<220> FEATURE:
<223> OTHER INFORMATION: A synthetic primer

<400> SEQUENCE: 81
atgtctgaca tcaatgccac ccgtcttccc gcttggcttg tagattgccc atgcgtcggt    60
gacgatgtca accgtctcct cactcgtggc gagagccttt gg                      102

<210> SEQ ID NO 82
<211> LENGTH: 30
<212> TYPE: DNA
<213> ORGANISM: Amanita bisporigera
<220> FEATURE:
<223> OTHER INFORMATION: A synthetic primer

<400> SEQUENCE: 82
atgtctgaca tcaatgccac ccgtcttccc                                     30

<210> SEQ ID NO 83
<211> LENGTH: 51
<212> TYPE: DNA
<213> ORGANISM: Amanita bisporigera
<220> FEATURE:
<223> OTHER INFORMATION: A synthetic primer

<400> SEQUENCE: 83
tgcatcggtg acgacgtcac tacactcctc actcgtggcg aggcccttttg t            51

<210> SEQ ID NO 84
<211> LENGTH: 51
<212> TYPE: DNA
<213> ORGANISM: Amanita bisporigera
<220> FEATURE:
<223> OTHER INFORMATION: A synthetic primer

<400> SEQUENCE: 84
tgcgtcggtg acgatgtcaa ccgtctcctc actcgtggcg agagcctttg g             51

<210> SEQ ID NO 85
<211> LENGTH: 24
<212> TYPE: DNA
<213> ORGANISM: Amanita bisporigera

<400> SEQUENCE: 85
atctggggta tcggttgcaa cccg                                           24

<210> SEQ ID NO 86
<211> LENGTH: 21
<212> TYPE: DNA
<213> ORGANISM: Amanita bisporigera

<400> SEQUENCE: 86
gcttggcttg tagattgccc a                                              21

<210> SEQ ID NO 87
<211> LENGTH: 33
<212> TYPE: PRT
<213> ORGANISM: Amanita bisporigera
<220> FEATURE:
<221> NAME/KEY: VARIANT
<222> LOCATION: (1)...(33)
<223> OTHER INFORMATION: X is any amino acid

<400> SEQUENCE: 87
```

```
Met Ser Asp Ile Asn Ala Thr Arg Leu Pro Xaa Trp Xaa Xaa Xaa Cys
1               5                   10                  15

Xaa Pro Cys Val Gly Asp Asp Val Xaa Xaa Leu Leu Thr Arg Ala Leu
            20                  25                  30

Cys
```

<210> SEQ ID NO 88
<211> LENGTH: 10
<212> TYPE: PRT
<213> ORGANISM: Amanita bisporigera

<400> SEQUENCE: 88

```
Met Ser Asp Ile Asn Ala Thr Arg Leu Pro
1               5                   10
```

<210> SEQ ID NO 89
<211> LENGTH: 17
<212> TYPE: PRT
<213> ORGANISM: Amanita bisporigera

<400> SEQUENCE: 89

```
Cys Ile Gly Asp Asp Val Thr Thr Leu Leu Thr Arg Gly Glu Ala Leu
1               5                   10                  15

Cys
```

<210> SEQ ID NO 90
<211> LENGTH: 17
<212> TYPE: PRT
<213> ORGANISM: Amanita bisporigera

<400> SEQUENCE: 90

```
Cys Val Gly Asp Asp Val Asn Arg Leu Leu Thr Arg Gly Glu Ser Leu
1               5                   10                  15

Cys
```

<210> SEQ ID NO 91
<211> LENGTH: 15
<212> TYPE: PRT
<213> ORGANISM: Amanita bisporigera
<220> FEATURE:
<221> NAME/KEY: VARIANT
<222> LOCATION: (2)..(2)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa can be any naturally occurring amino acid

<400> SEQUENCE: 91

```
Cys Xaa Gly Asp Asp Val Xaa Xaa Leu Leu Thr Arg Xaa Leu Cys
1               5                   10                  15
```

<210> SEQ ID NO 92
<211> LENGTH: 21
<212> TYPE: DNA
<213> ORGANISM: Artificial Sequence
<220> FEATURE:
<223> OTHER INFORMATION: A synthetic primer

<400> SEQUENCE: 92
agcatctgcc cgcaccttac g                                       21

<210> SEQ ID NO 93
<211> LENGTH: 22
<212> TYPE: DNA
<213> ORGANISM: Artificial Sequence
<220> FEATURE:
<223> OTHER INFORMATION: A synthetic primer

<400> SEQUENCE: 93
actgccttgt atcaccgtta tg                                            22

<210> SEQ ID NO 94
<211> LENGTH: 10
<212> TYPE: PRT
<213> ORGANISM: Amanita bisporigera
<220> FEATURE:
<221> NAME/KEY: VARIANT
<222> LOCATION: (1)...(10)
<223> OTHER INFORMATION: Xaa can be any amino acid

<400> SEQUENCE: 94

Met Ser Asp Ile Asn Xaa Xaa Arg Xaa Pro
1               5                   10

<210> SEQ ID NO 95
<211> LENGTH: 6
<212> TYPE: PRT
<213> ORGANISM: Amanita bisporigera
<220> FEATURE:
<221> NAME/KEY: VARIANT
<222> LOCATION: (1)...(6)
<223> OTHER INFORMATION: Xaa can be any amino acid

<400> SEQUENCE: 95

Cys Val Gly Asp Xaa Val
1               5

<210> SEQ ID NO 96
<211> LENGTH: 12
<212> TYPE: PRT
<213> ORGANISM: Amanita bisporigera
<220> FEATURE:
<221> NAME/KEY: VARIANT
<222> LOCATION: (1)...(12)
<223> OTHER INFORMATION: Xaa can be any amino acid

<400> SEQUENCE: 96

Cys Val Gly Asp Asp Val Xaa Xaa Xaa Asp Xaa Xaa
1               5                   10

<210> SEQ ID NO 97
<211> LENGTH: 23
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(23)
<223> OTHER INFORMATION: N is any nucleotide
<220> FEATURE:
<221> NAME/KEY: misc_feature
<222> LOCATION: (1)...(23)
<223> OTHER INFORMATION: Y is C or T

<400> SEQUENCE: 97
atgtcngaya tyaaygcnac ncg                                           23

<210> SEQ ID NO 98
<211> LENGTH: 33
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(33)
<223> OTHER INFORMATION: S is G or C
<220> FEATURE:
<221> NAME/KEY: misc_feature
<222> LOCATION: (1)...(33)
<223> OTHER INFORMATION: Y is C or T
<220> FEATURE:
<221> NAME/KEY: misc_feature
<222> LOCATION: (1)...(33)
<223> OTHER INFORMATION: W is A or T
<220> FEATURE:
<221> NAME/KEY: misc_feature
<222> LOCATION: (1)...(33)
<223> OTHER INFORMATION: K is G or T
<220> FEATURE:
<221> NAME/KEY: misc_feature
<222> LOCATION: (1)...(33)
<223> OTHER INFORMATION: R is A or G

<400> SEQUENCE: 98
aaggsyctcg ccacgagtga ggagwskrkt gac         33

<210> SEQ ID NO 99
<211> LENGTH: 102
<212> TYPE: DNA
<213> ORGANISM: Artificial Sequence
<220> FEATURE:
<223> OTHER INFORMATION: A synthetic primer

<400> SEQUENCE: 99
atgtctgata ttaatgcaac gcgtcttccc ttcaatattc tgccattcat gcttcccccg    60
tgcgtcagtg acgatgtcaa tatactcctc actcgtggcg ag                      102

<210> SEQ ID NO 100
<211> LENGTH: 34
<212> TYPE: PRT
<213> ORGANISM: Artificial Sequence
<220> FEATURE:
<223> OTHER INFORMATION: A synthetic peptide

<400> SEQUENCE: 100

Met Ser Asp Ile Asn Ala Thr Arg Leu Pro Phe Asn Ile Leu Pro Phe
 1               5                  10                  15

Met Leu Pro Pro Cys Val Ser Asp Asp Val Asn Ile Leu Leu Thr Arg
            20                  25                  30

Gly Glu

<210> SEQ ID NO 101
<211> LENGTH: 96
<212> TYPE: DNA
<213> ORGANISM: Artificial Sequence
<220> FEATURE:
<223> OTHER INFORMATION: A synthetic primer

<400> SEQUENCE: 101
atgtcagata tcaatgcgac gcgtcttccc atatggggaa taggttgcga cccgtgcatc    60
ggtgacgacg tcaccatact cctcactcgt ggcgag                              96

<210> SEQ ID NO 102

-continued

<211> LENGTH: 32
<212> TYPE: PRT
<213> ORGANISM: Artificial Sequence
<220> FEATURE:
<223> OTHER INFORMATION: A synthetic peptide

<400> SEQUENCE: 102

Met Ser Asp Ile Asn Ala Thr Arg Leu Pro Ile Trp Gly Ile Gly Cys
1               5                   10                  15

Asp Pro Cys Ile Gly Asp Asp Val Thr Ile Leu Leu Thr Arg Gly Glu
            20                  25                  30

<210> SEQ ID NO 103
<211> LENGTH: 96
<212> TYPE: DNA
<213> ORGANISM: Artificial Sequence
<220> FEATURE:
<223> OTHER INFORMATION: A synthetic primer

<400> SEQUENCE: 103
atgtcggata ttaatgctac acgtcttcca attattggga tcttacttcc cccgtgcatc    60
ggtgacgatg tcaccctact cctcactcgt ggcgag                              96

<210> SEQ ID NO 104
<211> LENGTH: 32
<212> TYPE: PRT
<213> ORGANISM: Artificial Sequence
<220> FEATURE:
<223> OTHER INFORMATION: A synthetic peptide

<400> SEQUENCE: 104

Met Ser Asp Ile Asn Ala Thr Arg Leu Pro Ile Ile Gly Ile Leu Leu
1               5                   10                  15

Pro Pro Cys Ile Gly Asp Asp Val Thr Leu Leu Leu Thr Arg Gly Glu
            20                  25                  30

<210> SEQ ID NO 105
<211> LENGTH: 73
<212> TYPE: DNA
<213> ORGANISM: Artificial Sequence
<220> FEATURE:
<223> OTHER INFORMATION: A synthetic primer

<400> SEQUENCE: 105
ccgtcttccc gcctggctcg ccacctgccc gtgcgccggt gacgacgtca accctctcct    60
cactcgtggc gag                                                       73

<210> SEQ ID NO 106
<211> LENGTH: 31
<212> TYPE: PRT
<213> ORGANISM: Artificial Sequence
<220> FEATURE:
<223> OTHER INFORMATION: A synthetic peptide

<400> SEQUENCE: 106

Met Ser Asp Ile Asn Ala Thr Arg Leu Pro Ala Trp Leu Ala Thr Cys
1               5                   10                  15

Pro Cys Ala Gly Asp Asp Val Asn Pro Leu Leu Thr Arg Gly Glu
            20                  25                  30

<210> SEQ ID NO 107
<211> LENGTH: 32
<212> TYPE: PRT
<213> ORGANISM: Amanita bisporigera

```
<400> SEQUENCE: 107

Met Ser Asp Ile Asn Ala Thr Arg Leu Pro Ile Trp Gly Ile Gly Cys
1               5                   10                  15

Asn Pro Cys Val Gly Asp Asp Val Thr Thr Leu Leu Thr Arg Gly Glu
            20                  25                  30

<210> SEQ ID NO 108
<211> LENGTH: 31
<212> TYPE: PRT
<213> ORGANISM: Amanita bisporigera

<400> SEQUENCE: 108

Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Gly Glu
            20                  25                  30

<210> SEQ ID NO 109
<211> LENGTH: 32
<212> TYPE: PRT
<213> ORGANISM: Amanita bisporigera
<220> FEATURE:
<221> NAME/KEY: VARIANT
<222> LOCATION: (1)...(32)
<223> OTHER INFORMATION: Xaa is any amino acid

<400> SEQUENCE: 109

Met Ser Asp Ile Asn Ala Thr Arg Leu Pro Xaa Trp Xaa Xaa Xaa Cys
1               5                   10                  15

Xaa Pro Cys Val Gly Asp Asp Val Xaa Xaa Leu Leu Thr Arg Gly Glu
            20                  25                  30

<210> SEQ ID NO 110
<211> LENGTH: 34
<212> TYPE: PRT
<213> ORGANISM: Amanita bisporigera

<400> SEQUENCE: 110

Met Ser Asp Ile Asn Ala Thr Arg Leu Pro Phe Asn Ile Leu Pro Phe
1               5                   10                  15

Met Leu Pro Pro Cys Val Ser Asp Asp Val Asn Ile Leu Leu Thr Arg
            20                  25                  30

Gly Glu

<210> SEQ ID NO 111
<211> LENGTH: 32
<212> TYPE: PRT
<213> ORGANISM: Amanita bisporigera

<400> SEQUENCE: 111

Met Ser Asp Ile Asn Ala Thr Arg Leu Pro Ile Trp Gly Ile Gly Cys
1               5                   10                  15

Asp Pro Cys Ile Gly Asp Asp Val Thr Ile Leu Leu Thr Arg Gly Glu
            20                  25                  30

<210> SEQ ID NO 112
<211> LENGTH: 32
<212> TYPE: PRT
<213> ORGANISM: Amanita bisporigera

<400> SEQUENCE: 112
```

```
Met Ser Asp Ile Asn Ala Thr Arg Leu Pro Ile Ile Gly Ile Leu Leu
1               5                   10                  15

Pro Pro Cys Ile Gly Asp Asp Val Thr Leu Leu Leu Thr Arg Gly Glu
            20                  25                  30
```

<210> SEQ ID NO 113
<211> LENGTH: 31
<212> TYPE: PRT
<213> ORGANISM: Amanita bisporigera

<400> SEQUENCE: 113

```
Met Ser Asp Ile Asn Ala Thr Arg Leu Pro Ala Trp Leu Ala Thr Cys
1               5                   10                  15

Pro Cys Ala Gly Asp Asp Val Asn Pro Leu Leu Thr Arg Gly Glu
            20                  25                  30
```

<210> SEQ ID NO 114
<211> LENGTH: 10
<212> TYPE: PRT
<213> ORGANISM: Amanita bisporigera

<400> SEQUENCE: 114

```
Phe Asn Ile Leu Pro Phe Met Leu Pro Pro
1               5                   10
```

<210> SEQ ID NO 115
<211> LENGTH: 15
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(15)
<223> OTHER INFORMATION: N is any nucleic acid
<220> FEATURE:
<221> NAME/KEY: misc_feature
<222> LOCATION: (1)...(15)
<223> OTHER INFORMATION: B is G, C, or T

<400> SEQUENCE: 115
tbgcncgngg ntacn                                               15

<210> SEQ ID NO 116
<211> LENGTH: 15
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(15)
<223> OTHER INFORMATION: N is any nucleic acid

<400> SEQUENCE: 116
gtanccncgn gcgan                                               15

<210> SEQ ID NO 117
<211> LENGTH: 8
<212> TYPE: PRT
<213> ORGANISM: Amanita bisporigera

<400> SEQUENCE: 117

```
Ile Ile Gly Ile Leu Leu Pro Pro
1               5
```

-continued

```
<210> SEQ ID NO 118
<211> LENGTH: 34
<212> TYPE: PRT
<213> ORGANISM: Amanita bisporigera

<400> SEQUENCE: 118

Met Ser Asp Ile Asn Ala Thr Arg Leu Pro His Pro Phe Pro Leu Gly
1               5                   10                  15

Leu Gln Pro Cys Ala Gly Asp Val Asp Asn Leu Thr Leu Thr Lys Gly
            20                  25                  30

Glu Gly

<210> SEQ ID NO 119
<211> LENGTH: 32
<212> TYPE: PRT
<213> ORGANISM: Amanita bisporigera

<400> SEQUENCE: 119

Met Ser Asp Ile Asn Ala Thr Arg Leu Pro Ile Trp Gly Ile Gly Cys
1               5                   10                  15

Asp Pro Cys Ile Gly Asp Asp Val Thr Ile Leu Leu Thr Arg Gly Glu
            20                  25                  30

<210> SEQ ID NO 120
<211> LENGTH: 31
<212> TYPE: PRT
<213> ORGANISM: Amanita bisporigera

<400> SEQUENCE: 120

Met Ser Asp Ile Asn Ala Thr Arg Leu Pro Ala Trp Leu Ala Thr Cys
1               5                   10                  15

Pro Cys Ala Gly Asp Asp Val Asn Pro Leu Leu Thr Arg Gly Glu
            20                  25                  30

<210> SEQ ID NO 121
<211> LENGTH: 29
<212> TYPE: PRT
<213> ORGANISM: Amanita bisporigera

<400> SEQUENCE: 121

Met Ser Asp Ile Asn Val Thr Arg Leu Pro Gly Phe Val Pro Ile Leu
1               5                   10                  15

Phe Pro Cys Val Gly Asp Asp Val Asn Thr Ala Leu Thr
            20                  25

<210> SEQ ID NO 122
<211> LENGTH: 35
<212> TYPE: PRT
<213> ORGANISM: Amanita bisporigera

<400> SEQUENCE: 122

Met Ser Asp Ile Asn Thr Ala Arg Leu Pro Phe Tyr Gln Phe Pro Asp
1               5                   10                  15

Phe Lys Tyr Pro Cys Val Gly Asp Asp Ile Glu Met Val Leu Ala Arg
            20                  25                  30

Gly Glu Arg
        35

<210> SEQ ID NO 123
<211> LENGTH: 33
<212> TYPE: PRT
<213> ORGANISM: Amanita bisporigera
```

<400> SEQUENCE: 123

Met Ser Asp Ile Asn Thr Ala Arg Leu Pro Phe Phe Gln Pro Pro Glu
1               5                   10                  15

Phe Arg Pro Pro Cys Val Gly Asp Asp Ile Glu Met Val Leu Thr Arg
            20                  25                  30

Gly

<210> SEQ ID NO 124
<211> LENGTH: 35
<212> TYPE: PRT
<213> ORGANISM: Amanita bisporigera

<400> SEQUENCE: 124

Met Ser Asp Ile Asn Thr Ala Arg Leu Pro Leu Phe Leu Pro Pro Val
1               5                   10                  15

Arg Met Pro Pro Cys Val Gly Asp Asp Ile Glu Met Val Leu Thr Arg
            20                  25                  30

Gly Glu Arg
        35

<210> SEQ ID NO 125
<211> LENGTH: 32
<212> TYPE: PRT
<213> ORGANISM: Amanita bisporigera

<400> SEQUENCE: 125

Met Ser Asp Ile Asn Thr Ala Arg Leu Pro Leu Phe Leu Pro Pro Val
1               5                   10                  15

Arg Leu Pro Pro Cys Val Gly Asp Asp Ile Glu Met Val Leu Thr Arg
            20                  25                  30

<210> SEQ ID NO 126
<211> LENGTH: 35
<212> TYPE: PRT
<213> ORGANISM: Amanita bisporigera

<400> SEQUENCE: 126

Met Ser Asp Ile Asn Thr Ala Arg Leu Pro Tyr Val Val Phe Met Ser
1               5                   10                  15

Phe Ile Pro Pro Cys Val Asn Asp Ile Gln Val Val Leu Thr Arg
            20                  25                  30

Gly Glu Glu
        35

<210> SEQ ID NO 127
<211> LENGTH: 30
<212> TYPE: PRT
<213> ORGANISM: Amanita bisporigera

<400> SEQUENCE: 127

Met Ser Asp Ile Asn Thr Ala Arg Leu Pro Cys Ile Gly Phe Leu Gly
1               5                   10                  15

Ile Pro Ser Val Gly Asp Asp Ile Glu Met Val Leu Arg His
            20                  25                  30

<210> SEQ ID NO 128
<211> LENGTH: 27
<212> TYPE: PRT
<213> ORGANISM: Amanita bisporigera

<400> SEQUENCE: 128

Met Ser Asp Ile Asn Thr Ala Arg Leu Pro Leu Ser Ser Pro Met Leu
1               5                   10                  15

Leu Pro Cys Val Gly Asp Asp Ile Leu Met Val
            20                  25

<210> SEQ ID NO 129
<211> LENGTH: 32
<212> TYPE: PRT
<213> ORGANISM: Amanita bisporigera

<400> SEQUENCE: 129

Met Ser Asp Ile Asn Ala Ile Arg Ala Pro Ile Leu Met Leu Ala Ile
1               5                   10                  15

Leu Pro Cys Val Gly Asp Asp Ile Glu Val Leu Arg Arg Gly Glu Gly
            20                  25                  30

<210> SEQ ID NO 130
<211> LENGTH: 35
<212> TYPE: PRT
<213> ORGANISM: Amanita bisporigera

<400> SEQUENCE: 130

Met Ser Asp Ile Asn Gly Thr Arg Leu Pro Ile Pro Gly Leu Ile Pro
1               5                   10                  15

Leu Gly Ile Pro Cys Val Ser Asp Asp Val Asn Pro Thr Leu Thr Arg
            20                  25                  30

Gly Glu Arg
        35

<210> SEQ ID NO 131
<211> LENGTH: 34
<212> TYPE: PRT
<213> ORGANISM: Amanita bisporigera

<400> SEQUENCE: 131

Met Ser Asp Ile Asn Ala Thr Arg Leu Pro Gly Ala Tyr Pro Pro Val
 1               5                  10                  15

Pro Met Pro Cys Val Gly Asp Ala Asp Asn Phe Thr Leu Thr Arg Gly
            20                  25                  30

Glu Lys

<210> SEQ ID NO 132
<211> LENGTH: 33
<212> TYPE: PRT
<213> ORGANISM: Amanita bisporigera

<400> SEQUENCE: 132

Met Ser Asp Ile Asn Ala Thr Arg Leu Pro Gly Met Glu Pro Pro Ser
 1               5                  10                  15

Pro Met Pro Cys Val Gly Asp Ala Asp Asn Phe Thr Leu Thr Arg Gly
            20                  25                  30

Asn

<210> SEQ ID NO 133
<211> LENGTH: 34
<212> TYPE: PRT
<213> ORGANISM: Amanita bisporigera

<400> SEQUENCE: 133

```
Met Ser Asp Ile Asn Ala Thr Arg Leu Pro His Pro Phe Pro Leu Gly
1               5                   10                  15
Leu Gln Pro Cys Ala Gly Asp Val Asp Asn Leu Thr Leu Thr Lys Gly
            20                  25                  30
Glu Gly
```

<210> SEQ ID NO 134
<211> LENGTH: 8
<212> TYPE: PRT
<213> ORGANISM: Amanita bisporigera

<400> SEQUENCE: 134

```
Ile Trp Gly Ile Gly Cys Asn Pro
1               5
```

<210> SEQ ID NO 135
<211> LENGTH: 8
<212> TYPE: PRT
<213> ORGANISM: Amanita bisporigera
<220> FEATURE:
<221> NAME/KEY: VARIANT
<222> LOCATION: (1)...(8)
<223> OTHER INFORMATION: Xaa can be any amino acid

<400> SEQUENCE: 135

```
Xaa Trp Xaa Xaa Xaa Cys Xaa Pro
1               5
```

<210> SEQ ID NO 136
<211> LENGTH: 7
<212> TYPE: PRT
<213> ORGANISM: Amanita bisporigera

<400> SEQUENCE: 136

```
Ala Trp Leu Ala Thr Cys Pro
1               5
```

<210> SEQ ID NO 137
<211> LENGTH: 8
<212> TYPE: PRT
<213> ORGANISM: Amanita bisporigera

<400> SEQUENCE: 137

```
Gly Phe Val Pro Ile Leu Phe Pro
1               5
```

<210> SEQ ID NO 138
<211> LENGTH: 10
<212> TYPE: PRT
<213> ORGANISM: Amanita bisporigera

<400> SEQUENCE: 138

```
Phe Tyr Gln Phe Pro Asp Phe Lys Tyr Pro
1               5                   10
```

<210> SEQ ID NO 139
<211> LENGTH: 10
<212> TYPE: PRT
<213> ORGANISM: Amanita bisporigera

<400> SEQUENCE: 139

```
Phe Phe Gln Pro Pro Glu Phe Arg Pro Pro
1               5                   10
```

```
<210> SEQ ID NO 140
<211> LENGTH: 10
<212> TYPE: PRT
<213> ORGANISM: Amanita bisporigera

<400> SEQUENCE: 140

Leu Phe Leu Pro Pro Val Arg Met Pro Pro
1               5                   10

<210> SEQ ID NO 141
<211> LENGTH: 10
<212> TYPE: PRT
<213> ORGANISM: Amanita bisporigera

<400> SEQUENCE: 141

Leu Phe Leu Pro Pro Val Arg Leu Pro Pro
1               5                   10

<210> SEQ ID NO 142
<211> LENGTH: 10
<212> TYPE: PRT
<213> ORGANISM: Amanita bisporigera

<400> SEQUENCE: 142

Tyr Val Val Phe Met Ser Phe Ile Pro Pro
1               5                   10

<210> SEQ ID NO 143
<211> LENGTH: 8
<212> TYPE: PRT
<213> ORGANISM: Amanita bisporigera

<400> SEQUENCE: 143

Cys Ile Gly Phe Leu Gly Ile Pro
1               5

<210> SEQ ID NO 144
<211> LENGTH: 8
<212> TYPE: PRT
<213> ORGANISM: Amanita bisporigera

<400> SEQUENCE: 144

Leu Ser Ser Pro Met Leu Leu Pro
1               5

<210> SEQ ID NO 145
<211> LENGTH: 8
<212> TYPE: PRT
<213> ORGANISM: Amanita bisporigera

<400> SEQUENCE: 145

Ile Leu Met Leu Ala Ile Leu Pro
1               5

<210> SEQ ID NO 146
<211> LENGTH: 10
<212> TYPE: PRT
<213> ORGANISM: Amanita bisporigera

<400> SEQUENCE: 146

Ile Pro Gly Leu Ile Pro Leu Gly Ile Pro
1               5                   10

<210> SEQ ID NO 147
<211> LENGTH: 9
```

-continued

<212> TYPE: PRT
<213> ORGANISM: Amanita bisporigera

<400> SEQUENCE: 147

Gly Ala Tyr Pro Pro Val Pro Met Pro
1               5

<210> SEQ ID NO 148
<211> LENGTH: 9
<212> TYPE: PRT
<213> ORGANISM: Amanita bisporigera

<400> SEQUENCE: 148

Gly Met Glu Pro Pro Ser Pro Met Pro
1               5

<210> SEQ ID NO 149
<211> LENGTH: 9
<212> TYPE: PRT
<213> ORGANISM: Amanita bisporigera

<400> SEQUENCE: 149

His Pro Phe Pro Leu Gly Leu Gln Pro
1               5

<210> SEQ ID NO 150
<211> LENGTH: 710
<212> TYPE: PRT
<213> ORGANISM: Homo sapiens

<400> SEQUENCE: 150

Met Leu Ser Leu Gln Tyr Pro Asp Val Tyr Arg Asp Glu Thr Ala Val
1               5                   10                  15

Gln Asp Tyr His Gly His Lys Ile Cys Asp Pro Tyr Ala Trp Leu Glu
            20                  25                  30

Asp Pro Asp Ser Glu Gln Thr Lys Ala Phe Val Glu Ala Gln Asn Lys
        35                  40                  45

Ile Thr Val Pro Phe Leu Glu Gln Cys Pro Ile Arg Gly Leu Tyr Lys
    50                  55                  60

Glu Arg Met Thr Glu Leu Tyr Asp Tyr Pro Lys Tyr Ser Cys His Phe
65                  70                  75                  80

Lys Lys Gly Lys Arg Tyr Phe Tyr Phe Tyr Asn Thr Gly Leu Gln Asn
                85                  90                  95

Gln Arg Val Leu Tyr Val Gln Asp Ser Leu Glu Gly Glu Ala Arg Val
            100                 105                 110

Phe Leu Asp Pro Asn Ile Leu Ser Asp Gly Thr Val Ala Leu Arg
            115                 120                 125

Gly Tyr Ala Phe Ser Glu Asp Gly Glu Tyr Phe Ala Tyr Gly Leu Ser
    130                 135                 140

Ala Ser Gly Ser Asp Trp Val Thr Ile Lys Phe Met Lys Val Asp Gly
145                 150                 155                 160

Ala Lys Glu Leu Pro Asp Val Leu Glu Arg Val Lys Phe Ser Cys Met
                165                 170                 175

Ala Trp Thr His Asp Gly Lys Gly Met Phe Tyr Asn Ser Tyr Pro Gln
            180                 185                 190

Gln Asp Gly Lys Ser Asp Gly Thr Glu Thr Ser Thr Asn Leu His Gln
        195                 200                 205

Lys Leu Tyr Tyr His Val Leu Gly Thr Asp Gln Ser Glu Asp Ile Leu
    210                 215                 220

-continued

```
Cys Ala Glu Phe Pro Asp Glu Pro Lys Trp Met Gly Ala Glu Leu
225                 230                 235                 240

Ser Asp Asp Gly Arg Tyr Val Leu Leu Ser Ile Arg Glu Gly Cys Asp
            245                 250                 255

Pro Val Asn Arg Leu Trp Tyr Cys Asp Leu Gln Gln Gly Ser Ser Gly
            260                 265                 270

Ile Ala Gly Ile Leu Lys Trp Val Lys Leu Ile Asp Asn Phe Glu Gly
            275                 280                 285

Glu Tyr Asp Tyr Val Thr Asn Glu Gly Thr Val Phe Thr Phe Lys Thr
290                 295                 300

Asn Arg Gln Ser Pro Asn Tyr Arg Val Ile Asn Ile Asp Phe Arg Asp
305                 310                 315                 320

Pro Glu Glu Ser Lys Trp Lys Val Leu Val Pro Glu His Glu Lys Asp
            325                 330                 335

Val Leu Glu Trp Ile Ala Cys Val Arg Ser Asn Phe Leu Val Leu Cys
            340                 345                 350

Tyr Leu His Asp Val Lys Asn Ile Leu Gln Leu His Asp Leu Thr Thr
            355                 360                 365

Gly Ala Leu Leu Lys Thr Phe Pro Leu Asp Val Gly Ser Ile Val Gly
370                 375                 380

Tyr Ser Gly Gln Lys Lys Asp Thr Glu Ile Phe Tyr Gln Phe Thr Ser
385                 390                 395                 400

Phe Leu Ser Pro Gly Ile Ile Tyr His Cys Asp Leu Thr Lys Glu Glu
            405                 410                 415

Leu Glu Pro Arg Val Phe Arg Glu Val Thr Val Lys Gly Ile Asp Ala
            420                 425                 430

Ser Asp Tyr Gln Thr Val Gln Ile Phe Tyr Pro Ser Lys Asp Gly Thr
            435                 440                 445

Lys Ile Pro Met Phe Ile Val His Lys Lys Gly Ile Lys Leu Asp Gly
450                 455                 460

Ser His Pro Ala Phe Leu Tyr Gly Tyr Gly Gly Phe Asn Ile Ser Ile
465                 470                 475                 480

Thr Pro Asn Tyr Ser Val Ser Arg Leu Ile Phe Val Arg His Met Gly
            485                 490                 495

Gly Ile Leu Ala Val Ala Asn Ile Arg Gly Gly Gly Glu Tyr Gly Glu
            500                 505                 510

Thr Trp His Lys Gly Gly Ile Leu Ala Asn Lys Gln Asn Cys Phe Asp
            515                 520                 525

Asp Phe Gln Cys Ala Ala Glu Tyr Leu Ile Lys Glu Gly Tyr Thr Ser
            530                 535                 540

Pro Lys Arg Leu Thr Ile Asn Gly Gly Ser Asn Gly Gly Leu Leu Val
545                 550                 555                 560

Ala Ala Cys Ala Asn Gln Arg Pro Asp Leu Phe Gly Cys Val Ile Ala
            565                 570                 575

Gln Val Gly Val Met Asp Met Leu Lys Phe His Lys Tyr Thr Ile Gly
            580                 585                 590

His Ala Trp Thr Thr Asp Tyr Gly Cys Ser Asp Ser Lys Gln His Phe
            595                 600                 605

Glu Trp Leu Val Lys Tyr Ser Pro Leu His Asn Val Lys Leu Pro Glu
            610                 615                 620

Ala Asp Asp Ile Gln Tyr Pro Ser Met Leu Leu Leu Thr Ala Asp His
625                 630                 635                 640
```

```
Asp Asp Arg Val Val Pro Leu His Ser Leu Lys Phe Ile Ala Thr Leu
            645                 650                 655

Gln Tyr Ile Val Gly Arg Ser Arg Lys Gln Ser Asn Pro Leu Leu Ile
        660                 665                 670

His Val Asp Thr Lys Ala Gly His Gly Ala Gly Lys Pro Thr Ala Lys
            675                 680                 685

Val Ile Glu Glu Val Ser Asp Met Phe Ala Phe Ile Ala Arg Cys Leu
        690                 695                 700

Asn Val Asp Trp Ile Pro
705             710

<210> SEQ ID NO 151
<211> LENGTH: 737
<212> TYPE: PRT
<213> ORGANISM: Coprinus cinereus

<400> SEQUENCE: 151

Met Ala Ala Lys Ala Trp Thr Pro Asn Thr Tyr Pro Pro Ala Arg Arg
 1               5                  10                  15

Ser Asp His Val Asp Thr Tyr Lys Ser Ala Ser Lys Gly Glu Val Lys
            20                  25                  30

Val Pro Asp Pro Tyr Arg Trp Met Glu Glu Tyr Thr Glu Glu Thr Asp
        35                  40                  45

Lys Trp Thr Thr Ala Gln Glu Ala Tyr Thr Arg Ala Tyr Ile Asp Glu
 50                  55                  60

Tyr Pro His Arg Lys Arg Leu Glu Asp Ala Phe Leu Ala Ser Gln Asp
 65                  70                  75                  80

Tyr Ala Arg Ala Gly Ala Pro Ile Leu Arg Asp Asp Lys Arg Trp Tyr
                85                  90                  95

Trp Phe His Asn Thr Gly Leu Gln Pro Gln Asp Val Met Phe Arg Ser
            100                 105                 110

Lys Asp Ser Gln Leu Pro Asp Arg Ser Lys Gly Ala Asp Asn Gly Glu
        115                 120                 125

Val Phe Leu Asp Gln Asn Leu Leu Ser Asp Asp Gly Thr Ala Ser Ile
    130                 135                 140

Ser Thr His Ala Phe Ser Asp Ser Gly Glu Tyr Tyr Ala Tyr Gly Ile
145                 150                 155                 160

Ser Tyr Ser Gly Ser Asp Phe Thr Thr Val Tyr Val Arg Arg Thr Asp
                165                 170                 175

Ser Pro Leu Ala Ser Lys Glu Gln Ala Ala Asn Asp Asn Gly Arg Leu
            180                 185                 190

Pro Glu Val Leu Lys Phe Val Lys Phe Ser Ser Leu Lys Trp Thr Pro
        195                 200                 205

Asp Ser Lys Gly Phe Phe Tyr Gln Arg Met Pro Asp Arg Ser Lys Gly
    210                 215                 220

Glu Lys Val Asn Gly Ser Gly Ile Glu Thr Gly Gly Asp Arg Asp Ala
225                 230                 235                 240

Met Leu Tyr Tyr His Arg Val Asn Thr Pro Gln Ser Glu Asp Val Leu
                245                 250                 255

Val Tyr His Asn Lys Asp Glu Pro Glu Trp Met Tyr Gly Ile Glu Ile
            260                 265                 270

Thr Asp Asp Asp Lys Tyr Ala Val Leu Thr Val Val Ala Asp Thr Ser
        275                 280                 285

Arg Lys Asn Leu Phe Trp Ile Ala Glu Leu Lys Glu Asp Ser Ile Glu
    290                 295                 300
```

-continued

```
Lys Gly Phe Lys Trp Asn Lys Val Val Asn Glu Tyr Glu Ala Glu Tyr
305                 310                 315                 320
Glu Tyr Val Thr Asn Tyr Gly Pro Val Phe Val Arg Thr Asn Asp
            325                 330                 335
Lys Ala Pro Lys Tyr Lys Ala Ile Thr Ile Asp Ile Ser Lys Gly Asn
            340                 345                 350
Glu Arg Lys Asp Phe Val Pro Glu Thr Asp Gly Phe Leu Asn Ser Ile
            355                 360                 365
Asp Ala Val Asn Lys Gly Glu Asn Phe Val Val Ser Tyr Lys Arg Asn
370                 375                 380
Val Lys Asp Glu Ala Tyr Val Tyr Ser Lys Glu Gly Lys Glu Leu Glu
385                 390                 395                 400
Arg Leu Leu Pro Asp Phe Ile Gly Ala Leu Thr Ile Thr Ala Arg Tyr
                405                 410                 415
Arg Asp Ser Trp Phe Phe Ile Asn Ala Val Gly Phe Thr Thr Pro Gly
                420                 425                 430
Thr Leu Gly Arg Tyr Asp Phe Thr Ala Pro Glu Gly Gln Arg Trp Ser
            435                 440                 445
Ile Tyr Ser Gln Thr Lys Val Lys Gly Leu Asn Pro Glu Glu Phe Ser
450                 455                 460
Ala Glu Gln Val Trp Tyr Glu Ser Lys Asp Gly Thr Lys Ile Pro Met
465                 470                 475                 480
Phe Ile Val Arg His Lys Ser Thr Pro Ile Asp Gly Thr Ala Pro Ala
                485                 490                 495
Ile Gln Tyr Gly Tyr Gly Gly Phe Ser Ile Ser Ile Asn Pro Ser Phe
            500                 505                 510
Ser Pro Thr Ile Leu Thr Phe Leu Lys Thr Tyr Gly Gly Val Tyr Ala
            515                 520                 525
Ile Ala Asn Ile Arg Gly Gly Gly Glu Phe Gly Glu Glu Trp His Glu
530                 535                 540
Gly Gly Tyr Arg Asp Lys Lys His Asn Cys Phe Asp Asp Phe Ile Ala
545                 550                 555                 560
Ala Thr Glu Tyr Leu His Lys Asn Lys Ile Ala Ala Pro Gly Lys Val
                565                 570                 575
Thr Ile Asn Gly Gly Ser Asn Gly Gly Leu Leu Val Ser Ala Cys Val
            580                 585                 590
Asn Arg Ala Pro Glu Gly Thr Phe Gly Ala Ala Val Ala Glu Val Gly
            595                 600                 605
Val His Asp Leu Leu Arg Phe His Lys Phe Thr Ile Gly Arg Ala Trp
610                 615                 620
Ile Ser Asp Tyr Gly Asp Pro Asp Pro Lys Asp Phe Asp Phe Ile
625                 630                 635                 640
His Pro Ile Ser Pro Leu His Asn Val Ser Pro Thr Lys Ile Leu Pro
                645                 650                 655
Pro Phe Met Leu Ile Thr Ala Asp His Asp Asp Arg Val Val Pro Ser
            660                 665                 670
His Ser Phe Lys Leu Ala Ala Thr Leu Gln His Leu Arg Ala Asp Asn
            675                 680                 685
Pro Asn Pro Ile Leu Leu Arg Val Asp Lys Ala Gly His Gly Ala
            690                 695                 700
Gly Lys Ser Thr Thr Lys Arg Met Gln Glu Ala Ala Asp Lys Trp Gly
705                 710                 715                 720
```

```
Phe Val Ala Lys Thr Leu Gly Leu Glu Trp Lys Asp Thr Ala Thr Lys
                725                 730                 735

Leu

<210> SEQ ID NO 152
<211> LENGTH: 923
<212> TYPE: PRT
<213> ORGANISM: Ustilago maydis

<400> SEQUENCE: 152

Met Asn Asn Leu Ile Ala His Thr Leu Leu Val Ala Pro Gln Arg Ala
  1               5                  10                  15

Arg Ser Pro Pro Ala Thr Glu Arg Met Tyr Ala Leu Gly Tyr Thr Lys
             20                  25                  30

Pro Ile Ala Arg Leu Arg Gly Val Val Asp Thr Asn Asn Asp Asp Lys
         35                  40                  45

His Glu Ala His Thr Asn Val Gly Lys Ala Asn Arg Gly Ser Leu Cys
     50                  55                  60

Gln Arg Arg Ser Phe Ile Leu Pro Ser Thr Ile Thr Ala Val Phe Val
 65                  70                  75                  80

Ser Pro His Leu Met Leu Ser Arg Phe Ala Arg Leu Tyr Leu Asp
                 85                  90                  95

Pro Ser Tyr Arg Ser Pro Leu Val Ser Ser Phe Arg Ser Cys Ser Asn
            100                 105                 110

Lys Ala Arg Ala His Ser Tyr Arg Ser Phe Ala Ser Thr Ala Thr Ala
        115                 120                 125

Met Thr Val Gln Asn Ala Pro Gly Trp Thr Thr Gln Pro Asn Pro Tyr
130                 135                 140

Pro Gln Ala Arg Arg Asp Asp Gln Ala Ser Leu Thr Tyr Lys Ser Ala
145                 150                 155                 160

Ala Asn Gly Ser Val Thr Val Pro Glu Pro Tyr Ile Trp Leu Glu Gln
                165                 170                 175

Pro Pro Ser Gln Ser Gln Glu Thr Lys Asp Trp Val His Ala Gln Ala
            180                 185                 190

Lys Leu Thr Gln Ser Tyr Leu Asp Gly Cys Gln Pro Asp Leu Asp Ile
        195                 200                 205

Leu Lys Ser Arg Ile Glu Lys Asn Phe Asp Phe Ala Arg Phe Ser Cys
210                 215                 220

Pro Ser Leu Lys Gly Asn Gly Lys Tyr Tyr Ser Phe Asn Ser Gly
225                 230                 235                 240

Leu Ser Pro Gln Ser Leu Ile Tyr Ser Ala Thr Lys Gln Gln Val Asp
                245                 250                 255

Ala Asn Ala Gly Lys Asn Gln Arg Asp Pro Ile Gly Glu Ile Phe Phe
            260                 265                 270

Asp Ser Asn Leu Leu Ser Ala Asp Gly Thr Val Ala Leu Ser Phe Thr
        275                 280                 285

Thr Phe Ser His Ser Gly Lys Tyr Leu Ala Tyr Gly Ile Ser Lys Ser
290                 295                 300

Gly Ser Asp Trp Val Glu Ile Phe Ile Arg Glu Thr Ser Lys Pro Phe
305                 310                 315                 320

Lys Leu Asp Asp Ala His Tyr Asn Ser Asn Gly Thr Ile Lys Leu Ser
                325                 330                 335

Lys Asp Glu Leu Ala Lys Phe Val Asp Ala Thr Gly Gly Lys Glu Arg
            340                 345                 350
```

```
Leu Asn Asp Arg Leu Glu His Val Lys Phe Ser Gly Ala Ala Phe Thr
            355                 360                 365

His Asp Asp Lys Gly Leu Phe Tyr Gln Thr Tyr Pro Ser Ala Ser Val
        370                 375                 380

Ser Asp Lys Gly Thr Glu Thr Asp Ala Asn Lys Asp Ala Gln Leu Trp
385                 390                 395                 400

Tyr His Arg Ile Gly Thr Asp Gln Ser Glu Asp Val Leu Val Val Ser
                405                 410                 415

Lys Asp Ile Lys Val Pro Glu Ser Met Trp Ser Thr Asn Val Ser His
                420                 425                 430

Asp Gly Asn Phe Leu Met Leu Tyr Asn Ser Lys Asp Thr Asp Ser Lys
            435                 440                 445

Glu Arg Val Tyr Val Leu Pro Leu Gln Asp His Gly Phe Ser Ala Ser
        450                 455                 460

Lys Gln Leu Lys Trp Ile Pro Leu Ala Leu Ser Phe Lys Tyr Val Leu
465                 470                 475                 480

Asn Tyr Val Thr Asn Lys Gly Asn Arg Phe Tyr Phe Met Thr Asn Lys
                485                 490                 495

Asp Ala Pro Asn Tyr Arg Leu Val Ser Val Asp Leu Asp Pro Ala Lys
                500                 505                 510

Gln Ala Gln Pro Thr Asp Asn Val Trp Glu Leu Thr Gly Gln Asp Val
        515                 520                 525

Glu Leu Thr Asp Val Ile Ala Glu Glu Lys Glu Ala Leu Leu Ser Ser
        530                 535                 540

Val Gln Val Ile Asp Asn Asn Lys Leu Leu Val Val Tyr Ser Arg Asp
545                 550                 555                 560

Val Lys Asp Glu Leu Tyr Gln Tyr Glu Leu Glu Ser Gly Lys Arg Val
                565                 570                 575

Glu Arg Leu Leu Pro His Leu Val Gly Thr Ile Glu Gln Ile Ala Ala
            580                 585                 590

Arg His Thr Asp Asp His Ala Phe Val Lys Phe Gly Ser Phe Val Asn
        595                 600                 605

Pro Gly Gln Val Val Arg Leu Asp Trp Gln Thr Asn Ser Glu Pro Asn
        610                 615                 620

Ala Thr Lys Val Lys Lys Val Ala Tyr Tyr Asp Thr Gln Val Asp Gly
625                 630                 635                 640

Ile Lys Ala Asp Asp Phe Val Ser Glu Gln Val Phe Ile Lys Ser Lys
                645                 650                 655

Asp Gly Thr Arg Val Pro Met Phe Val Thr His Pro Lys Thr Val Thr
            660                 665                 670

Lys Asp Gly Ser Ala Pro Ala Ile Leu Tyr Phe Tyr Gly Gly Phe Asn
        675                 680                 685

Ile Ser Ile Thr Pro Val Phe Ser Pro Ser Met Met Ser Trp Ile Ser
        690                 695                 700

Ser Tyr Asn Gly Val Leu Ala Phe Val Asn Cys Arg Gly Gly Gly Glu
705                 710                 715                 720

Tyr Gly Asp Lys Trp His Glu Ala Gly Thr Leu Leu Asn Lys Gln Asn
                725                 730                 735

Val Phe Asp Asp Ala Leu Ser Ala Ala Lys Phe Leu His Glu Ser Gly
            740                 745                 750

Tyr Ala Ala Lys Gly Lys Ile Ile Leu Ser Gly Gly Ser Asn Gly Gly
        755                 760                 765

Leu Gly Val Ala Ala Cys Ile Asn Gln Gln Leu Pro Glu His Gly Ile
```

```
            770                 775                 780
Gly Ala Gly Ile Ala Asp Val Gly Val Met Asp Met Leu Lys Phe His
785                 790                 795                 800

Thr Trp Thr Ile Gly Lys Ala Trp Thr Ala Asp Tyr Gly Asn Pro Ser
                805                 810                 815

Glu Asp Pro His Ile Phe Asp Tyr Val Tyr Lys Tyr Ser Pro Leu His
            820                 825                 830

Asn Val Asp Ser Asn Lys Val Tyr Pro Thr Thr Val Leu Ala Cys Ala
        835                 840                 845

Asp His Asp Asp Arg Val Val Pro Ala His Ser Phe Lys Leu Ile Ala
    850                 855                 860

Glu Met Gln His Lys Leu Ala Thr Asn Pro Asn Pro Leu Leu Leu Arg
865                 870                 875                 880

Val Glu Ile Asp Ala Gly His Gly Ala Gly Lys Ser Thr Gln Lys Arg
                885                 890                 895

Ile Gln Glu Ala Ala Glu Lys Tyr Ala Ile Val Gly Arg Ala Leu Arg
            900                 905                 910

Leu Lys Ile Thr Asp Asp Ala Ala Ser Arg Leu
        915                 920

<210> SEQ ID NO 153
<211> LENGTH: 803
<212> TYPE: PRT
<213> ORGANISM: Cryptococcus neoformans

<400> SEQUENCE: 153

Met Ser Gly Gln Gln Ala Ser His Ser Phe Ser Thr Asp Lys Thr Gly
  1               5                  10                  15

His Gly Thr Leu Lys Asn Val His Ala Ser Asp Phe Thr Ile Ser Pro
             20                  25                  30

Gly Gln Trp Lys Lys Asn Val Asn Phe Ser Pro Tyr Pro Val Pro Pro
         35                  40                  45

Gln His Gly Gly Ile Thr Glu Ile Ile His Gly Ile Glu Ile Glu Asp
     50                  55                  60

Pro Trp Arg Ala Leu Glu Asp Pro Asp Ser Glu Val Thr Lys Lys Phe
 65                  70                  75                  80

Val Lys Glu Gln Asn Asp Phe Ser Val Pro Arg Leu Thr Asn His Pro
                 85                  90                  95

Leu Arg Lys Glu Leu Glu Ala Ala Val Glu Gln Cys Tyr Asn His Glu
            100                 105                 110

Arg Met Thr Ser Pro Glu Leu Gln Gly Asp Gly Tyr Tyr Tyr Trp Lys
        115                 120                 125

Phe Asn Pro Gly Thr Ser Pro Arg Asp Val Ile Val Arg Ser Lys Asp
    130                 135                 140

Leu Lys Arg Asp Phe Gly Lys Ala Pro Gly Gly Ser Gly Pro Glu Ile
145                 150                 155                 160

Phe Tyr Asp Leu Asn Lys Glu Glu Asn Ile Ser Leu Tyr Ala His Ser
                165                 170                 175

Phe Ser Pro Ser Gly Lys Leu Trp Cys Ala Val Leu Gln Tyr Ala Gly
            180                 185                 190

Ser Asp Trp Gln Arg Ile Arg Val Ile Asp Thr Glu Ser Lys Ala Val
        195                 200                 205

Leu Glu Lys Asp Leu Gly Gly Ser Lys Phe Thr Phe Gly Val Thr Trp
    210                 215                 220
```

```
Gly Phe Ile Tyr Lys Arg Ser Ile Asp Tyr Asp Ala Thr Ser Asp Gly
225                 230                 235                 240

Tyr Asp Gly Ile Asp Gly Ser Phe Gly Met Phe Tyr His Ala Val Gly
            245                 250                 255

Gln His Gln Ser Thr Asp Val Ile Val Trp Ser Pro Pro Gly Glu
        260                 265                 270

Phe Gln Phe Ile Gly Lys Ala Lys Val Val Ala Val Asp Glu Lys Glu
        275                 280                 285

Glu Asn Asn Lys Arg Ala Phe Leu Ala Leu Asp Ile Tyr Lys Asn Thr
    290                 295                 300

Ser Pro Glu Thr Glu Leu Leu Leu Val Glu Leu Pro Gly Gly Thr Ala
305                 310                 315                 320

Gly Pro Ala Gly Val Leu Leu Pro Glu Leu Val Thr Lys Glu Met Lys
                325                 330                 335

Trp Val Ser Arg Gly Phe Thr Gly Glu Thr His Tyr Ile Gly Ser Ser
                340                 345                 350

Ser Ala Glu Arg His Phe Phe Thr Ser Phe Thr Asp Gly Val Ser Thr
        355                 360                 365

Gly Arg Ile Ile Ala Phe Asp Ser Ala Asp Trp Asp Ala Thr Asp Ile
370                 375                 380

Asp Ser Pro Leu Pro Met Gln Glu Ile Val Pro Ala Asp Pro Glu Gly
385                 390                 395                 400

His Gln Leu Gln Ser Ala Tyr Phe Ile Gly Asp Arg Leu Leu Ala Leu
                405                 410                 415

Ile Tyr Leu Lys His Ala Cys Ala Ser Val Val Phe Ile Asp Ala Arg
                420                 425                 430

Thr Gly Lys Pro Leu Gly Ser Ala Asp Ala Gln Gly Thr His Gly Asn
        435                 440                 445

Val Ala Ala Asp Pro Glu Thr Gln Val Pro Val Pro Glu Glu Glu Val
    450                 455                 460

Gln His Ala Lys Glu Gly Gln Val Val Ile Pro Glu His Gly Ala Ile
465                 470                 475                 480

Thr Ser Ile Ser Cys Arg Pro Asp Ala Asn Asp Phe Tyr Phe Thr Val
                485                 490                 495

Asp Thr Trp Val Ala Pro Ser Tyr Val Leu Lys Gly Glu Leu Ile Lys
                500                 505                 510

Asn Lys Ala Gly Arg Tyr Glu Val Asp Ile Ser Ser Val Asn Ser Ser
            515                 520                 525

Glu Thr Ala Ala Gln Glu Thr Leu Val Cys Ser Gln Val Phe Tyr Thr
530                 535                 540

Ser His Asp Gly Thr Arg Ile Pro Met Phe Ile Cys His Pro His Asp
545                 550                 555                 560

Leu Asp Leu Thr Arg Pro His Pro Leu Leu His Ala Tyr Gly Gly
                565                 570                 575

Phe Cys Ser Pro Leu Ile Pro His Phe Asp Pro Met Phe Ala Val Phe
            580                 585                 590

Met Arg Asn Leu Arg Gly Val Val Ala Ile Ala Gly Ile Arg Gly Gly
            595                 600                 605

Gly Glu Tyr Gly Lys Ala Trp His Glu Ala Ile Gly Ile Lys Arg
        610                 615                 620

Ser Val Gly Trp Asp Asp Phe Ala Ala Ala Ala Arg Tyr Val Gln Ser
625                 630                 635                 640

Arg Gly Leu Thr Thr Pro Ser Leu Thr Ala Ile Tyr Gly Ser Ser Asn
```

```
                645                 650                 655
Gly Gly Leu Leu Val Ser Ala Ala Thr Val Arg Asn Pro Glu Leu Tyr
            660                 665                 670

Ser Val Val Phe Ala Asp Val Ala Ile Thr Asp Leu Ile Arg Tyr His
            675                 680                 685

Lys Phe Thr Leu Gly Arg Met Trp Met Thr Glu Tyr Gly Ser Pro Glu
            690                 695                 700

Glu Pro Glu Thr Leu Ala Val Leu Arg Ala Asn Ser Pro Leu His Asn
705                 710                 715                 720

Ile Ser Arg Asp Pro Ser Val Gln Tyr Pro Ala Met Leu Leu Thr Thr
                725                 730                 735

Gly Asp His Asp Thr Arg Val Val Pro Gly His Ser Leu Lys Leu Leu
            740                 745                 750

Ala Glu Leu Gln Thr Leu Lys Ala Lys Asn His Gly Ala Ile Leu Gly
            755                 760                 765

Arg Val Tyr Ile Asn Ala Gly His Glu Gln Ser Thr Lys Ser Thr Glu
            770                 775                 780

Lys Lys Val Glu Glu Ala Val Asp Arg Leu Val Phe Ala Leu Asp Asn
785                 790                 795                 800

Ile Lys Ile

<210> SEQ ID NO 154
<211> LENGTH: 811
<212> TYPE: PRT
<213> ORGANISM: Cryptococcus neoformans

<400> SEQUENCE: 154

Met Ala Ile Glu Thr Ser Ala Ala His Asp Val Asp Ser Ala Pro His
1               5                   10                  15

Gly Leu Leu Lys Asn Ala Pro Thr Asp Asp Leu Thr Leu Glu Asp Glu
            20                  25                  30

Ser Trp Gln His Ser Val Cys Val His Ser Tyr Pro Ser Pro Pro Leu
        35                  40                  45

Asn Gly Gly Val Thr Glu Ile Ile Phe Asp Ile Glu Val Lys Asp Pro
    50                  55                  60

Trp Arg Ala Leu Glu Asp Gln Gly Ser Glu Val Thr Lys Lys Phe Ile
65              70                  75                  80

Glu Glu Gln Asn His Leu Ser Val Pro Arg Leu Ser Asn His Pro Leu
                85                  90                  95

Arg Thr Glu Leu Glu Ile Ala Val Glu Gln Cys Tyr Asn His Glu Arg
            100                 105                 110

Met Thr Cys Pro Glu Leu Gln Ala Ser Gly Tyr Tyr Tyr Trp Lys Tyr
        115                 120                 125

Asn Gln Gly Thr Ser Pro Arg Asp Val Ile Leu Arg Ser Lys Asn Leu
    130                 135                 140

Glu Ser Asp Phe Gly Lys Phe Ala Ser Glu Asp Gly Lys Gly Pro Glu
145                 150                 155                 160

Leu Phe Phe Asp Leu Asn Thr Glu Glu Asn Ile Ser Leu Tyr Ala His
                165                 170                 175

Ser Phe Ser Pro Ser Gly Lys Leu Trp Cys Ala Ile Leu Gln Gln Ser
            180                 185                 190

Gly Gly Asp Trp Leu Arg Leu Arg Val Tyr Asp Thr Gln Thr Lys Lys
        195                 200                 205

Ala Ile Glu Arg Ser Val Gly Gly Ala Lys Phe Thr Phe Gly Ala Thr
```

```
            210                 215                 220
Trp Val Gly Glu Lys Gly Phe Ile Tyr Lys Arg Val Ile Asp Tyr Asp
225                 230                 235                 240

Thr Thr Asp Gly Asn Tyr Gln Ala Lys Glu Gly Gln Phe Gly Leu Phe
                245                 250                 255

Tyr His Gln Ile Gly Thr Pro Gln Ser Glu Asp Val Leu Val Trp Lys
                260                 265                 270

Ala Pro Glu Gly Val Phe Gln Tyr Ile Gly Lys Pro Leu Ile Ile Thr
            275                 280                 285

Ser Asp Ala Lys Glu Asn Lys Lys Arg Ala Trp Phe Met Leu Asp
290                 295                 300

Ile Tyr Arg Asn Thr Ser Pro Glu Thr Glu Val Leu Met Val Glu Leu
305                 310                 315                 320

Pro Gly Gly Thr Ala Gly Pro Val Gly His Thr Leu Pro Ser Leu Val
                325                 330                 335

Leu His Gly Lys Lys Trp Val Ser Lys Gly Phe Thr Gly Met Thr Asn
                340                 345                 350

Tyr Ile Gly Ser Leu Ser Asp Asp Thr His Leu Phe Thr Ser Phe Thr
                355                 360                 365

Asp Gly Ile Ser Thr Gly Arg Ile Ile Ser Val Ser Ala Ala Asp Tyr
            370                 375                 380

Asp Ala Cys Gly Val Asn Glu Ala Ile Lys Phe Asn Thr Val Val Pro
385                 390                 395                 400

Ala Asn Ser Glu Gly His Gln Leu Arg His Ala Tyr Leu Ile Gly Asp
                405                 410                 415

Gln Val Ile Val Leu Asp Tyr Leu Lys His Gly Cys Ser Phe Leu Val
            420                 425                 430

Phe Leu Asp Ala Arg Thr Gly Lys Ser Val Gly Ser Ser Asp Ser Arg
                435                 440                 445

Gly Thr Arg Gly Asp Ala Ala Ile Asp Pro Asp Val Glu Val Pro Val
            450                 455                 460

Pro Glu Glu Glu Val Ala Glu Gln Ser Pro Thr Glu Asp Gln Val Ile
465                 470                 475                 480

Ile Pro Gln His Ala Ser Ile Asn Glu Leu Gln Ser Arg Pro Asp Ser
                485                 490                 495

Asn Asp Phe Tyr Phe Ser Val Asn Thr Phe Val Ala Pro Pro Tyr Val
                500                 505                 510

Leu Arg Gly Glu Leu Ile Lys Asn His Lys Val Glu Lys Gly Ile Lys
            515                 520                 525

Ile Ser Gly Ile Ser Lys Ser His Thr Met Pro Gln Glu Thr Leu Val
            530                 535                 540

Cys Ser Gln Leu Phe Tyr Glu Ser His Asp Gly Val Lys Ile Pro Met
545                 550                 555                 560

Phe Ile Cys His Ala His Asp Leu Asp Leu Thr Lys Pro Asn Pro Ala
                565                 570                 575

Leu Val His Ala Tyr Gly Gly Phe Cys Ser Pro Ser Leu Pro Arg Phe
                580                 585                 590

Asp Pro Met Phe Val Ala Phe Met Arg Asn Leu Arg Gly Ile Val Ala
            595                 600                 605

Val Ala Gly Ile Arg Gly Gly Gly Glu Tyr Gly Pro Glu Trp His Glu
            610                 615                 620

Ala Ala Leu Gly Ile Lys Arg Trp Val Gly Trp Asp Asp Phe Ala Trp
625                 630                 635                 640
```

```
Ala Ala Lys Tyr Leu Gln Gly Lys Gly Leu Thr Thr Pro Ala Leu Thr
            645                 650                 655

Ala Thr Tyr Gly Thr Ser Asn Gly Gly Leu Leu Val Ser Ala Ala Met
        660                 665                 670

Val Arg Asn Pro Ser Leu Tyr Ser Val Val Phe Pro Asp Val Ala Ile
            675                 680                 685

Thr Asp Leu Leu Arg Tyr His Lys Phe Thr Leu Gly Arg Ile Trp Met
    690                 695                 700

Asp Glu Tyr Gly Ser Pro Glu Lys Ala Glu Asp Phe Pro Ile Leu His
705                 710                 715                 720

Ser Thr Ser Pro Leu His Ser Val Asp Gly Asp Pro Ala Val Gln Tyr
                725                 730                 735

Pro Ala Val Leu Ile Thr Thr Ala Asp His Asp Thr Arg Val Val Pro
            740                 745                 750

Ser His Ser Leu Lys Phe Leu Ala Glu Leu Gln Ala Arg Lys Ser Glu
        755                 760                 765

Asn Lys Gly Val Phe Leu Gly Arg Ile Tyr Glu Asn Ala Gly His Glu
    770                 775                 780

Leu Gly Ser Lys Pro Thr Lys Lys Val Glu Glu Ala Val Asp Arg
785                 790                 795                 800

Leu Val Phe Val Leu Tyr Asn Leu Lys Glu Gln
                805                 810

<210> SEQ ID NO 155
<211> LENGTH: 669
<212> TYPE: DNA
<213> ORGANISM: Homo sapiens

<400> SEQUENCE: 155
cacttacgat gacaaattaa gaaatatctt actcagtaag gaagtatctt ttcctttctt      60
ccactaaggt acaagccata tatatagaag gtggaataat gaggaaactc ctgtcgaaat     120
tcaaaacatt acaggcaagc tttctcatgc acaaaatgct gcttttaatt ggttcttaac     180
taaattaatt aagctggtat gactcactct ccagtcacaa ctcaacttga aaaacacaaa     240
ggaatatggc tgggataaca aaagctaaga tccctgaatt actcctgatt tcatattaa      300 caagagagtt cagcctatag agaaaaggtt aatttgtttt ttaataggct tttgaaagac     360
gtgatcaggt ctagtgtgat aatttatggt taatcatatg tttagaggca aaagggatta     420 atctttaat attagagcaa ttttttctgt aatataaaac aaagttcttt tcatagtaac      480
attaaaagtc agatcaaact tccttttga gcaaagttgg caaattgaca agaaggaaga     540
agaaaatctg tctgaacagc agcatagtaa gaagatcaga ccagcatggt aactccctgc     600
aaaagcctct ttcccaatct gtctcctttt ttattttacc ataagtggtg taaaccaaaa     660
attaaattc                                                             669

<210> SEQ ID NO 156
<211> LENGTH: 2253
<212> TYPE: DNA
<213> ORGANISM: Phanerochaete chrysosporium

<400> SEQUENCE: 156
atgcgtacac cgtggacacc gaaccgctat cctccagcac gtcgctctga tcactatgat      60
gaatacaaga gcgagaagaa cggcgtggtc agagtacacg atccgtacaa ctggctggaa     120
cacaatacac aggaaactga gtcgtggacg tccgctcaag tcgcattcac caaagaatat     180
```

```
ctggaccaga atccagacag acagaagctc gaggacgaaa tcaggaggaa cactgactat      240
gccaagttct ccgcgccgag cctaaaggac gacggccgct ggtactggta ctataacagc      300
ggcctacagc cacagtcagg tgtgcatgca tttgtactac tcttgtgcca ctctgatatt      360
gatgtaccga cctcagtgat ataccgttcc cgagatagga acctacctac tatgagcaat      420
gaagagggac ctggcggaga ggtgttcttc gaccccaatc tcctctctaa cgatggcaca      480
gctgctctcg cggctactgc attctcgcgt gatggcaaat actttgcata tggtatatcc      540
cgctctggaa gcgactttta caccgtctat gtccgcccaa cttcggcacc gctcgcgtct      600
caaggcgagt cacgggtttc ccatgatgac gaacgtctgc aggacgaggt caggttcgtg      660
aagttctcga gcatctcctg gtcgcacgac tccaaaggat tcttctacca gcgatatcct      720
gagcgaaagt ctcatggatc tgcagacgag acaaagctg gtacagagac ggaaagcgac       780
aagcatgcta tgctctacta tcaccgtgta ggaacctcac agcttgagga cgtccttgtc      840
tataaggatg acgcgaatcc agaatggttc tggggtgcag agatctctga gaggatggc       900 cgttacctca ttctatctgt gtccagggac acttcaagaa aaaacctcct atggattgcg      960
gacctcgaga gcaatgcaat tggtcaggat atgcagtgga acaaattgat tgacgaattc     1020
gatgcctcat atgactacat cgcaaacaac ggcaacaagt tctacttcca gacgaacaaa     1080
gacgctccac aatacaagct agtcagcgtc gatatatctg cccctccggc acagcgcacc     1140
ttcgaggatg tcatacctga ggataagaat gctcatttgg aggacgtcct cgccatcgcc     1200
gacgacaagt ttgcggtcgt gtacaagcgc aatgtcaaag atgagatcta catttacgac     1260
atgaatggca agcagttgga gcgcgtggcg cccgactttg tcggagcagc cagtatcgct     1320
gggcgcaggt cacaaccgtg gttctttgcc acactcactg gctttacaaa ccccggcatc     1380
gtctcacggt acgacttcac tcagcaagat ccagcgaaga gatggagtac atatcgtacc     1440
acgctcttga agggcttgaa ggcggaggat ttcgaagcgc agcaggtttg gtaccatagc     1500
aaggacggca cgaagattcc catgttcatt gtccgccaca ggaataccaa atttgatgga     1560
acagcgccag ccatccaata tggctacggc ggattcacca tctcaatcaa tccgttcttc     1620
agcgcatctt tcttgacttt cctccaacgt tatgcgccg tgctcgccgt gccaaatatc       1680
cggggaggtg gtgagttcgg tgaagagtgg cacctggctg gcactcgaga gcgcaaggtc     1740
aactgcttcg acgattttat tgccgccaca caattttttga ttgacaacaa gtacgctgcg    1800
ccgggctgcg gtaattccga ttatgcgcca gactcaagag ttacaacagg tctcctggtc     1860
gctgcctgtg tgaatcgtgc tcccgagggg ctacttggcg ctgctgtcgc ggaggtcggt     1920
gtccttgatc tcctcaagtt cgcggacttc accatcggtc gggcgtggac gtcagattac     1980
ggtaatccac acgatccaca tgacttcgac ttcatctacc caatctctcc gctgcacaac     2040
gtgccgaagg acaaagatct tcctccaacc atcttgttga cggctgaccc aagcatagac     2100
gacgacaggg ttgtaccatt gcattcttac aagcatgctg ctacgctgca atacaccttg     2160
tcgcacaaca cgcatcccct tctcatccgc atagacaaga aggcgggcca tggtgctgga     2220
aagtccacgg accagaggca cgccattctc tga                                   2253
```

<210> SEQ ID NO 157
<211> LENGTH: 2207
<212> TYPE: DNA
<213> ORGANISM: Sporobolomyces roseus

<400> SEQUENCE: 157

```
atgtcgtccg cccgcaccgc gtgggatccg aaatcgactc cgtacccttc ggtacaccgc    60
tccgacactg tcgaagagtt caaatctgcc aaacacggta ccgtcaaggt cgcagatccg   120
tacgactggc tcgcgttccc agattcgaaa gagactcaac acttcgtcca gcagcaaggc   180
gacttcacca agaagtacct cgaccagtac caggacaagg agaagttctc gaaagagctc   240
gaaaagaact ggaactatgc gaggttctct tgcccttctc tcaaggggga tggatactac   300
tacttcacct acaactctgg actagccgct ccgaacctcc tcagcaccga cgggtccgtc   360
tctcgttcaa catcttcttt ctcggaagac ggaaagtact acgcgtatgc gctctcgcgt   420
tccggatccg actggaacac gatttacgtt cgagaaacgt cttcacctca cctctcgacc   480
caagccgtcg gatccgacga aggacgtctt ccgaacgacg ttctccgatt cgtcaagttt   540
tctggaatcg gttggacggc ggattcgaaa ggtttcttct accaaaggtt ccccgagcgc   600
aaagagcacg gaggagaaga ggatgacaag gctggtaccg agacggacaa agacttgaac   660
gcgagtctct actatcaccg agtcggtact cctcaaagtg aggacgtctt gattcaccaa   720
gacaaggaac accccgaatg gatgtttggc gccggagcta ccgaagatgg tcgataccte   780
gtcatgactt cgtcgcgaga cactgctcgc tcgaacctcc tctggattgc cgatttgcaa   840
gaccctcaaa actcggaaat cggtcccaac ctcaagtgga caaactcat caacgagtgg   900
ggtacctact ggtccgagtt gacgaacgac gggtccaagt ctacttttta caccaacgcc   960
gaagacagtc gaattacaa gatcgtcact ttcgacttgg agaaaccgga caaggattc   1020
aaagacttga tcgctcacaa cccgaaatcg cctctcactt cggctcacct cgccgcaaac  1080
gaccaactga tcctcctcta ctcgaacgac gtcaaggacg aactctacct tcactctctc  1140
gagacgggag aacgagtcaa gcgactcgcg tcagacttga tcggcacggt cgagcaattc  1200
agtggaaggc gagaacacaa ggagatgtgg ttctcgatga gcggattcac ttcacccggt  1260
actgtgtacc gttacgaatt cgagggagag aacgctggcg tcgagcagga gtacaggaaa  1320
gcgactgtcg aagggatcaa ggcggaagac tttgaaagct cgcaagtctt ttacgagagc  1380
aaggatggaa ccaaagtccc catgttcatc acgagaccga aaggagtcga aaaggaccg   1440
gttctcttat atgcctacgg tggattcagt cacgccatca ctcccttctt ctcaccctcg  1500
ctcatgacgt ggatcaagca ctacaaagct gcgttatgta ttgccaacat tcgaggtgga  1560
gacgagtacg gcgagaaatg gcatgaggct ggaacgaagg agcggaagca aaactgtttc  1620
gacgatttcc aatgggcagc gaagtacttg tacaaagagg gaatcgcaga agaaggcaag  1680
atcgcaatct cgggaggttc gaatggaggt ctgcttgtcg gagcgtgcgt gaatcaagcg  1740
cctgagttgt acggtgccgc gattgcagat gtcggagtac ttgacatgct ccgctttcat  1800
cgctacacga tcggtcgagc gtggtcctcg gactatggat gttcggacga gcccgaagga  1860
ttcgactatc tctacgctta ttcacctttg caaaacgtcg acccgagcaa gaagccgttc  1920
ccgccgacga tgctcttgac cgcggatcac gacgatcgtg tcgttcccct tcattcgttc  1980
aagcacatct cggaactgca gcacaaactt cccgacaacc ctcaccctct cctgttacga  2040
gtcgacacga atcaggtca cggtgccgga aagagtacgg cgaagaagat cgaggaagca  2100
tgcgagaagt atgggttcgt atctcagtcc atgggattac gatggcacga ctagatgtag  2160
cgatgtgacg gaccttggct ggaaaatgct tattctcttt tcgcgag              2207
```

<210> SEQ ID NO 158
<211> LENGTH: 723
<212> TYPE: PRT
<213> ORGANISM: Phaeosphaeria nodorum

<400> SEQUENCE: 158

```
Met Ala Glu Gln Asn Ser Ala Leu Ile Ala Gly Leu Gly Cys Gln Pro
 1               5                  10                  15

Val Glu Ser Ser Glu Ala Asp Ala Gly Ile Asn Trp Gln Trp Leu
             20                  25                  30

Glu Glu Pro Gln Gly Ala Thr Gly Leu Glu Trp Ala Lys His Glu Thr
             35                  40                  45

Glu Ile Thr Gln Glu His Leu Asp Arg Leu Pro Arg Ala His Lys Leu
         50                  55                  60

His Glu Lys Leu Glu Lys Met Ile Glu Gln Asn Ala Ala Pro Pro Thr
 65                  70                  75                  80

Tyr Ala Leu Cys Gly Arg Leu Phe Arg Leu Arg Arg Asp Ala Val Arg
                 85                  90                  95

Lys Ser Gly Ile Ile Glu Val Ala Ala Leu Glu Thr Pro Asp Glu Trp
                100                 105                 110

Thr Thr Val Ile Asp Ile Asp Asp Leu Arg Glu Arg Glu Gly Lys Pro
            115                 120                 125

Trp Gln Leu Ser Gln Thr Val Leu Pro Cys Phe Ser Ser Val Tyr Leu
130                 135                 140

Gly Gly Gln Ser Ser Arg Leu Leu Leu Gly Leu Ser Glu Gly Gly Ser
145                 150                 155                 160

Asp Glu Thr Thr Ile Arg Glu Phe Asp Val Asp Gln Ala Ala Trp Val
                165                 170                 175

Thr Asp Gly Phe Ala Ala Gly Pro Gly Arg Phe Ser Ala Ala Trp Leu
            180                 185                 190

Asp Leu Asp His Val Met Ile Thr His Ala Leu Asn Gly Gly Pro Thr
        195                 200                 205

Cys Asn Thr Gly Trp Pro Leu Asn Thr Tyr Ile Trp Ala Arg Gly Thr
210                 215                 220

Glu Leu Ala Asp Ala Lys Leu Val His Ser Gly Asp Pro Gly Asp Ala
225                 230                 235                 240

Ile Leu Tyr Cys Ser Ala Val Gly Thr Gly Arg Thr Arg Arg Gly Leu
                245                 250                 255

Ile Gly Gln Ala Ala Thr Phe Ala Asp Leu Lys Phe His Thr Val Ser
            260                 265                 270

Ile Asp Gly Thr Val Glu Arg Ala Ser Leu Pro Gln Gly Leu Ser Leu
        275                 280                 285

Ala Met Phe Leu Pro Ser Thr Ser Thr His Leu Phe Val Thr Thr Thr
290                 295                 300

Glu Glu Ser Thr Ile Gly Asn Lys Lys Ile Arg Lys Asp Ala Leu Leu
305                 310                 315                 320

Ala Trp Lys Tyr Thr His Gly Gln Thr Arg Thr Ser Val Val Tyr Val
                325                 330                 335

Pro Glu Ser Gly Glu Ala Ile Leu Asp Ala Val Thr Gly Gly Ile Ser
            340                 345                 350

Ala Gly Pro Ser Lys Val Tyr Phe Thr Leu Leu Lys Arg Asn Thr Glu
        355                 360                 365

Arg Arg Met Val Met Glu Tyr Val Asn Asp Glu Trp Lys Leu Cys Gln
370                 375                 380

Ala Ile Pro Thr Pro Thr Gly Ala Ser Ala Lys Val Gln Thr Ala Asp
385                 390                 395                 400

Pro Tyr Ser Asp Ser Ile Ile Val Glu Thr Ser Gly Leu Leu Asn Pro
```

-continued 405                 410                 415
Lys His Val Cys Leu Glu Asn Ala Gly Gly Ser Arg Lys Thr Asp Leu
            420                 425                 430

Tyr Ser Gln Lys Ala Ala Phe Asp His Ser Asn Cys Ala Val Glu Thr
            435                 440                 445

Gln Val Ala Thr Ser Lys Asp Gly Thr Glu Ile Asp Tyr Phe Ile Met
450                 455                 460

Ala Pro Lys Gln Gly Arg Glu Lys Leu Pro Val Leu Ile Thr Gly Tyr
465                 470                 475                 480

Gly Ala Phe Gly Met Asn Phe Asp Leu Ser Tyr Val Gly Pro Met Leu
                485                 490                 495

Gly Gly Leu Ser Leu Ala Leu Trp Leu Glu Leu Gly Gly Ala Leu Val
            500                 505                 510

Val Pro Leu Ile Arg Gly Gly Glu Arg Gly Glu Asp Trp His Gln
            515                 520                 525

Ala Ala Leu Arg Glu Asn Arg Gln Arg Ser Tyr Asp Asp Phe Ala Ala
            530                 535                 540

Val Ala Glu Ala Ile Ile Ser Asn Gly Leu Thr Ser Pro Gln Lys Leu
545                 550                 555                 560

Gly Val Phe Gly Phe Ser Asn Gly Gly Leu Leu Ala Ala Val Met Gly
                565                 570                 575

Thr Gln Arg Pro Asp Leu Phe Gly Ala Val Val Ser Asp Val Pro Leu
            580                 585                 590

Thr Asp Met Leu Arg Phe Pro Glu Leu Ala Met Gly Ser Ala Trp Leu
            595                 600                 605

Asn Glu Tyr Gly Asp Pro Lys Val Pro Glu Gln Ala Lys Ala Leu Arg
            610                 615                 620

Ala Tyr Ser Pro Phe His Asn Val Lys Gln Gly Thr Ala Tyr Pro Pro
625                 630                 635                 640

Met Leu Ile Thr Cys Ser Thr Leu Asp Asp Arg Val Gly Val Gly His
                645                 650                 655

Ser Arg Lys Leu Val Ala Arg Leu Lys Glu Val Glu Ser Pro Lys Thr
            660                 665                 670

Phe Leu Tyr Glu Glu Thr Glu Gly Gly His Ser Ser Tyr Arg Asp Leu
            675                 680                 685

Thr Thr Asn His Leu His Leu Phe Arg Asp Met Asp Asp Ser Pro
            690                 695                 700

Val Asn Ile Glu Ser Lys Val Gly Thr Ala Gly His Ile Lys Ile Ser
705                 710                 715                 720

Met Ser Gly

<210> SEQ ID NO 159
<211> LENGTH: 112
<212> TYPE: DNA
<213> ORGANISM: Amanita bisporigera

<400> SEQUENCE: 159
ttgagagcac acaagtctgg tatgagagca aagacggaac gaaagttcca atgttcatcg      60
ttcgtcacaa atcaacgaaa tttgacggaa cggcgccggc gattcaaaac gg             112

<210> SEQ ID NO 160
<211> LENGTH: 33
<212> TYPE: PRT
<213> ORGANISM: Amanita bisporigera

<400> SEQUENCE: 160

Glu Ser Thr Gln Val Trp Tyr Glu Ser Lys Asp Gly Thr Lys Val Pro
1               5                   10                  15

Met Phe Ile Val Arg His Lys Ser Thr Lys Phe Asp Gly Thr Ala Pro
            20                  25                  30

Ala

<210> SEQ ID NO 161
<211> LENGTH: 206
<212> TYPE: DNA
<213> ORGANISM: Amanita bisporigera

<400> SEQUENCE: 161
cgtatatcga actgccaagg tcaagggttt aaatccgaac gatttcgagg ctcgacaggt     60
gactagttgg ttttatattg catgaaaagt gcgtctcatg cggtctaggt gtggtatgac    120
agctacgacg gaacaaagat tccaatgttc atcgtccgtc acaagaatac caaatttaat    180
gggacggcgc cagctataca atatgg                                        206

<210> SEQ ID NO 162
<211> LENGTH: 32
<212> TYPE: PRT
<213> ORGANISM: Amanita bisporigera

<400> SEQUENCE: 162

Val Trp Tyr Asp Ser Tyr Asp Gly Thr Lys Ile Pro Met Phe Ile Val
1               5                   10                  15

Arg His Lys Asn Thr Lys Phe Asn Gly Thr Ala Pro Ala Ile Gln Tyr
            20                  25                  30

<210> SEQ ID NO 163
<211> LENGTH: 107
<212> TYPE: DNA
<213> ORGANISM: Amanita bisporigera

<400> SEQUENCE: 163
cgacaaacaa gtaacaccta cgcgcgaaaa actcgcgatc tccggcggca gcaacggcgg     60
actcctcgtc ggcgcaagcc gattgaccca gcgccccgac ctcttcg                 107

<210> SEQ ID NO 164
<211> LENGTH: 27
<212> TYPE: PRT
<213> ORGANISM: Amanita bisporigera

<400> SEQUENCE: 164

Glu Lys Leu Ala Ile Ser Gly Gly Ser Asn Gly Gly Leu Leu Val Gly
1               5                   10                  15

Ala Ser Arg Leu Thr Gln Arg Pro Asp Leu Phe
            20                  25

<210> SEQ ID NO 165
<211> LENGTH: 94
<212> TYPE: DNA
<213> ORGANISM: Amanita bisporigera

<400> SEQUENCE: 165
atcctcggat ggcacagcct cgctctccat gtatgatttc tcacactgtg gcaaatactt     60
cgcatatggt atttctcttt ccgtatgtaa tttt                                94

```
<210> SEQ ID NO 166
<211> LENGTH: 27
<212> TYPE: PRT
<213> ORGANISM: Amanita bisporigera

<400> SEQUENCE: 166

Ser Ser Asp Gly Thr Ala Ser Leu Ser Met Tyr Asp Phe Ser His Cys
 1               5                  10                  15

Gly Lys Tyr Phe Ala Tyr Gly Ile Ser Leu Ser
            20                  25

<210> SEQ ID NO 167
<211> LENGTH: 106
<212> TYPE: DNA
<213> ORGANISM: Amanita bisporigera

<400> SEQUENCE: 167
gggataatta attgcagcga gttatgacaa cggaaaaacc cacctcttct cagtagattt      60
tcctccgcca tgccccgctt tcttgtctac acgtagcaga agtgga                   106

<210> SEQ ID NO 168
<211> LENGTH: 20
<212> TYPE: PRT
<213> ORGANISM: Amanita bisporigera

<400> SEQUENCE: 168

Pro Leu Leu Leu Arg Val Asp Lys Lys Ala Gly His Gly Gly Gly Lys
 1               5                  10                  15

Ser Thr Glu Lys
            20

<210> SEQ ID NO 169
<211> LENGTH: 16
<212> TYPE: PRT
<213> ORGANISM: Amanita bisporigera

<400> SEQUENCE: 169

Asp Gly Thr Lys Val Pro Met Phe Ile Val Arg His Lys Ser Thr Lys
 1               5                  10                  15

<210> SEQ ID NO 170
<211> LENGTH: 3054
<212> TYPE: DNA
<213> ORGANISM: Amanita bisporigera

<400> SEQUENCE: 170
ggacacccca accatgtacc cttctgctcg ccgttcagac catatagaca catacaggag      60
cgaaacgaga ggcgaagtca aggtgccgga cccataccac tggctagagg aatattcaga    120
agagacggac aagtggacgt ccgaccagga ggagttcacg aggacatatt tggacagcaa    180
ccctgatcga aagaagctag aagacgcatt cagaaagagt atggattatc caaggtttc    240 ttcggcattc tattcattct gatggaatgg aatcgttgat ggctgccaat cttctttcct    300
tttatatagt tctccgctcc tttttgaat gatgacaagc gatggtattg gttttacaat     360
accggccttc aagcacaaac aggtaaacac atcaagctct gtcgtgcgaa atatttacaa    420
cttttggtag tcatctgcag atcaaaggat gagactcttc ccgacttctc agagagtgac    480
tacgtcgggg aaacattttt tgatgtaagt gtagtttgtc gctggcggtg ttcgatatca    540
atgatagcgt tttcgcagcc gaacctatta tcctcggatg gcacagcctc gctctccatg    600
tatgatttct cacactgtgg caaatacttc gcatatggta tttctctttc cgtatgtaat    660
```

```
tttcaacgag caaccatccc ttccgatgag atgaacttct tttttcgtcac aggggagcga    720 tttttcaact atatacgttc ggtcaacttc ctctccactg ccccctggca acgacagcat    780
tagaaatgac gacggtagac ttccagacga gcttagatat gtcaaatttt cctccatcag    840
ctggacaaag gactcccaag gatttttcta tcaggtacta cactatggaa agatctgcgg    900
acttgactaa attacttgca gcgctatccc ggtacaggca ctgtgaatgg acagaatggc    960
atccaaactc aaggcgatcg tgatgctatg atttactatc accggatagg gacatcacaa   1020 tgtataccccc gctcttttgt ccaatcctct catttcaatt cgctcttcta gccgatgata   1080
ttcttgtgca tgaagaccag gaacatcctg attgggtatt tggcgcagaa gtcacggaag   1140
atggtaaata tgtggccctg tacacaatga aggacacatc aagggtatgc tttaagtggt   1200
cccacctgcg ttgctaaccg gttcttgtag aaaaatctat tgtggattgc tgatcttgga   1260
caaaacgaag ttggacgaaa catgaaatgg aacaagattt gcaacgtttt tgactcagaa   1320
tacgacctgt aagtccctga acggtaatac ggttgttttt ttgcttattt gcgacagaat   1380
tggcaacgac ggttcattac tatacatcag aactaataaa gctgcacctc aatacaagat   1440 tgtcaccttta gatatagaga aaccagaatt agggtttaag gaattcatac cggaagatcc   1500
caaagcatat ctctctcaag tcaaaatttt taataaggat agactagcac tagtatacaa   1560
gcgtaacgtg agtccagaac acggcaatat atcgcaggag agcaaattga tggaaaaaat   1620
aggttatagg cgaactctac gtctacaata acactgggtc acgactaatg cgcctagccc   1680
gggactttgt tggctccatg acggtgaccg ctcgagaaac ggagccatgg ttttttgcca   1740
ctctcacggg cttcaatacc cctggaatcg tatgcaggta caatatccag cgaccggaag   1800
aacagcgttg gagcgtatat cgaactgcca aggtcaaggg tttaaatccg aacgatttcg   1860
aggctcgaca ggtgactagt tggttttata ttgcatgaaa agtgcgtctc atgcggtcta   1920
ggtgtggtat gacagctacg atggaacaaa gattccaatg ttcatcgtcc gtcacaagaa   1980
taccaaattt aatgggacgg cgccagctat acaatatggt aggctaaaga cagtgaattt   2040
attaccggat gacatgtcta attcactctg gcaaggttac ggtggcttta atatatctat   2100
aaatcccttc tttagtccaa cgattttgac gttcttgcaa aagtatggag caattctagc   2160
tgtacctaat atccgaggag gcggcgagtt cggcgagaca tggcatgatg ctggtatacg   2220
agagaaacga gtataacgca cgccttctcc acggtgatag ctctgacatt atttccaggc   2280
taatgtttac gatgatttca ttgcggcaac gtacgtgtca gttgtccttg aattctacat   2340
tgccatttac ttggtaccag tcagttcttg gtaaaaaaca agtatgccgc gggcggcaaa   2400
gtggccatca acgggggtc caatggaggt ctgttggcat gtctttatcc accctcagtc   2460
tcttatatta gccttaggac ttttggtcgc ggcctgtgtc aatcgtgcac ctgaaggaac   2520
ctttggagct gccattgctg aagttggggt cctagacttg ctcaaggttt gtccgatcgt   2580
gtcttacaga gatatatgct ccaactcata acctttgatt ttagttctcc aaatttacca   2640
taggtatatg atcaacactg ctcatgactt tgttcttaa gtcgatatca ggcaaagctt   2700
ggactagcga ctacggcgat ccagaagatc cgcgcgattt tgatttcatt tacacacatt   2760
caccacttca taatatacca aagaacatgg tcttacctcc gacgatgctt ctgacagctg   2820
atcgtgagtt ggctcccatg gtataattgc taggttcctg acgcgaccta gatgatgacc   2880
gtgtcgtccc aatgcattca tttaagtatg ctgcaatgct acaatacacc ctgccgcata   2940
atcgtcatcc acttctgcta cgtgtagaca agaaaggcgg ggcatggcgg aggaaaatct   3000
```
actgagaaga ggtgggtttt tccgttgtca taactcgctg caattaatta tccc    3054

<210> SEQ ID NO 171
<211> LENGTH: 3110
<212> TYPE: DNA
<213> ORGANISM: Amanita bisporigera

<400> SEQUENCE: 171
accaatggct ggaggagaat tcaaatgaag tagacgaatg gacgacggcg cagacagctt    60
tcacgcaagr ctatcttgat aagaatgcgg atagacagaa gctcgaggag aaatttcgtg   120
caagcaagga ctacgtcaag gtaatcgatg atcgatatag cgttgtgtct gtgctgaaga   180
ccttgcccat agttttctgc gccaactctg cttgatagtg gacactggta ttggttctac   240
aatagcggcg tacaatcgca agcaggtatg tacccatctg tctctggcga tgccgaattc   300
agacagtgtt cagtcctcta ccgctccaag aaacccgttc ttcctgattt ctcaaagagg   360
gacgaggaag tcggcgaagt atacttcgat gtagggatct ccacgacgtt tgaatacttc   420
tttgacttca ctcttgaaag ccaaacgtac tctctgctga tggcaccgca attatgggca   480
cgtgccgatt ctcccctagt ggcgagtatt tcgcatatgc agtgtcccac ttggtgagta   540
accacgttcc tacatgggcc aactccttgg tcttattttt tgcacaggga gttgattatt   600
ttactatcta tgttcgccct acgagttcat cattgtctca agctccggaa gctgaaggtg   660
gggatggtcg attgtcggat gaagtgaaat ggtgcaagtt tacgactata acgtggacaa   720
aggactccaa aggatttctt taccaggtat gatacatcca gccacccaac catccgttcg   780
ttaacctgtg tcatacagcg gtaccctgct cgggaatctc ttgtggcgaa agatcgtgat   840
aaagatgcta tggtatgcta tcatagggtt ggaacgactc aatgtaggga ttacttggcg   900
tcttgacttt ccccaaactg atccagtagt acagtggaag atatcattgt ccaacaagac   960
aaggagaacc cagactggac atatggaaca gatgcgtcag aggacggcaa atatatctac  1020
ttagtggtat acaaggatgc ctcgaaggca agagtttaag ttctatcgcc cgacatcaat  1080
aaccttcata ctaccagcaa atcttctgt gggttgcaga attcgacaag gacggggtca   1140
agccggaaat tccctggcga aaagtcatca atgagtttgg ggcggattac catgtgtgag  1200
tcctcccctc cttcacgtcc ccttcacgtc cccttttaa ctcggcatgg tatagtatca  1260
cgaaccacgg atctttgatc tatgtcaaga ctaacgtgaa tgcgcccaa tataaagttg   1320
tcactatcga cctttcgaca ggagaacccg aaattcgtga tttcatcccg gaacagaaag  1380
atgcgaagct cactcaagtc aaatgcgtca acaaggaata tttcgtcgcg atctacaagc  1440
gcaatgtatt ttcattgaca atttgatttc gaatttccct aacgtcgatt ttgcatccac  1500
aggtcaaaga tgaaatatat cttttactcca aagcaggcga tcaactcagt cgtctggcgt  1560
cggacttcat tggcgttgca tctataacta acagagagaa acaacctcat ttcttcctca  1620
ctttctctgg atttaacacg ccgggcacca tttctcgcta cgattttaca gctccagaga  1680
cacaacgtct cagcatcctt agaacgacga agctaaatgg tctgaatgca gatgactttg  1740
agagcacaca agtctggtat gagagcaaag acggaacgaa agttccaatg ttcatcgttc  1800
gtcacaaatc aacgaaattt gacggaacgg cgccggcgat tcaaaacggt aatcctttct  1860
catccatcac aaccagtagg aatctctgac aacctgtctt gcttcgcaca ggttatggtg  1920
gtttcgcgat tacagccgat ccattcttta gtcccatcat gctcaccttt atgcagacat  1980
atggcgcaat cctggctgtc ccgaacatca gaggtggagg tgaattcggc ggagaatggc  2040
acaaggcagg gagacgagaa accaaggttt gtgcccattg ccttatattt ctgttgcatg  2100

```
cagcctggac ctccgtaata gggaaatact tttgatgatt tcatcgctgc cgcgtatgtc    2160
cgccgctatt cgaattttcg tgatttcaca ggctcacgga ggtcttttgt tgctacagtc    2220
aatttcttgt caaaaacaag tacgcggctc caggcaaagg tggccatcac tggtgcatcc    2280
aatggcggta aagtgaccct cgttcttgtt ttcatcccgg tactcacctc gcgatggtgg    2340
aataggtttt cttgtctgtg gttccgtagt tcgggcacca gaggggacat tcggcgctgc    2400
tgtttccgaa ggtggtgtcg cggacctcct aaaggtatttt tggttgtcca cgatatccgt    2460
gctcgttctc taatttctgt atttgagttt aataaattta ccgggggtga gttgacattg    2520
gtcttgtgtc caccgctgat ttgattaatt acatcgtcag ggatggcgtg gacgagtgaa    2580
tatggaaacc cttttattaa ggaggacttc gactttgtcc aagcattgtc tcctgtgcat    2640
aacgtaccca aggatagggt tcttcctgcc acattactta tgaccaatgc gggtgggtga    2700
ctctctggag cccagattta ccagtacctg acgctcgact ctcatcaggt gacgatcgtg    2760
tagttccaat gcattcgctt aagttcgtcg caaaccttca gtacaatgtg cctcaaaatc    2820
ctcatccatt gctcatccgt gtggataaat cttggcttgg tcattggttt tggcaagaca    2880
acagacaagc agtaaattgc ccctcctttc tacgttccat tgcttatatt ttacagtact    2940
aaagatgctg cggacaagtg gagtttcgta gcgcaatcgt tagggctaga atggaaaacg    3000
gttgactagg ctgtcaaatt aacagatgcg ggctcaaaat accgtccacg ttagatgtat    3060
tcaatgtact ctgtttcctg taaccctgcg tacggcccaa tacagccatg                3110

<210> SEQ ID NO 172
<211> LENGTH: 24
<212> TYPE: DNA
<213> ORGANISM: Artificial Sequence
<220> FEATURE:
<223> OTHER INFORMATION: A synthetic primer

<400> SEQUENCE: 172
gaaacgagag gcgaagtcaa ggtg                                             24

<210> SEQ ID NO 173
<211> LENGTH: 24
<212> TYPE: DNA
<213> ORGANISM: Artificial Sequence
<220> FEATURE:
<223> OTHER INFORMATION: A synthetic primer

<400> SEQUENCE: 173
aagtggatga cgattatgcg gcag                                             24

<210> SEQ ID NO 174
<211> LENGTH: 27
<212> TYPE: DNA
<213> ORGANISM: Artificial Sequence
<220> FEATURE:
<223> OTHER INFORMATION: A synthetic primer

<400> SEQUENCE: 174
gattgggtat ttggcgcaga agtcacg                                          27

<210> SEQ ID NO 175
<211> LENGTH: 27
<212> TYPE: DNA
<213> ORGANISM: Artificial Sequence
<220> FEATURE:
<223> OTHER INFORMATION: A synthetic primer
```

```
<400> SEQUENCE: 175
atgtctcgcc gaactcgccg cctcctc                                        27

<210> SEQ ID NO 176
<211> LENGTH: 23
<212> TYPE: DNA
<213> ORGANISM: Artificial Sequence
<220> FEATURE:
<223> OTHER INFORMATION: A synthetic primer

<400> SEQUENCE: 176
tcaaatgaag tagacgaatg gac                                            23

<210> SEQ ID NO 177
<211> LENGTH: 23
<212> TYPE: DNA
<213> ORGANISM: Artificial Sequence
<220> FEATURE:
<223> OTHER INFORMATION: A synthetic primer

<400> SEQUENCE: 177
cacacggatg agcaatggat gag                                            23

<210> SEQ ID NO 178
<211> LENGTH: 26
<212> TYPE: DNA
<213> ORGANISM: Artificial Sequence
<220> FEATURE:
<223> OTHER INFORMATION: A synthetic primer

<400> SEQUENCE: 178
aaagttccaa tgttcatcgt tcgtca                                         26

<210> SEQ ID NO 179
<211> LENGTH: 28
<212> TYPE: DNA
<213> ORGANISM: Artificial Sequence
<220> FEATURE:
<223> OTHER INFORMATION: A synthetic primer

<400> SEQUENCE: 179
tgggactaaa gaatggatcg gctgtaat                                       28

<210> SEQ ID NO 180
<211> LENGTH: 101
<212> TYPE: DNA
<213> ORGANISM: Amanita bisporigera

<400> SEQUENCE: 180
atgtctgaca tcaatgctac ccgtctcccc atctggggta tcggttgcaa cccgtgcatc    60
ggtgacgacg tcactactct cctcactcgt gcccctttgta a                      101

<210> SEQ ID NO 181
<211> LENGTH: 99
<212> TYPE: DNA
<213> ORGANISM: Amanita bisporigera

<400> SEQUENCE: 181
atgtctgaca tcaatgccac ccgtcttccc gcttggcttg tagactgccc atgcgtcggt    60
gacgatgtca accgtctcct cactcgtagc ctttggtaa                           99

<210> SEQ ID NO 182
<211> LENGTH: 30
```

-continued

```
<212> TYPE: DNA
<213> ORGANISM: Amanita bisporigera

<400> SEQUENCE: 182
atgtctgaca tcaatgctac ccgtcttccc                                    30

<210> SEQ ID NO 183
<211> LENGTH: 115
<212> TYPE: DNA
<213> ORGANISM: Amanita bisporigera

<400> SEQUENCE: 183
ttggggtttg gcagtcggtt agtacccagt cctcttcgaa ctcggaaaac ctttactctc    60
aataaaccat gtctgacatc aatgccaccc gtcttcctat ctggtggtac atata        115

<210> SEQ ID NO 184
<211> LENGTH: 36
<212> TYPE: PRT
<213> ORGANISM: Amanita bisporigera

<400> SEQUENCE: 184

Gly Val Trp Gln Ser Val Ser Thr Gln Ser Ser Asn Ser Glu Asn
 1               5                  10                  15

Leu Tyr Ser Gln Thr Met Ser Asp Ile Asn Ala Thr Arg Leu Pro Ile
            20                  25                  30

Trp Trp Tyr Ile
        35

<210> SEQ ID NO 185
<211> LENGTH: 98
<212> TYPE: DNA
<213> ORGANISM: Amanita bisporigera

<400> SEQUENCE: 185
gtgggtacgc gccggggaga cgggtggcat tgatgtccga cattgcgatt gagagtagag    60
gatgctgtag gtttctgagg ggtcttgtga gtattgaa                            98

<210> SEQ ID NO 186
<211> LENGTH: 32
<212> TYPE: PRT
<213> ORGANISM: Amanita bisporigera

<400> SEQUENCE: 186

Ser Ile Leu Thr Arg Pro Leu Arg Asn Leu Gln His Pro Leu Leu Ser
 1               5                  10                  15

Ile Ala Met Ser Asp Ile Asn Ala Thr Arg Leu Pro Gly Ala Tyr Pro
            20                  25                  30

<210> SEQ ID NO 187
<211> LENGTH: 106
<212> TYPE: DNA
<213> ORGANISM: Amanita bisporigera

<400> SEQUENCE: 187
ctcacaagac cctcacgaaa cctacagcat cctctacttc tcaatcgcaa tgtcggacat    60
caatgccacc cgtctccccg gcgcgtaccc acctgttcct tggccg                  106

<210> SEQ ID NO 188
<211> LENGTH: 35
<212> TYPE: PRT
<213> ORGANISM: Amanita bisporigera
```

<400> SEQUENCE: 188

Ser Gln Asp Pro His Glu Thr Tyr Ser Ile Leu Tyr Phe Ser Ile Ala
1               5                   10                  15

Met Ser Asp Ile Asn Ala Thr Arg Leu Pro Gly Ala Tyr Pro Pro Val
            20                  25                  30

Pro Trp Pro
        35

<210> SEQ ID NO 189
<211> LENGTH: 1266
<212> TYPE: DNA
<213> ORGANISM: Amanita bisporigera

<400> SEQUENCE: 189

```
tgaggcacgg gaagtatatg aaccagaaga taggaagact ggtgacattg atgtcagaca      60
tggttatcag taaagagttt gacgaggact gggtactaat tgccaaaccc cagaaccttt     120
atgtgattcg acaagagcaa atataattgc agaacttgac ccaatgtttc aggtgttggc     180
gctgtctcag gcaatggtag cgccgccttg tgggtggctc tagggtgtaa cgtgtaacag     240
ttagcaatta ggctatatgc tgctctgcga acaggcttgc gacgcctgt caccttgccg      300
accgtactat ctagcaccat tcaacgccat gtgattatga tagcgtcggc attccgtgcc     360
agttgcatgt gctttgagtt ttccatgttt agtaaccgcg agccgcgagc gttcagaatc     420
atagtggtgg cggtgctaga gttacaacat gtatgtaaca tacgagtcag aataaaatta     480
ccataggaat ctagttctga tgtccattgg tcaactcgac ccagtacctt tcctccctct     540
ccttccaccg ccttcgtctc cttcattgtc cccaccactg gtatacaacg ccgacgtcga     600
ccgctgcgcc gtcctctcaa caatagacgt cccgtctcta atcttgccc taaacagcac      660
atttgcgttc gtaaacagcc cttccttcag tgacaccact ataaattgcg accccttgaa     720
ccgcgtccgg aacagctgtc caatatgctg cgtgtgcgat agatccaggg cagcgtcgat     780
ctcgtcgagg atgtacattg gcgctggttt gaattggagg agcgccatga tgagcgagag     840
cgcgatgaga gatctgcagc ataccgtcag acgaagcaac ttgggtgttc aaacgacata     900
cctctggccc ccacttaact cagtcaagct ctccttccaa acggtgccga gttgaacttt     960
gacttctaga ccgtccataa gatcttggcc ttcgggcggt accagtttgg caaaattgcc    1020
aggcaagagt tctgcaaaga tcccgccaaa gtcgctttac cacatgcctt caatccccctt   1080
gtcatacaaa tggtgacaaa gtgactcacc cgtcaacctt ttcccaagtt ttttgaagcg    1140
catccctctt gtaccggtct agttcttcga tagtctcttc aatctttttct ttatctttca   1200
gcacctgact aagcatcttt ttaagatgtg cctctctgct cacgacgcta gacacgtggc    1260
aggaaa                                                               1266
```

<210> SEQ ID NO 190
<211> LENGTH: 403
<212> TYPE: PRT
<213> ORGANISM: Amanita bisporigera

<400> SEQUENCE: 190

Ser Cys His Val Ser Ser Val Val Ser Arg Glu Ala His Leu Lys Lys
1               5                   10                  15

Met Leu Ser Gln Val Leu Lys Asp Lys Glu Lys Ile Glu Glu Thr Ile
            20                  25                  30

Glu Glu Leu Asp Arg Tyr Lys Arg Asp Ala Leu Gln Lys Thr Trp Glu

```
            35                  40                  45
Lys Val Asp Gly Val Thr Leu Ser Pro Phe Val Gln Gly Asp Arg His
 50                  55                  60
Val Val Lys Arg Leu Trp Arg Asp Leu Cys Arg Thr Leu Ala Trp Gln
 65                  70                  75                  80
Phe Cys Gln Thr Gly Thr Ala Arg Arg Pro Arg Ser Tyr Gly Arg Ser
                 85                  90                  95
Arg Ser Gln Ser Ser Thr Arg His Arg Leu Glu Gly Glu Leu Asp Val
                100                 105                 110
Lys Trp Gly Pro Glu Val Cys Arg Leu Asn Thr Gln Val Ala Ser Ser
                115                 120                 125
Asp Gly Met Leu Gln Ile Ser His Arg Ala Leu Ala His His Gly Ala
    130                 135                 140
Pro Pro Ile Gln Thr Ser Ala Asn Val His Pro Arg Arg Asp Arg Arg
145                 150                 155                 160
Cys Pro Gly Ser Ile Ala His Ala Ala Tyr Trp Thr Ala Val Pro Asp
                165                 170                 175
Ala Val Gln Gly Val Ala Ile Tyr Ser Gly Val Thr Glu Gly Arg Ala
                180                 185                 190
Val Tyr Glu Arg Lys Cys Ala Val Gly Lys Ile Arg Arg Asp Val Tyr
                195                 200                 205
Cys Glu Asp Gly Ala Ala Val Asp Val Gly Val Tyr Gln Trp Trp
    210                 215                 220
Gly Gln Arg Arg Arg Arg Trp Lys Glu Arg Glu Arg Tyr Trp
225                 230                 235                 240
Val Glu Leu Thr Asn Gly His Gln Asn Ile Pro Met Val Ile Tyr Ser
                245                 250                 255
Leu Val Cys Tyr Ile His Val Val Thr Leu Ala Pro Pro Leu Phe
            260                 265                 270
Thr Leu Ala Ala Arg Gly Tyr Thr Trp Lys Thr Gln Ser Thr Cys Asn
    275                 280                 285
Trp His Gly Met Pro Thr Leu Ser Ser His Gly Val Glu Trp Cys Ile
    290                 295                 300
Val Arg Ser Ala Arg Gln Ala Ser Gln Ala Cys Phe Ala Glu Gln His
305                 310                 315                 320
Ile Ala Leu Leu Thr Val Thr Arg Tyr Thr Leu Glu Pro Pro Thr Arg
                325                 330                 335
Arg Arg Tyr His Cys Leu Arg Gln Arg Gln His Leu Lys His Trp Val
                340                 345                 350
Lys Phe Cys Asn Tyr Ile Cys Ser Cys Arg Ile Thr Arg Phe Trp Gly
                355                 360                 365
Leu Ala Ile Ser Thr Gln Ser Ser Asn Ser Leu Ile Thr Met
    370                 375                 380
Ser Asp Ile Asn Val Thr Ser Leu Pro Ile Phe Trp Phe Ile Tyr Phe
385                 390                 395                 400
Pro Cys Leu

<210> SEQ ID NO 191
<211> LENGTH: 554
<212> TYPE: DNA
<213> ORGANISM: Amanita bisporigera

<400> SEQUENCE: 191
tatgctttta gtccaagctt ttacttcacc tggacgttgg gatacgtcag gaatatgtac    60
```

```
tgacaataaa tatcaccgca gcggcgccga aactcaccaa tctttacttc acctggacgt      120
tgggatagat gacgtattca ctggaaaagg gttagcggat aacatgggtc gcatgtcatc      180
atgaatatag ttagtgcgtc tccactcaca attgtccaag ttatttcgct tccgtcattc      240
gcggacagtt gaggtttgcc cctgcccaac tcggcaatgg gtcatgactg agacagataa      300
aagatgctgg gggcgcaagc attcaatact cagttcccct ccaaatttga atcgttcaga      360
aacctactac ttcatttact ctctcacaat gtctgacatc aatactgctc gtcttccttt      420
ctaccagttt cccgatttta agtatccctg cgttggtgac gacatcgaga tggtcctcgc      480
gcgtggcgag aggtgaatac aacatccggc caaggctgta tcaaacgact tacgtgctac      540
gtatcagcct ttgc                                                       554
```

```
<210> SEQ ID NO 192
<211> LENGTH: 181
<212> TYPE: PRT
<213> ORGANISM: Amanita bisporigera

<400> SEQUENCE: 192
```

```
Met Leu Leu Val Gln Ala Phe Thr Ser Pro Gly Arg Trp Asp Thr Ser
 1               5                  10                  15

Gly Ile Cys Thr Asp Asn Lys Tyr His Arg Ser Gly Ala Glu Thr His
            20                  25                  30

Gln Ser Leu Leu His Leu Asp Val Gly Ile Asp Val Phe Thr Gly
        35                  40                  45

Lys Gly Leu Ala Asp Asn Met Gly Arg Met Ser Ile Leu Val Arg
 50                  55                  60

Leu His Ser Gln Leu Ser Lys Leu Phe Arg Phe Arg His Ser Arg Thr
65                  70                  75                  80

Val Glu Val Cys Pro Cys Pro Thr Arg Gln Trp Val Met Thr Glu Thr
                85                  90                  95

Asp Lys Arg Cys Trp Gly Arg Lys His Ser Ile Leu Ser Ser Pro Pro
            100                 105                 110

Asn Leu Asn Arg Ser Glu Thr Tyr Tyr Phe Ile Tyr Ser Leu Thr Met
        115                 120                 125

Ser Asp Ile Asn Thr Ala Arg Leu Pro Phe Tyr Gln Phe Pro Asp Phe
130                 135                 140

Lys Tyr Pro Cys Val Gly Asp Asp Ile Glu Met Val Leu Ala Arg Gly
145                 150                 155                 160

Glu Arg Ile Gln His Pro Ala Lys Ala Val Ser Asn Asp Leu Arg Ala
                165                 170                 175

Thr Tyr Gln Pro Leu
            180
```

```
<210> SEQ ID NO 193
<211> LENGTH: 684
<212> TYPE: DNA
<213> ORGANISM: Amanita bisporigera

<400> SEQUENCE: 193
aatttgaatc tctcagaaac ctacttactc tctcacaatg tctgacatca atactgctcg       60
tcttcctttc ttccagcctc ccgaatttag gcctccctgc gtcggtgacg acatcgagat      120
ggtcctcacg cgtggtgaga ggtgagtaca catccggcca aggatgtatc aaaccactca      180
cgtgctacgt atcagccttt gctaaatgca cggcctatcg gtccactcct atggcatgaa      240
```

-continued

```
ggtgtcgccg tcgcatttca actacaacgt aaggcaattg tactgacttg aatgtagtag    300
tggtcattat gttgttgacg atatcaggct tggaccgttg agcctgcatc agaagtatga    360
ctttgcttgt ggtgaagaag cactggattt aacccatctt tttttcctaga taactcgctt    420 tcttttccaa gttatgtcg aatccgtttt gtagtaaaca tataaaaccc acgtcaacga     480
tcccgtgtta cttgttactt gttctttgtt cttgaaaccc tcgtcaatga tccgcgttat    540
agtcaataaa cttgttcttt gttccttgtca gtgtgagggc attttgtacg cgagtggttt    600
caagaaatca gtcaaaaggt gtctttccaa catatctgtt gagcctgtcc ggtcctgaag    660
cctgattgga gaatcaatca gtat                                             684
```

<210> SEQ ID NO 194
<211> LENGTH: 438
<212> TYPE: PRT
<213> ORGANISM: Amanita bisporigera

<400> SEQUENCE: 194

```
Ile Ile Ser Gln Lys Pro Thr Tyr Ser Leu Thr Met Ser Asp Ile Asn
  1               5                  10                  15

Thr Ala Arg Leu Pro Phe Phe Gln Pro Pro Glu Phe Arg Pro Pro Cys
             20                  25                  30

Val Gly Asp Asp Ile Glu Met Val Leu Thr Arg Gly Glu Arg Val His
         35                  40                  45

Ile Arg Pro Arg Met Tyr Gln Thr Thr His Val Leu Arg Ile Ser Leu
     50                  55                  60

Cys Met His Gly Leu Ser Val His Ser Tyr Gly Met Lys Val Ser Pro
 65                  70                  75                  80

Ser His Phe Asn Tyr Asn Val Arg Gln Leu Tyr Leu Glu Cys Ser Ser
                 85                  90                  95

Gly His Tyr Val Val Asp Asp Ile Arg Leu Gly Pro Leu Ser Leu His
            100                 105                 110

Gln Lys Tyr Asp Phe Ala Cys Gly Glu Glu Ala Leu Asp Leu Thr His
        115                 120                 125

Leu Phe Ser Ile Thr Arg Phe Leu Phe Gln Val Tyr Val Glu Ser Val
    130                 135                 140

Leu Thr Tyr Lys Thr His Val Asn Asp Pro Val Leu Val Thr Cys
145                 150                 155                 160

Ser Leu Phe Leu Lys Pro Ser Ser Met Ile Arg Val Ile Val Asn Lys
                165                 170                 175

Leu Val Leu Cys Ser Cys Gln Cys Glu Gly Ile Leu Tyr Ala Ser Gly
            180                 185                 190

Phe Lys Lys Ser Val Lys Arg Cys Leu Ser Asn Ile Ser Val Glu Pro
        195                 200                 205

Val Arg Ser Ser Leu Ile Gly Glu Ser Ile Ser Ile Ser Gln Lys
    210                 215                 220

Pro Thr Tyr Ser Leu Thr Met Ser Asp Ile Asn Thr Ala Arg Leu Pro
225                 230                 235                 240

Phe Phe Gln Pro Pro Glu Phe Arg Pro Pro Cys Val Gly Asp Asp Ile
                245                 250                 255

Glu Met Val Leu Thr Arg Gly Glu Arg Val His Ile Arg Pro Arg Met
            260                 265                 270

Tyr Gln Thr Thr His Val Leu Arg Ile Ser Leu Cys Met His Gly Leu
        275                 280                 285

Ser Val His Ser Tyr Gly Met Lys Val Ser Pro Ser His Phe Asn Tyr
```

```
                290                 295                 300
Asn Val Arg Gln Leu Tyr Leu Glu Cys Ser Ser Gly His Tyr Val Val
305                 310                 315                 320

Asp Asp Ile Arg Leu Gly Pro Leu Ser Leu His Gln Lys Tyr Asp Phe
                325                 330                 335

Ala Cys Gly Glu Glu Ala Leu Asp Leu Thr His Leu Phe Ser Ile Thr
                340                 345                 350

Arg Phe Leu Phe Gln Val Tyr Val Glu Ser Val Leu Thr Tyr Lys Thr
                355                 360                 365

His Val Asn Asp Pro Val Leu Leu Val Thr Cys Ser Leu Phe Leu Lys
                370                 375                 380

Pro Ser Ser Met Ile Arg Val Ile Val Asn Lys Leu Val Leu Cys Ser
385                 390                 395                 400

Cys Gln Cys Glu Gly Ile Leu Tyr Ala Ser Gly Phe Lys Lys Ser Val
                405                 410                 415

Lys Arg Cys Leu Ser Asn Ile Ser Val Glu Pro Val Arg Ser Ser Leu
                420                 425                 430

Ile Gly Glu Ser Ile Ser
        435

<210> SEQ ID NO 195
<211> LENGTH: 96
<212> TYPE: DNA
<213> ORGANISM: Amanita bisporigera

<400> SEQUENCE: 195
cacaatgtct gatatcaata ccgctcgtct tccttgcatc gggttccttg gcattccctc      60
cgtcggtgac gacatcgaga tggtcctcag gcatgg                               96

<210> SEQ ID NO 196
<211> LENGTH: 31
<212> TYPE: PRT
<213> ORGANISM: Amanita bisporigera

<400> SEQUENCE: 196

Thr Met Ser Asp Ile Asn Thr Ala Arg Leu Pro Cys Ile Gly Phe Leu
1               5                   10                  15

Gly Ile Pro Ser Val Gly Asp Asp Ile Glu Met Val Leu Arg His
            20                  25                  30

<210> SEQ ID NO 197
<211> LENGTH: 36
<212> TYPE: PRT
<213> ORGANISM: Amanita bisporigera

<400> SEQUENCE: 197

Pro Ser Ala Met Ser Asp Val Asn Asp Thr Arg Leu Pro Phe Asn Phe
1               5                   10                  15

Phe Arg Phe Pro Tyr Pro Cys Ile Gly Asp Asp Ser Gly Ser Val Leu
            20                  25                  30

Arg Leu Gly Glu
        35

<210> SEQ ID NO 198
<211> LENGTH: 93
<212> TYPE: DNA
<213> ORGANISM: Amanita bisporigera

<400> SEQUENCE: 198
```

```
cottccgaac caagaaccta cagatacctt tgcactctca caatgtctga catcaatgcc    60
atccgtgctc ccatcctgat gctcgcaatt ttg                                 93
```

<210> SEQ ID NO 199
<211> LENGTH: 31
<212> TYPE: PRT
<213> ORGANISM: Amanita bisporigera

<400> SEQUENCE: 199

Pro Ser Glu Pro Arg Thr Tyr Arg Tyr Leu Cys Thr Leu Thr Met Ser
1               5                   10                  15

Asp Ile Asn Ala Ile Arg Ala Pro Ile Leu Met Leu Ala Ile Leu
            20                  25                  30

<210> SEQ ID NO 200
<211> LENGTH: 816
<212> TYPE: DNA
<213> ORGANISM: Amanita bisporigera

<400> SEQUENCE: 200

```
ttcaatttaa tgcccccctg cgtcggtgac gacatcaaca tggtcctcac gcgtggcgag    60
aggtgagtac aaattccggc aacaatgta tcaaaccact tacgtgctac gtattagcct    120
ttgctagatg cattctatcg gtccactcct gtggcatgaa ggtgtcgccg tctcacttaa    180
attacaacgt aaagcaattg tactgacttg gatgtagtag tggacactgt tgttgacgat    240
atcaggctcg gaccattgag cctgcatcag aagtatgact ttggttgtgg taaagtactg    300
ggttaactcg tcttttcttc ctagataact cacgttcgtt ttcatttgaa tctgctttgt    360
aaacatataa aacccacgtc tacgatccgt gccatacttg ttctttgttc ttgtcagatt    420
tcgaaattgc caacgatatg ccagttttcc tgtgtctgca agcttggaac tgtgtgcgtc    480
ggatactgga tactggcgtt tcctcgtcct aaaggtagca agtgcgcat gcgggtgcta    540 acggttgcat gataaatcat cgcaagcatc aatgggttc gttggcaacg atccaaatga    600
acgactgagg gcttcgaaat gtgtagatgg ttgcaaaaac aaaacaaaaa accattaga    660 ccgtgaatat cgaatctctt agttactatt gatttcgact tggagtatca gccgcgatca    720
tttcgtcctc ggccctagta tcacaacata tgtaatatca tcctcaggat tacatgtatt    780
cttcaggtag cgtgactgtg atacctacct cccttc                              816
```

<210> SEQ ID NO 201
<211> LENGTH: 258
<212> TYPE: PRT
<213> ORGANISM: Amanita bisporigera

<400> SEQUENCE: 201

Phe Asn Leu Met Pro Pro Cys Val Gly Asp Asp Ile Asn Met Val Leu
1               5                   10                  15

Thr Arg Gly Glu Arg Val Gln Ile Pro Ala Asn Asn Val Ser Asn His
            20                  25                  30

Leu Arg Ala Thr Tyr Pro Leu Leu Asp Ala Phe Tyr Arg Ser Thr Pro
        35                  40                  45

Val Ala Arg Cys Arg Arg Leu Thr Ile Thr Thr Ser Asn Cys Thr Asp
    50                  55                  60

Leu Asp Val Val Asp Thr Val Val Asp Asp Ile Arg Leu Gly Pro
65                  70                  75                  80

Leu Ser Leu His Gln Lys Tyr Asp Phe Gly Cys Gly Lys Val Leu Gly

```
                    85                  90                  95
Leu Val Phe Ser Ser Ile Thr His Val Arg Phe His Leu Asn Leu Leu
                100                 105                 110

Cys Lys His Ile Lys Pro Thr Ser Thr Ile Arg Ala Ile Leu Val Leu
            115                 120                 125

Cys Ser Cys Gln Ile Ser Lys Leu Pro Thr Ile Cys Gln Phe Ser Cys
130                 135                 140

Val Cys Lys Leu Gly Thr Val Cys Val Gly Tyr Trp Ile Leu Ala Phe
145                 150                 155                 160

Pro Arg Pro Lys Gly Ser Lys Val Arg Met Arg Val Leu Thr Val Ala
                165                 170                 175

Ile Ile Ala Ser Ile Asn Gly Phe Arg Trp Gln Arg Ser Lys Thr Thr
                180                 185                 190

Glu Gly Phe Glu Met Cys Arg Trp Leu Gln Lys Gln Asn Lys Lys Thr
            195                 200                 205

Ile Arg Pro Ile Ser Asn Leu Leu Val Thr Ile Asp Phe Asp Leu Glu
210                 215                 220

Tyr Gln Pro Arg Ser Phe Arg Pro Arg Pro Tyr His Asn Ile Cys Asn
225                 230                 235                 240

Ile Ile Leu Arg Ile Thr Cys Ile Leu Gln Val Ala Leu Tyr Leu Pro
                245                 250                 255

Pro Phe

<210> SEQ ID NO 202
<211> LENGTH: 882
<212> TYPE: DNA
<213> ORGANISM: Amanita bisporigera

<400> SEQUENCE: 202
tctggtaaag gatgagttaa cccaatgctt caccacaagg aaactcatac ttctgatgca      60
ggctcaacgg tccaagcctg atatcgtcaa caacagtgtc cactactacg tccaagtcag     120
tacaattgcc ttcaatgcgt tgaagttgaa aagagacggc gacaccttca tgccatagga     180
gtggatcgat atactgtgca tttaggaaag gctaataata cgtagcacgt aagtcatttg     240
atacatcgtt ggccagatgt tgtactcacc tctcgccacg cgtgaggacc atctcgatgt     300
cgtcaccgac gcagggggc atccgaacgg gagggaggaa gagaggaaga cgagcagtat      360
tgatgtcaga catcgtaaaa ggaagctgta ggtttctgaa agattgaagt ttggagggga     420
actgagtttt gaacgctccg cccccagcat cttttatctg tcccagtcat ggcctattgc     480
tgatttgggc agaggcaaac ctcaatccgc cgacgacgga agcgaataac ttggataagc     540
gacggtgatt cttttttttat ttatttagag gaacttcggc atcaatcatg ttgatatctt    600
gcagaagtcg tatatcattg tgatatcatt gtgacaaatg tcacccacta tctctttcct     660
tgtgaatgtg ccatgtatcc aacgtccagg tgaagtaaac cttggtgatt ctcgccgccg     720
ctgcggtgat attgacagca taatgatctg aaaacgtact gatggaagcg tacttgacgg     780
cccgtccaaa ctgacatggg agtaatcgca cagtattact atgctatttg tattcagatt     840
ccacaattcc attacagtca cccgtgagtt ttccatatct gc                       882

<210> SEQ ID NO 203
<211> LENGTH: 285
<212> TYPE: PRT
<213> ORGANISM: Amanita bisporigera

<400> SEQUENCE: 203
```

Arg Tyr Gly Lys Leu Thr Gly Asp Cys Asn Gly Ile Val Glu Ser Glu
1               5                   10                  15

Tyr Lys His Ser Asn Thr Val Arg Leu Leu Pro Cys Gln Phe Gly Arg
                20                  25                  30

Ala Val Lys Tyr Ala Ser Ile Ser Thr Phe Ser Asp His Tyr Ala Val
            35                  40                  45

Asn Ile Thr Ala Ala Ala Arg Ile Thr Lys Val Tyr Phe Thr Trp
50                  55                  60

Thr Leu Asp Thr Trp His Ile His Lys Glu Arg Asp Ser Gly His Leu
65                  70                  75                  80

Ser Gln Tyr His Asn Asp Ile Arg Leu Leu Gln Asp Ile Asn Met Ile
                85                  90                  95

Asp Ala Glu Val Pro Leu Asn Lys Lys Asn His Arg Arg Leu Ser
            100                 105                 110

Lys Leu Phe Ala Ser Val Val Gly Gly Leu Arg Phe Ala Ser Ala Gln
        115                 120                 125

Ile Ser Asn Arg Pro Leu Gly Gln Ile Lys Asp Ala Gly Gly Ala
130                 135                 140

Phe Lys Thr Gln Phe Pro Ser Lys Leu Gln Ser Phe Arg Asn Leu Gln
145                 150                 155                 160

Leu Pro Phe Thr Met Ser Asp Ile Asn Thr Ala Arg Leu Pro Leu Phe
                165                 170                 175

Leu Pro Pro Val Arg Met Pro Pro Cys Val Gly Asp Asp Ile Glu Met
                180                 185                 190

Val Leu Thr Arg Gly Glu Arg Val Gln His Leu Ala Asn Asp Val Ser
        195                 200                 205

Asn Asp Leu Arg Ala Thr Tyr Tyr Pro Phe Leu Asn Ala Gln Tyr Ile
210                 215                 220

Asp Pro Leu Leu Trp His Glu Gly Val Ala Val Ser Phe Gln Leu Gln
225                 230                 235                 240

Arg Ile Glu Gly Asn Cys Thr Asp Leu Asp Val Val Asp Thr Val
            245                 250                 255

Val Asp Asp Ile Arg Leu Gly Pro Leu Ser Leu His Gln Lys Tyr Glu
            260                 265                 270

Phe Pro Cys Gly Glu Ala Leu Gly Leu Ile Leu Tyr Gln
        275                 280                 285

<210> SEQ ID NO 204
<211> LENGTH: 881
<212> TYPE: DNA
<213> ORGANISM: Amanita bisporigera

<400> SEQUENCE: 204
cctctgaaac ttgctgcgac ggcacgatct gactgggaga tcttcgttgc atctctaggt    60
tgagtgaatt cacaattcca gtattcagtt cggaggagca tgttggatcg attaccgtac   120
gttctggctc ttcatcgact ggctttagga acgaacctta ccaaacttgt atatcgtatt   180
gcaggtgaat cgagaaaaca ccttttacgt cgagtgttgt aacctggctc aaagattcaa   240
aaactctcaa cgacaagcag tttattgact ataacaccga tcgtcgacgt gggatttgtg   300
tttacagaac aaattcgaca gagaacgaga agaatgtaa gttatctggg agacaaatta   360
gaccagtgct tcgtgacgaa caaagtcata cttctgatgc aggctcagcg gtccaagcct   420
ggtatcgtca acagcagagt ccactactac atgcatttag caaaggctat acgtagcatg   480

-continued

```
taagtgattt gatacatcat tggtcagttg ttgtactcac tcctcgccac gcgtgaggac    540
cacctggatg tcgtcattga cacatggggg gatgaagctc atgaagacga cgtaaggaag    600
acgagcggta ttgatgtcag acattgtgag agttggaggg gaactgagta ttgaatattg    660
gatattgaac gctgcgtccc aagcaccttt tatctgtccc agccatggcc caggcccatt    720
cctagttgag gctcgatcta ttgcaaaatt tgacagcctg cgtggtatgg aagacgaagg    780
actgacgatg atgcttagtt gacatgtgtc aagcccacgt acgatatcga agccagagat    840
agatcgcgta ttcgtatatc gtacgaggga tgcttacttg g                       881
```

<210> SEQ ID NO 205
<211> LENGTH: 280
<212> TYPE: PRT
<213> ORGANISM: Amanita bisporigera

<400> SEQUENCE: 205

```
Lys Ala Ser Leu Val Arg Tyr Thr Asn Thr Arg Ser Ile Ser Gly Phe
  1               5                  10                  15

Asp Ile Val Arg Gly Leu Asp Thr Cys Gln Leu Ser Ile Ile Val Ser
             20                  25                  30

Pro Ser Ser Ile Pro Arg Arg Leu Ser Asn Phe Ala Ile Asp Arg
         35                  40                  45

Ala Ser Thr Arg Asn Gly Pro Gly Pro Trp Leu Gly Gln Ile Lys Gly
     50                  55                  60

Ala Trp Asp Ala Ala Phe Asn Ile Gln Tyr Ser Ile Leu Ser Ser Pro
 65                  70                  75                  80

Pro Thr Leu Thr Met Ser Asp Ile Asn Thr Ala Arg Leu Pro Tyr Val
                 85                  90                  95

Val Phe Met Ser Phe Ile Pro Pro Cys Val Asn Asp Asp Ile Gln Val
            100                 105                 110

Val Leu Thr Arg Gly Glu Glu Val Gln Gln Leu Thr Asn Asp Val Ser
        115                 120                 125

Asn His Leu His Ala Thr Tyr Ser Leu Cys Met His Val Val Val Asp
    130                 135                 140

Ser Ala Val Asp Asp Thr Arg Leu Gly Pro Leu Ser Leu His Gln Lys
145                 150                 155                 160

Tyr Asp Phe Val Arg His Glu Ala Leu Val Phe Val Ser Gln Ile Thr
                165                 170                 175

Tyr Ile Leu Ser Arg Ser Leu Ser Asn Leu Phe Cys Lys His Lys Ser
            180                 185                 190

His Val Asp Asp Arg Cys Tyr Ser Gln Thr Ala Cys Arg Glu Phe Leu
        195                 200                 205

Asn Leu Ala Arg Leu Gln His Ser Thr Lys Val Phe Ser Arg Phe Thr
    210                 215                 220

Cys Asn Thr Ile Tyr Lys Phe Gly Lys Val Arg Ser Ser Gln Ser Met
225                 230                 235                 240

Lys Ser Gln Asn Val Arg Ser Ile Gln His Ala Pro Asn Ile Leu
                245                 250                 255

Glu Leu Ile His Ser Thr Arg Cys Asn Glu Asp Leu Pro Val Arg Ser
            260                 265                 270

Cys Arg Arg Ser Lys Phe Gln Arg
        275                 280
```

<210> SEQ ID NO 206
<211> LENGTH: 172

```
<212> TYPE: DNA
<213> ORGANISM: Amanita bisporigera

<400> SEQUENCE: 206
ggaccatcag gatgtcgtca ccgacgcaag ggaggagcat tggcgaggag aggggaagac    60
gagcggtatt gatgtcagac attgtgagag agtaaaggaa gttgtaggtt tctgaaagat   120
tcaagtttgg aggggaggtg agtattgaac gctgcgcccc cagcacctcc ag           172

<210> SEQ ID NO 207
<211> LENGTH: 57
<212> TYPE: PRT
<213> ORGANISM: Amanita bisporigera

<400> SEQUENCE: 207

Leu Glu Val Leu Gly Ala Gln Arg Ser Ile Leu Thr Ser Pro Pro Asn
 1               5                  10                  15

Leu Asn Leu Ser Glu Thr Tyr Asn Phe Leu Tyr Ser Leu Thr Met Ser
             20                  25                  30

Asp Ile Asn Thr Ala Arg Leu Pro Leu Ser Ser Pro Met Leu Leu Pro
         35                  40                  45

Cys Val Gly Asp Asp Ile Leu Met Val
     50                  55

<210> SEQ ID NO 208
<211> LENGTH: 234
<212> TYPE: DNA
<213> ORGANISM: Amanita bisporigera

<400> SEQUENCE: 208
ccttccgaac caagaaccta cagatacctt tgcactctca caatgtctga catcaatgcc    60
atccgtgctc ccatcctgat gctcgcaatt ttgccctgcg tcggcgacga catcgaggtc   120
ctcaggcgtg gcgaggggtg agcctaacat ccgtcaacgg cgtacaaatg tacttatgcg   180
ctgcgtatca gcctttccta aatacccggt tcatcagctc gctcctatgg catg         234

<210> SEQ ID NO 209
<211> LENGTH: 75
<212> TYPE: PRT
<213> ORGANISM: Amanita bisporigera

<400> SEQUENCE: 209

Pro Ser Glu Pro Arg Thr Tyr Arg Tyr Leu Cys Thr Leu Thr Met Ser
 1               5                  10                  15

Asp Ile Asn Ala Ile Arg Ala Pro Ile Leu Met Leu Ala Ile Leu Pro
             20                  25                  30

Cys Val Gly Asp Asp Ile Glu Val Leu Arg Arg Gly Glu Gly Ala His
         35                  40                  45

Pro Ser Thr Ala Tyr Lys Cys Thr Tyr Ala Leu Arg Ile Ser Leu Ser
     50                  55                  60

Ile Pro Gly Ser Ser Ala Arg Ser Tyr Gly Met
 65                  70                  75

<210> SEQ ID NO 210
<211> LENGTH: 1706
<212> TYPE: DNA
<213> ORGANISM: Amanita bisporigera

<400> SEQUENCE: 210
cttctaacgt gggctttacg tgtttataaa tgtgaaaaac cttaaaagaa aaaaatcaga    60
```

```
gttgtccccc acagacaaaa taaggactta ctccgatgta ggctcaacgg tccaagcctc    120
atatcgtgaa caactttgaa aatttatcac tacataatac atacgagtca gaacggttgc    180
cttgtattat acgaggatgg cgacaccttt aatggcaccg agttctcagc agagactaac    240
gcacgcgaca taagtgtaca tcattgggta gatgatattg ctcacctctc gccacgagtg    300
agggtagggt tgacgtcgtc actgacgcac ggaattccga ggggtatcaa accagggatg    360
ggaagacgag tgccattgat atcagacatt gcgaatgaga gtaaaggagg ctctgagagg    420
tcttggattc aagttgggag aggaactggg tattgtacgc cctgcccgat gccttttat    480 ctgtctcagc caaggccaat tgcctagttg gcatagggga aacccaagag gcgcttcgag    540
ttcgtccgtg gtcattcaag ctcttttagg agagctggaa ccatgatggg cctaatgtag    600
ctcaaccagg tatggaatgg cgcaagaatt ccggccagaa cggatgatat gagtggttct    660
catcacgctg ttcgctgact tccaacgtcc aacgtctttg ggtacatgaa gtacggcatg    720
tcctcttaga aaaaaggcc ggtggacgat ggacagtagc gaacatcgtg gtgcctatag    780
gctatggcgt agccggatgt gggtagaaca aaggagcggt gcatgttgga cagtagtgaa    840
cagcgtggcg tcctcgtttc gcacgaggta ccgccgcact gactcgttgt gcgctgataa    900
aggatatcgg ccctcgatcg cgcaccgccc catcatgcgc tccattgcca ccacgaggat    960
gtgcatacag tgcaaccccc cgaggactgc acgacccagt tgatccgcga caagtactcc   1020
gcgcagaacg tggtcgggag gtactggcgc atacatcacc cggcccaagc gcaagcatcc   1080
gcggctgatc cgagcttgca caagctggtc gaagacgtag ctctcccaaa catgtctgtc   1140 cgcccttttcg caaactggtc gctcgacagc cctaaaatct gctccgcctt cgagtgcaga   1200
tccgtcccag cagccttagt ccaagtgtca tccaccccag tgtcgtcgcg tgatgcatcc   1260
caaattgcgc atccccatac agcttgaaat ctacacttcc tcagggtcca tgtccgcatc   1320
gactatcgcg tgcccaggcg gcacgcacca tcacggttct gcttcacatt caaccacgtc   1380
ttttcgatcg cgcgccgcat gatggcgcct atcgtgatcg atgatcacct ggggaagcct   1440
gaagatcatc ccccacgtag agaagcaaga atccacttca tcgtgacatc gcaccaccaa   1500
ccgcaagcgg aagaagcttc ctccaccagt cccaaccaat gccaaacatt ctcttgtctc   1560
tattccgctt gttgtcgtcg tcaccctcgt cgtcgcagag agcaggacta tttgactcgg   1620
gcgacccgcc caatccttcg atgctgacga tcttatgaca ttgcccgctt gccttctcac   1680
attaatttga ggacgaactg gattcg                                         1706
```

<210> SEQ ID NO 211
<211> LENGTH: 542
<212> TYPE: PRT
<213> ORGANISM: Amanita bisporigera

<400> SEQUENCE: 211

Arg Ile Gln Phe Val Leu Lys Leu Met Glu Gly Lys Arg Ala Met Ser
1               5                   10                  15

Asp Arg Gln His Arg Arg Ile Gly Arg Val Ala Arg Val Lys Ser Cys
            20                  25                  30

Ser Leu Arg Arg Arg Gly Arg Arg Gln Gln Ala Glu Arg Gln Glu Asn
        35                  40                  45

Val Trp His Trp Leu Gly Leu Val Glu Glu Ala Ser Ser Ala Cys Gly
    50                  55                  60

Trp Trp Cys Asp Val Thr Met Lys Trp Ile Leu Ala Ser Leu Arg Gly
65                  70                  75                  80

-continued

```
Gly Ser Ser Gly Phe Pro Arg Ser Ile Thr Ile Gly Ala Ile Met
                 85              90              95

Arg Arg Ala Ile Glu Lys Thr Trp Leu Asn Val Lys Gln Asn Arg Asp
            100             105             110

Gly Ala Cys Arg Leu Gly Thr Arg Ser Met Arg Thr Trp Thr Leu Arg
            115             120             125

Lys Cys Arg Phe Gln Ala Val Trp Gly Cys Ala Ile Trp Asp Ala Ser
130             135             140

Arg Asp Asp Thr Gly Val Asp Asp Thr Trp Thr Lys Ala Ala Gly Thr
145             150             155             160

Asp Leu His Ser Lys Ala Glu Gln Ile Leu Gly Leu Ser Ser Asp Gln
            165             170             175

Phe Ala Lys Gly Arg Thr Asp Met Phe Gly Arg Ala Thr Ser Ser Thr
            180             185             190

Ser Leu Cys Lys Leu Gly Ser Ala Ala Asp Ala Cys Ala Trp Ala Gly
            195             200             205

Cys Met Arg Gln Tyr Leu Pro Thr Thr Phe Cys Ala Glu Tyr Leu Ser
            210             215             220

Arg Ile Asn Trp Val Val Gln Ser Ser Gly Gly Cys Thr Val Cys Thr
225             230             235             240

Ser Ser Trp Trp Gln Trp Ser Ala Trp Gly Gly Ala Arg Ser Arg Ala
            245             250             255

Asp Ile Leu Tyr Gln Arg Thr Ser Gln Cys Gly Gly Thr Ser Cys
            260             265             270

Glu Thr Arg Thr Pro Arg Cys Ser Leu Leu Ser Asn Met His Arg Ser
            275             280             285

Phe Val Leu Pro Thr Ser Gly Tyr Ala Ile Ala Tyr Arg His His Asp
            290             295             300

Val Arg Tyr Cys Pro Ser Ser Thr Gly Leu Phe Phe Glu Asp Met Pro
305             310             315             320

Tyr Phe Met Tyr Pro Lys Thr Leu Asp Val Gly Ser Gln Arg Thr Ala
            325             330             335

Glu Pro Leu Ile Ser Ser Val Leu Ala Gly Ile Leu Ala Pro Phe His
            340             345             350

Thr Trp Leu Ser Tyr Ile Arg Pro Ile Met Val Pro Ala Leu Leu Lys
            355             360             365

Glu Leu Glu Pro Arg Thr Asn Ser Lys Arg Leu Leu Gly Phe Pro Met
370             375             380

Pro Asn Ala Ile Gly Leu Gly Asp Arg Lys Gly Ile Gly Gln Gly Val
385             390             395             400

Gln Tyr Pro Val Pro Leu Pro Thr Ile Gln Asp Leu Ser Glu Pro Pro
            405             410             415

Leu Leu Ser Phe Ala Met Ser Asp Ile Asn Gly Thr Arg Leu Pro Ile
            420             425             430

Pro Gly Leu Ile Pro Leu Gly Ile Pro Cys Val Ser Asp Val Asn
            435             440             445

Pro Thr Leu Thr Arg Gly Glu Arg Ala Ile Ser Ser Thr Gln Cys Thr
450             455             460

Leu Met Ser Arg Ala Leu Val Ser Ala Glu Asn Ser Val Pro Leu Lys
465             470             475             480

Val Ser Pro Ser Ser Tyr Asn Thr Arg Gln Pro Phe Leu Val Cys Ile
            485             490             495
```

```
Met Ile Phe Lys Val Val His Asp Met Arg Leu Gly Pro Leu Ser Leu
            500                 505                 510

His Arg Ser Lys Ser Leu Phe Cys Leu Trp Gly Thr Thr Leu Ile Phe
        515                 520                 525

Phe Phe Gly Phe Ser His Leu Thr Arg Lys Ala His Val Arg
    530                 535                 540

<210> SEQ ID NO 212
<211> LENGTH: 146
<212> TYPE: DNA
<213> ORGANISM: Amanita bisporigera

<400> SEQUENCE: 212
aatctcagcg ttcagtaccc aactcccatt cgaacctaac tccaagacct ctaaacctca      60
caatcccaat gtctgacatc aatgctaccc gtctccccat ctggggtatc ggttgcaacc     120
cgtgcgtcgg tgacgacgtc actacg                                          146

<210> SEQ ID NO 213
<211> LENGTH: 48
<212> TYPE: PRT
<213> ORGANISM: Amanita bisporigera

<400> SEQUENCE: 213

Ser Gln Arg Ser Val Pro Asn Ser His Ser Asn Leu Thr Pro Arg Pro
  1               5                  10                  15

Leu Asn Leu Thr Ile Pro Met Ser Asp Ile Asn Ala Thr Arg Leu Pro
             20                  25                  30

Ile Trp Gly Ile Gly Cys Asn Pro Cys Val Gly Asp Asp Val Thr Thr
         35                  40                  45

<210> SEQ ID NO 214
<211> LENGTH: 103
<212> TYPE: DNA
<213> ORGANISM: Amanita bisporigera

<400> SEQUENCE: 214
gtccgacatc aacgccactc gtcttcccat gatccaacgc ccttctacc cgtgcgccag       60 tgacgacgtc acctccaccc tcactcgtgg cgagaggtga gcg                       103

<210> SEQ ID NO 215
<211> LENGTH: 33
<212> TYPE: PRT
<213> ORGANISM: Amanita bisporigera

<400> SEQUENCE: 215

Ser Asp Ile Asn Ala Thr Arg Leu Pro Met Ile Gln Arg Pro Phe Tyr
  1               5                  10                  15

Pro Cys Ala Ser Asp Asp Val Thr Ser Thr Leu Thr Arg Gly Glu Arg
             20                  25                  30

Ala

<210> SEQ ID NO 216
<211> LENGTH: 103
<212> TYPE: DNA
<213> ORGANISM: Amanita bisporigera

<400> SEQUENCE: 216
ccgaacttaa atcccagacc tcacaaagcc tctttattct tgaatcgcaa tgtctgatat      60
caatgccgct cgtcttccca tcattttga accaatcatc ccg                        103
```

<210> SEQ ID NO 217
<211> LENGTH: 32
<212> TYPE: PRT
<213> ORGANISM: Amanita bisporigera

<400> SEQUENCE: 217

Arg Thr Ile Pro Asp Leu Thr Lys Pro Leu Tyr Ser Ile Ala Met Ser
1               5                   10                  15

Asp Ile Asn Ala Ala Arg Leu Pro Ile Ile Phe Glu Pro Ile Ile Pro
            20                  25                  30

<210> SEQ ID NO 218
<211> LENGTH: 168
<212> TYPE: DNA
<213> ORGANISM: Amanita bisporigera

<400> SEQUENCE: 218

```
tgctgggctc acttctcgcc cctagtgagg gtgaaattgt ccgcgtcacc gacgcacggc      60
ataggaacag gtgggtacgc gccggggaga cgggtggcat tgatgtccga cattgcgatt     120
gagagtagag gatgctgtag gtttctgagg ggtcttgtga gtattgaa                  168
```

<210> SEQ ID NO 219
<211> LENGTH: 54
<212> TYPE: PRT
<213> ORGANISM: Amanita bisporigera

<400> SEQUENCE: 219

Ser Ile Leu Thr Arg Pro Leu Arg Asn Leu Gln His Pro Leu Leu Ser
1               5                   10                  15

Ile Ala Met Ser Asp Ile Asn Ala Thr Arg Leu Pro Gly Ala Tyr Pro
            20                  25                  30

Pro Val Pro Met Pro Cys Val Gly Asp Ala Asp Asn Phe Thr Leu Thr
        35                  40                  45

Arg Gly Glu Lys Ala Gln
    50

<210> SEQ ID NO 220
<211> LENGTH: 105
<212> TYPE: DNA
<213> ORGANISM: Amanita bisporigera

<400> SEQUENCE: 220

```
atgtctgaca tcaatgccac ccgtctcccc catccgtttc cattaggatt gcaaccgtgt      60
gccggtgacg tggacaattt gaccctcact aaaggcgaag ggtga                    105
```

<210> SEQ ID NO 221
<211> LENGTH: 34
<212> TYPE: PRT
<213> ORGANISM: Amanita bisporigera

<400> SEQUENCE: 221

Met Ser Asp Ile Asn Ala Thr Arg Leu Pro His Pro Phe Pro Leu Gly
1               5                   10                  15

Leu Gln Pro Cys Ala Gly Asp Val Asp Asn Leu Thr Leu Thr Lys Gly
            20                  25                  30

Glu Gly

<210> SEQ ID NO 222

-continued

```
<211> LENGTH: 105
<212> TYPE: DNA
<213> ORGANISM: Amanita bisporigera

<400> SEQUENCE: 222
atgtctgaca tcaatgccac ccgtctcccc catccgtttc cattaggatt gcaaccgtgt      60
gccggtgacg tggacaattt gaccctcact aaaggcgaag gtga                     105

<210> SEQ ID NO 223
<211> LENGTH: 34
<212> TYPE: PRT
<213> ORGANISM: Amanita bisporigera

<400> SEQUENCE: 223

Met Ser Asp Ile Asn Ala Thr Arg Leu Pro His Pro Phe Pro Leu Gly
 1               5                  10                  15

Leu Gln Pro Cys Ala Gly Asp Val Asp Asn Leu Thr Leu Thr Lys Gly
            20                  25                  30

Glu Gly

<210> SEQ ID NO 224
<211> LENGTH: 96
<212> TYPE: DNA
<213> ORGANISM: Amanita phalloides

<400> SEQUENCE: 224
atgtcagata tcaatgcgac gcgtcttccc atatggggaa taggttgcga cccgtgcatc      60
ggtgacgacg tcaccatact cctcactcgt ggcgag                               96

<210> SEQ ID NO 225
<211> LENGTH: 32
<212> TYPE: PRT
<213> ORGANISM: Amanita phalloides

<400> SEQUENCE: 225

Met Ser Asp Ile Asn Ala Thr Arg Leu Pro Ile Trp Gly Ile Gly Cys
 1               5                  10                  15

Asp Pro Cys Ile Gly Asp Asp Val Thr Ile Leu Leu Thr Arg Gly Glu
            20                  25                  30

<210> SEQ ID NO 226
<211> LENGTH: 93
<212> TYPE: DNA
<213> ORGANISM: Amanita ocreata

<400> SEQUENCE: 226
atgtcagaca ttaacgcgac ccgtcttccc gcctggctcg ccacctgccc gtgcgccggt      60
gacgacgtca accctctcct cactcgtggc gag                                  93

<210> SEQ ID NO 227
<211> LENGTH: 31
<212> TYPE: PRT
<213> ORGANISM: Amanita ocreata

<400> SEQUENCE: 227

Met Ser Asp Ile Asn Ala Thr Arg Leu Pro Ala Trp Leu Ala Thr Cys
 1               5                  10                  15

Pro Cys Ala Gly Asp Asp Val Asn Pro Leu Leu Thr Arg Gly Glu
            20                  25                  30
```

<210> SEQ ID NO 228
<211> LENGTH: 33
<212> TYPE: PRT
<213> ORGANISM: Amanita bisporigera

<400> SEQUENCE: 228

Gln Thr Val Gln Ile Phe Tyr Pro Ser Lys Asp Gly Thr Lys Ile Pro
1               5                   10                  15

Met Phe Ile Val His Lys Lys Ser Ile Lys Leu Asp Gly Ser His Pro
            20                  25                  30

Ala

<210> SEQ ID NO 229
<211> LENGTH: 32
<212> TYPE: PRT
<213> ORGANISM: Amanita bisporigera

<400> SEQUENCE: 229

Ile Phe Tyr Pro Ser Lys Asp Gly Thr Lys Ile Pro Met Phe Ile Val
1               5                   10                  15

His Lys Lys Ser Ile Lys Leu Asp Gly Ser His Pro Ala Phe Leu Tyr
            20                  25                  30

<210> SEQ ID NO 230
<211> LENGTH: 26
<212> TYPE: PRT
<213> ORGANISM: Amanita bisporigera

<400> SEQUENCE: 230

Lys Arg Leu Thr Ile Asn Gly Gly Ser Asn Gly Gly Leu Leu Val Ala
1               5                   10                  15

Ala Cys Ala Asn Gln Arg Pro Asp Leu Phe
            20                  25

<210> SEQ ID NO 231
<211> LENGTH: 27
<212> TYPE: PRT
<213> ORGANISM: Amanita bisporigera

<400> SEQUENCE: 231

Ser Asp Asp Gly Thr Val Ala Leu Arg Gly Tyr Ala Phe Ser Glu Asp
1               5                   10                  15

Gly Glu Tyr Phe Ala Tyr Gly Leu Ser Ala Ser
            20                  25

<210> SEQ ID NO 232
<211> LENGTH: 20
<212> TYPE: PRT
<213> ORGANISM: Amanita bisporigera

<400> SEQUENCE: 232

Pro Leu Leu Ile His Val Asp Thr Lys Ala Gly His Gly Ala Gly Lys
1               5                   10                  15

Pro Thr Ala Lys
            20

<210> SEQ ID NO 233
<211> LENGTH: 16
<212> TYPE: PRT
<213> ORGANISM: Amanita bisporigera

<400> SEQUENCE: 233

Asp Gly Thr Lys Ile Pro Met Phe Ile Val His Lys Lys Ser Ile Lys
 1               5                  10                  15

<210> SEQ ID NO 234
<211> LENGTH: 2444
<212> TYPE: DNA
<213> ORGANISM: Amanita bisporigera

<400> SEQUENCE: 234

| | | | | | |
|---|---|---|---|---|---|
| acaccgtctc | aaattcaagc | catgcaccgt | tttttgcagc | ccgtaagaga | acgccttcgc | 60 |
| tctgctctcg | cccgctactt | tggttcgcgg | atcatgtctt | ctacacagtg | gacacccaac | 120 |
| atgtacccct | ctgctcgccg | ttcagaccat | atagacacat | acaggagcga | aacgagaggc | 180 |
| gaagtcaagg | tgccggaccc | gtaccactgg | ctagaggaat | attcagaaga | gacggacaag | 240 |
| tggacgtccg | accaggagga | gttcacgagg | acatatttgg | acagcaaccc | tgatcgaaag | 300 |
| aagctagaag | acgcattcag | aaagagtatg | gattatccca | agttctccgc | tccttttttg | 360 |
| aatgatgaca | agcgatggta | ttggttttac | aataccggcc | ttcaagcaca | aacagtcatc | 420 |
| tgcagatcaa | aggatgagac | tcttcccgac | ttctcagaga | gtgactacgt | cggggaaaca | 480 |
| ttttttgatc | cgaacctatt | atcctcggat | ggcacagcct | cgctctccat | gtatgatttc | 540 |
| tcacactgtg | gcaaatactt | cgcatatggt | atttctcttt | ccgggagcga | ttttcaact | 600 |
| atatacgtac | ggtcaacttc | ctctccactg | gcccctggca | acaacagcat | agaaatgac | 660 |
| gacggtagac | ttccagacga | gcttagatat | gtcaaatttt | cctccatcag | ctggacaaag | 720 |
| gactccaaag | gattttttcta | tcagcgctat | cccggtacag | gcactgtgaa | tggacagaat | 780 |
| ggcatccaaa | ctcaaggcga | tcgtgatgct | atgatttact | atcaccggat | agggacatca | 840 |
| caatccgatg | atattcttgt | gcatgaagac | caggaacatc | ctgattgggt | atttggcgca | 900 |
| gaagtcacgg | aagatggtaa | atatgtggcc | ctgtacacaa | tgaaggacac | atcaaggaaa | 960 |
| aatctattgt | ggattgctga | tcttggacaa | aacgaagttg | gacgaaacat | gaaatggaac | 1020 |
| aagatttgca | acgttttttga | ctcagaatac | gacctaattg | gcaacgacgg | ttcattacta | 1080 |
| tacatcagaa | ctaataaagc | tgcacctcaa | tacaagattg | tcaccttaga | tatagagaaa | 1140 |
| ccagaattag | ggtttaagga | attcataccg | gaagatccca | aagcatatct | ctctcaagtc | 1200 |
| aaaattttta | ataaggatag | actagcacta | gtatacaagc | gtaacgttat | aggcgaactc | 1260 |
| tacgtctaca | ataacactgg | gtcacgacta | atgcgcctag | cccgggactt | tgttggctcc | 1320 |
| atgacggtga | ccgctcgaga | aacggagcca | tggttttttg | ccactctcac | gggcttcaat | 1380 |
| accccctggaa | tcgtatgcag | gtacaatatc | cagcgaccgg | aagaacagcg | ttggagcgta | 1440 |
| tatcgaactg | ccaaggtcaa | gggtttaaat | ccgaacgatt | tcgaggctcg | acaggtgtgg | 1500 |
| tatgacagct | acgatggaac | aaagattcca | atgttcatcg | tccgtcacaa | gaatacccaa | 1560 |
| tttaatggga | cggcgccagc | tatacaatat | ggttacggtg | gctttaatat | atctataaat | 1620 |
| ccccttcttta | gtccaacgat | tttgacgttc | ttgcaaaagt | atggagcaat | tctagctgta | 1680 |
| cctaatatcc | gaggaggcgg | cgagttcggc | gagacatggc | atgatgctgg | tatacgagag | 1740 |
| aaacgagcta | atgtttacga | tgatttcatt | gcggcaactc | agttcttggt | aaaaaacaag | 1800 |
| tatgccgcgg | gcggcaaagt | ggccatcaac | gggggtccca | atgaggact | tttggtcgcg | 1860 |
| gcctgtgtca | atcgtgcacg | tgaaggaacc | tttggagctg | ccattgctga | agttggggtc | 1920 |
| ctagacttgc | tcaagttccc | caaatttacc | ataggcaaag | cttggattag | cgactacggc | 1980 |
| gatccagaag | atccgcgtga | ttttgattac | atttacacac | attcaccact | tcataatata | 2040 |

```
ccaaagaaca tggtcttacc tccgacgatg cttctgacag ctgatcatga tgaccgtgtc    2100
gtcccaatgc attcatttaa gtatgctgca atgctacaat acaccctgcc gcataatcgt    2160
catccacttc tgctacgtgt agacaagaaa gcggggcatg gcggaggaaa atctactgag    2220
aagaggttac aggaggctgc cgacaaatgg ggttttgccg cgcagtccat gggtcttgcg    2280
tggaaggata gacaagctaa tctgtgatga gtttcggcat gcattcagca tttagacatc    2340
tgttttactg tttgggctac attttacgac actcacgatt ccaggtatat tatttaacgc    2400
attgcacttg tgcaggctaa aaaaaaaaaa aaaaaaaaaa aaaa                     2444

<210> SEQ ID NO 235
<211> LENGTH: 2189
<212> TYPE: DNA
<213> ORGANISM: Amanita bisporigera

<400> SEQUENCE: 235 atgccccta caccatgggc tcctcacagt tatcctccta cccgtcgttc tgaccacgtt     60
gatgtatatc agagcgcatc cagaggcgaa gtaccagtac cggacccgta ccaatggctg    120
gaggagaatt caaatgaagt cgacgaatgg acgacggcgc agacagcttt cacgcaaggc    180
tatcttgata agaatgcgga tagacagaag ctcgaggaga atttcgtgc aagcaaggac     240 tacgtcaagt tttctgcgcc aactctgctt gatagtggac actggtattg gttctacaat    300
agcggcgtac aatcgcaagc agtcctctac cgctccaaga aacccgttct tcctgatttc    360
tcaaagaggg acgaggaaat cggcgaagta tacttcgatc caaacgtact ctctgctgat    420
ggcaccgcaa ttatgggcac gtgccgattc tcccctagtg gcgagtattt cgcatatgca    480
gtgtcccact gggagttga ttatttact atctatgttc gccctacgag ttcatcattg      540
tctcaagctc cggaagctga aggtggggat ggtcgattgt cggatgaagt gaatggtgc     600 aagtttacga ctataacgtg gacaaaggac tccaaaggat ttctttacca gcggtaccct    660
gctcgggaat ctcttgtggc gaaagatcgt gataaagatg ctatggtatg ctatcatagg    720
gttggaacga ctcaattgga agatatcatt gtccaacaag acaaggagaa cccagactgg    780
acatatggga cagatgcgtc agaggacggc aaatatatct acttagtggt atacaaggat    840
gcctcgaagc aaaatcttct gtgggttgca gaattcgaca aggacggggt caagccggaa    900
attccctggc gaaaagtcat caatgagttt ggggcggatt accatgttat cacgaaccac    960
ggatctttga tctatgtcaa gactaacgtg aatgcgcccc aatataaagt tgtcactatc   1020
gaccttccga caggagaacc cgaaattcgt gatttcatcc ggaacagaa agatgcgaag    1080 ctcactcaag tcaaatgcgt caacaaggaa tatttcgtcg gatctacaa gcgcaatgtc   1140 aaagatgaaa tatatctta ctccaaagca ggcgatcaac tcagtcgtct ggcgtcggac   1200
ttcattggcg ttgcatctat aactaacaga gagaacaac ctcatttctt cctcactttc   1260
tctggattta acacgccggg caccatttct cgctacgatt ttacagctcc agacacacaa   1320
cgtctcagca tccttaggac tacgaagcta atggtctga tgcagatga ctttgagagc    1380 acacaagtct ggtataagag caaagacgga acgaaagttc caatgttcat cgttcgtcac   1440
aaatcaacaa aatttgacgg aacgcgccgc gcgattcaaa acggttatgg tggtttcgct   1500
attacagccg atccattctt tagtcccatc atgctcacct ttatgcagac atatggcgca   1560
atcctggctg tcccgaacat cagaggtgga ggtgaattcg gcggagaatg gcacaaggca   1620
gggagacgag aaaccaaggg aaatactttt gatgatttca tcgctgccgc tcaatttctt   1680
gtcaaaaaca gtacgcggc tccaggcaag gtggccatca ctggtgcatc caatggcggt   1740
```

```
tttcttgtct gtggttccgt agttcggaca ccagagggaa cattcggcgc tgctgtttcc    1800
gaaggtggtg tcgcggacct cctaaagttt aataaattca ccgggggat ggcgtggacg     1860 agtgaatatg gaaacccttt tattaaggag gacttcgact ttgtccaagc attgtctcct    1920
gtgcataacg tacccaagga tagggttctt cctgccacat tacttatgac caatgcgggt    1980
gacgatcgtg tagttccaat gcattcgctc aagttcgtcg caaaccttca gtacaatgtg    2040
cctcaaaatc ctcatccatt gctcatccgt gtggataaat cttggcttgg tcatggtttt    2100
ggcaagacaa cagacaagca tactaaagat gctgcggaca agtggagttt cgtagcgcaa    2160
tcgttagggc tagaatggaa aacggttga                                      2189
```

<210> SEQ ID NO 236
<211> LENGTH: 761
<212> TYPE: PRT
<213> ORGANISM: Amanita bisporigera

<400> SEQUENCE: 236

```
Met His Arg Phe Leu Gln Pro Val Arg Glu Arg Leu Arg Ser Ala Leu
 1               5                  10                  15

Ala Arg Tyr Phe Gly Ser Arg Ile Met Ser Ser Thr Gln Trp Thr Pro
             20                  25                  30

Asn Met Tyr Pro Ser Ala Arg Arg Ser Asp His Ile Asp Thr Tyr Arg
         35                  40                  45

Ser Glu Thr Arg Gly Glu Val Lys Val Pro Asp Pro Tyr His Trp Leu
     50                  55                  60

Glu Glu Tyr Ser Glu Glu Thr Asp Lys Trp Thr Ser Asp Gln Glu Glu
 65                  70                  75                  80

Phe Thr Arg Thr Tyr Leu Asp Ser Asn Pro Asp Arg Lys Lys Leu Glu
                 85                  90                  95

Asp Ala Phe Arg Lys Ser Met Asp Tyr Pro Lys Phe Ser Ala Pro Phe
            100                 105                 110

Leu Asn Asp Asp Lys Arg Trp Tyr Trp Phe Tyr Asn Thr Gly Leu Gln
        115                 120                 125

Ala Gln Thr Val Ile Cys Arg Ser Lys Asp Glu Thr Leu Pro Asp Phe
    130                 135                 140

Ser Glu Ser Asp Tyr Val Gly Glu Thr Phe Phe Asp Pro Asn Leu Leu
145                 150                 155                 160

Ser Ser Asp Gly Thr Ala Ser Leu Ser Met Tyr Asp Phe Ser His Cys
                165                 170                 175

Gly Lys Tyr Phe Ala Tyr Gly Ile Ser Leu Ser Gly Ser Asp Phe Ser
            180                 185                 190

Thr Ile Tyr Val Arg Ser Thr Ser Ser Pro Leu Ala Pro Gly Asn Asn
        195                 200                 205

Ser Ile Arg Asn Asp Asp Gly Arg Leu Pro Asp Glu Leu Arg Tyr Val
    210                 215                 220

Lys Phe Ser Ser Ile Ser Trp Thr Lys Asp Ser Lys Gly Phe Phe Tyr
225                 230                 235                 240

Gln Arg Tyr Pro Gly Thr Gly Thr Val Asn Gly Gln Asn Gly Ile Gln
                245                 250                 255

Thr Gln Gly Asp Arg Asp Ala Met Ile Tyr Tyr His Arg Ile Gly Thr
            260                 265                 270

Ser Gln Ser Asp Asp Ile Leu Val His Glu Asp Gln Glu His Pro Asp
        275                 280                 285
```

```
Trp Val Phe Gly Ala Glu Val Thr Glu Asp Gly Lys Tyr Val Ala Leu
            290                 295                 300

Tyr Thr Met Lys Asp Thr Ser Arg Lys Asn Leu Leu Trp Ile Ala Asp
305                 310                 315                 320

Leu Gly Gln Asn Glu Val Gly Arg Asn Met Lys Trp Asn Lys Ile Cys
                325                 330                 335

Asn Val Phe Asp Ser Glu Tyr Asp Leu Ile Gly Asn Asp Gly Ser Leu
            340                 345                 350

Leu Tyr Ile Arg Thr Asn Lys Ala Ala Pro Gln Tyr Lys Ile Val Thr
        355                 360                 365

Leu Asp Ile Glu Lys Pro Glu Leu Gly Phe Lys Glu Phe Ile Pro Glu
370                 375                 380

Asp Pro Lys Ala Tyr Leu Ser Gln Val Lys Ile Phe Asn Lys Asp Arg
385                 390                 395                 400

Leu Ala Leu Val Tyr Lys Arg Asn Val Ile Gly Glu Leu Tyr Val Tyr
                405                 410                 415

Asn Asn Thr Gly Ser Arg Leu Met Arg Leu Ala Arg Asp Phe Val Gly
                420                 425                 430

Ser Met Thr Val Thr Ala Arg Glu Thr Glu Pro Trp Phe Phe Ala Thr
        435                 440                 445

Leu Thr Gly Phe Asn Thr Pro Gly Ile Val Cys Arg Tyr Asn Ile Gln
450                 455                 460

Arg Pro Glu Glu Gln Arg Trp Ser Val Tyr Arg Thr Ala Lys Val Lys
465                 470                 475                 480

Gly Leu Asn Pro Asn Asp Phe Glu Ala Arg Gln Val Trp Tyr Asp Ser
                485                 490                 495

Tyr Asp Gly Thr Lys Ile Pro Met Phe Ile Val Arg His Lys Asn Thr
            500                 505                 510

Gln Phe Asn Gly Thr Ala Pro Ala Ile Gln Tyr Gly Tyr Gly Gly Phe
        515                 520                 525

Asn Ile Ser Ile Asn Pro Phe Phe Ser Pro Thr Ile Leu Thr Phe Leu
530                 535                 540

Gln Lys Tyr Gly Ala Ile Leu Ala Val Pro Asn Ile Arg Gly Gly Gly
545                 550                 555                 560

Glu Phe Gly Glu Thr Trp His Asp Ala Gly Ile Arg Glu Lys Arg Ala
                565                 570                 575

Asn Val Tyr Asp Asp Phe Ile Ala Ala Thr Gln Phe Leu Val Lys Asn
            580                 585                 590

Lys Tyr Ala Ala Gly Lys Val Ala Ile Asn Gly Gly Ser Asn Gly Gly
        595                 600                 605

Gly Leu Leu Val Ala Ala Cys Val Asn Arg Ala Arg Glu Gly Thr Phe
610                 615                 620

Gly Ala Ala Ile Ala Glu Val Gly Val Leu Asp Leu Leu Lys Phe Pro
625                 630                 635                 640

Lys Phe Thr Ile Gly Lys Ala Trp Ile Ser Asp Tyr Gly Asp Pro Glu
                645                 650                 655

Asp Pro Arg Asp Phe Asp Tyr Ile Tyr Thr His Ser Pro Leu His Asn
            660                 665                 670

Ile Pro Lys Asn Met Val Leu Pro Pro Thr Met Leu Leu Thr Ala Asp
        675                 680                 685

His Asp Asp Arg Val Val Pro Met His Ser Phe Lys Tyr Ala Ala Met
690                 695                 700

Leu Gln Tyr Thr Leu Pro His Asn Arg His Pro Leu Leu Leu Arg Val
```

```
                705                 710                 715                 720
Asp Lys Lys Ala Gly His Gly Gly Lys Ser Thr Glu Lys Arg Leu
                    725                 730                 735

Gln Glu Ala Ala Asp Lys Trp Gly Phe Ala Ala Gln Ser Met Gly Leu
            740                 745                 750

Ala Trp Lys Asp Arg Gln Ala Asn Leu
            755                 760

<210> SEQ ID NO 237
<211> LENGTH: 730
<212> TYPE: PRT
<213> ORGANISM: Amanita bisporigera

<400> SEQUENCE: 237

Met Pro Pro Thr Pro Trp Ala Pro His Ser Tyr Pro Pro Thr Arg Arg
  1               5                  10                  15

Ser Asp His Val Asp Val Tyr Gln Ser Ala Ser Arg Gly Glu Val Pro
                 20                  25                  30

Val Pro Asp Pro Tyr Gln Trp Leu Glu Glu Asn Ser Asn Glu Val Asp
             35                  40                  45

Glu Trp Thr Thr Ala Gln Thr Ala Phe Thr Gln Gly Tyr Leu Asp Lys
 50                  55                  60

Asn Ala Asp Arg Gln Lys Leu Glu Glu Lys Phe Arg Ala Ser Lys Asp
 65                  70                  75                  80

Tyr Val Lys Phe Ser Ala Pro Thr Leu Leu Asp Ser Gly His Trp Tyr
                 85                  90                  95

Trp Phe Tyr Asn Ser Gly Val Gln Ser Gln Ala Val Leu Tyr Arg Ser
            100                 105                 110

Lys Lys Pro Val Leu Pro Asp Phe Gln Arg Gly Thr Arg Lys Val Gly
        115                 120                 125

Glu Val Tyr Phe Asp Pro Asn Val Leu Ser Ala Asp Gly Thr Ala Ile
    130                 135                 140

Met Gly Thr Cys Arg Phe Ser Pro Ser Gly Glu Tyr Phe Ala Tyr Ala
145                 150                 155                 160

Val Ser His Leu Gly Val Asp Tyr Phe Thr Ile Tyr Val Arg Pro Thr
                165                 170                 175

Ser Ser Ser Leu Ser Gln Ala Pro Glu Ala Glu Gly Gly Asp Gly Arg
            180                 185                 190

Leu Ser Asp Gly Val Lys Trp Cys Lys Phe Thr Thr Ile Thr Trp Thr
        195                 200                 205

Lys Asp Ser Lys Gly Phe Leu Tyr Gln Arg Tyr Pro Ala Arg Glu Ser
    210                 215                 220

Leu Val Ala Lys Asp Arg Asp Lys Asp Ala Met Val Cys Tyr His Arg
225                 230                 235                 240

Val Gly Thr Thr Gln Leu Glu Asp Ile Ile Val Gln Asp Lys Glu
                245                 250                 255

Asn Pro Asp Trp Thr Tyr Gly Thr Asp Ala Ser Glu Asp Gly Lys Tyr
            260                 265                 270

Ile Tyr Leu Val Val Tyr Lys Asp Ala Ser Lys Gln Asn Leu Leu Trp
        275                 280                 285

Val Ala Glu Phe Asp Lys Asp Gly Val Lys Pro Glu Ile Pro Trp Arg
    290                 295                 300

Lys Val Ile Asn Glu Phe Gly Ala Asp Tyr His Val Ile Thr Asn His
305                 310                 315                 320
```

```
Gly Ser Leu Ile Tyr Val Lys Thr Asn Val Asn Ala Pro Gln Tyr Lys
                325                 330                 335

Val Val Thr Ile Asp Leu Ser Thr Gly Glu Pro Glu Ile Arg Asp Phe
            340                 345                 350

Ile Pro Glu Gln Lys Asp Ala Lys Leu Thr Gln Val Lys Cys Val Asn
            355                 360                 365

Lys Gly Tyr Phe Val Ala Ile Tyr Lys Arg Asn Val Lys Asp Glu Ile
        370                 375                 380

Tyr Leu Tyr Ser Lys Ala Gly Asp Gln Leu Ser Arg Leu Ala Ser Asp
385                 390                 395                 400

Phe Ile Gly Val Ala Ser Ile Thr Asn Arg Glu Lys Gln Pro His Ser
                405                 410                 415

Phe Leu Thr Phe Ser Gly Phe Asn Thr Pro Gly Thr Ile Ser Arg Tyr
            420                 425                 430

Asp Phe Thr Ala Pro Asp Thr Gln Arg Leu Ser Ile Leu Arg Thr Thr
            435                 440                 445

Lys Leu Asn Gly Leu Asn Ala Asp Asp Phe Glu Ser Thr Gln Val Trp
        450                 455                 460

Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
                485                 490                 495

Gly Gly Phe Ala Ile Thr Ala Asp Pro Phe Phe Ser Pro Ile Met Leu
            500                 505                 510

Thr Phe Met Gln Thr Tyr Gly Ala Ile Leu Ala Val Pro Asn Ile Arg
            515                 520                 525

Gly Gly Gly Glu Phe Gly Gly Glu Trp His Lys Ala Gly Arg Arg Glu
        530                 535                 540

Thr Lys Gly Asn Thr Phe Asp Asp Phe Ile Ala Ala Gln Phe Leu
545                 550                 555                 560

Val Lys Asn Lys Tyr Ala Ala Pro Gly Lys Val Ala Ile Thr Gly Ala
                565                 570                 575

Ser Asn Gly Gly Phe Leu Val Cys Gly Ser Val Val Arg Ala Pro Glu
            580                 585                 590

Gly Thr Phe Gly Ala Ala Val Ser Glu Gly Gly Val Ala Asp Leu Leu
        595                 600                 605

Lys Phe Asn Lys Phe Thr Gly Gly Met Ala Trp Thr Ser Glu Tyr Gly
        610                 615                 620

Asn Pro Phe Ile Lys Glu Asp Phe Asp Phe Val Gln Ala Leu Ser Pro
625                 630                 635                 640

Val His Asn Val Pro Lys Asp Arg Val Leu Pro Ala Thr Leu Leu Met
                645                 650                 655

Thr Asn Ala Gly Asp Asp Arg Val Val Pro Met His Ser Leu Lys Phe
            660                 665                 670

Val Ala Asn Leu Gln Tyr Asn Val Pro Gln Asn Pro His Pro Leu Leu
        675                 680                 685

Ile Arg Val Asp Lys Ser Trp Leu Gly His Gly Phe Gly Lys Thr Thr
        690                 695                 700

Asp Lys His Thr Lys Asp Ala Ala Asp Lys Trp Ser Phe Val Ala Gln
705                 710                 715                 720

Ser Leu Gly Leu Glu Trp Lys Thr Val Asp
                725                 730
```

-continued

```
<210> SEQ ID NO 238
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: (1)...(20)
<223> OTHER INFORMATION: Y is C or T
<220> FEATURE:
<221> NAME/KEY: misc_feature
<222> LOCATION: (1)...(20)
<223> OTHER INFORMATION: R is A or G

<400> SEQUENCE: 238
gcngyratng artgnccncc                                                 20

<210> SEQ ID NO 239
<211> LENGTH: 14
<212> TYPE: PRT
<213> ORGANISM: Homo sapiens
<220> FEATURE:
<221> NAME/KEY: VARIANT
<222> LOCATION: (1)...(14)
<223> OTHER INFORMATION: Xaa can be any naturally occurring amino acid

<400> SEQUENCE: 239

Cys Val Gly Asp Asp Xaa Xaa Xaa Xaa Leu Thr Arg Gly Glu
  1               5                  10

<210> SEQ ID NO 240
<211> LENGTH: 248
<212> TYPE: DNA
<213> ORGANISM: Galerina marginata

<400> SEQUENCE: 240
acacattcaa caaatactaa cgcacaacgc atgagtacgt cgaacaagtc aacaacagaa      60
attgagctca ctcgttgcca ctaacgagag tttgatcgac gtgttcagca gtccatgggt     120
tgcagccaat accccagatt ggaagacgag tggagttggt gtcgaacatg gtagatatta     180
aggcaagggc gaagatcttt ggctgattga gttgacggtc ggaagattgg agactcggtt     240
ttcactgg                                                             248

<210> SEQ ID NO 241
<211> LENGTH: 99
<212> TYPE: DNA
<213> ORGANISM: Galerina marginata

<400> SEQUENCE: 241
atgttcgaca ccaactccac tcgtcttcca atctggggta ttggctgcaa cccatggact      60
gctgaacacg tcgatcaaac tctcgttagt ggcaacgag                             99

<210> SEQ ID NO 242
<211> LENGTH: 24
<212> TYPE: DNA
<213> ORGANISM: Galerina marginata

<400> SEQUENCE: 242
atctggggta ttggctgcaa ccca                                            24
```

-continued

```
<210> SEQ ID NO 243
<211> LENGTH: 81
<212> TYPE: PRT
<213> ORGANISM: Galerina marginata
<220> FEATURE:
<221> NAME/KEY: VARIANT
<222> LOCATION: (1)...(81)
<223> OTHER INFORMATION: Xaa is a nonsense codon

<400> SEQUENCE: 243
```

Gln Xaa Lys Pro Ser Leu Gln Ser Ser Asp Arg Gln Leu Asn Gln Pro
 1               5                  10                  15

Lys Ile Phe Ala Leu Ala Leu Ile Ser Thr Met Phe Asp Thr Asn Ser
             20                  25                  30

Thr Arg Leu Pro Ile Trp Gly Ile Gly Cys Asn Pro Trp Thr Ala Glu
         35                  40                  45

His Val Asp Gln Thr Leu Val Ser Gly Asn Glu Ala Gln Phe Leu Leu
     50                  55                  60

Leu Thr Cys Ser Thr Tyr Ser Cys Val Val Arg Xaa Tyr Leu Leu Asn
 65                  70                  75                  80

Val

```
<210> SEQ ID NO 244
<211> LENGTH: 33
<212> TYPE: PRT
<213> ORGANISM: Galerina marginata

<400> SEQUENCE: 244
```

Met Phe Asp Thr Asn Ser Thr Arg Leu Pro Ile Trp Gly Ile Gly Cys
 1               5                  10                  15

Thr Pro Trp Thr Ala Glu His Val Asp Gln Thr Leu Val Ser Gly Asn
             20                  25                  30

Glu

```
<210> SEQ ID NO 245
<211> LENGTH: 18
<212> TYPE: DNA
<213> ORGANISM: Artificial Sequence
<220> FEATURE:
<223> OTHER INFORMATION: A synthetic primer

<400> SEQUENCE: 245
cgccgtgatc gaatcccc                                                   18

<210> SEQ ID NO 246
<211> LENGTH: 614
<212> TYPE: DNA
<213> ORGANISM: Galerina amanitins

<400> SEQUENCE: 246
agcttacgtc tggcgacatt tgacccatga tagactaact ttggtagtcg aatcggtaca     60
atcacgactc cacggctttt tgccactgtt cggtgaatca ggttatctct ttataggagc    120
ctcttttctg ttatctgaaa actccaagcc atgtgaggat cgccgcgacc accttaggta    180
ctccttcgtg ccgtctgtca aagtggacaa agatacacct cggcgcgagt tttacttgac    240
ttaccaccga tctggaactt ccccatgggc tggtcagatg ccctcagatc acagaactcc    300
accaatgaag acagctcctc gtaatggcgt cgaaaatgtc ttggaccttt attctagaag    360
ttcacagtcc tgcggagtcg ttgctatttc ctaactcatc agctctattc ggtcctcgaa    420
agagataaaa ggcggtcgtc agtgcaggct gatctccaat cccccaacgc aaactcactt    480
```

```
aaccaaagat tcttttttgc tctaacatct acaatgttcg acaccaacgc cactcgyctc    540
ccaatctggg gtattggctg caacccatgg actgctgagc acgtcgacca gactctcgct    600
agtgcaacga gtaa                                                      614
```

<210> SEQ ID NO 247
<211> LENGTH: 9
<212> TYPE: PRT
<213> ORGANISM: Galerina amanitins

<400> SEQUENCE: 247

Ser Leu Arg Leu Ala Thr Phe Asp Pro
1               5

<210> SEQ ID NO 248
<211> LENGTH: 85
<212> TYPE: PRT
<213> ORGANISM: Galerina amanitins

<400> SEQUENCE: 248

Lys Phe Thr Val Leu Arg Ser Arg Cys Tyr Phe Leu Thr His Gln Leu
1               5                   10                  15

Tyr Ser Val Leu Glu Arg Asp Lys Arg Arg Ser Ser Val Gln Ala Asp
            20                  25                  30

Leu Gln Ser Pro Asn Ala Asn Ser Leu Asn Gln Arg Phe Phe Phe Ala
        35                  40                  45

Leu Thr Ser Thr Met Phe Asp Thr Asn Ala Thr Arg Leu Pro Ile Trp
    50                  55                  60

Gly Ile Gly Cys Asn Pro Trp Thr Ala Glu His Val Asp Gln Thr Leu
65                  70                  75                  80

Ala Ser Gly Asn Glu
            85

<210> SEQ ID NO 249
<211> LENGTH: 17
<212> TYPE: PRT
<213> ORGANISM: Artificial Sequence
<220> FEATURE:
<223> OTHER INFORMATION: A synthetic primer

<400> SEQUENCE: 249

Ala Thr Arg Leu Pro Ala Trp Leu Val Asp Cys Pro Cys Val Gly Asp
1               5                   10                  15

Asp

<210> SEQ ID NO 250
<211> LENGTH: 77
<212> TYPE: PRT
<213> ORGANISM: Amanita bisporigera

<400> SEQUENCE: 250

Ser Ser Ile Ala Trp Ala Pro Gly Asn Tyr Pro Ser Thr Arg Arg Ser
1               5                   10                  15

Asp His Val Asp Ser Tyr Gln Ser Ala Ser Lys Gly Glu Val Pro Val
            20                  25                  30

Pro Asp Pro Tyr Gln Trp Leu Glu Glu Ser Thr Asp Glu Val Asp Lys
        35                  40                  45

Trp Thr Thr Ala Gln Ala Asp Leu Ala Gln Ala Tyr Leu Asp Gln Asn
    50                  55                  60

```
Ala Asp Ile Gln Lys Leu Ala Asp Lys Phe Arg Ala Ser
 65                  70                  75
```

<210> SEQ ID NO 251
<211> LENGTH: 64
<212> TYPE: PRT
<213> ORGANISM: Amanita bisporigera

<400> SEQUENCE: 251

```
Val Asp Ile Tyr Lys Ser Ala Leu Arg Gly Asp Val His Val Gln Asp
 1               5                  10                  15

Pro Tyr Gln Trp Leu Glu Glu Tyr Thr Asp Glu Thr Asp Lys Trp Thr
             20                  25                  30

Thr Ala Gln Glu Val Phe Thr Arg Thr Tyr Leu Asp Lys Asn Pro Asp
         35                  40                  45

Leu Pro Arg Leu Glu Lys Ala Phe Gln Ala Cys Asn Asp Tyr Pro Lys
     50                  55                  60
```

<210> SEQ ID NO 252
<211> LENGTH: 70
<212> TYPE: PRT
<213> ORGANISM: Amanita bisporigera

<400> SEQUENCE: 252

```
Gly Ala Ala Ser Ile Ala Asn Arg Gln Lys Gln Thr His Phe Phe Leu
 1               5                  10                  15

Thr Leu Ser Gly Phe Asn Thr Pro Gly Thr Ile Ala Arg Tyr Asp Phe
             20                  25                  30

Thr Ala Pro Glu Thr Gln Arg Phe Ser Ile Leu Arg Thr Thr Lys Val
         35                  40                  45

Asn Glu Leu Asp Pro Asp Phe Glu Ser Thr Gln Val Trp Tyr Glu
     50                  55                  60

Ser Lys Asp Gly Asn Lys
 65                  70
```

<210> SEQ ID NO 253
<211> LENGTH: 50
<212> TYPE: PRT
<213> ORGANISM: Amanita bisporigera

<400> SEQUENCE: 253

```
Gly Gly Phe Ser Ile Ser Ile Asp Pro Phe Ser Ala Thr Ile Leu
 1               5                  10                  15

Thr Phe Leu Gln Lys Tyr Gly Val Val Phe Ala Leu Pro Asn Ile Arg
             20                  25                  30

Gly Gly Gly Glu Phe Gly Glu Asp Trp His Leu Ala Gly Cys Arg Glu
         35                  40                  45

Lys Lys
     50
```

<210> SEQ ID NO 254
<211> LENGTH: 46
<212> TYPE: PRT
<213> ORGANISM: Amanita bisporigera

<400> SEQUENCE: 254

```
Asp Asp Arg Val Val Pro Met His Ser Phe Lys Leu Ala Ala Glu Leu
 1               5                  10                  15

Gln Tyr Ser Leu Pro His Asn Pro Asn Pro Leu Leu Ile Arg Ile Asp
             20                  25                  30
```

-continued

```
Lys Lys Ala Gly His Gly Ala Gly Lys Ser Thr Gln Gln Lys
         35                  40                  45

<210> SEQ ID NO 255
<211> LENGTH: 34
<212> TYPE: PRT
<213> ORGANISM: Amanita bisporigera

<400> SEQUENCE: 255

Ala Ala Glu Leu Gln Tyr Ser Leu Pro His Asn Pro Asn Pro Leu Leu
  1               5                  10                  15

Ile Arg Ile Asp Lys Lys Thr Gly His Gly Ala Gly Lys Ser Thr Gln
             20                  25                  30

Gln Arg

<210> SEQ ID NO 256
<211> LENGTH: 34
<212> TYPE: PRT
<213> ORGANISM: Amanita bisporigera

<400> SEQUENCE: 256

Gln Val Trp Tyr Glu Ser Lys Asp Gly Thr Ser Ile Pro Met Phe Ile
  1               5                  10                  15

Val Arg His Lys Ser Thr Lys Phe Asp Gly Thr Ala Pro Val Ile Gln
             20                  25                  30

Tyr Gly

<210> SEQ ID NO 257
<211> LENGTH: 34
<212> TYPE: PRT
<213> ORGANISM: Amanita bisporigera

<400> SEQUENCE: 257

Gln Val Trp Tyr Glu Ser Lys Asp Gly Thr Ser Ile Pro Met Phe Ile
  1               5                  10                  15

Val Arg His Lys Ser Thr Lys Phe Asp Gly Thr Ala Pro Val Ile Gln
             20                  25                  30

Tyr Gly

<210> SEQ ID NO 258
<211> LENGTH: 59
<212> TYPE: PRT
<213> ORGANISM: Amanita bisporigera

<400> SEQUENCE: 258

Ser Asp Phe Val Thr Ile Tyr Val Trp Ser Thr Asp Ser Pro Leu Thr
  1               5                  10                  15

Asn Asp Val Asp Ser Lys Asn Asp Lys Gly Arg Leu Pro Glu Glu Ile
             20                  25                  30

Lys Phe Val Lys Phe Ser Ser Ile Gly Trp Thr Pro Asp Ser Lys Gly
         35                  40                  45

Phe Phe Ile Arg Ser Ile Pro Trp Thr Ala Ser
     50                  55

<210> SEQ ID NO 259
<211> LENGTH: 35
<212> TYPE: PRT
<213> ORGANISM: Amanita bisporigera

<400> SEQUENCE: 259
```

```
Lys Asn Asp Lys Gly Arg Leu Pro Glu Glu Ile Lys Phe Val Lys Phe
 1               5                  10                  15

Ser Ser Ile Gly Trp Thr Pro Asp Ser Lys Gly Phe Phe Ile Arg Ser
            20                  25                  30

Phe Pro Gly
        35

<210> SEQ ID NO 260
<211> LENGTH: 47
<212> TYPE: PRT
<213> ORGANISM: Amanita bisporigera

<400> SEQUENCE: 260

Asp Asp Arg Val Val Pro Met His Ser Phe Lys Phe Ile Ala Thr Leu
 1               5                  10                  15

Gln His Asn Val Pro Gln Asn Pro His Pro Leu Leu Ile Lys Ile Asp
            20                  25                  30

Lys Ser Trp Leu Gly His Gly Met Gly Lys Pro Thr Asp Lys Lys
        35                  40                  45

<210> SEQ ID NO 261
<211> LENGTH: 53
<212> TYPE: PRT
<213> ORGANISM: Amanita bisporigera

<400> SEQUENCE: 261

Gly Gly Asp Tyr Ser Thr Ile Tyr Val Arg Ser Thr Ser Ser Pro Leu
 1               5                  10                  15

Ser Gln Ser Ser Val Ala Gln Gly Val Asp Gly Arg Leu Ser Asp Glu
            20                  25                  30

Val Lys Trp Phe Lys Phe Ser Thr Ile Ile Trp Thr Lys Asp Phe Lys
        35                  40                  45

Gly Phe Leu Tyr Gln
        50

<210> SEQ ID NO 262
<211> LENGTH: 71
<212> TYPE: PRT
<213> ORGANISM: Amanita bisporigera

<400> SEQUENCE: 262

Val Phe Asp Ser Met Thr Phe Thr Ser Ile Thr Asn Lys Gly Ser Leu
 1               5                  10                  15

Phe Tyr Val Arg Thr Asn Glu Ser Ala Pro Gln Tyr Arg Val Ile Thr
            20                  25                  30

Val Asp Ile Ala Lys Arg Asn Glu Ile Lys Glu Leu Ile Pro Glu Thr
        35                  40                  45

Asp Ala Tyr Leu Ser Ser Ile Thr Ser Val Asn Lys Gly Tyr Phe Ala
    50                  55                  60

Leu Val Tyr Lys Arg Asn Val
65                  70

<210> SEQ ID NO 263
<211> LENGTH: 62
<212> TYPE: PRT
<213> ORGANISM: Amanita bisporigera

<400> SEQUENCE: 263

Ile Thr Asn Lys Gly Ser Leu Phe Tyr Val Arg Thr Asn Glu Ser Ala
```

-continued

```
                1               5                  10                 15
        Pro Gln Tyr Arg Val Ile Thr Val Asp Ile Ala Lys Arg Asn Glu Ile
                        20                  25                 30
        Lys Glu Leu Ile Pro Glu Thr Asp Ala Tyr Leu Ser Ser Ile Thr Ser
                        35                  40                 45
        Val Asn Lys Gly Tyr Phe Ala Leu Val Tyr Lys Arg Asn Val
                        50                  55                 60
```

<210> SEQ ID NO 264
<211> LENGTH: 73
<212> TYPE: PRT
<213> ORGANISM: Amanita bisporigera

<400> SEQUENCE: 264

```
        Ser Leu Gly Gln Ala Trp Ile Ser Glu Tyr Gly Asn Pro Ser Ile Pro
         1               5                  10                 15
        Glu Glu Phe Asp Tyr Ile Tyr Pro Leu Ser Pro Val His Asn Val Gln
                        20                  25                 30
        Thr Asp Lys Val Met Pro Ala Met Leu Ile Thr Val Asn Ile Gly Glu
                        35                  40                 45
        Gln Leu Thr Ser Ser Asn Leu Ile Met Pro His Thr Arg Pro Ser Pro
                        50                  55                 60
        Gly Asp Asp Arg Val Val Pro Met His
        65                      70
```

<210> SEQ ID NO 265
<211> LENGTH: 34
<212> TYPE: PRT
<213> ORGANISM: Amanita bisporigera

<400> SEQUENCE: 265

```
        Ala Ala Glu Leu Gln Tyr Ser Leu Pro His Asn Pro Asn Pro Leu Leu
         1               5                  10                 15
        Ile Arg Ile Asp Lys Lys Ala Gly His Gly Ala Gly Lys Ser Thr Gln
                        20                  25                 30
        Gln Lys
```

<210> SEQ ID NO 266
<211> LENGTH: 85
<212> TYPE: PRT
<213> ORGANISM: Amanita bisporigera

<400> SEQUENCE: 266

```
        Ala Val Thr His Ile Arg Gly Gly Ser Glu Lys Gly Trp Gly Trp Phe
         1               5                  10                 15
        Leu Asp Gly Arg Lys Asp Lys Lys Pro Asn Ser Phe Thr Asp Phe Ile
                        20                  25                 30
        Ala Cys Ala Glu Ala Leu Ile Ala Glu Gly Tyr Gly Thr Ala Gly Arg
                        35                  40                 45
        Ile Val Ala Glu Gly Arg Ser Ala Gly Gly Met Leu Met Gly Ala Val
                        50                  55                 60
        Ala Asn Leu Arg Pro Asp Leu Trp Ala Gly Val Ile Gly Gly Val Pro
        65                      70                  75                 80
        Phe Val Asp Val Leu
                        85
```

<210> SEQ ID NO 267
<211> LENGTH: 77

```
<212> TYPE: PRT
<213> ORGANISM: Amanita bisporigera

<400> SEQUENCE: 267

Gln Tyr Tyr Ala Pro Tyr Leu His Asp Asp Asn Arg Trp Tyr Trp Tyr
 1               5                  10                  15

Tyr Asn Ser Gly Leu Glu Pro Gln Thr Gly Glu Arg Phe Lys Gln Pro
                20                  25                  30

Phe Arg Pro Arg Trp Leu Thr Ser Val Pro Ala Lys Ala Leu Tyr Arg
            35                  40                  45

Ser Lys Asp Ser Asn Leu Pro Asp Leu Ser Thr Ala Asp Gly Ser Gly
        50                  55                  60

Gly Asp Leu Phe Phe Asp Val Gly Pro Leu Ser Ala Asn
65                  70                  75

<210> SEQ ID NO 268
<211> LENGTH: 38
<212> TYPE: PRT
<213> ORGANISM: Amanita bisporigera

<400> SEQUENCE: 268

Ala Glu Asp Ser Leu Ile Tyr Gln Asp Arg Glu His Arg Asp Trp Met
 1               5                  10                  15

Phe Ser Ile Asp Val Thr Asp Asp Gly Asn Tyr Leu Leu Tyr Ile
                20                  25                  30

Leu Lys Asp Ser Ser Arg
            35

<210> SEQ ID NO 269
<211> LENGTH: 30
<212> TYPE: PRT
<213> ORGANISM: Amanita bisporigera

<400> SEQUENCE: 269

Gly Leu Leu Val Ser Ala Cys Val Asn Arg Ala Pro Glu Gly Thr Phe
 1               5                  10                  15

Gly Cys Ala Val Ala Asp Val Gly Val His Asp Leu Leu Lys
                20                  25                  30

<210> SEQ ID NO 270
<211> LENGTH: 27
<212> TYPE: PRT
<213> ORGANISM: Amanita bisporigera

<400> SEQUENCE: 270

Glu Asp Ile Ile Val Tyr Gln Asp Asn Glu His Pro Glu Trp Ile Tyr
 1               5                  10                  15

Gly Ala Asp Thr Ser Glu Asp Gly Lys Tyr Leu
                20                  25

<210> SEQ ID NO 271
<211> LENGTH: 30
<212> TYPE: PRT
<213> ORGANISM: Amanita bisporigera

<400> SEQUENCE: 271

Met Ser Ser Ile Ala Trp Ala Pro Gly Asn Tyr Pro Ser Thr Arg Arg
 1               5                  10                  15

Ser Asp His Val Asp Ser Tyr Gln Ser Ala Ser Lys Gly Glu
                20                  25                  30
```

```
<210> SEQ ID NO 272
<211> LENGTH: 95
<212> TYPE: PRT
<213> ORGANISM: Amanita bisporigera

<400> SEQUENCE: 272

Phe Ser Ser Asp His Ile Arg Leu Arg Tyr Glu Ala Leu Asn Arg Pro
1               5                   10                  15

Ala Gln Ile Arg Arg Leu Ala Leu Ala Asp Gly Ala Gln Gln Val Leu
            20                  25                  30

Lys Glu Thr Pro Val Leu Gly Val Phe Asn Ala Asp Asp Tyr Val Ser
        35                  40                  45

Gln Arg Leu Trp Ala Thr Ser Val Asp Gly Thr Gln Val Pro Ile Ser
    50                  55                  60

Leu Val Val Arg His Asp Gln Leu Gly Gln Pro Thr Pro Leu Tyr Leu
65                  70                  75                  80

Tyr Gly Tyr Gly Ala Tyr Gly His Ser Leu Asp Pro Trp Phe Ser
                85                  90                  95

<210> SEQ ID NO 273
<211> LENGTH: 23
<212> TYPE: PRT
<213> ORGANISM: Amanita bisporigera

<400> SEQUENCE: 273

Gln Phe Leu Val Lys Asn Lys Tyr Ala Ala Pro Gly Lys Val Ala Ile
1               5                   10                  15

Asn Gly Ala Ser Asn Gly Gly
            20

<210> SEQ ID NO 274
<211> LENGTH: 38
<212> TYPE: PRT
<213> ORGANISM: Amanita bisporigera

<400> SEQUENCE: 274

Phe Ser Ala Pro Thr Leu Leu Asp Asp Gly His Trp Tyr Trp Phe Tyr
1               5                   10                  15

Asn Arg Gly Leu Gln Ser Gln Ser Gly Arg Tyr Leu Phe Ile Leu Arg
            20                  25                  30

Arg Cys Lys Thr Gln Thr
        35

<210> SEQ ID NO 275
<211> LENGTH: 62
<212> TYPE: PRT
<213> ORGANISM: Amanita bisporigera

<400> SEQUENCE: 275

Asn Asp Ser Arg Val Gln Tyr Trp Glu Ala Ala Lys Trp Val Ala Lys
1               5                   10                  15

Leu Arg Asp Thr Lys Thr Asp Asp His Pro Leu Leu Leu Lys Thr Glu
            20                  25                  30

Leu Gly Ala Gly His Gly Gly Met Ser Gly Arg Tyr Gln Gly Leu Arg
        35                  40                  45

Asp Val Ala Leu Glu Tyr Ala Phe Cys Phe Gln Gly Thr Gly
    50                  55                  60

<210> SEQ ID NO 276
```

```
<211> LENGTH: 34
<212> TYPE: PRT
<213> ORGANISM: Amanita bisporigera

<400> SEQUENCE: 276

Gln Lys Asn Leu Leu Trp Val Ala Glu Leu Asn Glu Asp Gly Val Lys
 1               5                  10                  15

Ser Gly Ile Gln Trp Arg Lys Val Val Asn Glu Tyr Val Ala Asp Tyr
            20                  25                  30

Asn Val

<210> SEQ ID NO 277
<211> LENGTH: 24
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(24)
<223> OTHER INFORMATION: Y is C or T
<220> FEATURE:
<221> NAME/KEY: misc_feature
<222> LOCATION: (1)...(24)
<223> OTHER INFORMATION: N is any nucleic acid
<220> FEATURE:
<221> NAME/KEY: misc_feature
<222> LOCATION: (1)...(24)
<223> OTHER INFORMATION: H is A, C, or T
<220> FEATURE:
<221> NAME/KEY: misc_feature
<222> LOCATION: (1)...(24)
<223> OTHER INFORMATION: S is G or C

<400> SEQUENCE: 277
caycaynnna thwsngaygg ntgg                                    24

<210> SEQ ID NO 278
<211> LENGTH: 24
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(24)
<223> OTHER INFORMATION: N is any nucleic acid
<220> FEATURE:
<221> NAME/KEY: misc_feature
<222> LOCATION: (1)...(24)
<223> OTHER INFORMATION: R is A or G
<220> FEATURE:
<221> NAME/KEY: misc_feature
<222> LOCATION: (1)...(24)
<223> OTHER INFORMATION: S is G or C
<220> FEATURE:
<221> NAME/KEY: misc_feature
<222> LOCATION: (1)...(24)
<223> OTHER INFORMATION: W is A or T

<400> SEQUENCE: 278
cctnccrtcn swnatnnnrt grtg                                    24

<210> SEQ ID NO 279
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
```

<220> FEATURE:
<221> NAME/KEY: misc_feature
<222> LOCATION: (1)...(17)
<223> OTHER INFORMATION: R is A or G
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: Y is C or T
<220> FEATURE:
<221> NAME/KEY: misc_feature
<222> LOCATION: (1)...(17)
<223> OTHER INFORMATION: M is A or C

<400> SEQUENCE: 279
garggncayg gnmgnga                                                    17

<210> SEQ ID NO 280
<211> LENGTH: 75
<212> TYPE: PRT
<213> ORGANISM: Amanita bisporigera

<400> SEQUENCE: 280

Trp Ala Pro Gly Asn Tyr Pro Ser Thr Arg Arg Ser Asp His Val Asp
1               5                   10                  15

Ser Tyr Gln Ser Ala Ser Lys Gly Glu Val Pro Val Pro Asp Pro Tyr
                20                  25                  30

Gln Trp Leu Glu Glu Ser Thr Asp Glu Val Asp Lys Trp Thr Thr Ala
            35                  40                  45

Gln Ala Asp Leu Ala Gln Ala Tyr Leu Asp Gln Asn Ala Asp Ile Gln
        50                  55                  60

Lys Leu Ala Asp Lys Phe Arg Ala Ser Arg Asn
65                  70                  75

<210> SEQ ID NO 281
<211> LENGTH: 47
<212> TYPE: PRT
<213> ORGANISM: Amanita bisporigera

<400> SEQUENCE: 281

Gly Asp Asp Arg Val Pro Met His Ser Phe Lys Phe Ile Ala Thr
1               5                   10                  15

Leu Gln His Asn Val Pro Gln Asn Pro His Pro Leu Leu Ile Lys Ile
                20                  25                  30

Asp Lys Ser Trp Leu Gly His Gly Met Gly Lys Pro Thr Asp Lys
            35                  40                  45

<210> SEQ ID NO 282
<211> LENGTH: 70
<212> TYPE: PRT
<213> ORGANISM: Amanita bisporigera

<400> SEQUENCE: 282

Val Asp Ile Tyr Lys Ser Ala Leu Arg Gly Asp Val His Val Gln Asp
1               5                   10                  15

Pro Tyr Gln Trp Leu Glu Glu Tyr Thr Asp Glu Thr Asp Lys Trp Thr
                20                  25                  30

Thr Ala Gln Glu Val Phe Thr Arg Thr Tyr Leu Asp Lys Asn Pro Asp
            35                  40                  45

Leu Pro Arg Leu Glu Lys Ala Phe Gln Ala Cys Asn Asp Tyr Pro Lys
        50                  55                  60

Val Leu Ser Ala Thr Ile
65                70

<210> SEQ ID NO 283
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: K is G or T
<220> FEATURE:
<221> NAME/KEY: misc_feature
<222> LOCATION: (1)...(17)
<223> OTHER INFORMATION: R is A or G
<220> FEATURE:
<221> NAME/KEY: misc_feature
<222> LOCATION: (1)...(17)
<223> OTHER INFORMATION: Y is C or T

<400> SEQUENCE: 283
tcncknccrt gnccytc                                                17

<210> SEQ ID NO 284
<211> LENGTH: 18
<212> TYPE: DNA
<213> ORGANISM: Artificial Sequence
<220> FEATURE:
<223> OTHER INFORMATION: A synthetic primer

<400> SEQUENCE: 284
gatgcctacc catgctcg                                               18

<210> SEQ ID NO 285
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: S is G or C
<220> FEATURE:
<221> NAME/KEY: misc_feature
<222> LOCATION: (1)...(20)
<223> OTHER INFORMATION: K is G or T
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: (1)...(20)
<223> OTHER INFORMATION: R is A or G
<220> FEATURE:
<221> NAME/KEY: misc_feature
<222> LOCATION: (1)...(20)
<223> OTHER INFORMATION: Y is C or T

<400> SEQUENCE: 285
gtkcangsrw anacrtcytc                                             20

<210> SEQ ID NO 286
<211> LENGTH: 63
<212> TYPE: PRT

-continued

<213> ORGANISM: Amanita bisporigera

<400> SEQUENCE: 286

Ile Thr Asn Lys Gly Ser Leu Phe Tyr Val Arg Thr Asn Glu Ser Ala
1               5                   10                  15
Pro Gln Tyr Arg Val Ile Thr Val Asp Ile Ala Lys Arg Asn Glu Ile
            20                  25                  30
Lys Glu Leu Ile Pro Glu Thr Asp Ala Tyr Leu Ser Ser Ile Thr Ser
        35                  40                  45
Val Asn Lys Gly Tyr Phe Ala Leu Val Tyr Lys Arg Asn Val Arg
    50                  55                  60

<210> SEQ ID NO 287
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: Y is C or T

<400> SEQUENCE: 287
ccntgyacnc cnytnca                                                17

<210> SEQ ID NO 288
<211> LENGTH: 71
<212> TYPE: PRT
<213> ORGANISM: Amanita bisporigera

<400> SEQUENCE: 288

Gly Gln Ala Trp Ile Ser Glu Tyr Gly Asn Pro Ser Ile Pro Glu Glu
1               5                   10                  15
Phe Asp Tyr Ile Tyr Pro Leu Ser Pro Val His Asn Val Gln Thr Asp
            20                  25                  30
Lys Val Met Pro Ala Met Leu Ile Thr Val Asn Ile Gly Glu Gln Leu
        35                  40                  45
Thr Ser Ser Asn Leu Ile Met Pro His Thr Arg Pro Ser Pro Gly Asp
    50                  55                  60
Asp Arg Val Val Pro Met His
65                  70

<210> SEQ ID NO 289
<211> LENGTH: 48
<212> TYPE: PRT
<213> ORGANISM: Amanita bisporigera

<400> SEQUENCE: 289

Asn Leu Asp Asp Asp Arg Val Val Pro Met His Ser Phe Lys Leu Ala
1               5                   10                  15
Ala Glu Leu Gln Tyr Ser Leu Pro His Asn Pro Asn Pro Leu Leu Ile
            20                  25                  30
Arg Ile Asp Lys Lys Ala Gly His Gly Ala Gly Lys Ser Thr Gln Gln
        35                  40                  45

<210> SEQ ID NO 290
<211> LENGTH: 32

<212> TYPE: PRT
<213> ORGANISM: Amanita bisporigera

<400> SEQUENCE: 290

Ala Glu Leu Gln Tyr Ser Leu Pro His Asn Pro Asn Pro Leu Leu Ile
1               5                   10                  15

Arg Ile Asp Lys Lys Thr Gly His Gly Ala Gly Lys Ser Thr Gln Gln
            20                  25                  30

<210> SEQ ID NO 291
<211> LENGTH: 27
<212> TYPE: PRT
<213> ORGANISM: Amanita bisporigera

<400> SEQUENCE: 291

Phe Ser Ala Pro Thr Leu Leu Asp Asp Gly His Trp Tyr Trp Phe Tyr
1               5                   10                  15

Asn Arg Gly Leu Gln Ser Gln Ser Gly Arg Tyr
            20                  25

<210> SEQ ID NO 292
<211> LENGTH: 46
<212> TYPE: PRT
<213> ORGANISM: Amanita bisporigera

<400> SEQUENCE: 292

Arg Ala Pro Glu Gly Thr Phe Gly Ala Ala Val Pro Glu Gly Gly Val
1               5                   10                  15

Ala Asp Leu Leu Lys Val Val Phe Val Phe Gln Leu Cys Asn Ser Gln
            20                  25                  30

Ser Leu Ile Leu Thr Leu Gln Phe His Lys Phe Thr Gly Gly
        35                  40                  45

<210> SEQ ID NO 293
<211> LENGTH: 61
<212> TYPE: PRT
<213> ORGANISM: Amanita bisporigera

<400> SEQUENCE: 293

Ala Val Thr His Ile Arg Gly Gly Ser Glu Lys Gly Trp Gly Trp Phe
1               5                   10                  15

Leu Asp Gly Arg Lys Asp Lys Lys Pro Asn Ser Phe Thr Asp Phe Ile
            20                  25                  30

Ala Cys Ala Glu Ala Leu Ile Ala Glu Gly Tyr Gly Thr Ala Gly Arg
        35                  40                  45

Ile Val Ala Glu Gly Arg Ser Ala Gly Gly Met Leu Met
50                  55                  60

<210> SEQ ID NO 294
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: R is A or G

<400> SEQUENCE: 294

```
tgnarnggng trcangg                                                    17

<210> SEQ ID NO 295
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: R is A or G
<220> FEATURE:
<221> NAME/KEY: misc_feature
<222> LOCATION: (1)...(17)
<223> OTHER INFORMATION: N is inosine

<400> SEQUENCE: 295
tgnarnggng trcangg                                                    17

<210> SEQ ID NO 296
<211> LENGTH: 54
<212> TYPE: PRT
<213> ORGANISM: Amanita bisporigera

<400> SEQUENCE: 296

Asp Phe Val Thr Ile Tyr Val Trp Ser Thr Asp Ser Pro Leu Thr Asn
  1               5                  10                  15

Asp Val Asp Ser Lys Asn Asp Lys Gly Arg Leu Pro Glu Glu Ile Lys
             20                  25                  30

Phe Val Lys Phe Ser Ser Ile Gly Trp Thr Pro Asp Ser Lys Gly Phe
         35                  40                  45

Phe Ile Arg Ser Ile Pro
     50

<210> SEQ ID NO 297
<211> LENGTH: 91
<212> TYPE: PRT
<213> ORGANISM: Amanita bisporigera

<400> SEQUENCE: 297

His Ile Arg Leu Arg Tyr Glu Ala Leu Asn Arg Pro Ala Gln Ile Arg
  1               5                  10                  15

Arg Leu Ala Leu Ala Asp Gly Ala Gln Gln Val Leu Lys Glu Thr Pro
             20                  25                  30

Val Leu Gly Val Phe Asn Ala Asp Asp Tyr Val Ser Gln Arg Leu Trp
         35                  40                  45

Ala Thr Ser Val Asp Gly Thr Gln Val Pro Ile Ser Leu Val Val Arg
     50                  55                  60

His Asp Gln Leu Gly Gln Pro Thr Pro Leu Tyr Leu Tyr Gly Tyr Gly
 65                  70                  75                  80

Ala Tyr Gly His Ser Leu Asp Pro Trp Phe Ser
                 85                  90

<210> SEQ ID NO 298
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is inosine
<220> FEATURE:
```

```
<221> NAME/KEY: misc_feature
<222> LOCATION: (1)...(17)
<223> OTHER INFORMATION: R is A or G

<400> SEQUENCE: 298
cargarggny tnatggc                                                17

<210> SEQ ID NO 299
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: Y is C or T

<400> SEQUENCE: 299
cgcatnagnc cytcctg                                                17

<210> SEQ ID NO 300
<211> LENGTH: 14
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(14)
<223> OTHER INFORMATION: K is G or T
<220> FEATURE:
<221> NAME/KEY: misc_feature
<222> LOCATION: (1)...(14)
<223> OTHER INFORMATION: R is A or G
<220> FEATURE:
<221> NAME/KEY: misc_feature
<222> LOCATION: (1)...(14)
<223> OTHER INFORMATION: N is any nucleic acid
<220> FEATURE:
<221> NAME/KEY: misc_feature
<222> LOCATION: (1)...(14)
<223> OTHER INFORMATION: W is a or T

<400> SEQUENCE: 300
karggnatga wngc                                                   14

<210> SEQ ID NO 301
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: W is A or T
<220> FEATURE:
<221> NAME/KEY: misc_feature
<222> LOCATION: (1)...(17)
<223> OTHER INFORMATION: Y is C or T
<220> FEATURE:
<221> NAME/KEY: misc_feature
<222> LOCATION: (1)...(17)
<223> OTHER INFORMATION: M is A or C
```

```
<400> SEQUENCE: 301
gcnwtcatnc cytmytg                                                17

<210> SEQ ID NO 302
<211> LENGTH: 37
<212> TYPE: PRT
<213> ORGANISM: Amanita bisporigera

<400> SEQUENCE: 302

Glu Asp Ser Leu Ile Tyr Gln Asp Arg Glu His Arg Asp Trp Met Phe
1               5                   10                  15

Ser Ile Asp Val Thr Asp Gly Asn Tyr Leu Leu Leu Tyr Ile Leu
            20                  25                  30

Lys Asp Ser Ser Arg
        35

<210> SEQ ID NO 303
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any naturally occurring amino acid

<400> SEQUENCE: 303

Met Ser Asp Ile Asn Ala Thr Arg Leu Pro Ile Trp Gly Ile Gly Cys
1               5                   10                  15

Asn Xaa Xaa Pro Cys Val Gly Asp Val Thr Leu Leu Thr Arg
            20                  25                  30

Gly Glu

<210> SEQ ID NO 304
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 304

Met Ser Asp Ile Asn Ala Thr Arg Leu Pro Ala Trp Leu Val Asp Cys
1               5                   10                  15

Xaa Xaa Xaa Pro Cys Val Gly Asp Val Asn Arg Leu Leu Thr Arg
            20                  25                  30

Gly Glu

<210> SEQ ID NO 305
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 305

Met Ser Asp Ile Asn Ala Thr Arg Leu Pro Ile Trp Gly Ile Gly Cys
1               5                   10                  15

Asp Xaa Xaa Pro Cys Ile Gly Asp Val Thr Ile Leu Leu Thr Arg
            20                  25                  30
```

Gly Glu

<210> SEQ ID NO 306
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 306

Met Ser Asp Ile Asn Ala Thr Arg Leu Pro Ile Ile Gly Ile Leu Leu
1               5                   10                  15

Pro Xaa Xaa Pro Cys Ile Gly Asp Asp Val Thr Leu Leu Leu Thr Arg
            20                  25                  30

Gly Glu

<210> SEQ ID NO 307
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: R is A or G
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: Y is C or T

<400> SEQUENCE: 307
tacarracng gngayct                                                  17

<210> SEQ ID NO 308
<211> LENGTH: 34
<212> TYPE: PRT
<213> ORGANISM: Amanita bisporigera

<400> SEQUENCE: 308

Met Ser Asp Ile Asn Thr Ala Arg Leu Pro Phe Tyr Gln Phe Pro Asp
1               5                   10                  15

Phe Lys Tyr Pro Cys Val Gly Asp Asp Ile Glu Met Val Leu Ala Arg
            20                  25                  30

Gly Glu

<210> SEQ ID NO 309
<211> LENGTH: 34
<212> TYPE: PRT
<213> ORGANISM: Amanita bisporigera

<400> SEQUENCE: 309

Met Ser Asp Ile Asn Thr Ala Arg Leu Pro Phe Phe Gln Pro Pro Glu
1               5                   10                  15

Phe Arg Pro Pro Cys Val Gly Asp Asp Ile Glu Met Val Leu Thr Arg
            20                  25                  30

Gly Glu

```
<210> SEQ ID NO 310
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 310

Met Ser Asp Val Asn Asp Thr Arg Leu Pro Phe Asn Phe Phe Arg Phe
 1               5                  10                  15

Pro Tyr Xaa Pro Cys Ile Gly Asp Asp Ser Gly Ser Val Leu Arg Leu
            20                  25                  30

Gly Glu

<210> SEQ ID NO 311
<211> LENGTH: 34
<212> TYPE: PRT
<213> ORGANISM: Amanita bisporigera

<400> SEQUENCE: 311

Met Ser Asp Ile Asn Thr Ala Arg Leu Pro Leu Phe Leu Pro Pro Val
 1               5                  10                  15

Arg Met Pro Pro Cys Val Gly Asp Asp Ile Glu Met Val Leu Thr Arg
            20                  25                  30

Gly Glu

<210> SEQ ID NO 312
<211> LENGTH: 34
<212> TYPE: PRT
<213> ORGANISM: Amanita bisporigera

<400> SEQUENCE: 312

Met Ser Asp Ile Asn Thr Ala Arg Leu Pro Tyr Val Val Phe Met Ser
 1               5                  10                  15

Phe Ile Pro Pro Cys Val Asn Asp Asp Ile Gln Val Val Leu Thr Arg
            20                  25                  30

Gly Glu

<210> SEQ ID NO 313
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 313

Met Ser Asp Ile Asn Ala Ile Arg Ala Pro Ile Leu Met Leu Ala Ile
 1               5                  10                  15

Leu Xaa Xaa Pro Cys Val Gly Asp Asp Ile Glu Val Leu Arg Arg Gly
            20                  25                  30

Glu Gly

<210> SEQ ID NO 314
<211> LENGTH: 34
<212> TYPE: PRT
<213> ORGANISM: Amanita bisporigera

<400> SEQUENCE: 314
```

Met Ser Asp Ile Asn Gly Thr Arg Leu Pro Ile Pro Gly Leu Ile Pro
1               5                   10                  15

Leu Gly Ile Pro Cys Val Ser Asp Val Asn Pro Thr Leu Thr Arg
            20                  25                  30

Gly Glu

<210> SEQ ID NO 315
<211> LENGTH: 34
<212> TYPE: PRT
<213> ORGANISM: Amanita bisporigera
<220> FEATURE:
<221> NAME/KEY: VARIANT
<222> LOCATION: (0)...(0)
<223> OTHER INFORMATION: Xaa can be any amino acid

<400> SEQUENCE: 315

Met Ser Asp Ile Asn Ala Thr Arg Leu Pro Gly Ala Tyr Pro Pro Val
1               5                   10                  15

Pro Met Xaa Pro Cys Val Gly Asp Ala Asp Asn Phe Thr Leu Thr Arg
            20                  25                  30

Gly Glu

<210> SEQ ID NO 316
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 316

Met Ser Asp Ile Asn Ala Thr Arg Leu Pro His Pro Phe Pro Leu Gly
1               5                   10                  15

Leu Gln Xaa Pro Val Ala Gly Asp Val Asp Asn Leu Thr Leu Thr Lys
            20                  25                  30

Gly Glu

<210> SEQ ID NO 317
<211> LENGTH: 34
<212> TYPE: PRT
<213> ORGANISM: Amanita bisporigera
<220> FEATURE:
<221> NAME/KEY: VARIANT
<222> LOCATION: (1)...(34)
<223> OTHER INFORMATION: Xaa can be any amino acid

<400> SEQUENCE: 317

Met Ser Asp Ile Asn Ala Thr Arg Leu Pro Ala Trp Leu Ala Thr Cys
1               5                   10                  15

Xaa Xaa Xaa Pro Cys Ala Gly Asp Asp Val Asn Pro Leu Leu Thr Arg
            20                  25                  30

Gly Glu

<210> SEQ ID NO 318
<211> LENGTH: 18
<212> TYPE: PRT
<213> ORGANISM: Artificial Sequence
<220> FEATURE:
<223> OTHER INFORMATION: A synthetic peptide

<400> SEQUENCE: 318

```
Ala Thr Arg Leu Pro Ile Trp Gly Ile Gly Cys Asn Pro Cys Val Gly
 1               5                  10                  15

Asp Asp

<210> SEQ ID NO 319
<211> LENGTH: 21
<212> TYPE: DNA
<213> ORGANISM: Artificial Sequence
<220> FEATURE:
<223> OTHER INFORMATION: A synthetic primer

<400> SEQUENCE: 319
ccagtgaaaa ccgagtctcc a                                           21

<210> SEQ ID NO 320
<211> LENGTH: 21
<212> TYPE: DNA
<213> ORGANISM: Artificial Sequence
<220> FEATURE:
<223> OTHER INFORMATION: A synthetic primer

<400> SEQUENCE: 320
caaagatctt cgcccttgcc t                                           21

<210> SEQ ID NO 321
<211> LENGTH: 21
<212> TYPE: DNA
<213> ORGANISM: Artificial Sequence
<220> FEATURE:
<223> OTHER INFORMATION: A synthetic primer

<400> SEQUENCE: 321
atgttcgaca ccaactccac t                                           21

<210> SEQ ID NO 322
<211> LENGTH: 21
<212> TYPE: DNA
<213> ORGANISM: Artificial Sequence
<220> FEATURE:
<223> OTHER INFORMATION: A synthetic primer

<400> SEQUENCE: 322
acacattcaa caaatactaa c                                           21

<210> SEQ ID NO 323
<211> LENGTH: 21
<212> TYPE: DNA
<213> ORGANISM: Artificial Sequence
<220> FEATURE:
<223> OTHER INFORMATION: A synthetic primer

<400> SEQUENCE: 323
gctgaacacg tcgatcaaac t                                           21

<210> SEQ ID NO 324
<211> LENGTH: 21
<212> TYPE: DNA
<213> ORGANISM: Artificial Sequence
<220> FEATURE:
<223> OTHER INFORMATION: A synthetic primer

<400> SEQUENCE: 324
tccatgggtt gcagccaata c                                           21

<210> SEQ ID NO 325
```

```
<211> LENGTH: 23
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(23)
<223> OTHER INFORMATION: R is A or G
<220> FEATURE:
<221> NAME/KEY: misc_feature
<222> LOCATION: (1)...(23)
<223> OTHER INFORMATION: N is any nucleic acid
<220> FEATURE:
<221> NAME/KEY: misc_feature
<222> LOCATION: (1)...(23)
<223> OTHER INFORMATION: Y is C or T

<400> SEQUENCE: 325
arrtcnccng tyttrtatct aga                                              23

<210> SEQ ID NO 326
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: Y is C or T
<220> FEATURE:
<221> NAME/KEY: misc_feature
<222> LOCATION: (1)...(20)
<223> OTHER INFORMATION: M is A or C
<220> FEATURE:
<221> NAME/KEY: misc_feature
<222> LOCATION: (1)...(20)
<223> OTHER INFORMATION: N is inosine

<400> SEQUENCE: 326
taymgnacng gngayytngt                                                  20

<210> SEQ ID NO 327
<211> LENGTH: 13254
<212> TYPE: DNA
<213> ORGANISM: Artificial Sequence
<220> FEATURE:
<223> OTHER INFORMATION: A synthetic sequence

<400> SEQUENCE: 327
gatcggagag aagtcagaga agtttcacta ttttcagcac atcgcagccg aagggcggcg      60
atgtccatga tgggagcgta gcataaccag aaatggatag aatcgataat cgatgatgga     120
aagtggagac ggtgacaggg gggagctagt aaatccaaaa gatacagtaa tgaagataat     180
gtgtctctca ccgaaaaaaa gggacgaatc ggaaccatca gtgcaaccta cgaaactcag     240
catcatcttc aatcggagat ttaaccgatc cacctacaag tttgaaacgt ttgcccgtta     300
ccaagttaat aacaatggtc gacttgcaca ccatctcgta ttcagctctc gtcactttca     360
ggcttatatt ccaattcctc aagctatctg cagctgcatt gactatctat ggactttaca     420
gagtcactcg tgtaatttat gttgagctga cttctccaat acgccatctc cccggtccag     480
caaacgccaa tatatttctt ggtaatctca aacagctctg gacagatgta agtacaaaat     540 caccccaccta cccacccatt gttaaccact attaccacag acatatcatt ggcattcaca     600
atatgggccg atgataagac taatggatt tctcggtgta agaaccaatc catttattct      660
gatatagata acaatcaagt ttagctttcg catttatatg tgacggatcc gcaggccttg     720
```

```
aaccacattt tgacgaatgg ttacgtttac accaaaccat cgttactcg ccgccagatc    780
ggcaagttgt ggggtccagg tgcttttca cctaccatac ttaagaggcg atgatccaac    840
catacgtcag gtctcccttt tgtcgaaggg gatcaacata aaaagcaggt gcgtacttcc   900
gttgcctcaa cctagttcgt attatgatat attacgttta acagcggaag attttggtga   960
ctatctatcc attccaaatc gtggtccatc agtgtctcaa tcacaaccag aatcctgcct  1020
ttggtccggt ccgcattcgc gaattcacag attgcttcgt aaaaaaatca aaacgggtcg  1080
gtttttacta ctcatccatg ctaccagtga tgaacttcgc ctagctccaa gactcttggg  1140
ctactgaatg ctcgaaacaa ggtggtactt gccgcttaga cattatggta ggccttggta  1200
aggtggtgat ggacatcatc agctcaacag gtatgtctga tgttgccagc atacttatta  1260
gtgtttaccg atgccattcg atggaaaggc ttccgttacg agcttgattc cctggatcgt  1320
gaaagtgact ttagccgtgt ggctacaatt ttatctcaat tgaacctgat tcgttggcaa  1380
ctccgaagat tcatcccact tctatggttc atagtatgga aattccaaat cactgtaacg  1440
gagttctcat cgcgttgtct agcctgatcc tgtagagaca caactagacg atatcaagca  1500
gaccctttct cggattacga gtcggcttct gaacgagagc aagggatccg tacgtacgaa  1560
taatgacaat tccggcagtc gagatctcct atcgcttttg gttcgcacca atatgtcccc  1620
cgatgtgcca gagcaccgtc gtctatccga tgacgaagtc aaagcgcgtg aggctgatgt  1680
atttgtcact gcgagtatac ctgatctttt tatttagagg ttatctcatt tgtaattgct  1740
ggacgtgaaa gtccgatgta agtctgagtc tgtttatctg tttaaggact attctcgaat  1800
atttgattgg tagtaacgta atggcgtggg ctttatttc tctggcaaaa aaccgtgaaa   1860
tccaggctaa gctgcgtaga gagctgctca cggtcgatac ctgtcagcca acgacggacc  1920
agctcaatgc actttcatat ttggatatgg taattaggga gacgctacgt ctgtatcctt  1980
catctaggcc actcgagggt gtgtgccaag gacgacattt tacctttggc taagccgatc  2040
accgaccgga gaggaaacct attctccagt attaggtgag gattcggtcg ttcccatatt  2100
tcttttagc gttcaccggt cttatagtat caaaagaggg caagtagtca taattcccat   2160
ttctgccatc cacaaggaca agtcgatatg gggtgaagat gctttagact tcaggtaaat  2220
attgcacgtc gctgttggct cctgagtcat tcagttttga tagaccagaa cgatgggaat  2280
gtctacctga aggcgtcaat accatcccag gcgtctggag ccatttgctc agttttggg   2340
gtggtccacg ttcgtgtatc ggattcagat ttgctatcgc cgagtgagca agttttctct  2400
agcatttcga agatatagtg ctgacactgg taacgacaag aatgaaagct ctactcttca  2460
cactagtccg tgccctcgaa tttgacttgg ctgtgccagc ggagcaaatt tctgtggaaa  2520
gtggactaag taaccgaccg attttgacca cggacccggg ccgttatcag ctcccgctgc  2580
tcatcaagcc atataaagct cgaagttaac gcgcctcgtg gttcattata cctagaggtc  2640
tagggaccac tgtgtggagt ttgtactggc atctatgata ttacatagca gtcaattacg  2700
aactgagttc ggggctgaga atgatgaga gtaaaatgtg gaggatggaa aagagcttga   2760
gcatgcgagc tgccgccgaa gtttagttca taaccagggt tctagcccgt caaagaaccg  2820
gttagcgatt gaatttgaca gaagcttctt gccactacta aatgcgttct gacggtgcag  2880
gcactgcgga tgacgcagca ttggaacgcg gcgttaatgg cgggagactt agcgcaagc   2940
ctcgagatgt cggttggttg aatgacatca gtggggccaa ctgttgcgac atgccatgac  3000
ttcccaagca aaaatttaca atacgactcg tatgagtcac caccgacttc atcgccccaa  3060
```

```
tgtcgtggtc tcttatgccc gtcatcgatt gacatggtgt ttcgcacgag tctgcttatc    3120
aagtaggcga gcaccaccac catgttttct accctagtac aaaaacagtg gtacggggaa    3180
cgcctatgtt aactttcgca caagaagagg aacttttgta ccatcctcgc cagctacctt    3240
ggggcgcgta aaatgccaac tcagttccgt cgatggccca ttggggagct caaaggcaaa    3300
atatctgacc agaaccgaca gcacagccta gagattgtgc agtcaaacaa ccaaaccgct    3360
gacatggggt tcaatcgtac cttcacctcc agtacggcga ggtctctgcc tggacacatc    3420
ctgggaccag caccgaaagt taagagaccc cggtagccag ctagttctcc cttgtttcct    3480
ttcttatgac cctcagcgtc cagccatctg cttggatcga acatgcccgc gtctggcccc    3540
cacaacgctt ccgacatatt cactcccccc aagggtatac ggacgaccat accttttcttc   3600
aaaaacaagc tatcgatcgt cgctccagat gcaatacgta tgggatttgt caacggtatc    3660
acatcgtctt cggctgcctg ccaagataat aggggggatgc gggaaggaat taaacaatga   3720
agacgaacca cacggattga ttgcatttcg ggggcatgga gtctcagtat ctcggctata    3780
aaagcatcga ggtatttcag atcctttgtt agctggtcgt atgtaggacg ttctcccttt    3840
gccaaacatt ctgagagctc agcacggagg ctctcttgga tttctggccg gcgtgcaagt    3900
tcaatgagag accactgagt gaaggctcag taatagaaca gcttgaacac tcgtaggcga    3960
agattaccgt taaggtgact atgagcagca cgggtcatag tttatgagat ctttgataaa    4020
caaggacaac cgttcgcaga acttacttgc tgttgtttca tatgcagcca tgaaaggaa     4080
actcttcggt tatattaact tacagagaat atcagaggag tggcaaaggt acgtacggcc    4140
tacaaagtat gttgattagg catcaagccg atgtgcactt gggctacata cctgggccgt    4200
gatctcggag agtgacaaac ggctgttggg atttgcgttt tctgacttga ctatacaggg    4260
aagcgtaggc acgaagaaac atcacctcat atattggtga catacccaga atcccaagga    4320
ctgattcgtt gacagtatct tccggttcct tacatgcctt gttcaggctg ttagttgtaa    4380
gcctattcaa gtgtgctact gattgtgcga gcttctcttc tctgacgctc atgagggtaa    4440
cttttaaacag gcatagagt atcggtgaca gaaagtgaat aagccttata aagggggaag    4500
gcttgactgt gtggatagag tcaaaggcgg ccatcatcaa ggacgtgcgg ccccttagag    4560
ttccaaagtc atgcgacaat atagcttcc ctatagtgtc caatctagga acatttcagg     4620
gcaagggcgg aatgaaggct gcgcaacgta cgtgacagaa ttcatccttg gcacagaga    4680
acaaggttaa ctaacaatgg gggagataga tacagcaact tgccatttca cgacatcaat    4740
tatgacgggg ttgtttgagt gctctgatga cggagaacat gaatcccatg ctgctttgag    4800
ctgtcattta tgttggtcaa tcggccgatt gtttttaagaa tggaaccatt ctaacctgat    4860
aggcagaatc caagcacacg ggagtgagat tgcgaattgc tgagaccgac agtgagaag    4920
acaggcctct ccgtagtctg cgatcatgtt aagtttatgc cctgatcgtt gagcgataaa    4980
gagtgaccga ccgcttgtga gtctcgccct cagaaataga tacaacatca ccatactgga    5040
acgtaaataa ggctggcagc taagaaaaat ggtgcaaaac agatactcgc caacttccgg    5100
ctcaaagcgg ttgtccctgc gagccgacaa tatgtggtgg tatccttgga atatatgtgt    5160
gtgagagcct tgggatcgct taatacaaca tggctggagc cgatgccagt gggtatctcg    5220
taaacgggcc catacattcg ttcccaatcc cgatatacca cactgaggtt cgccgaaggg    5280
aagatcttct tggtgttacc gaagatgaag ctctcgctgc gtggtccttg cagtctgggc    5340
gttctgatac ctcggcgtct tcgatagata gaaatgacga cgagcaacgt aaaggcagag    5400
gtcacaatcc tcatcgaatc gcctttgaaa tactctgcta catcaggcca gaggccgttg    5460
```

-continued

```
aagttgaggt tcaacatcac gaagtggacg agccgtggaa ggcgatcaag ttgcgcgaat    5520
gcgaggaaaa tgtttctgag gacccgaaac cgtaaccagg cgcgataaat gcttgaccta    5580
tctatctccg gggacggtgt tgggggtcca tcttaccgtg aaggtggata gggacagatc    5640
cgattccggg aaagaacaga cgaaacgttc gtatgatgca acacaagtgt gagcgcaaga    5700
tggagccgaa tgatcgggaa ctcggccgaa gggattctta atacacacg cccgataatc     5760 attctcatac atgtccattt tgggacaaaa cacctatcta tcggtctgta ggactgccac    5820
ttaactgttt aatctgtgac caccaggaca gacaaagaga ggctgtgcta agtggtgttc    5880
gaaacgcgtt atgcccagtt cggcataaat cgccaacacg caggatacga tgaaaagtgt    5940
aagcttaagg tcaagactcc cttgatgtga ttcaacaact tttgacgggg ttgccattgt    6000
attgcaccgt cttgcccggc tgaatgtccg cagaaaccga acgcccctaa aaacaaagaa    6060
gttcacggat tccatatagt aagcgtggag cctgtgtgat aaagagtggg ggacagcatg    6120
aatgattcat gggaagaccg atcagacaaa cgcttatgga gattttgcgc caatttgtct    6180
tctcatctcc gtgtcaggac aagattctct tatctatcgt actttctgcg gttttccaat    6240
cttgcgaatt cgtgactgaa acagataaaa ggcgttggat gcggctcagc tgtcaatatt    6300
acttacctcc cattcgaact cgaacccaag acctctactc taaatcacaa tgtctgacat    6360
caatgccacc cgtcttcctg cttggcttgt agactgccca tgcgtcggtg acgacgtcaa    6420
ccgtctcctc actcgtggtg agaggtgagc tcaaaattcc atttaataat gtagcaatgt    6480
acttatgtgt cgtgtaccag cctttgctaa atgtctcatc cactagtcaa ggtatccgcc    6540
tctgatttct tgatgacaat gcatggtcat ggtacttact tcgatgtagt agtggacgac    6600
gcaagttgtt gacaatgtta ggcttggagc gttgagcctg catcggaagt aaggccttca    6660
agtttttctg tgataagcag cgagccaact tggattagac gactcacgtt atttctcatt    6720
ctttctcatt ctcatataaa acccacgtaa atgatccgag ctgtactatg gaatgcaata    6780
tacttgtgtg tgtatgtgtg tgtgttgtca gtaagagagc gtttagcaat ccgagcgcat    6840
gctgctgtcg ccagagcttg accgtcctga ctgtccttat cattgctact tgtcagcaac    6900
atatcacata tcacataggc agctgttgta ccattgaaaa gccgtggggc gtataacctg    6960
gaggaatttc aaagaagggt ctttttatgat gagtttgata gctcgcatag ttgtggaagt    7020
cggcaagttc acaaaaacag tgaatttatg ttacattgcg tgacgaggag catgagacga    7080
gcaatttgca actttgaact acacccggga aaaagcaggc tcagcaaccc cgatgacgag    7140
ggggaggaga gaatggcgat gatgtaggca taatgcgatc gcatgtgtgt aggcgaacac    7200
gggcgacgat tggagagata gacacgctac gcgattacta cgccagtctc tcaagggccg    7260
ttcattaaag ttggctaaag tcgcggggga agggctggtg atgaggtatc ttgtgtcgac    7320
gcgggcacaa tggaccatgg gaggcagtcg ccgcatatct gaaaagctgg gctcccgacg    7380
tgaagtgagg aatcacgaaa atcatatttg cttggaagga aagcccatgc agctcagcaa    7440
actctagtaa gacaacggaa cgaaatcact ggcgatgttt gcgacatcag atctctggta    7500
tgaagtcagc ctgaaacctg ccctgtcaag gacatgcggc cgcaaccgcg actggttgat    7560
ggtaaatcca aatgcgacgc ccagttcgaa agatgagaca tacctgcgcc aaacagtgat    7620
taccacagcc acctacgagg cctcgtgagt tggcctcaat attcattagc tatcagtaga    7680
tgagcaccga agtagggctt ctgcgtgtag ttagggtgcg tgaatccgca gtgacgctca    7740
tttgtttggc tcagcgtggc cagtcgcgcc tcgggattta ccggcgcgat acaaacggaa    7800
```

```
agttctttcg cagcgttccc acccgcgcgg ccgtaagcgt gcaaaccgtc acccatagga    7860
aataaaccgt cggcaagaat agaatgtgat cccttcggcc gaatcgtcga aagcaatctg    7920
atcatagatc atcagtgacc tttcatcctt tttcagcgac agatcttgca ttcatgctgt    7980
ccgccactca tcatcttctt cttcacaata ttatactatt cacccacac tatccatatc    8040
cagttgggcc aatagtaaat cccgctgagg ctgtccgccc ttgatggaaa tgacttggag    8100
actcgccagt ttggcatcct tttttggtga ggaccccatt ttctatcttg agtcgtatcc    8160
atatctggat ggcctactgg tggtctcacc tctgtaacgg cccgcgatcg ctctcttcgc    8220
gatgttgaac ctcaatttca gcagcctttg gccttatgtc gcggagtacc tcaaagtcaa    8280
ttcgatgagg ataatagcct ctggcatatc cttgctcgtc gttgtttcca tttaccgaag    8340
ccgtcgaggt cctagaacgc cgagactgca aggaccacac atggagagct tcatcctcgg    8400
caatgctagg aagatcttcc cttcagccaa cctcagtttg gtgtatcaag gtttggagca    8460
gacttacggg cccgtctatg aaatagcctc tggctttggc tccaaccacg tcgtattgaa    8520
cgatcccaag gctctcacac acttattttc caaggacact gtcacatatt ctcagcctgc    8580
taggcagaaa gacatggggc ggaagttggt gagcgtttgt tccagcgttt cccgagctg    8640
tcagacttaa cttgttccag tttggtgata ttttggtgct cacggaaggg gagacccaca    8700
agaggttggt cgctcttgac tgcttgaaaa catggcataa atttaatatt gaacggatta    8760
tagaatacgg agggtcttgt cttctcccct gtcggtctcg gcaatccgca atttcactcc    8820
tatgtgtttg gattccgcct atcaggtcag gacggttcca gctttgagag tcagtcgatt    8880
gaacagcaca aatgatagct caaagcatca tgggattcat gtttccagtt gtcaaacaat    8940
tcgaaccgtg ctatcgtgct tgatgcagag aaatggtgag ttgctttcct tctagccttc    9000
atttaattgg ttcattatgt gcccaaggat gaactgttac acgtatgact cgcaacccttt   9060
actctgcccc attcttctca cctgcaatat attcctagca tggataatat tggaaaagct    9120
gtattgtcgt atgacttcgg caacatgagg ggccatacgt gttcgatctt agctgacttg    9180
gatgctttcc acgcagtcag cccttcaggc ctttacataa ggtttattgt gtttacccgc    9240
gagatacttt ataacctctt caagattacc ttaccgaatg ccaaagaaaa gcagtttgag    9300
gaactggcag cgcactttaa agtactcgcg actggctttc tgcgggaagc acgtgaggcg    9360
cctgaagata gcgccgttca ccaatcaatc cttggggtta tgcgtatgtt acctctatcc    9420
tgaccacgtg taaggagatt tcagcttttcc tatatatagt caagtccaaa aatgaaaatg    9480
ctaacgtccg tttatcactt cccgagatca cggcccaggt aagttgcttc acacatcggc    9540
gtcggtgctc gatcaacatc ctttgtaggc tgtatgtccc tatgcaatct cttttgtatc    9600
cactctgacc tgatataacc gaagggtggt cttgtcttgg ccgggtatga aactacggca    9660
agtaagttct atgactagca gtccgatgat ctcataatcc actaactatg ctgttcacag    9720
ttgccatgac ggtaatgtta tttatctaca agagatccat cgccgagctt ccctcagtg    9780
gtccctcatt gagcttgctc gccgggcaga aattcaagag actctccgtg ccgaactcaa    9840
ggagtgcttg gcagacggag aacgccctac atacgaccag ctgacaaagg atctgaaata    9900
cctcgatgct tttatatccg agatactgag gttacatccc tcagaaatgg tactaacccg    9960
cgtggttcgt ccccttccttt catccctatc tttttatgat gacgatcttt tcgactaggc   10020
agccgaagac gatgtgatac cgctgacgga tcccatacga actgcatctg gagcgatgat   10080
cgacagcttg ttcgtgagga aaggcaccgt ctccgcatcc ctttaggagg aatgaatata   10140
tcagagacgt tgtggggacc ggatgcggcg acattcgatc caagcaggtg gctggaagtt   10200
```

```
gatggtcata agaaaggaag aagggagaaa gtacccggct accgaaatct attgactttc   10260
ggtgctggcc aaaggctgtg tccgggaaga gacctcgcct tgctggagat gaaggtatgg   10320
cgaaactcct gccggttttt attcattttt gacttgacaa ttgccaggct gcgcttgtga   10380
ttctggtcct ccatttcagt tttgagttcc ccaatggacc atcgacgaaa ctgagttggc   10440
agttcgggcg gcccaaggta gccggcgagg atggtccgaa agtgcctatg ctgtgcgaga   10500
ctgacatagg atctcatgtg caacatcgtt cgtttcgtgt cttagtagag tttactgagt   10560
cgcatgggct ttccttccaa gcaaaaatga ctttcatgat tcctcacttc acgtggagga   10620
ccagcttttc agatgtgtgg cgatgaggct tagcatcgtg acgtaaatgg taggttggat   10680
gactggcata cccacatatt tcacatcatc cttatagacc tactagtacg ccaaacttgc   10740
ctcccatagt ccatcgtgcc acgcaccgac acaagatgca tcatcaccag cccactctaa   10800
ccaactttga tgaacgatca ttacagcctg agagggctgg cgtagtaatc acgtagcgtg   10860
tctatctctc ctcgagcacg cctgcagcct gcagtgtttt cccgcecccaa gcgacccttc   10920
cgcctcttcc caatcgtcgc cagcacatgc catcgcatgc ctatacatac atcatcacca   10980
tgattcttcc tcatcggcgt tgcatctttc tctcaggtgc tcggcccagt tcaaggttgc   11040
aaaatgctcg tctcatgctc tcattacctc ctcgtcacgc aatgtaacat aaaatcgctg   11100
tttttgtgga cttgccgctt ttacaactat gcgagctgtc aaactcatca ggaaggaccc   11160
ctgctggaaa ttcttccagg ctacacgccg caggactctt aaacggtaca aaagctgcca   11220
atgttgtatg tgatatgttc aagtaggcaa gtagcaatga cacggtcggt caggtcggtc   11280
tgctgtggat cgcggcatac aagctggcat tgataaatgt tgagatgcta tctctcacac   11340
ctcccccccc ttctctagtg cattgcattg cacagctcag agcatcattg aggggggtat   11400
tagagattga caaaggagaa tcagtaagaa gggtaatgta cttcagtcgt gttagccaag   11460
tgtccccgat gattatcacg acaatcttta agacgctggt tcagcggcac gatcatcgct   11520
ttgcaagcaa gacgtgttct acaatttgcc ttcgtcatag tcagcacaat caccccttcgt   11580
tatcatgaaa tccgaggcgg gtaccttgac tagtggatga gacatttagc aaaggctgat   11640
acacgacaca tgagtccatt gctacattat taaatggaat tttgagctca cctctcgcca   11700
cgagtgagga gacggttgac atcgtcaccg acgcatgggc aatctacaag ccaagcggga   11760
agacgggtgg cattgatgtc agacattgtg atttagagca gaggtcttgg gctcgagttc   11820
gaatgggagg taagtattga atattgaatg ctaagctgaa tccaacgcct tttatctgtc   11880
tcagtcacga attcgcatgg ttgcaaaaac cgcggaaagg acgatagata agagaatctt   11940
gtcctgacac ggagatgaag acgagttggc gcaaaatctc cataaacagt tgtctgatca   12000
tccttttttcg gtattcaata ttcatccccc attcatgctg tcagtcactg ttcatcacac   12060
attcttggca ggctccacaa aacttctttg ttctttcctg ttttttgggac gttctgtctt   12120
tgcgggcaca gccagtcggg caagacggtg caatacaatg gcaacccccc gtcaagaata   12180
gttgaatcgc atcaagggag tcttgaccct cactttttc gtcgtatcct gatcggcgac   12240
tgggcctaac gcgtttctcg ctggattaaa cacccccactg agcacagcct ttctctgtcc   12300
cggtggtcac agattgaaca gtcaagcagt ttgtaggatc aatagatagg ggttttgtcc   12360
tgaaatggac catgtagtaa tgattttcgt ccgtgtgacc cggtttgccg atgcaacaaa   12420
gacgcattat ctccatcgcg cacaggcgtg ttgcatcact tatgactatg tggctctaac   12480
tttcctggaa tcgaatccgc ccctatccac cttcacggta acatggaccc ccaacaccgt   12540
```

-continued

```
tcccggagat agataggtca agttctcgcg cctggttacg gtttcggctc ctcagaaacg    12600
ttttcctcgt attcgcgcaa ctcccaccct tcaatggcat ttccacgtct ggttgggttg    12660
gttgctatac tagtacttat ccgcgatggc cttccttcct tgcataacgg ctcgtccact    12720
ccgtcacccg tgatgttgaa cctcaactcc aacggcctct ggcctgatgt ggcagagtat    12780
ctcaaaggta attcgataag gattgtgacc tctgacattg ctcgtcgtca tttctatcta    12840
tcggagatgc cgaggtatca gaacgcccag actacaagga ccacgcagcg agagcttcag    12900
attcagtaac accaagatct tcccttccgc gaacctcagt acggtggtat atcgggattg    12960
ggaacgaatg tatgggcctt acgagatacc cactggcatc ggctacagcc atgttgtatt    13020
gagcgatccc aaggctcaca cacatatatt ccgaggatac caccacatat cctcggctcg    13080
cagggacaac cgctttgagc caggttggcg agtctttgtt ttgcaccatt tttcagctgc    13140
cagcctcatt gtcgttccag tatggtgatg ttatatctat ttctgagcgc gagactcaca    13200
aggggttggt cgctctttat cgctcaacga ttagggcata aacttaacat gatc          13254
```

<210> SEQ ID NO 328

<400> SEQUENCE: 328

000

<210> SEQ ID NO 329

<400> SEQUENCE: 329

000

<210> SEQ ID NO 330
<211> LENGTH: 10
<212> TYPE: PRT
<213> ORGANISM: Amanita bisporigera

<400> SEQUENCE: 330

Asn Cys Phe Asp Asp Phe Ile Ala Ala Thr
1               5                   10

<210> SEQ ID NO 331
<211> LENGTH: 22
<212> TYPE: PRT
<213> ORGANISM: Amanita bisporigera

<400> SEQUENCE: 331

Arg Ile Lys Glu Ser Ala Asp Lys Trp Gly Phe Val Ala Gln Ser Leu
1               5                   10                  15

Gly Leu Val Trp Lys Asp
            20

<210> SEQ ID NO 332
<211> LENGTH: 20
<212> TYPE: PRT
<213> ORGANISM: Amanita bisporigera

<400> SEQUENCE: 332

Ile Tyr Arg Thr Thr Lys Leu Asn Gly Leu Asn Thr Glu Asp Phe Lys
1               5                   10                  15

Ala Ser Gln Val
            20

<210> SEQ ID NO 333

```
<400> SEQUENCE: 333

000

<210> SEQ ID NO 334
<211> LENGTH: 26
<212> TYPE: PRT
<213> ORGANISM: Amanita bisporigera

<400> SEQUENCE: 334

Arg Tyr Pro Asp Thr Ser Thr Ala Thr Gln Glu Asn Gly Pro Ile Ala
1               5                   10                  15

Thr Glu Gly Asp Leu Asp Ala Met Val Tyr
            20                  25

<210> SEQ ID NO 335
<211> LENGTH: 12
<212> TYPE: PRT
<213> ORGANISM: Amanita bisporigera

<400> SEQUENCE: 335

Val Lys Asp Ala Ala Asp Lys Trp Gly Phe Ile Ala
1               5                   10

<210> SEQ ID NO 336
<211> LENGTH: 13
<212> TYPE: PRT
<213> ORGANISM: Amanita bisporigera

<400> SEQUENCE: 336

Met Met Cys Tyr His Lys Val Gly Thr Thr Gln Gly Glu
1               5                   10

<210> SEQ ID NO 337
<211> LENGTH: 13
<212> TYPE: PRT
<213> ORGANISM: Amanita bisporigera

<400> SEQUENCE: 337

Val Leu Tyr Arg Ser Lys Glu Pro Ala Leu Pro Asp Phe
1               5                   10

<210> SEQ ID NO 338
<211> LENGTH: 15
<212> TYPE: PRT
<213> ORGANISM: Amanita bisporigera

<400> SEQUENCE: 338

Lys Met Ala Thr Lys Ile Pro Met Phe Ile Val Arg His Lys Ser
1               5                   10                  15

<210> SEQ ID NO 339
<211> LENGTH: 11
<212> TYPE: PRT
<213> ORGANISM: Amanita bisporigera

<400> SEQUENCE: 339

Lys Asp Ala Ala Asp Lys Trp Gly Phe Ile Ala
1               5                   10

<210> SEQ ID NO 340

<400> SEQUENCE: 340
```

<210> SEQ ID NO 341

<400> SEQUENCE: 341

000

<210> SEQ ID NO 342

<400> SEQUENCE: 342

000

<210> SEQ ID NO 343
<211> LENGTH: 9
<212> TYPE: PRT
<213> ORGANISM: Amanita bisporigera

<400> SEQUENCE: 343

Asn Cys Phe Asp Asp Phe Ile Ala Ala
 1               5

<210> SEQ ID NO 344
<211> LENGTH: 19
<212> TYPE: PRT
<213> ORGANISM: Amanita bisporigera

<400> SEQUENCE: 344

Lys Glu Ser Ala Asp Lys Trp Gly Phe Val Ala Gln Ser Leu Gly Leu
 1               5                  10                  15

Val Trp Lys

<210> SEQ ID NO 345

<400> SEQUENCE: 345

000

<210> SEQ ID NO 346
<211> LENGTH: 19
<212> TYPE: PRT
<213> ORGANISM: Amanita bisporigera

<400> SEQUENCE: 346

Ser Ser Gly Gln Ala Trp Ile Ser Glu Tyr Gly Asn Pro Ser Ile Pro
 1               5                  10                  15

Glu Glu Phe

<210> SEQ ID NO 347

<400> SEQUENCE: 347

000

<210> SEQ ID NO 348
<211> LENGTH: 750
<212> TYPE: PRT
<213> ORGANISM: Amanita bisporigera

<400> SEQUENCE: 348

Met Arg Thr Pro Trp Thr Pro Asn Arg Tyr Pro Pro Ala Arg Arg Ser
 1               5                  10                  15

Asp His Tyr Asp Glu Tyr Lys Ser Glu Lys Asn Gly Val Val Arg Val

```
                20                  25                  30
His Asp Pro Tyr Asn Trp Leu Glu His Asn Thr Gln Glu Thr Glu Ser
            35                  40                  45

Trp Thr Ser Ala Gln Val Ala Phe Thr Lys Glu Tyr Leu Asp Gln Asn
 50                  55                  60

Pro Asp Arg Gln Lys Leu Glu Asp Glu Ile Arg Asn Thr Asp Tyr
 65              70                  75                  80

Ala Lys Phe Ser Ala Pro Ser Leu Lys Asp Asp Gly Arg Trp Tyr Trp
                85                  90                  95

Tyr Tyr Asn Ser Gly Leu Gln Pro Gln Ser Gly Val His Ala Phe Val
            100                 105                 110

Leu Leu Leu Cys His Ser Asp Ile Asp Val Pro Thr Ser Val Ile Tyr
            115                 120                 125

Arg Ser Arg Asp Arg Asn Leu Pro Thr Met Ser Asn Glu Glu Gly Pro
            130                 135                 140

Gly Gly Glu Val Phe Phe Asp Pro Asn Leu Leu Ser Asn Asp Gly Thr
145                 150                 155                 160

Ala Ala Leu Ala Ala Thr Ala Phe Ser Arg Asp Gly Lys Tyr Phe Ala
                165                 170                 175

Tyr Gly Ile Ser Arg Ser Gly Ser Asp Phe Tyr Thr Val Tyr Val Arg
            180                 185                 190

Pro Thr Ser Ala Pro Leu Ala Ser Gln Gly Glu Ser Arg Val Ser His
            195                 200                 205

Asp Asp Glu Arg Leu Gln Asp Glu Val Arg Phe Val Lys Phe Ser Ser
    210                 215                 220

Ile Ser Trp Ser His Asp Ser Lys Gly Phe Phe Tyr Gln Arg Tyr Pro
225                 230                 235                 240

Glu Arg Lys Ser His Gly Ser Ala Asp Glu Asp Lys Ala Gly Thr Glu
                245                 250                 255

Thr Glu Ser Asp Lys His Ala Met Leu Tyr Tyr His Arg Val Gly Thr
            260                 265                 270

Ser Gln Leu Glu Asp Val Leu Val Tyr Lys Asp Asp Ala Asn Pro Glu
            275                 280                 285

Trp Phe Trp Gly Ala Glu Ile Ser Glu Glu Asp Gly Arg Tyr Leu Ile
            290                 295                 300

Leu Ser Val Ser Arg Asp Thr Ser Arg Lys Asn Leu Leu Trp Ile Ala
305                 310                 315                 320

Asp Leu Glu Ser Asn Ala Ile Gly Gln Asp Met Gln Trp Asn Lys Leu
                325                 330                 335

Ile Asp Glu Phe Asp Ala Ser Tyr Asp Tyr Ile Ala Asn Asn Gly Asn
            340                 345                 350

Lys Phe Tyr Phe Gln Thr Asn Lys Asp Ala Pro Gln Tyr Lys Leu Val
            355                 360                 365

Ser Val Asp Ile Ser Ala Pro Pro Ala Gln Arg Thr Phe Glu Asp Val
            370                 375                 380

Ile Pro Glu Asp Lys Asn Ala His Leu Glu Asp Val Leu Ala Ile Ala
385                 390                 395                 400

Asp Asp Lys Phe Ala Val Val Tyr Lys Arg Asn Val Lys Asp Glu Ile
                405                 410                 415

Tyr Ile Tyr Asp Met Asn Gly Lys Gln Leu Glu Arg Val Ala Pro Asp
            420                 425                 430

Phe Val Gly Ala Ala Ser Ile Ala Gly Arg Arg Ser Gln Pro Trp Phe
            435                 440                 445
```

```
Phe Ala Thr Leu Thr Gly Phe Thr Asn Pro Gly Ile Val Ser Arg Tyr
            450                 455                 460

Asp Phe Thr Gln Gln Asp Pro Ala Lys Arg Trp Ser Thr Tyr Arg Thr
465                 470                 475                 480

Thr Leu Leu Lys Gly Leu Lys Ala Glu Asp Phe Glu Ala Gln Gln Val
                485                 490                 495

Trp Tyr His Ser Lys Asp Gly Thr Lys Ile Pro Met Phe Ile Val Arg
                500                 505                 510

His Arg Asn Thr Lys Phe Asp Gly Thr Ala Pro Ala Ile Gln Tyr Gly
            515                 520                 525

Tyr Gly Gly Phe Thr Ile Ser Ile Asn Pro Phe Phe Ser Ala Ser Phe
530                 535                 540

Leu Thr Phe Leu Gln Arg Tyr Gly Ala Val Leu Ala Val Pro Asn Ile
545                 550                 555                 560

Arg Gly Gly Gly Glu Phe Gly Glu Glu Trp His Leu Ala Gly Thr Arg
                565                 570                 575

Glu Arg Lys Val Asn Cys Phe Asp Asp Phe Ile Ala Ala Thr Gln Phe
            580                 585                 590

Leu Ile Asp Asn Lys Tyr Ala Ala Pro Gly Cys Gly Asn Ser Asp Tyr
        595                 600                 605

Ala Pro Asp Ser Arg Val Thr Thr Gly Leu Leu Val Ala Ala Cys Val
610                 615                 620

Asn Arg Ala Pro Glu Gly Leu Leu Gly Ala Ala Val Ala Glu Val Gly
625                 630                 635                 640

Val Leu Asp Leu Leu Lys Phe Ala Asp Phe Thr Ile Gly Arg Ala Trp
                645                 650                 655

Thr Ser Asp Tyr Gly Asn Pro His Asp Pro His Asp Phe Asp Phe Ile
                660                 665                 670

Tyr Pro Ile Ser Pro Leu His Asn Val Pro Lys Asp Lys Asp Leu Pro
            675                 680                 685

Pro Thr Ile Leu Leu Thr Ala Asp Pro Ser Ile Asp Asp Asp Arg Val
690                 695                 700

Val Pro Leu His Ser Tyr Lys His Ala Ala Thr Leu Gln Tyr Thr Leu
705                 710                 715                 720

Ser His Asn Thr His Pro Leu Leu Ile Arg Ile Asp Lys Lys Ala Gly
                725                 730                 735

His Gly Ala Gly Lys Ser Thr Asp Gln Arg His Ala Ile Leu
                740                 745                 750

<210> SEQ ID NO 349
<211> LENGTH: 2151
<212> TYPE: PRT
<213> ORGANISM: Amanita bisporigera

<400> SEQUENCE: 349

Met Ser Ser Ala Arg Thr Ala Trp Asp Pro Lys Ser Thr Pro Tyr Pro
  1               5                  10                  15

Ser Val His Arg Ser Asp Thr Val Glu Glu Phe Lys Ser Ala Lys His
                20                  25                  30

Gly Thr Val Lys Val Ala Asp Pro Tyr Asp Trp Leu Ala Phe Pro Asp
            35                  40                  45

Ser Lys Glu Thr Gln His Phe Val Gln Gln Gly Asp Phe Thr Lys
        50                  55                  60

Lys Tyr Leu Asp Gln Tyr Gln Asp Lys Glu Lys Phe Ser Lys Glu Leu
```

-continued

```
                65                   70                   75                   80
Glu Lys Asn Trp Asn Tyr Ala Arg Phe Ser Cys Pro Ser Leu Lys Gly
                    85                   90                   95

Asp Gly Tyr Tyr Tyr Phe Thr Tyr Asn Ser Gly Leu Ala Ala Pro Asn
                   100                  105                 110

Leu Leu Ser Thr Asp Gly Ser Val Ser Arg Ser Thr Ser Ser Phe Ser
                   115                  120                 125

Glu Asp Gly Lys Tyr Tyr Ala Tyr Ala Leu Ser Arg Ser Gly Ser Asp
        130                  135                  140

Trp Asn Thr Ile Tyr Val Arg Glu Thr Ser Ser Pro His Leu Ser Thr
145                  150                  155                 160

Gln Ala Val Gly Ser Asp Gly Arg Leu Pro Asn Asp Val Leu Arg
                    165                  170                 175

Phe Val Lys Phe Ser Gly Ile Gly Trp Thr Ala Asp Ser Lys Gly Phe
                    180                  185                 190

Phe Tyr Gln Arg Phe Pro Glu Arg Lys Glu His Gly Gly Glu Glu Asp
                    195                  200                 205

Asp Lys Ala Gly Thr Glu Thr Asp Lys Asp Leu Asn Ala Ser Leu Tyr
        210                  215                  220

Tyr His Arg Val Gly Thr Pro Gln Ser Glu Asp Val Leu Ile His Gln
225                  230                  235                 240

Asp Lys Glu His Pro Glu Trp Met Phe Gly Ala Gly Ala Thr Glu Asp
                    245                  250                 255

Gly Arg Tyr Leu Val Met Thr Ser Ser Arg Asp Thr Ala Arg Ser Asn
                    260                  265                 270

Leu Leu Trp Ile Ala Asp Leu Gln Asp Pro Gln Asn Ser Glu Ile Gly
            275                  280                  285

Pro Asn Leu Lys Trp Asn Lys Leu Ile Asn Glu Trp Gly Thr Tyr Trp
        290                  295                  300

Ser Glu Leu Thr Asn Asp Gly Ser Lys Phe Tyr Phe Tyr Thr Asn Ala
305                  310                  315                 320

Glu Asp Ser Pro Asn Tyr Lys Ile Val Thr Phe Asp Leu Glu Lys Pro
                    325                  330                 335

Glu Gln Gly Phe Lys Asp Leu Ile Ala His Asn Pro Lys Ser Pro Leu
                    340                  345                 350

Thr Ser Ala His Leu Ala Ala Asn Asp Gln Leu Ile Leu Leu Tyr Ser
            355                  360                  365

Asn Asp Val Lys Asp Glu Leu Tyr Leu His Ser Leu Glu Thr Gly Glu
        370                  375                  380

Arg Val Lys Arg Leu Ala Ser Asp Leu Ile Gly Thr Val Glu Gln Phe
385                  390                  395                 400

Ser Gly Arg Arg Glu His Lys Glu Met Trp Phe Ser Met Ser Gly Phe
                    405                  410                 415

Thr Ser Pro Gly Thr Val Tyr Arg Tyr Glu Phe Glu Gly Glu Asn Ala
                    420                  425                 430

Gly Val Glu Gln Glu Tyr Arg Lys Ala Thr Val Glu Gly Ile Lys Ala
            435                  440                  445

Glu Asp Phe Glu Ser Ser Gln Val Phe Tyr Glu Ser Lys Asp Gly Thr
        450                  455                  460

Lys Val Pro Met Phe Ile Thr Arg Pro Lys Gly Val Glu Lys Gly Pro
465                  470                  475                 480

Val Leu Leu Tyr Ala Tyr Gly Gly Phe Ser His Ala Ile Thr Pro Phe
                    485                  490                 495
```

```
Phe Ser Pro Ser Leu Met Thr Trp Ile Lys His Tyr Lys Ala Ala Leu
            500                 505                 510

Cys Ile Ala Asn Ile Arg Gly Gly Asp Glu Tyr Gly Glu Lys Trp His
        515                 520                 525

Glu Ala Gly Thr Lys Glu Arg Lys Gln Asn Cys Phe Asp Asp Phe Gln
    530                 535                 540

Trp Ala Ala Lys Tyr Leu Tyr Lys Glu Gly Ile Ala Glu Glu Gly Lys
545                 550                 555                 560

Ile Ala Ile Ser Gly Ser Asn Gly Gly Leu Leu Val Gly Ala Cys
                565                 570                 575

Val Asn Gln Ala Pro Glu Leu Tyr Gly Ala Ala Ile Ala Asp Val Gly
            580                 585                 590

Val Leu Asp Met Leu Arg Phe His Arg Tyr Thr Ile Gly Arg Ala Trp
        595                 600                 605

Ser Ser Asp Tyr Gly Cys Ser Asp Glu Pro Glu Gly Phe Asp Tyr Leu
    610                 615                 620

Tyr Ala Tyr Ser Pro Leu Gln Asn Val Asp Pro Ser Lys Lys Pro Phe
625                 630                 635                 640

Pro Pro Thr Met Leu Leu Thr Ala Asp His Asp Asp Arg Val Val Pro
                645                 650                 655

Leu His Ser Phe Lys His Ile Ser Glu Leu Gln His Lys Leu Pro Asp
            660                 665                 670

Asn Pro His Pro Leu Leu Leu Arg Val Asp Thr Lys Ser Gly His Gly
        675                 680                 685

Ala Gly Lys Ser Thr Ala Lys Lys Ile Glu Glu Ala Cys Glu Lys Tyr
    690                 695                 700

Gly Phe Val Ser Gln Ser Met Gly Leu Arg Trp His Asp Met Ser Ser
705                 710                 715                 720

Ala Arg Thr Ala Trp Asp Pro Lys Ser Thr Pro Tyr Pro Ser Val His
                725                 730                 735

Arg Ser Asp Thr Val Glu Glu Phe Lys Ser Ala Lys His Gly Thr Val
            740                 745                 750

Lys Val Ala Asp Pro Tyr Asp Trp Leu Ala Phe Pro Asp Ser Lys Glu
        755                 760                 765

Thr Gln His Phe Val Gln Gln Gln Gly Asp Phe Thr Lys Lys Tyr Leu
    770                 775                 780

Asp Gln Tyr Gln Asp Lys Glu Lys Phe Ser Lys Glu Leu Glu Lys Asn
785                 790                 795                 800

Trp Asn Tyr Ala Arg Phe Ser Cys Pro Ser Leu Lys Gly Asp Gly Tyr
                805                 810                 815

Tyr Tyr Phe Thr Tyr Asn Ser Gly Leu Ala Ala Pro Asn Leu Leu Ser
            820                 825                 830

Thr Asp Gly Ser Val Ser Arg Ser Thr Ser Phe Ser Glu Asp Gly
        835                 840                 845

Lys Tyr Tyr Ala Tyr Ala Leu Ser Arg Ser Gly Ser Asp Trp Asn Thr
    850                 855                 860

Ile Tyr Val Arg Glu Thr Ser Pro His Leu Ser Thr Gln Ala Val
865                 870                 875                 880

Gly Ser Asp Glu Gly Arg Leu Pro Asn Asp Val Leu Arg Phe Val Lys
                885                 890                 895

Phe Ser Gly Ile Gly Trp Thr Ala Asp Ser Lys Gly Phe Phe Tyr Gln
            900                 905                 910
```

```
Arg Phe Pro Glu Arg Lys Glu His Gly Gly Glu Asp Asp Lys Ala
            915                 920                 925
Gly Thr Glu Thr Asp Lys Asp Leu Asn Ala Ser Leu Tyr Tyr His Arg
        930                 935                 940
Val Gly Thr Pro Gln Ser Glu Asp Val Leu Ile His Gln Asp Lys Glu
945                 950                 955                 960
His Pro Glu Trp Met Phe Gly Ala Gly Ala Thr Glu Asp Gly Arg Tyr
                965                 970                 975
Leu Val Met Thr Ser Ser Arg Asp Thr Ala Arg Ser Asn Leu Leu Trp
            980                 985                 990
Ile Ala Asp Leu Gln Asp Pro Gln Asn Ser Glu Ile Gly Pro Asn Leu
        995                 1000                1005
Lys Trp Asn Lys Leu Ile Asn Glu Trp Gly Thr Tyr Trp Ser Glu Leu
    1010                1015                1020
Thr Asn Asp Gly Ser Lys Phe Tyr Phe Tyr Thr Asn Ala Glu Asp Ser
1025                1030                1035                1040
Pro Asn Tyr Lys Ile Val Thr Phe Asp Leu Glu Lys Pro Glu Gln Gly
                1045                1050                1055
Phe Lys Asp Leu Ile Ala His Asn Pro Lys Ser Pro Leu Thr Ser Ala
            1060                1065                1070
His Leu Ala Ala Asn Asp Gln Leu Ile Leu Tyr Ser Asn Asp Val
        1075                1080                1085
Lys Asp Glu Leu Tyr Leu His Ser Leu Glu Thr Gly Glu Arg Val Lys
    1090                1095                1100
Arg Leu Ala Ser Asp Leu Ile Gly Thr Val Glu Gln Phe Ser Gly Arg
1105                1110                1115                1120
Arg Glu His Lys Glu Met Trp Phe Ser Met Ser Gly Phe Thr Ser Pro
                1125                1130                1135
Gly Thr Val Tyr Arg Tyr Glu Phe Glu Gly Glu Asn Ala Gly Val Glu
            1140                1145                1150
Gln Glu Tyr Arg Lys Ala Thr Val Glu Gly Ile Lys Ala Glu Asp Phe
        1155                1160                1165
Glu Ser Ser Gln Val Phe Tyr Glu Ser Lys Asp Gly Thr Lys Val Pro
    1170                1175                1180
Met Phe Ile Thr Arg Pro Lys Gly Val Glu Lys Gly Pro Val Leu Leu
1185                1190                1195                1200
Tyr Ala Tyr Gly Gly Phe Ser His Ala Ile Thr Pro Phe Phe Ser Pro
                1205                1210                1215
Ser Leu Met Thr Trp Ile Lys His Tyr Lys Ala Ala Leu Cys Ile Ala
            1220                1225                1230
Asn Ile Arg Gly Gly Asp Glu Tyr Gly Glu Lys Trp His Glu Ala Gly
        1235                1240                1245
Thr Lys Glu Arg Lys Gln Asn Cys Phe Asp Asp Phe Gln Trp Ala Ala
    1250                1255                1260
Lys Tyr Leu Tyr Lys Glu Gly Ile Ala Glu Gly Lys Ile Ala Ile
1265                1270                1275                1280
Ser Gly Gly Ser Asn Gly Gly Leu Leu Val Gly Ala Cys Val Asn Gln
                1285                1290                1295
Ala Pro Glu Leu Tyr Gly Ala Ala Ile Ala Asp Val Gly Val Leu Asp
            1300                1305                1310
Met Leu Arg Phe His Arg Tyr Thr Ile Gly Arg Ala Trp Ser Ser Asp
        1315                1320                1325
Tyr Gly Cys Ser Asp Glu Pro Glu Gly Phe Asp Tyr Leu Tyr Ala Tyr
```

```
                1330                1335                1340
Ser Pro Leu Gln Asn Val Asp Pro Ser Lys Lys Pro Phe Pro Pro Thr
1345                1350                1355                1360

Met Leu Leu Thr Ala Asp His Asp Arg Val Val Pro Leu His Ser
            1365                1370                1375

Phe Lys His Ile Ser Glu Leu Gln His Lys Leu Pro Asp Asn Pro His
            1380                1385                1390

Pro Leu Leu Leu Arg Val Asp Thr Lys Ser Gly His Gly Ala Gly Lys
            1395                1400                1405

Ser Thr Ala Lys Lys Ile Glu Glu Ala Cys Glu Lys Tyr Gly Phe Val
            1410                1415                1420

Ser Gln Ser Met Gly Leu Arg Trp His Asp Met Ser Ser Ala Arg Thr
1425                1430                1435                1440

Ala Trp Asp Pro Lys Ser Thr Pro Tyr Pro Ser Val His Arg Ser Asp
            1445                1450                1455

Thr Val Glu Glu Phe Lys Ser Ala Lys His Gly Thr Val Lys Val Ala
            1460                1465                1470

Asp Pro Tyr Asp Trp Leu Ala Phe Pro Asp Ser Lys Glu Thr Gln His
            1475                1480                1485

Phe Val Gln Gln Gln Gly Asp Phe Thr Lys Lys Tyr Leu Asp Gln Tyr
            1490                1495                1500

Gln Asp Lys Glu Lys Phe Ser Lys Glu Leu Glu Lys Asn Trp Asn Tyr
1505                1510                1515                1520

Ala Arg Phe Ser Cys Pro Ser Leu Lys Gly Asp Gly Tyr Tyr Tyr Phe
            1525                1530                1535

Thr Tyr Asn Ser Gly Leu Ala Ala Pro Asn Leu Leu Ser Thr Asp Gly
            1540                1545                1550

Ser Val Ser Arg Ser Thr Ser Ser Phe Ser Glu Asp Gly Lys Tyr Tyr
            1555                1560                1565

Ala Tyr Ala Leu Ser Arg Ser Gly Ser Asp Trp Asn Thr Ile Tyr Val
            1570                1575                1580

Arg Glu Thr Ser Ser Pro His Leu Ser Thr Gln Ala Val Gly Ser Asp
1585                1590                1595                1600

Glu Gly Arg Leu Pro Asn Asp Val Leu Arg Phe Val Lys Phe Ser Gly
            1605                1610                1615

Ile Gly Trp Thr Ala Asp Ser Lys Gly Phe Phe Tyr Gln Arg Phe Pro
            1620                1625                1630

Glu Arg Lys Glu His Gly Gly Glu Glu Asp Lys Ala Gly Thr Glu
            1635                1640                1645

Thr Asp Lys Asp Leu Asn Ala Ser Leu Tyr Tyr His Arg Val Gly Thr
1650                1655                1660

Pro Gln Ser Glu Asp Val Leu Ile His Gln Asp Lys Glu His Pro Glu
1665                1670                1675                1680

Trp Met Phe Gly Ala Gly Ala Thr Glu Asp Gly Arg Tyr Leu Val Met
            1685                1690                1695

Thr Ser Ser Arg Asp Thr Ala Arg Ser Asn Leu Leu Trp Ile Ala Asp
            1700                1705                1710

Leu Gln Asp Pro Gln Asn Ser Glu Ile Gly Pro Asn Leu Lys Trp Asn
            1715                1720                1725

Lys Leu Ile Asn Glu Trp Gly Thr Tyr Trp Ser Glu Leu Thr Asn Asp
            1730                1735                1740

Gly Ser Lys Phe Tyr Phe Tyr Thr Asn Ala Glu Asp Ser Pro Asn Tyr
1745                1750                1755                1760
```

Lys Ile Val Thr Phe Asp Leu Glu Lys Pro Glu Gln Gly Phe Lys Asp
            1765                1770                1775

Leu Ile Ala His Asn Pro Lys Ser Pro Leu Thr Ser Ala His Leu Ala
            1780                1785                1790

Ala Asn Asp Gln Leu Ile Leu Leu Tyr Ser Asn Asp Val Lys Asp Glu
            1795                1800                1805

Leu Tyr Leu His Ser Leu Glu Thr Gly Glu Arg Val Lys Arg Leu Ala
            1810                1815                1820

Ser Asp Leu Ile Gly Thr Val Glu Gln Phe Ser Gly Arg Arg Glu His
1825                1830                1835                1840

Lys Glu Met Trp Phe Ser Met Ser Gly Phe Thr Ser Pro Gly Thr Val
            1845                1850                1855

Tyr Arg Tyr Glu Phe Glu Gly Glu Asn Ala Gly Val Glu Gln Glu Tyr
            1860                1865                1870

Arg Lys Ala Thr Val Glu Gly Ile Lys Ala Glu Asp Phe Glu Ser Ser
            1875                1880                1885

Gln Val Phe Tyr Glu Ser Lys Asp Gly Thr Lys Val Pro Met Phe Ile
            1890                1895                1900

Thr Arg Pro Lys Gly Val Glu Lys Gly Pro Val Leu Leu Tyr Ala Tyr
1905                1910                1915                1920

Gly Gly Phe Ser His Ala Ile Thr Pro Phe Phe Ser Pro Ser Leu Met
            1925                1930                1935

Thr Trp Ile Lys His Tyr Lys Ala Ala Leu Cys Ile Ala Asn Ile Arg
            1940                1945                1950

Gly Gly Asp Glu Tyr Gly Glu Lys Trp His Glu Ala Gly Thr Lys Glu
            1955                1960                1965

Arg Lys Gln Asn Cys Phe Asp Asp Phe Gln Trp Ala Ala Lys Tyr Leu
            1970                1975                1980

Tyr Lys Glu Gly Ile Ala Glu Glu Gly Lys Ile Ala Ile Ser Gly Gly
1985                1990                1995                2000

Ser Asn Gly Gly Leu Leu Val Gly Ala Cys Val Asn Gln Ala Pro Glu
            2005                2010                2015

Leu Tyr Gly Ala Ala Ile Ala Asp Val Gly Val Leu Asp Met Leu Arg
            2020                2025                2030

Phe His Arg Tyr Thr Ile Gly Arg Ala Trp Ser Ser Asp Tyr Gly Cys
            2035                2040                2045

Ser Asp Glu Pro Glu Gly Phe Asp Tyr Leu Tyr Ala Tyr Ser Pro Leu
            2050                2055                2060

Gln Asn Val Asp Pro Ser Lys Lys Pro Phe Pro Pro Thr Met Leu Leu
2065                2070                2075                2080

Thr Ala Asp His Asp Asp Arg Val Val Pro Leu His Ser Phe Lys His
            2085                2090                2095

Ile Ser Glu Leu Gln His Lys Leu Pro Asp Asn Pro His Pro Leu Leu
            2100                2105                2110

Leu Arg Val Asp Thr Lys Ser Gly His Gly Ala Gly Lys Ser Thr Ala
            2115                2120                2125

Lys Lys Ile Glu Glu Ala Cys Glu Lys Tyr Gly Phe Val Ser Gln Ser
            2130                2135                2140

Met Gly Leu Arg Trp His Asp
2145                2150

<210> SEQ ID NO 350
<211> LENGTH: 12

```
<212> TYPE: PRT
<213> ORGANISM: Amanita bisporigera

<400> SEQUENCE: 350

Ala Trp Leu Val Asp Cys Pro Cys Val Gly Asp Asp
 1               5                  10

<210> SEQ ID NO 351
<211> LENGTH: 12
<212> TYPE: PRT
<213> ORGANISM: Amanita bisporigera

<400> SEQUENCE: 351

Ala Thr Arg Leu Pro Ala Trp Leu Val Asp Cys Pro
 1               5                  10

<210> SEQ ID NO 352
<211> LENGTH: 60
<212> TYPE: PRT
<213> ORGANISM: Amanita bisporigera

<400> SEQUENCE: 352

Trp Ala Pro His Ser Tyr Pro Pro Thr Arg Arg Ser Asp His Val Asp
 1               5                  10                  15

Val Tyr Gln Ser Ala Ser Arg Gly Glu Val Pro Val Pro Asp Pro Tyr
             20                  25                  30

Gln Trp Leu Glu Glu Asn Ser Asn Glu Val Asp Glu Trp Thr Thr Ala
         35                  40                  45

Gln Thr Ala Phe Thr Gly Tyr Leu Asp Lys Asn
     50                  55                  60

<210> SEQ ID NO 353
<211> LENGTH: 60
<212> TYPE: PRT
<213> ORGANISM: Galerina marginata

<400> SEQUENCE: 353

Trp Ala Pro Gly Asn Tyr Pro Ser Thr Arg Arg Ser Asp His Val Asp
 1               5                  10                  15

Ser Tyr Gln Ser Ala Ser Lys Gly Glu Val Pro Val Pro Asp Pro Tyr
             20                  25                  30

Gln Trp Leu Glu Glu Ser Thr Asp Glu Val Asp Lys Trp Thr Thr Ala
         35                  40                  45

Gln Ala Asp Leu Ala Gln Ala Tyr Leu Asp Gln Asn
     50                  55                  60

<210> SEQ ID NO 354
<211> LENGTH: 60
<212> TYPE: PRT
<213> ORGANISM: Amanita bisporigera

<400> SEQUENCE: 354

Ser Ser Thr Gln Trp Thr Pro Asn Met Tyr Pro Ser Ala Arg Arg Ser
 1               5                  10                  15

Asp His Ile Asp Thr Tyr Arg Ser Glu Thr Arg Gly Glu Val Lys Val
             20                  25                  30

Pro Asp Pro Tyr His Trp Leu Glu Glu Tyr Ser Glu Glu Thr Asp Lys
         35                  40                  45

Trp Thr Ser Asp Gln Glu Glu Phe Thr Arg Thr Tyr
     50                  55                  60
```

<210> SEQ ID NO 355
<211> LENGTH: 17
<212> TYPE: PRT
<213> ORGANISM: Amanita bisporigera

<400> SEQUENCE: 355

Leu Asp Ser Asn Pro Asp Arg Lys Lys Leu Glu Asp Ala Phe Arg Lys
1               5                   10                  15

Ser

<210> SEQ ID NO 356
<211> LENGTH: 60
<212> TYPE: PRT
<213> ORGANISM: Galerina marginata

<400> SEQUENCE: 356

Ser Ser Ile Ala Trp Ala Pro Gly Asn Tyr Pro Ser Thr Arg Arg Ser
1               5                   10                  15

Asp His Val Asp Ser Tyr Gln Ser Ala Ser Lys Gly Glu Val Pro Val
            20                  25                  30

Pro Asp Pro Tyr Gln Trp Leu Glu Glu Ser Thr Asp Glu Val Asp Lys
        35                  40                  45

Trp Thr Thr Ala Gln Ala Asp Leu Ala Gln Ala Tyr
    50                  55                  60

<210> SEQ ID NO 357
<211> LENGTH: 17
<212> TYPE: PRT
<213> ORGANISM: Galerina marginata

<400> SEQUENCE: 357

Leu Asp Gln Asn Ala Asp Ile Gln Lys Leu Ala Asp Lys Phe Arg Ala
1               5                   10                  15

Ser

<210> SEQ ID NO 358
<211> LENGTH: 4
<212> TYPE: PRT
<213> ORGANISM: Amanita bisporigera

<400> SEQUENCE: 358

Asp Tyr Pro Lys
1

<210> SEQ ID NO 359
<211> LENGTH: 60
<212> TYPE: PRT
<213> ORGANISM: Amanita bisporigera

<400> SEQUENCE: 359

Ile Asp Thr Tyr Arg Ser Glu Thr Arg Gly Glu Val Lys Val Pro Asp
1               5                   10                  15

Pro Tyr His Trp Leu Glu Glu Tyr Ser Glu Glu Thr Asp Lys Trp Thr
            20                  25                  30

Ser Asp Gln Glu Glu Phe Thr Arg Thr Tyr Leu Asp Ser Asn Pro Asp
        35                  40                  45

Arg Lys Lys Leu Glu Asp Ala Phe Arg Lys Ser Met
    50                  55                  60

<210> SEQ ID NO 360

```
<211> LENGTH: 60
<212> TYPE: PRT
<213> ORGANISM: Galerina marginata

<400> SEQUENCE: 360

Val Asp Ile Tyr Lys Ser Ala Leu Arg Gly Asp Val His Val Gln Asp
1               5                   10                  15

Pro Tyr Gln Trp Leu Glu Glu Tyr Thr Asp Glu Thr Asp Lys Trp Thr
            20                  25                  30

Thr Ala Gln Glu Val Phe Thr Arg Thr Tyr Leu Asp Lys Asn Pro Asp
        35                  40                  45

Leu Pro Arg Leu Glu Lys Ala Phe Gln Ala Cys Asn
    50                  55                  60

<210> SEQ ID NO 361
<211> LENGTH: 60
<212> TYPE: PRT
<213> ORGANISM: Amanita bisporigera

<400> SEQUENCE: 361

Gly Ser Met Thr Val Thr Ala Arg Glu Thr Glu Pro Trp Phe Phe Ala
1               5                   10                  15

Thr Leu Thr Gly Phe Asn Thr Pro Gly Ile Val Cys Arg Tyr Asn Ile
            20                  25                  30

Gln Arg Pro Glu Glu Gln Arg Trp Ser Val Tyr Arg Thr Ala Lys Val
        35                  40                  45

Lys Gly Leu Asn Pro Asn Asp Phe Glu Ala Arg Gln
    50                  55                  60

<210> SEQ ID NO 362
<211> LENGTH: 10
<212> TYPE: PRT
<213> ORGANISM: Amanita bisporigera

<400> SEQUENCE: 362

Val Trp Tyr Asp Ser Tyr Asp Gly Thr Lys
1               5                   10

<210> SEQ ID NO 363
<211> LENGTH: 12
<212> TYPE: PRT
<213> ORGANISM: Amanita bisporigera

<400> SEQUENCE: 363

Thr Lys Ile Pro Met Phe Ile Val Arg His Lys Asn
1               5                   10

<210> SEQ ID NO 364
<211> LENGTH: 60
<212> TYPE: PRT
<213> ORGANISM: Galerina marginata

<400> SEQUENCE: 364

Gly Ala Ala Ser Ile Ala Asn Arg Gln Lys Gln Thr His Phe Phe Leu
1               5                   10                  15

Thr Leu Ser Gly Phe Asn Thr Pro Gly Thr Ile Ala Arg Tyr Asp Phe
            20                  25                  30

Thr Ala Pro Glu Thr Gln Arg Phe Ser Ile Leu Arg Thr Thr Lys Val
        35                  40                  45

Asn Glu Leu Asp Pro Asp Asp Phe Glu Ser Thr Gln
    50                  55                  60
```

<210> SEQ ID NO 365
<211> LENGTH: 12
<212> TYPE: PRT
<213> ORGANISM: Galerina marginata

<400> SEQUENCE: 365

Thr Lys Ile Pro Met Phe Ile Val Arg His Lys Ser
1               5                   10

<210> SEQ ID NO 366
<211> LENGTH: 10
<212> TYPE: PRT
<213> ORGANISM: Galerina marginata

<400> SEQUENCE: 366

Val Trp Tyr Glu Ser Lys Asp Gly Asn Lys
1               5                   10

<210> SEQ ID NO 367
<211> LENGTH: 50
<212> TYPE: PRT
<213> ORGANISM: Amanita bisporigera

<400> SEQUENCE: 367

Gly Gly Phe Asn Ile Ser Ile Asn Pro Phe Phe Ser Pro Thr Ile Leu
1               5                   10                  15

Thr Phe Leu Gln Lys Tyr Gly Ala Ile Leu Ala Val Pro Asn Ile Arg
            20                  25                  30

Gly Gly Gly Glu Phe Gly Glu Thr Trp His Asp Ala Gly Ile Arg Glu
        35                  40                  45

Lys Arg
    50

<210> SEQ ID NO 368
<211> LENGTH: 50
<212> TYPE: PRT
<213> ORGANISM: Galerina marginata

<400> SEQUENCE: 368

Gly Gly Phe Ser Ile Ser Ile Asp Pro Phe Phe Ser Ala Thr Ile Leu
1               5                   10                  15

Thr Phe Leu Gln Lys Tyr Gly Val Val Phe Ala Leu Pro Asn Ile Arg
            20                  25                  30

Gly Gly Gly Glu Phe Gly Glu Asp Trp His Leu Ala Gly Cys Arg Glu
        35                  40                  45

Lys Lys
    50

<210> SEQ ID NO 369
<211> LENGTH: 10
<212> TYPE: PRT
<213> ORGANISM: Amanita bisporigera

<400> SEQUENCE: 369

Asn Val Tyr Asp Asp Phe Ile Ala Ala Thr
1               5                   10

<210> SEQ ID NO 370
<211> LENGTH: 10
<212> TYPE: PRT
<213> ORGANISM: Galerina marginata

```
<400> SEQUENCE: 370

Asn Cys Phe Asp Asp Phe Ile Ala Ala Thr
 1               5                  10

<210> SEQ ID NO 371
<211> LENGTH: 46
<212> TYPE: PRT
<213> ORGANISM: Amanita bisporigera

<400> SEQUENCE: 371

Asp Asp Arg Val Val Pro Met His Ser Phe Lys Tyr Ala Ala Met Leu
 1               5                  10                  15

Gln Tyr Thr Leu Pro His Asn Arg His Pro Leu Leu Leu Arg Val Asp
            20                  25                  30

Lys Lys Ala Gly His Gly Gly Gly Lys Ser Thr Glu Lys Arg
        35                  40                  45

<210> SEQ ID NO 372
<211> LENGTH: 46
<212> TYPE: PRT
<213> ORGANISM: Galerina marginata

<400> SEQUENCE: 372

Asp Asp Arg Val Val Pro Met His Ser Phe Lys Leu Ala Ala Glu Leu
 1               5                  10                  15

Gln Tyr Ser Leu Pro His Asn Pro Asn Pro Leu Leu Ile Arg Ile Asp
            20                  25                  30

Lys Lys Ala Gly His Gly Ala Gly Lys Ser Thr Gln Gln Lys
        35                  40                  45

<210> SEQ ID NO 373
<211> LENGTH: 34
<212> TYPE: PRT
<213> ORGANISM: Amanita bisporigera

<400> SEQUENCE: 373

Ala Ala Met Leu Gln Tyr Thr Leu Pro His Asn Arg His Pro Leu Leu
 1               5                  10                  15

Leu Arg Val Asp Lys Lys Ala Gly His Gly Gly Gly Lys Ser Thr Glu
            20                  25                  30

Lys Arg

<210> SEQ ID NO 374
<211> LENGTH: 34
<212> TYPE: PRT
<213> ORGANISM: Galerina marginata

<400> SEQUENCE: 374

Ala Ala Glu Leu Gln Tyr Ser Leu Pro His Asn Pro Asn Pro Leu Leu
 1               5                  10                  15

Ile Arg Ile Asp Lys Lys Thr Gly His Gly Ala Gly Lys Ser Thr Gln
            20                  25                  30

Gln Arg

<210> SEQ ID NO 375
<211> LENGTH: 22
<212> TYPE: PRT
<213> ORGANISM: Amanita bisporigera

<400> SEQUENCE: 375
```

```
Arg Leu Gln Glu Ala Ala Asp Lys Trp Gly Phe Ala Ala Gln Ser Met
1               5                   10                  15

Gly Leu Ala Trp Lys Asp
            20
```

<210> SEQ ID NO 376
<211> LENGTH: 22
<212> TYPE: PRT
<213> ORGANISM: Galerina marginata

<400> SEQUENCE: 376

```
Arg Ile Lys Glu Ser Ala Asp Lys Trp Gly Phe Val Ala Gln Ser Leu
1               5                   10                  15

Gly Leu Val Trp Lys Asp
            20
```

<210> SEQ ID NO 377
<211> LENGTH: 34
<212> TYPE: PRT
<213> ORGANISM: Amanita bisporigera

<400> SEQUENCE: 377

```
Gln Val Trp Tyr Asp Ser Tyr Asp Gly Thr Lys Ile Pro Met Phe Ile
1               5                   10                  15

Val Arg His Lys Asn Thr Gln Phe Asn Gly Thr Ala Pro Ala Ile Gln
            20                  25                  30

Tyr Gly
```

<210> SEQ ID NO 378
<211> LENGTH: 34
<212> TYPE: PRT
<213> ORGANISM: Galerina marginata

<400> SEQUENCE: 378

```
Gln Val Trp Tyr Glu Ser Lys Asp Gly Thr Ser Ile Pro Met Phe Ile
1               5                   10                  15

Val Arg His Lys Ser Thr Lys Phe Asp Gly Thr Ala Pro Val Ile Gln
            20                  25                  30

Tyr Gly
```

<210> SEQ ID NO 379
<211> LENGTH: 20
<212> TYPE: PRT
<213> ORGANISM: Amanita bisporigera

<400> SEQUENCE: 379

```
Val Tyr Arg Thr Ala Lys Val Lys Gly Leu Asn Pro Asn Asp Phe Glu
1               5                   10                  15

Ala Arg Gln Val
            20
```

<210> SEQ ID NO 380
<211> LENGTH: 20
<212> TYPE: PRT
<213> ORGANISM: Galerina marginata

<400> SEQUENCE: 380

```
Ile Tyr Arg Thr Thr Lys Leu Asn Gly Leu Asn Thr Glu Asp Phe Lys
1               5                   10                  15

Ala Ser Gln Val
```

```
<210> SEQ ID NO 381

<400> SEQUENCE: 381

000

<210> SEQ ID NO 382
<211> LENGTH: 20
<212> TYPE: PRT
<213> ORGANISM: Galerina marginata

<400> SEQUENCE: 382

Val Tyr Arg Thr Ala Lys Val Lys Gly Leu Asn Pro Asn Asp Phe Glu
 1               5                  10                  15

Ala Arg Gln Val
            20

<210> SEQ ID NO 383

<400> SEQUENCE: 383

000

<210> SEQ ID NO 384

<400> SEQUENCE: 384

000

<210> SEQ ID NO 385
<211> LENGTH: 60
<212> TYPE: PRT
<213> ORGANISM: Amanita bisporigera

<400> SEQUENCE: 385

Ser Asp Phe Ser Thr Ile Tyr Val Arg Ser Thr Ser Pro Leu Ala
 1               5                  10                  15

Pro Gly Asn Asn Ser Ile Arg Asn Asp Asp Gly Arg Leu Pro Asp Glu
            20                  25                  30

Leu Arg Tyr Val Lys Phe Ser Ser Ile Ser Trp Thr Lys Asp Ser Lys
        35                  40                  45

Gly Phe Phe Tyr Gln Arg Tyr Pro Gly Thr Gly Thr
    50                  55                  60

<210> SEQ ID NO 386
<211> LENGTH: 59
<212> TYPE: PRT
<213> ORGANISM: Galerina marginata

<400> SEQUENCE: 386

Ser Asp Phe Val Thr Ile Tyr Val Trp Ser Thr Asp Ser Pro Leu Thr
 1               5                  10                  15

Asn Asp Val Asp Ser Lys Asn Asp Lys Gly Arg Leu Pro Glu Glu Ile
            20                  25                  30

Lys Phe Val Lys Phe Ser Ser Ile Gly Trp Thr Pro Asp Ser Lys Gly
        35                  40                  45

Phe Phe Ile Arg Ser Ile Pro Trp Thr Ala Ser
    50                  55

<210> SEQ ID NO 387
```

-continued

```
<211> LENGTH: 35
<212> TYPE: PRT
<213> ORGANISM: Amanita bisporigera

<400> SEQUENCE: 387

Arg Asn Asp Asp Gly Arg Leu Pro Asp Glu Leu Arg Tyr Val Lys Phe
1               5                   10                  15

Ser Ser Ile Ser Trp Thr Lys Asp Ser Lys Gly Phe Phe Tyr Gln Arg
            20                  25                  30

Tyr Pro Gly
        35

<210> SEQ ID NO 388
<211> LENGTH: 35
<212> TYPE: PRT
<213> ORGANISM: Galerina marginata

<400> SEQUENCE: 388

Lys Asn Asp Lys Gly Arg Leu Pro Glu Glu Ile Lys Phe Val Lys Phe
1               5                   10                  15

Ser Ser Ile Gly Trp Thr Pro Asp Ser Lys Gly Phe Phe Ile Arg Ser
            20                  25                  30

Phe Pro Gly
        35

<210> SEQ ID NO 389
<211> LENGTH: 25
<212> TYPE: PRT
<213> ORGANISM: Amanita bisporigera

<400> SEQUENCE: 389

Arg Tyr Pro Gly Thr Gly Thr Val Asn Gly Gln Asn Gly Ile Gln Thr
1               5                   10                  15

Gln Gly Asp Arg Asp Ala Met Ile Tyr
            20                  25

<210> SEQ ID NO 390
<211> LENGTH: 26
<212> TYPE: PRT
<213> ORGANISM: Galerina marginata

<400> SEQUENCE: 390

Arg Tyr Pro Asp Thr Ser Thr Ala Thr Gln Glu Asn Gly Pro Ile Ala
1               5                   10                  15

Thr Glu Gly Asp Leu Asp Ala Met Val Tyr
            20                  25

<210> SEQ ID NO 391
<211> LENGTH: 43
<212> TYPE: PRT
<213> ORGANISM: Amanita bisporigera

<400> SEQUENCE: 391

Ser Ser Leu Ser Gln Ala Pro Glu Ala Glu Gly Gly Asp Gly Arg Leu
1               5                   10                  15

Ser Asp Gly Val Lys Trp Cys Lys Phe Thr Thr Ile Trp Thr Lys
            20                  25                  30

Asp Ser Lys Gly Phe Leu Tyr Gln Arg Tyr Pro
        35                  40

<210> SEQ ID NO 392
```

-continued

<211> LENGTH: 43
<212> TYPE: PRT
<213> ORGANISM: Galerina marginata

<400> SEQUENCE: 392

Ser Pro Leu Thr Lys Asp Val Asp Ala Lys Asn Asp Lys Gly Arg Leu
1               5                   10                  15
Pro Glu Glu Ile Lys Phe Val Lys Phe Ser Ser Ile Gly Trp Thr Pro
            20                  25                  30
Asp Ser Lys Gly Phe Phe Ile Arg Ser Phe Pro
        35                  40

<210> SEQ ID NO 393

<400> SEQUENCE: 393

000

<210> SEQ ID NO 394
<211> LENGTH: 47
<212> TYPE: PRT
<213> ORGANISM: Galerina marginata

<400> SEQUENCE: 394

Asp Asp Arg Val Val Pro Met His Ser Phe Lys Phe Ile Ala Thr Leu
1               5                   10                  15
Gln His Asn Val Pro Gln Asn Pro His Pro Leu Leu Ile Lys Ile Asp
            20                  25                  30
Lys Ser Trp Leu Gly His Gly Met Gly Lys Pro Thr Asp Lys Lys
        35                  40                  45

<210> SEQ ID NO 395

<400> SEQUENCE: 395

000

<210> SEQ ID NO 396
<211> LENGTH: 12
<212> TYPE: PRT
<213> ORGANISM: Galerina marginata

<400> SEQUENCE: 396

Leu Gln Glu Ala Ala Asp Lys Trp Gly Phe Ala Ala
1               5                   10

<210> SEQ ID NO 397
<211> LENGTH: 54
<212> TYPE: PRT
<213> ORGANISM: Amanita bisporigera

<400> SEQUENCE: 397

Gly Ser Asp Phe Ser Thr Ile Tyr Val Arg Ser Thr Ser Ser Pro Leu
1               5                   10                  15
Ala Pro Gly Asn Asn Ser Ile Arg Asn Asp Asp Gly Arg Leu Pro Asp
            20                  25                  30
Glu Leu Arg Tyr Val Lys Phe Ser Ser Ile Ser Trp Thr Lys Asp Ser
        35                  40                  45
Lys Gly Phe Phe Tyr Gln
    50

<210> SEQ ID NO 398

```
<211> LENGTH: 53
<212> TYPE: PRT
<213> ORGANISM: Galerina marginata

<400> SEQUENCE: 398

Gly Gly Asp Tyr Ser Thr Ile Tyr Val Arg Ser Thr Ser Ser Pro Leu
 1               5                  10                  15

Ser Gln Ser Ser Val Ala Gln Gly Val Asp Gly Arg Leu Ser Asp Glu
             20                  25                  30

Val Lys Trp Phe Lys Phe Ser Thr Ile Ile Trp Thr Lys Asp Phe Lys
         35                  40                  45

Gly Phe Leu Tyr Gln
     50

<210> SEQ ID NO 399
<211> LENGTH: 58
<212> TYPE: PRT
<213> ORGANISM: Amanita bisporigera

<400> SEQUENCE: 399

Val Phe Asp Ser Glu Tyr Asp Leu Ile Gly Asn Asp Gly Ser Leu Leu
 1               5                  10                  15

Tyr Ile Arg Thr Asn Lys Ala Ala Pro Gln Tyr Lys Ile Val Thr Leu
             20                  25                  30

Asp Ile Glu Lys Pro Glu Leu Gly Phe Lys Gly Phe Ile Pro Glu Asp
         35                  40                  45

Pro Lys Ala Tyr Leu Ser Gln Val Lys Ile
     50                  55

<210> SEQ ID NO 400
<211> LENGTH: 57
<212> TYPE: PRT
<213> ORGANISM: Galerina marginata

<400> SEQUENCE: 400

Val Phe Asp Ser Met Thr Phe Thr Ser Ile Thr Asn Lys Gly Ser Leu
 1               5                  10                  15

Phe Tyr Val Arg Thr Asn Glu Ser Ala Pro Gln Tyr Arg Val Ile Thr
             20                  25                  30

Val Asp Ile Ala Lys Arg Asn Glu Ile Lys Glu Leu Ile Pro Glu Thr
         35                  40                  45

Asp Ala Tyr Leu Ser Ser Ile Thr Ser
     50                  55

<210> SEQ ID NO 401
<211> LENGTH: 14
<212> TYPE: PRT
<213> ORGANISM: Amanita bisporigera

<400> SEQUENCE: 401

Val Asn Lys Gly Tyr Phe Ala Leu Val Tyr Lys Arg Asn Val
 1               5                  10

<210> SEQ ID NO 402
<211> LENGTH: 14
<212> TYPE: PRT
<213> ORGANISM: Galerina marginata

<400> SEQUENCE: 402

Val Asn Lys Gly Tyr Phe Ala Leu Val Tyr Lys Arg Asn Val
 1               5                  10
```

-continued

<210> SEQ ID NO 403
<211> LENGTH: 60
<212> TYPE: PRT
<213> ORGANISM: Amanita bisporigera

<400> SEQUENCE: 403

Ile Gly Asn Asp Gly Ser Leu Leu Tyr Ile Arg Thr Asn Lys Ala Ala
1               5                   10                  15

Pro Gln Tyr Lys Ile Val Thr Leu Asp Ile Glu Lys Pro Glu Leu Gly
            20                  25                  30

Phe Lys Glu Phe Ile Pro Glu Asp Pro Lys Ala Tyr Leu Ser Gln Val
        35                  40                  45

Lys Ile Phe Asn Lys Asp Arg Leu Ala Leu Val Tyr
    50                  55                  60

<210> SEQ ID NO 404
<211> LENGTH: 58
<212> TYPE: PRT
<213> ORGANISM: Galerina marginata

<400> SEQUENCE: 404

Ile Thr Asn Lys Gly Ser Leu Phe Tyr Val Arg Thr Asn Glu Ser Ala
1               5                   10                  15

Pro Gln Tyr Arg Val Ile Thr Val Asp Ile Ala Lys Arg Asn Glu Ile
            20                  25                  30

Lys Glu Leu Ile Pro Glu Thr Asp Ala Tyr Leu Ser Ser Ile Thr Ser
        35                  40                  45

Val Asn Lys Gly Tyr Phe Ala Leu Val Tyr
    50                  55

<210> SEQ ID NO 405
<211> LENGTH: 4
<212> TYPE: PRT
<213> ORGANISM: Amanita bisporigera

<400> SEQUENCE: 405

Lys Arg Asn Val
1

<210> SEQ ID NO 406
<211> LENGTH: 4
<212> TYPE: PRT
<213> ORGANISM: Galerina marginata

<400> SEQUENCE: 406

Lys Arg Asn Val
1

<210> SEQ ID NO 407
<211> LENGTH: 46
<212> TYPE: PRT
<213> ORGANISM: Amanita bisporigera

<400> SEQUENCE: 407

Thr Ile Gly Lys Ala Trp Ile Ser Asp Tyr Gly Asp Pro Glu Asp Pro
1               5                   10                  15

Arg Asp Phe Asp Tyr Ile Tyr Thr His Ser Pro Leu His Asn Ile Pro
            20                  25                  30

Lys Asn Met Val Leu Pro Pro Thr Met Leu Leu Thr Ala Asp
        35                  40                  45

<210> SEQ ID NO 408
<211> LENGTH: 59
<212> TYPE: PRT
<213> ORGANISM: Galerina marginata

<400> SEQUENCE: 408

Ser Leu Gly Gln Ala Trp Ile Ser Glu Tyr Gly Asn Pro Ser Ile Pro
1               5                   10                  15

Glu Glu Phe Asp Tyr Ile Tyr Pro Leu Ser Pro Val His Asn Val Gln
            20                  25                  30

Thr Asp Lys Val Met Pro Ala Met Leu Ile Thr Val Asn Ile Gly Glu
        35                  40                  45

Gln Leu Thr Ser Ser Asn Leu Ile Met Pro His
    50                  55

<210> SEQ ID NO 409
<211> LENGTH: 9
<212> TYPE: PRT
<213> ORGANISM: Amanita bisporigera

<400> SEQUENCE: 409

His Asp Asp Arg Val Val Pro Met His
1               5

<210> SEQ ID NO 410
<211> LENGTH: 14
<212> TYPE: PRT
<213> ORGANISM: Galerina marginata

<400> SEQUENCE: 410

Thr Arg Pro Ser Pro Gly Asp Asp Arg Val Val Pro Met His
1               5                   10

<210> SEQ ID NO 411

<400> SEQUENCE: 411

000

<210> SEQ ID NO 412
<211> LENGTH: 34
<212> TYPE: PRT
<213> ORGANISM: Galerina marginata

<400> SEQUENCE: 412

Ala Ala Glu Leu Gln Tyr Ser Leu Pro His Asn Pro Asn Pro Leu Leu
1               5                   10                  15

Ile Arg Ile Asp Lys Lys Ala Gly His Gly Ala Gly Lys Ser Thr Gln
            20                  25                  30

Gln Lys

<210> SEQ ID NO 413
<211> LENGTH: 60
<212> TYPE: PRT
<213> ORGANISM: Amanita bisporigera

<400> SEQUENCE: 413

Ala Val Pro Asn Ile Arg Gly Gly Glu Phe Gly Glu Thr Trp His
1               5                   10                  15

Asp Ala Gly Ile Arg Glu Lys Arg Ala Asn Val Tyr Asp Asp Phe Ile
            20                  25                  30

Ala Ala Thr Gln Phe Leu Val Lys Asn Lys Tyr Ala Ala Gly Gly Lys
         35                  40                  45

Val Ala Ile Asn Gly Gly Ser Asn Gly Gly Leu Leu
 50                  55                  60

<210> SEQ ID NO 414
<211> LENGTH: 60
<212> TYPE: PRT
<213> ORGANISM: Galerina marginata

<400> SEQUENCE: 414

Ala Val Thr His Ile Arg Gly Gly Ser Glu Lys Gly Trp Gly Trp Phe
 1               5                  10                  15

Leu Asp Gly Arg Lys Asp Lys Lys Pro Asn Ser Phe Thr Asp Phe Ile
             20                  25                  30

Ala Cys Ala Glu Ala Leu Ile Ala Glu Gly Tyr Gly Thr Ala Gly Arg
         35                  40                  45

Ile Val Ala Glu Gly Arg Ser Ala Gly Gly Met Leu
 50                  55                  60

<210> SEQ ID NO 415
<211> LENGTH: 26
<212> TYPE: PRT
<213> ORGANISM: Amanita bisporigera

<400> SEQUENCE: 415

Val Ala Ala Cys Val Asn Arg Ala Arg Glu Gly Thr Phe Gly Ala Ala
 1               5                  10                  15

Ile Ala Glu Val Gly Val Leu Asp Leu Leu
             20                  25

<210> SEQ ID NO 416
<211> LENGTH: 25
<212> TYPE: PRT
<213> ORGANISM: Galerina marginata

<400> SEQUENCE: 416

Met Gly Ala Val Ala Asn Leu Arg Pro Asp Leu Trp Ala Gly Val Ile
 1               5                  10                  15

Gly Gly Val Pro Phe Val Asp Val Leu
             20                  25

<210> SEQ ID NO 417
<211> LENGTH: 41
<212> TYPE: PRT
<213> ORGANISM: Amanita bisporigera

<400> SEQUENCE: 417

Lys Phe Ser Ala Pro Phe Leu Asn Asp Asp Lys Arg Trp Tyr Trp Phe
 1               5                  10                  15

Tyr Asn Thr Gly Leu Gln Ala Gln Thr Val Ile Cys Arg Ser Lys Asp
             20                  25                  30

Glu Thr Leu Pro Asp Phe Ser Glu Ser
         35                  40

<210> SEQ ID NO 418
<211> LENGTH: 60
<212> TYPE: PRT
<213> ORGANISM: Galerina marginata

<400> SEQUENCE: 418

```
Gln Tyr Tyr Ala Pro Tyr Leu His Asp Asp Asn Arg Trp Tyr Trp Tyr
1               5                   10                  15

Tyr Asn Ser Gly Leu Glu Pro Gln Thr Gly Glu Arg Phe Lys Gln Pro
            20                  25                  30

Phe Arg Pro Arg Trp Leu Thr Ser Val Pro Ala Lys Ala Leu Tyr Arg
        35                  40                  45

Ser Lys Asp Ser Asn Leu Pro Asp Leu Ser Thr Ala
    50                  55                  60

<210> SEQ ID NO 419
<211> LENGTH: 16
<212> TYPE: PRT
<213> ORGANISM: Amanita bisporigera

<400> SEQUENCE: 419

Asp Tyr Val Gly Glu Thr Phe Phe Asp Pro Asn Leu Leu Ser Ser Asp
1               5                   10                  15

<210> SEQ ID NO 420
<211> LENGTH: 17
<212> TYPE: PRT
<213> ORGANISM: Galerina marginata

<400> SEQUENCE: 420

Asp Gly Ser Gly Gly Asp Leu Phe Phe Asp Val Gly Pro Leu Ser Ala
1               5                   10                  15

Asn

<210> SEQ ID NO 421
<211> LENGTH: 38
<212> TYPE: PRT
<213> ORGANISM: Amanita bisporigera

<400> SEQUENCE: 421

Ser Asp Asp Ile Leu Val His Glu Asp Gln His Pro Asp Trp Val
1               5                   10                  15

Phe Gly Ala Glu Val Thr Glu Asp Gly Lys Tyr Val Ala Leu Tyr Thr
            20                  25                  30

Met Lys Asp Thr Ser Arg
        35

<210> SEQ ID NO 422
<211> LENGTH: 38
<212> TYPE: PRT
<213> ORGANISM: Galerina marginata

<400> SEQUENCE: 422

Ala Glu Asp Ser Leu Ile Tyr Gln Asp Arg Glu His Arg Asp Trp Met
1               5                   10                  15

Phe Ser Ile Asp Val Thr Asp Asp Gly Asn Tyr Leu Leu Tyr Ile
            20                  25                  30

Leu Lys Asp Ser Ser Arg
        35

<210> SEQ ID NO 423
<211> LENGTH: 30
<212> TYPE: PRT
<213> ORGANISM: Amanita bisporigera

<400> SEQUENCE: 423
```

-continued

```
Gly Leu Leu Val Ala Ala Cys Val Asn Arg Ala Arg Glu Gly Thr Phe
1               5                   10                  15
Gly Ala Ala Ile Ala Glu Val Gly Val Leu Asp Leu Leu Lys
            20                  25                  30

<210> SEQ ID NO 424
<211> LENGTH: 30
<212> TYPE: PRT
<213> ORGANISM: Galerina marginata

<400> SEQUENCE: 424

Gly Leu Leu Val Ser Ala Cys Val Asn Arg Ala Pro Glu Gly Thr Phe
1               5                   10                  15
Gly Cys Ala Val Ala Asp Val Gly Val His Asp Leu Leu Lys
            20                  25                  30

<210> SEQ ID NO 425
<211> LENGTH: 30
<212> TYPE: PRT
<213> ORGANISM: Amanita bisporigera

<400> SEQUENCE: 425

Gly Phe Leu Val Cys Gly Ser Val Val Arg Ala Pro Glu Gly Thr Phe
1               5                   10                  15
Gly Ala Ala Val Ser Glu Gly Gly Val Ala Asp Leu Leu Lys
            20                  25                  30

<210> SEQ ID NO 426

<400> SEQUENCE: 426

000

<210> SEQ ID NO 427
<211> LENGTH: 27
<212> TYPE: PRT
<213> ORGANISM: Amanita bisporigera

<400> SEQUENCE: 427

Asp Asp Ile Leu Val His Glu Asp Gln Glu His Pro Asp Trp Val Phe
1               5                   10                  15
Gly Ala Glu Val Thr Glu Asp Gly Lys Tyr Val
            20                  25

<210> SEQ ID NO 428
<211> LENGTH: 27
<212> TYPE: PRT
<213> ORGANISM: Galerina marginata

<400> SEQUENCE: 428

Glu Asp Ile Ile Val Tyr Gln Asp Asn Glu His Pro Glu Trp Ile Tyr
1               5                   10                  15
Gly Ala Asp Thr Ser Glu Asp Gly Lys Tyr Leu
            20                  25

<210> SEQ ID NO 429
<211> LENGTH: 13
<212> TYPE: PRT
<213> ORGANISM: Amanita bisporigera

<400> SEQUENCE: 429

Met Ile Tyr Tyr His Arg Ile Gly Thr Ser Gln Ser Asp
1               5                   10
```

<210> SEQ ID NO 430
<211> LENGTH: 13
<212> TYPE: PRT
<213> ORGANISM: Galerina marginata

<400> SEQUENCE: 430

Met Met Cys Tyr His Lys Val Gly Thr Thr Gln Gly Glu
1               5                   10

<210> SEQ ID NO 431
<211> LENGTH: 30
<212> TYPE: PRT
<213> ORGANISM: Amanita bisporigera

<400> SEQUENCE: 431

Met Ser Ser Thr Gln Trp Thr Pro Asn Met Tyr Pro Ser Ala Arg Arg
1               5                   10                  15

Ser Asp His Ile Asp Thr Tyr Arg Ser Glu Thr Arg Gly Glu
            20                  25                  30

<210> SEQ ID NO 432
<211> LENGTH: 30
<212> TYPE: PRT
<213> ORGANISM: Galerina marginata

<400> SEQUENCE: 432

Met Ser Ser Ile Ala Trp Ala Pro Gly Asn Tyr Pro Ser Thr Arg Arg
1               5                   10                  15

Ser Asp His Val Asp Ser Tyr Gln Ser Ala Ser Lys Gly Glu
            20                  25                  30

<210> SEQ ID NO 433
<211> LENGTH: 50
<212> TYPE: PRT
<213> ORGANISM: Amanita bisporigera

<400> SEQUENCE: 433

Phe Asn Thr Pro Gly Ile Val Cys Arg Tyr Asn Ile Gln Arg Pro Glu
1               5                   10                  15

Glu Gln Arg Trp Ser Val Tyr Arg Thr Ala Lys Val Lys Gly Leu Asn
            20                  25                  30

Pro Asn Asp Phe Glu Ala Arg Gln Val Trp Tyr Asp Ser Tyr Asp Gly
        35                  40                  45

Thr Lys
    50

<210> SEQ ID NO 434
<211> LENGTH: 60
<212> TYPE: PRT
<213> ORGANISM: Galerina marginata

<400> SEQUENCE: 434

Phe Ser Ser Asp His Ile Arg Leu Arg Tyr Glu Ala Leu Asn Arg Pro
1               5                   10                  15

Ala Gln Ile Arg Arg Leu Ala Leu Ala Asp Gly Ala Gln Gln Val Leu
            20                  25                  30

Lys Glu Thr Pro Val Leu Gly Val Phe Asn Ala Asp Asp Tyr Val Ser
        35                  40                  45

Gln Arg Leu Trp Ala Thr Ser Val Asp Gly Thr Gln
    50                  55                  60

<210> SEQ ID NO 435
<211> LENGTH: 36
<212> TYPE: PRT
<213> ORGANISM: Amanita bisporigera

<400> SEQUENCE: 435

Ile Pro Met Phe Ile Val Arg His Lys Asn Thr Gln Phe Asn Gly Thr
1               5                   10                  15

Ala Pro Ala Ile Gln Tyr Gly Tyr Gly Gly Phe Asn Ile Ser Ile Asn
            20                  25                  30

Pro Phe Phe Ser
        35

<210> SEQ ID NO 436
<211> LENGTH: 35
<212> TYPE: PRT
<213> ORGANISM: Galerina marginata

<400> SEQUENCE: 436

Val Pro Ile Ser Leu Val Val Arg His Asp Gln Leu Gly Gln Pro Thr
1               5                   10                  15

Pro Leu Tyr Leu Tyr Gly Tyr Gly Ala Tyr Gly His Ser Leu Asp Pro
            20                  25                  30

Trp Phe Ser
        35

<210> SEQ ID NO 437
<211> LENGTH: 23
<212> TYPE: PRT
<213> ORGANISM: Amanita bisporigera

<400> SEQUENCE: 437

Gln Phe Leu Val Lys Asn Lys Tyr Ala Ala Gly Gly Lys Val Ala Ile
1               5                   10                  15

Asn Gly Gly Ser Asn Gly Gly
            20

<210> SEQ ID NO 438
<211> LENGTH: 23
<212> TYPE: PRT
<213> ORGANISM: Galerina marginata

<400> SEQUENCE: 438

Gln Phe Leu Val Lys Asn Lys Tyr Ala Ala Pro Gly Lys Val Ala Ile
1               5                   10                  15

Asn Gly Ala Ser Asn Gly Gly
            20

<210> SEQ ID NO 439
<211> LENGTH: 33
<212> TYPE: PRT
<213> ORGANISM: Amanita bisporigera

<400> SEQUENCE: 439

Phe Ser Ala Pro Phe Leu Asn Asp Asp Lys Arg Trp Tyr Trp Phe Tyr
1               5                   10                  15

Asn Thr Gly Leu Gln Ala Gln Thr Val Ile Cys Arg Ser Lys Asp Glu
            20                  25                  30

Thr

```
<210> SEQ ID NO 440
<211> LENGTH: 38
<212> TYPE: PRT
<213> ORGANISM: Galerina marginata

<400> SEQUENCE: 440

Phe Ser Ala Pro Thr Leu Leu Asp Asp Gly His Trp Tyr Trp Phe Tyr
1               5                   10                  15

Asn Arg Gly Leu Gln Ser Gln Ser Gly Arg Tyr Leu Phe Ile Leu Arg
            20                  25                  30

Arg Cys Lys Thr Gln Thr
        35

<210> SEQ ID NO 441
<211> LENGTH: 13
<212> TYPE: PRT
<213> ORGANISM: Amanita bisporigera

<400> SEQUENCE: 441

Val Ile Cys Arg Ser Lys Asp Glu Thr Leu Pro Asp Phe
1               5                   10

<210> SEQ ID NO 442
<211> LENGTH: 13
<212> TYPE: PRT
<213> ORGANISM: Galerina marginata

<400> SEQUENCE: 442

Val Leu Tyr Arg Ser Lys Glu Pro Ala Leu Pro Asp Phe
1               5                   10

<210> SEQ ID NO 443
<211> LENGTH: 60
<212> TYPE: PRT
<213> ORGANISM: Amanita bisporigera

<400> SEQUENCE: 443

His Asp Asp Arg Val Val Pro Met His Ser Phe Lys Tyr Ala Ala Met
1               5                   10                  15

Leu Gln Tyr Thr Leu Pro His Asn Arg His Pro Leu Leu Leu Arg Val
            20                  25                  30

Asp Lys Lys Ala Gly His Gly Gly Lys Ser Thr Glu Lys Arg Leu
        35                  40                  45

Gln Glu Ala Ala Asp Lys Trp Gly Phe Ala Ala Gln
    50                  55                  60

<210> SEQ ID NO 444
<211> LENGTH: 59
<212> TYPE: PRT
<213> ORGANISM: Galerina marginata

<400> SEQUENCE: 444

Asn Asp Ser Arg Val Gln Tyr Trp Glu Ala Ala Lys Trp Val Ala Lys
1               5                   10                  15

Leu Arg Asp Thr Lys Thr Asp Asp His Pro Leu Leu Leu Lys Thr Glu
            20                  25                  30

Leu Gly Ala Gly His Gly Gly Met Ser Gly Arg Tyr Gln Gly Leu Arg
        35                  40                  45

Asp Val Ala Leu Glu Tyr Ala Phe Cys Phe Gln
    50                  55
```

<210> SEQ ID NO 445
<211> LENGTH: 4
<212> TYPE: PRT
<213> ORGANISM: Amanita bisporigera

<400> SEQUENCE: 445

Gln Ser Met Gly
 1

<210> SEQ ID NO 446
<211> LENGTH: 4
<212> TYPE: PRT
<213> ORGANISM: Galerina marginata

<400> SEQUENCE: 446

Gln Gly Thr Gly
 1

<210> SEQ ID NO 447
<211> LENGTH: 34
<212> TYPE: PRT
<213> ORGANISM: Amanita bisporigera

<400> SEQUENCE: 447

Arg Lys Asn Leu Leu Trp Ile Ala Asp Leu Gly Gln Asn Glu Val Gly
 1               5                  10                  15

Arg Asn Met Lys Trp Asn Lys Ile Cys Asn Val Phe Asp Ser Glu Tyr
                20                  25                  30

Asp Leu

<210> SEQ ID NO 448
<211> LENGTH: 34
<212> TYPE: PRT
<213> ORGANISM: Galerina marginata

<400> SEQUENCE: 448

Gln Lys Asn Leu Leu Trp Val Ala Glu Leu Asn Glu Asp Gly Val Lys
 1               5                  10                  15

Ser Gly Ile Gln Trp Arg Lys Val Val Asn Glu Tyr Val Ala Asp Tyr
                20                  25                  30

Asn Val

<210> SEQ ID NO 449
<211> LENGTH: 47
<212> TYPE: PRT
<213> ORGANISM: Amanita bisporigera

<400> SEQUENCE: 449

Gly Asp Asp Arg Val Val Pro Met His Ser Leu Lys Phe Val Ala Asn
 1               5                  10                  15

Leu Gln Tyr Asn Val Pro Gln Asn Pro His Pro Leu Leu Ile Arg Val
                20                  25                  30

Asp Lys Ser Trp Leu Gly His Gly Phe Gly Lys Thr Thr Asp Lys
                35                  40                  45

<210> SEQ ID NO 450
<211> LENGTH: 47
<212> TYPE: PRT
<213> ORGANISM: Galerina marginata

<400> SEQUENCE: 450

-continued

Gly Asp Asp Arg Val Pro Met His Ser Phe Lys Phe Ile Ala Thr
1               5                   10                  15

Leu Gln His Asn Val Pro Gln Asn Pro His Pro Leu Leu Ile Lys Ile
            20                  25                  30

Asp Lys Ser Trp Leu Gly His Gly Met Gly Lys Pro Thr Asp Lys
        35                  40                  45

<210> SEQ ID NO 451
<211> LENGTH: 11
<212> TYPE: PRT
<213> ORGANISM: Amanita bisporigera

<400> SEQUENCE: 451

Lys Asp Ala Ala Asp Lys Trp Ser Phe Val Ala
1               5                   10

<210> SEQ ID NO 452
<211> LENGTH: 11
<212> TYPE: PRT
<213> ORGANISM: Galerina marginata

<400> SEQUENCE: 452

Lys Asp Ala Ala Asp Lys Trp Gly Phe Ile Ala
1               5                   10

<210> SEQ ID NO 453
<211> LENGTH: 34
<212> TYPE: PRT
<213> ORGANISM: Amanita bisporigera

<400> SEQUENCE: 453

Gln Val Trp Tyr Lys Ser Lys Asp Gly Thr Lys Val Pro Met Phe Ile
1               5                   10                  15

Val Arg His Lys Ser Thr Lys Phe Asp Gly Thr Ala Pro Ala Ile Gln
            20                  25                  30

Asn Gly

<210> SEQ ID NO 454

<400> SEQUENCE: 454

000

<210> SEQ ID NO 455
<211> LENGTH: 20
<212> TYPE: PRT
<213> ORGANISM: Amanita bisporigera

<400> SEQUENCE: 455

Ile Leu Arg Thr Thr Lys Leu Asn Gly Leu Asn Ala Asp Asp Phe Glu
1               5                   10                  15

Ser Thr Gln Val
            20

<210> SEQ ID NO 456

<400> SEQUENCE: 456

000

<210> SEQ ID NO 457

<400> SEQUENCE: 457

```
000

<210> SEQ ID NO 458
<400> SEQUENCE: 458

000

<210> SEQ ID NO 459
<400> SEQUENCE: 459

000

<210> SEQ ID NO 460
<400> SEQUENCE: 460

000

<210> SEQ ID NO 461
<211> LENGTH: 53
<212> TYPE: PRT
<213> ORGANISM: Amanita bisporigera

<400> SEQUENCE: 461

Gly Val Asp Tyr Phe Thr Ile Tyr Val Arg Pro Thr Ser Ser Ser Leu
  1               5                  10                  15

Ser Gln Ala Pro Glu Ala Glu Gly Gly Asp Gly Arg Leu Ser Asp Gly
             20                  25                  30

Val Lys Trp Cys Lys Phe Thr Thr Ile Thr Trp Thr Lys Asp Ser Lys
         35                  40                  45

Gly Phe Leu Tyr Gln
         50

<210> SEQ ID NO 462
<211> LENGTH: 50
<212> TYPE: PRT
<213> ORGANISM: Amanita bisporigera

<400> SEQUENCE: 462

Gly Gly Phe Ala Ile Thr Ala Asp Pro Phe Phe Ser Pro Ile Met Leu
  1               5                  10                  15

Thr Phe Met Gln Thr Tyr Gly Ala Ile Leu Ala Val Pro Asn Ile Arg
             20                  25                  30

Gly Gly Gly Glu Phe Gly Gly Glu Trp His Lys Ala Gly Arg Arg Glu
         35                  40                  45

Thr Lys
    50

<210> SEQ ID NO 463
<400> SEQUENCE: 463

000

<210> SEQ ID NO 464
<400> SEQUENCE: 464

000
```

```
<210> SEQ ID NO 465
<211> LENGTH: 9
<212> TYPE: PRT
<213> ORGANISM: Amanita bisporigera

<400> SEQUENCE: 465

Asn Thr Phe Asp Asp Phe Ile Ala Ala
 1               5

<210> SEQ ID NO 466
<211> LENGTH: 9
<212> TYPE: PRT
<213> ORGANISM: Galerina marginata

<400> SEQUENCE: 466

Asn Cys Phe Asp Asp Phe Ile Ala Ala
 1               5

<210> SEQ ID NO 467
<211> LENGTH: 60
<212> TYPE: PRT
<213> ORGANISM: Amanita bisporigera

<400> SEQUENCE: 467

Ile Thr Asn His Gly Ser Leu Ile Tyr Val Lys Thr Asn Val Asn Ala
 1               5                  10                  15

Pro Gln Tyr Lys Val Val Thr Ile Asp Leu Ser Thr Gly Glu Pro Glu
             20                  25                  30

Ile Arg Asp Phe Ile Pro Glu Gln Lys Asp Ala Lys Leu Thr Gln Val
         35                  40                  45

Lys Cys Val Asn Lys Gly Tyr Phe Val Ala Ile Tyr
     50                  55                  60

<210> SEQ ID NO 468

<400> SEQUENCE: 468

000

<210> SEQ ID NO 469
<211> LENGTH: 5
<212> TYPE: PRT
<213> ORGANISM: Amanita bisporigera

<400> SEQUENCE: 469

Lys Arg Asn Val Lys
 1               5

<210> SEQ ID NO 470
<211> LENGTH: 5
<212> TYPE: PRT
<213> ORGANISM: Galerina marginata

<400> SEQUENCE: 470

Lys Arg Asn Val Arg
 1               5

<210> SEQ ID NO 471

<400> SEQUENCE: 471

000

<210> SEQ ID NO 472
```

```
<400> SEQUENCE: 472

000

<210> SEQ ID NO 473

<400> SEQUENCE: 473

000

<210> SEQ ID NO 474

<400> SEQUENCE: 474

000

<210> SEQ ID NO 475
<211> LENGTH: 43
<212> TYPE: PRT
<213> ORGANISM: Amanita bisporigera

<400> SEQUENCE: 475

Gly Met Ala Trp Thr Ser Glu Tyr Gly Asn Pro Phe Ile Lys Glu Asp
 1               5                   10                  15

Phe Asp Phe Val Gln Ala Leu Ser Pro Val His Asn Val Pro Lys Asp
            20                  25                  30

Arg Val Leu Pro Ala Thr Leu Leu Met Thr Asn
        35                  40

<210> SEQ ID NO 476
<211> LENGTH: 60
<212> TYPE: PRT
<213> ORGANISM: Galerina marginata

<400> SEQUENCE: 476

Gly Gln Ala Trp Ile Ser Glu Tyr Gly Asn Pro Ser Ile Pro Glu Glu
 1               5                   10                  15

Phe Asp Tyr Ile Tyr Pro Leu Ser Pro Val His Asn Val Gln Thr Asp
            20                  25                  30

Lys Val Met Pro Ala Met Leu Ile Thr Val Asn Ile Gly Glu Gln Leu
        35                  40                  45

Thr Ser Ser Asn Leu Ile Met Pro His Thr Arg Pro
    50                  55                  60

<210> SEQ ID NO 477
<211> LENGTH: 10
<212> TYPE: PRT
<213> ORGANISM: Amanita bisporigera

<400> SEQUENCE: 477

Ala Gly Asp Asp Arg Val Val Pro Met His
 1               5                   10

<210> SEQ ID NO 478
<211> LENGTH: 11
<212> TYPE: PRT
<213> ORGANISM: Galerina marginata

<400> SEQUENCE: 478

Ser Pro Gly Asp Asp Arg Val Val Pro Met His
 1               5                   10
```

```
<210> SEQ ID NO 479
<211> LENGTH: 49
<212> TYPE: PRT
<213> ORGANISM: Amanita bisporigera

<400> SEQUENCE: 479

Asn Ala Gly Asp Asp Arg Val Val Pro Met His Ser Leu Lys Phe Val
1               5                   10                  15

Ala Asn Leu Gln Tyr Asn Val Pro Gln Asn Pro His Pro Leu Leu Ile
            20                  25                  30

Arg Val Asp Lys Ser Trp Leu Gly His Gly Phe Gly Lys Thr Thr Asp
        35                  40                  45

Lys

<210> SEQ ID NO 480
<211> LENGTH: 48
<212> TYPE: PRT
<213> ORGANISM: Galerina marginata

<400> SEQUENCE: 480

Asn Leu Asp Asp Asp Arg Val Val Pro Met His Ser Phe Lys Leu Ala
1               5                   10                  15

Ala Glu Leu Gln Tyr Ser Leu Pro His Asn Pro Asn Pro Leu Leu Ile
            20                  25                  30

Arg Ile Asp Lys Lys Ala Gly His Gly Ala Gly Lys Ser Thr Gln Gln
        35                  40                  45

<210> SEQ ID NO 481
<211> LENGTH: 33
<212> TYPE: PRT
<213> ORGANISM: Amanita bisporigera

<400> SEQUENCE: 481

Ala Asn Leu Gln Tyr Asn Val Pro Gln Asn Pro His Pro Leu Leu Ile
1               5                   10                  15

Arg Val Asp Lys Ser Trp Leu Gly His Gly Phe Gly Lys Thr Thr Asp
            20                  25                  30

Lys

<210> SEQ ID NO 482
<211> LENGTH: 32
<212> TYPE: PRT
<213> ORGANISM: Galerina marginata

<400> SEQUENCE: 482

Ala Glu Leu Gln Tyr Ser Leu Pro His Asn Pro Asn Pro Leu Leu Ile
1               5                   10                  15

Arg Ile Asp Lys Lys Thr Gly His Gly Ala Gly Lys Ser Thr Gln Gln
            20                  25                  30

<210> SEQ ID NO 483
<211> LENGTH: 19
<212> TYPE: PRT
<213> ORGANISM: Amanita bisporigera

<400> SEQUENCE: 483

Lys Asp Ala Ala Asp Lys Trp Ser Phe Val Ala Gln Ser Leu Gly Leu
1               5                   10                  15

Glu Trp Lys
```

<210> SEQ ID NO 484
<211> LENGTH: 19
<212> TYPE: PRT
<213> ORGANISM: Galerina marginata

<400> SEQUENCE: 484

Lys Glu Ser Ala Asp Lys Trp Gly Phe Val Ala Gln Ser Leu Gly Leu
1               5                   10                  15

Val Trp Lys

<210> SEQ ID NO 485
<211> LENGTH: 27
<212> TYPE: PRT
<213> ORGANISM: Amanita bisporigera

<400> SEQUENCE: 485

Phe Ser Ala Pro Thr Leu Leu Asp Ser Gly His Trp Tyr Trp Phe Tyr
1               5                   10                  15

Asn Ser Gly Val Gln Ser Gln Ala Val Leu Tyr
            20                  25

<210> SEQ ID NO 486
<211> LENGTH: 27
<212> TYPE: PRT
<213> ORGANISM: Galerina marginata

<400> SEQUENCE: 486

Phe Ser Ala Pro Thr Leu Leu Asp Asp Gly His Trp Tyr Trp Phe Tyr
1               5                   10                  15

Asn Arg Gly Leu Gln Ser Gln Ser Gly Arg Tyr
            20                  25

<210> SEQ ID NO 487
<211> LENGTH: 13
<212> TYPE: PRT
<213> ORGANISM: Amanita bisporigera

<400> SEQUENCE: 487

Val Leu Tyr Arg Ser Lys Lys Pro Val Leu Pro Asp Phe
1               5                   10

<210> SEQ ID NO 488

<400> SEQUENCE: 488

000

<210> SEQ ID NO 489
<211> LENGTH: 28
<212> TYPE: PRT
<213> ORGANISM: Amanita bisporigera

<400> SEQUENCE: 489

Arg Ala Pro Glu Gly Thr Phe Gly Ala Ala Val Ser Glu Gly Gly Val
1               5                   10                  15

Ala Asp Leu Leu Lys Phe Asn Lys Phe Thr Gly Gly
            20                  25

<210> SEQ ID NO 490
<211> LENGTH: 46
<212> TYPE: PRT
<213> ORGANISM: Galerina marginata

<400> SEQUENCE: 490

-continued

```
Arg Ala Pro Glu Gly Thr Phe Gly Ala Val Pro Glu Gly Gly Val
1               5                   10                  15

Ala Asp Leu Leu Lys Val Val Phe Val Phe Gln Leu Cys Asn Ser Gln
                20                  25                  30

Ser Leu Ile Leu Thr Leu Gln Phe His Lys Phe Thr Gly Gly
        35                  40                  45
```

<210> SEQ ID NO 491
<211> LENGTH: 19
<212> TYPE: PRT
<213> ORGANISM: Amanita bisporigera

<400> SEQUENCE: 491

```
Thr Gly Gly Met Ala Trp Thr Ser Glu Tyr Gly Asn Pro Phe Ile Lys
1               5                   10                  15

Glu Asp Phe
```

<210> SEQ ID NO 492
<211> LENGTH: 19
<212> TYPE: PRT
<213> ORGANISM: Galerina marginata

<400> SEQUENCE: 492

```
Ser Ser Gly Gln Ala Trp Ile Ser Glu Tyr Gly Asn Pro Ser Ile Pro
1               5                   10                  15

Glu Glu Phe
```

<210> SEQ ID NO 493
<211> LENGTH: 60
<212> TYPE: PRT
<213> ORGANISM: Amanita bisporigera

<400> SEQUENCE: 493

```
Ala Val Pro Asn Ile Arg Gly Gly Glu Phe Gly Gly Glu Trp His
1               5                   10                  15

Lys Ala Gly Arg Arg Glu Thr Lys Gly Asn Thr Phe Asp Asp Phe Ile
                20                  25                  30

Ala Ala Ala Gln Phe Leu Val Lys Asn Lys Tyr Ala Ala Pro Gly Lys
        35                  40                  45

Val Ala Ile Thr Gly Ala Ser Asn Gly Gly Phe Leu
        50                  55                  60
```

<210> SEQ ID NO 494

<400> SEQUENCE: 494

000

<210> SEQ ID NO 495
<211> LENGTH: 5
<212> TYPE: PRT
<213> ORGANISM: Amanita bisporigera

<400> SEQUENCE: 495

```
Gly Gly Phe Leu Val
1               5
```

<210> SEQ ID NO 496
<211> LENGTH: 5
<212> TYPE: PRT
<213> ORGANISM: Galerina marginata

```
<400> SEQUENCE: 496

Gly Gly Met Leu Met
1               5

<210> SEQ ID NO 497
<211> LENGTH: 27
<212> TYPE: PRT
<213> ORGANISM: Amanita bisporigera

<400> SEQUENCE: 497

Glu Asp Ile Ile Val Gln Gln Asp Lys Glu Asn Pro Asp Trp Thr Tyr
1               5                   10                  15

Gly Thr Asp Ala Ser Glu Asp Gly Lys Tyr Ile
            20                  25

<210> SEQ ID NO 498

<400> SEQUENCE: 498

000

<210> SEQ ID NO 499
<211> LENGTH: 13
<212> TYPE: PRT
<213> ORGANISM: Amanita bisporigera

<400> SEQUENCE: 499

Met Val Cys Tyr His Arg Val Gly Thr Thr Gln Leu Glu
1               5                   10

<210> SEQ ID NO 500

<400> SEQUENCE: 500

000

<210> SEQ ID NO 501
<211> LENGTH: 34
<212> TYPE: PRT
<213> ORGANISM: Amanita bisporigera

<400> SEQUENCE: 501

Lys Gln Asn Leu Leu Trp Val Ala Glu Phe Asp Lys Asp Gly Val Lys
1               5                   10                  15

Pro Glu Ile Pro Trp Arg Lys Val Ile Asn Glu Phe Gly Ala Asp Tyr
            20                  25                  30

His Val

<210> SEQ ID NO 502

<400> SEQUENCE: 502

000

<210> SEQ ID NO 503
<211> LENGTH: 54
<212> TYPE: PRT
<213> ORGANISM: Amanita bisporigera

<400> SEQUENCE: 503

Asp Tyr Phe Thr Ile Tyr Val Arg Pro Thr Ser Ser Ser Leu Ser Gln
1               5                   10                  15
```

```
Ala Pro Glu Ala Glu Gly Gly Asp Gly Arg Leu Ser Asp Gly Val Lys
            20                  25                  30

Trp Cys Lys Phe Thr Thr Ile Thr Trp Thr Lys Asp Ser Lys Gly Phe
        35                  40                  45

Leu Tyr Gln Arg Tyr Pro
    50

<210> SEQ ID NO 504
<211> LENGTH: 54
<212> TYPE: PRT
<213> ORGANISM: Galerina marginata

<400> SEQUENCE: 504

Asp Phe Val Thr Ile Tyr Val Trp Ser Thr Asp Ser Pro Leu Thr Asn
1               5                   10                  15

Asp Val Asp Ser Lys Asn Asp Lys Gly Arg Leu Pro Glu Glu Ile Lys
            20                  25                  30

Phe Val Lys Phe Ser Ser Ile Gly Trp Thr Pro Asp Ser Lys Gly Phe
        35                  40                  45

Phe Ile Arg Ser Ile Pro
    50

<210> SEQ ID NO 505
<211> LENGTH: 60
<212> TYPE: PRT
<213> ORGANISM: Amanita bisporigera

<400> SEQUENCE: 505

His Ser Phe Leu Thr Phe Ser Gly Phe Asn Thr Pro Gly Thr Ile Ser
1               5                   10                  15

Arg Tyr Asp Phe Thr Ala Pro Asp Thr Gln Arg Leu Ser Ile Leu Arg
            20                  25                  30

Thr Thr Lys Leu Asn Gly Leu Asn Ala Asp Asp Phe Glu Ser Thr Gln
        35                  40                  45

Val Trp Tyr Lys Ser Lys Asp Gly Thr Lys Val Pro
    50                  55                  60

<210> SEQ ID NO 506
<211> LENGTH: 58
<212> TYPE: PRT
<213> ORGANISM: Galerina marginata

<400> SEQUENCE: 506

His Ile Arg Leu Arg Tyr Glu Ala Leu Asn Arg Pro Ala Gln Ile Arg
1               5                   10                  15

Arg Leu Ala Leu Ala Asp Gly Ala Gln Gln Val Leu Lys Glu Thr Pro
            20                  25                  30

Val Leu Gly Val Phe Asn Ala Asp Asp Tyr Val Ser Gln Arg Leu Trp
        35                  40                  45

Ala Thr Ser Val Asp Gly Thr Gln Val Pro
    50                  55

<210> SEQ ID NO 507
<211> LENGTH: 33
<212> TYPE: PRT
<213> ORGANISM: Amanita bisporigera

<400> SEQUENCE: 507

Ile Ser Leu Val Val Arg His Asp Gln Leu Gly Gln Pro Thr Pro Leu
1               5                   10                  15
```

```
-continued

Tyr Leu Tyr Gly Tyr Gly Ala Tyr Gly His Ser Leu Asp Pro Trp Phe
            20                  25                  30
Ser

<210> SEQ ID NO 508
<211> LENGTH: 34
<212> TYPE: PRT
<213> ORGANISM: Galerina marginata

<400> SEQUENCE: 508

Met Phe Ile Val Arg His Lys Ser Thr Lys Phe Asp Gly Thr Ala Pro
1               5                   10                  15

Ala Ile Gln Asn Gly Tyr Gly Gly Phe Ala Ile Thr Ala Asp Pro Phe
            20                  25                  30

Phe Ser

<210> SEQ ID NO 509
<211> LENGTH: 30
<212> TYPE: PRT
<213> ORGANISM: Amanita bisporigera

<400> SEQUENCE: 509

Met Pro Pro Thr Pro Trp Ala Pro His Ser Tyr Pro Pro Thr Arg Arg
1               5                   10                  15

Ser Asp His Val Asp Val Tyr Gln Ser Ala Ser Arg Gly Glu
            20                  25                  30

<210> SEQ ID NO 510

<400> SEQUENCE: 510

000

<210> SEQ ID NO 511
<211> LENGTH: 41
<212> TYPE: PRT
<213> ORGANISM: Amanita bisporigera

<400> SEQUENCE: 511

Lys Phe Ser Ala Pro Thr Leu Leu Asp Ser Gly His Trp Tyr Trp Phe
1               5                   10                  15

Tyr Asn Ser Gly Val Gln Ser Gln Ala Val Leu Tyr Arg Ser Lys Lys
            20                  25                  30

Pro Val Leu Pro Asp Phe Gln Arg Gly
        35                  40

<210> SEQ ID NO 512

<400> SEQUENCE: 512

000

<210> SEQ ID NO 513
<211> LENGTH: 17
<212> TYPE: PRT
<213> ORGANISM: Amanita bisporigera

<400> SEQUENCE: 513

Thr Arg Lys Val Gly Glu Val Tyr Phe Asp Pro Asn Val Leu Ser Ala
1               5                   10                  15

Asp
```

<210> SEQ ID NO 514

<400> SEQUENCE: 514

000

<210> SEQ ID NO 515
<211> LENGTH: 23
<212> TYPE: PRT
<213> ORGANISM: Amanita bisporigera

<400> SEQUENCE: 515

Gln Phe Leu Val Lys Asn Lys Tyr Ala Ala Pro Gly Lys Val Ala Ile
1               5                   10                  15

Thr Gly Ala Ser Asn Gly Gly
            20

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519
<211> LENGTH: 37
<212> TYPE: PRT
<213> ORGANISM: Amanita bisporigera

<400> SEQUENCE: 519

Glu Asp Ile Ile Val Gln Gln Asp Lys Glu Asn Pro Asp Trp Thr Tyr
1               5                   10                  15

Gly Thr Asp Ala Ser Glu Asp Gly Lys Tyr Ile Tyr Leu Val Val Tyr
            20                  25                  30

Lys Asp Ala Ser Lys
        35

<210> SEQ ID NO 520
<211> LENGTH: 37
<212> TYPE: PRT
<213> ORGANISM: Galerina marginata

<400> SEQUENCE: 520

Glu Asp Ser Leu Ile Tyr Gln Asp Arg Glu His Arg Asp Trp Met Phe
1               5                   10                  15

Ser Ile Asp Val Thr Asp Gly Asn Tyr Leu Leu Leu Tyr Ile Leu
            20                  25                  30

Lys Asp Ser Ser Arg
        35

<210> SEQ ID NO 521

```
<211> LENGTH: 30
<212> TYPE: DNA
<213> ORGANISM: Rattus norvegicus

<400> SEQUENCE: 521
tgtcaaccgt ctcctctgtc gtttcctttg                                    30

<210> SEQ ID NO 522
<211> LENGTH: 33
<212> TYPE: PRT
<213> ORGANISM: Agrobacterium tumefaciens

<400> SEQUENCE: 522

Thr Cys Thr Gly Thr Gly Ala Cys Gly Ala Thr Gly Thr Cys Ala Thr
 1               5                  10                  15

Cys Cys Ala Gly Thr Cys Thr Cys Thr Cys Ala Cys Thr Cys Gly Thr
            20                  25                  30

Ala

<210> SEQ ID NO 523
<211> LENGTH: 23
<212> TYPE: DNA
<213> ORGANISM: Vitis vinifera

<400> SEQUENCE: 523
ttgtagactg cccatgcgtc tgt                                           23

<210> SEQ ID NO 524
<211> LENGTH: 30
<212> TYPE: DNA
<213> ORGANISM: Amanita bisporigera

<400> SEQUENCE: 524
atgtctgaca tcaatgctac ccgtctcccc                                    30

<210> SEQ ID NO 525
<211> LENGTH: 45
<212> TYPE: DNA
<213> ORGANISM: Amanita bisporigera

<400> SEQUENCE: 525
tgcatcggtg acgacgtcac tactctcctc actcgtgccc tttgt                   45

<210> SEQ ID NO 526
<211> LENGTH: 17
<212> TYPE: PRT
<213> ORGANISM: Salmo salar

<400> SEQUENCE: 526

Ala Thr Cys Gly Gly Thr Gly Ala Cys Gly Ala Cys Gly Thr Cys Ala
 1               5                  10                  15

Cys

<210> SEQ ID NO 527
<211> LENGTH: 17
<212> TYPE: DNA
<213> ORGANISM: Burkholderia cenocepacia

<400> SEQUENCE: 527
atcggtgacg acgtcac                                                  17

<210> SEQ ID NO 528
```

```
<211> LENGTH: 26
<212> TYPE: DNA
<213> ORGANISM: Chaetomium globosum

<400> SEQUENCE: 528
ggtgacgatg acaaccgcct cctcac                                          26

<210> SEQ ID NO 529
<211> LENGTH: 18
<212> TYPE: DNA
<213> ORGANISM: Chaetomium globosum

<400> SEQUENCE: 529
ctcctcactc gtgcccctt                                                  18

<210> SEQ ID NO 530
<211> LENGTH: 18
<212> TYPE: DNA
<213> ORGANISM: Ciona intestinalis

<400> SEQUENCE: 530
atgtctgaca tcaatgct                                                   18

<210> SEQ ID NO 531
<211> LENGTH: 17
<212> TYPE: DNA
<213> ORGANISM: Ciona intestinalis

<400> SEQUENCE: 531
atgtctgaca tcaatgc                                                    17

<210> SEQ ID NO 532
<211> LENGTH: 16
<212> TYPE: DNA
<213> ORGANISM: Aspergillus oryzae

<400> SEQUENCE: 532
ctgacatcaa tgctac                                                     16

<210> SEQ ID NO 533
<211> LENGTH: 18
<212> TYPE: DNA
<213> ORGANISM: Oryza sativa

<400> SEQUENCE: 533
tctgacatca atgccacc                                                   18

<210> SEQ ID NO 534
<211> LENGTH: 6
<212> TYPE: PRT
<213> ORGANISM: Amanita bisporigera

<400> SEQUENCE: 534

Cys Val Gly Asp Asp Val
 1               5

<210> SEQ ID NO 535

<400> SEQUENCE: 535

000

<210> SEQ ID NO 536
<211> LENGTH: 19
```

```
<212> TYPE: DNA
<213> ORGANISM: Homo sapiens

<400> SEQUENCE: 536
atgtctgaca tcaatgcca                                                    19

<210> SEQ ID NO 537
<211> LENGTH: 16
<212> TYPE: DNA
<213> ORGANISM: Neurospora crassa

<400> SEQUENCE: 537
tgtctgacat caatgc                                                       16

<210> SEQ ID NO 538
<211> LENGTH: 17
<212> TYPE: DNA
<213> ORGANISM: Homo sapiens

<400> SEQUENCE: 538
gtctgacatc aatgcca                                                      17

<210> SEQ ID NO 539

<400> SEQUENCE: 539

000

<210> SEQ ID NO 540
<211> LENGTH: 21
<212> TYPE: DNA
<213> ORGANISM: Otolemur garnettii

<400> SEQUENCE: 540
tgtctgacat caatgccacc c                                                 21

<210> SEQ ID NO 541
<211> LENGTH: 21
<212> TYPE: DNA
<213> ORGANISM: Phytophthora sojae

<400> SEQUENCE: 541
cggtgacgat gtcaaccgtc t                                                 21

<210> SEQ ID NO 542
<211> LENGTH: 19
<212> TYPE: DNA
<213> ORGANISM: Mus musculus

<400> SEQUENCE: 542
atgtctgaca tcaatgcca                                                    19

<210> SEQ ID NO 543
<211> LENGTH: 17
<212> TYPE: DNA
<213> ORGANISM: Helianthus annuus

<400> SEQUENCE: 543
aatgccaccc gtcttcc                                                      17

<210> SEQ ID NO 544
<211> LENGTH: 20
<212> TYPE: PRT
<213> ORGANISM: Amanita bisporigera
```

<400> SEQUENCE: 544

Gly Cys Asn Gly Tyr Arg Ala Thr Asn Gly Ala Arg Thr Gly Asn Cys
1               5                   10                  15

Cys Asn Cys Cys
            20

<210> SEQ ID NO 545
<211> LENGTH: 25
<212> TYPE: DNA
<213> ORGANISM: Gibberella zeae

<400> SEQUENCE: 545
cgtcggtgac gatgtcctcc gtctc                                          25

<210> SEQ ID NO 546
<211> LENGTH: 18
<212> TYPE: DNA
<213> ORGANISM: Homo sapiens

<400> SEQUENCE: 546
tcactactct cctcactc                                                  18

<210> SEQ ID NO 547
<211> LENGTH: 17
<212> TYPE: DNA
<213> ORGANISM: Ornithorhynchus anatinus

<400> SEQUENCE: 547
acgtcactac tctcctc                                                   17

<210> SEQ ID NO 548
<211> LENGTH: 18
<212> TYPE: DNA
<213> ORGANISM: Ostreococcus lucimarinus

<400> SEQUENCE: 548
gcatcggtga cgacgtca                                                  18

<210> SEQ ID NO 549
<211> LENGTH: 16
<212> TYPE: PRT
<213> ORGANISM: Amanita bisporigera

<400> SEQUENCE: 549

Thr Arg Leu Pro Ile Trp Gly Ile Gly Cys Asn Pro Cys Ile Gly Asp
1               5                   10                  15

<210> SEQ ID NO 550
<400> SEQUENCE: 550

000

<210> SEQ ID NO 551
<211> LENGTH: 12
<212> TYPE: PRT
<213> ORGANISM: Amanita bisporigera

<400> SEQUENCE: 551

Thr Arg Leu Pro Ile Trp Gly Ile Gly Cys Asn Pro
1               5                   10

<210> SEQ ID NO 552
<211> LENGTH: 12
<212> TYPE: PRT
<213> ORGANISM: Amanita bisporigera

<400> SEQUENCE: 552

Ile Trp Gly Ile Gly Cys Asn Pro Cys Ile Gly Asp
1               5                   10

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558
<211> LENGTH: 45
<212> TYPE: DNA
<213> ORGANISM: Amanita bisporigera

<400> SEQUENCE: 558
tgcgtcggtg acgatgtcaa ccgtctcctc actcgtagcc tttgg        45

<210> SEQ ID NO 559
<211> LENGTH: 35
<212> TYPE: PRT
<213> ORGANISM: Amanita bisporigera

<400> SEQUENCE: 559

Met Ser Asp Ile Asn Ala Thr Arg Leu Pro Ile Trp Gly Ile Gly Cys
1               5                   10                  15

Asn Pro Cys Ile Gly Asp Asp Val Thr Thr Leu Leu Thr Arg Gly Glu
                20                  25                  30

Ala Leu Cys
        35

<210> SEQ ID NO 560
<211> LENGTH: 17
<212> TYPE: PRT
<213> ORGANISM: Amanita bisporigera

<400> SEQUENCE: 560

```
Ala Thr Arg Leu Pro Ala Trp Leu Val Asp Cys Pro Cys Val Gly Asp
1               5                   10                  15

Asp

<210> SEQ ID NO 561
<211> LENGTH: 17
<212> TYPE: DNA
<213> ORGANISM: Rattus norvegicus

<400> SEQUENCE: 561
acgtcactac tctcctc                                                  17

<210> SEQ ID NO 562
<211> LENGTH: 18
<212> TYPE: DNA
<213> ORGANISM: Amanita bisporigera

<400> SEQUENCE: 562
caatgccacc cgtcttcc                                                 18

<210> SEQ ID NO 563
<211> LENGTH: 20
<212> TYPE: DNA
<213> ORGANISM: Strongylocentrotus purpuratus

<400> SEQUENCE: 563
tgtctgacat caatggtacc                                               20

<210> SEQ ID NO 564
<211> LENGTH: 17
<212> TYPE: DNA
<213> ORGANISM: Monodelphis domestica

<400> SEQUENCE: 564
gtctgacatc aatgcta                                                  17

<210> SEQ ID NO 565
<211> LENGTH: 16
<212> TYPE: DNA
<213> ORGANISM: Aspergillus nidulans

<400> SEQUENCE: 565
tgtctgacat caatgc                                                   16

<210> SEQ ID NO 566
<211> LENGTH: 18
<212> TYPE: DNA
<213> ORGANISM: Aspergillus nidulans

<400> SEQUENCE: 566
tgtctgacat caatgcca                                                 18

<210> SEQ ID NO 567
<211> LENGTH: 21
<212> TYPE: DNA
<213> ORGANISM: Ustilago maydis

<400> SEQUENCE: 567
catcaatgcc acccgccttc c                                             21

<210> SEQ ID NO 568
<211> LENGTH: 16
```

<212> TYPE: DNA
<213> ORGANISM: Amanita bisporigera

<400> SEQUENCE: 568
aatgctaccc gtctcc                                                     16

<210> SEQ ID NO 569
<211> LENGTH: 14
<212> TYPE: PRT
<213> ORGANISM: Ustilago maydis

<400> SEQUENCE: 569

Gly Asp Asp Val Ala Ala Leu Leu Ser Arg Arg Val Leu Cys
1               5                   10

<210> SEQ ID NO 570
<211> LENGTH: 12
<212> TYPE: PRT
<213> ORGANISM: Prosthecochloris aestuarii

<400> SEQUENCE: 570

Gly Asp Asp Val Glu Thr Ile Leu Thr Arg Leu Leu
1               5                   10

<210> SEQ ID NO 571
<211> LENGTH: 21
<212> TYPE: DNA
<213> ORGANISM: Rhizobium leguminosarum

<400> SEQUENCE: 571
cgtcggtgac gaggtcaacc g                                               21

<210> SEQ ID NO 572
<211> LENGTH: 32
<212> TYPE: DNA
<213> ORGANISM: Rhodococcus

<400> SEQUENCE: 572
cgggtacaac acgtgcatcg gtgacgccgt ca                                   32

<210> SEQ ID NO 573
<211> LENGTH: 19
<212> TYPE: DNA
<213> ORGANISM: Strongylocentrotus purpuratus

<400> SEQUENCE: 573
catcggtgac gacgtcact                                                  19

<210> SEQ ID NO 574
<211> LENGTH: 19
<212> TYPE: DNA
<213> ORGANISM: Amanita bisporigera

<400> SEQUENCE: 574
gatgtcaacc gtctcctca                                                  19

<210> SEQ ID NO 575
<211> LENGTH: 10
<212> TYPE: PRT
<213> ORGANISM: Amanita bisporigera

<400> SEQUENCE: 575

Met Ser Asp Ile Asn Thr Ala Arg Leu Pro
1               5                   10

<210> SEQ ID NO 576

<400> SEQUENCE: 576

000

<210> SEQ ID NO 577

<400> SEQUENCE: 577

000

<210> SEQ ID NO 578
<211> LENGTH: 28
<212> TYPE: DNA
<213> ORGANISM: Gibberella zeae

<400> SEQUENCE: 578
cgtcggtgac gatgtcctcc gtctcttc         28

<210> SEQ ID NO 579
<211> LENGTH: 33
<212> TYPE: DNA
<213> ORGANISM: Danio rerio

<400> SEQUENCE: 579
cgacactacc ctcaccactc gtgcccttag tta         33

<210> SEQ ID NO 580
<211> LENGTH: 33
<212> TYPE: DNA
<213> ORGANISM: Mycobacterium avium

<400> SEQUENCE: 580
cgtcggtgac gatgtacacc gtcgccacgc tcg         33

<210> SEQ ID NO 581
<211> LENGTH: 15
<212> TYPE: PRT
<213> ORGANISM: Amanita bisporigera
<220> FEATURE:
<221> NAME/KEY: VARIANT
<222> LOCATION: (1)...(15)
<223> OTHER INFORMATION: Xaa can be any amino acid

<400> SEQUENCE: 581

Cys Val Gly Asp Asp Val Xaa Xaa Leu Leu Thr Arg Ala Leu Cys
 1               5                  10                  15

<210> SEQ ID NO 582
<211> LENGTH: 10
<212> TYPE: PRT
<213> ORGANISM: Botryotinia fuckeliana

<400> SEQUENCE: 582

Met Arg Glu Ile Asn Ser Thr Arg Leu Pro
 1               5                  10

<210> SEQ ID NO 583
<211> LENGTH: 10
<212> TYPE: PRT
<213> ORGANISM: Frankia

<400> SEQUENCE: 583

```
Met Ser Asn Ile Ala Ala Pro Arg Leu Pro
1               5                   10
```

<210> SEQ ID NO 584
<211> LENGTH: 13
<212> TYPE: PRT
<213> ORGANISM: Coprinopsis cinerea

<400> SEQUENCE: 584

```
Met Ser Asp Ile Ala Trp His Pro Asp Asn Ala Thr Arg
1               5                   10
```

<210> SEQ ID NO 585
<211> LENGTH: 9
<212> TYPE: PRT
<213> ORGANISM: Ustilago maydis

<400> SEQUENCE: 585

```
Ser Asp Val Asn Ala Pro Arg Leu Pro
1               5
```

<210> SEQ ID NO 586
<211> LENGTH: 8
<212> TYPE: PRT
<213> ORGANISM: Saccharopolyspora erythraea

<400> SEQUENCE: 586

```
Ser Asp Ile Ala Thr Arg Leu Pro
1               5
```

<210> SEQ ID NO 587
<211> LENGTH: 5
<212> TYPE: PRT
<213> ORGANISM: Amanita bisporigera

<400> SEQUENCE: 587

```
Met Ser Asp Ile Asn
1               5
```

<210> SEQ ID NO 588
<211> LENGTH: 60
<212> TYPE: PRT
<213> ORGANISM: Amanita bisporigera

<400> SEQUENCE: 588

```
Gly Val Ala Ser Ile Thr Asn Arg Glu Lys Gln Pro His Ser Phe Leu
1               5                   10                  15

Thr Phe Ser Gly Phe Asn Thr Pro Gly Thr Ile Ser Arg Tyr Asp Phe
                20                  25                  30

Thr Ala Pro Asp Thr Gln Arg Leu Ser Ile Leu Arg Thr Thr Lys Leu
            35                  40                  45

Asn Gly Leu Asn Ala Asp Asp Phe Glu Ser Thr Gln
        50                  55                  60
```

<210> SEQ ID NO 589
<211> LENGTH: 10
<212> TYPE: PRT
<213> ORGANISM: Amanita bisporigera

<400> SEQUENCE: 589

```
Val Trp Tyr Lys Ser Lys Asp Gly Thr Lys
1               5                   10
```

```
<210> SEQ ID NO 590
<211> LENGTH: 15
<212> TYPE: PRT
<213> ORGANISM: Amanita bisporigera

<400> SEQUENCE: 590

Lys Asp Gly Thr Lys Val Pro Met Phe Ile Val Arg His Lys Ser
1               5                   10                  15

<210> SEQ ID NO 591
<211> LENGTH: 15
<212> TYPE: PRT
<213> ORGANISM: Amanita bisporigera

<400> SEQUENCE: 591

Ala Asp Arg Gln Lys Leu Glu Glu Lys Phe Arg Ala Ser Lys Asp
1               5                   10                  15

<210> SEQ ID NO 592
<211> LENGTH: 15
<212> TYPE: PRT
<213> ORGANISM: Galerina marginata

<400> SEQUENCE: 592

Ala Asp Ile Gln Lys Leu Ala Asp Lys Phe Arg Ala Ser Arg Asn
1               5                   10                  15

<210> SEQ ID NO 593
<211> LENGTH: 60
<212> TYPE: PRT
<213> ORGANISM: Amanita bisporigera

<400> SEQUENCE: 593

Val Asp Val Tyr Gln Ser Ala Ser Arg Gly Glu Val Pro Val Pro Asp
1               5                   10                  15

Pro Tyr Gln Trp Leu Glu Glu Asn Ser Asn Glu Val Asp Glu Trp Thr
                20                  25                  30

Thr Ala Gln Thr Ala Phe Thr Gln Gly Tyr Leu Asp Lys Asn Ala Asp
            35                  40                  45

Arg Gln Lys Leu Glu Glu Lys Phe Arg Ala Ser Lys
        50                  55                  60

<210> SEQ ID NO 594
<211> LENGTH: 10
<212> TYPE: PRT
<213> ORGANISM: Amanita bisporigera

<400> SEQUENCE: 594

Asp Tyr Val Lys Phe Ser Ala Pro Thr Leu
1               5                   10

<210> SEQ ID NO 595
<211> LENGTH: 10
<212> TYPE: PRT
<213> ORGANISM: Galerina marginata

<400> SEQUENCE: 595

Asp Tyr Pro Lys Val Leu Ser Ala Thr Ile
1               5                   10

<210> SEQ ID NO 596
<211> LENGTH: 1572
<212> TYPE: DNA
<213> ORGANISM: Galerina marginata
```

<400> SEQUENCE: 596

```
atggtcgact tgcacaccat ctcgtattca gctctcgtca ctttcaggct tatattccaa      60
ttcctcaagc tatctgcagc tgcattgact atctatggac tttacagagt cactcgtgta     120
atttatgttg agctgacttc tccaatacgc catctccccg tccagcaaa cgccaatata     180
tttcttggta atctcaaaca gctctggaca gatctttcgc atttatatgt gacggatccg     240
caggccttga accacatttt gacgaatggt tacgtttaca ccaaaccatc gtttactcgc     300
cgccagatcg gcaagttgtg gggtccaggt ctcccttttg tcgaagggga tcaacataaa     360
aagcagcgga gattttggt gactatctat ccattccaaa tcgtggtcca tcagtgtctc     420
aatcacaacc agaatcctgc ctttggtccg ctccaagact cttgggctac tgaatgctcg     480
aaacaaggtg gtacttgccg cttagacatt atggtaggcc ttggtaaggt ggtgatggac     540
atcatcagct caacagtgtt taccgatgcc attcgatgga aaggcttccg ttacgagctt     600
gattccctgg atcgtgaaag tgactttagc cgtgtggcta caattttatc tcaattgaac     660
ctgattcgtt ggcaactccg aagattcatc ccacttctat ggttcatacc tgatcctgta     720
gagacacaac tagacgatat caagcagacc ctttctcgga ttacgagtcg gcttctgaac     780
gagagcaagg gatccgtacg tacgaataat gacaattccg gcagtcgaga tctcctatcg     840
cttttggttc gcaccaatat gtcccccgat gtgccagagc accgtcgtct atccgatgac     900
gaagtcaaag cgcaggttat ctcatttgta attgctggac gtgaaagtcc gattaacgta     960
atggcgtggg ctttatttc tctggcaaaa aaccgtgaaa tccaggctaa gctgcgtaga    1020
gagctgctca cggtcgatac ctgtcagcca acgacggacc agctcaatgc actttcatat    1080
ttggatatgg taattaggga gacgctacgc cactcgaggg tgtgtgccaa ggacgacatt    1140
ttacctttgg ctaagccgat caccgaccgg agaggaaacc tattctccag tattagtatc    1200
aaaagagggc aagtagtcat aattcccatt tctgccatcc acaaggacaa gtcgatatgg    1260
ggtgaagatg ctttagactt cagaccagaa cgatgggaat gtctacctga aggcgtcaat    1320
accatcccag cgtctggag ccatttgctc agttttggg gtggtccacg ttcgtgtatc    1380
ggattcagat ttgctatcgc cgaaatgaaa gctctactct tcacactagt ccgtgccctc    1440
gaatttgact ggctgtgcc agcggagcaa atttctgtgg aaagtggact aagtaaccga    1500
ccgatttga ccacggaccc gggccgttat cagctcccgc tgctcatcaa gccatataaa    1560
gctcgaagtt aa                                                       1572
```

<210> SEQ ID NO 597
<211> LENGTH: 523
<212> TYPE: PRT
<213> ORGANISM: Galerina marginata

<400> SEQUENCE: 597

```
Met Val Asp Leu His Thr Ile Ser Tyr Ser Ala Leu Val Thr Phe Arg
  1               5                  10                  15

Leu Ile Phe Gln Phe Leu Lys Leu Ser Ala Ala Ala Leu Thr Ile Tyr
             20                  25                  30

Gly Leu Tyr Arg Val Thr Arg Val Ile Tyr Val Glu Leu Thr Ser Pro
         35                  40                  45

Ile Arg His Leu Pro Gly Pro Ala Asn Ala Asn Ile Phe Leu Gly Asn
     50                  55                  60

Leu Lys Gln Leu Trp Thr Asp Leu Ser His Leu Tyr Val Thr Asp Pro
 65                  70                  75                  80
```

-continued

```
Gln Ala Leu Asn His Ile Leu Thr Asn Gly Tyr Val Tyr Thr Lys Pro
                 85                  90                  95
Ser Phe Thr Arg Arg Gln Ile Gly Lys Leu Trp Gly Pro Gly Leu Pro
            100                 105                 110
Phe Val Glu Gly Asp Gln His Lys Lys Gln Arg Lys Ile Leu Val Thr
        115                 120                 125
Ile Tyr Pro Phe Gln Ile Val Val His Gln Cys Leu Asn His Asn Gln
    130                 135                 140
Asn Pro Ala Phe Gly Pro Leu Gln Asp Ser Trp Ala Thr Glu Cys Ser
145                 150                 155                 160
Lys Gln Gly Gly Thr Cys Arg Leu Asp Ile Met Val Gly Leu Gly Lys
                165                 170                 175
Val Val Met Asp Ile Ile Ser Ser Thr Val Phe Thr Asp Ala Ile Arg
            180                 185                 190
Trp Lys Gly Phe Arg Tyr Glu Leu Asp Ser Leu Asp Arg Glu Ser Asp
        195                 200                 205
Phe Ser Arg Val Ala Thr Ile Leu Ser Gln Leu Asn Leu Ile Arg Trp
    210                 215                 220
Gln Leu Arg Arg Phe Ile Pro Leu Leu Trp Phe Ile Pro Asp Pro Val
225                 230                 235                 240
Glu Thr Gln Leu Asp Asp Ile Lys Gln Thr Leu Ser Arg Ile Thr Ser
                245                 250                 255
Arg Leu Leu Asn Glu Ser Lys Gly Ser Val Arg Thr Asn Asn Asp Asn
            260                 265                 270
Ser Gly Ser Arg Asp Leu Leu Ser Leu Leu Val Arg Thr Asn Met Ser
        275                 280                 285
Pro Asp Val Pro Glu His Arg Arg Leu Ser Asp Glu Val Lys Ala
    290                 295                 300
Gln Val Ile Ser Phe Val Ile Ala Gly Arg Glu Ser Pro Ile Asn Val
305                 310                 315                 320
Met Ala Trp Ala Leu Phe Ser Leu Ala Lys Asn Arg Glu Ile Gln Ala
                325                 330                 335
Lys Leu Arg Arg Glu Leu Leu Thr Val Asp Thr Cys Gln Pro Thr Thr
            340                 345                 350
Asp Gln Leu Asn Ala Leu Ser Tyr Leu Asp Met Val Ile Arg Glu Thr
        355                 360                 365
Leu Arg His Ser Arg Val Cys Ala Lys Asp Asp Ile Leu Pro Leu Ala
    370                 375                 380
Lys Pro Ile Thr Asp Arg Gly Asn Leu Phe Ser Ser Ile Ser Ile
385                 390                 395                 400
Lys Arg Gly Gln Val Val Ile Ile Pro Ile Ser Ala Ile His Lys Asp
                405                 410                 415
Lys Ser Ile Trp Gly Glu Asp Ala Leu Asp Phe Arg Pro Glu Arg Trp
            420                 425                 430
Glu Cys Leu Pro Glu Gly Val Asn Thr Ile Pro Gly Val Trp Ser His
        435                 440                 445
Leu Leu Ser Phe Trp Gly Gly Pro Arg Ser Cys Ile Gly Phe Arg Phe
    450                 455                 460
Ala Ile Ala Glu Met Lys Ala Leu Leu Phe Thr Leu Val Arg Ala Leu
465                 470                 475                 480
Glu Phe Asp Leu Ala Val Pro Ala Glu Gln Ile Ser Val Glu Ser Gly
                485                 490                 495
```

Leu Ser Asn Arg Pro Ile Leu Thr Thr Asp Pro Gly Arg Tyr Gln Leu
            500                 505                 510

Pro Leu Leu Ile Lys Pro Tyr Lys Ala Arg Ser
            515                 520

<210> SEQ ID NO 598
<211> LENGTH: 545
<212> TYPE: PRT
<213> ORGANISM: Galerina marginata

<400> SEQUENCE: 598

Met Gly Arg Thr Cys Leu Leu Val Val Ser Ala Thr Ala Thr Leu Gly
  1               5                  10                  15

Val Tyr Gly Leu Tyr Lys Ile Ala Gly Ile Val Tyr Arg Glu Trp Leu
             20                  25                  30

Ser Pro Leu Arg Val Leu Pro Gly Thr Lys Ser Pro Ser Phe Leu Tyr
         35                  40                  45

Gly Asp Leu Lys Glu Leu Trp Glu Glu Glu Asp Thr Gly Thr Ser Gly
 50                  55                  60

Ile Leu Val Glu Lys Tyr Gly Thr Thr Phe Arg Tyr Lys Ser Leu Leu
 65                  70                  75                  80

Gly Ile Ser Arg Leu Tyr Thr Ala Asp Thr Arg Ala Leu Asn His Ile
                 85                  90                  95

Leu Met Asn Ser Tyr Asp Tyr Glu Lys Leu Pro Glu Ser Arg Ala Ala
            100                 105                 110

Leu Thr Asn Ile Leu Gly Ala Gly Leu Leu Val Val Glu Gly Asp Lys
        115                 120                 125

His Lys Gln Gln Arg Lys Ile Met Asn Pro Ala Phe Gly Pro Ala Gln
130                 135                 140

Ile Arg Glu Leu Thr Asp Ile Phe Val Arg Lys Ser Ile Gln Leu Arg
145                 150                 155                 160

Asp Leu Trp Ala Glu Glu Cys Thr Lys Gln Gly Gly Gln Gly Arg Ile
                165                 170                 175

Glu Ile Leu Ser Trp Leu Thr Trp Thr Thr Leu Asp Val Ile Gly Leu
            180                 185                 190

Ala Gly Phe Asn Tyr Lys Phe Asn Ala Leu Met Arg Asp Ser Lys Ala
        195                 200                 205

Asn Glu Leu Ser Glu Ala Phe Asn Thr Ile Phe Gln Ala Gly Thr Ser
    210                 215                 220

Val Asn Val Met Leu Ile Leu Arg Ala Phe Ile Pro Ala Leu Ser Trp
225                 230                 235                 240

Ile Leu Pro Glu Ala Gly Asp Val Glu Ala Lys Lys Ala Ser Ser Thr
                245                 250                 255

Met Ser Arg Ile Gly Lys Glu Leu Leu Ser Asn Ser Lys Ala Ala Val
            260                 265                 270

Ser Gln Gln Glu Ser Leu Glu Lys Asp Thr Trp Lys Thr Arg Asp Leu
        275                 280                 285

Leu Ser Leu Leu Val Arg Ala Asn Val Ala Thr Asp Leu Thr Glu Ser
    290                 295                 300

Gln Arg Met Leu Asp Glu Asp Val Leu Ala Gln Ile Pro Thr Phe Ile
305                 310                 315                 320

Val Ala Gly His Glu Thr Thr Ser Asn Ala Thr Thr Trp Ala Leu Phe
                325                 330                 335

Ala Leu Asn Ser Gln Asn Pro Asp Ala Gln Ile Lys Leu Arg Asn Glu
            340                 345                 350

```
Leu Leu Thr Val Ser Thr Asp Asn Pro Thr Met Asp Glu Leu Asn Ala
            355                 360                 365

Leu Pro Tyr Leu Asp Ala Val Val Arg Glu Thr Leu Arg Leu His Ala
    370                 375                 380

Pro Val Ser Met Thr Ser Arg Val Ala Met Lys Asp Asp Val Leu Pro
385                 390                 395                 400

Leu Ala Ile Pro Phe Thr Asp Ser Lys Gly Val Ile His His Glu Ile
                405                 410                 415

Arg Ile Arg Lys Gly Glu Pro Leu Leu Ile Pro Ile Leu Ala Leu Asn
            420                 425                 430

Arg Asp Lys Ser Ile Trp Gly Glu Asp Ala His Glu Phe Arg Pro Glu
            435                 440                 445

Arg Trp Glu Ser Ile Pro Asp Ala Ala Ser Ser Ile Pro Gly Val Trp
        450                 455                 460

Gly His Met Leu Thr Phe Leu Gly Gly Pro His Ser Cys Ile Gly Tyr
465                 470                 475                 480

Arg Phe Ala Leu Val Glu Met Lys Ala Leu Leu Phe Thr Leu Ile Arg
                485                 490                 495

Ser Phe Glu Phe Glu Leu Ala Val Pro Ala Ser Asp Ile Gly Lys Lys
            500                 505                 510

Ala Gly Ile Val His Arg Pro Ile Leu Leu Ser Asn Pro Glu Gly Gly
            515                 520                 525

Ser Gln Met Pro Leu Phe Val Lys Ala Tyr Gln Pro Pro Leu Glu Glu
            530                 535                 540

Ala
545

<210> SEQ ID NO 599
<211> LENGTH: 514
<212> TYPE: PRT
<213> ORGANISM: Galerina marginata

<400> SEQUENCE: 599

Met Gly Leu Val Trp Met Val Ala Ala Val Ala Ala Val Leu Ala
 1               5                  10                  15

Ser Trp Ala Phe Asp Ala Leu Val Tyr Leu Val Trp Arg Pro Arg Ala
            20                  25                  30

Ile Thr Arg Gln Leu Arg Ala Gln Gly Val Gly Gly Pro Gly Tyr Arg
        35                  40                  45

Phe Phe Ala Gly Asn Leu Ala Glu Ile Lys Gln Leu Arg Ala Asp Ser
    50                  55                  60

Ala Gly Ala Ala Leu Asp Ile Gly Asp His Asp Phe Val Pro Arg Val
65                  70                  75                  80

Gln Pro His Phe Arg Lys Trp Ile Pro Ile His Gly Arg Thr Phe Leu
                85                  90                  95

Tyr Trp Phe Gly Ala Lys Pro Thr Leu Cys Ile Ala Asp Val Asn Val
            100                 105                 110

Val Lys Gln Val Leu Ser Asp Arg Gly Gly Leu Tyr Pro Lys Ser Ile
        115                 120                 125

Gly Asn Pro His Ile Ala Arg Leu Leu Gly Lys Gly Leu Val Leu Thr
    130                 135                 140

Asp Gly Asp Asp Trp Lys Arg His Arg Lys Val Val His Pro Ala Phe
145                 150                 155                 160

Asn Met Asp Lys Leu Lys Met Met Thr Val Thr Met Ser Asp Cys Ala
```

```
                    165                 170                 175
Gly Ser Met Met Ser Glu Trp Lys Ala Lys Met Asp Lys Gly Gly Ser
                180                 185                 190
Val Glu Ile Asp Leu Ser Ser Gln Phe Glu Leu Thr Ala Asp Val
            195                 200                 205
Ile Ser His Thr Ala Phe Gly Ser Ser Tyr Glu Gln Gly Lys Lys Val
            210                 215                 220
Phe Leu Ala Gln Arg Glu Leu Gln Phe Leu Ala Phe Ser Thr Val Phe
225                 230                 235                 240
Asn Val Gln Ile Pro Ser Phe Arg Tyr Leu Pro Thr Glu Lys Asn Leu
                245                 250                 255
Lys Ile Trp Lys Leu Asp Lys Glu Val Arg Thr Met Leu Met Asn Ile
            260                 265                 270
Ile Lys Gly Arg Leu Ala Thr Lys Asp Thr Met Gly Tyr Gly Asn Asp
            275                 280                 285
Leu Leu Gly Leu Met Leu Glu Ala Cys Ala Pro Glu Asp Gly Gln Asn
            290                 295                 300
Pro Leu Leu Ser Met Asp Glu Ile Ile Asp Glu Cys Lys Thr Phe Phe
305                 310                 315                 320
Phe Ala Gly His Asp Thr Ser Ser His Leu Leu Thr Trp Thr Met Phe
                325                 330                 335
Leu Leu Ser Thr His Pro Glu Trp Gln Glu Lys Leu Arg Glu Glu Val
            340                 345                 350
Leu Arg Glu Cys Gly Asn Gly Ile Pro Thr Gly Asp Met Leu Asn Lys
            355                 360                 365
Leu Gln Leu Val Asn Met Phe Leu Leu Glu Thr Leu Arg Leu Tyr Ala
            370                 375                 380
Pro Val Ser Ala Ile Gln Arg Lys Ala Gly Ser Asp Leu Glu Val Gly
385                 390                 395                 400
Gly Ile Lys Val Thr Glu Gly Thr Phe Leu Thr Ile Pro Ile Ala Thr
                405                 410                 415
Ile His Arg Asp Lys Glu Val Trp Gly Glu Asp Ala Asn Lys Phe Lys
                420                 425                 430
Pro Met Arg Phe Glu Asn Gly Val Thr Arg Ala Gly Lys His Pro Asn
            435                 440                 445
Ala Leu Leu Ser Phe Ser Ser Gly Pro Arg Ser Cys Ile Gly Gln Asn
            450                 455                 460
Phe Ala Met Ile Glu Ala Lys Ala Val Ile Ala Val Ile Leu Gln Arg
465                 470                 475                 480
Phe Ser Phe Ser Leu Ser Pro Lys Tyr Val His Ala Pro Met Asp Val
                485                 490                 495
Ile Thr Leu Arg Pro Lys Phe Gly Leu Pro Met Ile Leu Lys Ser Leu
            500                 505                 510
Glu Met

<210> SEQ ID NO 600
<211> LENGTH: 1875
<212> TYPE: DNA
<213> ORGANISM: Amanita bisporigera

<400> SEQUENCE: 600
atgttgaacc tcaacttcaa cggcctctgg cctgatgtag cagagtattt caaaggcgat      60
tcgatgagga ttgtgaccctc tgcctttacg ttgctcgtcg tcatttctat ctatcgaaga     120
```

```
cgccgaggta tcagaacgcc cagactgcaa ggaccacgca gcgagagctt catcttcggt    180
aacaccaaga agatcttccc ttcggcgaac ctcagtgtgg tatatcggga ttgggaacga    240
atgtatgggc ccgtttacga gatacccact ggcatcggct ccagccatgt tgtattaagc    300
gatcccaagg ctctcacaca catatattcc aaggatacca ccacatattg tcggctcgca    360
gggacaaccg ctttgagccg gaagttggcg agtatctgtt ttgcaccatt tttcttagct    420
gccagcctta tttacgttcc aactacggag aggcctgtct tctccactgt cggtctcagc    480
aattcgcaat ctcactcccg tgtgcttgga ttctgcctat cagggaaagc tatattgtcg    540
catgactttg gaactctaag ggccgcacg tccttgatga tggccgcctt tgactctatc    600
cacacagtca agccttcccc ctttataagg cttattcact ttctgtcacc gatactctat    660
gccctgttta aagttaccct catgagcgtc agagaagaga agctcgcaca atcagtagca    720
cacttgaata ggcttacaac taacagcctg aacaaggcat gtaaggaacc ggaagatact    780
gtcaacgaat cagtccttgg gattctggtc aagtcagaaa acgcaaatcc caacagccgt    840
ttgtcactct ccgagatcac ggcccaggcc gtacgtacct ttgccactcc tctgatattc    900
tctcaatggt ctctcattga acttgcacgc cggccagaaa tccaagagag cctccgtgct    960
gagctctcag aatgtttggc aaagggagaa cgtcctacat acgaccagct aacaaaggat   1020
ctgaaatacc tcgatgcttt tatagccgag atactgagac tccatgcccc cgaaatgcaa   1080
tcaatccgtg tggcagccga agacgatgtg ataccgttga caaatcccat acgtattgca   1140
tctggagcga cgatcgatag cttgtttttg aagaaaggta tggtcgtccg tataccettg   1200 gggggagtga atatgtcgga agcgttgtgg gggccagacg cgggcatgtt cgatccaagc   1260
agatggctgg acgctgaggg tcataagaaa ggaaacaagg gagaactagc tggctaccgg   1320
ggtctcttaa ctttcggtgc tggtcccagg atgtgtccag gcagagacct cgccgtactg   1380
gaggtgaagg ctgtgctgtc ggttctggtc agatattttg cctttgagct ccccaatggg   1440
ccatcgacgg aactgagttg gcattttacg cgccccaagg tagctggcga ggatggtaca   1500
aaagttcctc ttcttgtgcg aaaggtagaa aacatggtgg tggtgctcgc ctacttgata   1560
agcagactcg tgcgaaacac catgtcaatc gatgacgggc ataagagacc acgacattgg   1620
ggcgatgaag tcggtggtga ctcatacgag tcgtattgta aatttttgct tgggaagtca   1680
tggcatgtcg caacagttgg ccccactgat gtcattcaac caaccgacat ctcgaggctt   1740
gcgctaaagt ctcccgccat taacgccgcg ttccaatgct gcgtcatccg cagtgcctgc   1800
accgtcagaa cgcatttagt agtggcaaga agcttctgtc aaattcaatc gctaaccggt   1860
tctttgacgg gctag                                                    1875

<210> SEQ ID NO 601
<211> LENGTH: 624
<212> TYPE: PRT
<213> ORGANISM: Galerina marginata
<400> SEQUENCE: 601

Met Leu Asn Leu Asn Phe Asn Gly Leu Trp Pro Asp Val Ala Glu Tyr
1               5                   10                  15

Phe Lys Gly Asp Ser Met Arg Ile Val Thr Ser Ala Phe Thr Leu Leu
            20                  25                  30

Val Val Ile Ser Ile Tyr Arg Arg Arg Arg Gly Ile Arg Thr Pro Arg
        35                  40                  45

Leu Gln Gly Pro Arg Ser Glu Ser Phe Ile Phe Gly Asn Thr Lys Lys
    50                  55                  60

```
Ile Phe Pro Ser Ala Asn Leu Ser Val Val Tyr Arg Asp Trp Glu Arg
 65                  70                  75                  80

Met Tyr Gly Pro Val Tyr Glu Ile Pro Thr Gly Ile Gly Ser Ser His
                 85                  90                  95

Val Val Leu Ser Asp Pro Lys Ala Leu Thr His Ile Tyr Ser Lys Asp
                100                 105                 110

Thr Thr Thr Tyr Cys Arg Leu Ala Gly Thr Thr Ala Leu Ser Arg Lys
                115                 120                 125

Leu Ala Ser Ile Cys Phe Ala Pro Phe Phe Leu Ala Ala Ser Leu Ile
130                 135                 140

Tyr Val Pro Thr Thr Glu Arg Pro Val Phe Ser Thr Val Gly Leu Ser
145                 150                 155                 160

Asn Ser Gln Ser His Ser Arg Val Leu Gly Phe Cys Leu Ser Gly Lys
                165                 170                 175

Ala Ile Leu Ser His Asp Phe Gly Thr Leu Arg Gly Arg Thr Ser Leu
                180                 185                 190

Met Met Ala Ala Phe Asp Ser Ile His Thr Val Lys Pro Ser Pro Phe
                195                 200                 205

Ile Arg Leu Ile His Phe Leu Ser Pro Ile Leu Tyr Ala Leu Phe Lys
                210                 215                 220

Val Thr Leu Met Ser Val Arg Glu Glu Lys Leu Ala Gln Ser Val Ala
225                 230                 235                 240

His Leu Asn Arg Leu Thr Thr Asn Ser Leu Asn Lys Ala Cys Lys Glu
                245                 250                 255

Pro Glu Asp Thr Val Asn Glu Ser Val Leu Gly Ile Leu Val Lys Ser
                260                 265                 270

Glu Asn Ala Asn Pro Asn Ser Arg Leu Ser Leu Ser Glu Ile Thr Ala
                275                 280                 285

Gln Ala Val Arg Thr Phe Ala Thr Pro Leu Ile Phe Ser Gln Trp Ser
                290                 295                 300

Leu Ile Glu Leu Ala Arg Arg Pro Glu Ile Gln Glu Ser Leu Arg Ala
305                 310                 315                 320

Glu Leu Ser Glu Cys Leu Ala Lys Gly Glu Arg Pro Thr Tyr Asp Gln
                325                 330                 335

Leu Thr Lys Asp Leu Lys Tyr Leu Asp Ala Phe Ile Ala Glu Ile Leu
                340                 345                 350

Arg Leu His Ala Pro Glu Met Gln Ser Ile Arg Val Ala Ala Glu Asp
                355                 360                 365

Asp Val Ile Pro Leu Thr Asn Pro Ile Arg Ile Ala Ser Gly Ala Thr
                370                 375                 380

Ile Asp Ser Leu Phe Leu Lys Lys Gly Met Val Val Arg Ile Pro Leu
385                 390                 395                 400

Gly Gly Val Asn Met Ser Glu Ala Leu Trp Gly Pro Asp Ala Gly Met
                405                 410                 415

Phe Asp Pro Ser Arg Trp Leu Asp Ala Glu Gly His Lys Lys Gly Asn
                420                 425                 430

Lys Gly Glu Leu Ala Gly Tyr Arg Gly Leu Leu Thr Phe Gly Ala Gly
                435                 440                 445

Pro Arg Met Cys Pro Gly Arg Asp Leu Ala Val Leu Glu Val Lys Ala
                450                 455                 460

Val Leu Ser Val Leu Val Arg Tyr Phe Ala Phe Glu Leu Pro Asn Gly
465                 470                 475                 480
```

```
Pro Ser Thr Glu Leu Ser Trp His Phe Thr Arg Pro Lys Val Ala Gly
            485                 490                 495

Glu Asp Gly Thr Lys Val Pro Leu Leu Val Arg Lys Val Glu Asn Met
        500                 505                 510

Val Val Val Leu Ala Tyr Leu Ile Ser Arg Leu Val Arg Asn Thr Met
        515                 520                 525

Ser Ile Asp Asp Gly His Lys Arg Pro Arg His Trp Gly Asp Glu Val
    530                 535                 540

Gly Gly Asp Ser Tyr Glu Ser Tyr Cys Lys Phe Leu Leu Gly Lys Ser
545                 550                 555                 560

Trp His Val Ala Thr Val Gly Pro Thr Asp Val Ile Gln Pro Thr Asp
            565                 570                 575

Ile Ser Arg Leu Ala Leu Lys Ser Pro Ala Ile Asn Ala Ala Phe Gln
            580                 585                 590

Cys Cys Val Ile Arg Ser Ala Cys Thr Val Arg Thr His Leu Val Val
            595                 600                 605

Ala Arg Ser Phe Cys Gln Ile Gln Ser Leu Thr Gly Ser Leu Thr Gly
        610                 615                 620

<210> SEQ ID NO 602
<211> LENGTH: 405
<212> TYPE: DNA
<213> ORGANISM: Galerina marginata

<400> SEQUENCE: 602
atgagaaata caaaaacttt gaaggcctta cttccgatgc aggctcaacg ctccaagcct      60
aacattgtca acaacttgcg tcgtccacta ctacatcgaa tggatgagac atttagcaaa    120
ggctggtaca cgacacataa gtacattgct acattattaa atggaatttt gagctcacct    180
ctcaccacga gtgaggagac ggttgacgtc gtcaccgacg catgggcagt ctacaagcca    240
agcaggaaga cgggtggcat tgatagtaga ggtcttgggt tcgagttcga atgggagtca    300
cgaattcgca agattggaaa accgcagaaa gggcgttcgg tttctgcgga cattcagccg    360
ggcaagacgg tgcaatacaa tggcaaccccc gtcaaaagtt gttga              405

<210> SEQ ID NO 603
<211> LENGTH: 134
<212> TYPE: PRT
<213> ORGANISM: Galerina marginata

<400> SEQUENCE: 603

Met Arg Asn Asn Lys Asn Leu Lys Ala Leu Leu Pro Met Gln Ala Gln
1               5                   10                  15

Arg Ser Lys Pro Asn Ile Val Asn Asn Leu Arg Arg Pro Leu Leu His
            20                  25                  30

Arg Met Asp Glu Thr Phe Ser Lys Gly Trp Tyr Thr Thr His Lys Tyr
        35                  40                  45

Ile Ala Thr Leu Leu Asn Gly Ile Leu Ser Ser Pro Leu Thr Thr Ser
    50                  55                  60

Glu Glu Thr Val Asp Val Val Thr Asp Ala Trp Ala Val Tyr Lys Pro
65                  70                  75                  80

Ser Arg Lys Thr Gly Gly Ile Asp Ser Arg Gly Leu Gly Phe Glu Phe
            85                  90                  95

Glu Trp Glu Ser Arg Ile Arg Lys Ile Gly Lys Pro Gln Lys Gly Arg
            100                 105                 110

Ser Val Ser Ala Asp Ile Gln Pro Gly Lys Thr Val Gln Tyr Asn Gly
```

```
                 115                 120                 125

Asn Pro Val Lys Ser Cys
    130

<210> SEQ ID NO 604
<211> LENGTH: 1689
<212> TYPE: DNA
<213> ORGANISM: Galerina marginata

<400> SEQUENCE: 604
atgcgatcgc attctctcaa gggccgttca ttaaagttgg ctaaagtcgc gggggaaggg     60
ctggtgatga ggtatcttgt gtcgacgcgg gcacaatgga ccatgggagg cagtcgccgc    120
atatctgaaa agctgggctc ccgacgtgaa gtgaggaatc acgaaaatca tatttgcttg    180
gaaggaaagc ccatgcagct cagcaaactc tacctgaaac ctgccctgtc aaggacatgc    240
ggccgcaacc gcgactggtt gatggtaaat ccaaatgcga cgcccagttc gaaagatgag    300
acatacctgc gccaaacagt gattaccaca gccacctacg aggcctccgt ggccagtcgc    360
gcctcgggat ttaccggcgc gatacaaacg gaaagttctt tcgcagcgtt cccacccgcg    420
cggccccttt ggccttatgt cgcggagtac ctcaaagtca attcgatgag gataatagcc    480
tctggcatat ccttgctcgt cgttgtttcc atttaccgaa gccgtcgagg tcctagaacg    540
ccgagactgc aaggaccaca catggagagc ttcatcctcg gcaatgctag gaagatcttc    600
ccttcagcca acctcagttt ggtgtatcaa ggtttggagc agacttacgg gcccgtctat    660
gaaatagcct ctggctttgg ctccaaccac gtcgtattga acgatcccaa ggctctcaca    720
cacttatttt ccaaggacac tgtcacatat tctcagcctg ctaggcagaa agacatgggg    780
cggaagttga atacggaggg tcttgtcttc tcccctgtcg gtctcggcaa tccgcaattt    840
cactcctatg tgtttggatt ccgcctatca ggtcaggacg gttccagctt tgagacatca    900
tgggattcat gtttccagtt gtcaaacaat tcgaaccgtg ctatcgtgct tgatgcagag    960
aaatgcatgg ataatattgg aaaagctgta ttgtcgtatg acttcggcaa catgaggggc   1020
catacgtgtt cgatcttagc tgacttggat gctttccacg cagtcagccc ttcaggcctt   1080
tacataaggt ttattgtgtt tacccgcgag atactttata acctcttcaa gattaccttc   1140
ccgaatgcca agaaaaagca gtttgaggaa ctggcagcgc actttaaagt actcgcgact   1200
ggctttctgc gggaagcacg tgaggcgcct gaagatagcg ccgttcacca atcaatcctt   1260
ggggttatgc tcaagtccaa aaatgaaaat gctaacgtcc gtttatcact tcccgagatc   1320
acggcccagg ctggtggtct tgtcttggcc gggtatgaaa ctacggcaaa gatccatcgc   1380
cgagctttcc ctcagtggtc cctcattgag cttgctcgcc gggcagaaat tcaagagact   1440
ctccgtgccg aactcaagga gtgcttggca gacggagaac gccctacata cgaccagctg   1500
acaaaggatc tgaaatacct cgatgctttt atatccgaga tactgaggtt acatccctca   1560
gaaatggtac taacccgcgt ggcagccgaa gacgatgtga taccgctgac ggatcccata   1620
cgaactgcat ctggagcgat gatcgacagc ttgttcgtga ggaaaggcac cgtctccgca   1680
tcccttttag                                                           1689

<210> SEQ ID NO 605
<211> LENGTH: 562
<212> TYPE: PRT
<213> ORGANISM: Galerina marginata

<400> SEQUENCE: 605
```

-continued

```
Met Arg Ser His Ser Leu Lys Gly Arg Ser Leu Lys Leu Ala Lys Val
 1               5                  10                  15

Ala Gly Glu Gly Leu Val Met Arg Tyr Leu Val Ser Thr Arg Ala Gln
             20                  25                  30

Trp Thr Met Gly Gly Ser Arg Arg Ile Ser Glu Lys Leu Gly Ser Arg
         35                  40                  45

Arg Glu Val Arg Asn His Glu Asn His Ile Cys Leu Glu Gly Lys Pro
     50                  55                  60

Met Gln Leu Ser Lys Leu Tyr Leu Lys Pro Ala Leu Ser Arg Thr Cys
65                  70                  75                  80

Gly Arg Asn Arg Asp Trp Leu Met Val Asn Pro Asn Ala Thr Pro Ser
                 85                  90                  95

Ser Lys Asp Glu Thr Tyr Leu Arg Gln Thr Val Ile Thr Thr Ala Thr
             100                 105                 110

Tyr Glu Ala Ser Val Ala Ser Arg Ala Ser Gly Phe Thr Gly Ala Ile
         115                 120                 125

Gln Thr Glu Ser Ser Phe Ala Ala Phe Pro Pro Ala Arg Pro Leu Trp
     130                 135                 140

Pro Tyr Val Ala Glu Tyr Leu Lys Val Asn Ser Met Arg Ile Ile Ala
145                 150                 155                 160

Ser Gly Ile Ser Leu Leu Val Val Ser Ile Tyr Arg Ser Arg Arg
                 165                 170                 175

Gly Pro Arg Thr Pro Arg Leu Gln Gly Pro His Met Glu Ser Phe Ile
                 180                 185                 190

Leu Gly Asn Ala Arg Lys Ile Phe Pro Ser Ala Asn Leu Ser Leu Val
                 195                 200                 205

Tyr Gln Gly Leu Glu Gln Thr Tyr Gly Pro Val Tyr Glu Ile Ala Ser
     210                 215                 220

Gly Phe Gly Ser Asn His Val Val Leu Asn Asp Pro Lys Ala Leu Thr
225                 230                 235                 240

His Leu Phe Ser Lys Asp Thr Val Thr Tyr Ser Gln Pro Ala Arg Gln
                 245                 250                 255

Lys Asp Met Gly Arg Lys Leu Asn Thr Glu Gly Leu Val Phe Ser Pro
                 260                 265                 270

Val Gly Leu Gly Asn Pro Gln Phe His Ser Tyr Val Phe Gly Phe Arg
         275                 280                 285

Leu Ser Gly Gln Asp Gly Ser Ser Phe Glu Thr Ser Trp Asp Ser Cys
     290                 295                 300

Phe Gln Leu Ser Asn Asn Ser Asn Arg Ala Ile Val Leu Asp Ala Glu
305                 310                 315                 320

Lys Cys Met Asp Asn Ile Gly Lys Ala Val Leu Ser Tyr Asp Phe Gly
             325                 330                 335

Asn Met Arg Gly His Thr Cys Ser Ile Leu Ala Asp Leu Asp Ala Phe
             340                 345                 350

His Ala Val Ser Pro Ser Gly Leu Tyr Ile Arg Phe Ile Val Phe Thr
         355                 360                 365

Arg Glu Ile Leu Tyr Asn Leu Phe Lys Ile Thr Leu Pro Asn Ala Lys
     370                 375                 380

Glu Lys Gln Phe Glu Leu Ala Ala His Phe Lys Val Leu Ala Thr
385                 390                 395                 400

Gly Phe Leu Arg Glu Ala Arg Glu Ala Pro Glu Asp Ser Ala Val His
                 405                 410                 415

Gln Ser Ile Leu Gly Val Met Leu Lys Ser Lys Asn Glu Asn Ala Asn
```

```
            420             425             430
Val Arg Leu Ser Leu Pro Glu Ile Thr Ala Gln Ala Gly Gly Leu Val
            435             440             445

Leu Ala Gly Tyr Glu Thr Thr Ala Lys Ile His Arg Arg Ala Phe Pro
            450             455             460

Gln Trp Ser Leu Ile Glu Leu Ala Arg Arg Ala Glu Ile Gln Glu Thr
465             470             475             480

Leu Arg Ala Glu Leu Lys Glu Cys Leu Ala Asp Gly Glu Arg Pro Thr
            485             490             495

Tyr Asp Gln Leu Thr Lys Asp Leu Lys Tyr Leu Asp Ala Phe Ile Ser
            500             505             510

Glu Ile Leu Arg Leu His Pro Ser Glu Met Val Leu Thr Arg Val Ala
            515             520             525

Ala Glu Asp Asp Val Ile Pro Leu Thr Asp Pro Ile Arg Thr Ala Ser
530             535             540

Gly Ala Met Ile Asp Ser Leu Phe Val Arg Lys Gly Thr Val Ser Ala
545             550             555             560

Ser Leu

<210> SEQ ID NO 606
<211> LENGTH: 105
<212> TYPE: DNA
<213> ORGANISM: Galerina marginata

<400> SEQUENCE: 606
atgtctgaca tcaatgccac ccgtcttccc gcttggcttg tagattgccc atgcgtcggt      60
gacgatgtca accgtctcct cactcgtggc gagagccttt gctaa                    105

<210> SEQ ID NO 607
<211> LENGTH: 34
<212> TYPE: PRT
<213> ORGANISM: Galerina marginata

<400> SEQUENCE: 607

Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Gly Glu Ser
            20                  25                  30

Leu Cys

<210> SEQ ID NO 608
<211> LENGTH: 105
<212> TYPE: DNA
<213> ORGANISM: Galerina marginata

<400> SEQUENCE: 608
ttagcaaagg ctctcgccac gagtgaggag acggttgaca tcgtcaccga cgcatgggca      60
atctacaagc caagcgggaa gacgggtggc attgatgtca gacat                    105

<210> SEQ ID NO 609
<211> LENGTH: 258
<212> TYPE: DNA
<213> ORGANISM: Galerina marginata

<400> SEQUENCE: 609
atggtgcaaa acaaagactc gccaacctgg ctcaaagcgg ttgtccctgc gagccgagga      60
tatgtggtgg tatcctcgga atatatgtgt gtgagccttg ggatcgctca atacaacatg    120
```

```
gctgtagccg atgccagtgg gtatctcgta aggcccatac attcgttccc aatcccgata    180
taccaccgta ctgaggttcg cggaagggaa gatcttggtg ttactgaatc tgaagctctc    240
gctgcgtggt ccttgtag                                                  258
```

<210> SEQ ID NO 610
<211> LENGTH: 85
<212> TYPE: PRT
<213> ORGANISM: Galerina marginata

<400> SEQUENCE: 610

| Met | Val | Gln | Asn | Lys | Asp | Ser | Pro | Thr | Trp | Leu | Lys | Ala | Val | Val | Pro |
|---|---|---|---|---|---|---|---|---|---|---|---|---|---|---|---|
| 1 | | | | 5 | | | | | 10 | | | | | 15 | |
| Ala | Ser | Arg | Gly | Tyr | Val | Val | Ser | Ser | Glu | Tyr | Met | Cys | Val | Ser | |
| | | | 20 | | | | 25 | | | | | 30 | | | |
| Leu | Gly | Ile | Ala | Gln | Tyr | Asn | Met | Ala | Val | Ala | Asp | Ala | Ser | Gly | Tyr |
| | | | 35 | | | | 40 | | | | 45 | | | | |
| Leu | Val | Arg | Pro | Ile | His | Ser | Phe | Pro | Ile | Pro | Ile | Tyr | His | Arg | Thr |
| | 50 | | | | | 55 | | | | | 60 | | | | |
| Glu | Val | Arg | Gly | Arg | Glu | Asp | Leu | Gly | Val | Thr | Glu | Ser | Glu | Ala | Leu |
| 65 | | | | | 70 | | | | | 75 | | | | | 80 |
| Ala | Ala | Trp | Ser | Leu | | | | | | | | | | | |
| | | | | 85 | | | | | | | | | | | |

<210> SEQ ID NO 611
<211> LENGTH: 582
<212> TYPE: PRT
<213> ORGANISM: Cryptococcus

<400> SEQUENCE: 611

| Met | Thr | Met | Glu | Leu | Leu | Lys | Val | Leu | His | His | Glu | Ala | Ser | Gln | Leu |
|---|---|---|---|---|---|---|---|---|---|---|---|---|---|---|---|
| 1 | | | | 5 | | | | | 10 | | | | | 15 | |
| Phe | Pro | Asn | Cys | Ile | Arg | Ser | Ser | Pro | Val | Ala | Cys | Ile | Val | Leu | Tyr |
| | | | 20 | | | | 25 | | | | | 30 | | | |
| Ser | Phe | Gly | Gly | Ile | Ala | Ile | Leu | Leu | Phe | Ser | Val | Tyr | Leu | Trp | Leu |
| | | | 35 | | | | 40 | | | | | 45 | | | |
| Trp | Pro | Phe | Gln | Tyr | Ala | Lys | Leu | Tyr | Phe | Arg | Asn | Leu | Pro | Gly | Pro |
| | 50 | | | | | 55 | | | | | 60 | | | | |
| Pro | Ser | Asp | Ser | Trp | Phe | Trp | Gly | Val | Val | Pro | Thr | Leu | Ile | Lys | Ser |
| 65 | | | | | 70 | | | | | 75 | | | | | 80 |
| Pro | Pro | Ser | Val | Pro | His | Ser | Met | Trp | Thr | Asp | Glu | Tyr | Gly | Pro | Thr |
| | | | | 85 | | | | | 90 | | | | | 95 | |
| Val | Arg | Tyr | Arg | Val | Ala | Leu | Gly | Ala | Gln | Arg | Phe | Leu | Thr | Ile | Asp |
| | | | 100 | | | | | 105 | | | | | 110 | | |
| Pro | Thr | Ala | Leu | Asn | Tyr | Ile | Leu | Ser | His | Ala | Asp | Leu | Phe | Pro | Lys |
| | | | 115 | | | | | 120 | | | | | 125 | | |
| Pro | Ser | Arg | Val | Arg | Lys | Ala | Leu | Ser | Asp | Leu | Leu | Gly | Asn | Gly | Leu |
| | | 130 | | | | | 135 | | | | | 140 | | | |
| Leu | Thr | Ala | Glu | Gly | His | Thr | His | Lys | Lys | Gln | Arg | Lys | Ala | Leu | Asn |
| 145 | | | | | 150 | | | | | 155 | | | | | 160 |
| Pro | Ser | Phe | Ser | Pro | Ala | Ala | Val | Arg | Gly | Met | Ile | Pro | Val | Phe | Tyr |
| | | | | 165 | | | | | 170 | | | | | 175 | |
| Asp | Lys | Ala | Tyr | Glu | Leu | Lys | Ala | Lys | Leu | Leu | Gly | Ile | Ile | Glu | Gly |
| | | | 180 | | | | | 185 | | | | | 190 | | |
| Asp | Glu | Thr | Glu | Gln | Ala | Ser | Pro | Thr | Pro | Cys | Lys | Glu | Glu | Asp | Glu |
| | | | 195 | | | | | 200 | | | | | 205 | | |

```
Val Glu Gly Gly Lys Lys Ile Asp Val Met Lys Tyr Leu Gly Lys Thr
    210                 215                 220
Thr Leu Asp Val Ile Gly Ile Val Gly Phe Ser Tyr Asp Phe Lys Ala
225                 230                 235                 240
Leu Ser Glu Pro Arg Asn Glu Leu Ser Glu Ala Tyr Ser Lys Met Phe
                245                 250                 255
Gln Ala Gly Met Asp Ala Asn Phe Trp Asp Phe Leu Arg Gly Ala Ile
            260                 265                 270
Pro Leu Val Asn Lys Leu Pro Asn Lys Arg Ala Thr Glu Ile Ala Ala
        275                 280                 285
Arg Lys Ala Val Thr Leu Arg Ile Ser Lys Lys Ile Val Glu Asp Lys
    290                 295                 300
Lys Arg Glu Val Met Ser Ala His Ser Glu Gly Leu Glu Lys Arg Glu
305                 310                 315                 320
Asp Ile Gly Asp Asp Leu Leu Ser Ile Leu Ile Lys Ala Asn Met Ala
                325                 330                 335
Ser Asp Val Lys Pro Glu Gln Lys Leu Ser Asp Glu Val Leu Asp
            340                 345                 350
Gln Ile Thr Thr Phe Met Leu Ala Gly Asn Glu Thr Ser Ser Thr Ala
        355                 360                 365
Leu Thr Trp Ile Leu Tyr Ser Leu Thr Gln His Pro Glu Cys Gln Thr
    370                 375                 380
Arg Leu Arg Glu Glu Val Leu Ala Val Pro Asp Asp Arg Pro Ser Leu
385                 390                 395                 400
Glu Thr Leu Asn Asn Leu Pro Tyr Met Asp Ala Val Ile Arg Glu Ala
                405                 410                 415
Leu Arg Leu His Ala Pro Ala Pro Gly Thr Met Arg Glu Ala Lys Glu
            420                 425                 430
Asp Thr Val Ile Pro Leu Ser Met Pro Val Ile Gly Arg Asp Gly Lys
        435                 440                 445
Gln Ile Asp Ser Val Lys Ile Asn Lys Gly Thr Met Val Phe Ile Pro
    450                 455                 460
Ile Ile Thr Val Asn Thr Ser Pro Ala Ile Trp Gly Pro Asp Ala Arg
465                 470                 475                 480
Val Phe Asn Pro Asp Arg His Leu Lys Thr Ser Ser Asp Ser Phe Gly
                485                 490                 495
Gly Ala Asn Met His Val Pro Gly Val Trp Gly Asn Met Leu Ser Phe
            500                 505                 510
Leu Gly Gly Ala Arg Asn Cys Ile Gly Tyr Lys Leu Ala Leu Ala Glu
        515                 520                 525
Ile Ser Thr Ile Leu Phe Val Leu Ile Arg Ser Phe Glu Phe Gln Glu
    530                 535                 540
Leu Lys Ser Lys Pro Glu Val Glu Lys Ala Ser Val Val Met Arg
545                 550                 555                 560
Pro Arg Ile Lys Gly Glu Glu Ser Ala Gly Leu Gln Met Pro Leu Met
                565                 570                 575
Val Lys Pro Leu Leu Met
            580

<210> SEQ ID NO 612
<211> LENGTH: 13254
<212> TYPE: DNA
<213> ORGANISM: Amanita bisporigera
```

<400> SEQUENCE: 612

```
gatcatgtta agtttatgcc ctaatcgttg agcgataaag agcgaccaac cccttgtgag        60
tctcgcgctc agaaatagat ataacatcac catactggaa cgacaatgag gctggcagct       120
gaaaaatggt gcaaaacaaa gactcgccaa cctggctcaa agcggttgtc cctgcgagcc       180
gaggatatgt ggtggtatcc tcggaatata tgtgtgtgag ccttgggatc gctcaataca       240
acatggctgt agccgatgcc agtgggtatc tcgtaaggcc catacattcg ttcccaatcc       300
cgatatacca ccgtactgag gttcgcggaa gggaagatct tggtgttact gaatctgaag       360
ctctcgctgc gtggtccttg tagtctgggc gttctgatac ctcggcatct ccgatagata       420
gaaatgacga cgagcaatgt cagaggtcac aatccttatc gaattacctt tgagatactc       480
tgccacatca ggccagaggc cgttggagtt gaggttcaac atcacgggtg acggagtgga       540
cgagccgtta tgcaaggaag gaaggccatc gcggataagt actagtatag caaccaaccc       600
aaccagacgt ggaaatgcca ttgaagggtg ggagttgcgc gaatacgagg aaaacgtttc       660
tgaggagccg aaaccgtaac caggcgcgag aacttgacct atctatctcc gggaacggtg       720
ttggggtcc atgttaccgt gaaggtggat aggggcggat tcgattccag gaaagttaga       780
gccacatagt cataagtgat gcaacacgcc tgtgcgcgat ggagataatg cgtctttgtt       840
gcatcggcaa accgggtcac acggacgaaa atcattacta catggtccat ttcaggacaa       900
aaccccctatc tattgatcct acaaactgct tgactgttca atctgtgacc accgggacag       960
agaaaggctg tgctcagtgg ggtgtttaat ccagcgagaa acgcgttagg cccagtcgcc      1020
gatcaggata cgacgaaaaa gtgtagggtc aagactccct tgatgcgatt caactattct      1080
tgacgggggg ttgccattgt attgcaccgt cttgcccgac tggctgtgcc cgcaaagaca      1140
gaacgtccca aaaacaggaa agaacaaaga agttttgtgg agcctgccaa gaatgtgtga      1200
tgaacagtga ctgacagcat gaatggggga tgaatattga ataccgaaaa aggatgatca      1260
gacaactgtt tatggagatt ttgcgccaac tcgtcttcat ctccgtgtca ggacaagatt      1320
ctcttatcta tcgtcctttc cgcggttttt gcaaccatgc gaattcgtga ctgagacaga      1380
taaaaggcgt tggattcagc ttagcattca atattcaata cttacctccc attcgaactc      1440
gagcccaaga cctctgctct aaatcacaat gtctgacatc aatgccaccc gtcttcccgc      1500
ttggcttgta gattgcccat gcgtcggtga cgatgtcaac cgtctcctca ctcgtggcga      1560
gaggtgagct caaaattcca tttaataatg tagcaatgga ctcatgtgtc gtgtatcagc      1620
ctttgctaaa tgtctcatcc actagtcaag gtacccgcct cggatttcat gataacgaag      1680
ggtgattgtg ctgactatga cgaaggcaaa ttgtagaaca cgtcttgctt gcaaagcgat      1740
gatcgtgccg ctgaaccagc gtcttaaaga ttgtcgtgat aatcatcggg gacacttggc      1800
taacacgact gaagtacatt acccttctta ctgattctcc tttgtcaatc tctaataccc      1860
ccctcaatga tgctctgagc tgtgcaatgc aatgcactag agaaggggggg ggaggtgtga      1920
gagatagcat ctcaacattt atcaatgcca gcttgtatgc cgcgatccac agcagaccga      1980
cctgaccgac cgtgtcattg ctacttgcct acttgaacat atcacataca acattggcag      2040
cttttgtacc gttaagagt cctgcggcgt gtagcctgga agaatttcca gcaggggtcc      2100
ttcctgatga gtttgacagc tcgcatagtt gtaaaagcgg caagtccaca aaaacagcga      2160
ttttatgtta cattgcgtga cgaggaggta atgagagcat gagacgagca ttttgcaacc      2220
ttgaactggg ccgagcacct gagagaaaga tgcaacgccg atgaggaaga atcatggtga      2280
tgatgtatgt ataggcatgc gatggcatgt gctggcgacg attgggaaga ggcggaaggg      2340
```

```
tcgcttgggg cgggaaaaca ctgcaggctg caggcgtgct cgaggagaga tagacacgct    2400
acgtgattac tacgccagcc ctctcaggct gtaatgatcg ttcatcaaag ttggttagag    2460
tgggctggtg atgatgcatc ttgtgtcggt gcgtggcacg atggactatg ggaggcaagt    2520
ttggcgtact agtaggtcta taaggatgat gtgaaatatg tgggtatgcc agtcatccaa    2580
cctaccattt acgtcacgat gctaagcctc atcgccacac atctgaaaag ctggtcctcc    2640
acgtgaagtg aggaatcatg aaagtcattt ttgcttggaa ggaaagccca tgcgactcag    2700
taaactctac taagacacga aacgaacgat gttgcacatg agatcctatg tcagtctcgc    2760
acagcatagg cactttcgga ccatcctcgc cggctacctt gggccgcccg aactgccaac    2820
tcagttccgt cgatggtcca ttggggaact caaaactgaa atggaggacc agaatcacaa    2880
gcgcagcctg gcaattgtca agtcaaaaat gaataaaaac cggcaggagt ttcgccatac    2940
cttcatctcc agcaaggcga ggtctcttcc cggacacagc ctttggccag caccgaaagt    3000
caatagattt cggtagccgg gtactttctc ccttcttcct ttcttatgac catcaacttc    3060
cagccacctg cttggatcga atgtcgccgc atccggtccc cacaacgtct ctgatatatt    3120
cattcctcct aaagggatgc ggagacggtg cctttcctca cgaacaagct gtcgatcatc    3180
gctccagatg cagttcgtat gggatccgtc agcggtatca catcgtcttc ggctgcctag    3240
tcgaaaagat cgtcatcata aaaagatagg gatgaaagga agggacgaac cacgcgggtt    3300
agtaccattt ctgagggatg taacctcagt atctcggata taaaagcatc gaggtatttc    3360
agatcctttg tcagctggtc gtatgtaggg cgttctccgt ctgccaagca ctccttgagt    3420
tcggcacgga gagtctcttg aatttctgcc cggcgagcaa gctcaatgag ggaccactga    3480
gggaaagctc ggcgatggat ctcttgtaga taaataacat taccgtcatg gcaactgtga    3540
acagcatagt tagtggatta tgagatcatc ggactgctag tcatagaact tacttgccgt    3600
agtttcatac ccggccaaga caagaccacc cttcggttat atcaggtcag agtggataca    3660
aaagagattg catagggaca tacagcctac aaaggatgtt gatcgagcac cgacgccgat    3720
gtgtgaagca acttacctgg gccgtgatct cgggaagtga taaacggacg ttagcatttt    3780 cattttttgga cttgactata tataggaaag ctgaaatctc cttacacgtg gtcaggatag    3840
aggtaacata cgcataaccc caaggattga ttggtgaacg cgctatctt caggcgcctc    3900 acgtgcttcc cgcagaaagc cagtcgcgag tactttaaag tgcgctgcca gttcctcaaa    3960
ctgcttttct ttggcattcg gtaaggtaat cttgaagagg ttataaagta tctcgcgggt    4020
aaacacaata aacctatgt aaaggcctga agggctgact gcgtggaaag catccaagtc    4080
agctaagatc gaacacgtat ggcccctcat gttgccgaag tcatacgaca atacagcttt    4140
tccaatatta tccatgctag gaatatattg caggtgagaa gaatggggca gagtaaaggt    4200
tgcgagtcat acgtgtaaca gttcatcctt gggcacataa tgaaccaatt aaatgaaggc    4260
tagaaggaaa gcaactcacc atttctctgc atcaagcacg atagcacggt tcgaattgtt    4320
tgacaactgg aaacatgaat cccatgatgc tttgagctat catttgtgct gttcaatcga    4380
ctgactctca aagctggaac cgtcctgacc tgataggcgg aatccaaaca cataggagtg    4440
aaattgcgga ttgccgagac cgacagggga gaagacaaga ccctccgtat tctataatcc    4500
gttcaatatt aaatttatgc catgttttca agcagtcaag agcgaccaac ctcttgtggg    4560
tctccccttc cgtgagcacc aaaatatcac caaactggaa caagttaagt ctgacagctc    4620
gggaaaacgc tggaacaaac gctcaccaac ttccgcccca tgtctttctg cctagcaggc    4680
```

```
tgagaatatg tgacagtgtc cttggaaaat aagtgtgtga gagccttggg atcgttcaat    4740
acgacgtggt tggagccaaa gccagaggct atttcataga cgggcccgta agtctgctcc    4800
aaaccttgat acaccaaact gaggttggct gaagggaaga tcttcctagc attgccgagg    4860
atgaagctct ccatgtgtgg tccttgcagt ctcggcgttc taggacctcg acggcttcgg    4920
taaatggaaa caacgacgag caaggatatg ccagaggcta ttatcctcat cgaattgact    4980
ttgaggtact ccgcgacata aggccaaagg ctgctgaaat tgaggttcaa catcgcgaag    5040
agagcgatcg cgggccgtta cagaggtgag accaccagta ggccatccag atatggatac    5100
gactcaagat agaaaatggg gtcctcacca aaaaaggatg ccaaactggc gagtctccaa    5160
gtcatttcca tcaagggcgg acagcctcag cgggatttac tattggccca actggatatg    5220
gatagtgtgg ggtgaatagt ataatattgt gaagaagaag atgatgagtg gcggacagca    5280
tgaatgcaag atctgtcgct gaaaaaggat gaaaggtcac tgatgatcta tgatcagatt    5340
gctttcgacg attcggccga agggatcaca ttctattctt gccgacggtt tatttcctat    5400
gggtgacggt ttgcacgctt acggccgcgc gggtgggaac gctgcgaaag aacttccgt    5460 ttgtatcgcg ccggtaaatc ccgaggcgcg actggccacg ctgagccaaa caaatgagcg    5520
tcactgcgga ttcacgcacc ctaactacac gcagaagccc tacttcggtg ctcatctact    5580
gatagctaat gaatattgag gccaactcac gaggcctcgt aggtggctgt ggtaatcact    5640
gtttggcgca ggtatgtctc atctttcgaa ctgggcgtcg catttggatt taccatcaac    5700
cagtcgcggt tgcggccgca tgtccttgac agggcaggtt tcaggctgac ttcataccag    5760
agatctgatg tcgcaaacat cgccagtgat ttcgttccgt tgtcttacta gagttttgctg   5820 agctgcatgg gctttccttc caagcaaata tgattttcgt gattcctcac ttcacgtcgg    5880
gagcccagct tttcagatat gcggcgactg cctcccatgg tccattgtgc ccgcgtcgac    5940
acaagatacc tcatcaccag cccttccccc gcgactttag ccaactttaa tgaacggccc    6000
ttgagagact ggcgtagtaa tcgcgtagcg tgtctatctc tccaatcgtc gcccgtgttc    6060
gcctacacac atgcgatcgc attatgccta catcatcgcc attctctcct cccctcgtc    6120 atcggggttg ctgagcctgc tttttcccgg gtgtagttca agttgcaaa ttgctcgtct    6180 catgctcctc gtcacgcaat gtaacataaa ttcactgttt ttgtgaactt gccgacttcc    6240
acaactatgc gagctatcaa actcatcata aaagacccct tcttttgaaatt cctccaggtt   6300 atacgcccca cggcttttca atggtacaac agctgcctat gtgatatgtg atatgttgct    6360
gacaagtagc aatgataagg acagtcagga cggtcaagct ctggcgacag cagcatgcgc    6420
tcggattgct aaacgctctc ttactgacaa cacacacaca tacacacaca agtatattgc    6480
attccatagt acagctcgga tcatttacgt gggttttata tgagaatgag aaagaatgag    6540
aaataacgtg agtcgtctaa tccaagttgg ctcgctgctt atcacagaaa aacttgaagg    6600
ccttacttcc gatgcaggct caacgctcca agcctaacat tgtcaacaac ttgcgtcgtc    6660
cactactaca tcgaagtaag taccatgacc atgcattgtc atcaagaaat cagaggcgga    6720
taccttgact agtggatgag acatttagca aaggctggta cacgacacat aagtacattg    6780
ctacattatt aaatggaatt ttgagctcac ctctcaccac gagtgaggag acggttgacg    6840
tcgtcaccga cgcatgggca gtctacaagc caagcaggaa gacgggtggc attgatgtca    6900
gacattgtga tttagagtag aggtcttggg ttcgagttcg aatgggaggt aagtaatatt    6960
gacagctgag ccgcatccaa cgccttttat ctgtttcagt cacgaattcg caagattgga    7020
aaaccgcaga aagtacgata gataagagaa tcttgtcctg acacggagat gagaagacaa    7080
```

```
attggcgcaa aatctccata agcgtttgtc tgatcggtct tcccatgaat cattcatgct   7140
gtcccccact ctttatcaca caggctccac gcttactata tggaatccgt gaacttcttt   7200
gtttttaggg gcgttcggtt tctgcggaca ttcagccggg caagacggtg caatacaatg   7260
gcaaccccgt caaaagttgt tgaatcacat caagggagtc ttgaccttaa gcttacactt   7320
ttcatcgtat cctgcgtgtt ggcgatttat gccgaactgg gcataacgcg tttcgaacac   7380
cacttagcac agcctctctt tgtctgtcct ggtggtcaca gattaaacag ttaagtggca   7440
gtcctacaga ccgatagata ggtgttttgt cccaaaatgg acatgtatga gaatgattat   7500
cgggcgtgtg tatttaagaa tcccttcggc cgagttcccg atcattcggc tccatcttgc   7560
gctcacactt gtgttgcatc atacgaacgt tcgtctgtt ctttcccgga atcggatctg    7620
tccctatcca ccttcacggt aagatggacc cccaacaccg tccccggaga tagataggtc   7680
aagcatttat cgcgcctggt tacggtttcg ggtcctcaga aacattttcc tcgcattcgc   7740
gcaacttgat cgccttccac ggctcgtcca cttcgtgatg ttgaacctca acttcaacgg   7800
cctctggcct gatgtagcag agtatttcaa aggcgattcg atgaggattg tgacctctgc   7860
ctttacgttg ctcgtcgtca tttctatcta tcgaagacgc cgaggtatca gaacgcccag   7920
actgcaagga ccacgcagcg agagcttcat cttcggtaac accaagaaga tcttcccttc   7980
ggcgaacctc agtgtggtat atcgggattg ggaacgaatg tatgggcccg tttacgagat   8040
acccactggc atcggctcca gccatgttgt attaagcgat cccaaggctc tcacacacat   8100
atattccaag gataccacca catattgtcg gctcgcaggg acaaccgctt tgagccggaa   8160
gttggcgagt atctgttttg caccattttt cttagctgcc agccttattt acgttccagt   8220
atggtgatgt tgtatctatt tctgagggcg agactcacaa gcggtcggtc actctttatc   8280
gctcaacgat cagggcataa acttaacatg atcgcagact acggagaggc ctgtcttctc   8340
cactgtcggt ctcagcaatt cgcaatctca ctcccgtgtg cttggattct gcctatcagg   8400
ttagaatggt tccattctta aaacaatcgg ccgattgacc aacataaatg acagctcaaa   8460
gcagcatggg attcatgttc tccgtcatca gagcactcaa acaacccgt cataattgat    8520
gtcgtgaaat ggcaagttgc tgtatctatc tcccccattg ttagttaacc ttgttctctg   8580
tgcccaagga tgaattctgt cacgtacgtt gcgcagcctt cattccgccc ttgccctgaa   8640
atgttcctag attggacact atagggaaag ctatattgtc gcatgacttt ggaactctaa   8700
ggggccgcac gtccttgatg atggccgcct ttgactctat ccacacagtc aagccttccc   8760
cctttataag gcttattcac tttctgtcac cgatactcta tgccctgttt aaagttaccc   8820
tcatgagcgt cagagaagag aagctcgcac aatcagtagc acacttgaat aggcttacaa   8880
ctaacagcct gaacaaggca tgtaaggaac cggaagatac tgtcaacgaa tcagtccttg   8940
ggattctggg tatgtcacca atatatgagg tgatgtttct tcgtgcctac gcttccctgt   9000
atagtcaagt cagaaaacgc aaatcccaac agccgtttgt cactctccga gatcacggcc   9060
caggtatgta gcccaagtgc acatcggctt gatgcctaat caacatactt tgtaggccgt   9120
acgtaccttt gccactcctc tgatattctc tgtaagttaa tataaccgaa gagtttcctt   9180
ttcatggctg catatgaaac aacagcaagt aagttctgcg aacggttgtc cttgtttatc   9240
aaagatctca taaactatga cccgtgctgc tcatagtcac cttaacggta atcttcgcct   9300
acgagtgttc aagctgttct attactgagc cttcactcag tggtctctca ttgaacttgc   9360
acgccggcca gaaatccaag agagcctccg tgctgagctc tcagaatgtt tggcaaaggg   9420
```

```
agaacgtcct acatacgacc agctaacaaa ggatctgaaa tacctcgatg cttttatagc    9480
cgagatactg agactccatg cccccgaaat gcaatcaatc cgtgtggttc gtcttcattg    9540
tttaattcct tcccgcatcc ccctattatc ttggcaggca gccgaagacg atgtgatacc    9600
gttgacaaat cccatacgta ttgcatctgg agcgacgatc gatagcttgt ttttgaagaa    9660
aggtatggtc gtccgtatac ccttgggggg agtgaatatg tcggaagcgt tgtggggggcc   9720
agacgcgggc atgttcgatc caagcagatg gctggacgct gagggtcata agaaaggaaa    9780
caagggagaa ctagctggct accggggtct cttaactttc ggtgctggtc ccaggatgtg    9840
tccaggcaga gacctcgccg tactggaggt gaaggtacga ttgaacccca tgtcagcggt    9900
ttggttgttt gactgcacaa tctctaggct gtgctgtcgg ttctggtcag atattttgcc    9960
tttgagctcc ccaatgggcc atcgacggaa ctgagttggc attttacgcg ccccaaggta   10020
gctggcgagg atggtacaaa agttcctctt cttgtgcgaa agttaacata ggcgttcccc   10080
gtaccactgt ttttgtacta gggtagaaaa catggtggtg gtgctcgcct acttgataag   10140
cagactcgtg cgaaacacca tgtcaatcga tgacgggcat aagagaccac gacattgggg   10200
cgatgaagtc ggtggtgact catacgagtc gtattgtaaa ttttttgcttg ggaagtcatg   10260
gcatgtcgca acagttggcc ccactgatgt cattcaacca accgacatct cgaggcttgc   10320
gctaaagtct cccgccatta acgccgcgtt ccaatgctgc gtcatccgca gtgcctgcac   10380
cgtcagaacg catttagtag tggcaagaag cttctgtcaa attcaatcgc taaccggttc   10440
tttgacgggc tagaaccctg gttatgaact aaacttcggc ggcagctcgc atgctcaagc   10500
tcttttccat cctccacatt ttactctcat catttctcag ccccgaactc agttcgtaat   10560
tgactgctat gtaatatcat agatgccagt acaaactcca cacagtggtc cctagacctc   10620
taggtataat gaaccacgag gcgcgttaac ttcgagcttt atatggcttg atgagcagcg   10680
ggagctgata acggcccggg tccgtggtca aaatcggtcg gttacttagt ccactttcca   10740
cagaaatttg ctccgctggc acagccaagt caaattcgag ggcacggact agtgtgaaga   10800
gtagagcttt cattcttgtc gttaccagtg tcagcactat atcttcgaaa tgctagagaa   10860
aacttgctca ctcggcgata gcaaatctga atccgataca cgaacgtgga ccaccccaaa   10920
aactgagcaa atggctccag acgcctggga tggtattgac gccttcaggt agacattccc   10980
atcgttctgg tctatcaaaa ctgaatgact caggagccaa cagcgacgtg caatatttac   11040
ctgaagtcta aagcatcttc accccatatc gacttgtcct tgtggatggc agaaatggga   11100
attatgacta cttgccctct tttgatacta taagaccggt gaacgctaaa agaaatatg    11160
ggaacgaccg aatcctcacc taatactgga gaataggttt cctctccggt cggtgatcgg   11220
cttagccaaa ggtaaaatgt cgtccttggc acacaccctc gagtggccta gatgaaggat   11280
acagacgtag cgtctcccta attaccatat ccaaatatga aagtgcattg agctggtccg   11340
tcgttggctg acaggtatcg accgtgagca gctctctacg cagcttagcc tggatttcac   11400
ggttttttgc cagagaaaat aaagcccacg ccattacgtt actaccaatc aaatattcga   11460
gaatagtcct taaacagata aacagactca gacttacatc ggactttcac gtccagcaat   11520
tacaaatgag ataacctcta aataaaaaga tcaggtatac tcgcagtgac aaatacatca   11580
gcctcacgcg ctttgacttc gtcatcggat agacgacggt gctctggcac atcggggac    11640
atattggtgc gaaccaaaag cgataggaga tctcgactgc cggaattgtc attattcgta   11700
cgtacggatc ccttgctctc gttcagaagc cgactcgtaa tccagaaaag ggtctgcttg   11760
atatcgtcta gttgtgtctc tacaggatca ggctagacaa cgcgatgaga actccgttac   11820
```

```
agtgatttgg aatttccata ctatgaacca tagaagtggg atgaatcttc ggagttgcca    11880
acgaatcagg ttcaattgag ataaaattgt agccacacgg ctaaagtcac tttcacgatc    11940
cagggaatca agctcgtaac ggaagccttt ccatcgaatg gcatcggtaa acactaataa    12000
gtatgctggc aacatcagac atacctgttg agctgatgat gtccatcacc accttaccaa    12060
ggcctaccat aatgtctaag cggcaagtac caccttgttt cgagcattca gtagcccaag    12120
agtcttggag ctaggcgaag ttcatcactg gtagcatgga tgagtagtaa aaaccgaccc    12180
gttttgattt ttttacgaag caatctgtga attcgcgaat gcggaccgga ccaaaggcag    12240
gattctggtt gtgattgaga cactgatgga ccacgatttg gaatggatag atagtcacca    12300
aaatcttccg ctgttaaacg taatatatca taatacgaac taggttgagg caacggaagt    12360
acgcacctgc tttttatgtt gatccccttc gacaaaaggg agacctgacg tatggttgga    12420
tcatcgcctc ttaagtatgg taggtgaaaa agcacctgga ccccacaact tgccgatctg    12480
gcggcgagta aacgatggtt tggtgtaaac gtaaccattc gtcaaaatgt ggttcaaggc    12540
ctgcggatcc gtcacatata aatgcgaaag ctaaacttga ttgttatcta tatcagaata    12600
aatggattgg ttcttacacc gagaaatcca tttagtctta tcatcggccc atattgtgaa    12660
tgccaatgat atgtctgtgg taatagtggt taacaatggg tgggtaggtg ggtgattttg    12720
tacttacatc tgtccagagc tgtttgagat taccaagaaa tatattggcg tttgctggac    12780
cggggagatg gcgtattgga gaagtcagct caacataaat tacacgagtg actctgtaaa    12840
gtccatagat agtcaatgca gctgcagata gcttgaggaa ttggaatata agcctgaaag    12900
tgacgagagc tgaatacgag atggtgtgca agtcgaccat tgttattaac ttggtaacgg    12960
gcaaacgttt caaacttgta ggtggatcgg ttaaatctcc gattgaagat gatgctgagt    13020 tcgtaggtt gcactgatgg ttccgattcg tcccttttttt tcggtgagag acacattatc    13080
ttcattactg tatctttttgg atttactagc tccccccctgt caccgtctcc actttccatc    13140
atcgattatc gattctatcc atttctggtt atgctacgct cccatcatgg acatcgccgc    13200
ccttcggctg cgatgtgctg aaaatagtga aacttctctg acttctctcc gatc          13254
```

<210> SEQ ID NO 613
<211> LENGTH: 226
<212> TYPE: PRT
<213> ORGANISM: Galerina marginata

<400> SEQUENCE: 613

```
Ala Pro Thr Arg Leu His Leu Arg Val Arg Thr Arg Phe Ser Tyr Leu
 1               5                  10                  15

Ser Ser Phe Pro Arg Phe Leu Gln Pro Cys Glu Phe Val Thr Glu Thr
            20                  25                  30

Asp Lys Arg Arg Trp Ile Gln Leu Ser Ile Gln Tyr Ser Ile Leu Thr
        35                  40                  45

Ser His Ser Asn Ser Ser Pro Arg Pro Leu Leu Ile Thr Met Ser Asp
    50                  55                  60

Ile Asn Ala Thr Arg Leu Pro Ala Trp Leu Val Asp Cys Pro Cys Val
65                  70                  75                  80

Gly Asp Asp Val Asn Arg Leu Leu Thr Arg Gly Glu Arg Ala Gln Asn
                85                  90                  95

Ser Ile Cys Ser Asn Gly Leu Met Cys Arg Val Ser Ala Phe Ala Lys
            100                 105                 110

Cys Leu Ile His Ser Arg Tyr Pro Pro Arg Ile Ser Arg Arg Val Ile
```

```
        115                 120                 125
Val Leu Thr Met Thr Lys Ala Asn Cys Arg Thr Arg Leu Ala Cys Lys
    130                 135                 140

Ala Met Ile Val Pro Leu Asn Gln Arg Leu Lys Asp Cys Arg Asp Asn
145                 150                 155                 160

His Arg Gly His Leu Ala Asn Thr Thr Glu Val His Tyr Pro Ser Tyr
                165                 170                 175

Phe Ser Phe Val Asn Leu Tyr Pro Pro Gln Cys Ser Glu Leu Cys Asn
            180                 185                 190

Ala Met His Arg Arg Gly Gly Arg Cys Glu Arg His Leu Asn Ile Tyr
        195                 200                 205

Gln Cys Gln Leu Val Cys Arg Asp Pro Gln Gln Thr Asp Leu Thr Asp
210                 215                 220

Arg Val
225

<210> SEQ ID NO 614
<211> LENGTH: 260
<212> TYPE: PRT
<213> ORGANISM: Galerina marginata

<400> SEQUENCE: 614

Leu Cys Asp Lys Glu Trp Gly Thr Ala Met Ile His Gly Lys Thr Asp
  1               5                  10                  15

Gln Thr Asn Ala Tyr Gly Asp Phe Ala Pro Ile Cys Leu Leu Ile Ser
                 20                  25                  30

Val Ser Gly Gln Asp Ser Leu Ile Tyr Arg Thr Phe Cys Gly Phe Pro
             35                  40                  45

Ile Leu Arg Ile Arg Asp Asn Arg Lys Ala Leu Asp Ala Ala Gln Leu
         50                  55                  60

Ser Ile Leu Leu Thr Ser His Ser Asn Ser Asn Pro Arg Pro Leu Leu
 65                  70                  75                  80

Ile Thr Met Ser Asp Ile Asn Ala Thr Arg Leu Pro Ala Trp Leu Val
                 85                  90                  95

Asp Cys Pro Cys Val Gly Asp Asp Val Asn Arg Leu Leu Thr Arg Gly
                100                 105                 110

Glu Arg Ala Gln Asn Ser Ile Cys Ser Asn Val Leu Met Cys Arg Val
            115                 120                 125

Pro Ala Phe Ala Lys Cys Leu Ile His Ser Arg Tyr Pro Pro Leu Ile
        130                 135                 140

Ser Gln Cys Met Val Met Val Leu Thr Ser Met Trp Thr Thr Gln Val
145                 150                 155                 160

Val Asp Asn Val Arg Leu Gly Ala Leu Ser Leu His Arg Lys Gly Leu
                165                 170                 175

Gln Val Phe Leu Ala Ala Ser Gln Leu Gly Leu Asp Asp Ser Arg Tyr
            180                 185                 190

Phe Ser Phe Phe Leu Ile Leu Ile Asn Pro Arg Lys Ser Glu Leu Tyr
        195                 200                 205

Tyr Gly Met Gln Tyr Thr Cys Val Cys Met Cys Val Cys Cys Gln Glu
    210                 215                 220

Ser Val Gln Ser Glu Arg Met Leu Leu Ser Pro Glu Leu Asp Arg Pro
225                 230                 235                 240

Asp Cys Pro Tyr His Cys Tyr Leu Ser Ala Thr Tyr His Ile Ser His
                245                 250                 255
```

Arg Gln Leu Leu
        260

<210> SEQ ID NO 615
<211> LENGTH: 1512
<212> TYPE: DNA
<213> ORGANISM: Galerina marginata

<400> SEQUENCE: 615

| | | | | | |
|---|---|---|---|---|---|
| atgtttgcga | catcagatct | ctggtatgaa | gtcagcctga | aacctgccct | gtcaaggaca | 60 |
| tgcggccgca | accgcgactg | gttgatggta | aatccaaatg | cgacgcccag | ttcgaaagat | 120 |
| gagacatacc | tgcgccaaac | agtgattacc | acagccacct | acgaggcctc | cgtggccagt | 180 |
| cgcgcctcgg | gatttaccgg | cgcgatacaa | acggaaagtt | ctttcgcagc | gttcccaccc | 240 |
| gcgcggcccc | tttggcctta | tgtcgcggag | tacctcaaag | tcaattcgat | gaggataata | 300 |
| gcctctggca | tatccttgct | cgtcgttgtt | tccatttacc | gaagccgtcg | aggtcctaga | 360 |
| acgccgagac | tgcaaggacc | acacatggag | agcttcatcc | tcggcaatgc | taggaagatc | 420 |
| ttcccttcag | ccaacctcag | tttggtgtat | caaggtttgg | agcagactta | cgggcccgtc | 480 |
| tatgaaatag | cctctggctt | tggctccaac | acgtcgtat | tgaacgatcc | caaggctctc | 540 |
| acacacttat | tttccaagga | cactgtcaca | tattctcagc | ctgctaggca | gaaagacatg | 600 |
| gggcggaagt | tgaatacgga | gggtcttgtc | ttctcccctg | tcggtctcgg | caatccgcaa | 660 |
| tttcactcct | atgtgtttgg | attccgccta | tcaggtcagg | acggttccag | ctttgagaca | 720 |
| tcatgggatt | catgtttcca | gttgtcaaac | aattcgaacc | gtgctatcgt | gcttgatgca | 780 |
| gagaaatgca | tggataatat | tggaaaagct | gtattgtcgt | atgacttcgg | caacatgagg | 840 |
| ggccatacgt | gttcgatctt | agctgacttg | gatgctttcc | acgcagtcag | cccttcaggc | 900 |
| ctttacataa | ggtttattgt | gtttacccgc | gagatacttt | ataacctctt | caagattacc | 960 |
| ttaccgaatg | ccaaagaaaa | gcagtttgag | gaactggcag | cgcactttaa | agtactcgcg | 1020 |
| actggctttc | tgcgggaagc | acgtgaggcg | cctgaagata | gcgccgttca | ccaatcaatc | 1080 |
| cttggggtta | tgctcaagtc | caaaaatgaa | aatgctaacg | tccgtttatc | acttcccgag | 1140 |
| atcacggccc | aggctggtgg | tcttgtcttg | gccgggtatg | aaaactacgg | caaagatcca | 1200 |
| cgccgagctt | tccctcagtg | gtccctcatt | gagcttgctc | gccgggcaga | aattcaagag | 1260 |
| actctccgtg | ccgaactcaa | ggagtgcttg | gcagacggaa | acgccctac | atacgaccag | 1320 |
| ctgacaaagg | atctgaaata | cctcgatgct | tttatatccg | agatactgag | gttacatccc | 1380 |
| tcagaaatgg | tactaacccg | cgtggcagcc | gaagacgatg | tgataccgct | gacggatccc | 1440 |
| atacgaactg | catctggagc | gatgatcgac | agcttgttcg | tgaggaaagg | caccgtctcc | 1500 |
| gcatcccttt | ag | | | | | 1512 |

<210> SEQ ID NO 616
<211> LENGTH: 503
<212> TYPE: PRT
<213> ORGANISM: Galerina marginata

<400> SEQUENCE: 616

Met Phe Ala Thr Ser Asp Leu Trp Tyr Glu Val Ser Leu Lys Pro Ala
 1               5                  10                  15

Leu Ser Arg Thr Cys Gly Arg Asn Arg Asp Trp Leu Met Val Asn Pro
            20                  25                  30

Asn Ala Thr Pro Ser Ser Lys Asp Glu Thr Tyr Leu Arg Gln Thr Val
        35                  40                  45

```
Ile Thr Thr Ala Thr Tyr Glu Ala Ser Val Ala Ser Arg Ala Ser Gly
 50                  55                  60
Phe Thr Gly Ala Ile Gln Thr Glu Ser Ser Phe Ala Ala Phe Pro Pro
 65                  70                  75                  80
Ala Arg Pro Leu Trp Pro Tyr Val Ala Glu Tyr Leu Lys Val Asn Ser
                 85                  90                  95
Met Arg Ile Ile Ala Ser Gly Ile Ser Leu Leu Val Val Ser Ile
            100                 105                 110
Tyr Arg Ser Arg Arg Gly Pro Arg Thr Pro Arg Leu Gln Gly Pro His
            115                 120                 125
Met Glu Ser Phe Ile Leu Gly Asn Ala Arg Lys Ile Phe Pro Ser Ala
130                 135                 140
Asn Leu Ser Leu Val Tyr Gln Gly Leu Glu Gln Thr Tyr Gly Pro Val
145                 150                 155                 160
Tyr Glu Ile Ala Ser Gly Phe Gly Ser Asn His Val Val Leu Asn Asp
                165                 170                 175
Pro Lys Ala Leu Thr His Leu Phe Ser Lys Asp Thr Val Thr Tyr Ser
            180                 185                 190
Gln Pro Ala Arg Gln Lys Asp Met Gly Arg Lys Leu Asn Thr Glu Gly
            195                 200                 205
Leu Val Phe Ser Pro Val Gly Leu Gly Asn Pro Gln Phe His Ser Tyr
210                 215                 220
Val Phe Gly Phe Arg Leu Ser Gly Gln Asp Gly Ser Ser Phe Glu Thr
225                 230                 235                 240
Ser Trp Asp Ser Cys Phe Gln Leu Ser Asn Asn Ser Asn Arg Ala Ile
                245                 250                 255
Val Leu Asp Ala Glu Lys Cys Met Asp Asn Ile Gly Lys Ala Val Leu
            260                 265                 270
Ser Tyr Asp Phe Gly Asn Met Arg Gly His Thr Cys Ser Ile Leu Ala
            275                 280                 285
Asp Leu Asp Ala Phe His Ala Val Ser Pro Ser Gly Leu Tyr Ile Arg
            290                 295                 300
Phe Ile Val Phe Thr Arg Glu Ile Leu Tyr Asn Leu Phe Lys Ile Thr
305                 310                 315                 320
Leu Pro Asn Ala Lys Glu Lys Gln Phe Glu Glu Leu Ala Ala His Phe
                325                 330                 335
Lys Val Leu Ala Thr Gly Phe Leu Arg Glu Ala Arg Glu Ala Pro Glu
            340                 345                 350
Asp Ser Ala Val His Gln Ser Ile Leu Gly Val Met Leu Lys Ser Lys
            355                 360                 365
Asn Glu Asn Ala Asn Val Arg Leu Ser Leu Pro Glu Ile Thr Ala Gln
370                 375                 380
Ala Gly Gly Leu Val Leu Ala Gly Tyr Glu Thr Thr Ala Lys Ile His
385                 390                 395                 400
Arg Arg Ala Phe Pro Gln Trp Ser Leu Ile Glu Leu Ala Arg Arg Ala
                405                 410                 415
Glu Ile Gln Glu Thr Leu Arg Ala Glu Leu Lys Glu Cys Leu Ala Asp
            420                 425                 430
Gly Glu Arg Pro Thr Tyr Asp Gln Leu Thr Lys Asp Leu Lys Tyr Leu
            435                 440                 445
Asp Ala Phe Ile Ser Glu Ile Leu Arg Leu His Pro Ser Glu Met Val
450                 455                 460
```

-continued

Leu Thr Arg Val Ala Ala Glu Asp Asp Val Ile Pro Leu Thr Asp Pro
465                 470                 475                 480

Ile Arg Thr Ala Ser Gly Ala Met Ile Asp Ser Leu Phe Val Arg Lys
            485                 490                 495

Gly Thr Val Ser Ala Ser Leu
            500

<210> SEQ ID NO 617
<211> LENGTH: 35
<212> TYPE: PRT
<213> ORGANISM: Galerina marginata

<400> SEQUENCE: 617

Met Ser Asp Ile Asn Ala Thr Arg Leu Pro Ile Trp Gly Ile Gly Cys
1               5                   10                  15

Asn Pro Cys Ile Gly Asp Asp Val Thr Thr Leu Leu Thr Arg Gly Glu
            20                  25                  30

Ala Leu Cys
        35

<210> SEQ ID NO 618
<211> LENGTH: 17
<212> TYPE: PRT
<213> ORGANISM: Galerina marginata

<400> SEQUENCE: 618

Cys Ile Gly Asp Asp Val Thr Thr Leu Leu Thr Arg Gly Glu Ala Leu
1               5                   10                  15

Cys

<210> SEQ ID NO 619
<211> LENGTH: 34
<212> TYPE: PRT
<213> ORGANISM: Galerina marginata

<400> SEQUENCE: 619

Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Gly Glu Ser
            20                  25                  30

Leu Cys

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623
<211> LENGTH: 17

```
<212> TYPE: PRT
<213> ORGANISM: Galerina marginata

<400> SEQUENCE: 623

Met Ser Asp Ile Asn Ala Thr Arg Leu Pro Ala Trp Leu Val Asp Cys
1               5                   10                  15

Pro

<210> SEQ ID NO 624

<400> SEQUENCE: 624

000

<210> SEQ ID NO 625
<211> LENGTH: 15
<212> TYPE: PRT
<213> ORGANISM: Galerina marginata

<400> SEQUENCE: 625

Cys Val Gly Asp Asp Val Asn Arg Leu Leu Thr Arg Ser Leu Cys
1               5                   10                  15

<210> SEQ ID NO 626
<211> LENGTH: 33
<212> TYPE: PRT
<213> ORGANISM: Galerina marginata

<400> SEQUENCE: 626

Met Ala Asp Ile Asn Ala Thr Arg Leu Pro Ile Trp Gly Ile Gly Cys
1               5                   10                  15

Asn Pro Cys Ile Gly Asp Asp Val Thr Thr Leu Leu Thr Arg Ala Leu
            20                  25                  30

Cys

<210> SEQ ID NO 627
<211> LENGTH: 24
<212> TYPE: PRT
<213> ORGANISM: Galerina marginata

<400> SEQUENCE: 627

Met Ser Asp Ile Asn Ala Thr Arg Leu Pro Trp Cys Pro Cys Gly Asp
1               5                   10                  15

Asp Val Leu Leu Thr Arg Leu Cys
            20

<210> SEQ ID NO 628
<211> LENGTH: 32
<212> TYPE: PRT
<213> ORGANISM: Galerina marginata

<400> SEQUENCE: 628

Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Ser Leu Cys
            20                  25                  30

<210> SEQ ID NO 629
<211> LENGTH: 110
<212> TYPE: DNA
<213> ORGANISM: Amanita bisporigera

<400> SEQUENCE: 629
```

```
acccttccgc aatgtctgac gtcaatgaca cccgtcttcc cttcaacttc ttccgctttc      60
cctacccctg catcggtgac gacagcggaa gtgtcctcag gctcggcgag                110

<210> SEQ ID NO 630
<211> LENGTH: 3237
<212> TYPE: DNA
<213> ORGANISM: Puccinia graminis

<400> SEQUENCE: 630
atgaccaaac ctactaagaa cccatgggac cctaaggcaa caccttatcc ccccgttcgc      60

```
gtttcgatcg tcaagaggat caggaattgg tcgaattcag gaagactctg attccgggat    2040
tcaattccaa cgatttcgtt tccaaacagg tattctatga atcaaaggac gggaccaaag    2100
tcccgatgtt tatcgttcac aagaaagact tccagcagga cggtactgcg ccagctcttc    2160
agtacggata cgtaggcccc ccttttttta catattcttt ccatcatccg gtcagctcgc    2220
gaaaaccgga cagctaaggt gaactgttct ccagggtgga ttttcgatca gtatctcgcc    2280
ctacttttcg ccctctttca tgagctttgt agcccattat ggaggggtat tggctgtccc    2340
taacatccga gggggtggag agtatggaga ggactggcac ttggcaggct ggtcagtacc    2400
ctgaatgttc tcccttgaag ggtgtaaatt aaacgctaat tgattcgatg aatctcatg     2460 gatcgtggat gggtacagct ttgagaaaaa acagaacgtg ttcgacgact ccagtacgc     2520 taccaaatat ctggttgcca atcagtacgc ggcgcccgac aaggtgacca tcatgggcgg    2580
cagtaacgga ggtctcctgg tggcagcctg cgtgaaccag gctcccgagc tctttggagc    2640
cgcgcttgcc gaggtgggcg tgttggacat gttgaggttc catcggttca cgattgggta    2700
agggtcactt tatccaatca ccgccatcct ctctctctct ccgttctctt gagcttgagc    2760
ttactctccc cgcgccctgc gtcacgtttc cagacgggct tggatcgctg actatggaga    2820
cccagaagac cccgaagcat tcgactactt gatcaaatat tcccccttac ataacgtcaa    2880
cccggccgcg gaatatccgg ctctcatgct actcacagcg ggtcagtgcc agacccatcc    2940
catctcatct atcgacacgc cacatgatta ttcttaggat ctgttggagc cccactactg    3000
atgaggaggt tcgaatatct acaacatata gaccatgacg atcgggtggt ccctctgcac    3060
agcttcaagt acgctgctgc cgttcaacac gccctcccga cgaacaaaca accttgcttg    3120
ttgaggctcg atctcaaggc aggtcatgga gccgggaaga gcacggagat gaagatcaac    3180
tcggtcgtcg accaacgtct gtcctccagt ccttcaactt cttccccttg tttttga      3237

<210> SEQ ID NO 631
<211> LENGTH: 2190
<212> TYPE: DNA
<213> ORGANISM: Puccinia graminis

<400> SEQUENCE: 631
atgaccaaac ctactaagaa cccatgggac cctaaggcaa caccttatcc ccccgttcgc     60
agggatccag actcatcgga ggtcttccag agtaagcaga atggctcggt caccgtccca    120
gatcccttac agttggctac acgagccacc caagcagagc aaagacactc agtcacaaag    180
acttgggact atgctcgatt cagttgtcca tcgctgaagc cggatggata ctactatttc    240
agcttcaact ctggcctcca gcccagtcg atcatctatc gggtcaagaa ggggcaggaa     300
gaggatgcac tcaagcgggc caccgacccc aaacagcccg caggcgagct cttcctcgat    360
cccaacctgt tctccatcga tggcactacc gcactctcat tctccgccac atccgagtca    420
ggcatctata tggcgtacgg tgtctcccgc tctggaagcg acagtcagac tatctacgtc    480
cgtcgcaccg actctcccca cacaaagtct gccgccgatg tggcaagag gggcgaggac    540 cctggccgga tggaggacac agtcgagaag gttaaattca gtagcctcag ttggatgaaa    600
gacgattctg tgttctttta ttcaagattc cctgacgaac aggccaaagc tgagaagccc    660
tccgggcccg ggcggatgt tcaaggagaa gtagagattg atgccgggac agatactaag    720
gctgatctca atcacatgct ctactttcac aaacttggtg agccacagag taaagatctg    780
ttgatagtcg aggatccagc gaatccatcc tatatgtggg gagctgaagt ctcggatgac    840
gccaagtacc tcatcttgac gacctccaag gataccggcc gttcgaatcg actctgggtt    900
```

```
gccgatctga cctctcaacc cctatcgagt gagatgaaat ggcaaaagat tgtcaatgag    960
tttggcaacg agtacatctt cgcggccaat gatggcagtc aactatattt catgaccaac   1020
aaggacgcgc ctaaacgcaa ggtggtgacg tatgacttga gtaagcccga agaaggcttt   1080
aaagacttga tcccagagga tcctcaggcg gtcctggagg gttattatcc caccaacaaa   1140
gaattcaccg ttctgagcta ttctcgagat gtcaaagatg agctatacct ccacgagatc   1200
aagtcgggca gcggatcaa acggatcggc ggagacttga ttggcacgat cgggggcctt   1260
tccggccgcc gtaaacacga cgagttcttc ttccagatca gtagcttctt gagccccggc   1320
acggtctacc gctaccgttt cgatcgtcaa gaggatcagg aattggtcga attcaggaag   1380
actctgattc cgggattcaa ttccaacgat tcgtttcca aacaggtatt ctatgaatca    1440
aaggacggga ccaaagtccc gatgtttatc gttcacaaga aagacttcca gcaggacggt   1500
actgcgccag ctcttcatat ctcgccctac ttttcgccct cttcatgag ctttgtagcc    1560 cattatggag gggtattggc tgtccctaac atccgagggg gtggagagta tggagaggac   1620
tggcacttgg caggctgctt tgagaaaaaa cagaacgtgt cgacgactt ccagtacgct    1680 accaaatatc tggttgccaa tcagtacgcg gcgcccgaca aggtgaccat catgggcggc   1740
agtaacggag gtctcctggt ggcagcctgc gtgaaccagg ctcccgagct ctttggagcc   1800
gcgcttgccg aggtgggcgt gttggacatg ttgaggttcc atcggttcac gattggacgg   1860
gcttggatcg ctgactatgg agacccagaa gaccccgaag cattcgacta cttgatcaaa   1920
tattccccct tacataacgt caacccggcc gcggaatatc cggctctcat gctactcaca   1980
gcggaccatg acgatcgggt ggtccctctg cacagcttca agtacgctgc tgccgttcaa   2040
cacgccctcc cgacgaacaa acaaccttgc ttgttgaggc tcgatctcaa ggcaggtcat   2100
ggagccggga agagcacgga gatgaagatc aactcggtcg tcgaccaacg tctgtcctcc   2160
agtccttcaa cttcttcccc ttgttttga                                     2190
```

```
<210> SEQ ID NO 632
<211> LENGTH: 40
<212> TYPE: PRT
<213> ORGANISM: Puccinia graminis

<400> SEQUENCE: 632

Met Thr Lys Pro Thr Lys Asn Pro Trp Asp Pro Lys Ala Thr Pro Tyr
1               5                   10                  15

Pro Pro Val Arg Arg Asp Pro Asp Ser Ser Glu Val Phe Gln Ser Lys
            20                  25                  30

Gln Asn Gly Ser Val Thr Val Pro
        35                  40

<210> SEQ ID NO 633
<211> LENGTH: 8
<212> TYPE: PRT
<213> ORGANISM: Artificial Sequence
<220> FEATURE:
<223> OTHER INFORMATION: A synthetic protein
<220> FEATURE:
<221> NAME/KEY: VARIANT
<222> LOCATION: (1)...(8)
<223> OTHER INFORMATION: Xaa is any amino acid

<400> SEQUENCE: 633

Ala Ile Xaa Lys Ala Gly Xaa Ala
1               5
```

```
<210> SEQ ID NO 634
<211> LENGTH: 6
<212> TYPE: PRT
<213> ORGANISM: Artificial Sequence
<220> FEATURE:
<223> OTHER INFORMATION: A synthetic protein

<400> SEQUENCE: 634

Arg Gly Lys Pro Lys Gly
 1               5

<210> SEQ ID NO 635
<211> LENGTH: 6
<212> TYPE: PRT
<213> ORGANISM: Artificial Sequence
<220> FEATURE:
<223> OTHER INFORMATION: A synthetic protein

<400> SEQUENCE: 635

Thr Gly Lys Pro Lys Gly
 1               5

<210> SEQ ID NO 636
<211> LENGTH: 7
<212> TYPE: PRT
<213> ORGANISM: Artificial Sequence
<220> FEATURE:
<223> OTHER INFORMATION: A synthetic protein

<400> SEQUENCE: 636

Phe Thr Ser Gly Ser Thr Gly
 1               5

<210> SEQ ID NO 637
<211> LENGTH: 7
<212> TYPE: PRT
<213> ORGANISM: Artificial Sequence
<220> FEATURE:
<223> OTHER INFORMATION: A synthetic protein

<400> SEQUENCE: 637

Tyr Thr Ser Gly Ser Thr Gly
 1               5

<210> SEQ ID NO 638
<211> LENGTH: 5
<212> TYPE: PRT
<213> ORGANISM: Artificial Sequence
<220> FEATURE:
<223> OTHER INFORMATION: A synthetic protein

<400> SEQUENCE: 638

Tyr Gly Pro Thr Glu
 1               5

<210> SEQ ID NO 639
<211> LENGTH: 6
<212> TYPE: PRT
<213> ORGANISM: Artificial Sequence
<220> FEATURE:
<223> OTHER INFORMATION: A synthetic protein

<400> SEQUENCE: 639

Pro Cys Thr Pro Leu Gln
 1               5
```

```
<210> SEQ ID NO 640
<211> LENGTH: 7
<212> TYPE: PRT
<213> ORGANISM: Artificial Sequence
<220> FEATURE:
<223> OTHER INFORMATION: A synthetic protein

<400> SEQUENCE: 640

Tyr Arg Thr Gly Asp Leu Val
1               5

<210> SEQ ID NO 641
<211> LENGTH: 6
<212> TYPE: PRT
<213> ORGANISM: Artificial Sequence
<220> FEATURE:
<223> OTHER INFORMATION: A synthetic protein
<220> FEATURE:
<221> NAME/KEY: VARIANT
<222> LOCATION: (1)...(6)
<223> OTHER INFORMATION: Xaa is any amino acid

<400> SEQUENCE: 641

Glu Leu Xaa Glu Ile Glu
1               5

<210> SEQ ID NO 642
<211> LENGTH: 5
<212> TYPE: PRT
<213> ORGANISM: Artificial Sequence
<220> FEATURE:
<223> OTHER INFORMATION: A synthetic protein

<400> SEQUENCE: 642

Ile Ser Asp Gly Trp
1               5

<210> SEQ ID NO 643
<211> LENGTH: 6
<212> TYPE: PRT
<213> ORGANISM: Artificial Sequence
<220> FEATURE:
<223> OTHER INFORMATION: A synthetic protein

<400> SEQUENCE: 643

Glu Gly His Gly Arg Glu
1               5

<210> SEQ ID NO 644
<211> LENGTH: 6
<212> TYPE: PRT
<213> ORGANISM: Artificial Sequence
<220> FEATURE:
<223> OTHER INFORMATION: A synthetic protein

<400> SEQUENCE: 644

Gln Glu Gly Met Leu Ala
1               5

<210> SEQ ID NO 645
<211> LENGTH: 6
<212> TYPE: PRT
<213> ORGANISM: Artificial Sequence
<220> FEATURE:
<223> OTHER INFORMATION: A synthetic protein

<400> SEQUENCE: 645

Gln Glu Gly Leu Met Ala
```

```
1               5

<210> SEQ ID NO 646

<400> SEQUENCE: 646

000

<210> SEQ ID NO 647
<211> LENGTH: 7
<212> TYPE: PRT
<213> ORGANISM: Artificial Sequence
<220> FEATURE:
<223> OTHER INFORMATION: A synthetic protein

<400> SEQUENCE: 647

Gly Glu Leu Ile Ile Gly Gly
1               5

<210> SEQ ID NO 648
<211> LENGTH: 6
<212> TYPE: PRT
<213> ORGANISM: Artificial Sequence
<220> FEATURE:
<223> OTHER INFORMATION: A synthetic protein

<400> SEQUENCE: 648

Tyr Lys Thr Gly Asp Leu
1               5

<210> SEQ ID NO 649
<211> LENGTH: 6
<212> TYPE: PRT
<213> ORGANISM: Artificial Sequence
<220> FEATURE:
<223> OTHER INFORMATION: A synthetic protein

<400> SEQUENCE: 649

Lys Asp Thr Gln Val Lys
1               5

<210> SEQ ID NO 650
<211> LENGTH: 7
<212> TYPE: PRT
<213> ORGANISM: Artificial Sequence
<220> FEATURE:
<223> OTHER INFORMATION: A synthetic protein
<220> FEATURE:
<221> NAME/KEY: VARIANT
<222> LOCATION: 6
<223> OTHER INFORMATION: Xaa can be Ala or Thr

<400> SEQUENCE: 650

Gly Gly Asp Ser Ile Xaa Ala
1               5

<210> SEQ ID NO 651
<211> LENGTH: 7
<212> TYPE: PRT
<213> ORGANISM: Artificial Sequence
<220> FEATURE:
<223> OTHER INFORMATION: A synthetic protein
<220> FEATURE:
<221> NAME/KEY: VARIANT
<222> LOCATION: 6
<223> OTHER INFORMATION: Xaa can be Ala or Thr

<400> SEQUENCE: 651
```

Gly Gly His Ser Ile Xaa Ala
1               5

<210> SEQ ID NO 652
<211> LENGTH: 99
<212> TYPE: DNA
<213> ORGANISM: Amanita bisporigera

<400> SEQUENCE: 652
atgtctgaca tcaatgccac ccgtcttccc gcttggcttg tagactgccc atgcgtcggt 60
gacgatgtca accgtctcct cactcgtagc ctttggtaa 99

<210> SEQ ID NO 653
<211> LENGTH: 7
<212> TYPE: PRT
<213> ORGANISM: Artificial Sequence
<220> FEATURE:
<223> OTHER INFORMATION: A synthetic protein
<220> FEATURE:
<221> NAME/KEY: VARIANT
<222> LOCATION: 4
<223> OTHER INFORMATION: Xaa at this position can be Tyr or Phe
<220> FEATURE:
<221> NAME/KEY: VARIANT
<222> LOCATION: 5
<223> OTHER INFORMATION: Xaa at this position can be Ala or Pro

<400> SEQUENCE: 653

Glu Asp Val Xaa Xaa Cys Thr
 1 5

<210> SEQ ID NO 654
<211> LENGTH: 10
<212> TYPE: PRT
<213> ORGANISM: Amanita

<400> SEQUENCE: 654

Met Ser Asp Ile Asn Val Thr Arg Leu Pro
 1 5 10

<210> SEQ ID NO 655
<211> LENGTH: 8
<212> TYPE: PRT
<213> ORGANISM: Amanita

<400> SEQUENCE: 655

Ile Trp Gly Ile Gly Cys Val Leu
 1 5

<210> SEQ ID NO 656
<211> LENGTH: 6
<212> TYPE: PRT
<213> ORGANISM: Burkholderia ambifaria

<400> SEQUENCE: 656

Ala Trp Leu Val Asp Cys
 1 5

<210> SEQ ID NO 657
<211> LENGTH: 7
<212> TYPE: PRT
<213> ORGANISM: Pseudomonas aeruginosa

<400> SEQUENCE: 657

Ala Trp Val Val Asp Cys Pro
 1 5

<210> SEQ ID NO 658
<211> LENGTH: 5
<212> TYPE: PRT
<213> ORGANISM: Galerina marginata

<400> SEQUENCE: 658

Tyr Leu Leu Asn Val
1               5

<210> SEQ ID NO 659
<211> LENGTH: 20
<212> TYPE: PRT
<213> ORGANISM: Amanita bisporigera

<400> SEQUENCE: 659

Thr Asn Phe Gly Ser Arg Ile Gly Thr Ile Thr Pro Arg Leu Phe
1               5                   10                  15

Ala Thr Val Arg
            20

<210> SEQ ID NO 660
<211> LENGTH: 13
<212> TYPE: PRT
<213> ORGANISM: Amanita bisporigera

<400> SEQUENCE: 660

Ile Arg Leu Ser Leu Tyr Arg Ser Leu Phe Ser Val Ile
1               5                   10

<210> SEQ ID NO 661
<211> LENGTH: 5
<212> TYPE: PRT
<213> ORGANISM: Amanita bisporigera

<400> SEQUENCE: 661

Lys Leu Gln Ala Met
1               5

<210> SEQ ID NO 662
<211> LENGTH: 6
<212> TYPE: PRT
<213> ORGANISM: Amanita bisporigera

<400> SEQUENCE: 662

Gly Ser Pro Arg Pro Pro
1               5

<210> SEQ ID NO 663
<211> LENGTH: 48
<212> TYPE: PRT
<213> ORGANISM: Amanita bisporigera

<400> SEQUENCE: 663

Val Leu Leu Arg Ala Val Cys Gln Ser Gly Gln Arg Tyr Thr Ser Ala
1               5                   10                  15

Arg Val Leu Leu Asp Leu Pro Pro Ile Trp Asn Phe Pro Met Gly Trp
            20                  25                  30

Ser Asp Ala Leu Arg Ser Gln Asn Ser Thr Asn Glu Asp Ser Ser Ser
        35                  40                  45

<210> SEQ ID NO 664
<211> LENGTH: 10

```
<212> TYPE: PRT
<213> ORGANISM: Amanita bisporigera

<400> SEQUENCE: 664

Trp Arg Arg Lys Cys Leu Gly Pro Leu Phe
1               5                   10

<210> SEQ ID NO 665
<211> LENGTH: 85
<212> TYPE: PRT
<213> ORGANISM: Amanita bisporigera

<400> SEQUENCE: 665

Lys Phe Thr Val Leu Arg Ser Arg Cys Tyr Phe Leu Thr His Gln Leu
1               5                   10                  15

Tyr Ser Val Leu Glu Arg Asp Lys Arg Arg Ser Ser Val Gln Ala Asp
            20                  25                  30

Leu Gln Ser Pro Asn Ala Asn Ser Leu Asn Gln Arg Phe Phe Ala
        35                  40                  45

Leu Thr Ser Thr Met Phe Asp Thr Asn Ala Thr Arg Leu Pro Ile Trp
50                  55                  60

Gly Ile Gly Cys Asn Pro Trp Thr Ala Glu His Val Asp Gln Thr Leu
65                  70                  75                  80

Ala Ser Gly Asn Glu
                85

<210> SEQ ID NO 666
<211> LENGTH: 33
<212> TYPE: PRT
<213> ORGANISM: Homo sapiens

<400> SEQUENCE: 666

Gln Thr Val Gln Ile Phe Tyr Pro Ser Lys Asp Gly Thr Lys Ile Pro
1               5                   10                  15

Met Phe Ile Val His Lys Lys Ser Thr Lys Leu Asp Gly Ser His Pro
            20                  25                  30

Ala

<210> SEQ ID NO 667
<211> LENGTH: 32
<212> TYPE: PRT
<213> ORGANISM: Homo sapiens

<400> SEQUENCE: 667

Ile Phe Tyr Pro Ser Lys Asp Gly Thr Lys Ile Pro Met Phe Ile Val
1               5                   10                  15

His Lys Lys Ser Ile Lys Leu Asp Gly Ser His Pro Ala Phe Leu Tyr
            20                  25                  30

<210> SEQ ID NO 668
<211> LENGTH: 26
<212> TYPE: PRT
<213> ORGANISM: Homo sapiens

<400> SEQUENCE: 668

Lys Arg Leu Thr Ile Asn Gly Gly Ser Asn Gly Gly Leu Leu Val Ala
1               5                   10                  15

Ala Cys Ala Asn Gln Arg Pro Asp Leu Phe
            20                  25
```

```
<210> SEQ ID NO 669
<211> LENGTH: 27
<212> TYPE: PRT
<213> ORGANISM: Homo sapiens

<400> SEQUENCE: 669

Ser Asp Asp Gly Thr Val Ala Leu Arg Gly Tyr Ala Phe Ser Glu Asp
1               5                   10                  15

Gly Glu Tyr Phe Ala Tyr Gly Leu Ser Ala Ser
            20                  25

<210> SEQ ID NO 670
<211> LENGTH: 20
<212> TYPE: PRT
<213> ORGANISM: Homo sapiens

<400> SEQUENCE: 670

Pro Leu Leu Ile His Val Asp Thr Lys Ala Gly His Ala Gly Lys
1               5                   10                  15

Pro Thr Ala Lys
            20

<210> SEQ ID NO 671
<211> LENGTH: 16
<212> TYPE: PRT
<213> ORGANISM: Homo sapiens

<400> SEQUENCE: 671

Asp Gly Thr Lys Ile Pro Met Phe Ile Val His Lys Lys Ser Thr Lys
1               5                   10                  15

<210> SEQ ID NO 672
<211> LENGTH: 23
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(23)
<223> OTHER INFORMATION: W is A or T
<220> FEATURE:
<221> NAME/KEY: misc_feature
<222> LOCATION: (1)...(23)
<223> OTHER INFORMATION: Y is C or T
<220> FEATURE:
<221> NAME/KEY: misc_feature
<222> LOCATION: (1)...(23)
<223> OTHER INFORMATION: N is inosine
<220> FEATURE:
<221> NAME/KEY: misc_feature
<222> LOCATION: (1)...(23)
<223> OTHER INFORMATION: K is G or T

<400> SEQUENCE: 672
twygcnacng gngayykngk ncg                                       23

<210> SEQ ID NO 673
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: R is A or G
<220> FEATURE:
<221> NAME/KEY: misc_feature
```

```
<222> LOCATION: (1)...(17)
<223> OTHER INFORMATION: Y is C or T
<220> FEATURE:
<221> NAME/KEY: misc_feature
<222> LOCATION: (1)...(17)
<223> OTHER INFORMATION: N is any nucleic acid
<220> FEATURE:
<221> NAME/KEY: misc_feature
<222> LOCATION: (1)...(17)
<223> OTHER INFORMATION: H is A, C, or T
<220> FEATURE:
<221> NAME/KEY: misc_feature
<222> LOCATION: (1)...(17)
<223> OTHER INFORMATION: R is A or G

<400> SEQUENCE: 673
garytngsng arathga                                                  17

<210> SEQ ID NO 674
<211> LENGTH: 17
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(17)
<223> OTHER INFORMATION: N is inosine
<220> FEATURE:
<221> NAME/KEY: misc_feature
<222> LOCATION: (1)...(17)
<223> OTHER INFORMATION: Y is C or T
<220> FEATURE:
<221> NAME/KEY: misc_feature
<222> LOCATION: (1)...(17)
<223> OTHER INFORMATION: R is A or G

<400> SEQUENCE: 674
ggnacytgnt grtcytt                                                  17

<210> SEQ ID NO 675
<211> LENGTH: 26
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(26)
<223> OTHER INFORMATION: W is A or T
<220> FEATURE:
<221> NAME/KEY: misc_feature
<222> LOCATION: (1)...(26)
<223> OTHER INFORMATION: N is any nucleic acid
<220> FEATURE:
<221> NAME/KEY: misc_feature
<222> LOCATION: (1)...(26)
<223> OTHER INFORMATION: R is A or G
<220> FEATURE:
<221> NAME/KEY: misc_feature
<222> LOCATION: (1)...(26)
<223> OTHER INFORMATION: K is G or T
<220> FEATURE:
<221> NAME/KEY: misc_feature
<222> LOCATION: (1)...(26)
<223> OTHER INFORMATION: S is G or C
<220> FEATURE:
<221> NAME/KEY: misc_feature
<222> LOCATION: (1)...(26)
<223> OTHER INFORMATION: M is A or C

<400> SEQUENCE: 675
awngarksnc cnccnrrsnm raaraa                                        26
```

```
<210> SEQ ID NO 676
<211> LENGTH: 18
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(18)
<223> OTHER INFORMATION: N is any nucleic acid
<220> FEATURE:
<221> NAME/KEY: misc_feature
<222> LOCATION: (1)...(18)
<223> OTHER INFORMATION: Y is C or T
<220> FEATURE:
<221> NAME/KEY: misc_feature
<222> LOCATION: (1)...(18)
<223> OTHER INFORMATION: R is A or G

<400> SEQUENCE: 676
ggnggngayt cnatyrcn                                                 18

<210> SEQ ID NO 677
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: N is any nucleic acid
<220> FEATURE:
<221> NAME/KEY: misc_feature
<222> LOCATION: (1)...(20)
<223> OTHER INFORMATION: Y is C or T
<220> FEATURE:
<221> NAME/KEY: misc_feature
<222> LOCATION: (1)...(20)
<223> OTHER INFORMATION: D is A, G, or T
<220> FEATURE:
<221> NAME/KEY: misc_feature
<222> LOCATION: (1)...(20)
<223> OTHER INFORMATION: W is A or T
<220> FEATURE:
<221> NAME/KEY: misc_feature
<222> LOCATION: (1)...(20)
<223> OTHER INFORMATION: R is A or G

<400> SEQUENCE: 677
gcngydatns wrtcnccncc                                               20
```